(12) United States Patent
Gege et al.

(10) Patent No.: US 12,291,523 B2
(45) Date of Patent: *May 6, 2025

(54) LXR MODULATORS WITH BICYCLIC CORE MOIETY

(71) Applicant: OrsoBio, Inc., Menlo Park, CA (US)

(72) Inventors: Christian Gege, Ehingen (DE); Olaf Kinzel, Heidelberg (DE); Eva Hambruch, Mannheim (DE); Manfred Birkel, Seeheim-Jugenheim (DE); Claus Kremoser, Heidelberg (DE); Ulrich Deuschle, Speyer (DE)

(73) Assignee: ORSOBIO, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/596,586

(22) Filed: Mar. 5, 2024

(65) Prior Publication Data

US 2024/0317726 A1    Sep. 26, 2024

Related U.S. Application Data

(60) Continuation of application No. 18/166,831, filed on Feb. 9, 2023, now Pat. No. 11,970,484, which is a division of application No. 17/255,821, filed as application No. PCT/EP2019/067351 on Jun. 28, 2019, now Pat. No. 11,618,747.

(30) Foreign Application Priority Data

Jun. 28, 2018 (EP) ................................. 18180450

(51) Int. Cl.
| | |
|---|---|
| C07D 409/14 | (2006.01) |
| A61P 1/16 | (2006.01) |
| C07D 209/18 | (2006.01) |
| C07D 401/04 | (2006.01) |
| C07D 403/04 | (2006.01) |
| C07D 403/10 | (2006.01) |
| C07D 405/04 | (2006.01) |
| C07D 405/10 | (2006.01) |
| C07D 405/14 | (2006.01) |
| C07D 409/04 | (2006.01) |
| C07D 413/04 | (2006.01) |
| C07D 417/04 | (2006.01) |
| C07D 417/14 | (2006.01) |
| C07D 451/02 | (2006.01) |
| C07D 471/04 | (2006.01) |
| C07D 495/04 | (2006.01) |

(52) U.S. Cl.
CPC .............. *C07D 409/14* (2013.01); *A61P 1/16* (2018.01); *C07D 209/18* (2013.01); *C07D 401/04* (2013.01); *C07D 403/04* (2013.01); *C07D 403/10* (2013.01); *C07D 405/04* (2013.01); *C07D 405/10* (2013.01); *C07D 405/14* (2013.01); *C07D 409/04* (2013.01); *C07D 413/04* (2013.01); *C07D 417/04* (2013.01); *C07D 417/14* (2013.01); *C07D 451/02* (2013.01); *C07D 471/04* (2013.01); *C07D 495/04* (2013.01); *C07B 2200/05* (2013.01)

(58) Field of Classification Search
CPC .. C07D 409/14; C07D 209/18; C07D 401/04; C07D 403/04; C07D 403/10; C07D 405/04; C07D 405/10; C07D 405/14; C07D 409/04; C07D 413/04; C07D 417/04; C07D 417/14; C07D 451/02; C07D 471/04; C07D 495/04; A61P 1/16; C07B 2200/05
USPC .................................................... 514/210.18
See application file for complete search history.

(56) References Cited

U.S. PATENT DOCUMENTS

| | | | |
|---|---|---|---|
| 9,464,044 B2 | 10/2016 | Ahn et al. | |
| 9,708,316 B2 | 7/2017 | Fink et al. | |
| 11,136,290 B2 | 10/2021 | Farand et al. | |
| 11,618,747 B2 | 4/2023 | Gege et al. | |
| 11,970,484 B2 * | 4/2024 | Gege .................... | C07D 409/04 |
| 2007/0072911 A1 | 3/2007 | Avolio et al. | |
| 2007/0293547 A1 | 12/2007 | Molteni et al. | |
| 2010/0184598 A1 | 7/2010 | Selles et al. | |
| 2011/0288074 A1 | 11/2011 | Schann et al. | |
| 2015/0210635 A1 | 7/2015 | Ahn et al. | |
| 2015/0291563 A1 | 10/2015 | Park et al. | |
| 2017/0226053 A1 | 8/2017 | Gauvry et al. | |
| 2019/0359565 A1 | 11/2019 | Farand et al. | |
| 2020/0397807 A1 | 12/2020 | Pranesh et al. | |
| 2021/0147398 A1 | 5/2021 | Gege et al. | |

(Continued)

FOREIGN PATENT DOCUMENTS

| | | |
|---|---|---|
| AU | 2019272538 A1 | 11/2020 |
| CA | 3099051 A1 | 11/2019 |
| CN | 1476432 A | 2/2004 |

(Continued)

OTHER PUBLICATIONS

Abulizi et al. "A controlled-release mitochondrial protonophore reverses hypertriglyceridemia, nonalcoholic steatohepatitis, and diabetes in lipodystrophic mice," FASEB J. (2017); 31(7):2916-2924.

(Continued)

*Primary Examiner* — Kristin A Vajda
(74) *Attorney, Agent, or Firm* — COOLEY LLP

(57) ABSTRACT

The present invention relates to bicyclic compounds (e.g. indoles) containing a sulfonyl moiety, which bind to the liver X receptor (LXRa and/or LXKJ3) and act preferably as inverse agonists of LXR.

2 Claims, 1 Drawing Sheet

Specification includes a Sequence Listing.

(56) References Cited

U.S. PATENT DOCUMENTS

| | | | |
|---|---|---|---|
| 2022/0055985 A1 | 2/2022 | Farand et al. | |
| 2023/0357214 A1 | 11/2023 | Gege et al. | |

FOREIGN PATENT DOCUMENTS

| | | | |
|---|---|---|---|
| CN | 1863528 A | 11/2006 | |
| CN | 1950365 A | 4/2007 | |
| CN | 101184731 A | 5/2008 | |
| CN | 101213194 A | 7/2008 | |
| CN | 105209039 A | 12/2015 | |
| CN | 108137497 A | 6/2018 | |
| CN | 110914248 A | 3/2020 | |
| EP | 0535925 A1 | 4/1993 | |
| EP | 0535926 A1 | 4/1993 | |
| EP | 2865664 A1 | 4/2015 | |
| JP | H06145150 A | 5/1994 | |
| JP | 2007508286 A | 4/2007 | |
| JP | 2007523087 A | 8/2007 | |
| JP | 2010506954 A | 3/2010 | |
| JP | 2012515759 A | 7/2012 | |
| JP | 2012529436 A | 11/2012 | |
| JP | 2015525238 A | 9/2015 | |
| TW | 200602320 A | 1/2006 | |
| TW | 200637816 A | 11/2006 | |
| TW | 200745031 A | 12/2007 | |
| TW | 202003457 A | 1/2020 | |
| WO | WO-9822452 A1 | 5/1998 | |
| WO | WO-9822457 A1 | 5/1998 | |
| WO | WO-9857931 A2 | 12/1998 | |
| WO | WO-9921851 A1 | 5/1999 | |
| WO | WO-0046195 A1 | 8/2000 | |
| WO | WO-0046197 A1 | 8/2000 | |
| WO | WO-0046199 A2 | 8/2000 | |
| WO | WO-0130343 A1 | 5/2001 | |
| WO | WO-0218335 A1 | 3/2002 | |
| WO | WO-0232863 A1 | 4/2002 | |
| WO | WO-0236562 A2 | 5/2002 | |
| WO | WO-02051837 A2 | 7/2002 | |
| WO | WO-03082802 A1 | 10/2003 | |
| WO | WO-2004000831 A1 | 12/2003 | |
| WO | WO-2005014000 A1 | 2/2005 | |
| WO | WO-2005034941 A1 | 4/2005 | |
| WO | WO-2005085188 A2 | 9/2005 | |
| WO | WO-2006050236 A2 | 5/2006 | |
| WO | WO-2007075555 A2 | 7/2007 | |
| WO | WO-2007134169 A2 | 11/2007 | |
| WO | WO-2008003736 A1 | 1/2008 | |
| WO | WO-2008049047 A2 | 4/2008 | |
| WO | WO-2008116833 A1 | 10/2008 | |
| WO | WO-2008119657 A1 | 10/2008 | |
| WO | WO-2008132434 A2 | 11/2008 | |
| WO | WO-2009032116 A1 | 3/2009 | |
| WO | WO-2009032125 A1 | 3/2009 | |
| WO | WO-2009064848 A1 | 5/2009 | |
| WO | WO-2009064852 A1 | 5/2009 | |
| WO | WO-2010010186 A1 | 1/2010 | |
| WO | WO-2010124793 A1 | 11/2010 | |
| WO | WO-2010144452 A1 | 12/2010 | |
| WO | WO-2013012649 A1 | 1/2013 | |
| WO | WO-2013028999 A1 | 2/2013 | |
| WO | WO-2013111150 A1 | 8/2013 | |
| WO | WO-2014085453 A2 | 6/2014 | |
| WO | WO-2016081599 A1 | 5/2016 | |
| WO | WO-2016106266 A1 | 6/2016 | |
| WO | WO-2016207217 A1 | 12/2016 | |
| WO | WO-2017201313 A1 | 11/2017 | |
| WO | WO-2018188795 A1 | 10/2018 | |
| WO | WO-2019016269 A1 | 1/2019 | |
| WO | WO-2019226490 A1 | 11/2019 | |
| WO | WO-2020002611 A1 | 1/2020 | |
| WO | WO-2024097897 A1 | 5/2024 | |

OTHER PUBLICATIONS

Ahn, Sang Bong, et al., "Expression of Liver X Receptor Correlates with Intrahepatic Inflammation and Fibrosis in Patients with Nonalcoholic Fatty Liver Disease," Digestive Diseases and Sciences (2014); 59(12):2975-2982.

Attie, K. M., et al., "Increased lean mass and muscle volume in healthy post-menopausal women treated with ACE-031 (Soluble activin type IIB receptor), an inhibitor of myostatin and other negative regulators of muscle," Muscle Disease: Myopathy: Therapeutic Issues, Neurology, 2011, 76(9), Suppl. 4, pp. A281-A282 (P04.019).

Aurora Fine Chemicals. https://aurorafinechemicals.com/about.html, downloaded on Jul. 16, 2020 (Year: 2020), 1 page.

Aurora Fine Chemicalss. [retrieved online] http://online.aurorafinechemicals.com/StrSearch-new.asp?S2=&R1=&C1=&C2=&C3=ON&C4=ON&R2=V2& T1=70& T2=1 00&mol In=&B1=Search&N DISPLAY=20&ALLFIELDS=K24.833.925, downloaded on Jul. 16, 2020 (Year: 2020), 2 pages.

Bakir, F., et al. "Discovery and Structure-activity Relationship Studies of Indole Derivatives as Liver X Receptor (LXR) Agonists," Bioorganic & Medicinal Chemistry Letters, (2007); 17(12):3473-3479.

Capitta et al. "'Quick and click' assembly of functionalised indole rings via metal-promoted cyclative tandem reactions," RSC Advances (2014); 4(103):59297-59301.

Childress, E.S., et al., "Small Molecule Mitochondrial Uncouplers and Their Therapeutic Potential," Journal of Medicinal Chemistry, Jun. 14, 2018, vol. 61(11), pp. 4641-4655.

Collins, Jon L., et al. "Identification of a Nonsteroidal Liver X Receptor Agonist through Parallel Array Synthesis of Tertiary Amines," Journal of Medicinal Chemistry (2002); 45(10):1963-1966.

Database Registry [Online] Chemical Abstracts Service (2018) Retrieved from STN Database Accession No. 2030852-21-0: Abstract, 1 page.

Database Registry [Online] Chemical Abstracts Service (2018) Retrieved from STN Database Accession No. 2039648-43-4: Abstract, 1 page.

Database Registry [Online] Chemical Abstracts Service (2018) Retrieved from STN Database Accession No. 2177727-62-5: Abstract, 1 page.

Database Registry [Online] Chemical Abstracts Service (2018) Retrieved from STN Database Accession No. 2188864-14-2: Abstract, 1 page.

Database Registry [Online] Chemical Abstracts Service (2018) Retrieved from STN Database Accession No. 2192710-60-2: Abstract, 1 page.

Database Registry [Online] Chemical Abstracts Service (2018) Retrieved from STN Database Accession No. 2196006-39-8: Abstract, 1 page.

Database Registry [Online] Chemical Abstracts Service (2018) Retrieved from STN Database Accession No. 2196723-55-2: Abstract, 1 page.

Day, Christopher P., and James, Oliver F. W., "Steatohepatitis: A tale of two "Hits"?" Gastroenterology (1998); 114(4):842-845.

Estes, Chris, et al., "Modeling NAFLD disease burden in China, France, Germany, Italy, Japan, Spain, United Kingdom, and United States for the period 2016-2030," Journal of Hepatology (2018) 69(4):896-904.

Estes, Chris, et al., "Modeling the epidemic of nonalcoholic fatty liver disease demonstrates an exponential increase in burden of disease," Hepatology (2018); 67(1):123-133.

Extended European Search Report mailed Nov. 22, 2018, issued in corresponding Application No. 18180450.1, filed Jun. 28, 2018, 8 pages.

Faucher, Anne-Marie, et al., "Discovery of Small-Molecule Inhibitors of the ATPase Activity of Human Papillomavirus E1 Helicase," Journal of Medicinal Chemistry (2004); 47(1):18-21.

Flaveny, Colin A., et al., "Broad Anti-tumor Activity of a Small Molecule that Selectively Targets the Warburg Effect and Lipogenesis," Cancer Cell (2015); 28(1):42-56.

Foster "Deuterium Isotope Effects in Studies of Drug Metabolism," Trends Pharmacol. Sci. (1984); 5(12):524-527.

(56) References Cited

OTHER PUBLICATIONS

García-Mediavilla, Maria Victoria, et al. "Liver X receptor a-mediated regulation of lipogenesis by core and NS5A proteins contributes to HCV-induced liver steatosis and HCV replication." Laboratory Investigation 92.8 (2012): 1191-1202.

Giesbrecht, Heath E., et al. "Thieme Chemistry Journal Awardees—Where Are They Now? Stereoselective Synthesis of Z-Configured α,β-Unsaturated Macrocyclic Lactones and Diolides by Intramolecular Julia-Kocienski Olefination," Synlett (2010) 3:374-378.

Griffett, Kristine, and Burris, Thomas P., "Promiscuous activity of the LXR antagonist GSK2033 in a mouse model of fatty liver disease," Biochemical and Biophysical Research Communications (2016); 479(3):424-428.

Griffett, Kristine, et al. "A Liver-Selective LXR Inverse Agonist That Suppresses Hepatic Steatosis," ACS Chemical Biology (2013); 8(3):559-567.

Griffett, Kristine, et al. "The LXR inverse agonist SR9238 suppresses fibrosis in a model of non-alcoholic steatohepatitis." Molecular Metabolism (2015); 4(4):353-357.

Gronemeyer, Hinrich, et al. "Principles for modulation of the nuclear receptor superfamily," Nature Reviews Drug Discovery (2004); 3(11):950-964.

Guo, T., et al., "Myostatin inhibition prevents diabetes and hyperphagia in a mouse model of lipodystrophy," Diabetes, Oct. 2012, vol. 61(10), pp. 2414-2423, doi: 10.2337/db11-0915.

He, Y.P., et al.; "Palladium-Catalyzed Enantioselective Cacchi Reaction: Asymmetric Synthesis of Axially Chiral 2,3-Disubstituted Indoles," Angewandte Chemie International Edition (2020); 59(5):2105-2109.

Huang, Peng, et al. "Liver X Receptor Inverse Agonist SR9243 Suppresses Nonalcoholic Steatohepatitis Intrahepatic Inflammation and Fibrosis," BioMed Research International (2018); 2018: Article 8071093, 8 pages.

International Preliminary Report on Patentability dated Nov. 24, 2020, for PCT/US2019/032925, 9 pages.

International Preliminary Report on Patentability for PCT/EP2019/067351 mailed Jan. 7, 2021, 7 pages.

International Search Report and Written Opinion dated Jan. 29, 2024, for PCT/US2023/078547, 12 pages.

International Search Report and Written Opinion dated Jul. 19, 2019, for PCT/US2019/032925, 13 pages.

International Search Report mailed Aug. 12, 2019, issued in corresponding Application No. PCT/EP2019/067351, filed Jun. 28, 2019, 5 pages.

Kim, J., et al., "Ruthenium-Catalyzed Direct C-H Amidation of Arenes Including Weakly Coordinating Aromatic Ketones," Chemistry—A European Journal, (2013); 19(23):7328-7333.

Kirchgessner, Todd G., et al., "Beneficial and Adverse Effects of an LXR Agonist on Human Lipid and Lipoprotein Metabolism and Circulating Neutrophils," Cell Metabolism (2016); 24(2):223-233.

Kremoser, Claus, et al. "Panning for SNURMs: using cofactor profiling for the rational discovery of selective nuclear receptor modulators," Drug Discovery Today (2007); 12(19-20):860-869.

Li, X., et al.; "Construction of Atropisomeric 3-Arylindoles via Enantioselective Cacchi Reaction," Organic Letters. (2021); 23(15):5901-5905.

Liberti, Maria V., and Jason W. Locasale. "The Warburg Effect: How Does it Benefit Cancer Cells?" Trends in Biochemical Sciences (2016); 41(3):211-218.

Liu, Shuman, and Vaziri, Nosratola D., "Role of PCSK9 and Idol in the pathogenesis of acquired LDL receptor deficiency and hypercholesterolemia in nephrotic syndrome," Nephrology Dialysis Transplantation (2014); 29(3):538-543.

Papageorgiou, Anna-Pia, et al., "Liver X receptor activation enhances CVB3 viral replication during myocarditis by stimulating lipogenesis," Cardiovascular Research (2015); 107(1):78-88.

Patel, Rucha, et al. "Separating the Anti-Inflammatory and Diabetogenic Effects of Glucocorticoids Through LXRβ Antagonism," Endocrinology (2017); 158(4):1034-1047.

Peet, Daniel J., et al., "Cholesterol and Bile Acid Metabolism are Impaired in Mice Lacking the Nuclear Oxysterol Receptor LXRα," Cell (1998); 9(5):693-704.

Qu., C, et al. "Cascade photoredox/gold catalysis: access to multisubstituted indoles via aminoarylation of alkynes," Chemical Communications, (2016); 52(100):14400-14403.

RN 1005134-02-0 and RN 1005178-70-0 (both publicly available in 2008) (Year: 2008), 1 page.

RN: 2216852 37 6 to RN: 313373 56 7 all 35 compounds, Database Registry [Online] Retrieved from STN, Apr. 22, 2018, 20 pages.

Schultz, Joshua R., et al., "Role of LXRs in control of lipogenesis," Genes & Development (2000); 14(22):2831-2838.

Sci Finder entry for RN 2036868-48-9, downloaded on Jul. 16, 2020 (Year: 2020), 1 page.

Sreenivasa, G.M., et al. "Synthesis and Characterization of 2-Benzene Sulphonamido-N(2'-Benzothiazolyl 6'-Fluoro-7'-Substituted) Benzamide and 2-(2-Phenyl-4-Benzylidenyl-5-Oxo-Imidazolin-1-YL) N-(2'-Amino (1', 3') Benzothiazolyl 6'- Fluoro 7'-Substituted) Benzamide," Rapports De Pharmacie, (2015); 1(1):9-16.

Steffensen, Knut R. "Are Synthetic Compounds that Silence the Liver-X-Receptor the Next Generation of Anti-cancer Drugs?" Cancer Cell (2015); 28(1):3-4.

STN file for RN 2036868-48-9, publicly available since Nov. 24, 2016 (Year: 2016), 1 page.

Taiwan Office Action mailed Apr. 6, 2020, issued in corresponding Application No. 108121075 filed Jun. 18, 2019, with English Translation, 12 pages.

Tanko L.B. "Does Activin Receptor Blockade by Bimagrumab (BYM338) Pose Detrimental Effects on Bone Healing in a Rat Fibula Osteotomy Model?" Calcified Tissue International, (2016); 99(3):310-321.

Tian, M., et al.; "Rh(III)-Catalyzed Asymmetric Synthesis of Axially Chiral Biindolyls by Merging C-H Activation and Nucleophilic Cyclization," Journal of the American Chemical Society (2019); 141(24):9527-9532.

Traversari, Catia, et al. "LXR-dependent and -independent effects of oxysterols on immunity and tumor growth," European Journal of Immunology (2014); 44(7):1896-1903.

Voth, C.N., et al.; "Nickel-Catalyzed Arylative Additions on 2-Alkynyl-N-Arylsulfonylanilides to Construct Functionalized Indoles," European Journal of Organic Chemistry (2020); 2020(6):744-748.

Wang, et al. "Dual gold/photoredox-catalyzed bis-arylative cyclization of chiral homopropargyl sulfonamides with diazonium salts: rapid access to enantioenriched 2,3-dihydropyrroles," Chemical Communications, (2017); 53(51):6848-6851.

Wang, Yuhui, et al. "Transcriptional regulation of hepatic lipogenesis," Nature Reviews Molecular Cell Biology (2015); 16(11):678-689.

Ward, Patrick S., and Thompson, Craig B., "Metabolic Reprogramming: A Cancer Hallmark Even Warburg Did Not Anticipate," Cancer Cell (2012); 21(3):297-308.

Yang, Chendong, et al., "Sterol Intermediates from Cholesterol Biosynthetic Pathway as Liver X Receptor Ligands," Journal of Biological Chemistry (2006); 281(38):27816-27826.

Youn, et al. "Unusual 1,2-Aryl Migration and Depalladation of Alkylpalladium Intermediates Containing a syn-b-Hydrogen Atom," Chemistry Select, (2016); 1(18):5749-5757.

Yu, R., et al. "Palladium-Catalyzed Sequential Vinylic C-H Arylation/Amination of 2-Vinylanilines with Aryl boronic Acids: Access to 2-Arylindoles," Journal of Organic Chemistry, (2018); 83(1):323-329.

Zheng, Fenping, et al., "Regulation of Insulin Resistance and Adiponectin Signaling in Adipose Tissue by Liver X Receptor Activation Highlights a Cross-Talk with PPARγ," PLoS One (Jun. 2014); 9(6):e101269, 11 pages.

Zhou, Xiaoye, et al. "Genetic Deletion of Low Density Lipoprotein Receptor Impairs Sterol-induced Mouse Macrophage ABCA1 Expression: a new SREBP1-dependent mechanism," Journal of Biological Chemistry (2008); 283(4):2129-2138.

Zuercher, William J., et al., "Discovery of Tertiary Sulfonamides as Potent Liver X Receptor Antagonists," Journal of Medicinal Chemistry (2010); 53(8):3412-3416.

\* cited by examiner

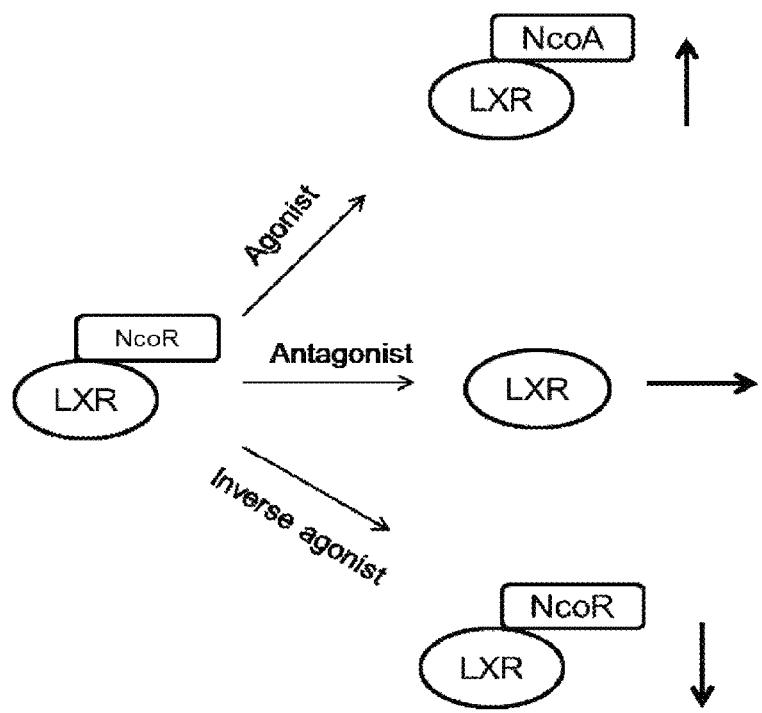
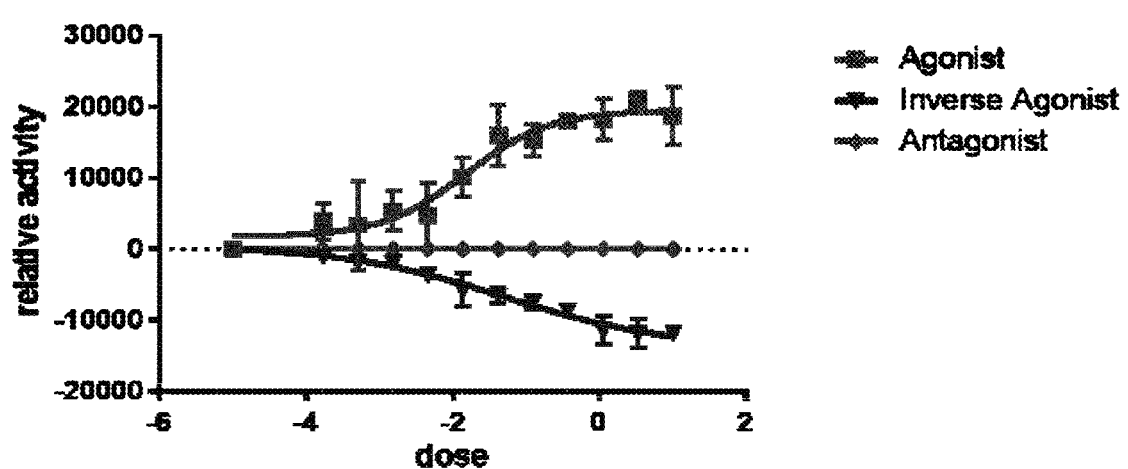

LXR MODULATORS WITH BICYCLIC CORE MOIETY

CROSS REFERENCE TO RELATED APPLICATIONS

This application is a continuation of U.S. application Ser. No. 18/166,831, filed Feb. 9, 2023, which is a divisional of U.S. application Ser. No. 17/255,821, filed Jun. 28, 2019, U.S. Pat. No. 11,618,747, which is a U.S. National Phase of PCT Application No. PCT/EP2019/067351, filed Jun. 28, 2019, which claims priority to European Application No. 18180450.1, filed Jun. 28, 2018, the disclosures of each of which are incorporated by reference herein in their entirety.

INCORPORATION OF SEQUENCE LISTING

The Sequence Listing associated with this application is provided electronically in XML file format and is hereby incorporated by reference into the specification. The name of the XML file containing the Sequence Listing is LIVR_004_03US_SeqList_ST26.xml. The XML file is 31,817 bytes, was created on Mar. 5, 2024, and is being submitted electronically via the USPTO Patent Center.

BACKGROUND

The Liver X Receptors, LXRα (NR1H3) and LXRβ (NR1H2) are members of the nuclear receptor protein superfamily. Both receptors form heterodimeric complexes with Retinoid X Receptor (RXRα, β or γ) and bind to LXR response elements (e.g. DR4-type elements) located in the promoter regions of LXR responsive genes. Both receptors are transcription factors that are physiologically regulated by binding ligands such as oxysterols or intermediates of the cholesterol biosynthetic pathways such as desmosterol. In the absence of a ligand, the LXR-RXR heterodimer is believed to remain bound to the DR4-type element in complex with co-repressors, such as NCOR1, resulting in repression of the corresponding target genes. Upon binding of an agonist ligand, either an endogenous one such as the oxysterols or steroid intermediates mentioned before or a synthetic, pharmacological ligand, the conformation of the heterodimeric complex is changed, leading to the release of corepressor proteins and to the recruitment of coactivator proteins such as NCOA1 (SRC1), resulting in transcriptional stimulation of the respective target genes. While LXRβ is expressed in most tissues, LXRα is expressed more selectively in cells of the liver, the intestine, adipose tissue and macrophages. The relative expression of LXRα and LXRβ at the mRNA or the protein level may vary between different tissues in the same species or between different species in a given tissue. The LXR's control reverse cholesterol transport, i.e. the mobilization of tissue-bound peripheral cholesterol into HDL and from there into bile and feces, through the transcriptional control of target genes such as ABCA1 and ABCG1 in macrophages and ABCG5 and ABCG8 in liver and intestine. This explains the anti-atherogenic activity of LXR agonists in dietary LDLR-KO mouse models. The LXRs, however, do also control the transcription of genes involved in lipogenesis (e.g. Srebp1c, Scd1, Fasn) which accounts for the liver steatosis observed following prolonged treatment with LXR agonists.

The liver steatosis liability is considered a main barrier for the development of non-selective LXR agonists for atherosclerosis treatment.

Non-alcoholic fatty liver disease (NAFLD) is regarded as a manifestation of metabolic syndrome in the liver and NAFLD has reached epidemic prevalences worldwide (Estes et al., Hepatology 2018; 67:123; Estes et al., J. Hepatol. 2018; 69:896). The pathologies of NAFLD range from benign and reversible steatosis to steatohepatitis (nonalcoholic steatohepatitis, NASH) that can develop towards fibrosis, cirrhosis and potentially further towards hepatocellular carcinogenesis. Classically, a two-step model has been employed to describe the progression of NAFLD into NASH, with hepatic steatosis as an initiating first step sensitizing towards secondary signals (exogenous or endogenous) that lead to inflammation and hepatic damage (Day et al., Gastroenterology 1998; 114:842). Nowadays, the transition from benign NAFLD towards the more aggressive state NASH is regarded as multifactorial with genetic, environmental, lifestyle and nutritional influences playing different roles in different individual setups. Independent from the etiology of the disease there is a very strong unmet medical need to stop progression of NAFLD because of the detrimental sequelae such as liver cirrhosis, hepatocellular carcinoma or other forms of liver related modalities.

LXR expression levels are firmly associated with the state of NAFLD. Notably, LXR expression was shown to correlate with the degree of fat deposition, as well as with hepatic inflammation and fibrosis in NAFLD patients (Ahn et al., Dig. Dis. Sci. 2014; 59:2975). Furthermore, serum and liver desmosterol levels are increased in patients with NASH but not in people with simple liver steatosis. Desmosterol has been characterized as a potent endogenous LXR agonist (Yang et al., J. Biol. Chem. 2006; 281:27816). Given the known involvement of the LXRs as master regulators of hepatic lipidogenesis and lipid metabolism, in general and the aforementioned association of LXR expression levels with the stage of fatty liver disease, NAFLD/NASH patients might therefore benefit from blocking the increased LXR activity in the livers of these patients through small molecule antagonists or inverse agonists that shut off LXRs' activity. While doing so it needs to be taken care that such LXR antagonists or inverse agonists do not interfere with LXRs in peripheral tissues or macrophages to avoid disruption of the anti-atherosclerotic reverse cholesterol transport governed by LXR in these tissues or cells.

Certain publications (e.g. Peet et al., Cell 1998; 93:693 and Schultz et al., Genes Dev. 2000; 14:2831) have highlighted the role of LXRα, in particular, for the stimulation of lipidogenesis and hence establishment of NAFLD in the liver. They indicate that it is mainly LXRα being responsible for the hepatic steatosis, hence an LXRα-specific antagonist or inverse agonist might suffice or be desirable to treat just hepatic steatosis. These data, however, were generated only by comparing LXRα, LXRβ or double knockout with wild-type mice with regards to their susceptibility to develop steatosis on a high fat diet. They do not account for a major difference in the relative expression levels of LXRα and LXRβ in the human as opposed to the murine liver. Whereas LXRα is the predominant LXR subtype in the rodent liver, LXRβ is expressed to about the same if not higher levels in the human liver compared to LXRα (data from Unigene or other expression databases). This was exemplified by testing an LXRβ selective agonist in human phase I clinical studies (Kirchgessner et al., Cell Metab. 2016; 24:223) which resulted in the induction of strong hepatic steatosis although it was shown to not activate human LXRα.

Hence it can be assumed that it should be desirable to have no strong preference of an LXR modulator designed to treat NAFLD or NASH for a particular LXR subtype. A certain degree of LXR-subtype selectivity might be allowed if the pharmacokinetic profile of such a compound clearly ensures sufficient liver exposure and resident time to cover both LXRs in clinical use.

In summary, the treatment of diseases such as NAFLD or NASH would need LXR modulators that block LXRs in a hepato-selective fashion and this could be achieved through hepatotropic pharmacokinetic and tissue distribution properties that have to be built into such LXR modulators.

The master control on lipidogenesis is exerted by LXRs in all major cell types studied so far. Cancer cells are also highly dependent on de novo lipidogenesis and therefore Flaveny et al. tested the LXR inverse agonist tool compound SR9243 in cancer cells and in animal cancer models (Cancer Cell 2015; 28:42). They could show that SR9243 inhibited lipidogenesis along with the Warburg glycolysis effect, in general, and that this molecular effect led to apoptosis and diminished tumor growth in vivo.

PRIOR ART

Zuercher et al. describes with the structurally unrelated tertiary sulfonamide GSK2033 the first potent, cell-active LXR antagonists (J. Med. Chem. 2010; 53:3412). Later, this compound was reported to display a significant degree of promiscuity, targeting a number of other nuclear receptors (Griffett & Burris, Biochem. Biophys. Res. Commun. 2016; 479:424). It is stated, that GSK2033 showed rapid clearance ($Cl_{int}$>1.0 mL/min/mg protein) in rat and human liver microsomal assays and that this rapid hepatic metabolism of GSK2033 precludes its use in vivo. As such GSK2033 is a useful chemical probe for LXR in cellular studies only.

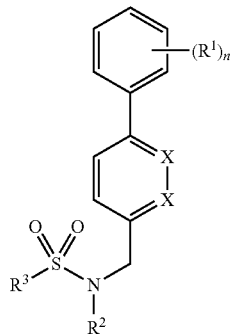

Example 9 (A)

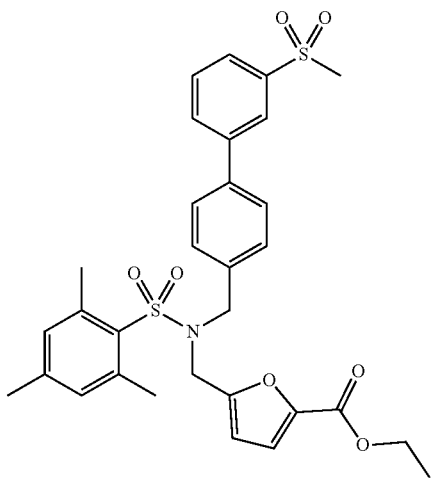

SR9238

GSK2033

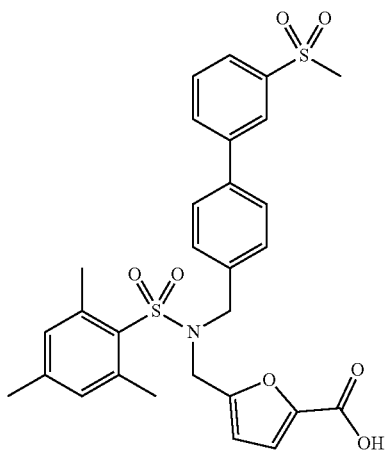

SR10389

WO2014/085453 describes the preparation of structurally unrelated small molecule LXR inverse agonists of Formula (A) in addition to structure GSK2033 above:

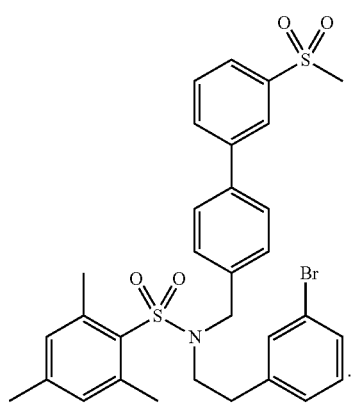

SR9243

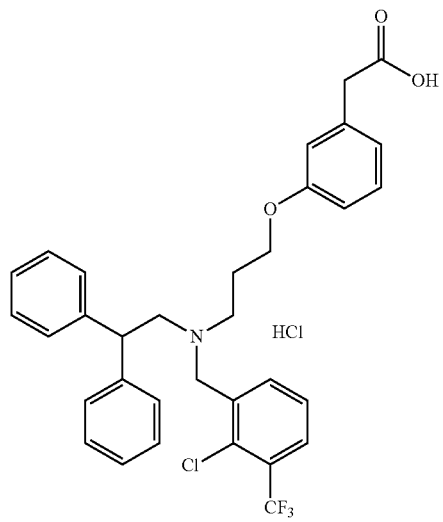

GW3965

The following compounds from this application, in particular, are further described in some publications, mainly from the same group of inventors/authors: SR9238 is described as a liver-selective LXR inverse agonist that suppresses hepatic steatosis upon parenteral administration (Griffett et al., ACS Chem. Biol. 2013; 8:559). After ester saponification of SR9238 the LXR inactive acid derivative SR10389 is formed. This compound then has systemic exposure. In addition, it was described, that SR9238 suppresses fibrosis in a model of NASH again after parenteral administration (Griffett et al., Mol. Metab. 2015; 4:35). With related SR9243 the effects on aerobic glycolysis (Warburg effect) and lipogenesis were described (Flaveny et al., Cancer Cell 2015; 28:42) and the NASH-suppressing data obtained with SR9238 was confirmed by Huang et al. (BioMed Res. Int. 2018; 8071093) using SR9243.

WO2003/082802 describes structurally unrelated LXR agonists of general Formula (B):

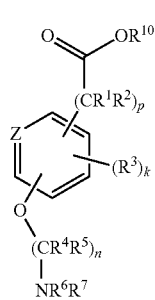

(B)

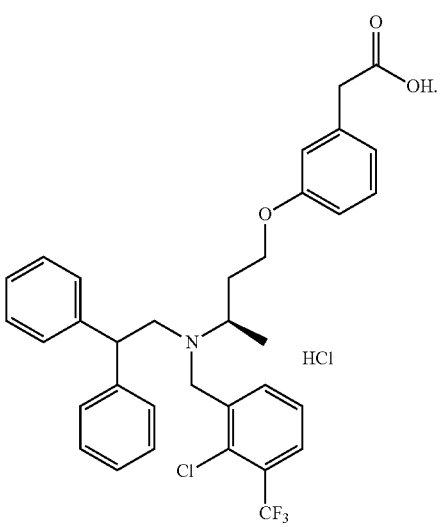

RGX-104

In all examples the acid containing (hetero)aryl moiety is linked via an oxygen atom to the rest of the molecule. Most interesting examples are GW3965 (Collins et al. J. Med. Chem. 2002; 45: 1963) and clinical candidate RGX-104 from Rgenix.

Yu et al. (J. Org. Chem. 2018; 83:323) describes the synthesis of 2,3-disubstituted indoles via the following reaction scheme. The only example with an ortho-substituted aryl in 3-position of the indole is structure C1.

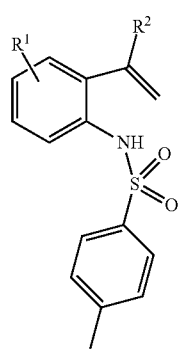

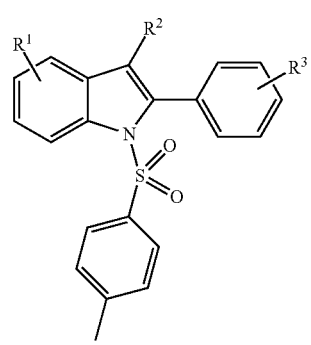

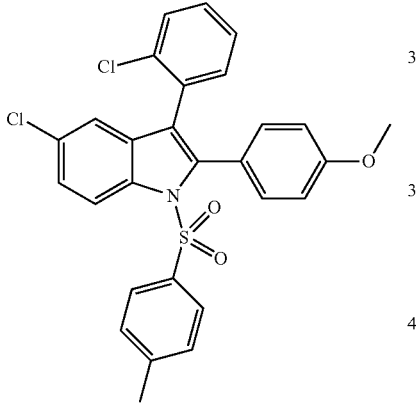

WO2016/207217 discloses bicyclic derivatives of Formula (D), which does not fall within the scope of the present invention, since no-SO₂-linked residue is possible for A, which may represent a bicyclic structure including indole. However intermediate D1 is disclosed (Example 69, Step E), which is the only example with an ortho-substituted aryl in 3-position of the indole.

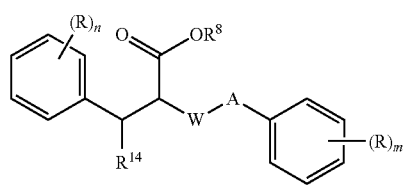

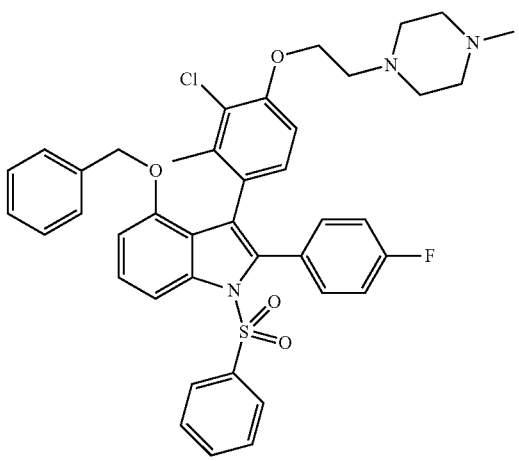

WO2016/106266 discloses azaindoles of Formula (E) as TGFβ antagonists

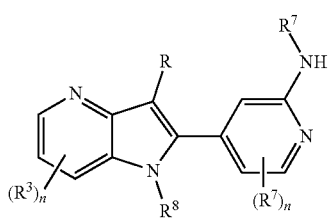

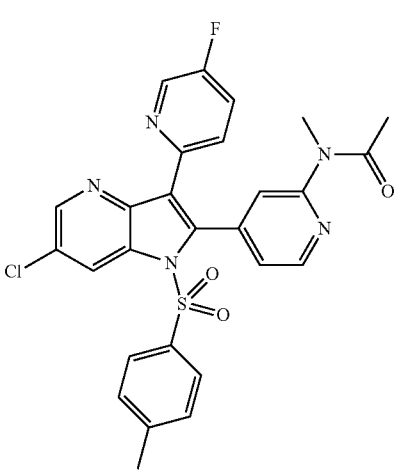

-continued

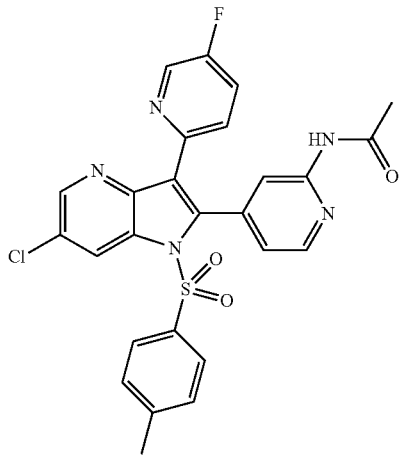

E2 wherein R is an optionally substituted heterocyclic or heterobicyclic group, $R^8$ is selected from a broad range of substituents including —$SO_2R^9$. Residue $R^9$ can be selected from a broad range of substituents including $C_3$-$C_8$-cycloalkyl and heterocycloalkyl. The only examples wherein both the 2- and 3-position of the azaindole is substituted with a cyclic moiety is structure E1 and E2.

WO2013/111150 discloses adamantane derivatives of Formula (F) as 17β-hydroxysteroid dehydrogenase type 1 inhibitors

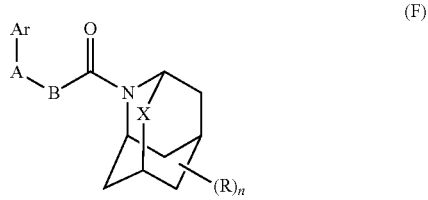

(F)

wherein Ar is an optionally substituted $C_1$-$C_{18}$-heteroaryl group, A can be —$SO_2$— and B can be absent. No examples are shown, which fall within the scope of the present invention.

WO2013/028999 discloses structures of Formula (G) as potential therapeutics for neuropsychiatric disorders

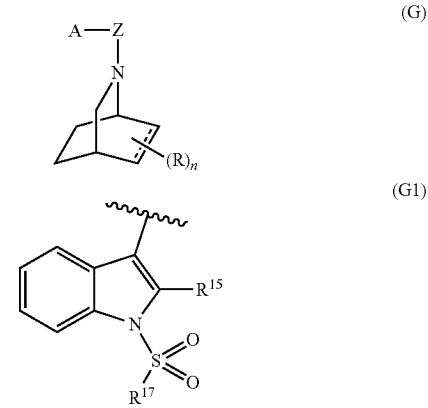

(G)

(G1)

wherein Z may be absent and A represents a ring structure, e.g. 3-substituted indole of Formula (G1). Here $R^{15}$ and $R^{17}$ can be selected from an optionally substituted aryl and heteroaryl moiety. However for this case, no examples are shown.

WO2013/012649 discloses azaindoles of Formula (H) for the treatment of HIV

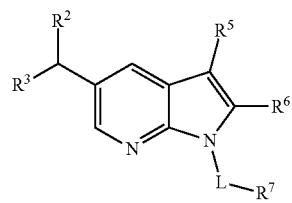

(H)

wherein linker element L can be —$SO_2$—, $R^5$ and $R^6$ can independently be selected from a broad range of substituents including an optionally substituted cycloalkyl, heterocycloalkyl, aryl and heteroaryl. In most cases, $R^2$ is a carboxylic acid or bioisostere thereof. No examples are shown, which fall within the scope of the present invention.

WO2010/124793 and WO2008/132434 disclose azaindoles of Formula (J) as fungicides

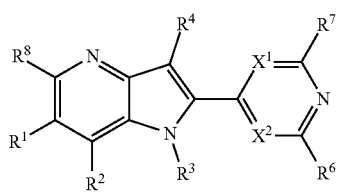

(J)

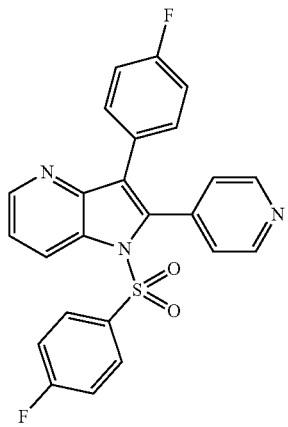

J1 wherein $R^4$ can be selected from a broad range of substituents including an optionally substituted cyclyl, heterocyclyl, aryl and heteroaryl. $R^3$ can be selected from a broad range of substituents including —$SO_2R^{12}$, with $R^{12}$ again can be selected from a broad range of substituents including an optionally substituted cyclyl, heterocyclyl, aryl and heteroaryl. The only example wherein both the 2- and 3-position of the azaindole is substituted with a cyclic moiety is structure J1.

WO2010/010186 discloses JAK kinase inhibitors of Formula (K)

(K)

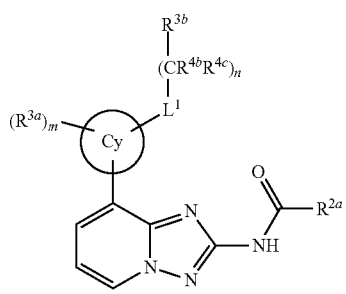

wherein ring Cy is selected from aryl and heteroaryl. With $L^1$ equals $SO_2$, n equals 0, $R^{3a}$ e.g. unsubstituted cycloalkyl, heterocycloalkyl, aryl or heteroaryl and $R^{3b}$ selected from optionally substituted cycloalkyl, heterocycloalkyl, aryl or heteroaryl derivatives falling in the scope of the present invention can be constructed, however no examples are shown.

WO2009/032116 discloses indoles of Formula (L) for treating viral infections (L)

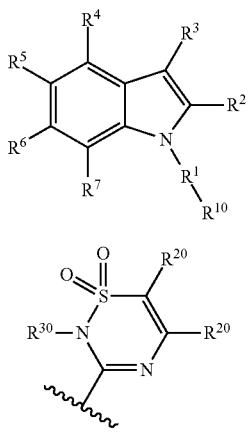

L1

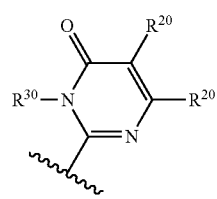

L2

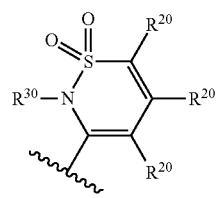

L3

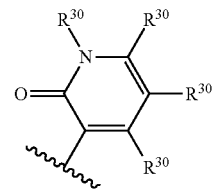

L4

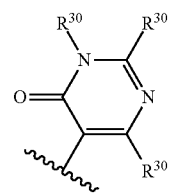

L5

L6 wherein $R^1$ can be selected from a broad range of substituents including —$SO_2$—. For $R^2$ the cyclic moieties (L1 to L3) and for $R^3$ the cyclic moieties (L4 and L5) are possible. In related application WO2009/032125 and WO2009/064848 even more cyclic moieties for $R^3$ are possible. $R^{10}$ can be selected from optionally substituted cycloalkyl, cycloalkenyl, heterocycloalkyl, heterocycloalkenyl, aryl and heteroaryl. In WO2009/064852, a cyclic moiety of structure L6 is possible for $R^3$. In all applications, no examples are shown, which fall within the scope of the present invention.

WO2008/116833 discloses azetidine compounds of Formula (M) for treating disorders that respond to modulation of the serotonin 5-hydroxytryptamine-6 (5-HT$_6$) receptor (M)

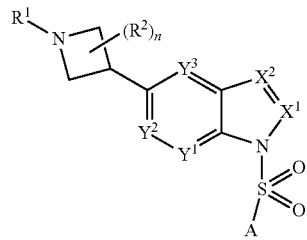

wherein $X^1$ and $X^2$ are independently N or $CR^x$. Residue $R^x$ can be selected from a broad range of substituents including an optionally substituted phenyl or $C_{3-6}$-cycloalkyl. Residue A can be selected from optionally substituted $C_{3-6}$-cycloalkyl, aryl or heteroaryl. No examples, wherein both the 2- and 3-position of the indole is directly substituted by a cyclic moiety, are disclosed.

WO2008/003736 discloses azaindoles of Formula (N)

(N)

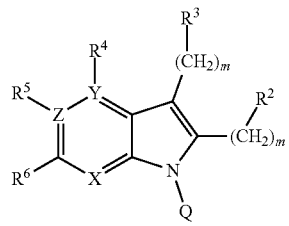

wherein $R^2$ and $R^3$ can independently comprise a saturated nitrogen-containing heterocyclic moiety (e.g. piperidine)

while m can be 0. Q can represent the protecting group —SO$_2$-Ph. No examples, wherein both the 2- and 3-position of the indole is directly substituted by a cyclic moiety, are disclosed.

WO2007/075555 discloses CB$_1$ antagonists of Formula (P)

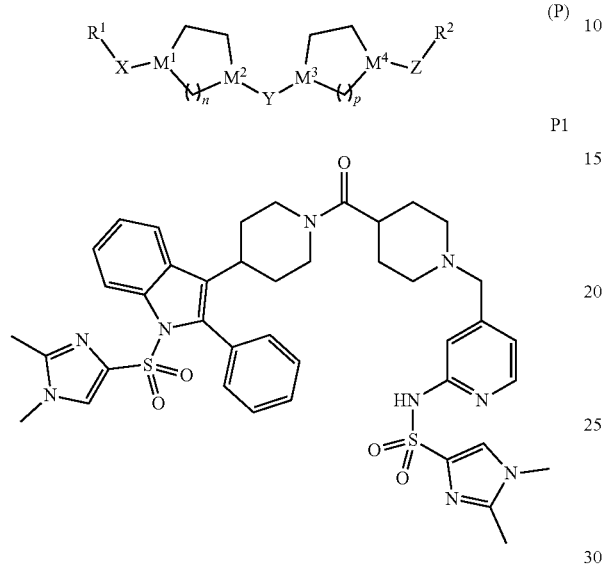

wherein R$^1$ can be selected from a broad range of substituents including a substituted indole while X can represent a bond. The only example where a cyclic moiety is linked to the 3-position of the indole is structure P1. More specifically, indole derivatives of Formula (P) are described in WO2004/000831 as histamine H3 antagonist, again with structure P1 as example.

WO2007/134169 and WO2006/050236 disclose indole derivatives of Formula (Q) as inhibitors of TNF-α production

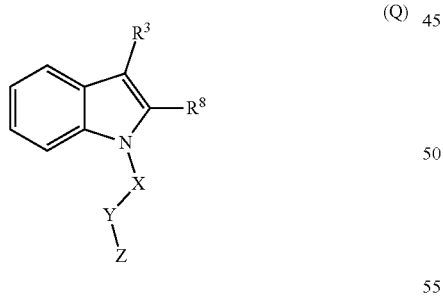

wherein X can be SO$_2$, Y can be selected from a broad range of substituents including cycloalkyl, heterocycloalkyl, aryl and heterocycle while Z has to be selected from —B(OR)$_2$, —CONROR and —N(OR)COR (with R=H or alkyl). R$^3$ and R$^8$ can be independently selected from a broad range of substituents including cycloalkyl and a 5- or 6-membered organic ring. No examples, wherein both the 2- and 3-position of the indole is substituted by a cyclic moiety, are disclosed.

WO2005/034941 discloses bicyclic structures of Formula (R) as inhibitors for hepatitis C virus polymerase

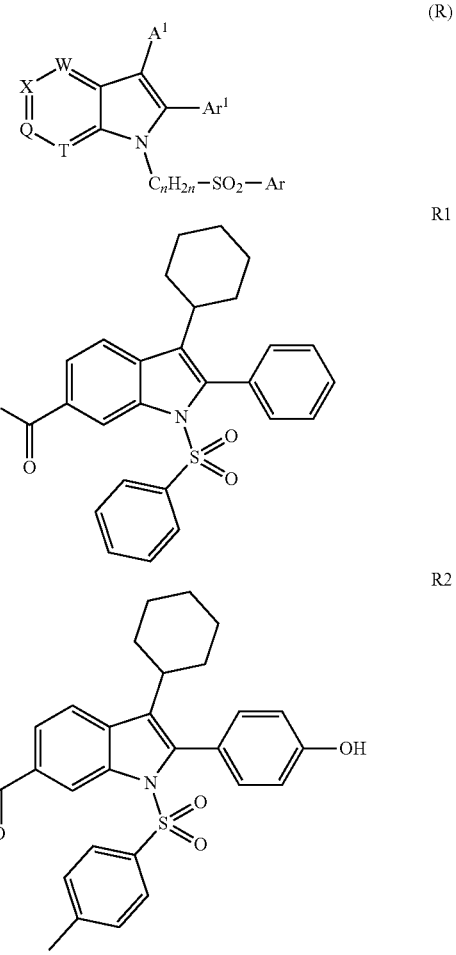

wherein Ar$^1$ and Ar are 5- to 10-membered aromatic rings, A$^1$ can be a cycloalkyl (optionally substituted with alkoxy) and n can be 0. The closest examples to the present invention are structure R1 and R2.

WO2005/14000 discloses indoles of Formula (S) for the treatment of 5-HT$_6$-receptor-related diseases such as obesity and CNS disorders

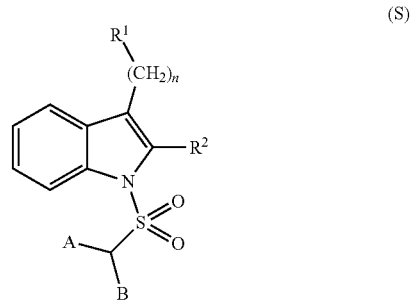

wherein R$^1$ represents a nitrogen-attached saturated or unsaturated heterocyclic ring system, R$^2$ can be selected from a broad range of substituents including a saturated or unsaturated cycloalkyl, n is selected from 0 to 4 and residue A and B form a saturated or unsaturated cycloalkyl ring. No examples, wherein both the 2- and 3-position of the indole is directly substituted (i.e. n=0) by a cyclic moiety, are disclosed.

WO2002/51837 and WO2002/36562 disclose bicyclic structures of Formulae (T) and (T1), respectively, for the treatment of 5-HT$_6$-receptor-related diseases

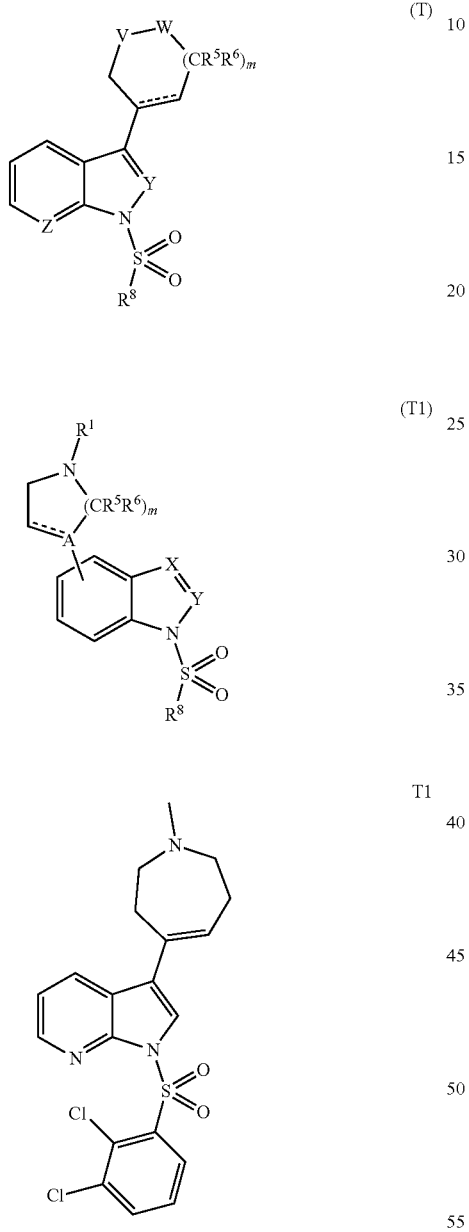

wherein X and Y can independently represent a carbon atom, which is optionally substituted with an aryl or heteroaryl moiety, R$^8$ may also represent an optionally substituted aryl or heteroaryl moiety. The cyclic moiety on the left-hand-side of Formula (T1) is usually piperazine. No examples, wherein both the 2- and 3-position of the (aza)indole is substituted by a cyclic moiety (e.g. aryl or heteroaryl), are disclosed. The closest example is structure T1.

WO2002/32863 discloses indoles of Formula (U) for the treatment of 5-HT$_6$-receptor-related diseases

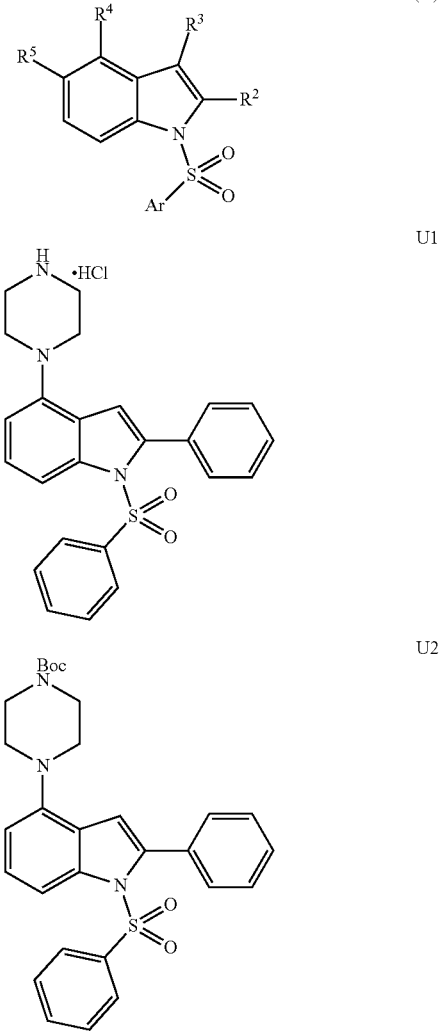

wherein Ar can be selected from optionally substituted phenyl, naphthyl or 5- to 10-membered mono- or bicyclic heterocyclic moieties, R$^2$ can be an unsubstituted phenyl and R$^3$ is selected from hydrogen or 3-(1-azabicyclo[2.2.2]oct-2-en)yl. However no example with suitable substitution at 2- and 3-position of the indole is shown—the closest examples are structure U1 and U2.

WO9921851 discloses structures of Formula (V) as agricultural or horticultural fungicides

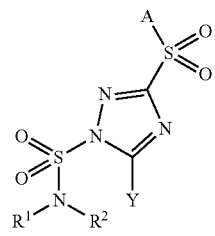

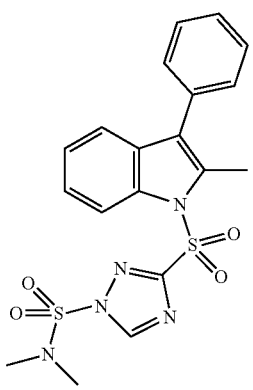

wherein A can be selected from a very broad range of cyclic systems including optionally substituted indole. However no example with suitable substitution at 2- and 3-position of the indole is shown; the closest example is structure V1.

WO9857931 and WO9822452 disclose bicyclic structures of Formulae (W) and (W1), respectively, as antimicrobial agents

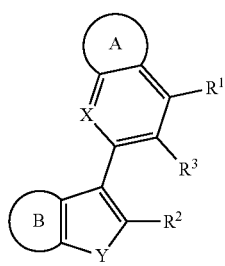

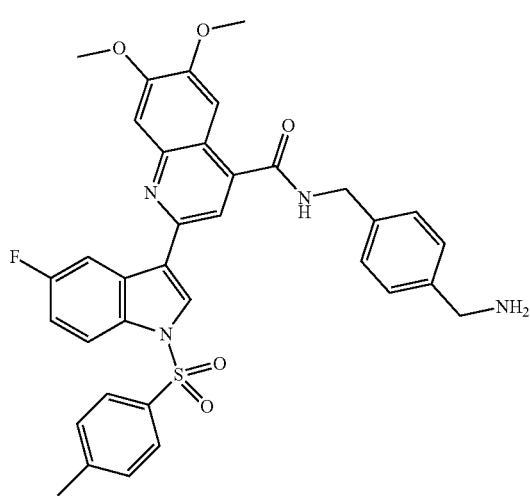

wherein $R^2$ can be selected from a very broad range of residues including aryl and heteroaryl; and Y can represent NR, with R selected from a very broad range of residues including a arylsulfonyl moiety.

No example with substitution at 2- and 3-position of the indole is shown; the closest example is structure W1.

WO9822457 discloses bicyclic structures of Formula (X) as anti-inflammatory agents

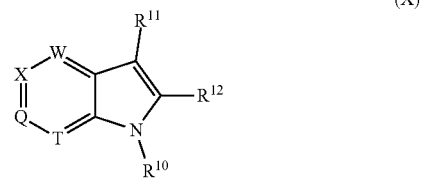

wherein $R_{10}$ can be selected from a very broad range of substituents including $SO_2R^{30}$; and wherein $R^{11}$, $R^{12}$, $R^{30}$ can be selected from optionally substituted aryl and heteroaryl. However no example is shown, where $R^{10}$ has indeed a $SO_2$-connected moiety.

WO2001/30343, WO2000/46199, WO2000/46197, WO2000/46195, JP06145150, EP0535926, EP0535925 describe indole derivatives, where in 2-position of the indole moiety a 1H- or 2H-tetrazol-5-yl moiety can be attached as only possible cyclic moiety, which functions as a carboxylic acid bioisostere. The only example with such a directly connected tetrazole moiety is disclosed in JP06145150 (Structure Y1).

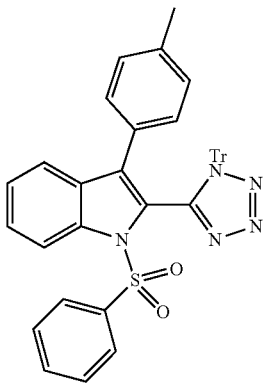

WO2008/119657 describes imidazolidinone derivatives of Formula (Z) binding to LXR with representative example (Z1):

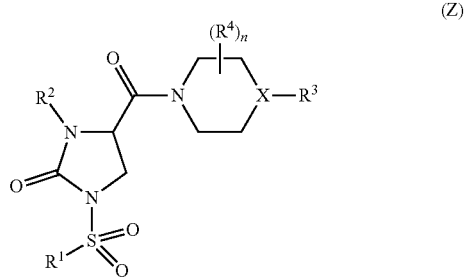

-continued

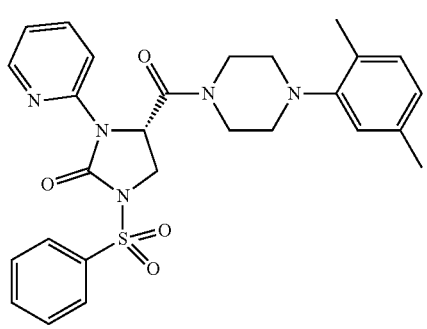

(Z1)

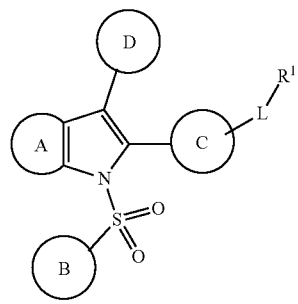

(I)

The following four structures were found to be weak binder on another nuclear receptor target and therefor were mentioned as initial hits in a confidential collaboration with another pharma company:

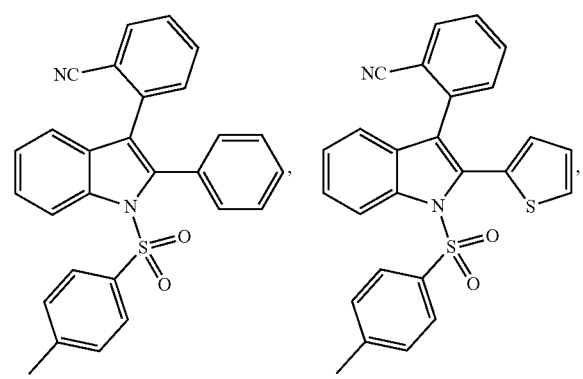

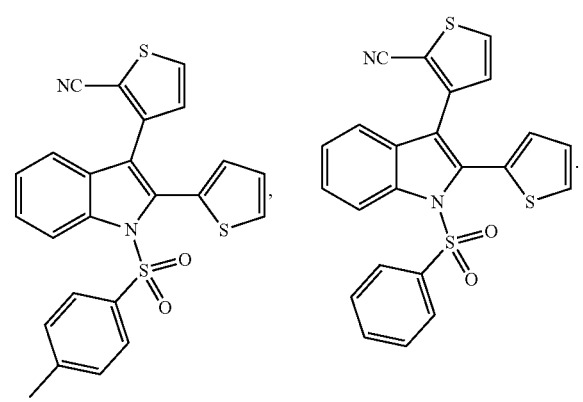

SUMMARY OF THE INVENTION

The present invention relates to compounds according to Formula (I)

a glycine conjugate, tauro conjugate, enantiomer, diastereomer, tautomer, N-oxide, solvate, prodrug and pharmaceutically acceptable salt thereof, wherein cycle A, B, C, D and residue L and $R^1$ are defined as in claim 1.

The compounds of the present invention have a similar or better LXR inverse agonistic activity compared to the known LXR inverse agonists. Furthermore, the compounds of the present invention exhibit an advantageous liver/blood-ratio after oral administration so that disruption of the anti-atherosclerotic reverse cholesterol transport governed by LXR in peripheral macrophages can be avoided. The incorporation of an acidic moiety (or a bioisoster thereof) can improve additional parameters, e.g. microsomal stability, solubility and lipophilicity.

Thus, the present invention further relates to a pharmaceutical composition comprising a compound according to Formula (I) and at least one pharmaceutically acceptable carrier or excipient.

The present invention is further directed to compounds according to Formula (I) for use in the prophylaxis and/or treatment of diseases mediated by LXRs.

Accordingly, the present invention relates to the prophylaxis and/or treatment of non-alcoholic fatty liver disease, non-alcoholic steatohepatitis, liver inflammation, liver fibrosis, obesity, insulin resistance, type II diabetes, familial hypercholesterolemia, hypercholesterolemia in nephrotic syndrome, metabolic syndrome, cardiac steatosis, cancer, viral myocarditis and hepatitis C virus infection.

BRIEF DESCRIPTION OF THE DRAWINGS

FIG. 1 illustrates the differences between LXR agonists, antagonists and inverse agonists exemplified by their different capabilities to recruit coactivators or corepressors.

DETAILED DESCRIPTION OF THE INVENTION

The desired properties of a LXR modulator in conjunction with hepatoselectivity, can be yielded with compounds that follow the structural pattern represented by Formula (I)

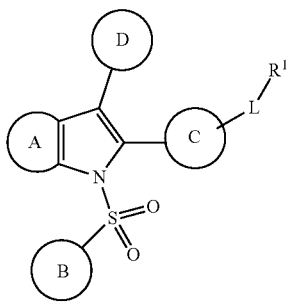
(I)

a glycine conjugate, tauro conjugate, enantiomer, diastereomer, tautomer, N-oxide, solvate, prodrug and pharmaceutically acceptable salt thereof, wherein

is an annelated 5- to 6-membered cycle forming a 6-membered aryl or a 5- to 6-membered heteroaryl containing 1 to 3 heteroatoms independently selected from N, O and S, wherein this cycle is unsubstituted or substituted with 1 to 4 substituents independently selected from the group consisting of halogen, CN, $SF_5$, $NO_2$, $C_{1-6}$-alkyl, oxo, $C_{0-6}$-alkylene-$OR^{11}$, $C_{0-6}$-alkylene-(3- to 6-membered cycloalkyl), $C_{0-6}$-alkylene-(3- to 6-membered heterocycloalkyl), $C_{0-6}$-alkylene-$S(O)_nR^{11}$, $C_{0-6}$-alkylene-$NR^{11}S(O)_2R^{11}$, $C_{0-6}$-alkylene-$S(O)_2NR^{11}R^{12}$, $C_{0-6}$-alkylene-$NR^{11}S(O)_2NR^{11}R^{12}$, $C_{0-6}$-alkylene-$CO_2R^{11}$, O—$C_{1-6}$-alkylene-$CO_2R^{11}$, $C_{0-6}$-alkylene-O—$COR^{11}$, $C_{0-6}$-alkylene-$CONR^{11}R^{12}$, $C_{0-6}$-alkylene-$NR^{11}$—$COR^{11}$, $C_{0-6}$-alkylene-$NR^{11}$—$CONR^{11}R^{12}$, $C_{0-6}$-alkylene-O—$CONR^{11}R^{12}$, $C_{0-6}$-alkylene-$NR^{11}$—$CO_2R^{11}$ and $C_{0-6}$-alkylene-$NR^{11}R^{12}$, wherein alkyl, alkylene, cycloalkyl and heterocycloalkyl is unsubstituted or substituted with 1 to 6 substituents independently selected from halogen, CN, oxo, hydroxy, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl; and wherein optionally two adjacent substituents on the aryl or heteroaryl moiety form a 5- to 8-membered partially unsaturated cycle optionally containing 1 to 3 heteroatoms independently selected from O, S or N, and wherein the new formed cycle is unsubstituted or substituted with 1 to 3 substituents independently selected from halogen, CN, $C_{1-4}$-alkyl, halo-$C_{1-4}$-alkyl, 3- to 6-membered cycloalkyl, halo-(3- to 6-membered cycloalkyl), 3- to 6-membered heterocycloalkyl, halo-(3- to 6-membered heterocycloalkyl), OH, oxo, $CO_2H$, $CO_2$-$C_{1-4}$-alkyl, $CONHCH_2CO_2H$, $CONH(CH_2)_2SO_3H$, O—$C_{1-4}$-alkyl and O-halo-$C_{1-4}$-alkyl;

is selected from the group consisting of 3- to 10-membered cycloalkyl, 3- to 10-membered heterocycloalkyl containing 1 to 3 heteroatoms independently selected from N, O and S, 6- to 14-membered aryl and 5- to 14-membered heteroaryl containing 1 to 4 heteroatoms independently selected from N, O and S, wherein cycloalkyl, heterocycloalkyl, aryl and heteroaryl are unsubstituted or substituted with 1 to 6 substituents independently selected from the group consisting of halogen, CN, $SF_5$, $NO_2$, oxo, $C_{1-4}$-alkyl, $C_{0-6}$-alkylene-$OR^{21}$, $C_{0-6}$-alkylene-(3- to 6-membered cycloalkyl), $C_{0-6}$-alkylene-(3- to 6-membered heterocycloalkyl), $C_{0-6}$-alkylene-$S(O)NR^{21}$, $C_{0-6}$-alkylene-$NR^{21}S(O)_2R^{21}$, $C_{0-6}$-alkylene-$S(O)_2NR^{21}R^{22}$, $C_{0-6}$-alkylene-$NR^{21}S(O)_2NR^{21}R^{22}$, $C_{0-6}$-alkylene-$CO_2R^{21}$, O—$C_{1-6}$-alkylene-$CO_2R^{21}$, $C_{0-6}$-alkylene-O—$COR^{21}$, $C_{0-6}$-alkylene-$CONR^{21}R^{22}$, $C_{0-6}$-alkylene-$NR^{21}$—$COR^{21}$, $C_{0-6}$-alkylene-$NR^{21}$—$CONR^{21}R^{22}$, $C_{0-6}$-alkylene-O—$CONR^{21}R^{22}$, $C_{0-6}$-alkylene-$NR^{21}$—$CO_2R^{21}$ and $C_{0-6}$-alkylene-$NR^{21}R^{22}$, wherein alkyl, alkylene, cycloalkyl and heterocycloalkyl is unsubstituted or substituted with 1 to 6 substituents independently selected from halogen, CN, oxo, hydroxy, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl;

and wherein optionally two adjacent substituents on the aryl or heteroaryl moiety form a 5- to 8-membered partially unsaturated cycle optionally containing 1 to 3 heteroatoms independently selected from O, S or N, and wherein this additional cycle is unsubstituted or substituted with 1 to 4 substituents independently selected from halogen, CN, oxo, OH, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl;

and wherein optionally two adjacent substituents on the cycloalkyl or heterocycloalkyl moiety form a 5- to 6-membered unsaturated cycle optionally containing 1 to 3 heteroatoms independently selected from O, S or N, wherein this additional cycle is unsubstituted or substituted with 1 to 4 substituents independently selected from halogen, CN, oxo, OH, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl;

is selected from the group consisting of 6- or 10-membered aryl and 5- to 10-membered heteroaryl containing 1 to 3 heteroatoms independently selected from N, O and S, wherein cycloalkyl, heterocycloalkyl, aryl and heteroaryl are unsubstituted or substituted with 1 to 4 substituents independently selected from the group consisting of halogen, CN, $SF_5$, $NO_2$, oxo, $C_{1-4}$-alkyl, $C_{0-6}$-alkylene-$OR^{31}$, $C_{0-6}$-alkylene-(3- to 6-membered cycloalkyl), $C_{0-6}$-alkylene-(3- to 6-membered heterocycloalkyl), $C_{0-6}$-alkylene-(6- membered aryl), $C_{0-6}$-alkylene-(5- to 6-membered heteroaryl), $C_{0-6}$-alkylene-S(O)$_n$R$^{31}$, $C_{0-6}$-alkylene-NR$^{31}$S(O)$_2$R$^{31}$, $C_{0-6}$-alkylene-S(O)$_2$NR$^{31}$R$^{32}$, $C_{0-6}$-alkylene-NR$^{31}$S(O)$_2$NR$^{31}$R$^{32}$, $C_{0-6}$-alkylene-CO$_2$R$^{31}$, O—C$_{1-6}$-alkylene-CO$_2$R$^{31}$, $C_{0-6}$-alkylene-O—COR$^{31}$, $C_{0-6}$-alkylene-CONR$^{31}$R$^{32}$, $C_{0-6}$-alkylene-NR$^{31}$—COR$^{31}$, $C_{0-6}$-alkylene-NR$^{31}$—CONR$^{31}$R$^{32}$, $C_{0-6}$-alkylene-O—CONR$^{31}$R$^{32}$, $C_{0-6}$-alkylene-NR$^{31}$—CO$_2$R$^{31}$ and $C_{0-6}$-alkylene-NR$^{31}$R$^{32}$, wherein alkyl, alkylene, cycloalkyl, heterocycloalkyl, aryl and heteroaryl is unsubstituted or substituted with 1 to 6 substituents independently selected from halogen, CN, oxo, hydroxy, CO$_2$H, CO$_2$-C$_{1-4}$-alkyl, CONHCH$_2$CO$_2$H, CONH(CH$_2$)$_2$SO$_3$H, C$_{1-4}$-alkyl, halo-C$_{1-4}$-alkyl, O—C$_{1-4}$-alkyl and O-halo-C$_{1-4}$-alkyl;

and wherein optionally two adjacent substituents on the aryl or heteroaryl moiety form a 5- to 8-membered partially unsaturated cycle optionally containing 1 to 3 heteroatoms independently selected from O, S or N, and wherein this additional cycle is unsubstituted or substituted with 1 to 4 substituents independently selected from halogen, CN, oxo, OH, CO$_2$H, CO$_2$-C$_{1-4}$-alkyl, CONHCH$_2$CO$_2$H, CONH(CH$_2$)$_2$SO$_3$H, C$_{1-4}$-alkyl, halo-C$_{1-4}$-alkyl, O—C$_{1-4}$-alkyl and O-halo-C$_{1-4}$-alkyl;

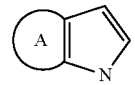

is selected from the group consisting of 3- to 10-membered cycloalkyl, 3- to 10-membered heterocycloalkyl containing 1 to 3 heteroatoms independently selected from N, O and S, 6- to 14-membered aryl and 5- to 14-membered heteroaryl containing 1 to 4 heteroatoms independently selected from N, O and S, wherein cycloalkyl, heterocycloalkyl, aryl and heteroaryl are unsubstituted or substituted with 1 to 6 substituents independently selected from the group consisting of halogen, CN, SF$_5$, NO$_2$, oxo, C$_{1-4}$-alkyl, $C_{0-6}$-alkylene-OR$^{21}$, $C_{0-6}$-alkylene-(3- to 6-membered cycloalkyl), $C_{0-6}$-alkylene-(3- to 6-membered heterocycloalkyl), $C_{0-6}$-alkylene-S(O)$_n$R$^{21}$, $C_{0-6}$-alkylene-NR$^{21}$S(O)$_2$R$^{21}$, $C_{0-6}$-alkylene-S(O)$_2$NR$^{21}$R$^{22}$, $C_{0-6}$-alkylene-NR$^{21}$S(O)$_2$NR$^{21}$R$^{22}$, $C_{0-6}$-alkylene-CR$^{41}$(=N—OR$^{41}$), $C_{0-6}$-alkylene-CO$_2$R$^{21}$, O—C$_{1-6}$-alkylene-CO$_2$R$^{21}$, $C_{0-6}$-alkylene-O—COR$^{21}$, $C_{0-6}$-alkylene-CONR$^{21}$R$^{22}$, $C_{0-6}$-alkylene-NR$^{21}$—COR$^{21}$, $C_{0-6}$-alkylene-NR$^{21}$—CONR$^{21}$R$^{22}$, $C_{0-6}$-alkylene-O—CONR$^{21}$R$^{22}$, $C_{0-6}$-alkylene-NR$^{21}$—CO$_2$R$^{21}$ and $C_{0-6}$-alkylene-NR$^{21}$R$^{22}$, wherein alkyl, alkylene, cycloalkyl and heterocycloalkyl is unsubstituted or substituted with 1 to 6 substituents independently selected from halogen, CN, oxo, hydroxy, CO$_2$H, CO$_2$-C$_{1-4}$-alkyl, CONHCH$_2$CO$_2$H, CONH(CH$_2$)$_2$SO$_3$H, CO—OC$_{1-4}$-alkyl, C$_{1-4}$-alkyl, halo-C$_{1-4}$-alkyl, O—C$_{1-4}$-alkyl and O-halo-C$_{1-4}$-alkyl;

and wherein optionally two adjacent substituents on the aryl or heteroaryl moiety form a 5- to 8-membered partially unsaturated cycle optionally containing 1 to 3 heteroatoms independently selected from O, S or N, and wherein this additional cycle is unsubstituted or substituted with 1 to 4 substituents independently selected from halogen, CN, oxo, OH, CO$_2$H, CO$_2$-C$_{1-4}$-alkyl, CONHCH$_2$CO$_2$H, CONH(CH$_2$)$_2$SO$_3$H, C$_{1-4}$-alkyl, halo-C$_{1-4}$-alkyl, O—C$_{1-4}$-alkyl and O-halo-C$_{1-4}$-alkyl;

and wherein optionally two adjacent substituents on the cycloalkyl or heterocycloalkyl moiety form a 5- to 6-membered unsaturated cycle optionally containing 1 to 3 heteroatoms independently selected from O, S or N, wherein this additional cycle is unsubstituted or substituted with 1 to 4 substituents independently selected from halogen, CN, oxo, OH, CO$_2$H, CO$_2$-C$_{1-4}$-alkyl, CONHCH$_2$CO$_2$H, CONH(CH$_2$)$_2$SO$_3$H, C$_{1-4}$-alkyl, halo-C$_{1-4}$-alkyl, O—C$_{1-4}$-alkyl and O-halo-C$_{1-4}$-alkyl;

wherein

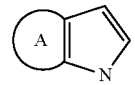

has a substituent from above in 1,2-orientation regarding to the connection towards or has an annelated additional cycle in 1,2-orientation;

L is selected from the group consisting of a bond, C$_{1-6}$-alkylene, C$_{2-6}$-alkenylene, C$_{2-6}$-alkinylene, 3- to 10-membered cycloalkylene, 3- to 10-membered heterocycloalkylene containing 1 to 4 heteroatoms independently selected from N, O and S, 6- or 10-membered arylene and 5- to 10-membered heteroarylene containing 1 to 4 heteroatoms independently selected from N, O and S, wherein alkylene, alkenylene, alkinylene, cycloalkylene, heterocycloalkylene, arylene and heteroarylene are unsubstituted or substituted with 1 to 6 substituents independently selected from the group consisting of halogen, CN, SF$_5$, NO$_2$, oxo, C$_{1-4}$-alkyl, $C_{0-6}$-alkylene-OR$^{41}$, $C_{0-6}$-alkylene-(3- to 6-membered cycloalkyl), $C_{0-6}$-alkylene-(3- to 6-membered heterocycloalkyl), $C_{0-6}$-alkylene-S(O)$_n$R$^{41}$, $C_{0-6}$-alkylene-NR$^{41}$S(O)$_2$R$^{41}$, $C_{0-6}$-alkylene-S(O)$_2$NR$^{41}$R$^{42}$, $C_{0-6}$-alkylene-NR$^{41}$S(O)$_2$NR$^{41}$R$^{42}$, $C_{0-6}$-alkylene-CO$_2$R$^{41}$, O—C$_{1-6}$-alkylene-CO$_2$R$^{41}$, $C_{0-6}$-alkylene-O—COR$^{41}$, $C_{0-6}$-alkylene-CONR$^{41}$R$^{42}$, $C_{0-6}$-alkylene-NR$^{41}$—COR$^{41}$, $C_{0-6}$-alkylene-NR$^{41}$—CONR$^{41}$R$^{42}$, $C_{0-6}$-alkylene-O—CONR$^{41}$R$^{42}$, $C_{0-6}$-alkylene-NR$^{41}$—CO$_2$R$^{41}$ and $C_{0-6}$-alkylene-NR$^{41}$R$^{42}$, wherein alkyl, alkylene, cycloalkyl and heterocycloalkyl is unsubstituted or substituted with 1 to 6 substituents independently selected from halogen, CN, oxo, hydroxy, CO$_2$H, CO$_2$-C$_{1-4}$-alkyl, CONHCH$_2$CO$_2$H, CONH(CH$_2$)$_2$SO$_3$H, C$_{1-4}$-alkyl, halo-C$_{1-4}$-alkyl, O—C$_{1-4}$-alkyl and O-halo-C$_{1-4}$-alkyl;

and wherein optionally two adjacent substituents on the arylene and heteroarylene moiety form a 5- to 8-membered partially unsaturated cycle optionally containing 1 to 3 heteroatoms independently selected from O, S or N, and
wherein this additional cycle is unsubstituted or substituted with 1 to 4 substituents independently selected from halogen, CN, oxo, OH, $CO_2H$, $CO_2$-$C_{1-4}$-alkyl, $C_{1-4}$-alkyl, halo-$C_{1-4}$-alkyl, O—$C_{1-4}$-alkyl and O-halo-$C_{1-4}$-alkyl;

$R^1$ is selected from the group consisting of H, halogen, CN, $SF_5$, $NO_2$, oxo, $C_{1-4}$-alkyl, $C_{0-6}$-alkylene-$OR^{41}$, Y—$C_{0-6}$-alkylene-(3- to 6-membered cycloalkyl), Y—$C_{0-6}$-alkylene-(3- to 6-membered heterocycloalkyl), Y—$C_{0-6}$-alkylene-(6-membered aryl), Y—$C_{0-6}$-alkylene-(5- to 6-membered heteroaryl), $C_{0-6}$-alkylene-S(=O)(=$R^{41}$)=N—$R^{75}$, X—$C_{1-6}$-alkylene-S(=O)(=$R^{41}$)=N—$R^{75}$, $C_{0-6}$-alkylene-S(O)$_n R^{41}$, X—$C_{1-6}$-alkylene-S(O)$_n R^{41}$, $C_{0-6}$-alkylene-S(=$NR^{71}$)$R^{41}$, X—$C_{1-6}$-alkylene-S(=$NR^{71}$)$R^{41}$, $C_{0-6}$-alkylene-S(O)(=$NR^{71}$)$R^{41}$, X—$C_{1-6}$-alkylene-S(O)(=$NR^{71}$)$R^{41}$, $C_{0-6}$-alkylene-S(=$NR^{71}$)$_2 R^{41}$, X—$C_{1-6}$-alkylene-S(=$NR^{71}$)$_2 R^{41}$, $C_{0-6}$-alkylene-$NR^{41}$S(O)$_2 R^{41}$, X—$C_{1-6}$-alkylene-$NR^{41}$S(O)$_2 R^{41}$, $C_{0-6}$-alkylene-S(O)$_2 NR^{41} R^{42}$, X—$C_{1-6}$-alkylene-S(O)$_2 NR^{41} R^{42}$, $C_{0-6}$-alkylene-$NR^{41}$S(O)$_2 NR^{41} R^{42}$, X—$C_{1-6}$-alkylene-$NR^{41}$S(O)$_2 NR^{41} R^{42}$, $C_{0-6}$-alkylene-$SO_3 R^{41}$, X—$C_{1-6}$-alkylene-$SO_3 R^{41}$, $C_{0-6}$-alkylene-$CO_2 R^{41}$, X—$C_{1-6}$-alkylene-$CO_2 R^{41}$, $C_{0-6}$-alkylene-O—$COR^{41}$, X—$C_{1-6}$-alkylene-O—$COR^{41}$, $C_{0-6}$-alkylene-$CONR^{41} R^{42}$, X—$C_{1-6}$-alkylene-$CONR^{41} R^{42}$, $C_{0-6}$-alkylene-$CONR^{41} OR^{41}$, X—$C_{1-6}$-alkylene-$CONR^{41} OR^{41}$, $C_{0-6}$-alkylene-$CONR^{41} SO_2 R^{41}$, X—$C_{1-6}$-alkylene-$CONR^{41} SO_2 R^{41}$, $C_{0-6}$-alkylene-$NR^{41}$—$COR^{41}$, X—$C_{1-6}$-$C_{0-6}$-alkylene-$NR^{41}$—$COR^{41}$, $C_{0-6}$-alkylene-$NR^{41}$—$CONR^{41} R^{42}$, X—$C_{1-6}$-alkylene-$NR^{41}$—$CONR^{41} R^{42}$, $C_{0-6}$-alkylene-O—$CONR^{41} R^{42}$, X—$C_{1-6}$-alkylene-O—$CONR^{41} R^{42}$, $C_{0-6}$-alkylene-$NR^{41}$—$CO_2 R^{41}$, X—$C_{1-6}$-alkylene-$NR^{41}$—$CO_2 R^{41}$, $C_{0-6}$-alkylene-$NR^{41} R^{42}$, X—$C_{1-6}$-alkylene-$NR^{41} R^{42}$,
wherein alkyl, alkylene, cycloalkyl, heterocycloalkyl, aryl and heteroaryl is unsubstituted or substituted with 1 to 6 substituents independently selected from halogen, CN, oxo, hydroxy, $CO_2H$, $CO_2$-$C_{1-4}$-alkyl, $CONHCH_2 CO_2 H$, $CONH(CH_2)_2 SO_3 H$, $C_{1-4}$-alkyl, halo-$C_{1-4}$-alkyl, O—$C_{1-4}$-alkyl and O-halo-$C_{1-4}$-alkyl;
and wherein optionally two adjacent substituents on the aryl and heteroaryl moiety form a 5- to 8-membered partially unsaturated cycle optionally containing 1 to 3 heteroatoms independently selected from O, S or N, and
wherein this additional cycle is unsubstituted or substituted with 1 to 4 substituents independently selected from halogen, CN, oxo, OH, $CO_2H$, $CO_2$-$C_{1-4}$-alkyl, $CONHCH_2 CO_2 H$, $CONH(CH_2)_2 SO_3 H$, $C_{1-4}$-alkyl, halo-$C_{1-4}$-alkyl, O—$C_{1-4}$-alkyl and O-halo-$C_{1-4}$-alkyl;

$R^{11}$, $R^{12}$, $R^{21}$, $R^{22}$, $R^{31}$, $R^{32}$, $R^{41}$, $R^{42}$, $R^{51}$ are independently selected from H and $C_{1-4}$-alkyl,
wherein alkyl is unsubstituted or substituted with 1 to 3 substituent independently selected from halogen, CN, $C_{1-4}$-alkyl, halo-$C_{1-4}$-alkyl, 3- to 6-membered cycloalkyl, halo-(3- to 6-membered cycloalkyl), 3- to 6-membered heterocycloalkyl, halo-(3- to 6-membered heterocycloalkyl), OH, oxo, $CO_2H$, $CO_2$-$C_{1-4}$-alkyl, $CONHCH_2 CO_2 H$, $CONH(CH_2)_2 SO_3 H$, $SO_3 H$, O—$C_{1-4}$-alkyl and O-halo-$C_{1-4}$-alkyl;

or $R^{11}$ and $R^{12}$, $R^{21}$ and $R^{22}$, $R^{31}$ and $R^{32}$, $R^{41}$ and $R^{42}$, respectively, when taken together with the nitrogen to which they are attached complete a 3- to 6-membered ring containing carbon atoms and optionally containing 1 or 2 heteroatoms independently selected from O, S or N; and
wherein the new formed cycle is unsubstituted or substituted with 1 to 3 substituents independently selected from halogen, CN, $C_{1-4}$-alkyl, halo-$C_{1-4}$-alkyl, 3- to 6-membered cycloalkyl, halo-(3- to 6-membered cycloalkyl), 3- to 6-membered heterocycloalkyl, halo-(3- to 6-membered heterocycloalkyl), OH, oxo, $CO_2H$, $CO_2$-$C_{1-4}$-alkyl, $CONHCH_2 CO_2 H$, $CONH(CH_2)_2 SO_3 H$, $SO_3 H$, O—$C_{1-4}$-alkyl and O-halo-$C_{1-4}$-alkyl;

$R^{71}$ is independently selected from H, CN; $NO_2$, $C_{1-4}$-alkyl and C(O)—$OC_{1-4}$-alkyl,
wherein alkyl is unsubstituted or substituted with 1 to 3 substituents independently selected from halogen, CN, $C_{1-4}$-alkyl, halo-$C_{1-4}$-alkyl, 3- to 6-membered cycloalkyl, halo-(3- to 6-membered cycloalkyl), 3- to 6-membered heterocycloalkyl, halo-(3- to 6-membered heterocycloalkyl), OH, oxo, $CO_2H$, $CO_2$-$C_{1-4}$-alkyl, $CONHCH_2 CO_2 H$, $CONH(CH_2)_2 SO_3 H$, $SO_3 H$, O—$C_{1-4}$-alkyl and O-halo-$C_{1-4}$-alkyl;

$R^{75}$ is independently selected from $C_{1-4}$-alkyl, 3- to 6-membered cycloalkyl, 3- to 6-membered heterocycloalkyl, 6-membered aryl and 5- to 6-membered heteroaryl,
wherein alkyl, cycloalkyl, heterocycloalkyl, aryl and heteroaryl is unsubstituted or substituted with 1 to 3 substituents independently selected from halogen, CN, Me, Et, $CHF_2$, $CF_3$, OH, oxo, $CO_2H$, $CONHCH_2 CO_2 H$, $CONH(CH_2)_2 SO_3 H$, $SO_3 H$, OMe, OEt, $OCHF_2$, and $OCF_3$;

X is independently selected from O, $NR^{51}$, S(O)$_n$, S(=$NR^{71}$), S(O)(=$NR^{71}$) and S(=$NR^{71}$)$_2$;

Y is independently selected from a bond, O, $NR^{51}$, S(O)$_n$, S(=$NR^{71}$), S(O)(=$NR^{71}$) and S(=$NR^{71}$)$_2$;

n is independently selected from 0 to 2;

and with the proviso, that the following structures are excluded:

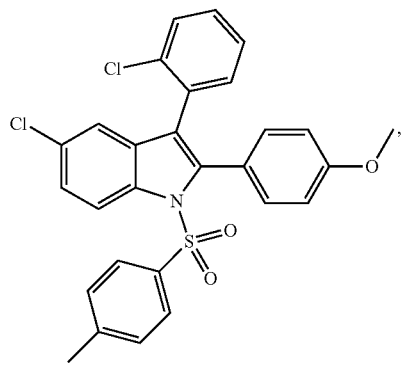

-continued

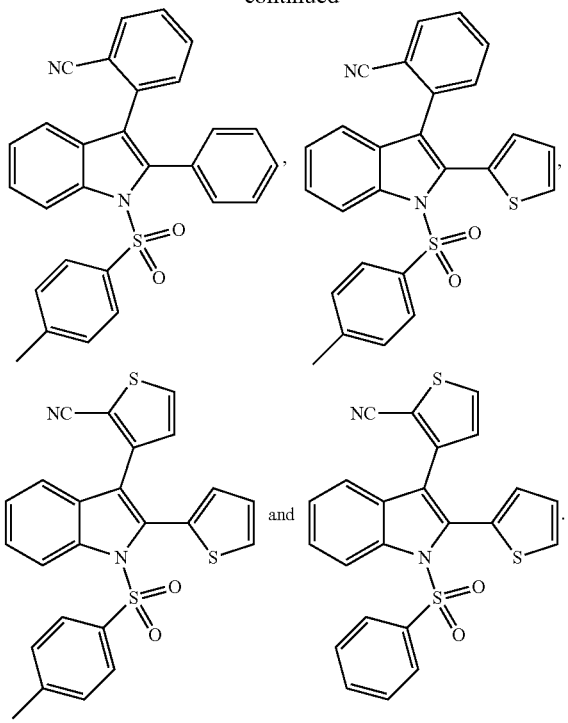

In a preferred embodiment in combination with any of the above or below embodiments

is an annelated 5- to 6-membered cycle forming a 6-membered aryl or a 5- to 6-membered heteroaryl containing 1 to 3 heteroatoms independently selected from N, O and S, wherein this cycle is unsubstituted or substituted with 1 to 4 substituents independently selected from the group consisting of halogen, CN, SF$_5$, NO$_2$, C$_{1-6}$-alkyl, oxo, C$_{0-6}$-alkylene-OR$^{11}$, C$_{0-6}$-alkylene-(3- to 6-membered cycloalkyl), C$_{0-6}$-alkylene-(3- to 6-membered heterocycloalkyl), C$_{0-6}$-alkylene-S(O)NR$^{11}$, C$_{0-6}$-alkylene-NR$^{11}$S(O)$_2$R$^{11}$, C$_{0-6}$-alkylene-S(O)$_2$NR$^{11}$R$^{12}$, C$_{0-6}$-alkylene-NR$^{11}$S(O)$_2$NR$^{11}$R$^{12}$, C$_{0-6}$-alkylene-CO$_2$R$^{11}$, O—C$_{1-6}$-alkylene-CO$_2$R$^{11}$, C$_{0-6}$-alkylene-O—COR$^{11}$, C$_{0-6}$-alkylene-CONR$^{11}$R$^{12}$, C$_{0-6}$-alkylene-NR$^{11}$—COR$^{11}$, C$_{0-6}$-alkylene-NR$^{11}$—CONR$^{11}$R$^{12}$, C$_{0-6}$-alkylene-O—CONR$^{11}$R$^{12}$, C$_{0-6}$-alkylene-NR$^{11}$—CO$_2$R$^{11}$ and C$_{0-6}$-alkylene-NR$^{11}$R$^{12}$,
wherein alkyl, alkylene, cycloalkyl and heterocycloalkyl is unsubstituted or substituted with 1 to 6 substituents independently selected from halogen, CN, oxo, hydroxy, CO$_2$H, CO$_2$-C$_{1-4}$-alkyl, CONHCH$_2$CO$_2$H, CONH(CH$_2$)$_2$SO$_3$H, C$_{1-4}$-alkyl, halo-C$_{1-4}$-alkyl, O—C$_{1-4}$-alkyl and O-halo-C$_{1-4}$-alkyl; and
wherein optionally two adjacent substituents on the aryl or heteroaryl moiety form a 5- to 8-membered partially unsaturated cycle optionally containing 1 to 3 heteroatoms independently selected from O, S or N, and wherein the new formed cycle is unsubstituted or substituted with 1 to 3 substituents independently selected from halogen, CN, C$_{1-4}$-alkyl, halo-C$_{1-4}$-alkyl, 3- to 6-membered cycloalkyl, halo-(3- to 6-membered cycloalkyl), 3- to 6-membered heterocycloalkyl, halo-(3- to 6-membered heterocycloalkyl), OH, oxo, CO$_2$H, CO$_2$-C$_{1-4}$-alkyl, CONHCH$_2$CO$_2$H, CONH(CH$_2$)$_2$SO$_3$H, O—C$_{1-4}$-alkyl and O-halo-C$_{1-4}$-alkyl.

In a more preferred embodiment in combination with any of the above or below embodiments

is an annelated phenyl, thiophenyl, thiazolyl, pyridyl, pyrimidinyl, pyridazinyl and pyrazinyl, wherein this cycle is unsubstituted or substituted with 1 to 4 substituents independently selected from the group consisting of halogen, CN, SF$_5$, NO$_2$, C$_{1-6}$-alkyl, oxo, C$_{0-6}$-alkylene-OR$^{11}$, C$_{0-6}$-alkylene-(3- to 6-membered cycloalkyl), C$_{0-6}$-alkylene-(3- to 6-membered heterocycloalkyl), C$_{0-6}$-alkylene-S(O)NR$^{11}$, C$_{0-6}$-alkylene-NR$^{11}$S(O)$_2$R$^{11}$, C$_{0-6}$-alkylene-S(O)$_2$NR$^{11}$R$^{12}$, C$_{0-6}$-alkylene-NR$^{11}$S(O)$_2$NR$^{11}$R$^{12}$, C$_{0-6}$-alkylene-CO$_2$R$^{11}$, O—C$_{1-6}$-alkylene-CO$_2$R$^{11}$, C$_{0-6}$-alkylene-O—COR$^{11}$, C$_{0-6}$-alkylene-CONR$^{11}$R$^{12}$, C$_{0-6}$-alkylene-NR$^{11}$—COR$^{11}$, C$_{0-6}$-alkylene-NR$^{11}$—CONR$^{11}$R$^{12}$, C$_{0-6}$-alkylene-O—CONR$^{11}$R$^{12}$, C$_{0-6}$-alkylene-NR$^{11}$—CO$_2$R$^{11}$ and C$_{0-6}$-alkylene-NR$^{11}$R$^{12}$,
wherein alkyl, alkylene, cycloalkyl and heterocycloalkyl is unsubstituted or substituted with 1 to 6 substituents independently selected from halogen, CN, oxo, hydroxy, CO$_2$H, CO$_2$-C$_{1-4}$-alkyl, CONHCH$_2$CO$_2$H, CONH(CH$_2$)$_2$SO$_3$H, C$_{1-4}$-alkyl, halo-C$_{1-4}$-alkyl, O—C$_{1-4}$-alkyl and O-halo-C$_{1-4}$-alkyl.

In an even more preferred embodiment in combination with any of the above or below embodiments

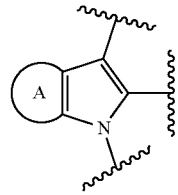

is selected from

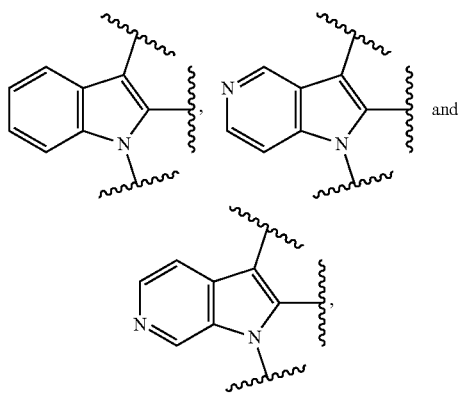

wherein

is unsubstituted or substituted with 1 to 3 substituents independently selected from the group consisting of F, Cl, Br, CN, OH, oxo, $C_{1-4}$-alkyl, halo-$C_{1-4}$-alkyl, O—$C_{1-4}$-alkyl, O-halo-$C_{1-4}$-alkyl, $NH_2$, $NHC_{1-4}$-alkyl, $N(C_{1-4}$-alkyl$)_2$, $SO_2$-$C_{1-4}$-alkyl and $SO_2$-halo-$C_{1-4}$-alkyl.

In a most preferred embodiment in combination with any of the above or below embodiments

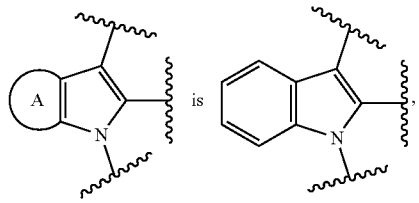

wherein

is unsubstituted or substituted with 1 to 3 substituents independently selected from the group consisting of F, Cl, Br, CN, Me, Et, $CF_3$, $CHF_2$, OH, OMe, $OCF_3$ and $OCHF_2$.

In a preferred embodiment in combination with any of the above or below embodiments

is selected from the group consisting of 3- to 10-membered cycloalkyl, 3- to 10-membered heterocycloalkyl containing 1 to 3 heteroatoms independently selected from N, O and S, 6- to 14-membered aryl and 5- to 14-membered heteroaryl containing 1 to 4 heteroatoms independently selected from N, O and S,
wherein cycloalkyl, heterocycloalkyl, aryl and heteroaryl are unsubstituted or substituted with 1 to 6 substituents independently selected from the group consisting of halogen, CN, $SF_5$, $NO_2$, oxo, $C_{1-4}$-alkyl, $C_{0-6}$-alkylene-$OR^{21}$, $C_{0-6}$-alkylene-(3- to 6-membered cycloalkyl), $C_{0-6}$-alkylene-(3- to 6-membered heterocycloalkyl), $C_{0-6}$-alkylene-$S(O)_nR^{21}$, $C_{0-6}$-alkylene-$NR^{21}S(O)_2R^{21}$, $C_{0-6}$-alkylene-$S(O)_2NR^{21}R^{22}$, $C_{0-6}$-alkylene-$NR^{21}S(O)_2NR^{21}R^{22}$, $C_{0-6}$-alkylene-$CO_2R^{21}$, O—$C_{1-6}$-alkylene-$CO_2R^{21}$, $C_{0-6}$-alkylene-O—$COR^{21}$, $C_{0-6}$-alkylene-$CONR^{21}R^{22}$, $C_{0-6}$-alkylene-$NR^{21}$—$COR^{21}$, $C_{0-6}$-alkylene-$NR^{21}$—$CONR^{21}R^{22}$, $C_{0-6}$-alkylene-$NR^{21}$—$CO_2R^{21}$ and $C_{0-6}$-alkylene-$NR^{21}R^{22}$,
wherein alkyl, alkylene, cycloalkyl and heterocycloalkyl is unsubstituted or substituted with 1 to 6 substituents independently selected from halogen, CN, oxo, hydroxy, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl;
and wherein optionally two adjacent substituents on the aryl or heteroaryl moiety form a 5- to 8-membered partially unsaturated cycle optionally containing 1 to 3 heteroatoms independently selected from O, S or N, and
wherein this additional cycle is unsubstituted or substituted with 1 to 4 substituents independently selected from halogen, CN, oxo, OH, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl;
and wherein optionally two adjacent substituents on the cycloalkyl or heterocycloalkyl moiety form a 5- to 6-membered unsaturated cycle optionally containing 1 to 3 heteroatoms independently selected from O, S or N,
wherein this additional cycle is unsubstituted or substituted with 1 to 4 substituents independently selected from halogen, CN, oxo, OH, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl.

In a more preferred embodiment in combination with any of the above or below embodiments

is selected from the group consisting of phenyl, pyridyl and thiophenyl,
wherein phenyl, pyridyl and thiophenyl are substituted with 1 to 4 substituents independently selected from the group consisting of halogen, CN, $SF_5$, $NO_2$, oxo, $C_{1-4}$-alkyl, $C_{0-6}$-alkylene-$OR^{21}$, $C_{0-6}$-alkylene-(3- to 6-membered cycloalkyl), $C_{0-6}$-alkylene-(3- to 6-membered heterocycloalkyl), $C_{0-6}$-alkylene-$S(O)_nR^{21}$, $C_{0-6}$-alkylene-$NR^{21}S(O)_2R^{21}$, $C_{0-6}$-alkylene-$S(O)_2NR^{21}R^{22}$, $C_{0-6}$-alkylene-$NR^{21}S(O)_2NR^{21}R^{22}$, $C_{0-6}$-alkylene-$CO_2R^{21}$, O—$C_{1-6}$-alkylene-$CO_2R^{21}$, $C_{0-6}$-alkylene-O—$COR^{21}$, $C_{0-6}$-alkylene-$CONR^{21}R^{22}$, $C_{0-6}$-alkylene-$NR^{21}$—$COR^{21}$, $C_{0-6}$-alkylene-$NR^{21}$—$CONR^{21}R^{22}$, $C_{0-6}$-alkylene-O—$CONR^{21}R^{22}$, $C_{0-6}$-alkylene-$NR^{21}$—$CO_2R^{21}$ and $C_{0-6}$-alkylene-$NR^{21}R^{22}$,
wherein alkyl, alkylene, cycloalkyl and heterocycloalkyl is unsubstituted or substituted with 1 to 6 substituents independently selected from halogen, CN, oxo, hydroxy, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl;
and wherein optionally two adjacent substituents on the phenyl and pyridyl moiety form a 5- to 8-membered partially unsaturated cycle optionally containing 1 to 3 heteroatoms independently selected from O, S or N, and
wherein this additional cycle is unsubstituted or substituted with 1 to 4 substituents independently selected from halogen, CN, oxo, OH, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl.

In a similar more preferred embodiment in combination with any of the above or below embodiments

is selected from the group consisting of phenyl, naphthyl, pyridyl, pyrimidinyl, thiophenyl, thiazolyl, cyclopentyl, cyclohexyl, bicyclo[1.1.1]pentyl, bicyclo[2.2.2]octyl, bicyclo[2.2.1]heptyl, pentacyclo[4.2.0.0$^{2,5}$.0$^{3,8}$.0$^{4,7}$]octyl and piperidinyl,
wherein the cycle is unsubstituted or substituted with 1 to 3 substituents independently selected from the group consisting of F, Cl, Br, CN, OH, oxo, $C_{1-4}$-alkyl, halo-$C_{1-4}$-alkyl, O—$C_{1-4}$-alkyl, O-halo-$C_{1-4}$-alkyl, $C_{1-4}$-alkyl-OH and halo-$C_{1-4}$-alkyl-OH; and wherein optionally two adjacent substituents on the phenyl ring form together a —(CH$_2$)$_3$—, —(CH$_2$)$_4$—, —OCF$_2$O— and —OCH$_2$O— group.

In an even more preferred embodiment in combination with any of the above or below embodiments

is selected from the group consisting of phenyl and pyridyl,
wherein phenyl and pyridyl is substituted with 1 to 2 substituents independently selected from the group consisting of F, Cl, CN, CF$_3$, CH$_2$F and CHF$_2$.

In a most preferred embodiment in combination with any of the above or below embodiments

is 4-difluoromethylphenyl.

In a preferred embodiment in combination with any of the above or below embodiments

is selected from the group consisting of 6- or 10-membered aryl and 5- to 10-membered heteroaryl containing 1 to 3 heteroatoms independently selected from N, O and S,
wherein cycloalkyl, heterocycloalkyl, aryl and heteroaryl are unsubstituted or substituted with 1 to 4 substituents independently selected from the group consisting of halogen, CN, SF$_5$, NO$_2$, oxo, $C_{1-4}$-alkyl, $C_{0-6}$-alkylene-OR$^{31}$, $C_{0-6}$-alkylene-(3- to 6-membered cycloalkyl), $C_{0-6}$-alkylene-(3- to 6-membered heterocycloalkyl), $C_{0-6}$-alkylene-(6-membered aryl), $C_{0-6}$-alkylene-(5- to 6-membered heteroaryl), $C_{0-6}$-alkylene-S(O)$_n$R$^{31}$, $C_{0-6}$-alkylene-NR$^{31}$S(O)$_2$R$^{31}$, $C_{0-6}$-alkylene-S(O)$_2$NR$^{31}$R$^{32}$, $C_{0-6}$-alkylene-NR$^{31}$S(O)$_2$NR$^{31}$R$^{32}$, $C_{0-6}$-alkylene-CO$_2$R$^{31}$, O—$C_{1-6}$-alkylene-CO$_2$R$^{31}$, $C_{0-6}$-alkylene-O—COR$^{31}$, $C_{0-6}$-alkylene-CONR$^{31}$R$^{32}$, $C_{0-6}$-alkylene-NR$^{31}$—COR$^{31}$, $C_{0-6}$-alkylene-NR$^{31}$—CONR$^{31}$R$^{32}$, $C_{0-6}$-alkylene-O—CONR$^{31}$R$^{32}$, $C_{0-6}$-alkylene-NR$^{31}$—CO$_2$R$^{31}$ and $C_{0-6}$-alkylene-NR$^{31}$R$^{32}$,
wherein alkyl, alkylene, cycloalkyl, heterocycloalkyl, aryl and heteroaryl is unsubstituted or substituted with 1 to 6 substituents independently selected from halogen, CN, oxo, hydroxy, CO$_2$H, CO$_2$-$C_{1-4}$-alkyl, CONHCH$_2$CO$_2$H, CONH(CH$_2$)$_2$SO$_3$H, $C_{1-4}$-alkyl, halo-$C_{1-4}$-alkyl, O—$C_{1-4}$-alkyl and O-halo-$C_{1-4}$-alkyl;
and wherein optionally two adjacent substituents on the aryl or heteroaryl moiety form a 5- to 8-membered partially unsaturated cycle optionally containing 1 to 3 heteroatoms independently selected from O, S or N, and
wherein this additional cycle is unsubstituted or substituted with 1 to 4 substituents independently selected from halogen, CN, oxo, OH, CO$_2$H, CO$_2$-$C_{1-4}$-alkyl, CONHCH$_2$CO$_2$H, CONH(CH$_2$)$_2$SO$_3$H, $C_{1-4}$-alkyl, halo-$C_{1-4}$-alkyl, O—$C_{1-4}$-alkyl and O-halo-$C_{1-4}$-alkyl.

In a more preferred embodiment in combination with any of the above or below embodiments

is selected from the group consisting of phenyl, pyridyl and thiophenyl,
wherein phenyl, pyridyl and thiophenyl are unsubstituted or substituted with 1 to 4 substituents independently selected from the group consisting of halogen, CN, SF$_5$, NO$_2$, oxo, $C_{1-4}$-alkyl, $C_{0-6}$-alkylene-OR$^{31}$, $C_{0-6}$-alkylene-(3- to 6-membered cycloalkyl), $C_{0-6}$-alkylene-(3- to 6-membered heterocycloalkyl), $C_{0-6}$-alkylene-(6-membered aryl), $C_{0-6}$-alkylene-(5- to 6-membered heteroaryl), $C_{0-6}$-alkylene-S(O)$_n$R$^{31}$, $C_{0-6}$-alkylene-NR$^{31}$S(O)$_2$R$^{31}$, $C_{0-6}$-alkylene-S(O)$_2$NR$^{31}$R$^{32}$, $C_{0-6}$-alkylene-NR$^{31}$S(O)$_2$NR$^{31}$R$^{32}$, $C_{0-6}$-alkylene-CO$_2$R$^{31}$, O—$C_{1-6}$-alkylene-CO$_2$R$^{31}$, $C_{0-6}$-alkylene-O—COR$^{31}$, $C_{0-6}$-alkylene-CONR$^{31}$R$^{32}$, $C_{0-6}$-alkylene-NR$^{31}$—COR$^{31}$, $C_{0-6}$-alkylene-NR$^{31}$—CONR$^{31}$R$^{32}$, $C_{0-6}$-alkylene-O—CONR$^{31}$R$^{32}$, $C_{0-6}$-alkylene-NR$^{31}$—CO$_2$R$^{31}$ and $C_{0-6}$-alkylene-NR$^{31}$R$^{32}$,
wherein alkyl, alkylene, cycloalkyl, heterocycloalkyl, aryl and heteroaryl is unsubstituted or substituted with 1 to 6 substituents independently selected from halogen, CN, oxo, hydroxy, CO$_2$H, CO$_2$-$C_{1-4}$-alkyl, CONHCH$_2$CO$_2$H, CONH(CH$_2$)$_2$SO$_3$H, $C_{1-4}$-alkyl, halo-$C_{1-4}$-alkyl, O—$C_{1-4}$-alkyl and O-halo-$C_{1-4}$-alkyl;
and wherein residue-L-R$^1$ is linked in 1,3-orientation regarding the connection towards

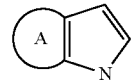

and L is not a bond.

In an even more preferred embodiment in combination with any of the above or below embodiments

is selected from phenyl, pyridyl and thiophenyl; wherein phenyl, pyridyl and thiophenyl is unsubstituted or substituted with 1 to 3 substituents independently selected from the group consisting of F, Cl, CN, OH, oxo, $C_{1-4}$-alkyl, halo-$C_{1-4}$-alkyl, O—$C_{1-4}$-alkyl and O-halo-$C_{1-4}$-alkyl; and wherein the residue-L-$R^1$ is linked in 1,3-orientation regarding the connection towards

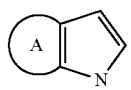

and L is not a bond.

In a most preferred embodiment in combination with any of the above or below embodiments

is phenyl, wherein phenyl is unsubstituted or substituted with F, Cl and Me; and wherein the residue-L-$R^1$ is linked in 1,3-orientation regarding the connection towards

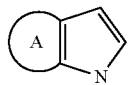

and L is not a bond.

In a preferred embodiment in combination with any of the above or below embodiments L is selected from the group consisting of a bond, $C_{1-6}$-alkylene, $C_{2-6}$-alkenylene, $C_{2-6}$-alkinylene, 3- to 10-membered cycloalkylene, 3- to 10-membered heterocycloalkylene containing 1 to 4 heteroatoms independently selected from N, O and S, 6- or 10-membered arylene and 5- to 10-membered heteroarylene containing 1 to 4 heteroatoms independently selected from N, O and S, wherein alkylene, alkenylene, alkinylene, cycloalkylene, heterocycloalkylene, arylene and heteroarylene are unsubstituted or substituted with 1 to 6 substituents independently selected from the group consisting of halogen, CN, $SF_5$, $NO_2$, oxo, $C_{1-4}$-alkyl, $C_{0-6}$-alkylene-$OR^{41}$, $C_{0-6}$-alkylene-(3- to 6-membered cycloalkyl), $C_{0-6}$-alkylene-(3- to 6-membered heterocycloalkyl), $C_{0-6}$-alkylene-$S(O)_nR^{41}$, $C_{0-6}$-alkylene-$NR^{41}S(O)_2R^{41}$, $C_{0-6}$-alkylene-$S(O)_2NR^{41}R^{42}$, $C_{0-6}$-alkylene-$NR^{41}S(O)_2NR^{41}R^{42}$, $C_{0-6}$-alkylene-$CO_2R^{41}$, O—$C_{1-6}$-alkylene-$CO_2R^{41}$, $C_{0-6}$-alkylene-O—$COR^{41}$, $C_{0-6}$-alkylene-$CONR^{41}R^{42}$, $C_{0-6}$-alkylene-$NR^{41}$—$COR^{41}$, $C_{0-6}$-alkylene-$NR^{41}$—$CONR^{41}R^{42}$, $C_{0-6}$-alkylene-O—$CONR^{41}R^{42}$, $C_{0-6}$-alkylene-$NR^{41}$—$CO_2R^{41}$ and $C_{0-6}$-alkylene-$NR^{41}R^{42}$, wherein alkyl, alkylene, cycloalkyl and heterocycloalkyl is unsubstituted or substituted with 1 to 6 substituents independently selected from halogen, CN, oxo, hydroxy, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl;

and wherein optionally two adjacent substituents on the arylene and heteroarylene moiety form a 5- to 8-membered partially unsaturated cycle optionally containing 1 to 3 heteroatoms independently selected from O, S or N, and wherein this additional cycle is unsubstituted or substituted with 1 to 4 substituents independently selected from halogen, CN, oxo, OH, $CO_2H$, $CO_2$-$C_{1-4}$-alkyl, $C_{1-4}$-alkyl, halo-$C_{1-4}$-alkyl, O—$C_{1-4}$-alkyl and O-halo-$C_{1-4}$-alkyl.

In a more preferred embodiment in combination with any of the above or below embodiments L is selected from the group consisting of 3- to 10-membered cycloalkylene, 3- to 10-membered heterocycloalkylene containing 1 to 4 heteroatoms independently selected from N, O and S, 6-membered arylene and 5- to 6-membered heteroarylene containing 1 to 2 heteroatoms independently selected from N, O and S, wherein cycloalkylene, heterocycloalkylene, arylene and heteroarylene are unsubstituted or substituted with 1 to 6 substituents independently selected from the group consisting of halogen, CN, $SF_5$, $NO_2$, oxo, $C_{1-4}$-alkyl, $C_{0-6}$-alkylene-$OR^{41}$, $C_{0-6}$-alkylene-(3- to 6-membered cycloalkyl), $C_{0-6}$-alkylene-(3- to 6-membered heterocycloalkyl), $C_{0-6}$-alkylene-$S(O)_nR^{41}$, $C_{0-6}$-alkylene-$NR^{41}S(O)_2R^{41}$, $C_{0-6}$-alkylene-$S(O)_2NR^{41}R^{42}$, $C_{0-6}$-alkylene-$NR^{41}S(O)_2NR^{41}R^{42}$, $C_{0-6}$-alkylene-$CO_2R^{41}$, O—$C_{1-6}$-alkylene-$CO_2R^{41}$, $C_{0-6}$-alkylene-O—$COR^{41}$, $C_{0-6}$-alkylene-$CONR^{41}R^{42}$, $C_{0-6}$-alkylene-$NR^{41}$—$COR^{41}$, $C_{0-6}$-alkylene-$NR^{41}$—$CONR^{41}R^{42}$, $C_{0-6}$-alkylene-O—$CONR^{41}R^{42}$, $C_{0-6}$-alkylene-$NR^{41}$—$CO_2R^{41}$ and $C_{0-6}$-alkylene-$NR^{41}R^{42}$, wherein alkyl, alkylene, cycloalkyl and heterocycloalkyl is unsubstituted or substituted with 1 to 6 substituents independently selected from halogen, CN, oxo, hydroxy, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl;

and wherein optionally two adjacent substituents on the arylene and heteroarylene moiety form a 5- to 8-membered partially unsaturated cycle optionally containing 1 to 3 heteroatoms independently selected from O, S or N, and wherein this additional cycle is unsubstituted or substituted with 1 to 4 substituents independently selected from halogen, CN, oxo, OH, $CO_2H$, $CO_2$-$C_{1-4}$-alkyl, $C_{1-4}$-alkyl, halo-$C_{1-4}$-alkyl, O—$C_{1-4}$-alkyl and O-halo-$C_{1-4}$-alkyl.

In an even more preferred embodiment in combination with any of the above or below embodiments
-L-R$^1$ is selected from

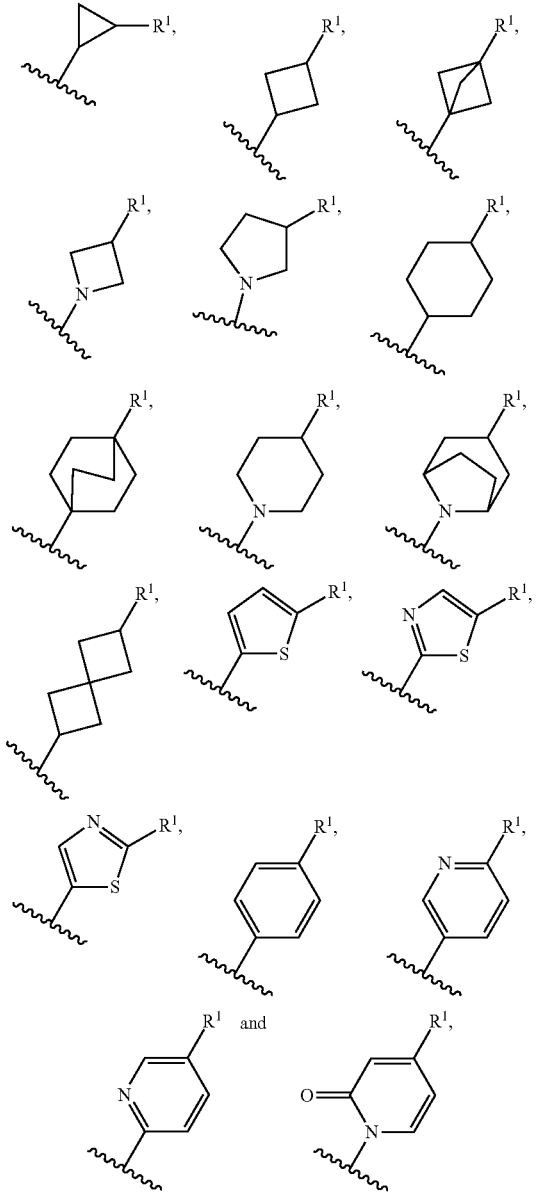

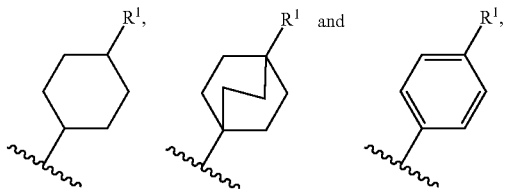

wherein the cycle is unsubstituted or substituted with 1 to 4 substituents independently selected from the group consisting of F, Cl, Br, CN, OH, oxo, $C_{1-4}$-alkyl, halo-$C_{1-4}$-alkyl, O—$C_{1-4}$-alkyl, O-halo-$C_{1-4}$-alkyl, $C_{1-4}$-alkyl-OH, halo-$C_{1-4}$-alkyl-OH, $SO_2$-$C_{1-4}$-alkyl and $SO_2$-halo-$C_{1-4}$-alkyl; and wherein optionally two adjacent substituents on the phenyl ring form together a —$(CH_2)_3$—, —$(CH_2)_4$—, —$OCF_2O$— and —$OCH_2O$— group.

In a most preferred embodiment in combination with any of the above or below embodiments -L-R$^1$ is selected from wherein phenyl is unsubstituted or substituted with 1 to 4 substituents independently selected from the group consisting of F, Cl, CN, OH, Me and OMe.

In a preferred embodiment in combination with any of the above or below embodiments R$^1$ is selected from the group consisting of H, halogen, CN, SF$_5$, NO$_2$, oxo, $C_{1-4}$-alkyl, $C_{0-6}$-alkylene-OR$^{41}$, Y—$C_{0-6}$-alkylene-(3- to 6-membered cycloalkyl), Y—$C_{0-6}$-alkylene-(3- to 6-membered heterocycloalkyl), Y—$C_{0-6}$-alkylene-(6-membered aryl), Y—$C_{0-6}$-alkylene-(5- to 6-membered heteroaryl), $C_{0-6}$-alkylene-S(=O)(=R$^{41}$)=N—R$^{75}$, X—$C_{1-6}$-alkylene-S(=O)(=R$^{41}$)=N—R$^{75}$, $C_{0-6}$-alkylene-S(O)$_n$R$^{41}$, X—$C_{1-6}$-alkylene-S(O)$_n$R$^{41}$, $C_{0-6}$-alkylene-S(=NR$^{71}$) R$^{41}$, X—$C_{1-6}$-alkylene-S(=NR$^{71}$)R$^{41}$, $C_{0-6}$-alkylene-S(O)(=NR$^{71}$)R$^{41}$, X—$C_{1-6}$-alkylene-S(O)(=NR$^{71}$)R$^{41}$, $C_{0-6}$-alkylene-S(=NR$^{71}$)$_2$R$^{41}$, X—$C_{1-6}$-alkylene-S(=NR$^{71}$)$_2$R$^{41}$, $C_{0-6}$-alkylene-NR$^{41}$S(O)$_2$R$^{41}$, X—$C_{1-6}$-alkylene-NR$^{41}$S(O)$_2$R$^{41}$, $C_{0-6}$-alkylene-S(O)$_2$NR$^{41}$R$^{42}$, X—$C_{1-6}$-alkylene-S(O)$_2$NR$^{41}$R$^{42}$, $C_{0-6}$-alkylene-NR$^{41}$S(O)$_2$NR$^{41}$R$^{42}$, X—$C_{1-6}$-alkylene-NR$^{41}$S(O)$_2$NR$^{41}$R$^{42}$, $C_{0-6}$-alkylene-SO$_3$R$^{41}$, X—$C_{1-6}$-alkylene-SO$_3$R$^{41}$, $C_{0-6}$-alkylene-CO$_2$R$^{41}$, X—$C_{1-6}$-alkylene-CO$_2$R$^{41}$, $C_{0-6}$-alkylene-O—COR$^{41}$, X—$C_{1-6}$-alkylene-O—COR$^{41}$, $C_{0-6}$-alkylene-CONR$^{41}$R$^{42}$, X—$C_{1-6}$-alkylene-CONR$^{41}$R$^{42}$, $C_{0-6}$-alkylene-CONR$^{41}$OR$^{41}$, X—$C_{1-6}$-alkylene-CONR$^{41}$OR$^{41}$, $C_{0-6}$-alkylene-CONR$^{41}$SO$_2$R$^{41}$, X—$C_{1-6}$-alkylene-CONR$^{41}$SO$_2$R$^{41}$, $C_{0-6}$-alkylene-NR$^{41}$—COR$^{41}$, X—$C_{1-6}$-$C_{0-6}$-alkylene-NR$^{41}$—COR$^{41}$, $C_{0-6}$-alkylene-NR$^{41}$—CONR$^{41}$R$^{42}$, X—$C_{1-6}$-alkylene-NR$^{41}$—CONR$^{41}$R$^{42}$, $C_{0-6}$-alkylene-O—CONR$^{41}$R$^{42}$, X—$C_{1-6}$-alkylene-O—CONR$^{41}$R$^{42}$, $C_{0-6}$-alkylene-NR$^{41}$—CO$_2$R$^{41}$, X—$C_{1-6}$-alkylene-NR$^{41}$—CO$_2$R$^{41}$, $C_{0-6}$-alkylene-NR$^{41}$R$^{42}$, X—$C_{1-6}$-alkylene-NR$^{41}$R$^{42}$, wherein alkyl, alkylene, cycloalkyl, heterocycloalkyl, aryl and heteroaryl is unsubstituted or substituted with 1 to 6 substituents independently selected from halogen, CN, oxo, hydroxy, CO$_2$H, CO$_2$-$C_{1-4}$-alkyl, CONHCH$_2$CO$_2$H, CONH(CH$_2$)$_2$SO$_3$H, $C_{1-4}$-alkyl, halo-$C_{1-4}$-alkyl, O—$C_{1-4}$-alkyl and O-halo-$C_{1-4}$-alkyl;

and wherein optionally two adjacent substituents on the aryl and heteroaryl moiety form a 5- to 8-membered partially unsaturated cycle optionally containing 1 to 3 heteroatoms independently selected from O, S or N, and wherein this additional cycle is unsubstituted or substituted with 1 to 4 substituents independently selected from halogen, CN, oxo, OH, CO$_2$H, CO$_2$-$C_{1-4}$-alkyl, CONHCH$_2$CO$_2$H, CONH(CH$_2$)$_2$SO$_3$H, $C_{1-4}$-alkyl, halo-$C_{1-4}$-alkyl, O—$C_{1-4}$-alkyl and O-halo-$C_{1-4}$-alkyl.

In a more preferred embodiment in combination with any of the above or below embodiments R$^1$ is selected from CO$_2$H, tetrazole, CH$_2$CO$_2$H, OCH$_2$CO$_2$H, SO$_2$CH$_2$CO$_2$H, CHMeCO$_2$H, $CMe_2CO_2H$, $C(OH)MeCO_2H$, $CONHSO_2Me$ and $CONH(OH)$; and optionally the glycine and tauro conjugate thereof.

In a most preferred embodiment in combination with any of the above or below embodiments $R^1$ is selected from $CO_2H$ and $C(OH)MeCO_2H$; and optionally the glycine and tauro conjugate thereof.

In a preferred embodiment in combination with any of the above or below embodiments $-L-R^1$ is selected from

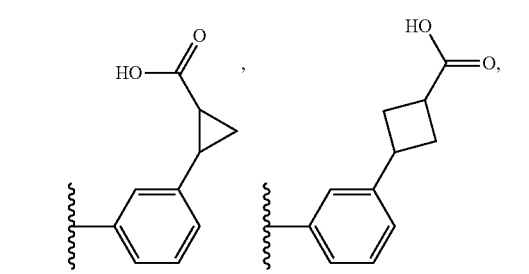

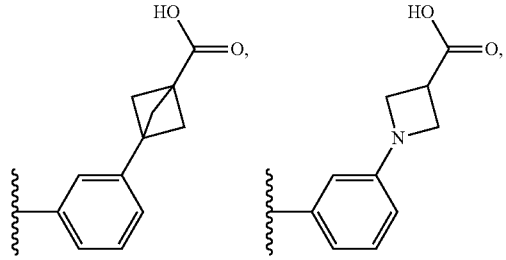

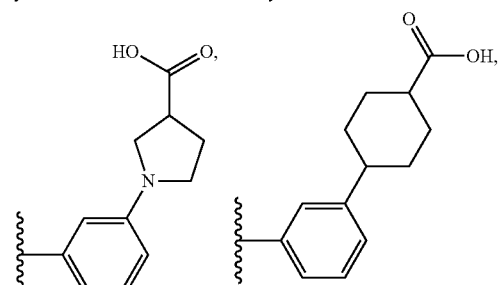

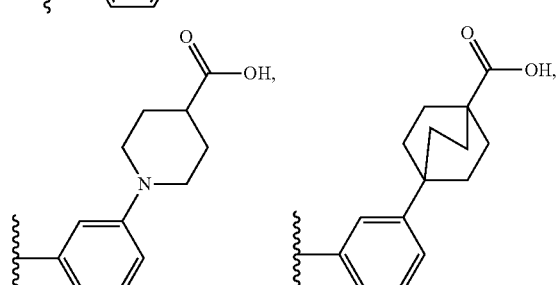

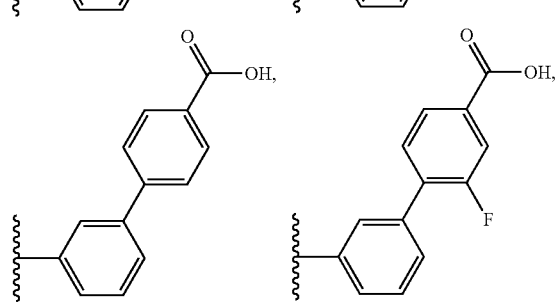

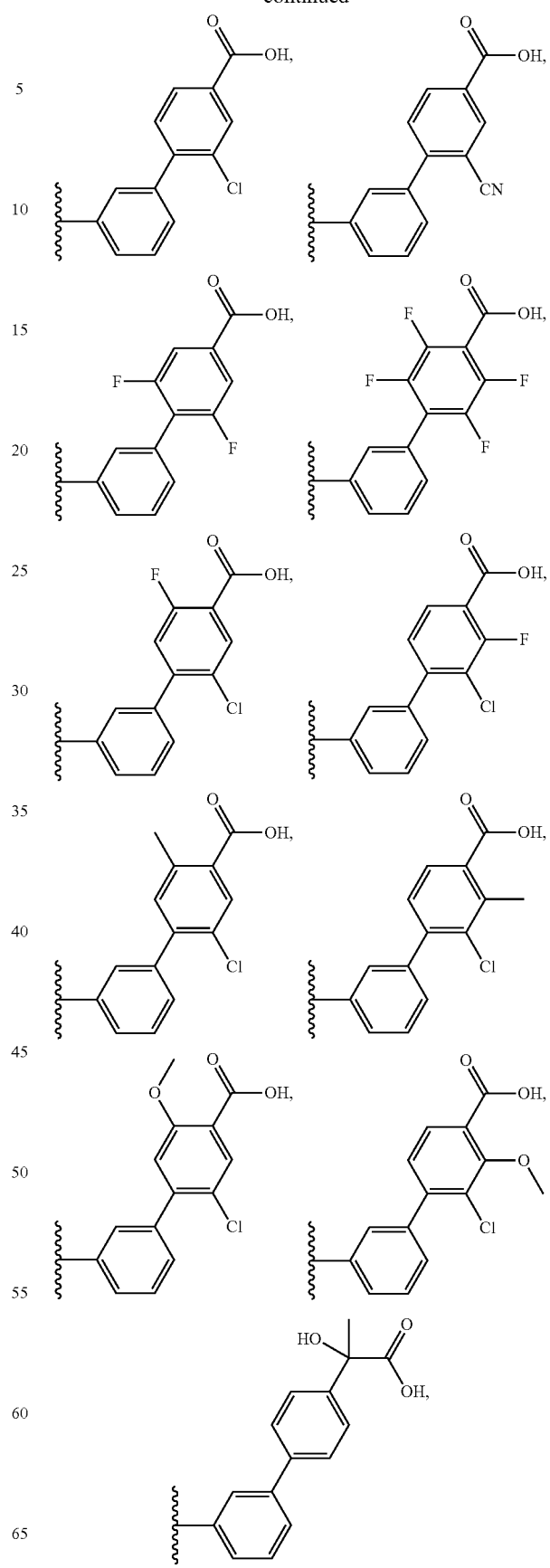

-continued
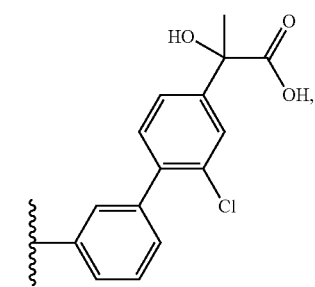
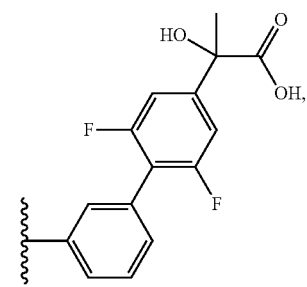
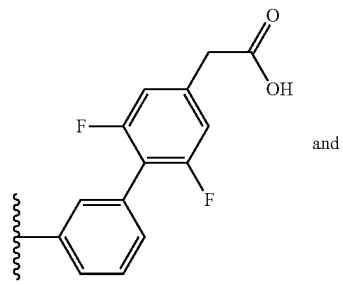
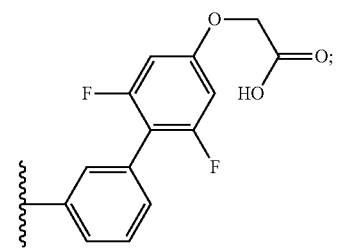
and optionally the glycine and tauro conjugate thereof.
In a more preferred embodiment in combination with any of the above or below embodiments
-L-R¹ is selected from
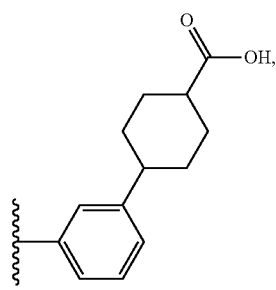
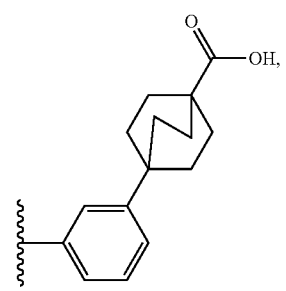
-continued
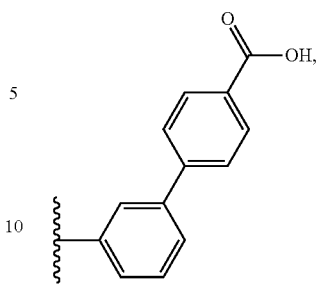
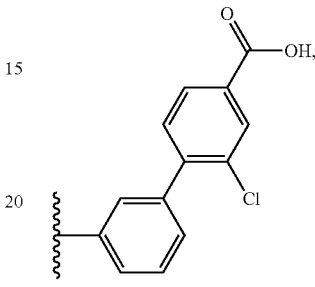
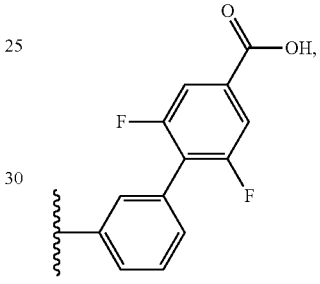
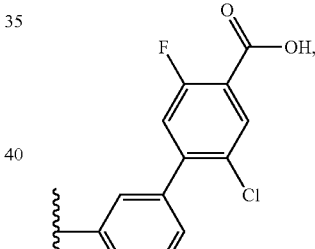
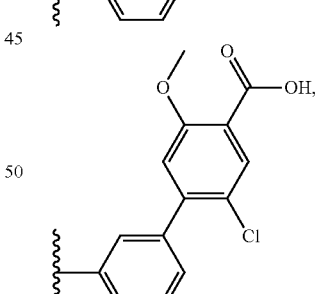
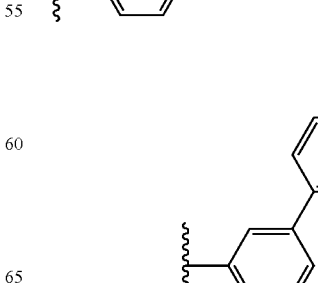

-continued

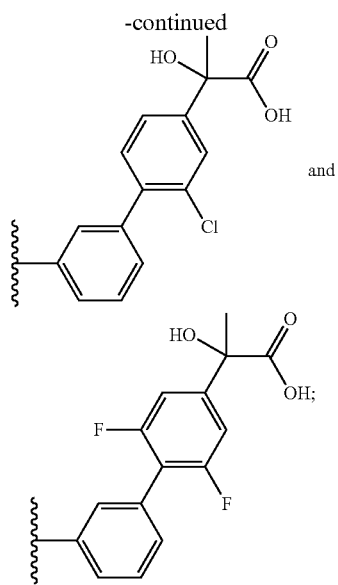

and

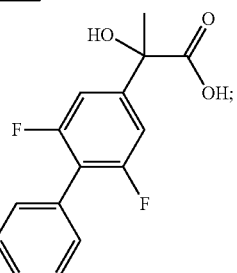

and optionally the glycine and tauro conjugate thereof.

In a most preferred embodiment in combination with any of the above or below embodiments -L-R¹ is selected from

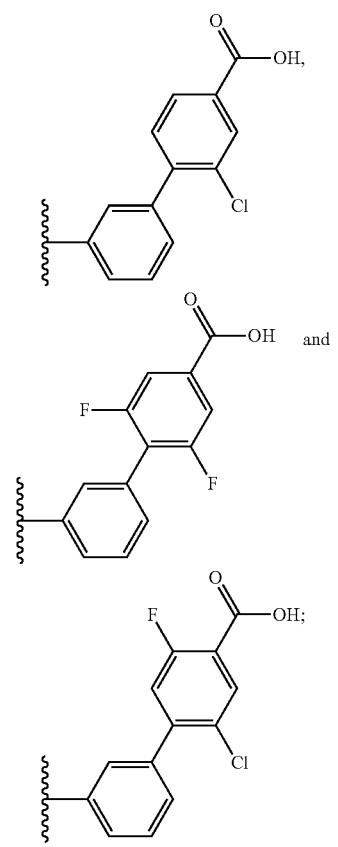

and

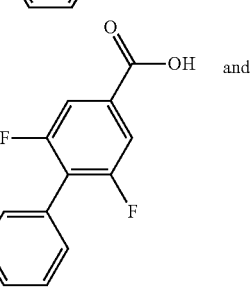

and optionally the glycine and tauro conjugate thereof.

In a preferred embodiment in combination with any of the above or below embodiments (D)

is selected form the group consisting of 3- to 10-membered cycloalkyl, 3- to 10-membered heterocycloalkyl containing 1 to 3 heteroatoms independently selected from N, O and S, 6- to 14-membered aryl and 5- to 14-membered heteroaryl containing 1 to 4 heteroatoms independently selected from N, O and S, wherein cycloalkyl, heterocycloalkyl, aryl and heteroaryl are unsubstituted or substituted with 1 to 6 substituents independently selected from the group consisting of halogen, CN, $SF_5$, $NO_2$, oxo, $C_{1-4}$-alkyl, $C_{0-6}$-alkylene-$OR^{21}$, $C_{0-6}$-alkylene-(3- to 6-membered cycloalkyl), $C_{0-6}$-alkylene-(3- to 6-membered heterocycloalkyl), $C_{0-6}$-alkylene-$S(O)_nR^{21}$, $C_{0-6}$-alkylene-$NR^{21}S(O)_2R^{21}$, $C_{0-6}$-alkylene-$S(O)_2NR^{21}R^{22}$, $C_{0-6}$-alkylene-$NR^{21}S(O)_2NR^{21}R^{22}$, $C_{0-6}$-alkylene-$CR^{41}(=N-OR^{41})$, $C_{0-6}$-alkylene-$CO_2R^{21}$, $O-C_{1-6}$-alkylene-$CO_2R^{21}$, $C_{0-6}$-alkylene-$O-COR^{21}$, $C_{0-6}$-alkylene-$CONR^{21}R^{22}$, $C_{0-6}$-alkylene-$NR^{21}-COR^{21}$, $C_{0-6}$-alkylene-$NR^{21}-CONR^{21}R^{22}$, $C_{0-6}$-alkylene-$O-CONR^{21}R^{22}$, $C_{0-6}$-alkylene-$NR^{21}-CO_2R^{21}$ and $C_{0-6}$-alkylene-$NR^{21}R^{22}$, wherein alkyl, alkylene, cycloalkyl and heterocycloalkyl is unsubstituted or substituted with 1 to 6 substituents independently selected from halogen, CN, oxo, hydroxy, $CO_2H$, $CO_2$-$C_{1-4}$-alkyl, $CONHCH_2CO_2H$, $CONH(CH_2)_2SO_3H$, $CO-OC_{1-4}$-alkyl, $C_{1-4}$-alkyl, halo-$C_{1-4}$-alkyl, $O-C_{1-4}$-alkyl and O-halo-$C_{1-4}$-alkyl;

and wherein optionally two adjacent substituents on the aryl or heteroaryl moiety form a 5- to 8-membered partially unsaturated cycle optionally containing 1 to 3 heteroatoms independently selected from O, S or N, and wherein this additional cycle is unsubstituted or substituted with 1 to 4 substituents independently selected from halogen, CN, oxo, OH, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, $O-C_{1-4}$-alkyl and O-halo-$C_{1-4}$-alkyl;

and wherein optionally two adjacent substituents on the cycloalkyl or heterocycloalkyl moiety form a 5- to 6-membered unsaturated cycle optionally containing 1 to 3 heteroatoms independently selected from O, S or N, wherein this additional cycle is unsubstituted or substituted with 1 to 4 substituents independently selected from halogen, CN, oxo, OH, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, $O-C_{1-4}$-alkyl and O-halo-$C_{1-4}$-alkyl;

wherein (D)

has a substituent from above in 1,2-orientation regarding to the connection towards

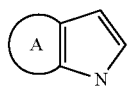

or has an annelated additional cycle in 1,2-orientation.
In a more preferred embodiment in combination with any of the above or below embodiments

is selected from the group consisting of 6- or 10-membered aryl and 5- to 10-membered heteroaryl containing 1 to 4 heteroatoms independently selected from N, O and S,
  wherein aryl and heteroaryl are unsubstituted or substituted with 1 to 6 substituents independently selected from the group consisting of halogen, CN, $SF_5$, $NO_2$, oxo, $C_{1-4}$-alkyl, $C_{0-6}$-alkylene-$OR^{21}$, $C_{0-6}$-alkylene-(3- to 6-membered cycloalkyl), $C_{0-6}$-alkylene-(3- to 6-membered heterocycloalkyl), $C_{0-6}$-alkylene-$S(O)_nR^{21}$, $C_{0-6}$-alkylene-$NR^{21}S(O)_2R^{21}$, $C_{0-6}$-alkylene-$S(O)_2NR^{21}R^{22}$, $C_{0-6}$-alkylene-$NR^{21}S(O)_2NR^{21}R^{22}$, $C_{0-6}$-alkylene-$CR^{41}(=N-OR^{41})$, $C_{0-6}$-alkylene-$CO_2R^{21}$, O—$C_{1-6}$-alkylene-$CO_2R^{21}$, $C_{0-6}$-alkylene-O—$COR^{21}$, $C_{0-6}$-alkylene-$CONR^{21}R^{22}$, $C_{0-6}$-alkylene-$NR^{21}$—$COR^{21}$, $C_{0-6}$-alkylene-$NR^{21}$—$CONR^{21}R^{22}$, $C_{0-6}$-alkylene-O—$CONR^{21}R^{22}$, $C_{0-6}$-alkylene-$NR^{21}$—$CO_2R^{21}$ and $C_{0-6}$-alkylene-$NR^{21}R^{22}$,
    wherein alkyl, alkylene, cycloalkyl and heterocycloalkyl is unsubstituted or substituted with 1 to 6 substituents independently selected from halogen, CN, oxo, hydroxy, $CO_2H$, $CO_2$-$C_{1-4}$-alkyl, $CONHCH_2CO_2H$, $CONH(CH_2)_2SO_3H$, CO—$OC_{1-4}$-alkyl, $C_{1-4}$-alkyl, halo-$C_{1-4}$-alkyl, O—$C_{1-4}$-alkyl and O-halo-$C_{1-4}$-alkyl;
  and wherein optionally two adjacent substituents on the aryl or heteroaryl moiety form a 5- to 8-membered partially unsaturated cycle optionally containing 1 to 3 heteroatoms independently selected from O, S or N, and
    wherein this additional cycle is unsubstituted or substituted with 1 to 4 substituents independently selected from halogen, CN, oxo, OH, $CO_2H$, $CO_2$-$C_{1-4}$-alkyl, $CONHCH_2CO_2H$, $CONH(CH_2)_2SO_3H$, $C_{1-4}$-alkyl, halo-$C_{1-4}$-alkyl, O—$C_{1-4}$-alkyl and O-halo-$C_{1-4}$-alkyl;
wherein

has a substituent from above in 1,2-orientation regarding to the connection towards

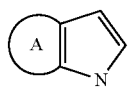

or has an annelated additional cycle in 1,2-orientation.

In an even more preferred embodiment in combination with any of the above or below embodiments

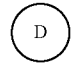

is selected from the group consisting

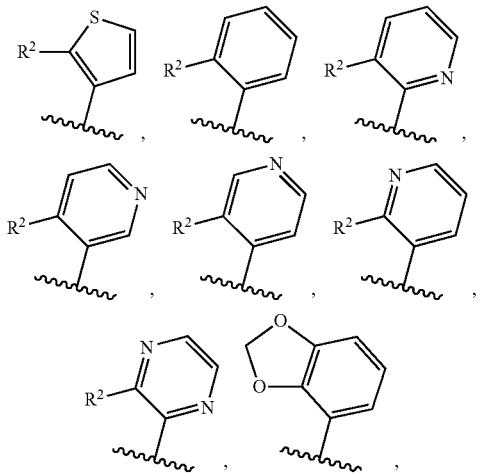

wherein
$R^2$ is selected from Me, F, Cl, CN, Me, CHO, $CHF_2$, $CF_3$, $SO_2Me$,

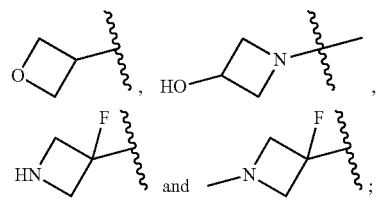

and
wherein

is not further substituted or further substituted with 1 to 2 substituents selected from the group consisting F, Cl, CN, Me, OMe, CHO, $CHF_2$ and $CF_3$.

In a most preferred embodiment in combination with any of the above or below embodiments

is selected from the group consisting of

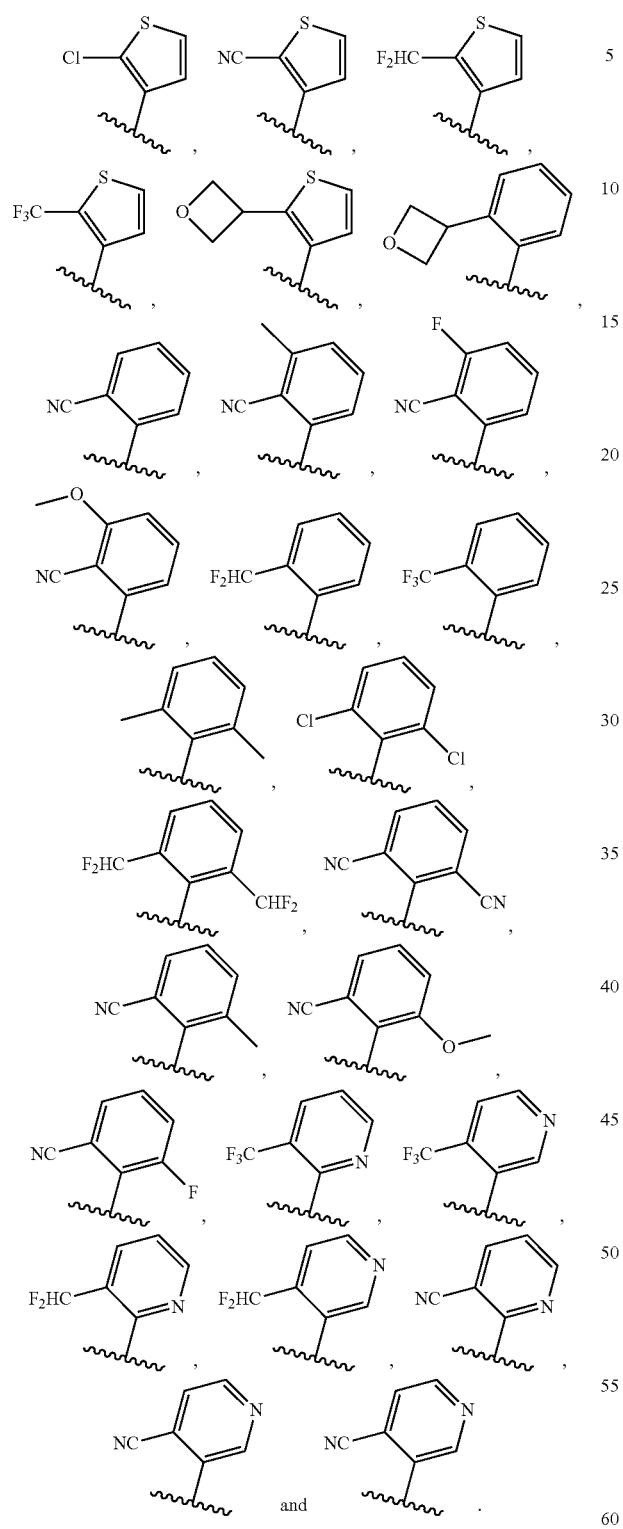

In a preferred embodiment in combination with any of the above or below embodiments Formula (I) contains a substituent selected from the group consisting of CO₂H, tetrazole, CONHSO₂Me and CONH(OH); and optionally the glycine and tauro conjugate thereof.

In a more preferred embodiment in combination with any of the above or below embodiments Formula (I) contains a carboxylic acid moiety and optionally the glycine and tauro conjugate thereof.

In a most preferred embodiment, the compound is selected from

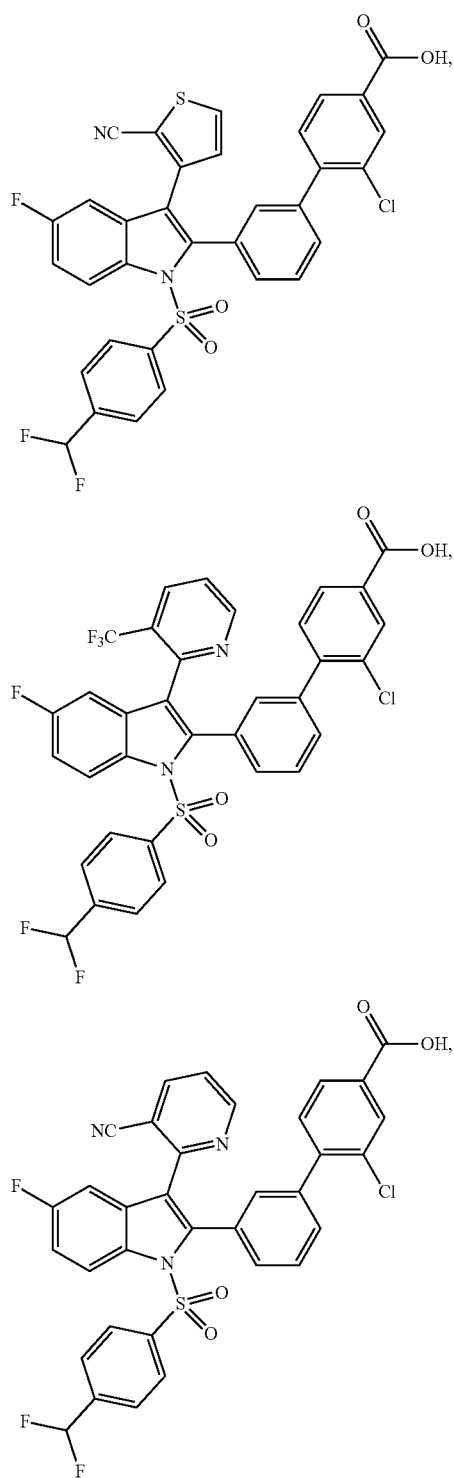

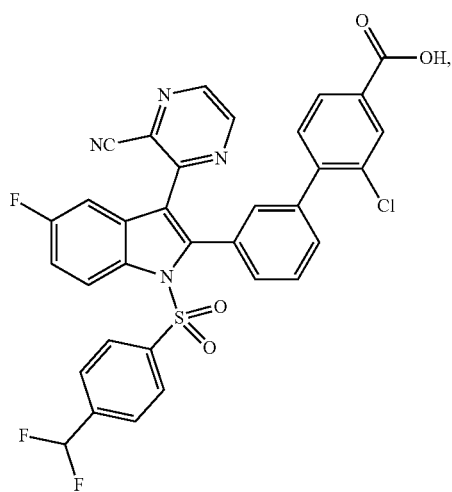
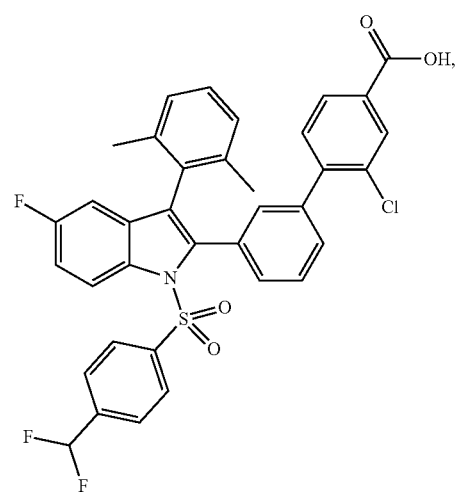
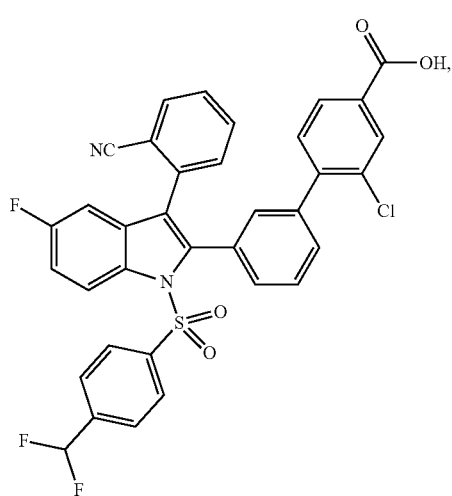
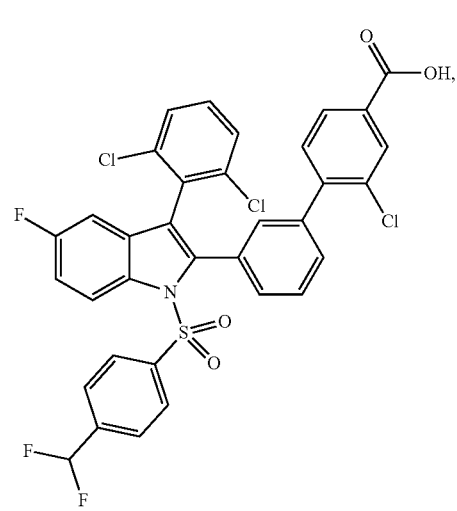
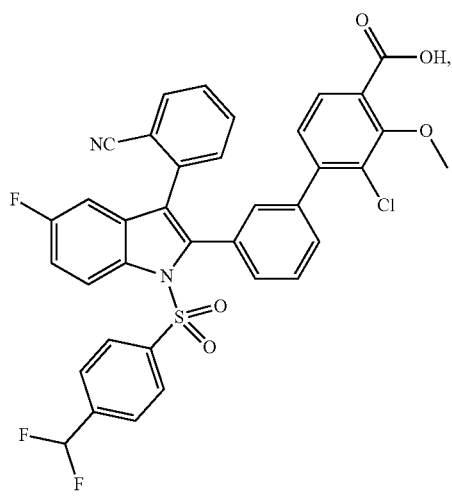
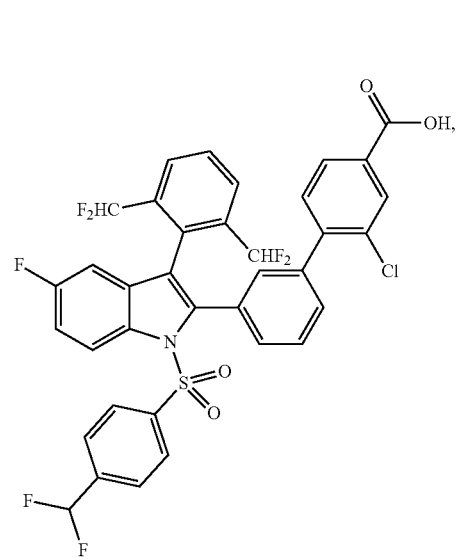

49
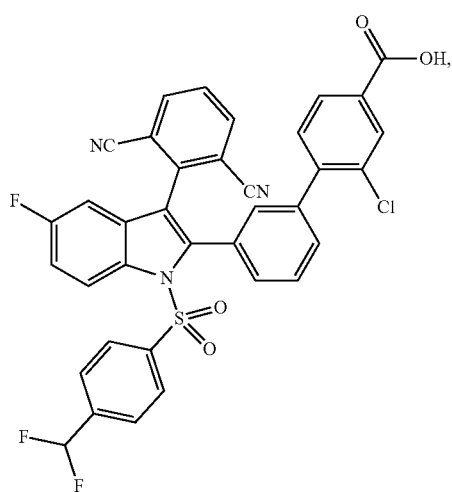
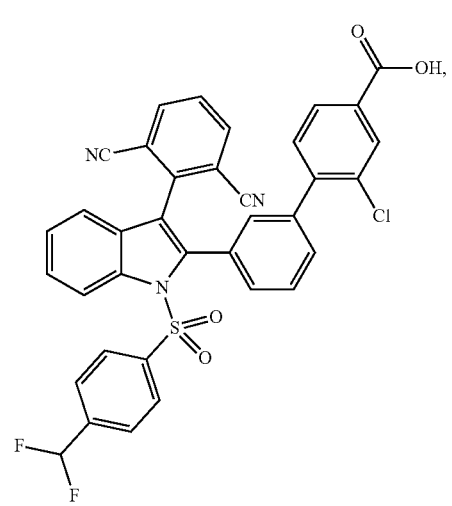
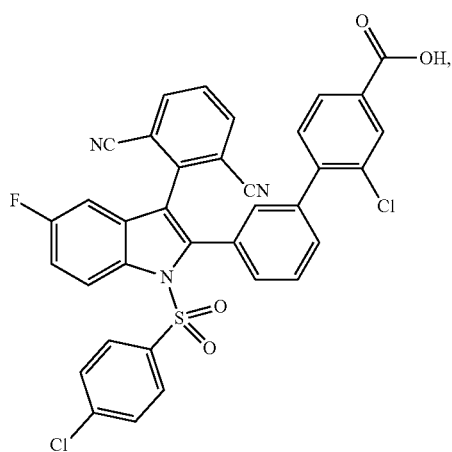
50
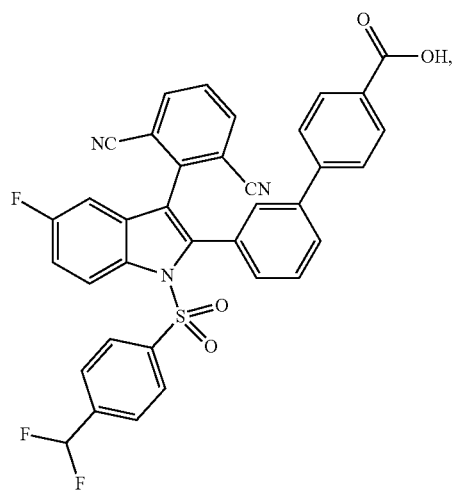
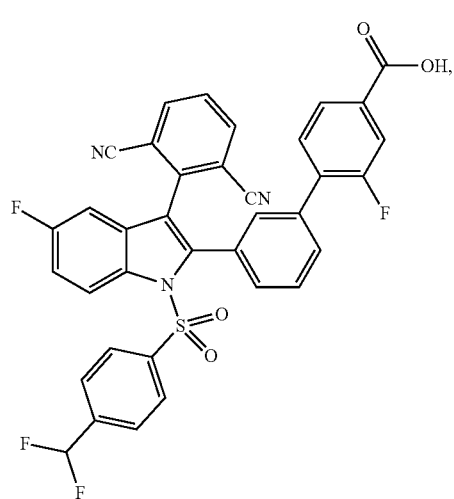
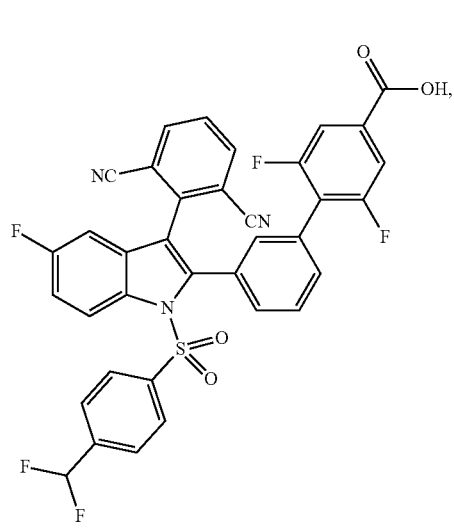

51
-continued
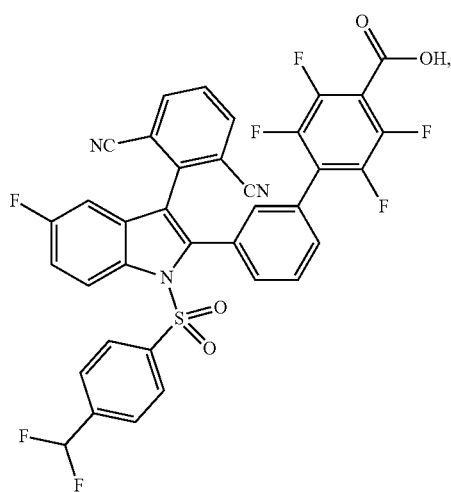
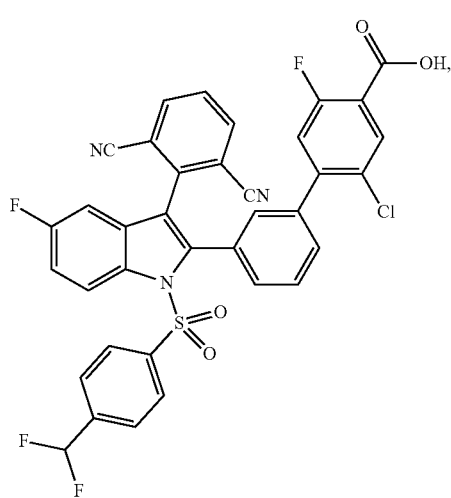
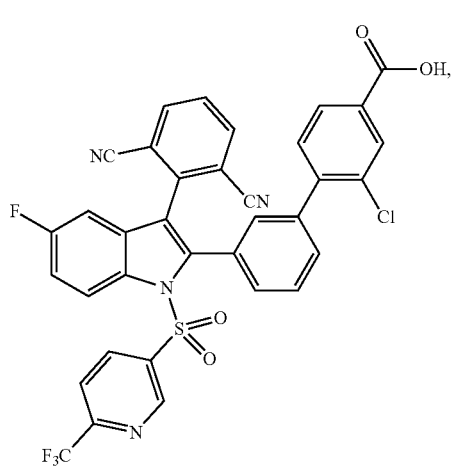
52
-continued
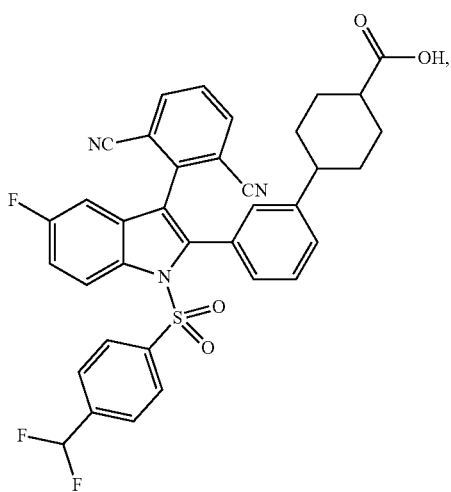
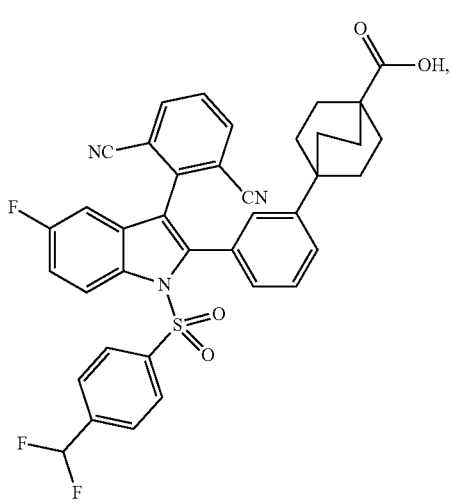
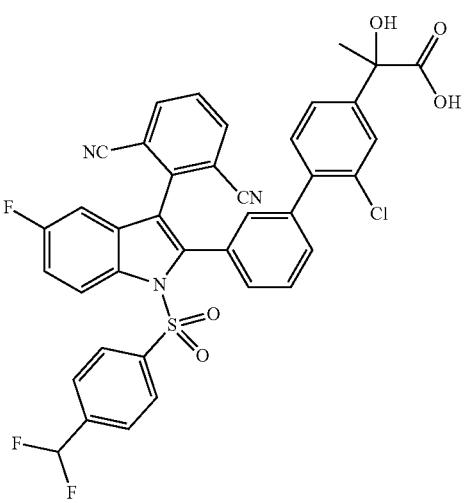 [SMILES: CC(O)(C(=O)O)c1cc(F)c(-c2cccc(-c3c(-c4c(C#N)cccc4C#N)c4cc(F)ccc4n3S(=O)(=O)c3ccc(C(F)F)cc3)c2)c(F)c1]
and

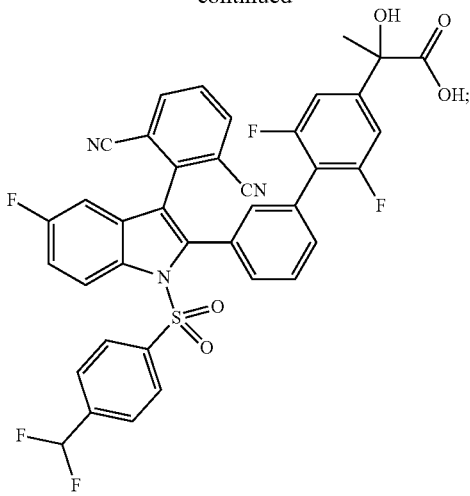

or a glycine conjugate or tauro conjugate thereof; and
an enantiomer, diastereomer, tautomer, N-oxide, solvate, prodrug and pharmaceutically acceptable salt thereof.

In an upmost preferred embodiment, the compound is 2-chloro-3'-(3-(2-cyanothiophen-3-yl)-1-((4-(difluoromethyl)phenyl)sulfonyl)-5-fluoro-1H-indol-2-yl)-[1,1'-biphenyl]-4-carboxylic acid or a glycine conjugate or tauro conjugate thereof and optionally a pharmaceutically acceptable salt thereof. Even more preferred is 2-chloro-3'-(3-(2-cyanothiophen-3-yl)-1-((4-(difluoromethyl)phenyl)sulfonyl)-5-fluoro-1H-indol-2-yl)-[1,1'-biphenyl]-4-carboxylic acid and optionally a pharmaceutically acceptable salt thereof.

In a similar upmost preferred embodiment, the compound is 2-chloro-3'-(3-(3-cyanopyrazin-2-yl)-1-((4-(difluoromethyl)phenyl)sulfonyl)-5-fluoro-1H-indol-2-yl)-[1,1'-biphenyl]-4-carboxylic acid or a glycine conjugate or tauro conjugate thereof and optionally a pharmaceutically acceptable salt thereof. Even more preferred is 2-chloro-3'-(3-(3-cyanopyrazin-2-yl)-1-((4-(difluoro-methyl)phenyl)sulfonyl)-5-fluoro-1H-indol-2-yl)-[1,1'-biphenyl]-4-carboxylic acid and optionally a pharmaceutically acceptable salt thereof.

In a similar upmost preferred embodiment, the compound is 2-chloro-3'-(3-(2-cyanophenyl)-1-((4-(difluoromethyl)phenyl)sulfonyl)-5-fluoro-1H-indol-2-yl)-[1,1'-biphenyl]-4-carboxylic acid or a glycine conjugate or tauro conjugate thereof and optionally a pharmaceutically acceptable salt thereof. Even more preferred is 2-chloro-3'-(3-(2-cyanophenyl)-1-((4-(difluoromethyl)phenyl)sulfonyl)-5-fluoro-1H-indol-2-yl)-[1,1'-biphenyl]-4-carboxylic acid and optionally a pharmaceutically acceptable salt thereof.

In a similar upmost preferred embodiment, the compound is 2-chloro-3'-(3-(2,6-dicyanophenyl)-1-((4-(difluoromethyl)phenyl)sulfonyl)-5-fluoro-1H-indol-2-yl)-[1,1'-biphenyl]-4-carboxylic acid or a glycine conjugate or tauro conjugate thereof and optionally a pharmaceutically acceptable salt thereof. Even more preferred is 2-chloro-3'-(3-(2,6-dicyanophenyl)-1-((4-(difluoromethyl)phenyl)sulfonyl)-5-fluoro-1H-indol-2-yl)-[1,1'-biphenyl]-4-carboxylic acid and optionally a pharmaceutically acceptable salt thereof.

In a similar upmost preferred embodiment, the compound is 3'-(3-(2,6-dicyanophenyl)-1-((4-(difluoromethyl)phenyl)sulfonyl)-5-fluoro-1H-indol-2-yl)-2,6-difluoro-[1,1'-biphenyl]-4-carboxylic acid or a glycine conjugate or tauro conjugate thereof and optionally a pharmaceutically acceptable salt thereof. Even more preferred is 3'-(3-(2,6-dicyanophenyl)-1-((4-(difluoromethyl)phenyl)sulfonyl)-5-fluoro-1H-indol-2-yl)-2,6-difluoro-[1,1'-biphenyl]-4-carboxylic acid and optionally a pharmaceutically acceptable salt thereof.

In a similar upmost preferred embodiment, the compound is 2-chloro-3'-(3-(2,6-dicyanophenyl)-1-((4-(difluoromethyl)phenyl)sulfonyl)-5-fluoro-1H-indol-2-yl)-5-fluoro-[1,1'-biphenyl]-4-carboxylic acid or a glycine conjugate or tauro conjugate thereof and optionally a pharmaceutically acceptable salt thereof. Even more preferred is 2-chloro-3'-(3-(2,6-dicyanophenyl)-1-((4-(difluoro-methyl)phenyl)sulfonyl)-5-fluoro-1H-indol-2-yl)-5-fluoro-[1,1'-biphenyl]-4-carboxylic acid and optionally a pharmaceutically acceptable salt thereof.

The invention also provides the compound of the invention for use as a medicament.

Also provided is the compound of the present invention for use in the prophylaxis and/or treatment of diseases amenable for treatment with LXR modulators.

Also provided is the compound of the invention for use in treating a LXR mediated disease selected from non-alcoholic fatty liver disease, non-alcoholic steatohepatitis, liver inflammation, liver fibrosis, obesity, insulin resistance, type II diabetes, familial hypercholesterolemia, hypercholesterolemia in nephrotic syndrome, metabolic syndrome, cardiac steatosis, cancer, viral myocarditis, hepatitis C virus infection or its complications, and unwanted side-effects of long-term glucocorticoid treatment in diseases such as rheumatoid arthritis, inflammatory bowel disease and asthma.

In a preferred embodiment, the disease is selected from non-alcoholic fatty liver disease, non-alcoholic steatohepatitis, liver inflammation, liver fibrosis, obesity, insulin resistance, type II diabetes, familial hypercholesterolemia, hypercholesterolemia in nephrotic syndrome, metabolic syndrome or cardiac steatosis.

In a similar preferred embodiment, the disease is cancer.

In a similar preferred embodiment, the disease is selected from viral myocarditis, hepatitis C virus infection or its complications.

The invention further relates to a method for preventing and/or treating diseases mediated by LXRs, the method comprising administering a compound of the present invention in an effective amount to a subject in need thereof.

More specifically, the invention relates to a method for preventing and treating diseases selected from non-alcoholic fatty liver disease, non-alcoholic steatohepatitis, liver inflammation, liver fibrosis, obesity, insulin resistance, type II diabetes, familial hypercholesterolemia, hypercholesterolemia in nephrotic syndrome, metabolic syndrome, cardiac steatosis, cancer, viral myocarditis, hepatitis C virus infection or its complications, and unwanted side-effects of long-term glucocorticoid treatment in diseases such as rheumatoid arthritis, inflammatory bowel disease and asthma.

Moreover, the invention also relates to the use of a compound according to the present invention in the preparation of a medicament for the prophylaxis and/or treatment of a LXR mediated disease.

More specifically, the invention relates to the use of a compound according to the present invention in the preparation of a medicament for the prophylaxis and/or treatment of a LXR mediated disease, wherein the disease is selected from non-alcoholic fatty liver disease, non-alcoholic steatohepatitis, liver inflammation, liver fibrosis, obesity, insulin resistance, type II diabetes, familial hypercholesterolemia, hypercholesterolemia in nephrotic syndrome, metabolic syndrome, cardiac steatosis, cancer, viral myocarditis, hepatitis C virus infection or its complications, and unwanted side-effects of long-term glucocorticoid treatment in diseases such as rheumatoid arthritis, inflammatory bowel disease and asthma.

Also provided is a pharmaceutical composition comprising the compound of the invention and a pharmaceutically acceptable carrier or excipient.

In the context of the present invention "$C_{1-6}$-alkyl" means a saturated alkyl chain having 1 to 6 carbon atoms which may be straight chained or branched. Examples thereof include methyl, ethyl, propyl, isopropyl, n-butyl, isobutyl, tert-butyl, n-pentyl, isopentyl, n-hexyl and isohexyl. Similarly, "$C_{1-4}$-alkyl" means a saturated alkyl chain having 1 to 4 carbon atoms which may be straight chained or branched. Examples thereof include methyl, ethyl, propyl, isopropyl, n-butyl, isobutyl, and tert-butyl.

The term "halo-$C_{1-4}$-alkyl" means that one or more hydrogen atoms in the alkyl chain are replaced by a halogen. A preferred example thereof is $CH_2F$, $CHF_2$ and $CF_3$.

A "$C_{0-6}$-alkylene" means that the respective group is divalent and connects the attached residue with the remaining part of the molecule. Moreover, in the context of the present invention, "$C_0$-alkylene" is meant to represent a bond, whereas $C_1$-alkylene means a methylene linker, $C_2$-alkylene means a ethylene linker or a methyl-substituted methylene linker and so on. In the context of the present invention, a $C_{0-6}$-alkylene preferably represents a bond, a methylene, a ethylene group or a propylene group.

Similarly, a "$C_{2-6}$-alkenylene" and a "$C_{2-6}$-alkinylene" means a divalent alkenyl or alkynyl group which connects two parts of the molecule.

A 3- to 10-membered cycloalkyl group means a saturated or partially unsaturated mono-, bi-, spiro- or multicyclic ring system comprising 3 to 10 carbon atoms. Examples include cyclopropyl, cyclobutyl, cyclopentyl, cyclohexyl, cyclohexenyl, bicyclo[2.2.2]octyl, bicyclo[3.2.1]octanyl, spiro[3.3]heptyl, bicyclo[2.2.1]heptyl, adamantyl and pentacyclo[4.2.0.0$^{2,5}$.0$^{3,8}$.0$^{4,7}$]octyl. Consequently, a 3- to 6-membered cycloalkyl group means a saturated or partially unsaturated mono- bi-, or spirocyclic ring system comprising 3 to 6 carbon atoms whereas a 5- to 8-membered cycloalkyl group means a saturated or partially unsaturated mono-, bi-, or spirocyclic ring system comprising 5 to 8 carbon atoms.

A 3- to 10-membered heterocycloalkyl group means a saturated or partially unsaturated 3 to 10 membered carbon mono-, bi-, spiro- or multicyclic ring wherein 1, 2, 3 or 4 carbon atoms are replaced by 1, 2, 3 or 4 heteroatoms, respectively, wherein the heteroatoms are independently selected from N, O, S, SO and $SO_2$. Examples thereof include epoxidyl, oxetanyl, pyrrolidinyl, tetrahydrofuranyl, piperidinyl, piperazinyl tetrahydropyranyl, 1,4-dioxanyl, morpholinyl, 4-quinuclidinyl, 1,4-dihydropyridinyl and 6-azabicyclo[3.2.1]octanyl. The heterocycloalkyl group can be connected with the remaining part of the molecule via a carbon, nitrogen (e.g. in morpholine or piperidine) or sulfur atom. An example for a S-linked heterocycloalkyl is the cyclic sulfonimidamide

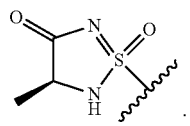

A 5- to 14-membered mono-, bi- or tricyclic heteroaromatic ring system (within the application also referred to as heteroaryl) means an aromatic ring system containing up to 6 heteroatoms independently selected from N, O, S, SO and $SO_2$. Examples of monocyclic heteroaromatic rings include pyrrolyl, imidazolyl, furanyl, thiophenyl (thienyl), pyridinyl, pyrimidinyl, pyrazinyl, pyrazolyl, oxazolyl, isoxazolyl, triazolyl, oxadiazolyl and thiadiazolyl. It further means a bicyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzofuranyl, benzoxazolyl, indolyl, indolizinyl 1,5-naphthyridinyl, 1,7-naphthyridinyl and pyrazolo[1,5-a]pyrimidinyl. Examples of tricyclic heteroaromatic rings include acridinyl, benzo[b][1,5]naphthyridinyl and pyrido[3,2-b][1,5]naphthyridinyl.

The nitrogen or sulphur atom of the heteroaryl system may also be optionally oxidized to the corresponding N-oxide, S-oxide or S,S-dioxide.

If not stated otherwise, the heteroaryl system can be connected via a carbon or nitrogen atom. Examples for N-linked heterocycles are

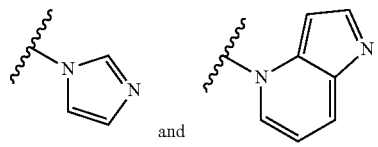

and

A 6- to 14-membered mono-, bi- or tricyclic aromatic ring system (within the application also referred to as aryl) means an aromatic carbon cycle such as phenyl, naphthyl, anthracenyl or phenanthrenyl.

The term "N-oxide" denotes compounds, where the nitrogen in the heteroaromatic system (preferably pyridinyl) is oxidized. Such compounds can be obtained in a known manner by reacting a compound of the present invention (such as in a pyridinyl group) with $H_2O_2$ or a peracid in an inert solvent.

Halogen is selected from fluorine, chlorine, bromine and iodine, more preferably fluorine or chlorine and most preferably fluorine.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C. are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds of Formula (I) in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula (I) when administered to a mammal, e.g. a human. See, for example, Foster in Trends Pharmacol. Sci. 1984:5; 524. Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Furthermore, the compounds of the present invention are partly subject to tautomerism. For example, if a heteroaromatic group containing a nitrogen atom in the ring is substituted with a hydroxy group on the carbon atom adjacent to the nitrogen atom, the following tautomerism can appear:

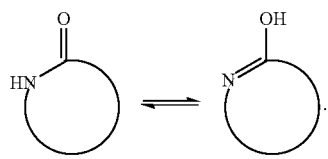

A cycloalkyl or heterocycloalkyl group can be connected straight or spirocyclic, e.g. when cyclohexane is substituted with the heterocycloalkyl group oxetane, the following structures are possible:

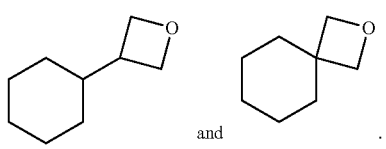 [SMILES: C1CCC(C2COC2)CC1 ; C1CCC2(CC1)COC2]

The term "1,3-orientation" means that on a ring the substituents have at least one possibility, where 3 atoms are between the two substituents attached to the ring system, e.g.

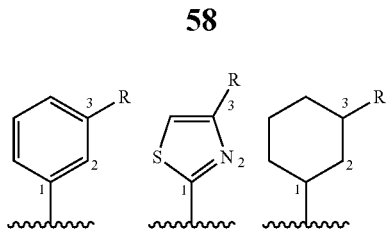

The term "1,2-orientation" (ortho) means that on a ring the substituents have one possibility, where 2 atoms are between the two substituents attached to the ring system, e.g.

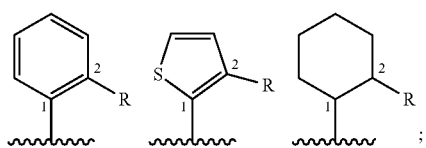

alternatively the residue R can be incorporated in an annelated additional cycle, e.g.

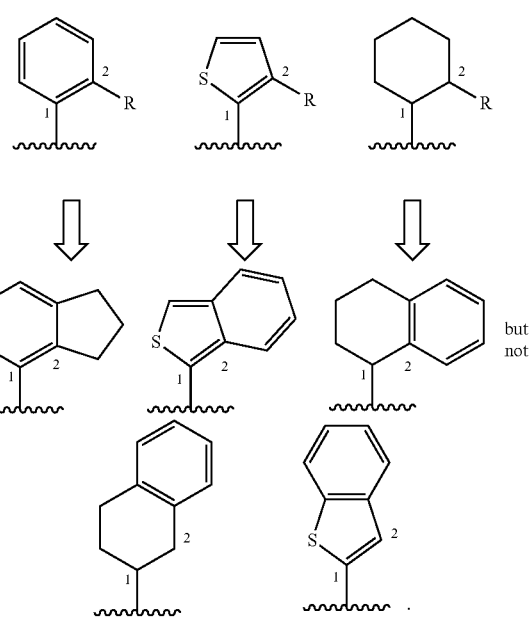

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

The compounds of the present invention can be in the form of a prodrug compound. "Prodrug compound" means a derivative that is converted into a compound according to the present invention by a reaction with an enzyme, gastric acid or the like under a physiological condition in the living body, e.g. by oxidation, reduction, hydrolysis or the like, each of which is carried out enzymatically.

Examples of the prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods. Other examples of the prodrug are compounds (referred to as "ester prodrug" in the application, wherein the carboxylate in a compound of the present invention is, for example, converted into an alkyl-, aryl-, arylalkylene-, amino-, choline-, acyloxyalkyl-, 1-((alkoxycarbonyl)oxy)-2-alkyl, or linolenoyl-ester. Exemplary structures for prodrugs of carboxylic acids are prodrugs:

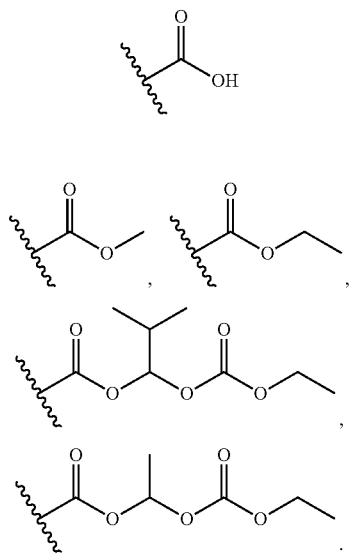

A ester prodrug can also be formed, when a carboxylic acid forms a lactone with a hydroxy group from the molecule. An exemplary example is prodrug:

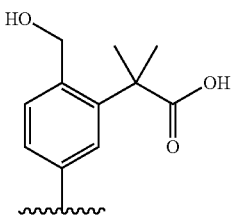

The term "—CO$_2$H or an ester thereof" means that the carboxylic acid and the alkyl esters are intended, e.g.

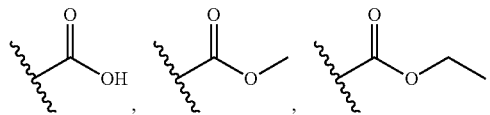

The term "glycine conjugate or tauro conjugate thereof" means, that the carboxylic acid moiety in the molecule is connected with glycine or taurine, respectively, to form the conjugate (and potentially a prodrug, solvate or pharmaceutically acceptable salt thereof):

conjugates:

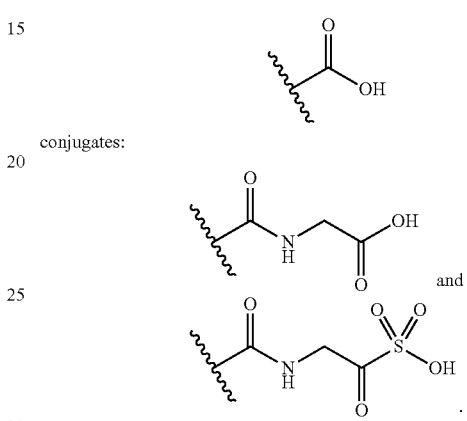

Metabolites of compounds of the present invention are also within the scope of the present invention.

Where tautomerism, like e.g. keto-enol tautomerism, of compounds of the present invention or their prodrugs may occur, the individual forms, like e.g. the keto and enol form, are each within the scope of the invention as well as their mixtures in any ratio. Same applies for stereoisomers, like e.g. enantiomers, cis/trans-isomers, atropisomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials. Another way to obtain pure enantiomers from racemic mixtures would use enantioselective crystallization with chiral counterions.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present on these groups and can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Further the compounds of the present invention may be present in the form of solvates, such as those which include as solvate water, or pharmaceutically acceptable solvates, such as alcohols, in particular ethanol.

Furthermore, the present invention provides pharmaceutical compositions comprising at least one compound of the present invention, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier.

The pharmaceutical composition of the present invention may additionally comprise one or more other compounds as active ingredients like a prodrug compound or other nuclear receptor modulators.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

The compounds of the present invention act as LXR modulators.

Ligands to nuclear receptors including LXR ligands can either act as agonists, antagonists or inverse agonists. An agonist in this context means a small molecule ligand that binds to the receptor and stimulates its transcriptional activity as determined by e.g. an increase of mRNAs or proteins that are transcribed under control of an LXR response element. Transcriptional activity can also be determined in biochemical or cellular in vitro assays that employ just the ligand binding domain of LXRα or LXRβ but use the interaction with a cofactor (i.e. a corepressor or a coactivator), potentially in conjunction with a generic DNA-binding element such as the Gal4 domain, to monitor agonistic, antagonistic or inverse agonistic activity.

Whereas an agonist by this definition stimulates LXR- or LXR-Gal4-driven transcriptional activity, an antagonist is defined as a small molecule that binds to LXRs and thereby inhibits transcriptional activation that would otherwise occur through an endogenous LXR ligand.

An inverse agonist differs from an antagonist in that it not only binds to LXRs and inhibits transcriptional activity but in that it actively shuts down transcription directed by LXR, even in the absence of an endogenous agonist. Whereas it is difficult to differentiate between LXR antagonistic and inverse agonistic activity in vivo, given that there are always some levels of endogenous LXR agonist present, biochemical or cellular reporter assays can more clearly distinguish between the two activities. At a molecular level an inverse agonist does not allow for the recruitment of a coactivator protein or active parts thereof whereas it should lead to an active recruitment of corepressor proteins are active parts thereof. An LXR antagonist in this context would be defined as an LXR ligand that neither leads to coactivator nor to corepressor recruitment but acts just through displacing LXR agonists. Therefore, the use of assays such as the Gal4-mammalian-two-hybrid assay is mandatory in order to differentiate between coactivator or corepressor-recruiting LXR compounds (Kremoser et al., Drug Discov. Today 2007; 12:860; Gronemeyer et al., Nat. Rev. Drug Discov. 2004; 3:950).

Since the boundaries between LXR agonists, LXR antagonists and LXR inverse agonists are not sharp but fluent, the term "LXR modulator" was coined to encompass all compounds which are not clean LXR agonists but show a certain degree of corepressor recruitment in conjunction with a reduced LXR transcriptional activity. LXR modulators therefore encompass LXR antagonists and LXR inverse agonists and it should be noted that even a weak LXR agonist can act as an LXR antagonist if it prevents a full agonist from full transcriptional activation.

FIG. 1 illustrates the differences between LXR agonists, antagonists and inverse agonists exemplified by their different capabilities to recruit coactivators or corepressors. In FIG. 1, NcoR is a corepressor and NcoA is a coactivator.

The compounds are useful for the prophylaxis and/or treatment of diseases which are mediated by LXRs. Preferred diseases are all disorders associated with steatosis, i.e. tissue fat accumulation. Such diseases encompass the full spectrum of non-alcoholic fatty liver disease including non-alcoholic steatohepatitis, liver inflammation and liver fibrosis, furthermore insulin resistance, metabolic syndrome and cardiac steatosis. An LXR modulator based medicine might also be useful for the treatment of hepatitis C virus infection or its complications and for the prevention of unwanted side-effects of long-term glucocorticoid treatment in diseases such as rheumatoid arthritis, inflammatory bowel disease and asthma.

A different set of applications for LXR modulators might be in the treatment of cancer. LXR antagonists or inverse agonists might useful to counteract the so-called Warburg effect which is associated with a transition from normal differentiated cells towards cancer cells (see Liberti et al., Trends Biochem. Sci. 2016; 41:211; Ward & Thompson, Cancer Cell 2012; 21:297-308). Furthermore, LXR is known to modulate various components of the innate and adaptive immune system. Oxysterols, which are known as endogenous LXR agonists were identified as mediators of an LXR-dependent immunosuppressive effect found in the tumor microenvironment (Traversari et al., Eur. J. Immunol. 2014; 44: 1896). Therefore, it is reasonable to assume that LXR antagonists or inverse agonists might be capable of stimulating the immune system and antigen-presenting cells, in particular, to elicit an anti-tumor immune response. The latter effects of LXR antagonists or inverse agonists might be used for a treatment of late stage cancer, in general, and in particular for those types of cancerous solid tumors that show a poor immune response and highly elevated signs of Warburg metabolism.

In more detail, anti-cancer activity of the LXR inverse agonist SR9243 was shown to be mediated by interfering with the Warburg effect and lipogenesis in different tumor cells in vitro and SW620 colon tumor cells in athymic mice in vivo (see Flaveny et al. Cancer Cell. 2015; 28:42; Steffensen, Cancer Cell 2015; 28:3).

Therefore, LXR modulators (preferably LXR inverse agonists) may by useful for the treatment of Warburg-dependent cancers.

LXR modulators (preferably LXR inverse agonists) may counteract the diabetogenic effects of glucocorticoids without compromising the anti-inflammatory effects of glucocorticoids and could therefore be used to prevent unwanted side-effects of long-term glucocorticoid treatment in diseases such as rheumatoid arthritis, inflammatory bowel disease and asthma (Patel et al. Endocrinology 2017:158: 1034).

LXR modulators (preferably LXR inverse agonists) may be useful for the treatment of hepatitis C virus mediated liver steatosis (see Garcia-Mediavilla et al. Lab. Invest. 2012; 92:1191).

LXR modulators (preferably LXR inverse agonists) may be useful for the treatment of viral myocarditis (see Papageorgiou et al. Cardiovasc. Res. 2015; 107:78).

LXR modulators (preferably LXR inverse agonists) may be useful for the treatment of insulin resistance (see Zheng et al. PLOS One 2014; 9:e101269).

LXR modulators (preferably LXR inverse agonists) may be useful for the treatment of familial hypercholesterolemia (see Zhou et al. J. Biol. Chem. 2008; 283:2129).

LXR modulators (preferably LXR inverse agonists) may be useful for the treatment of hypercholesterolemia in nephrotic syndrome (see Liu & Vazizi in Nephrol. Dial. Transplant. 2014; 29:538).

EXPERIMENTAL SECTION

The compounds of the present invention can be prepared by a combination of methods known in the art including the procedures described in Schemes I to V below.

The synthetic route depicted in Scheme I starts with the preparation of alkynes I-c by Sonogashira couplings. Subsequently, the free amino group of I-c is reacted with sulfonyl chlorides I-d in the presence of an appropriate base and appropriate solvent to afford alkynesulfonamides I-e. I-e undergoes cyclization and concomitant reaction with aromatic halides I-f in the presence of appropriate catalyst (e.g. Pd-catalysts), appropriate solvent and temperature to afford compounds of the present invention (I). Further manipulation of functional groups present in $R^1$ by standard methods, known to persons skilled in the art (e.g. ester hydrolysis, amide bond formation), can give rise to further compounds of the present invention. Alternatively, alkyneamine I-c can be transformed into alkynetrifluoroacetamides I-g which can also undergo aforementioned cyclization and concomitant reaction with aromatic halides I-f to afford intermediates I-h with an unsubstituted NH. Reaction with sulfonyl chlorides I-d in the presence of an appropriate base and appropriate solvent also affords compounds of Formula (I).

Scheme I: Synthesis of compounds of the present invention.

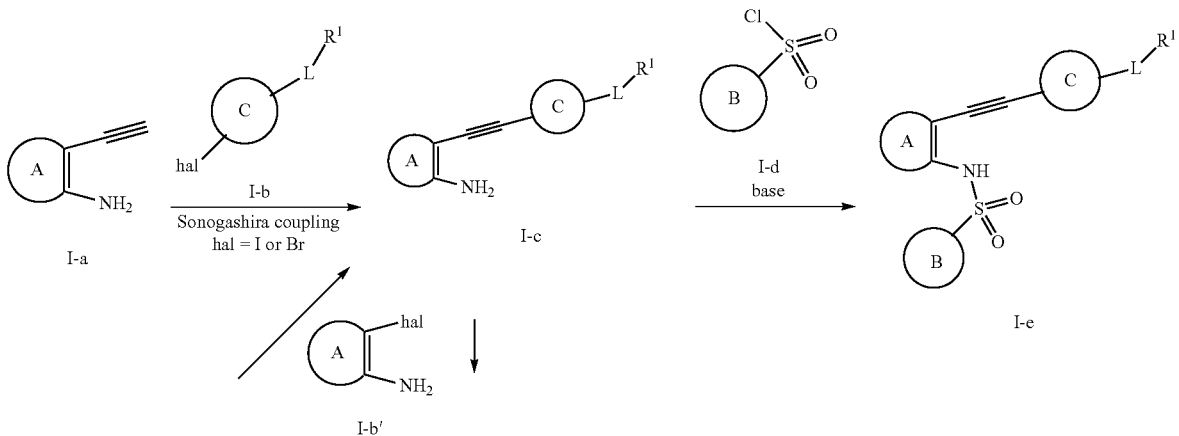

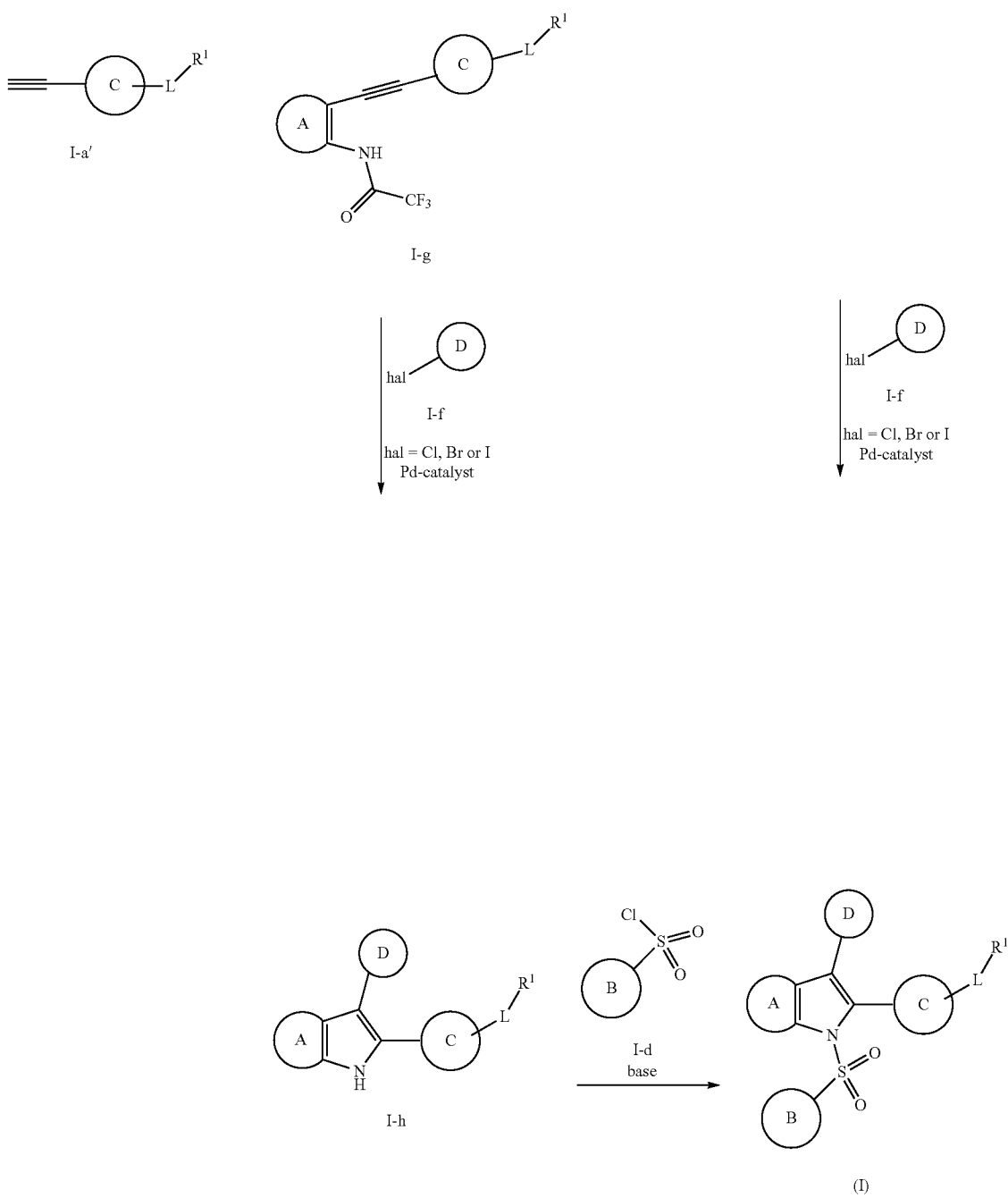

A variation of the routes shown in Scheme I is shown in Scheme II. Alkynesulfonamide I-e is reacted in the presence of NIS to afford iodinated intermediates II-b which can be substrates for Suzuki couplings to afford compounds (I). Alternatively, cyclization of alkynesulfonamide I-e in the presence of appropriate catalyst (e.g. Pd-catalysts), appropriate solvent and temperature but without the presence of halides I-f afford 3-unsubstituted intermediates II-d. Reactions with NBS afford brominated intermediates II-e which are likewise substrates for Suzuki coupling reactions to afford compounds of Formula (I).

Scheme II: Synthetic route for compounds of the present invetntion, with introduction of moiety D via Suzuki coupling.

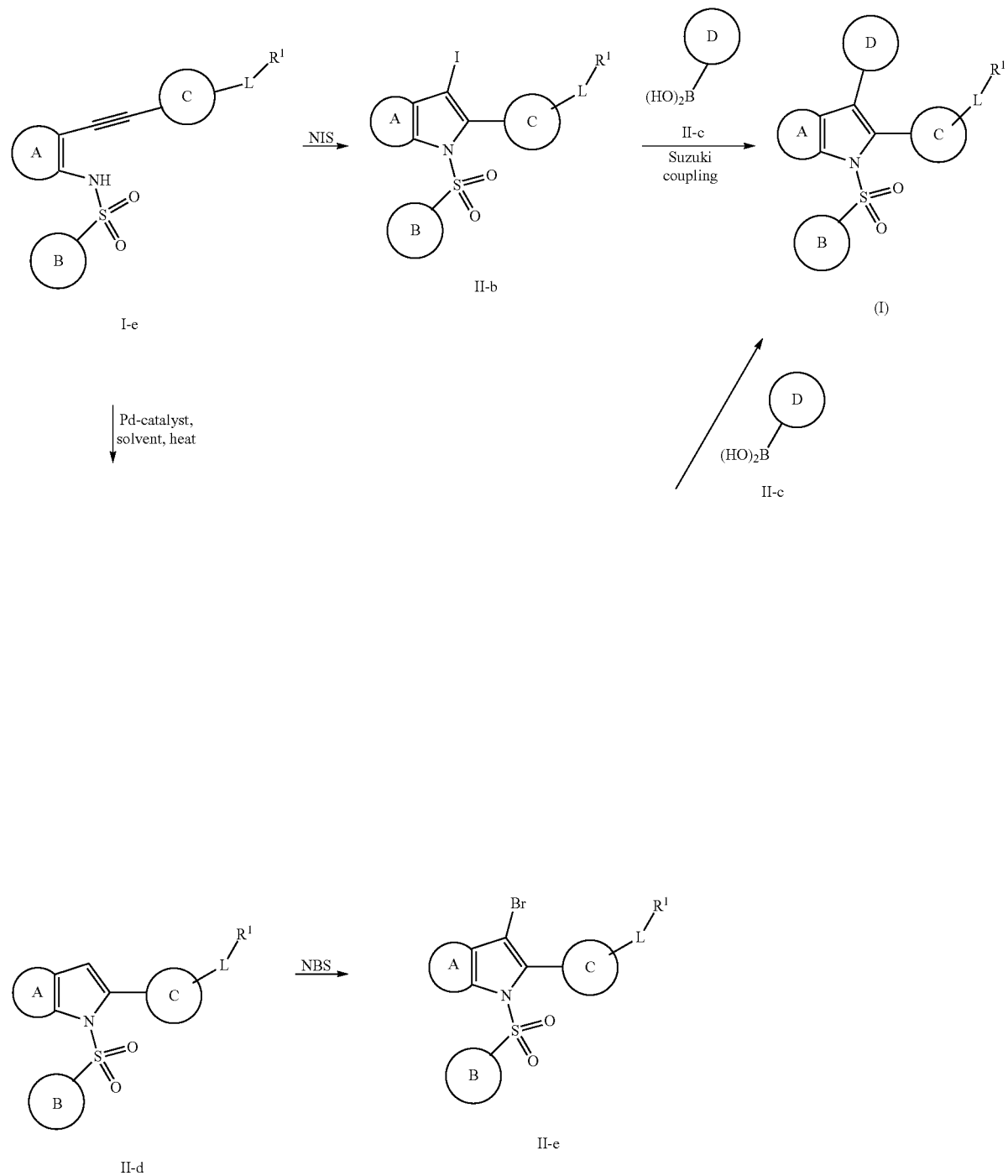

A further variation of the synthetic route depicted in Schemes I and II is shown in Scheme III. In the presence of B₂Pin₂, appropriate catalyst (e.g. Pd-catalysts), appropriate solvent, additives and temperature, intermediates I-e can undergo cyclization and concomitant formation of 3-pinacolyl boronic esters III-b. These can be substrates for Suzuki coupling reactions to afford compounds of the present invention with Formula (I).

Scheme III: Alternative synthetic route for compounds of the present invention, with introduction of D via Suzuki coupling.

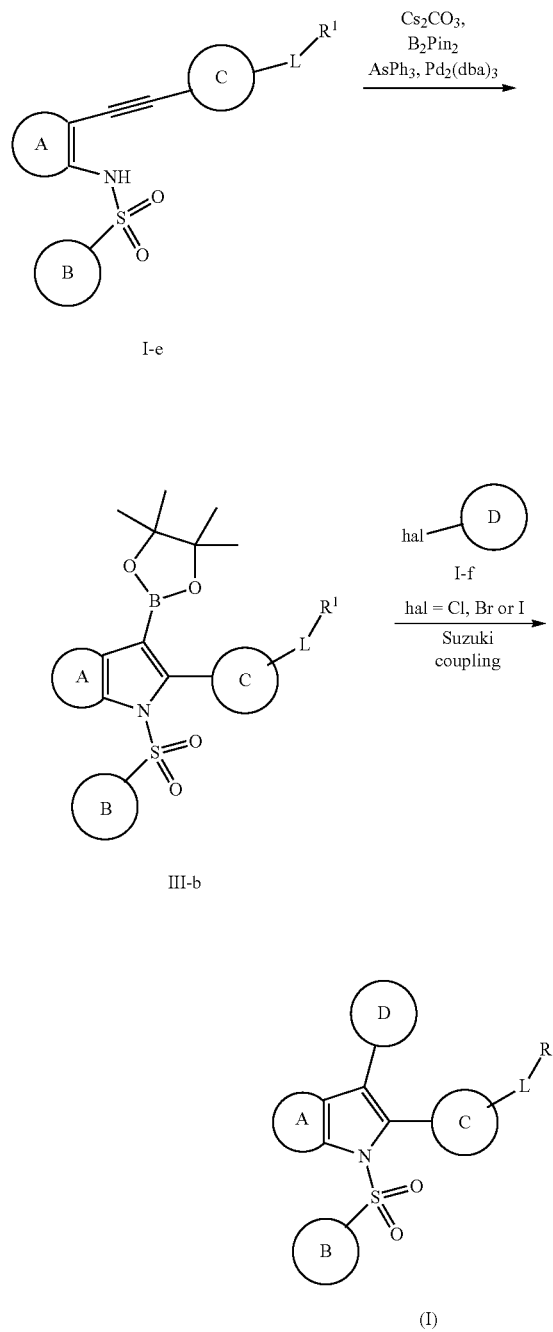

Scheme IV: Synthetic route for compounds of the present invention, with final introduction of —L—R¹ via Suzuki coupling.

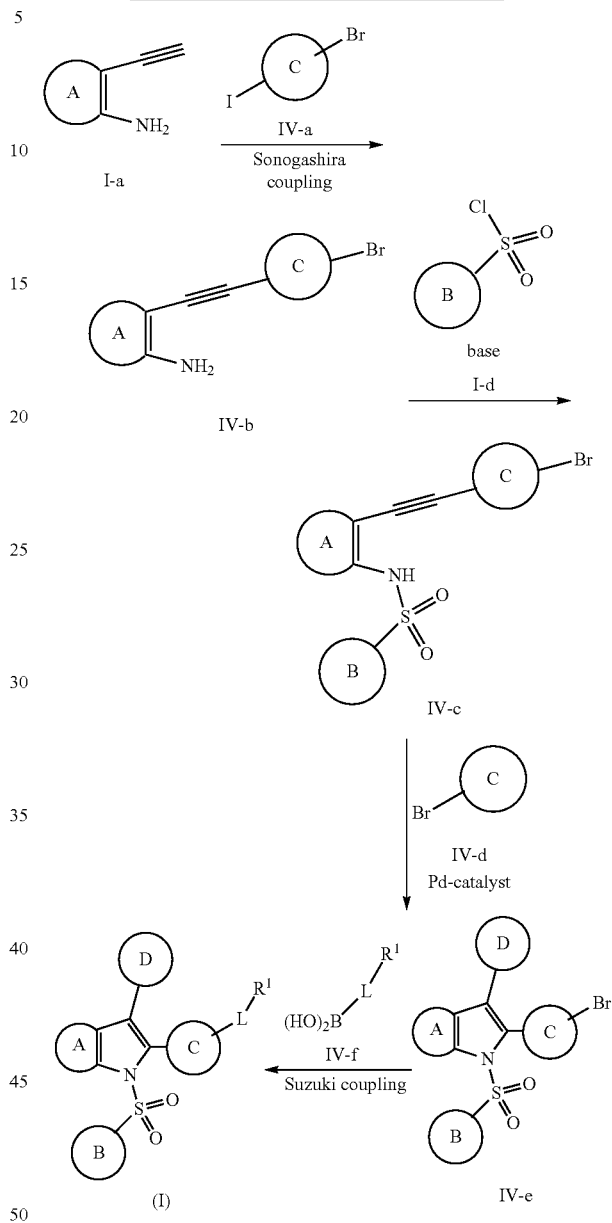

In Scheme IV is depicted a synthetic route for the late stage introduction of the right hand side moieties -L-R¹ to the compounds of the present invention. Sonogashira coupling of I-a with bromo-iodo-aromatics IV-a afford bromo-alkyneamines IV-b which can be transformed to sulfonamides IV-c. These can undergo cyclization and concomitant reaction with aromatic bromides IV-d in the presence of appropriate catalysts (e.g. Pd-catalysts), appropriate solvent and temperature to afford advanced intermediates IV-e with a bromo substituent on ring C. Finally, intermediates IV-e can be used as substrates for Suzuki couplings to afford compounds of Formula (I).

In Scheme V are summarized the synthetic routes for the preparation of the compounds of the present invention starting from the preformed central pyrrolo-annelated bicyclic aromatic. N-protected 2-pinacolyl boronic esters V-a can undergo Suzuki coupling with halides V-b to afford intermediates V-c. After bromination with NBS the 3-bromo intermediates V-d are obtained, which, after a second Suzuki coupling, are converted to N-protected advanced intermediates V-e. When starting with N-protected 3-pinacolyl boronic esters V-a, first Suzuki coupling and then bromination of the 2-position and subsequent second Suzuki coupling affords likewise intermediates V-e. After deprotection and reaction of the free NH with sulfonyl chlorides I-d, in the presence of an appropriate base and solvent, compounds (I) are obtained.

Scheme V: Synthesis of compounds of the present invention, starting from preformed core aromatic.

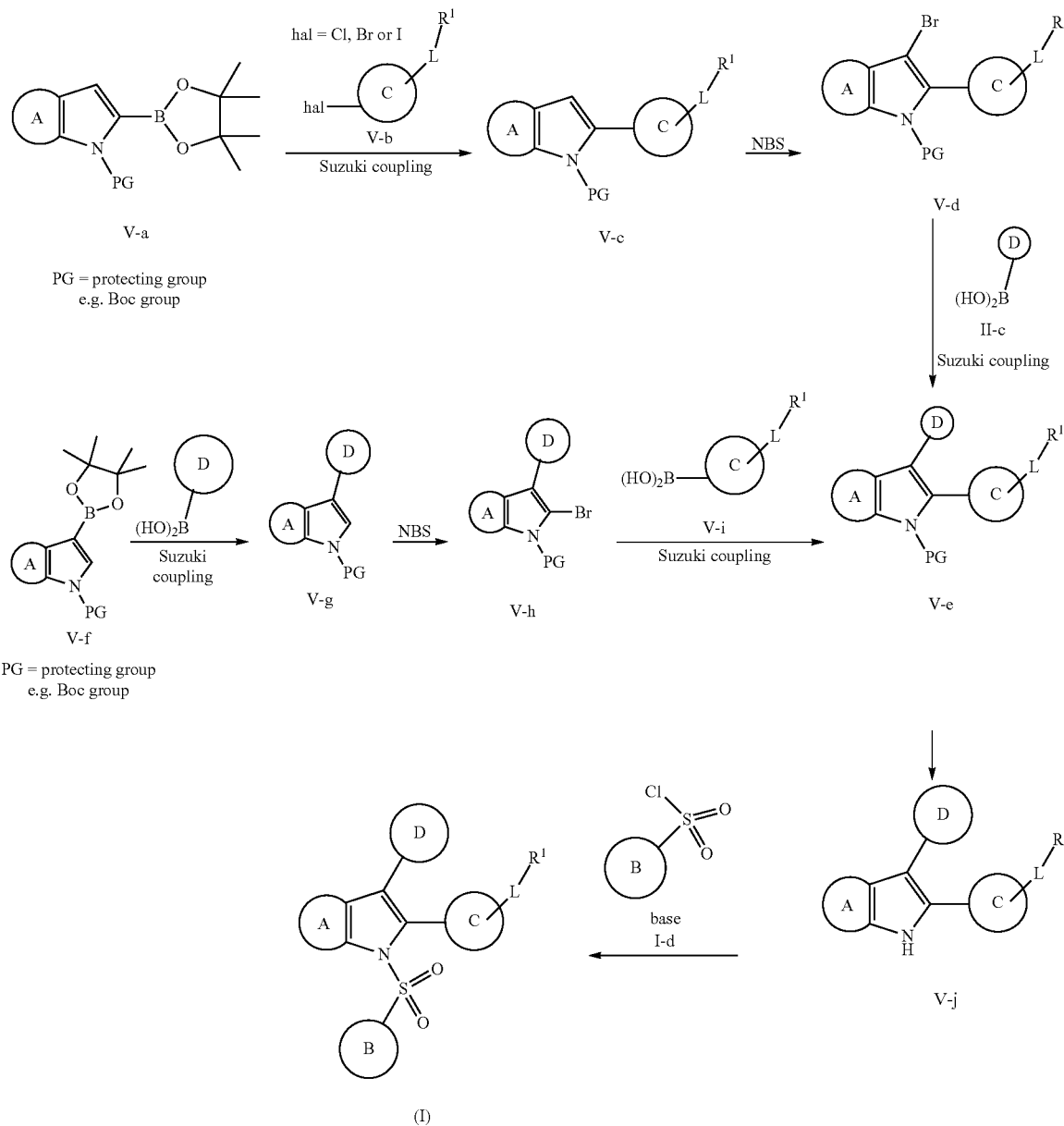

Abbreviations

Ac acetyl
ACN acetonitrile
AIBN azobisisobutyronitrile
aq. aqueous
BINAP (2,2'-bis(diphenylphosphino)-1,1'-binaphthyl)
$B_2Pin_2$ 4,4,4',4',5,5,5',5'-octamethyl-2,2'-bi-1,3,2-dioxaborolane
Boc tert-butyloxycarbonyl
BPO dibenzoyl peroxide
m-CPBA meta-chloroperbenzoic acid
Cy cyclohexyl
DAST diethylaminosulfur trifluoride
dba dibenzylideneacetone
DBU 1,8-diazabicyclo[5.4.0]undec-7-ene
DCM dichloromethane
DEA diethanolamine
DEAD diethyl azodicarboxylate
DIEA or DIPEA diisopropylethylamine
DMAP 4-N,N-dimethylaminopyridine
N,N-dimethylformamide DMF
dppf 1,1'-bis(diphenylphosphino)ferrocene
EA ethyl acetate
EDCI 1-ethyl-3-(3-dimethylaminopropyl)carbodiimide
FCC flash column chromatography on silica gel
h hour(s)
HATU O-(7-azabenzotriazole-1-yl)-N,N,N',N'-tetramethyluronium hexafluorophosphate
HOBt hydroxybenzotriazole IBX 2-iodoxybenzoic acid
LDA lithium diisopropylamide
LiHMDS lithium bis(trimethylsilyl)amide
NBS N-bromosuccinimide
NIS N-iodosuccinimide
pinacolato (OCMe$_2$CMe$_2$O) Pin
PE petroleum ether
prep preparative
sat. saturated (aqueous)
Sphos 2-dicyclohexylphosphino-2',6'-dimethoxybiphenyl
TBAF tetra-n-butylammonium fluoride
TEA triethylamine
TFA trifluoroacetic acid
TFAA trifluoroacetic acid anhydride
THF tetrahydrofuran
TLC thin layer chromatography
Tr Trityl
Xantphos 4,5-bis(diphenylphosphino)-9,9-dimethylxanthene
XPhos 2-dicyclohexylphosphino-2',4',6'-triisopropylbiphenyl Preparative Example P1

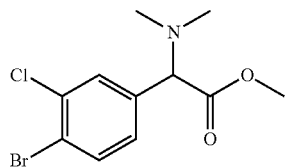

P1

Methyl 2-(4-bromo-3-chlorophenyl)-2-(dimethylamino)acetate (P1)

To a solution of methyl 2-amino-2-(4-bromo-3-chlorophenyl)acetate (300 mg, 1.08 mmol) in MeOH (6 mL) was added CH$_2$O (37 wt. % in H$_2$O; 0.5 mL) and HCOOH (2.0 mL). The mixture was stirred at rt for 30 min, then NaBH(OAc)$_3$ (572 mg, 2.7 mmol) was added. The mixture was stirred at rt for 2 h, diluted with EA (150 mL) and washed with water (15 mL), sat. NaHCO$_3$ (15 mL) and brine (10 mL). The organic layer was dried over Na$_2$SO$_4$, filtered, concentrated and purified by prep-TLC (EA:PE=1:4) to afford compound P1 as a colorless oil.

Preparative Example P2

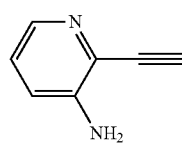

P2

Step 1: 2-((Trimethylsilyl)ethynyl)pyridin-3-amine (P2a)

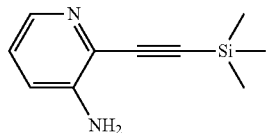

P2a

Pd(PPh$_3$)$_4$ (993 mg, 0.86 mmol), CuI (164 mg, 0.86 mmol) and PPh$_3$ (225 mg, 0.86 mmol) were combined in a round-bottom flask, then degassed and refilled with N$_2$ three times. To the mixture was added TEA (43 mL), 2-bromopyridin-3-amine (1.49 g, 8.59 mmol) and ethynyltrimethylsilane (2.43 mL, 18.0 mmol). The mixture was stirred at 60° C. for 6 h, cooled to rt, filtered through Celite and washed with EA (40 mL). The filtrate was concentrated to give compound P2a as a black solid, which was used in the next step without further purification.

Step 2: 2-Ethynylpyridin-3-amine (P2)

To a solution of compound P2a (2.16 g, 8.59 mmol) in THF (26 mL) was added TBAF (26 mL, 1M in THF, 26 mmol) and the mixture was stirred at rt for 3 h, concentrated and purified by FCC (EA/PE=1:19 to 1:0) to give compound P2 as a white solid.

Preparative Example P2/1 to P2/9

The following Preparative Examples were prepared similar as described for Preparative Example P2 using the appropriate building blocks.

| # | building block | structure |
|---|---|---|
| P2/1 | 4-bromopyridin-3-amine | 4-ethynylpyridin-3-amine |
| P2/2 | 3-bromopyridin-2-amine | 3-ethynylpyridin-2-amine |
| P2/3 | 2-bromothiophen-3-amine | 2-ethynylthiophen-3-amine |
| P2/4 | 2-bromo-4-fluoro-5-chloroaniline | 4-fluoro-5-chloro-2-ethynylaniline |

-continued

| # | building block | structure |
|---|---|---|
| P2/5 | 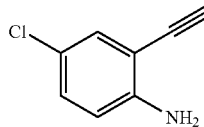 | 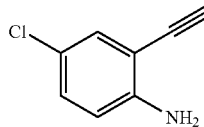 |
| P2/6 | | 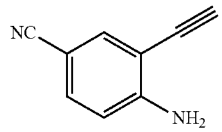 |
| P2/7 | | 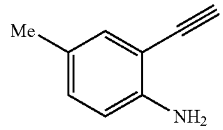 |
| P2/8 | | 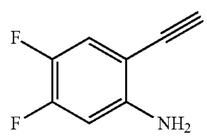 |
| P2/9 | | 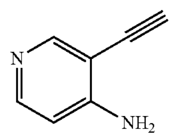 |

Preparative Example P3

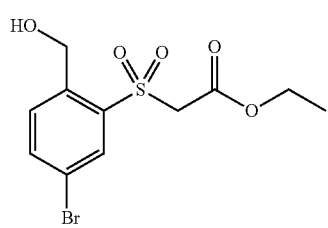

Step 1: (4-Bromo-2-mercaptophenyl)methanol (P32)

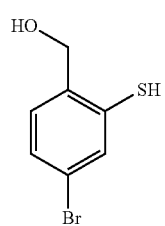

To a solution of 4-bromo-2-mercaptobenzoic acid (1.5 g, 6.5 mmol) in THF (30 mL) was added BH$_3$ (13 mL, 1M in THF). This mixture was stirred overnight and quenched with water (30 mL) and diluted with EA (20 mL). The organic layer was separated and the aq. layer was washed with EA (3×20 mL). The combined organic layer was washed with brine (30 mL), dried over Na$_2$SO$_4$, filtered and concentrated. The yellow solid was used in the next step without purification.

Step 2: Ethyl 2-((5-bromo-2-(hydroxymethyl)phenyl)thio)acetate (P3b)

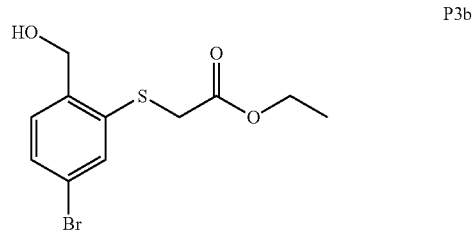 [SMILES: CCOC(=O)CSc1cc(Br)ccc1CO]

To a mixture of compound P3a (436 mg, 2.0 mmol) and ethyl 2-bromoacetate (306 mg, 2.0 mmol) in DMF (10 mL) was added Cs$_2$CO$_3$ (2.0 g, 6.0 mmol). The mixture was stirred at rt overnight, diluted with water (100 mL) and extracted with EA (3×30 mL). The combined organic layer was washed with brine (30 mL), dried over Na$_2$SO$_4$, filtered, concentrated and purified by FCC (PE:EA=5:1) to afford compound P3b as a white solid.

Step 3: Ethyl 2-((5-bromo-2-(hydroxymethyl)phenyl) sulfonyl)acetate (P3)

To a stirred solution of compound P3b (290 mg, 1.0 mmol) in DCM (5 mL) at 0° C. was added m-CPBA (610 mg, 3.0 mmol, 85%) and the resulting mixture was stirred at rt for 16 h, diluted with aq. sat. NaHCO$_3$ solution and extracted with EA (3×20 mL). The combined organic layer was dried over Na$_2$SO$_4$, filtered, concentrated and purified by FCC (PE:EA=5:1) to afford compound P3 as a white solid.

Preparative Example P3-1

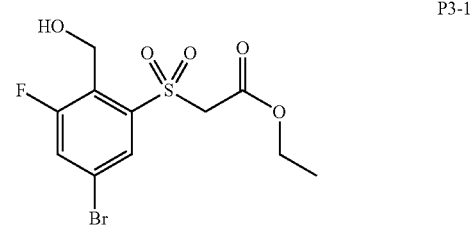 [SMILES: CCOC(=O)CS(=O)(=O)c1cc(Br)cc(F)c1CO]

Step 1: 4-Bromo-2-((2-ethoxy-2-oxoethyl)thio)-6-fluorobenzoic Acid (P3-1a)

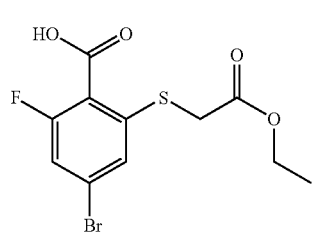

P3-1a

To a mixture of 4-bromo-2,6-difluorobenzoic acid (10.0 g, 42.4 mmol) and ethyl 2-mercaptoacetate (5.10 g, 42.4 mmol) in DMF (100 mL) was added $Cs_2CO_3$ (41.5 g, 127 mmol) and the mixture was stirred at 80° C. overnight, diluted with water (1 L) and adjusted to pH=3 with 2M HCl and extracted with EA (3×300 mL). The combined organic layer was washed with brine (300 mL), dried over $Na_2SO_4$, filtered, concentrated and purified by FCC (PE:EA=1:1) to give compound P3-1a as a yellow oil.

Step 2: Ethyl 2-((5-bromo-3-fluoro-2-(hydroxymethyl)phenyl)thio)acetate (P3-1b)

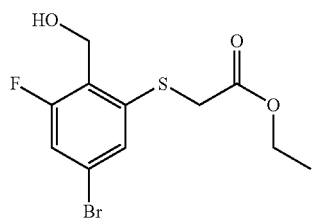

P3-1b

To the solution of compound P3-1a (4.10 g, 12.2 mmol) in THF (40 mL) was added $B_2H_6$ (24.4 mL, 1M in THF). This mixture was stirred at 70° C. overnight, quenched with water (100 mL) and extracted with EA (4×40 mL). The combined organic layer was washed with brine (50 mL), dried over $Na_2SO_4$, filtered, concentrated and purified by FCC (PE:EA=5:1) to give compound P3-1b as a white solid.

Step 3: Ethyl 2-((5-bromo-3-fluoro-2-(hydroxymethyl)phenyl)sulfonyl)acetate (P3-1)

To a stirred solution of compound P3-1b (1.00 g, 3.40 mmol) in DCM (30 mL) at 0° C. was added m-CPBA (1.80 g, 10.2 mmol, 85%) and the mixture was stirred at rt for 16 h, diluted with aq. sat. $NaHCO_3$ solution and extracted with EA (3×20 mL). The combined organic layer was dried over $Na_2SO_4$, concentrated and purified by FCC (PE:EA=5:1) to give compound P3-1 as a white solid.

Preparative Example P4

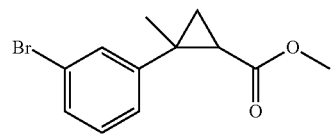

P4

Methyl 2-(3-bromophenyl)-2-methylcyclopropane-1-carboxylate (P4)

To a solution of compound P16 (1.00 g, 3.92 mmol) in DMF (15 mL) was added MeI (1.11 g, 7.84 mmol) and $K_2CO_3$ (1.35 g, 9.80 mmol). The mixture was stirred for 2 h at 50° C., cooled, diluted with EA (100 mL) and washed with water (3×20 mL) and brine (20 mL), dried over $Na_2SO_4$, filtered, concentrated and purified by prep-TLC (EA:PE=1:6) to give compound P4 as a yellow oil.

Preparative Example P5

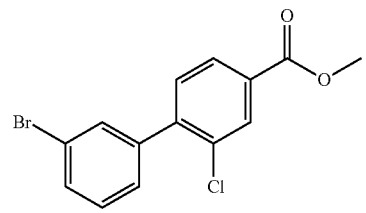

P5

Methyl 3'-bromo-2-chloro-[1,1'-biphenyl]-4-carboxylate (P5)

To a solution of methyl 3-chloro-4-(4,4,5,5-tetramethyl-1,3,2-dioxaborolan-2-yl)benzoate (47.7 g, 161 mmol) in dioxane (300 mL) was added 1-bromo-3-iodobenzene (50.0 g, 177 mmol), $Na_2CO_3$ (35.7 g, 337 mmol) and $Pd(PPh_3)_4$ (11.7 g, 10.1 mmol) under $N_2$. The mixture was stirred at 90° C. overnight under $N_2$, cooled, filtered, concentrated and purified by FCC (EA:PE=1:50) to give compound P5 as a white solid.

Preparative Example P5/1 to P5/3

The following Preparative Examples were prepared similar as described for Preparative Example P5 using the appropriate building blocks.

| # | building block(s) | structure |
|---|---|---|
| P5/1 | 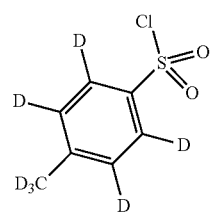 (P8) | 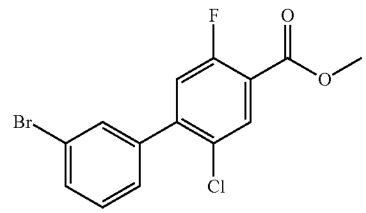 [SMILES: COC(=O)c1cc(Cl)c(-c2cccc(Br)c2)cc1F] |
| P5/2 | | 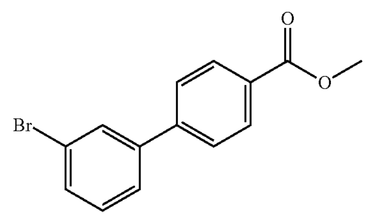 [SMILES: COC(=O)c1ccc(-c2cccc(Br)c2)cc1] |
| P5/3 | | 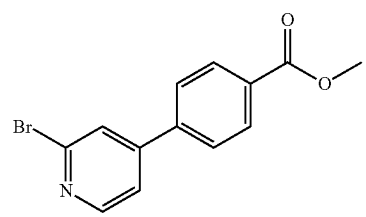 [SMILES: COC(=O)c1ccc(-c2ccnc(Br)c2)cc1] |

Preparative Example P6

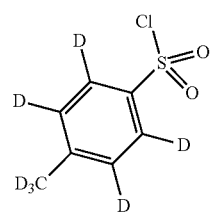

4-(Methyl-d3)benzenesulfonyl chloride-2,3,5,6-d4 (P6)

To a solution of toluene-d8 (1.00 g, 10.0 mmol) in DCM (10 mL) was added ClSO₃H (5 mL) and the mixture was stirred at rt for 2 h, poured into water (100 mL) and extracted with DCM (100 mL). The organic layer was concentrated to give compound P6 as a white solid.

Preparative Example P7

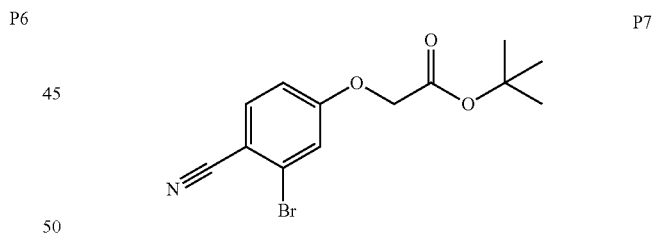

tert-Butyl 2-(3-bromo-4-cyanophenoxy)acetate (P7)

A mixture of 2-(3-bromo-4-cyanophenoxy)acetic acid (200 mg 0.78 mmol), Boc₂O (204 mg 0.94 mmol), DMAP (10 mg, 80 μmol) and pyridine (0.4 mL) in tert-BuOH (10 mL) was stirred at rt overnight, concentrated and purified by FCC (PE:EA=50:1) to give compound P7 as a yellow oil.

Preparative Example P7/1

The following Preparative Example was prepared similar as described for Preparative Example P7 using the appropriate building block.

| # | building block | structure |
|---|---|---|
| P7/1 | 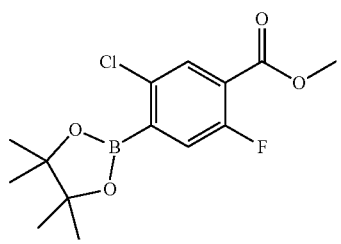 | 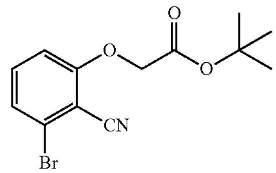 [SMILES: CC(C)(C)OC(=O)COc1cccc(Br)c1C#N] |

Preparative Example P8

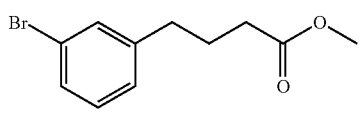

Methyl 5-chloro-2-fluoro-4-(4,4,5,5-tetramethyl-1,3,2-dioxaborolan-2-yl)benzoate (P8)

To a solution of methyl 4-bromo-5-chloro-2-fluorobenzoate (2.66 g, 10.0 mmol) in dioxane (30 mL) was added $B_2Pin_2$ (2.79 g, 11.0 mmol), KOAc (2.45 g, 25.0 mmol) and $Pd(dppf)Cl_2$ (260 mg) under $N_2$. The mixture was stirred at 80° C. overnight under $N_2$, diluted with water (50 mL) and extracted with EA (3×50 mL). The combined organic layer was washed with brine, dried over $Na_2SO_4$, filtered, concentrated and purified by FCC (EA:PE=1:40) to give compound P8 as a white solid.

Preparative Example P9

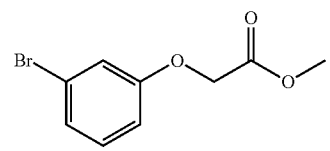

Methyl 4-(3-bromophenyl)butanoate (P9)

To a solution of 4-(3-bromophenyl)butanoic acid (500 mg, 2.06 mmol) in DMF (50 mL) was added $K_2CO_3$ (569 mg, 4.11 mmol) and $CH_3I$ (438 mg, 3.09 mmol). The mixture was stirred for 2 h at rt. Insoluble salts were filtered off and washed with EA. The combined organic layer was washed with water (3×50 mL), brine (2×50 mL), dried over $Na_2SO_4$ and filtered. The solvents were removed under reduced pressure to afford compound P9 as a yellow solid, which was used in the next step without further purification.

Preparative Example P10

P10

Methyl 2-(3-bromophenoxy)acetate (P10)

To a solution of 3-bromophenol (1.72 g, 10.0 mmol) and methyl-bromoacetate (1.01 mL, 11.0 mmol) in ACN (60 mL) was added $K_2CO_3$ (2.07 g, 15.0 mmol) and the mixture was stirred at 50° C. overnight. After insoluble salts are filtered off and washed with ACN, the solvent is removed under reduced pressure and the remainder is taken up in EA and washed subsequently with water and brine. The organic layer is dried over $Na_2SO_4$, filtered and concentrated to give compound P10 as a colorless semi-solid.

Preparative Examples P10/1

The following Example was prepared similar as described for Preparative Example P10 using the appropriate building blocks.

| # | building block | structure |
|---|---|---|
| P10/1 | 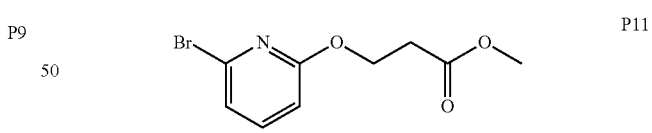 | 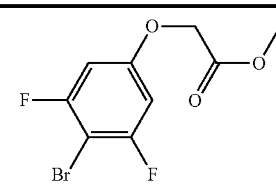 |

Preparative Example P11

P11

Methyl 3-((6-bromopyridin-2-yl)oxy)propanoate (P11)

To a solution of 6-bromopyridin-2(1H)-one (800 mg, 4.59 mmol) and $PPh_3$ (2.39 g, 9.19 mmol) in dry THF (30 mL) under $N_2$ was added DEAD (1.20 g, 6.89 mmol) and methyl 3-hydroxypropanoate (479 mg, 4.59 mmol). The mixture was stirred at rt overnight, quenched with sat. $NH_4Cl$ (60 mL) and extracted with EA (2×30 mL). The combined organic layer was washed with brine (2×30 mL), dried over $Na_2SO_4$, concentrated and purified by prep-TLC (EA:PE=1:4) to give compound P11 as a white solid.

Preparative Example P12

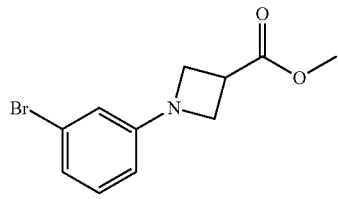

Methyl 1-(3-bromophenyl)azetidine-3-carboxylate (P12)

To a solution of 1-bromo-3-iodobenzene (500 mg, 1.77 mmol) in dioxane (8 mL) was added methyl azetidine-3-carboxylate hydrochloride (295 mg, 1.94 mol), $Pd_2(dba)_3$ (35 mg, 40 μmol), XPhos (17 mg, 40 μmol) and $Na_2CO_3$ (375 mg, 3.53 mmol). The mixture was stirred at 100° C. overnight, cooled to rt, filtered, concentrated and purified by prep-TLC (PE:EA=2:1) to give compound P12 as a yellow oil.

Preparative Example P12/1

The following Preparative Example was prepared similar as described for Preparative Example P12 using the appropriate building block.

| # | building block | structure |
|---|---|---|
| P12/1 | (methyl pyrrolidine-3-carboxylate · HCl) | (methyl 1-(3-bromophenyl)pyrrolidine-3-carboxylate) |

Preparative Example P13

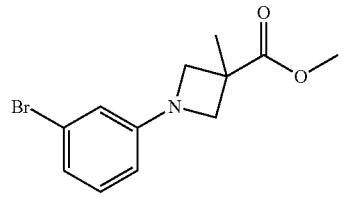

Methyl 1-(3-bromophenyl)-3-methylazetidine-3-carboxylate (P13)

To a solution of 1-bromo-3-iodobenzene (500 mg, 1.77 mmol) in dioxane (15 mL) was added methyl 3-methylazetidine-3-carboxylate hydrochloride (293 mg, 1.77 mmol), $Pd_2(dba)_3$ (32 mg, 35 μmol), Xantphos (20 mg, 35 μmol) and $Cs_2CO_3$ (1.35 g, 3.54 mmol). The mixture was stirred at 100° C. overnight under $N_2$, cooled to rt, diluted with water (150 mL) and extracted with EA (3×200 mL). The combined organic layer was washed with brine (2×50 mL), dried over $Na_2SO_4$, concentrated and purified by FCC (EA:PE=1:5) to afford compound P13 as a yellow oil.

Preparative Example P13/1 to P13/4

The following Preparative Examples were prepared similar as described for Preparative Example P13 using the appropriate building blocks.

| # | building blocks | | structure |
|---|---|---|---|
| P13/1 | (methyl piperidine-4-carboxylate · HCl) | (1-bromo-3-iodobenzene) | (methyl 1-(3-bromophenyl)piperidine-4-carboxylate) |
| P13/2 | (methyl azetidine-3-carboxylate · HCl) | (1-bromo-2-chloro-4-iodobenzene) | (methyl 1-(3-bromo-4-chlorophenyl)azetidine-3-carboxylate) |

| # | building blocks | | structure |
|---|---|---|---|
| P13/3 | methyl azetidine-3-carboxylate·HCl | 2-bromo-1-fluoro-4-iodobenzene | methyl 1-(3-bromo-4-fluorophenyl)azetidine-3-carboxylate |
| P13/4 | methyl 4-methylpiperidine-4-carboxylate·HCl | 1-bromo-3-iodobenzene | methyl 1-(3-bromophenyl)-4-methylpiperidine-4-carboxylate |

Preparative Example P14

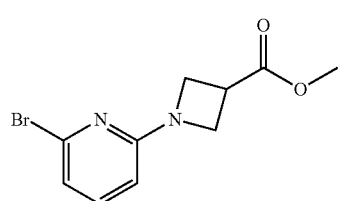

P14

Methyl 1-(6-bromopyridin-2-yl)azetidine-3-carboxylate (P14)

To a solution of 2,6-dibromopyridine (500 mg, 2.11 mmol) in DMF (20 mL) was added methyl azetidine-3-carboxylate hydrochloride (384 mg, 2.53 mmol) and $K_2CO_3$ (729 mg, 5.28 mmol) and the mixture was stirred overnight at 80° C. After cooling to rt insoluble salts were filtered off and washed with EA. The combined organic solvents were washed with water (3×50 mL), brine (2×50 mL), dried over $Na_2SO_4$, filtered and concentrated. The residue was purified by prep-TLC (PE:EA=4:1) to afford compound P14 as a yellow oil.

Preparative Example P15

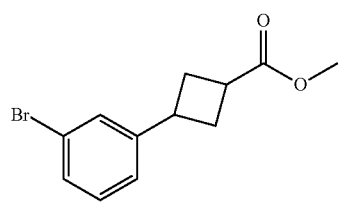

P15

Step 1: 3-(3-Bromophenyl)-3-hydroxycyclobutane-1-carboxylic Acid (P15a)

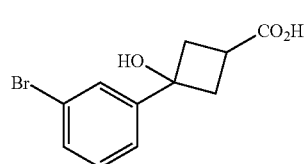

P15a

To a solution of 1-bromo-3-iodobenzene (2.82 g, 10.0 mmol) and 3-oxocyclobutane-1-carboxylic acid (1.14 g, 10.0 mmol) in THF (30 mL) at −78° C. was added n-BuLi (8 mL, 20 mmol, 2.5 M in THF) and the mixture was stirred at −78° C. for 4 h, quenched with $NH_4Cl$ (50 mL), neutralized with 1N aq. HCl and extracted with EA (3×). The combined organic layer was washed with brine, dried over $Na_2SO_4$, filtered, concentrated and purified by FCC (EA:PE=1:1) to give compound P15a as a colorless oil.

Step 2: Methyl 3-(3-bromophenyl)-3-hydroxycyclobutane-1-carboxylate (P15b)

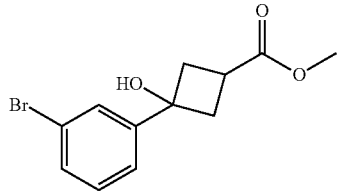

P15b

To a solution of compound P15a (1.35 g, 5.00 mmol) in DMF (20 mL) was added $K_2CO_3$ (1.38 g, 10.0 mmol) and $CH_3I$ (710 mg, 5.00 mmol) and the mixture was stirred at rt for 2 h. Water was added (200 mL) and the mixture was extracted with EA. The combined EA extracts were washed with brine, dried over $Na_2SO_4$ and filtered. The solvent was removed under reduced pressure and the residue was purified by FCC (EA:PE=1:10) to give compound P15b as a colorless oil.

Step 3: Methyl 3-(3-bromophenyl)cyclobutane-1-carboxylate (P15)

To a solution of compound P15b (1.10 g, 3.90 mmol) in TFA (20 mL) at 0° C. was added triethylsilane (680 mg, 5.85 mmol) and the mixture was stirred for 2 h. Water was added to the mixture (200 mL) and the mixture extracted with EA. The solvent was removed under reduced pressure and the residue was purified by FCC (EA:PE=1:10) to give compound P15 as a colorless oil.

Preparative Example P16

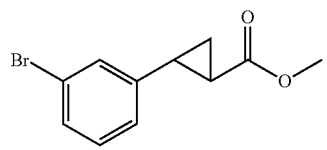

P16

Step 1: Methyl (E)-3-(3-bromophenyl) acrylate (P16a)

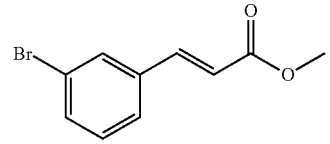

P16a (E)-3-(3-Bromophenyl)acrylic acid (3.00 g, 13.2 mmol) was dissolved in DMF (50 mL), MeI (3.75 g, 26.4 mmol) and $K_2CO_3$ (2.74 g, 19.8 mmol) were added and the mixture was stirred for 2 h at rt. After insoluble salts were filtered and washed with EA, the solvent was washed with water (3×50 mL), brine (2×50 mL), dried over $Na_2SO_4$, filtered and concentrated to give compound P16a as a yellow solid which was used in the next step without any purification.

Step 2: rac-Methyl (1R,2R)-2-(3-bromophenyl)cyclopropane-1-carboxylate (P16)

Under argon, NaH (60%, 680 mg, 17.0 mmol) was initially charged in DMSO (30 mL) and trimethylsulphoxonium iodide (3.74 g, 17.0 mmol) was added in one portion at rt. After the evolution of gas had ceased, compound P16a (3.15 g, 13.1 mmol), dissolved in DMSO (10 mL), was slowly added drop-wise. After stirring overnight at 50° C., the mixture was partitioned between EA and water. The aq. layer was extracted with EA. The combined organic layer was dried over $Na_2SO_4$, filtered, concentrated and purified by FCC (EA:PE=1:20) to give compound P16 as a colorless oil.

Preparative Example P16/1 to P16/2

The following Preparative Examples were prepared similar as described for Preparative Example P16 using the appropriate building blocks.

| # | building block | structure | chemical name |
|---|---|---|---|
| P16/1 | {Br-thiophene-CH=CH-C(O)OMe} | {Br-thiophene-cyclopropane-C(O)OMe} | rac-methyl (1R,2R)-2-(5-bromothiophen-2-yl)cyclopropane-1-carboxylate |
| P16/2 | {Br,Cl-phenyl-CH=CH-C(O)OMe} | {Br,Cl-phenyl-cyclopropane-C(O)OMe} | rac-methyl (1R,2R)-2-(3-bromo-5-chlorophenyl)cyclopropane-1-carboxylate |

Preparative Example P17

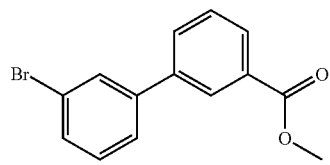

P17

Methyl 3'-bromo-[1,1'-biphenyl]-3-carboxylate (P17)

To a solution of (3-bromophenyl)boronic acid (1.50 g, 7.47 mmol) in dioxane (30 mL) was added methyl 3-bromobenzoate (1.93 g, 8.96 mmol), Pd(PPh$_3$)$_4$ (173 mg, 0.15 mmol) and Na$_2$CO$_3$ (1.58 g, 14.9 mmol). The mixture was stirred at 100° C. overnight. After cooling to rt the reaction was filtered, concentrated and purified by FCC to give compound P17 as a yellow oil.

Preparative Examples P17/1 to P17/4

The following Examples were prepared similar as described for Preparative Example P17 using the appropriate building blocks.

| # | building block | structure |
|---|---|---|
| P17/1 | | 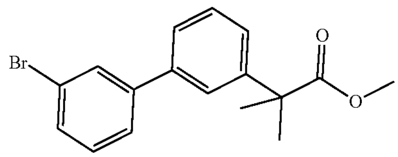 [SMILES: COC(=O)C(C)(C)c1cccc(-c2cccc(Br)c2)c1] |
| P17/2 | | 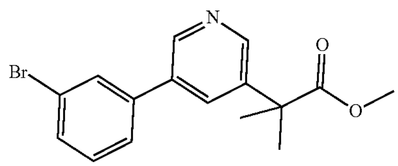 [SMILES: COC(=O)C(C)(C)c1cncc(-c2cccc(Br)c2)c1] |
| P17/3 | | 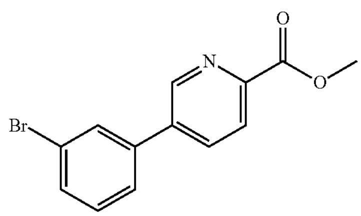 [SMILES: COC(=O)c1ccc(-c2cccc(Br)c2)cn1] |
| P17/4 | | 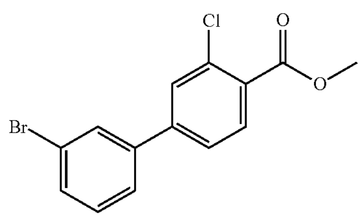 [SMILES: COC(=O)c1ccc(-c2cccc(Br)c2)cc1Cl] |

Preparative Example P18

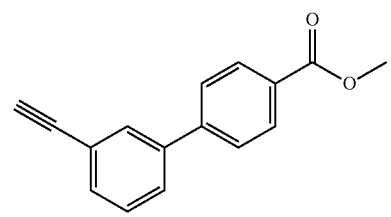
P18

Step 1: Methyl 3'-((trimethylsilyl)ethynyl)-[1,1'-biphenyl]-4-carboxylate (P18a)

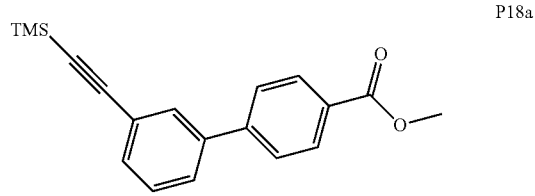 [SMILES: COC(=O)c1ccc(-c2cccc(C#C[Si](C)(C)C)c2)cc1]
P18a

Pd(PPh₃)₄ (1.98 g, 1.72 mmol), CuI (327 mg, 1.72 mmol) and PPh₃ (450 mg, 1.72 mmol) were combined in a round-bottom flask and the flask was degassed and refilled with N₂ three times. TEA (86 mL), methyl 3'-bromo-[1,1'-biphenyl]-4-carboxylate (P5/2, 5.00 g, 17.2 mmol) and ethynyltrimethylsilane (4.86 mL, 36.1 mmol) were added and the mixture was stirred at 60° C. for 6 h. After filtration through kieselgur the filtrate was concentrated under reduced pressure to give compound P18a as a black solid, which was used in the next step without further purification.

Step 2: Methyl 3'-ethynyl-[1,1'-biphenyl]-4-carboxylate (P18)

To a solution of compound P18a (6.21 g, 17.2 mmol) in THF (25 mL) was added TBAF (25 mL, 1M in THF) and the mixture was stirred at rt for 3 h. After concentration under reduced pressure the residue was purified by FCC (EA: PE=1:20) to give compound P18 as a white solid.

Preparative Example P19

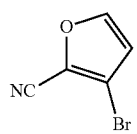
P19

Step 1: 3-Bromofuran-2-carboxamide (P19a)

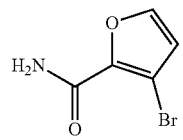

P19a

To a solution of 3-bromofuran-2-carboxylic acid (1.00 g, 5.24 mmol) in DMF (10 mL) was added HATU (2.98 g, 7.85 mmol) and DIPEA (1.69 g, 13.1 mmol) and the mixture was stirred at rt for 1 h. NH$_4$Cl (333 mg, 6.29 mmol) was added and stirring was continued overnight. Water (30 mL) was added, and the mixture was extracted with EA (3×30 mL). The combined organic layer was dried over Na$_2$SO$_4$, concentrated and purified by FCC to give compound P19a as a yellow solid.

Step 2: 3-Bromofuran-2-carbonitrile (P19)

To a solution of compound 19a (906 mg, 4.77 mmol) in DCM (10 mL) at 0° C. was added TFAA (2.50 g, 11.9 mmol) and the mixture was stirred for 2 h, diluted with water (30 mL) and extracted with DCM (3×30 mL). The combined organic layer was dried over Na$_2$SO$_4$, concentrated and purified by FCC (EA:PE=1:20) to give compound P19 as a white solid.

Preparative Example P20

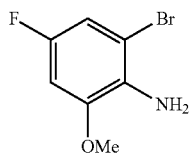

P20

2-Bromo-4-fluoro-6-methoxyaniline (P20)

NBS (12.4 g, 69.4 mmol) was added to a solution of 4-fluoro-2-methoxyaniline (8.90 g, 63.1 mmol) in dry DCM (217 mL) at −78° C. and the mixture was stirred at −78° C. for 2 h, then allowed to warm to 0° C. and stirred for 2 h. The solvent was removed in vacuum and the resulting residue was purified by FCC (EA:PE=1:10) to give compound P20 as a yellow oil.

Preparative Example P21

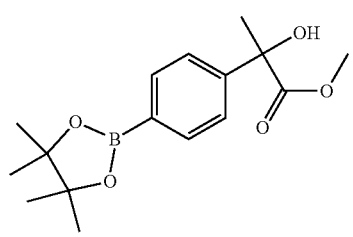

P21

Step 1: 2-(4-Bromophenyl)-2-((trimethylsilyl)oxy)propanenitrile (P21a)

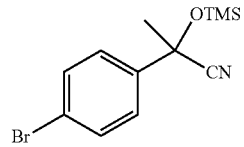

P21a

Trimethylsilyl cyanide (4.96 g, 50.0 mmol) and zinc iodide (50 mg) were added to 1-(4-bromophenyl)ethan-1-one (5.00 g, 50.0 mmol) in DCM (200 mL). This mixture was stirred for 5 h at rt. The mixture was washed with water (2×20 mL) and brine (20 mL). The organic layer was dried over Na$_2$SO$_4$ and concentrated to afford crude compound P21a, which was used in the next step without any purification.

Step 2: 2-(4-Bromophenyl)-2-hydroxypropanoic Acid (P21b)

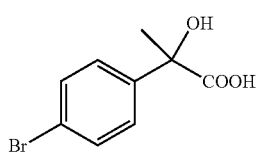

P21b

To the solution of compound P21a (12.2 g, 40.9 mmol) in AcOH (50 mL) was added conc. HCl (50 mL). The mixture was stirred overnight at rt and heated at 100° C. for 2 h. The solvent was removed under reduced pressure. H$_2$O was added and the mixture was extracted with EA (3×200 mL). The organic layer was dried over Na$_2$SO$_4$ and concentrated to give crude compound P21b as a yellow oil, which was used in the next step without any purification.

Step 3: Methyl 2-(4-bromophenyl)-2-hydroxypropanoate (P21c)

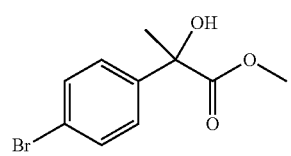

P21c

To a solution of compound P21b (6.50 g, 26.5 mmol) in MeOH (60 mL) was added conc. H$_2$SO$_4$ (3 mL). The mixture was stirred overnight at rt. The solvent was removed under reduced pressure, dissolved in EA (300 mL) and washed with H$_2$O (30 mL) and sat. NaHCO$_3$ (30 mL). The organic layer was dried over Na$_2$SO$_4$, concentrated and purified by FCC (EA:PE=1:2) to give compound P21c as a colorless oil.

Step 4: Methyl 2-hydroxy-2-(4-(4,4,5,5-tetramethyl-1,3,2-dioxaborolan-2-yl)phenyl)propanoate (P21)

To a solution of compound P21c (200 mg, 0.77 mmol) in dioxane (10 mL) was added B$_2$Pin$_2$ (209 mg, 0.93 mmol), KOAc (151 mg, 1.54 mmol) and Pd(dppf)Cl$_2$ (56 mg, 0.08 mmol). The mixture was stirred at 100° C. overnight under N$_2$. After cooling to rt, the mixture was filtered and the solvent was removed under reduced pressure. The residue was purified by prep-TLC (EA:PE=1:1) to afford compound P21 as a white solid.

Preparative Examples P21/1

The following Example was prepared similar as described for Preparative Example P21 using the appropriate building block.

| # | building block | structure |
|---|---|---|
| P21/1 | 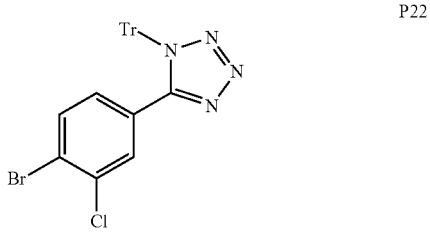 | 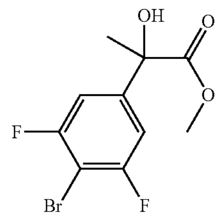 [SMILES: COC(=O)C(C)(O)c1cc(F)c(Br)c(F)c1] |

Preparative Example P22 (Mixture of 1- and 2-Trityl Isomer)

Step 1: 5-(4-Bromo-3-chlorophenyl)-1H-tetrazole (P22a)

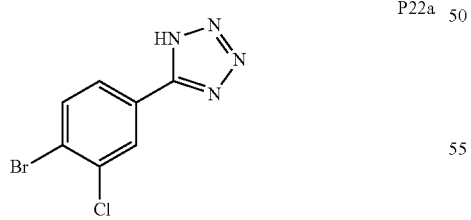

To a solution of 4-bromo-3-chlorobenzonitrile (500 mg, 2.33 mmol) in DMF (10 mL) was added NaN$_3$ (1.50 g, 23.3 mmol) and NH$_4$Cl (1.20 g, 23.3 mmol). The mixture was stirred at 100° C. under N$_2$ overnight. Then DCM (100 mL) was added and the mixture was washed with brine (30 mL). The organic layer was dried over Na$_2$SO$_4$, concentrated and purified by FCC (EA:PE=1:3) to give compound P22a as a white solid.

Step 2: 5-(4-Bromo-3-chlorophenyl)-1-trityl-1H-tetrazole (P22), (Mixture of 1- and 2-Trityl Isomers)

To a solution of compound P22a (350 mg, 1.36 mmol) in DCM (50 mL) was added triphenylmethyl chloride (556 mg, 2.00 mmol) and TEA (202 mg, 2.00 mmol). The mixture was stirred at rt for 12 h. Then DCM (50 mL) was added and the mixture was washed with brine (30 mL). The organic layer was dried over Na$_2$SO$_4$, concentrated and purified by FCC (EA:PE=1:7) to afford compound P22 as a white solid.

Preparative Example P23 (Mixture of 1- and 2-Trityl Isomers)

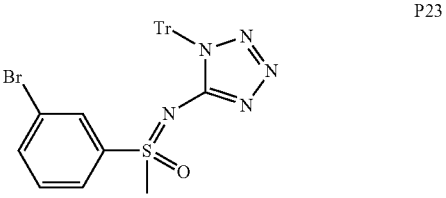

Step 1: N-((3-Bromophenyl)(methyl)(oxo)-$\lambda^6$-sulfaneylidene)-2,2,2-trifluoroacetamide (P23a)

To a solution of 1-bromo-3-(methylsulfinyl)benzene (950 mg, 4.38 mmol) in DCM (10 mL) was added MgO (697 mg, 17.4 mmol), 2,2,2-trifluoroacetamide (742 mg, 6.57 mmol), Rh$_2$(OAc)$_4$ (100 mg) and (diacetoxy)iodobenzene (2.82 g, 8.76 mmol). The mixture was stirred at 40° C. overnight and filtered through a pad of Celite. The solvent was removed under reduced pressure and the crude product was purified by FCC (PE:EA=1:2) to give compound P23a as a white solid.

Step 2: (3-Bromophenyl)(imino)(methyl)-$\lambda^6$-sulfanone (P23b)

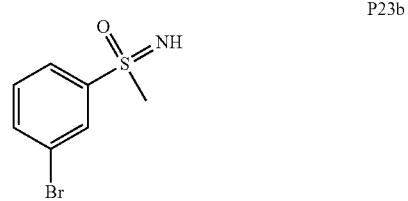

To a stirred solution of compound P23a (680 mg, 2.07 mmol) in MeOH (5 mL) was added $K_2CO_3$ (713 mg, 5.17 mmol) and stirring was continued at rt for 1 h. Then water was added and the mixture was extracted with EA (3×20 mL). The combined organic layer was washed with brine (20 mL), dried over $Na_2SO_4$ and concentrated to give compound P23b as a white solid.

Step 3: N-((3-Bromophenyl)(methyl)(oxo)-$\lambda^6$-sulfaneylidene)cyanamide (P23c)

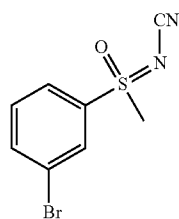

P23c

To a solution of compound P23b (430 mg, 1.86 mmol) in DCM (5 mL) was added cyanic bromide (235 mg, 2.24 mmol) and TEA (376 mg, 3.72 mmol). The mixture was stirred at rt for 3 h, diluted with water and extracted with EA (3×20 mL). The combined organic layer was washed with sat. aq. $NaHCO_3$ (20 mL), dried over $Na_2SO_4$ and concentrated to give compound P23c as a yellow solid.

Step 4: ((1H-Tetrazol-5-yl)imino)(3-bromophenyl)(methyl)-$\lambda^6$-sulfanone (P23d)

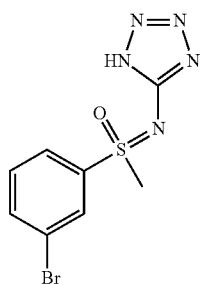

P23d

To a stirred solution of compound P23c (420 mg, 1.63 mmol) in DMF (5 mL) was added $NaN_3$ (1.06 g, 16.3 mmol) and $NH_4Cl$ (864 mg, 16.3 mmol). The mixture was stirred and heated to 100° C. overnight. After cooling to rt, water was added and the mixture was extracted with EA (3×20 mL). The combined organic layer was dried over $Na_2SO_4$, filtered, concentrated and purified by prep-TLC (PE:EA=1:1) to give compound P23d as a white solid.

Step 5: (3-Bromophenyl)(methyl)((1-trityl-1H-tetrazol-5-yl)imino)-$\lambda^6$-sulfanone (P23) (Mixture of 1- and 2-Trityl Isomer)

To a stirred solution of compound P23d (350 mg, 1.16 mmol) in DCM (20 mL) was added trityl chloride (388 mg, 1.39 mmol) and TEA (0.3 mL, 2.3 mmol). Stirring was continued at rt overnight. Then water was added and the mixture was extracted with DCM (3×50 mL). The combined organic layer was washed with brine (20 mL), dried over $Na_2SO_4$, concentrated and purified by FCC (EA:PE=1:3) to give compound P23 as a white solid.

Preparative Example P24

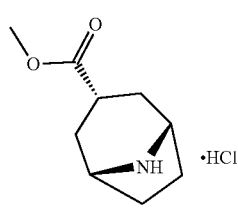

P24 rel-Methyl (1R,3r,5S)-8-azabicyclo[3.2.1]octane-3-carboxylate Hydrochloride (P24)

rel-(1R,3r,5S)-8-(tert-Butoxycarbonyl)-8-azabicyclo[3.2.1]octane-3-carboxylic acid (500 mg, 1.96 mmol) was dissolved in HCl in MeOH (20 mL). The solution was stirred at rt for 5 h. The solvent was removed under reduced pressure to afford compound P24 as a white solid.

Preparative Example P25

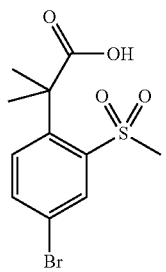

P25

Step 1: (4-Bromo-2-(methylsulfonyl)phenyl)methanol (P25a)

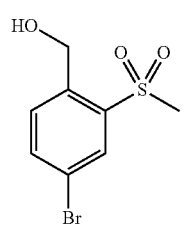

P25a

To a solution of methyl 4-bromo-2-(methylsulfonyl)benzoate (3.00 g, 10.2 mmol) in MeOH (20 mL) was added $LiBH_4$ (4.00 g, 100 mmol) slowly at 0° C. The mixture was stirred at 80° C. overnight. Water (40 mL) was added slowly under cooling with an ice bath and the mixture was extracted with EA (3×30 mL). The combined organic layer was washed with brine (30 mL), dried over Na$_2$SO$_4$, filtered and concentrated under reduced pressure to give compound P25a as a pale yellow solid, which was directly used in the next step.

Step 2: 2-(4-Bromo-2-(methylsulfonyl)phenyl)acetonitrile (P25b)

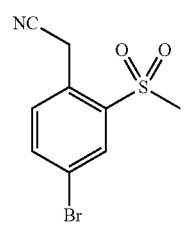

P25b

To a solution of cyanic bromide (712 mg, 6.70 mmol) and PPh$_3$ (1.76 g, 6.70 mmol) in DCM (30 mL) was added a solution of compound P25a (1.50 g, 5.60 mmol) in DCM (50 mL). The mixture was stirred at 15° C. for 1 h, then DBU (1.10 g, 6.70 mmol) was added at 0° C. The resulting mixture was stirred at 0~15° C. for another 16 h. The solvent was concentrated in vacuum. The residue was purified by FCC (PE:EA=4:1) to give compound P25b as a yellow solid.

Step 3: 2-(4-Bromo-2-(methylsulfonyl)phenyl)-2-methylpropanenitrile (P25c)

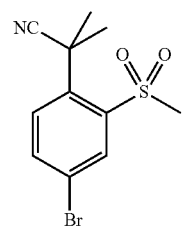

P25c

To a solution of compound P25b (200 mg, 1.10 mmol) in THF (20 mL) were added potassium tert-butoxide (502 mg, 4.40 mmol) and iodomethane (624 mg, 4.40 mmol) at −78° C. The mixture was warmed to −20° C. and stirred overnight, diluted with aq. NH$_4$Cl (30 mL) and extracted with EA (3×30 mL). The combined organic layer was washed with brine (100 mL), dried over Na$_2$SO$_4$, filtered, concentrated and purified by FCC (PE:EA=100:8) to give compound P25c as a yellow solid.

Step 4: 2-(4-Bromo-2-(methylsulfonyl)phenyl)-2-methylpropanoic Acid (P25)

To a solution of compound P25c (850 mg, 2.80 mmol) in EtOH (5 mL) and H$_2$O (5 mL) was added KOH (1.20 g, 22.4 mmol). The mixture was stirred at 80° C. for 2 d. The pH was adjusted to ca. 5 by addition of 1N aq. HCl and the mixture was extracted with DCM/MeOH (10/1, 3×40 mL). The combined organic layer was washed with brine (100 mL), dried over Na$_2$SO$_4$, filtered and concentrated to give compound P25 as a yellow solid.

Preparative Example P26

P26

4-Bromo-3-(trifluoromethyl)-1-trityl-1H-pyrazole (P26)

To a stirred solution of 4-bromo-5-(trifluoromethyl)-1H-pyrazole (428 mg, 2.00 mmol) in DCM (10 mL) was added TEA (606 mg, 6.00 mmol) and (chloromethanetriyl)tribenzene (1.11 g, 4.00 mmol) and stirring was continued at rt overnight. Then the solvent was removed and H$_2$O (50 mL) was added and the mixture was extracted with EA (3×50 mL). The combined organic layer was washed with brine, dried over Na$_2$SO$_4$, filtered, concentrated and purified by FCC (PE:EA=5:1) to give compound P26 as a white solid.

Preparative Example P27

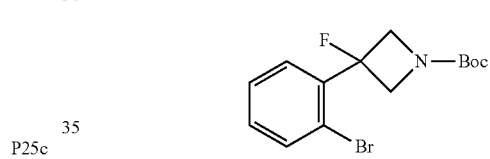

P27

Step 1: tert-Butyl 3-(2-bromophenyl)-3-hydroxyazetidine-1-carboxylate (P27a)

P27a

To a solution of 1-bromo-2-iodobenzene (8.43 g, 30.0 mmol) in THF (50 mL) at −78° C. was slowly added i-PrMgBr in THF (0.90M, 33 mL, 30.0 mmol). After stirring for 2 h, a solution of tert-butyl 3-oxoazetidine-1-carboxylate (3.20 g, 19.0 mmol) in THF (20 mL) was added dropwise to the mixture at −78° C. The mixture was stirred at rt for 3 h, diluted with sat. aq. NH$_4$Cl and extracted with EA. The organic layer was washed with water and brine, dried over Na$_2$SO$_4$, concentrated and purified by FCC (PE:DCM=2:1) to afford compound P27a as a white solid.

Step 2: tert-Butyl 3-(2-bromophenyl)-3-fluoroazetidine-1-carboxylate (P27)

To a stirred solution of compound P27a (4.30 g, 13.1 mmol) in DCM (50 mL) at 0° C. was slowly added DAST (4.20 g, 26.2 mmol). After stirring for 4 h, the mixture was poured into water and extracted with EA. The organic layer was washed with brine, dried over Na₂SO₄, concentrated and purified by FCC (PE:DCM=3:1) to give compound P27 as a colorless oil.

Preparative Example P28

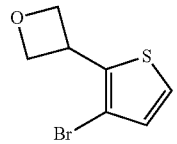

P28

Step 1: 3-(3-Bromothiophen-2-yl)oxetan-3-ol (P28a)

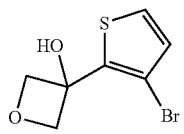

P28a

To a suspension of 3-bromothiophene (13.0 g, 80.2 mmol) in THF (20 mL) was added LDA (48.0 mL, 2.0M in THF, 96.0 mmol) under N₂ at −60° C. The mixture was stirred at −60° C. for 45 min. Then oxetan-3-one (8.70 g, 121 mmol) was added and stirring was continued for 30 min at −60° C. Water was added slowly and the mixture was extracted with EA (3×). The combined organic layer was dried over Na₂SO₄, filtered, concentrated and purified by FCC (PE: EA=10:1 to 5:1) to give compound P28a as a brown oil.

Step 2: 3-(3-Bromothiophen-2-yl)oxetane (P28)

To a mixture of compound P28a (17.0 g, 72.6 mmol) in DCM (120 mL) was added BF₃·Et₂O (18.5 mL, 146 mmol) at 0° C. under N₂. The mixture was stirred at 0° C. for 30 min. Then triethylsilane (35.0 mL, 220 mmol) was added and the mixture was stirred at 0° C. for 30 min. Further triethylsilane (35.0 mL, 220 mmol) was added and the mixture was stirred at 0° C. for 30 min. A third portion of triethylsilane (35.0 mL, 220 mmol) was added and stirring was continued at 0° C. 30 min. The mixture was added to a solution aq. NaOH (10%, 200 g) under cooling with an ice bath and extracted with EA (3×). The combined organic layer was dried over Na₂SO₄, filtered, concentrated and purified by FCC (PE/DCM=10:1 to 3:1) to give compound P28 as a yellow oil. ¹H-NMR (CDCl₃, 400 MHz) δ: 7.23 (d, J=5.2 Hz, 1H), 6.94 (d, J=5.2 Hz, 1H), 5.08-5.04 (m, 2H), 4.80-4.77 (m, 2H), 4.67-4.59 (m, 1H).

Preparative Example P29

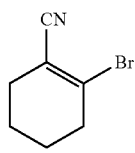

P29

Step 1: 2-Bromocyclohex-1-ene-1-carboxamide (P29a)

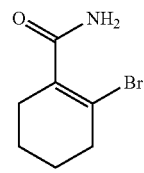

P29a

To a solution of 2-bromocyclohex-1-ene-1-carboxylic acid (1.20 g, 5.88 mmol) in DCM (20 mL) was added HATU (3.35 g, 8.82 mmol), DIPEA (2.16 g, 16.7 mmol) and NH₄Cl (3.20 g, 58.9 mmol). The mixture was stirred at rt for 24 h, filtered, concentrated and purified by FCC (PE:EA=1:1) to give compound P29a as a colorless oil.

Step 2: 2-Bromocyclohex-1-ene-1-carbonitrile (P29)

To a solution of compound P29a (510 mg, 2.51 mmol) in DCM (20 mL) was added TFAA (1.05 g, 5.02 mmol) at 0° C. The mixture was stirred at rt for 12 h, poured into water (50 mL) and extracted with DCM (3×20 mL). The combined the organic layer was washed with brine (30 mL), dried over Na₂SO₄, filtered, concentrated and purified by FCC (PE: EA=2:1) to give compound P29 as a white solid.

Preparative Example P30

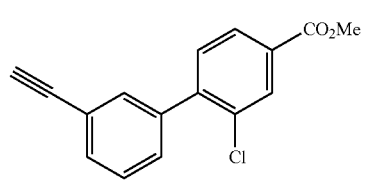

P30

Step 1: Methyl 2-chloro-3'-((trimethylsilyl)ethynyl)-[1,1'-biphenyl]-4-carboxylate (P30a)

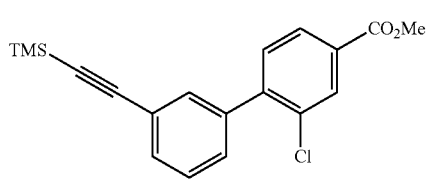

P30a

Pd(PPh₃)₄ (553 mg, 0.48 mmol), CuI (93 mg, 0.48 mmol) and PPh₃ (126 mg, 0.48 mmol) were combined in a round-bottom flask, then degassed and refilled with N₂ three times. To the mixture was added TEA (45 mL), compound P5 (2.00 g, 6.10 mmol), ethynyltrimethylsilane (786 mg, 10.2 mmol) and then the mixture was stirred at 60° C. for 6 h, cooled, filtered through kieselguhr and washed with EA (40 mL). The filtrate was concentrated and purified by FCC (PE: EA=20:1) to give compound P30a as a yellow solid.

Step 2: Methyl 2-chloro-3'-ethynyl-[1,1'-biphenyl]-4-carboxylate (P30)

To a solution of compound P30a (2.05 g, 5.89 mmol) in MeOH (5 mL) was added K$_2$CO$_3$ (778 mg, 7.07 mmol) and the mixture was stirred at rt for 30 min, poured into ice water (50 mL) and extracted with DCM (2×50 mL). The combined organic layer was dried over Na$_2$SO$_4$, filtered and concentrated to give compound P30 as a yellow solid.

Preparative Example P31

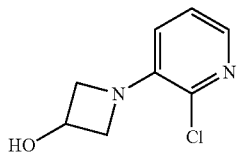

1-(2-Chloropyridin-3-yl)azetidin-3-ol (P31)

To a solution of 2-chloro-3-iodopyridine (1.20 g, 5.00 mmol) in toluene (20 mL) was added azetidin-3-ol hydrochloride (1.09 g, 10.0 mmol), Cs$_2$CO$_3$ (6.52 g, 20.0 mmol), BINAP (311 mg, 0.50 mmol) and Pd$_2$(dba)$_3$ (200 mg) under N$_2$. The mixture was stirred at 110° C. overnight under N$_2$. After cooling to rt the mixture was filtered and the solvent was removed under reduced pressure. The residue was purified by FCC (EA:PE=1:3) to give compound P31 as a yellow solid.

Preparative Example P32

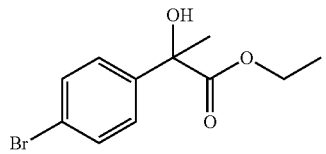 [SMILES: CCOC(=O)C(C)(O)c1ccc(Br)c(Cl)c1]

Ethyl 2-(4-bromophenyl)-2-hydroxypropanoate (P32)

To a solution of ethyl 2-(4-bromophenyl)-2-oxoacetate (512 mg, 2.00 mmol) in THF (30 mL) was added MeMgBr (2 mL, 1M in THF) at 0° C. The mixture was stirred at 0° C. for 1 h, diluted with water (50 mL) and extracted with EA (3×50 mL). The combined organic layer was washed with brine, dried over Na$_2$SO$_4$, filtered, concentrated and purified by FCC (PE:EA=5:1) to give compound P32 as a white solid.

Preparative Examples P32/1

The following Preparative Example was prepared similar as described for Preparative Example P32 using the appropriate building block.

| # | building block | structure |
|---|---|---|
| P32/1 | -C(O)-C(O)-O-Et) | -C(OH)(Me)-C(O)-O-Et) |

Preparative Example P33

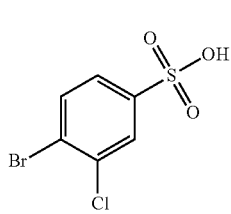

4-Bromo-3-chlorobenzenesulfonic Acid (P31)

A solution of 4-bromo-3-chlorobenzenesulfonyl chloride (576 mg, 2.00 mmol) in H$_2$O (30 mL) was stirred at 100° C. for 16 h and concentrated to give compound P33 as a white solid.

Preparative Example P34

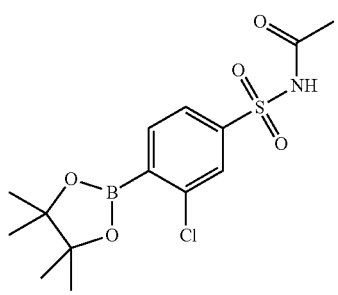

Step 1:
N-((4-Bromo-3-chlorophenyl)sulfonyl)acetamide (P34a)

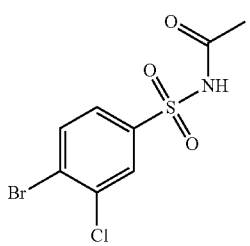

4-Bromo-3-chlorobenzenesulfonamide (1.5 g, 5.5 mmol) was dissolved in pyridine (5 mL). Then DMAP (22 mg, 0.18 mmol) and Ac$_2$O (1.1 mL, 12 mmol) were added and the mixture was stirred for 3 h at rt, diluted with EA and washed with aq. NH$_4$Cl solution (3×) and water. The organic layer was dried over Na$_2$SO$_4$ and concentrated. The resulting oil was triturated with PE and the precipitate was collected by filtration to afford compound P34a as a white solid.

Step 2: N-((3-Chloro-4-(4,4,5,5-tetramethyl-1,3,2-dioxaborolan-2-yl)phenyl)sulfonyl)acetamide (P34)

To a solution of compound P34a (310 mg, 1.00 mmol) in dioxane (5 mL) was added B$_2$Pin$_2$ (381 mg, 1.50 mmol), KOAc (276 mg, 2.00 mmol) and Pd(dppf)Cl$_2$ (120 mg). The mixture was stirred under N$_2$ at 90° C. for 8 h, cooled, filtrated, concentrated and purified by FCC (PE:EA=5:1) to give compound P34 as a yellow solid.

Preparative Example P35

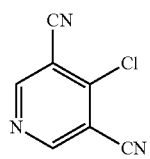

P35

Step 1: 4-Bromopyridine-3,5-dicarboxylic Acid (P35a)

P35a

To a solution of 4-bromo-3,5-dimethylpyridine (1.24 g, 6.72 mmol) in water (15 mL) was added KMnO$_4$ (1.59 g, 10.1 mmol) and the mixture was stirred at 100° C. for 1 h. Then an additional amount of KMnO$_4$ (1.59 g, 10.1 mmol) in water (15 mL) was added and stirring at 100° C. was continued for 2 h. Then the mixture was filtered and the solvent concentrated to about 5 mL, adjusted to pH=2 with conc. HCl and concentrated to give compound P35a as a white solid.

Step 2: 4-Chloropyridine-3,5-dicarboxamide (P35b)

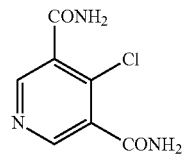

P35b

To a solution of compound P35a (1.30 g, 5.30 mmol) in DCM (15 mL) was added SOCl$_2$ (1.5 mL) and DMF (3 drops). The mixture was stirred at 45° C. for 2 h, concentrated and redissolved in dioxane (5 mL). NH$_3$·H$_2$O (20 mL) was added dropwise to the solution at 0° C. and then concentrated to give compound P35b as a yellow solid.

Step 3: 4-Chloropyridine-3,5-dicarbonitrile (P35)

To a solution of compound P35b (188 mg, 0.94 mmol) in DMF (5 mL) was added POCl$_3$ (1 mL) and the mixture was stirred at rt overnight, diluted with water (30 mL) and extracted with EA (3×50 mL). The combined organic layer was washed with aq. NaHCO$_3$ (30 mL), concentrated and purified by FCC (PE:EA=5:1) to give compound P35 as a white solid.

General remarks: A "C" before the example number means that it is a comparative example while a "P" before the example number means that the example contains a protection group. These examples are not falling within the scope of the claims.

Example 1

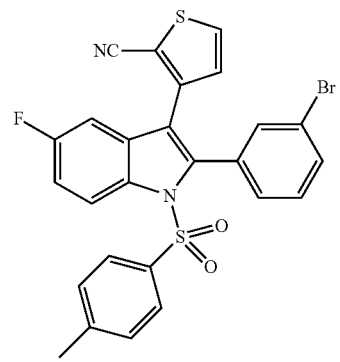

1

Step 1: 2-((3-Bromophenyl)ethynyl)-4-fluoroaniline (1a)

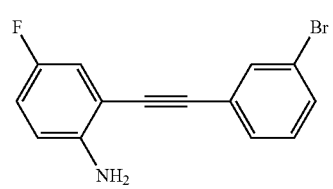

1a

To a solution of 1-bromo-3-iodobenzene (5.00 g, 17.7 mmol) in Et$_3$N (50 mL) was added Pd(PPh$_3$)$_4$ (1.22 g, 1.06 mmol), CuI (269 mg, 1.41 mmol), PPh$_3$ (278 mg, 1.06 mmol) and 2-ethynyl-4-fluoroaniline (2.86 g, 21.2 mmol). The mixture was stirred at 60° C. under N$_2$ for 4 h, cooled, filtered, concentrated and purified by FCC (PE:EA=8:1) to give compound 1a as a yellow solid.

Step 2: N-(2-((3-Bromophenyl)ethynyl)-4-fluorophenyl)-4-methylbenzenesulfonamide (1b)

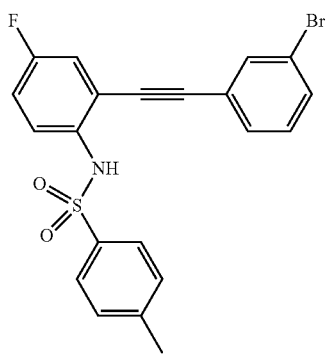

1b

To a solution of compound 1a (3.50 g, 12.1 mmol) in DCM (50 mL) was added pyridine (3.5 mL), 4-methylbenzene-1-sulfonyl chloride (4.58 g, 24.1 mmol) and DMAP (350 mg). The mixture was stirred at rt overnight, diluted with CH$_2$Cl$_2$ (300 mL) and subsequently washed with 2N HCl (3×30 mL) and brine (30 mL). The organic layer was dried over Na$_2$SO$_4$, filtered, concentrated and purified by FCC (PE:EA=5:1) to give compound 1b as a white solid.

Step 3: 3-(2-(3-Bromophenyl)-5-fluoro-1-tosyl-1H-indol-3-yl)thiophene-2-carbonitrile (1)

To a solution of compound 1b (4.20 g, 9.48 mmol) in CH$_3$CN (60 mL) was added 3-bromothiophene-2-carbonitrile (3.67 g, 14.2 mmol), K$_2$CO$_3$ (2.62 g, 10.0 mmol) and Pd(PPh$_3$)$_4$ (1.09 g, 0.95 mmol) under N$_2$. The mixture was stirred at 100° C. for 2 h, cooled, poured into EA (400 mL) and washed with water (50 mL) and brine (50 mL). The organic layer was dried over Na$_2$SO$_4$, filtered, concentrated and purified by FCC (EA:PE=1:3) to give compound 1 as a white solid.

Example 1/1 to 1/149

The following Examples were prepared similar as described for Example 1 using the appropriate building blocks.

| # | building block(s) | structure | analytical data |
|---|---|---|---|
| 1/1 | | 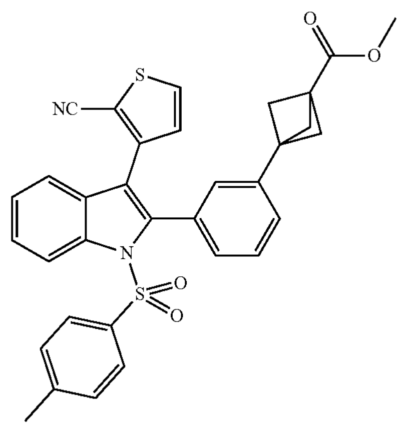 [SMILES: COC(=O)C12CC(c3cccc(-c4c(-c5ccsc5C#N)c5ccccc5n4S(=O)(=O)c4ccc(C)cc4)c3)(C1)C2] | |
| 1/2 | P5/2 | 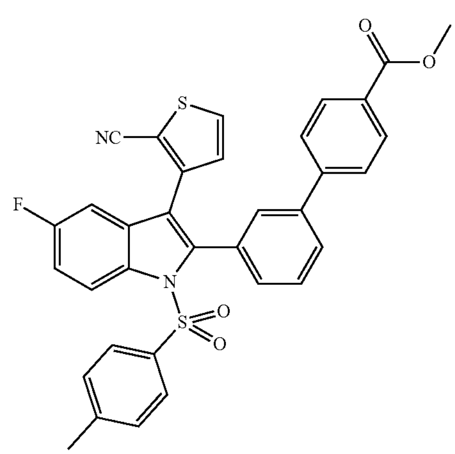 | |

-continued

| # | building block(s) | structure | analytical data |
|---|---|---|---|
| 1/3 | 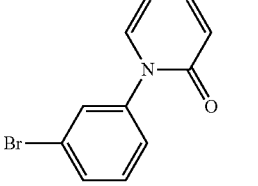 | 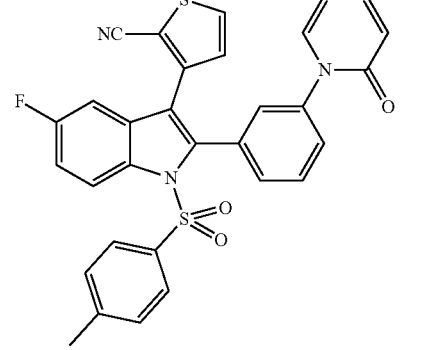 | |
| 1/4 | 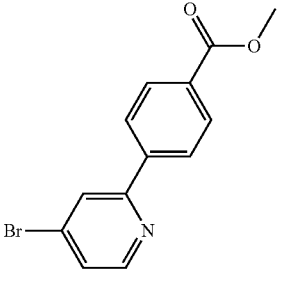 [SMILES: COC(=O)c1ccc(-c2cc(Br)ccn2)cc1] | 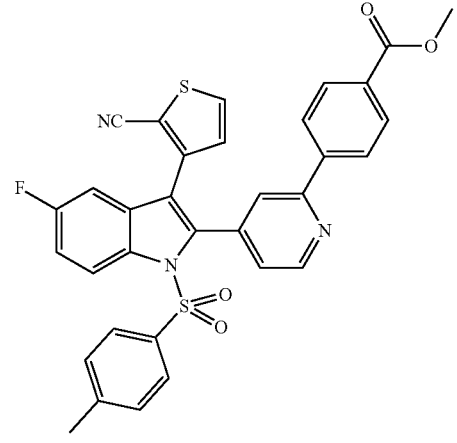 [SMILES: COC(=O)c1ccc(-c2cc(-c3c(-c4ccsc4C#N)c4cc(F)ccc4n3S(=O)(=O)c3ccc(C)cc3)ccn2)cc1] | |
| 1/5 | 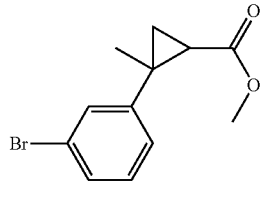<br>P4 | 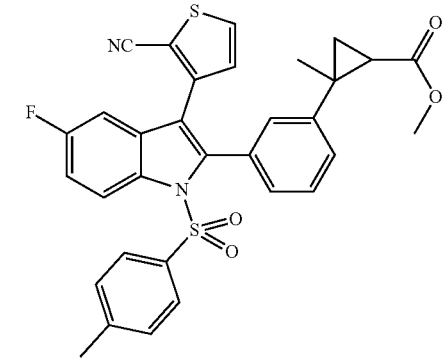<br>first eluting isomer<br>retention time 1.67 min | Separation of both isomers under the following conditions:<br>Instrument: SFC-80 (Thar, Waters)<br>Column: OJ 20 × 250 mm, 10 μm (Daicel)<br>Column temperature: 35° C. Mobile phase: $CO_2$/MeOH (0.2% $NH_4^+OMe^-$) = 70/30<br>Flow rate: 80 g/min<br>Back pressure: 100 bar<br>Detection wavelength: 214 nm<br>Cycle time: 2 min<br>Sample solution: 180 mg dissolved in 30 mL MeOH<br>Injection volume: 1 mL |

| # | building block(s) | structure | analytical data |
|---|---|---|---|
| 1/6 | | 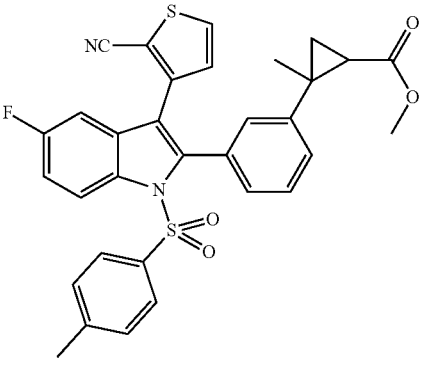
second eluting isomer
retention time 2.16 min | |
| 1/7 | 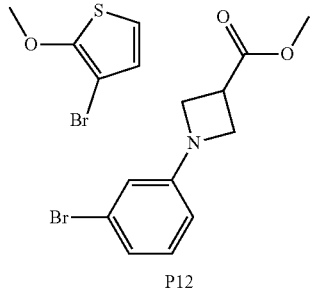
P12 | 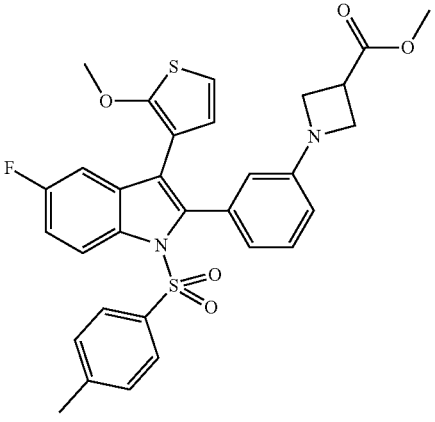 | |
| 1/8 | 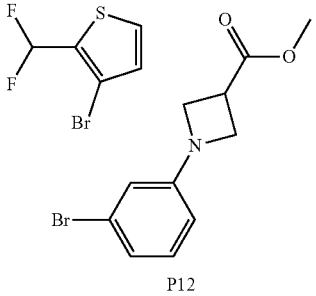
P12 | 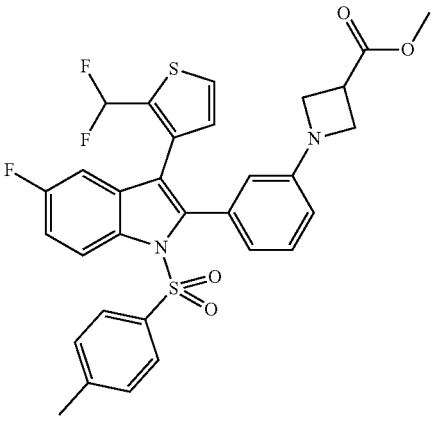 [SMILES: COC(=O)C1CN(c2cccc(-c3c(-c4ccsc4C(F)F)c4cc(F)ccc4n3S(=O)(=O)c3ccc(C)cc3)c2)C1] | |

-continued
| # | building block(s) | structure | analytical data |
|---|---|---|---|
| 1/9 | 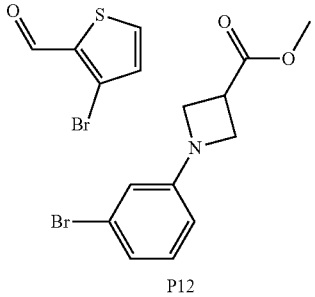 P12 | 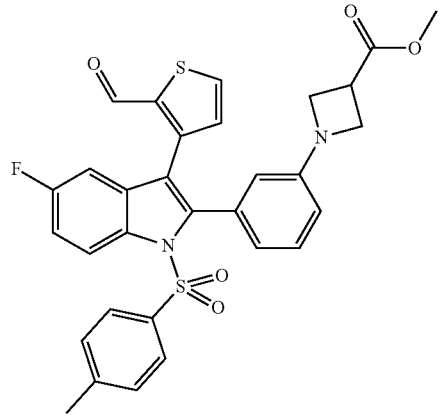 [SMILES: COC(=O)C1CN(c2cccc(-c3c(-c4ccsc4C=O)c4cc(F)ccc4n3S(=O)(=O)c3ccc(C)cc3)c2)C1] | |
| 1/10 | 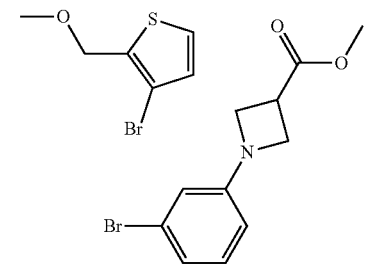 P12 | 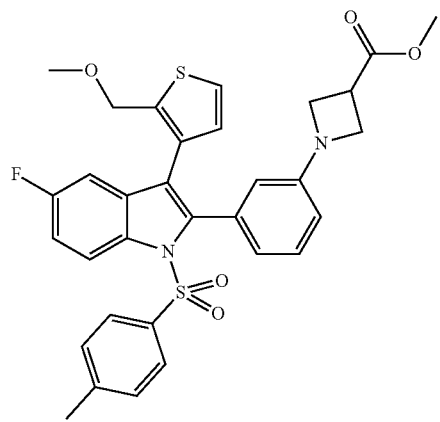 [SMILES: COCc1sccc1-c1c(-c2cccc(N3CC(C(=O)OC)C3)c2)n(S(=O)(=O)c2ccc(C)cc2)c2ccc(F)cc12] | |
| 1/11 | 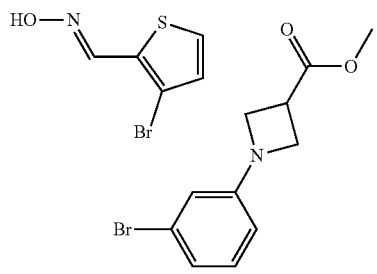 P12 | 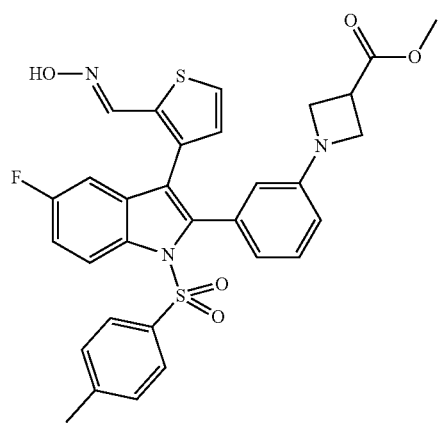 [SMILES: COC(=O)C1CN(c2cccc(-c3c(-c4ccsc4/C=N/O)c4cc(F)ccc4n3S(=O)(=O)c3ccc(C)cc3)c2)C1] | |

| # | building block(s) | structure | analytical data |
|---|---|---|---|
| 1/12 | P12 | 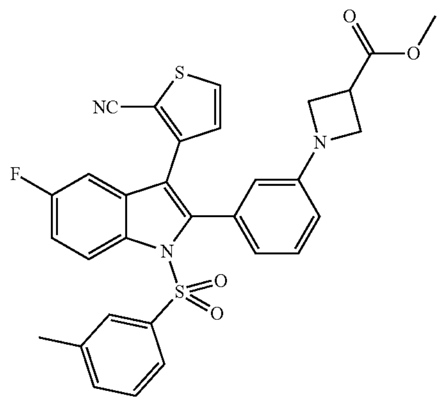 [SMILES: COC(=O)C1CN(c2cccc(-c3c(-c4ccsc4C#N)c4cc(F)ccc4n3S(=O)(=O)c3cccc(C)c3)c2)C1] | |
| 1/13 | P12 | 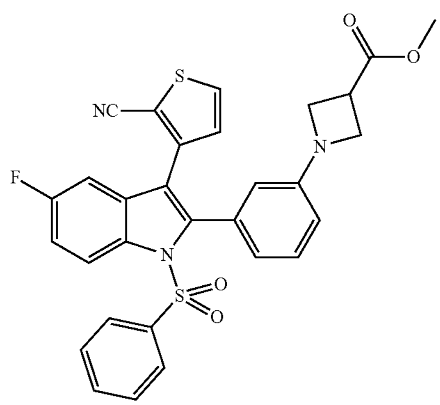 [SMILES: COC(=O)C1CN(c2cccc(-c3c(-c4ccsc4C#N)c4cc(F)ccc4n3S(=O)(=O)c3ccccc3)c2)C1] | |
| 1/14 | P12 | 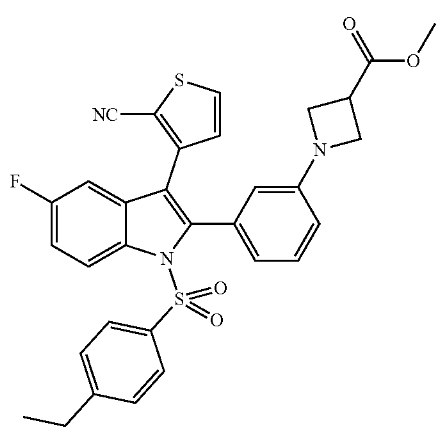 [SMILES: CCc1ccc(S(=O)(=O)n2c(-c3cccc(N4CC(C(=O)OC)C4)c3)c(-c3ccsc3C#N)c3cc(F)ccc32)cc1] | |

-continued

| # | building block(s) | structure | analytical data |
|---|---|---|---|
| 1/15 | P12 | 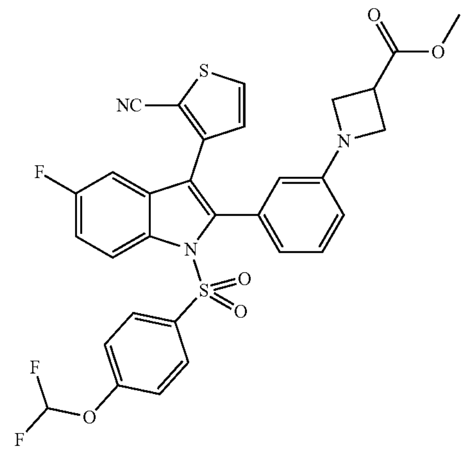 [SMILES: COC(=O)C1CN(c2cccc(-c3c(-c4ccsc4C#N)c4cc(F)ccc4n3S(=O)(=O)c3ccc(OC(F)F)cc3)c2)C1] | |
| 1/16 | P12 | 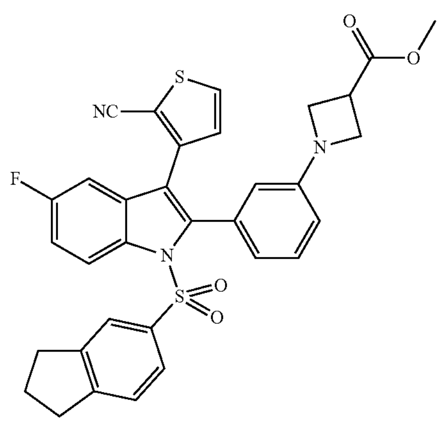 [SMILES: COC(=O)C1CN(c2cccc(-c3c(-c4ccsc4C#N)c4cc(F)ccc4n3S(=O)(=O)c3ccc4c(c3)CCC4)c2)C1] | |
| 1/17 | P12 | 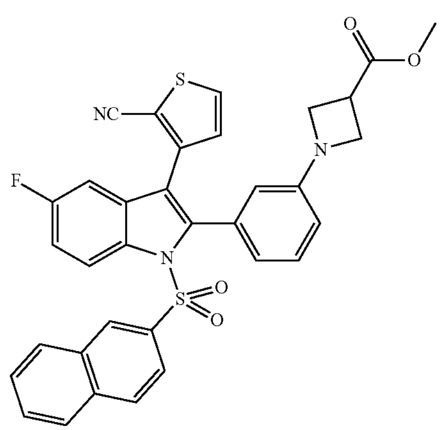 [SMILES: COC(=O)C1CN(c2cccc(-c3c(-c4ccsc4C#N)c4cc(F)ccc4n3S(=O)(=O)c3ccc4ccccc4c3)c2)C1] | |

-continued
| # | building block(s) | structure | analytical data |
|---|---|---|---|
| 1/18 | 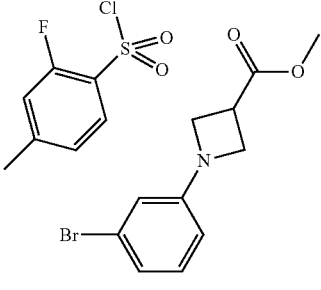 P12 | 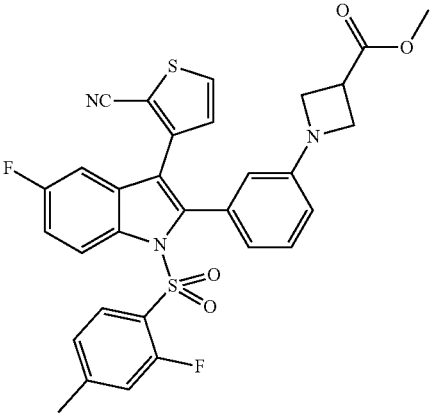 [SMILES: COC(=O)C1CN(c2cccc(-c3c(-c4ccsc4C#N)c4cc(F)ccc4n3S(=O)(=O)c3ccc(C)cc3F)c2)C1] | |
| 1/19 | 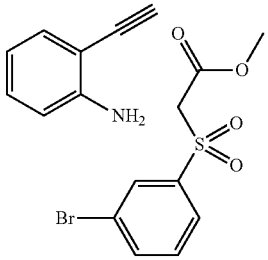 | 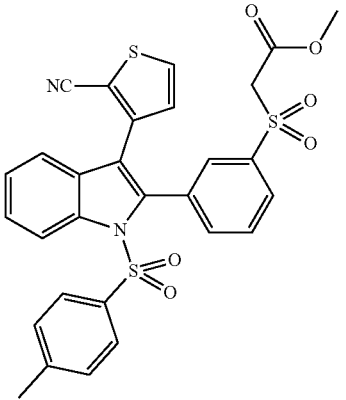 [SMILES: COC(=O)CS(=O)(=O)c1cccc(-c2c(-c3ccsc3C#N)c3ccccc3n2S(=O)(=O)c2ccc(C)cc2)c1] | |
| 1/20 | 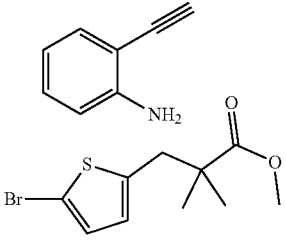 | 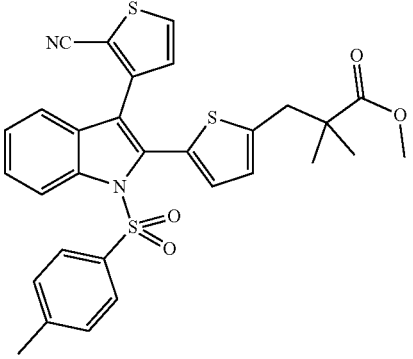 [SMILES: COC(=O)C(C)(C)Cc1ccc(-c2c(-c3ccsc3C#N)c3ccccc3n2S(=O)(=O)c2ccc(C)cc2)s1] | |
| 1/21 | 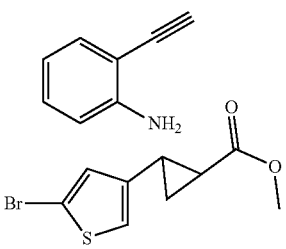 | 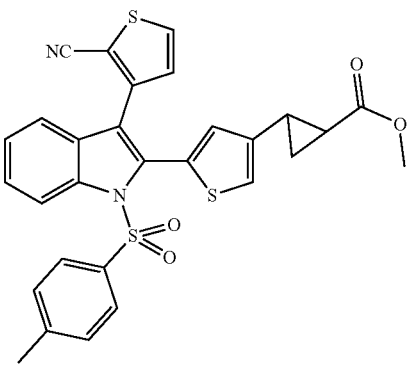 [SMILES: COC(=O)C1CC1c1csc(-c2c(-c3ccsc3C#N)c3ccccc3n2S(=O)(=O)c2ccc(C)cc2)c1] | |

| # | building block(s) | structure | analytical data |
|---|---|---|---|
| 1/22 | 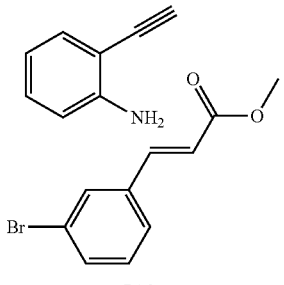 P16a | 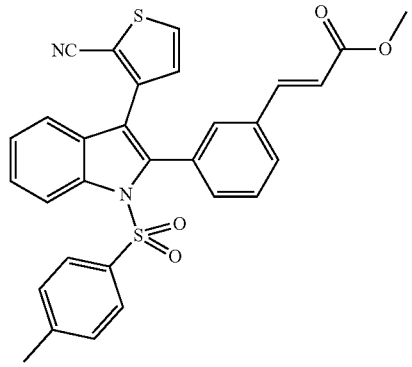 [SMILES: COC(=O)/C=C/c1cccc(-c2c(-c3ccsc3C#N)c3ccccc3n2S(=O)(=O)c2ccc(C)cc2)c1] | |
| 1/23 | 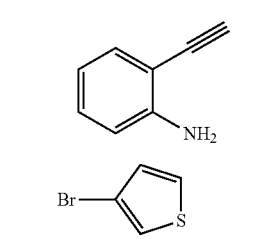 | 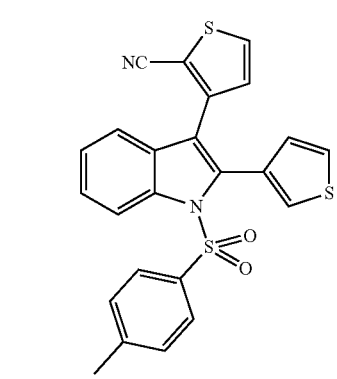 [SMILES: Cc1ccc(S(=O)(=O)n2c(-c3ccsc3)c(-c3ccsc3C#N)c3ccccc32)cc1] | ¹H-NMR (500 MHz, DMSO-d₆) δ: 8.25 (d, J = 8.5 Hz, 1H), 8.02 (d, J = 5.5 Hz, 1H), 7.57 (dd, J = 3.0, 5.0 Hz, 1H), 7.49 (dd, J = 4.5, 8.5 Hz, 1H), 7.45-7.43 (m, 3H), 7.36 (d, J = 4.0 Hz, 2H), 7.32 (d, J = 8.5 Hz, 2H), 7.11 (dd, J = 1.3, 4.8 Hz, 1H), 6.98 (d, J = 5.0 Hz, 1H), 2.31 (s, 3H); MS: 482.7 (M + Na)⁺. |
| 1/24 | 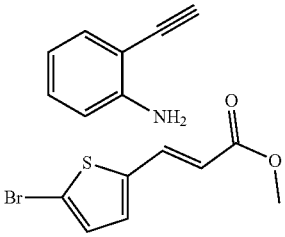 | 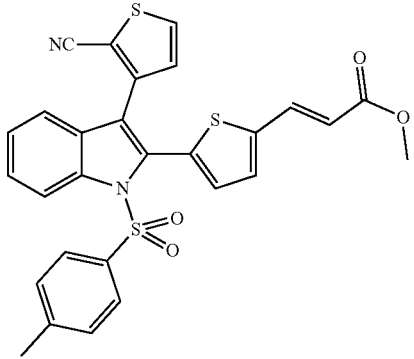 [SMILES: COC(=O)/C=C/c1ccc(-c2c(-c3ccsc3C#N)c3ccccc3n2S(=O)(=O)c2ccc(C)cc2)s1] | |
| 1/25 | 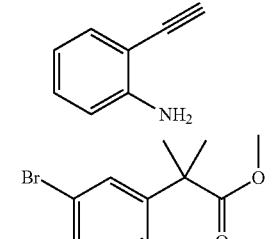 | 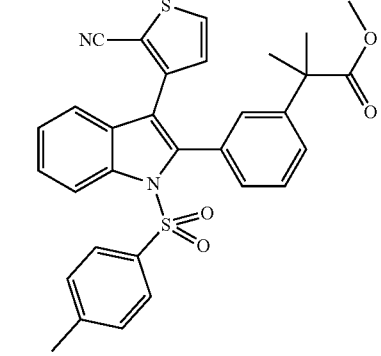 [SMILES: COC(=O)C(C)(C)c1cccc(-c2c(-c3ccsc3C#N)c3ccccc3n2S(=O)(=O)c2ccc(C)cc2)c1] | |

-continued
| # | building block(s) | structure | analytical data |
|---|---|---|---|
| 1/26 | 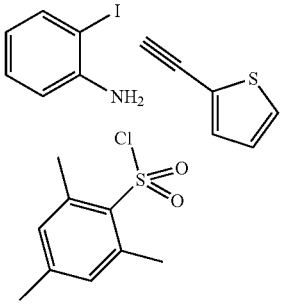 | 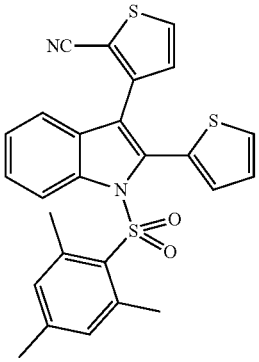 [SMILES: Cc1cc(C)c(S(=O)(=O)n2c(-c3cccs3)c(-c3ccsc3C#N)c3ccccc32)c(C)c1] | ¹H-NMR (500 MHz, DMSO-d₆) δ: 8.21 (d, J = 8.5 Hz, 1H), 7.99 (d, J = 5.0 Hz, 1H), 7.55-7.51 (m, 2H), 7.46 (d, J = 7.5 Hz 1H), 7.40 (t, J = 7.5 Hz, 1H), 6.99 (d, J = 5.0 Hz, 1H), 6.94-6.89 (m, 4H), 2.23 (s, 3H), 2.06 (s, 6H); MS: 510.8 (M + Na)⁺. |
| 1/27 | 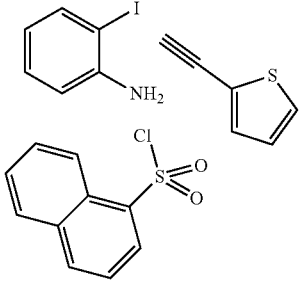 | 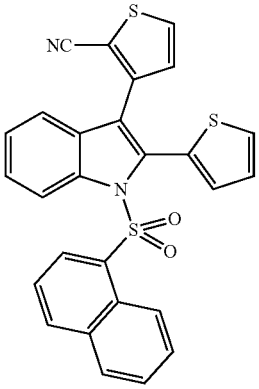 [SMILES: N#Cc1sccc1-c1c(-c2cccs2)n(S(=O)(=O)c2cccc3ccccc23)c2ccccc12] | ¹H-NMR (500 MHz, DMSO-d₆) δ: 8.33 (d, J = 8.0 Hz, 1H), 8.24 (d, J = 8.0 Hz, 1H), 8.08 (d, J = 8.0 Hz, 1H), 8.02 (d, J = 8.0 Hz, 1H), 7.98 (d, J = 5.0 Hz, 1H), 7.70 (d, J = 7.5 Hz, 1H), 7.63-7.43 (m, 7H), 7.05-6.95 (m, 3H); MS: 519.3 (M + Na)⁺. |
| 1/28 | 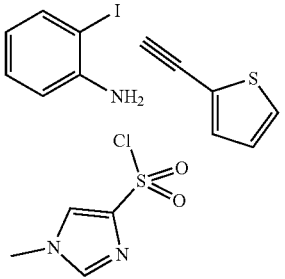 | 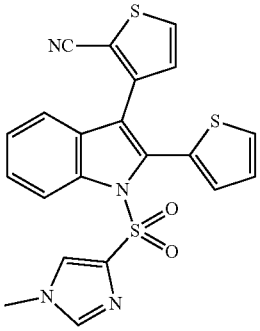 [SMILES: Cn1cnc(S(=O)(=O)n2c(-c3cccs3)c(-c3ccsc3C#N)c3ccccc32)c1] | ¹H-NMR (500 MHz, DMSO-d₆) δ: 8.20 (d, J = 10.5 Hz, 1H), 8.02 (d, J = 6.5 Hz, 1H), 7.81 (s, 1H), 7.78 (s, 1H), 7.67-7.66 (m, 1H), 7.50-7.30 (m, 4H), 7.09 (dd, J = 4.5, 6.5 Hz, 1H), 7.04 (d, J = 6.0 Hz, 1H), 3.63 (s, 3H); MS: 450.8 (M + 1)⁺. |
| 1/29 | 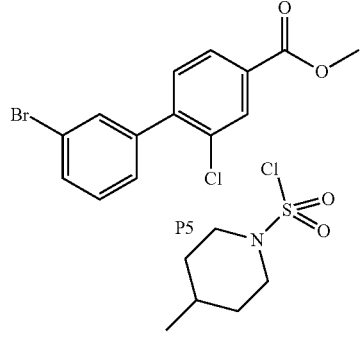 | 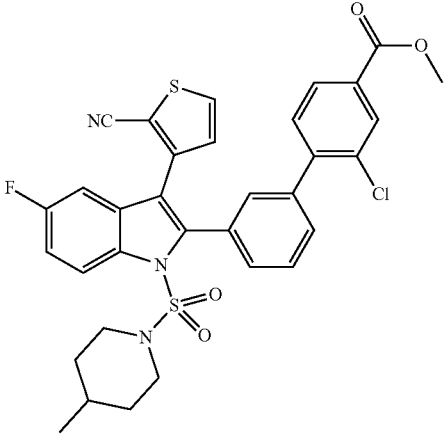 [SMILES: COC(=O)c1ccc(-c2cccc(-c3c(-c4ccsc4C#N)c4cc(F)ccc4n3S(=O)(=O)N3CCC(C)CC3)c2)c(Cl)c1] | |

-continued
| # | building block(s) | structure | analytical data |
|---|---|---|---|
1/30 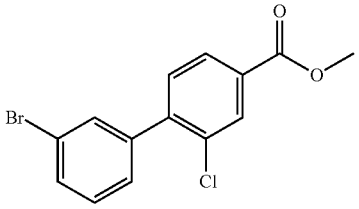
1/31 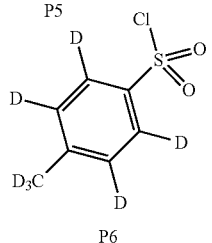
1/32 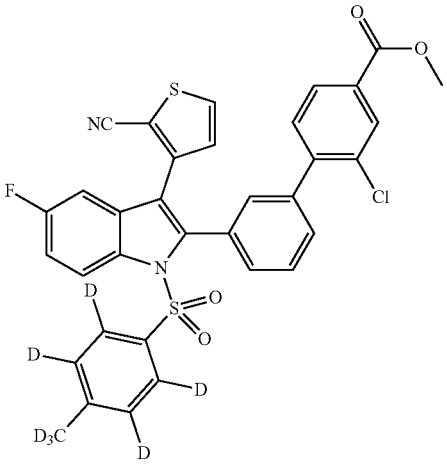 [SMILES: [2H]c1c([2H])c(S(=O)(=O)n2c(-c3cccc(-c4ccc(C(=O)OC)cc4Cl)c3)c(-c3ccsc3C#N)c3cc(F)ccc32)c([2H])c([2H])c1C([2H])([2H])[2H]]

-continued
| # | building block(s) | structure | analytical data |
|---|---|---|---|
| 1/33 | 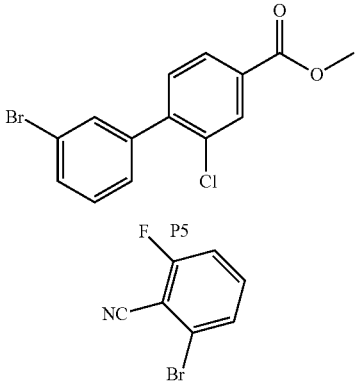 | 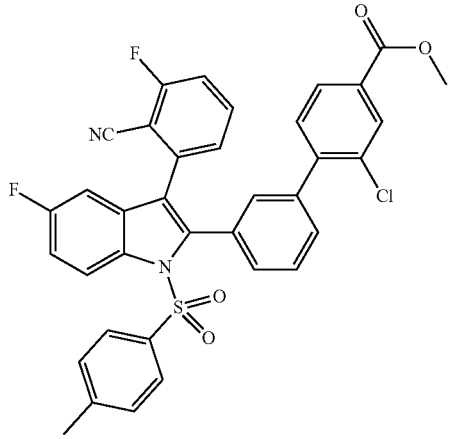 [SMILES: COC(=O)c1ccc(-c2cccc(-c3c(-c4cccc(F)c4C#N)c4cc(F)ccc4n3S(=O)(=O)c3ccc(C)cc3)c2)c(Cl)c1] | |
| 1/34 | 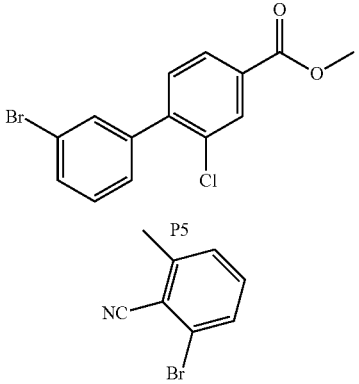 | 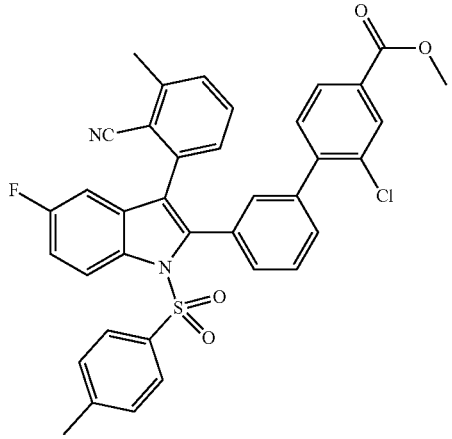 | |
| 1/35 | 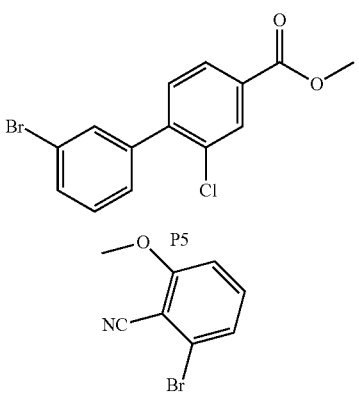 | 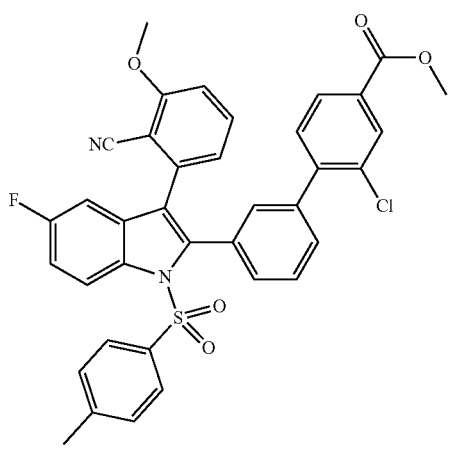 [SMILES: COC(=O)c1ccc(-c2cccc(-c3c(-c4cccc(OC)c4C#N)c4cc(F)ccc4n3S(=O)(=O)c3ccc(C)cc3)c2)c(Cl)c1] | |

| # | building block(s) | structure | analytical data |
|---|---|---|---|
| 1/36 | 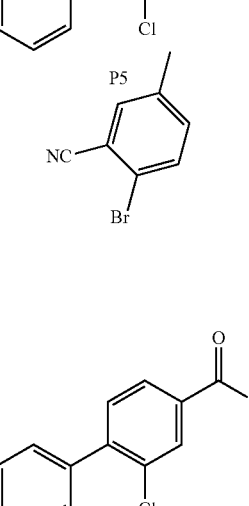 | 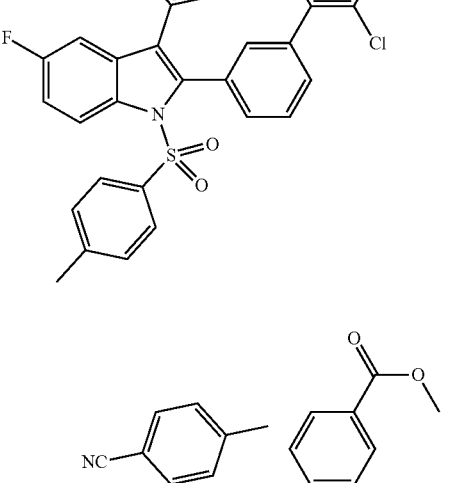 | |
| 1/37 | 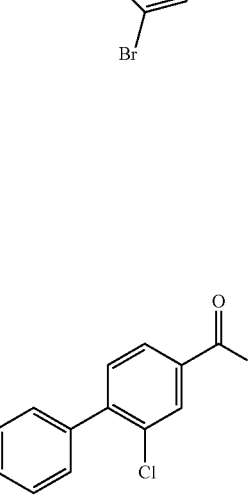 | 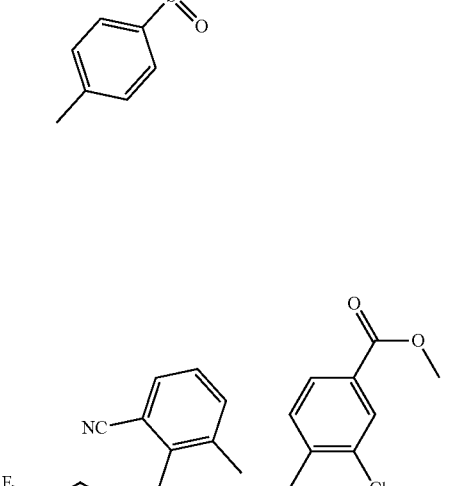 | |
| 1/38 |  | 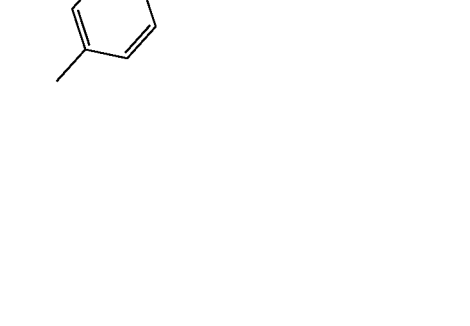 | |

-continued

| # | building block(s) | structure | analytical data |
|---|---|---|---|
| 1/39 | | 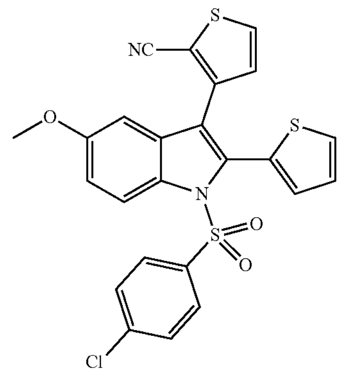 [SMILES: COc1ccc2c(c1)c(-c1ccsc1C#N)c(-c1cccs1)n2S(=O)(=O)c1ccc(Cl)cc1] | ¹H-NMR (500 MHz, DMSO-d₆) δ: 8.16 (d, J = 9.5 Hz, 1H), 8.04 (d, J = 5.0 Hz, 1H), 7.74 (d, J = 4.5 Hz, 1H), 7.60 (d, J = 8.5 Hz, 2H), 7.49 (d, J = 8.5 Hz, 2H), 7.22-7.21 (m, 1H). 7.16-7.12 (m, 2H), 7.03 (d, J = 5.5 Hz, 1H), 6.78 (s, 1H), 3.76 (s, 3H); MS: 510.8 (M + 1)⁺. |
| 1/40 | | 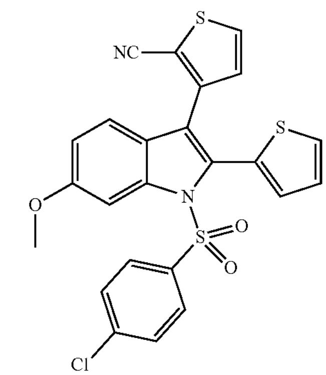 [SMILES: COc1ccc2c(-c3ccsc3C#N)c(-c3cccs3)n(S(=O)(=O)c3ccc(Cl)cc3)c2c1] | ¹H-NMR (500 MHz, DMSO-d₆) δ: 8.03 (d, J = 5.0 Hz, 1H), 7.76 (d, J = 1.5 Hz, 1H), 7.72 (d, J = 5.0 Hz, 1H), 7.61 (d, J = 8.5 Hz, 2H), 7.55 (d, J = 8.5 Hz, 2H), 7.27 (d, J = 9.0 Hz, 1H), 7.19-7.17 (m, 1H), 7.11-7.09 (m, 1H), 7.05 (dd, J = 2.5, 8.5 Hz, 1H), 7.01 (d, J = 5.5 Hz, 1H), 3.91 (s, 3H); MS: 510.8 (M + 1)⁺. |
| 1/41 | | 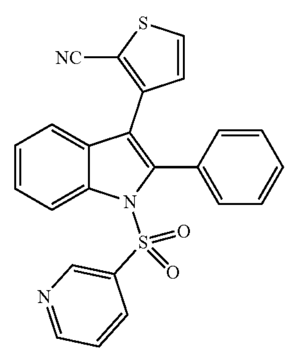 [SMILES: N#Cc1sccc1-c1c(-c2ccccc2)n(S(=O)(=O)c2cccnc2)c2ccccc12] | ¹H-NMR (500 MHz, DMSO-d₆) δ: 8.82 (d, 4.0 Hz, 1H), 8.62 (s, 1H), 8.30 (d, J = 8.0 Hz, 1H), 8.01 (d, J = 4.5 Hz, 1H), 7.87 (d, J = 8.5 Hz, 1H), 7.58-7.53 (m, 2H), 7.46-7.35 (m, 5H), 7.30 (d, J = 7.0 Hz, 2H), 6.97 (d, J = 4.5 Hz, 1H); MS: 441.9 (M + 1)⁺. |
| 1/42 | | 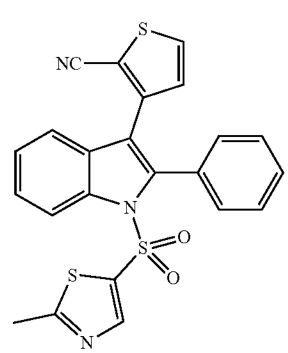 [SMILES: Cc1ncc(S(=O)(=O)n2c(-c3ccccc3)c(-c3ccsc3C#N)c3ccccc32)s1] | ¹H-NMR (500 MHz, DMSO-d₆) δ: 8.19 (d, J = 8.5 Hz, 1H), 8.05-8.02 (m, 2H), 7.57-7.54 (m, 1H), 7.46-7.33 (m, 7H), 6.97 (d, J = 5.0 Hz, 1H), 2.63 (s, 3H); MS: 462.1 (M + 1)⁺. |

| # | building block(s) | structure | analytical data |
|---|---|---|---|
| 1/43 | | 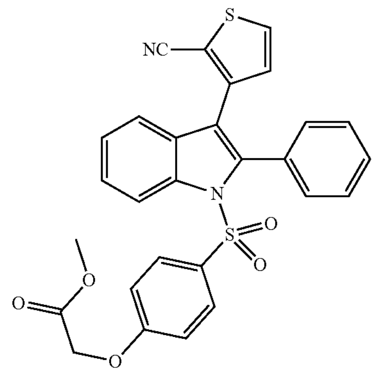 [SMILES: COC(=O)COc1ccc(S(=O)(=O)n2c(-c3ccccc3)c(-c3ccsc3C#N)c3ccccc32)cc1] | |
| 1/44 | | 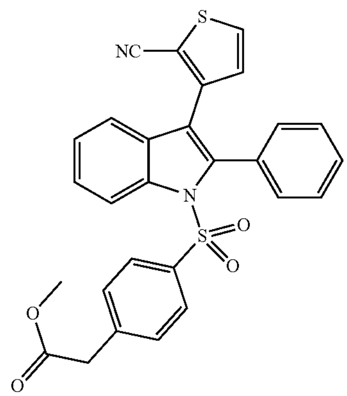 [SMILES: COC(=O)Cc1ccc(S(=O)(=O)n2c(-c3ccccc3)c(-c3ccsc3C#N)c3ccccc32)cc1] | |
| 1/45 | | 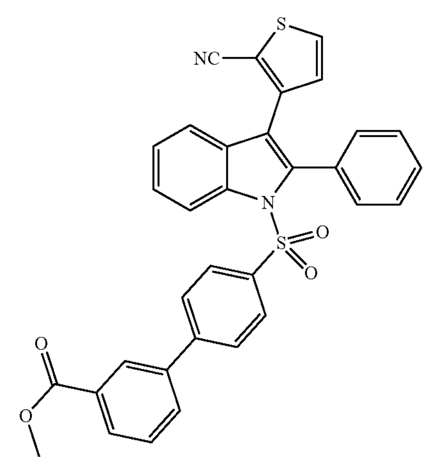 [SMILES: COC(=O)c1cccc(-c2ccc(S(=O)(=O)n3c(-c4ccccc4)c(-c4ccsc4C#N)c4ccccc43)cc2)c1] | |
| 1/46 | | 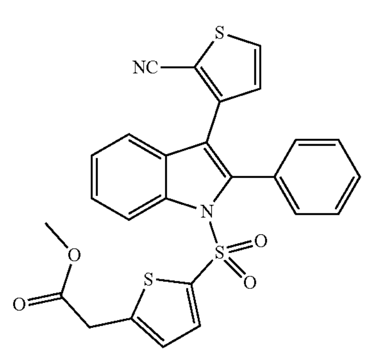 [SMILES: COC(=O)Cc1ccc(S(=O)(=O)n2c(-c3ccccc3)c(-c3ccsc3C#N)c3ccccc32)s1] | |

-continued

| # | building block(s) | structure | analytical data |
|---|---|---|---|
| 1/47 | | 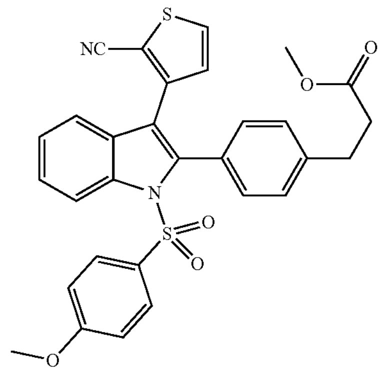 [SMILES: COC(=O)CCc1ccc(-c2c(-c3ccsc3C#N)c3ccccc3n2S(=O)(=O)c2ccc(OC)cc2)cc1] | |
| 1/48 | | 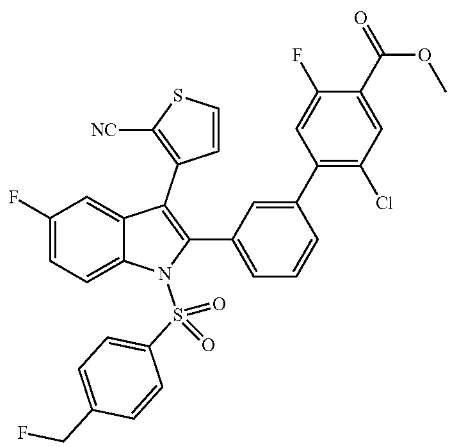 [SMILES: COC(=O)c1cc(Cl)c(-c2cccc(-c3c(-c4ccsc4C#N)c4cc(F)ccc4n3S(=O)(=O)c3ccc(CF)cc3)c2)cc1F] | |
| 1/49 | | 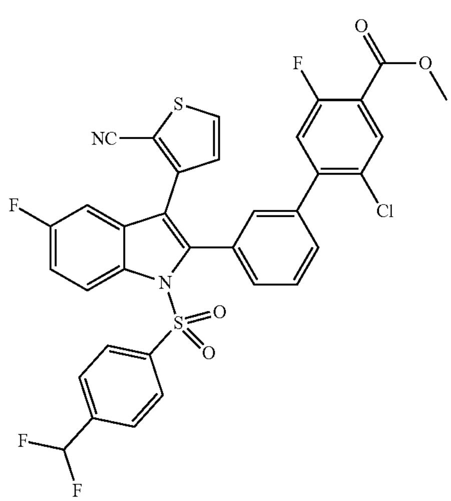 [SMILES: COC(=O)c1cc(Cl)c(-c2cccc(-c3c(-c4ccsc4C#N)c4cc(F)ccc4n3S(=O)(=O)c3ccc(C(F)F)cc3)c2)cc1F] | |

| # | building block(s) | structure | analytical data |
|---|---|---|---|
| 1/50 | 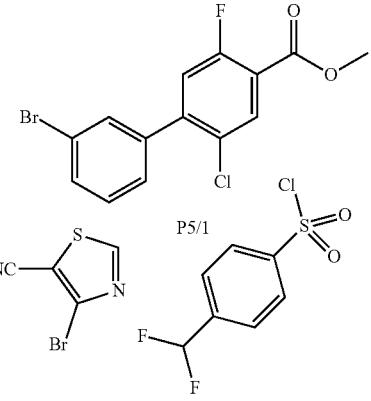 P5/1 | 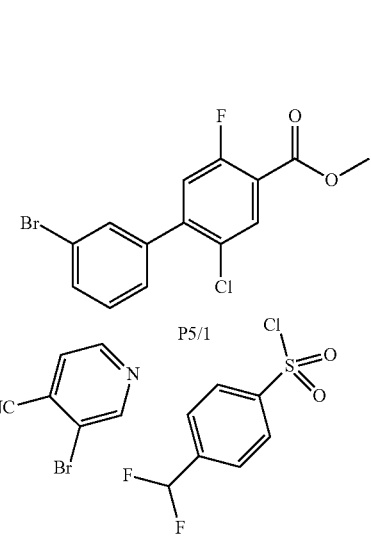 | |
| 1/51 | 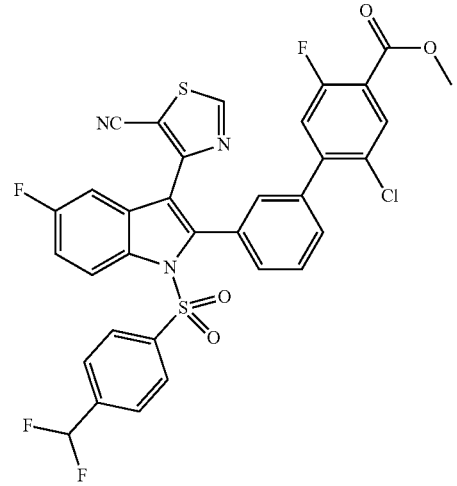 P5/1 | 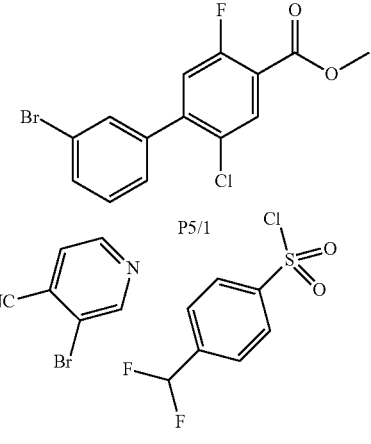 | |
| 1/52 | 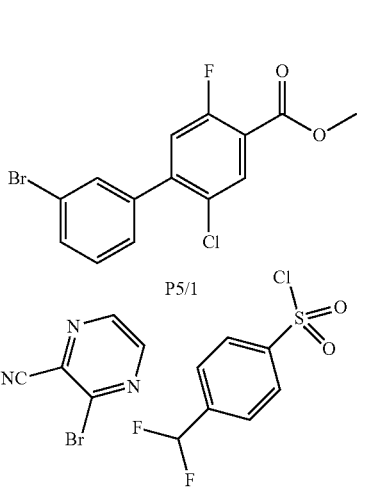 P5/1 | 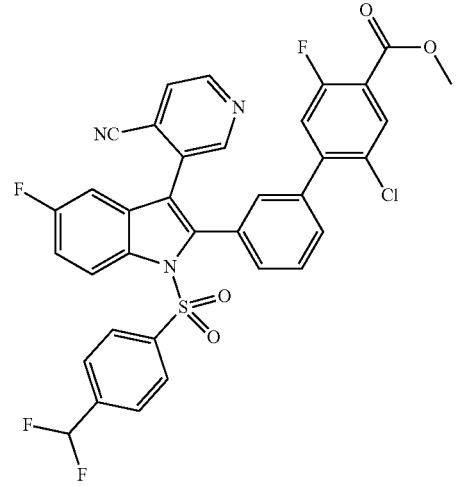 [SMILES: COC(=O)c1cc(Cl)c(-c2cccc(-c3c(-c4cnccc4C#N)c4cc(F)ccc4n3S(=O)(=O)c3ccc(C(F)F)cc3)c2)cc1F] | |

| # | building block(s) | structure | analytical data |
|---|---|---|---|
| 1/53 | | 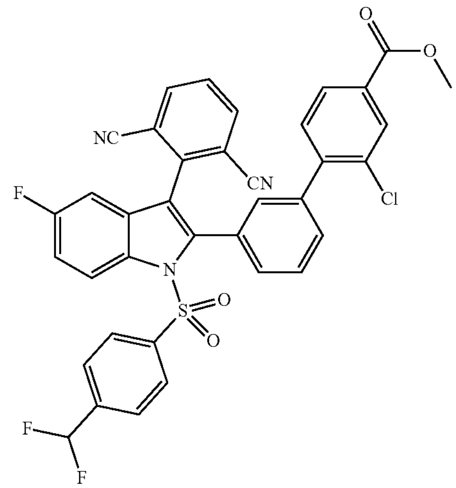 [SMILES: COC(=O)c1ccc(-c2cccc(-c3c(-c4c(C#N)cccc4C#N)c4cc(F)ccc4n3S(=O)(=O)c3ccc(C(F)F)cc3)c2)c(Cl)c1] | |
| 1/54 | | 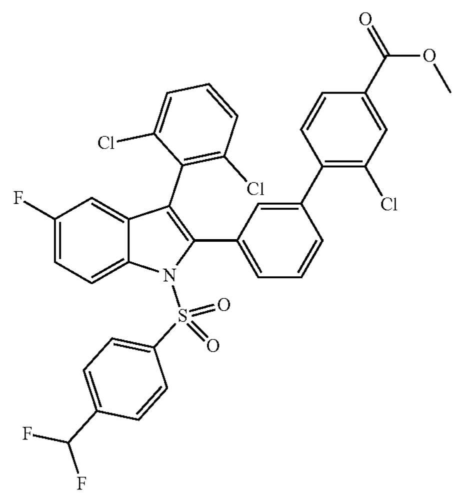 [SMILES: COC(=O)c1ccc(-c2cccc(-c3c(-c4c(Cl)cccc4Cl)c4cc(F)ccc4n3S(=O)(=O)c3ccc(C(F)F)cc3)c2)c(Cl)c1] | |
| 1/55 | | 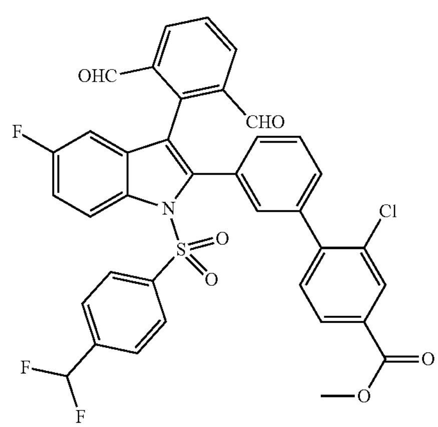 [SMILES: COC(=O)c1ccc(-c2cccc(-c3c(-c4c(C=O)cccc4C=O)c4cc(F)ccc4n3S(=O)(=O)c3ccc(C(F)F)cc3)c2)c(Cl)c1] | |

| # | building block(s) | structure | analytical data |
|---|---|---|---|
| 1/56 | P16 | 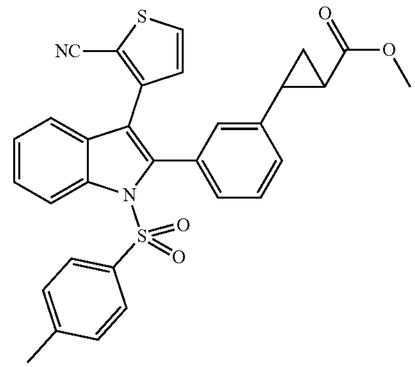 | |
| 1/57 | P17 | 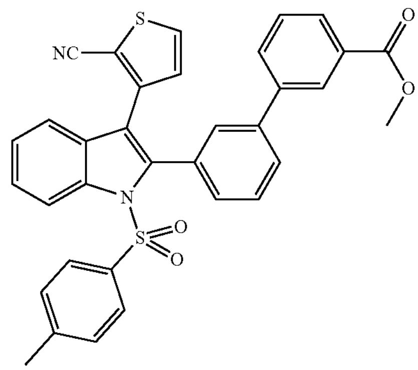 | |
| 1/58 | P17/1 | 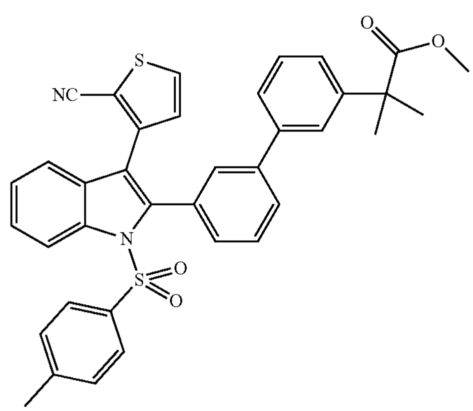 | |
| 1/59 | P17/2 | 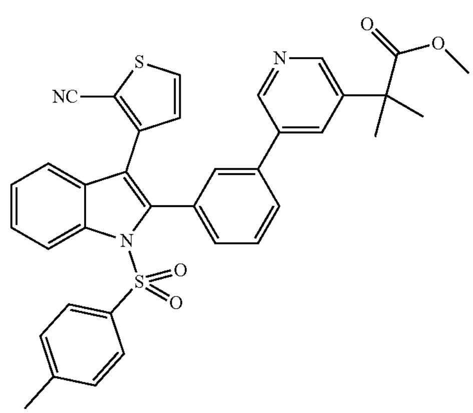 | |
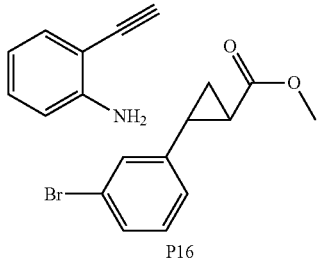
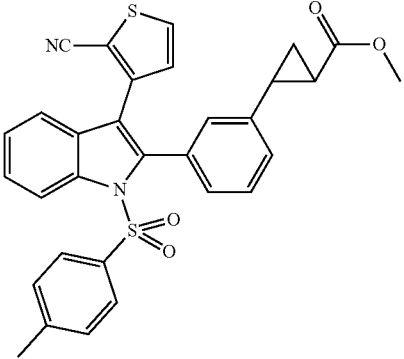 [SMILES: COC(=O)C1CC1c1cccc(-c2c(-c3ccsc3C#N)c3ccccc3n2S(=O)(=O)c2ccc(C)cc2)c1]
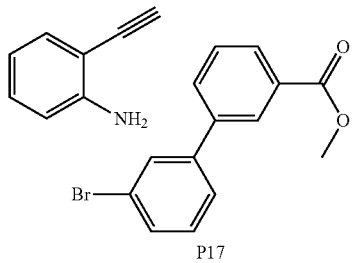
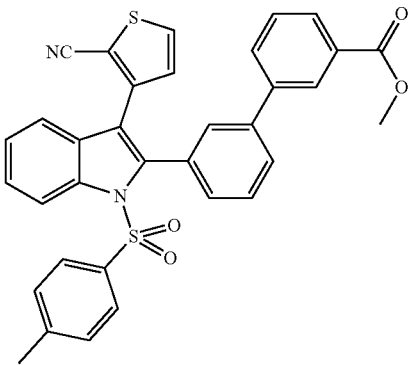 [SMILES: COC(=O)c1cccc(-c2cccc(-c3c(-c4ccsc4C#N)c4ccccc4n3S(=O)(=O)c3ccc(C)cc3)c2)c1]
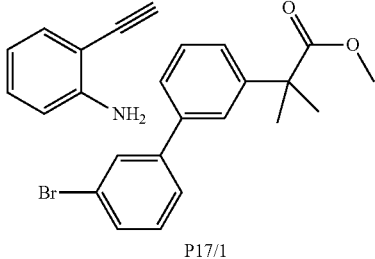
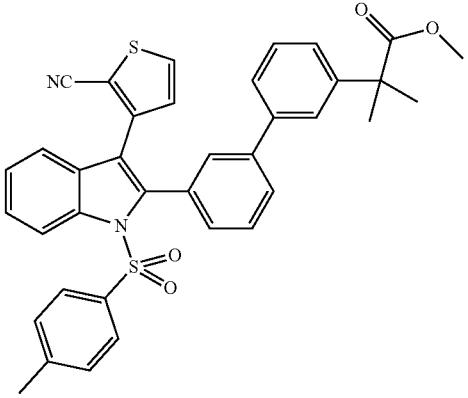 [SMILES: COC(=O)C(C)(C)c1cccc(-c2cccc(-c3c(-c4ccsc4C#N)c4ccccc4n3S(=O)(=O)c3ccc(C)cc3)c2)c1]
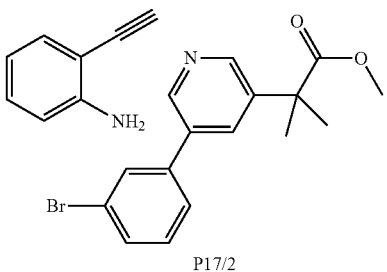
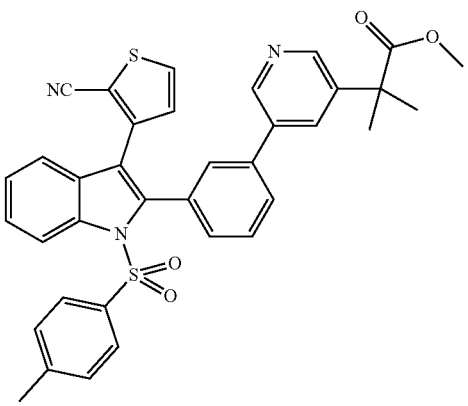 [SMILES: COC(=O)C(C)(C)c1cncc(-c2cccc(-c3c(-c4ccsc4C#N)c4ccccc4n3S(=O)(=O)c3ccc(C)cc3)c2)c1]

| # | building block(s) | structure | analytical data |
|---|---|---|---|
| 1/60 | 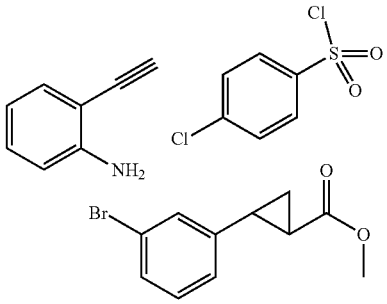 P16 | 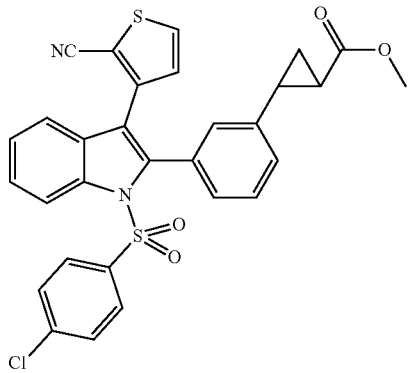 [SMILES: COC(=O)C1CC1c1cccc(-c2c(-c3ccsc3C#N)c3ccccc3n2S(=O)(=O)c2ccc(Cl)cc2)c1] | |
| 1/61 | 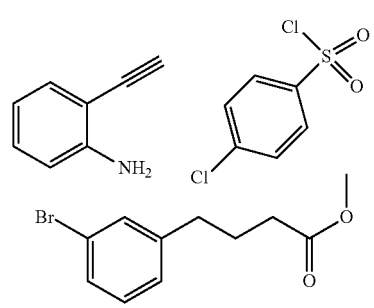 P9 | 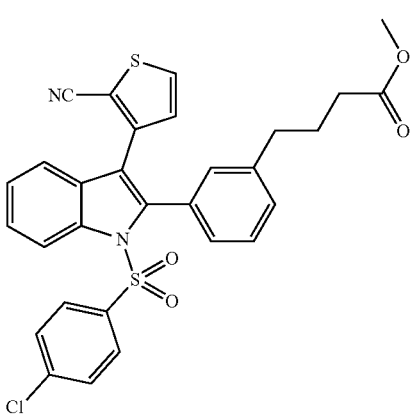 [SMILES: COC(=O)CCCc1cccc(-c2c(-c3ccsc3C#N)c3ccccc3n2S(=O)(=O)c2ccc(Cl)cc2)c1] | |
| 1/62 | 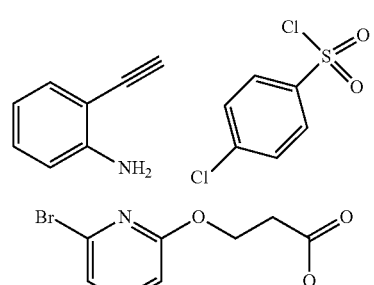 P11 | 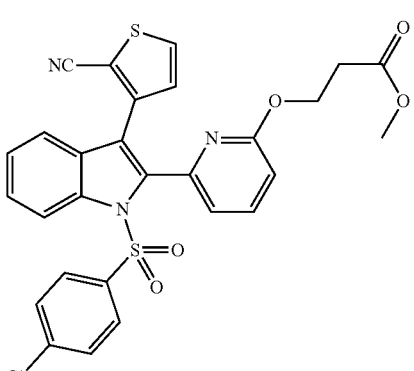 | |
| 1/63 | 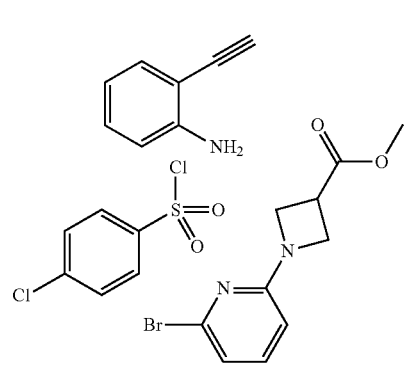 P14 | 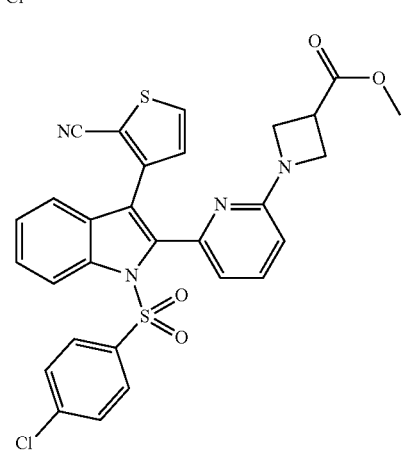 | |

-continued
| # | building block(s) | structure | analytical data |
|---|---|---|---|
| 1/64 | 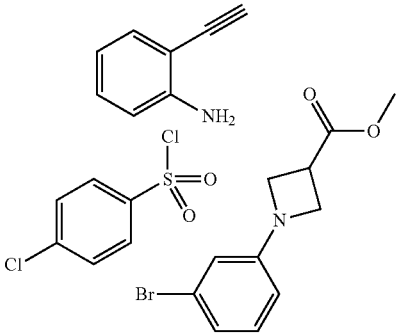 P12 | 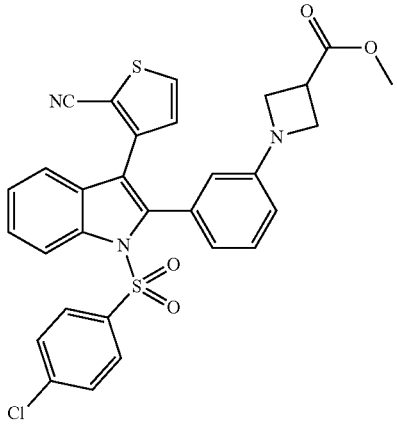 [SMILES: COC(=O)C1CN(c2cccc(-c3c(-c4ccsc4C#N)c4ccccc4n3S(=O)(=O)c3ccc(Cl)cc3)n2)C1] | |
| 1/65 | 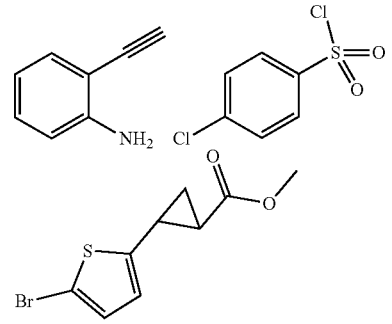 P16/1 | 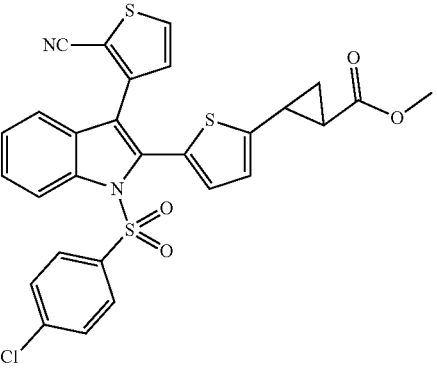 [SMILES: COC(=O)C1CC1c1ccc(-c2c(-c3ccsc3C#N)c3ccccc3n2S(=O)(=O)c2ccc(Cl)cc2)s1] | |
| 1/66 | 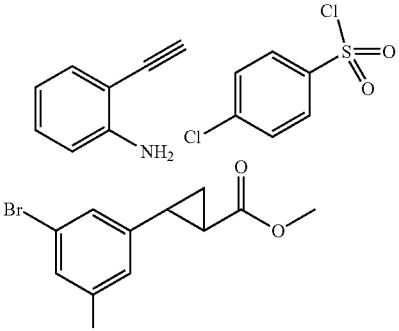 P16/2 | 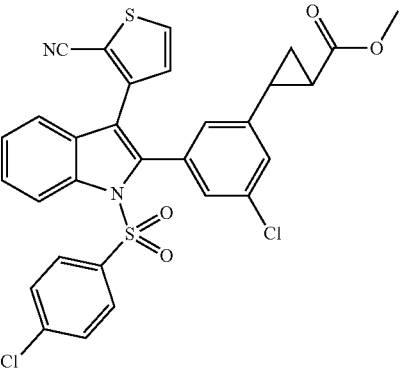 [SMILES: COC(=O)C1CC1c1cc(Cl)cc(-c2c(-c3ccsc3C#N)c3ccccc3n2S(=O)(=O)c2ccc(Cl)cc2)c1] | |
| 1/67 | 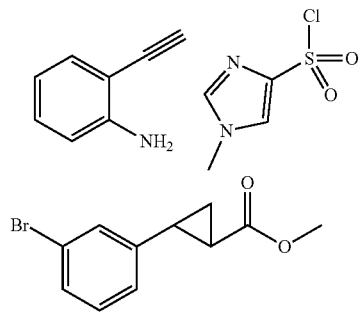 P16 | 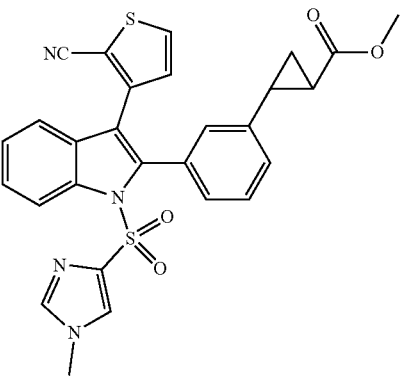 [SMILES: COC(=O)C1CC1c1cccc(-c2c(-c3ccsc3C#N)c3ccccc3n2S(=O)(=O)c2cn(C)cn2)c1] | |

-continued
| # | building block(s) | structure | analytical data |
|---|---|---|---|
| 1/68 | 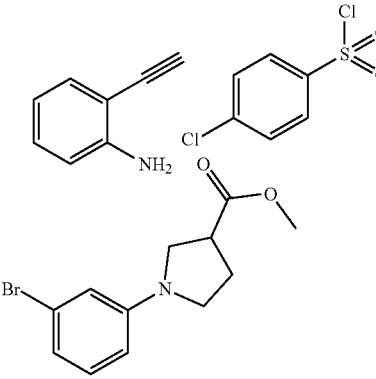 P12/1 | 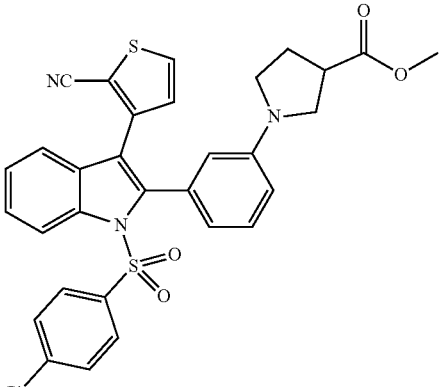 | |
| 1/69 | 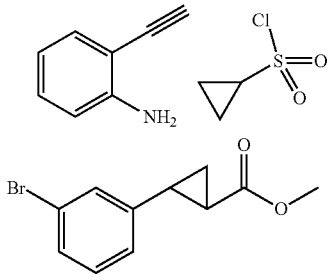 P16 | 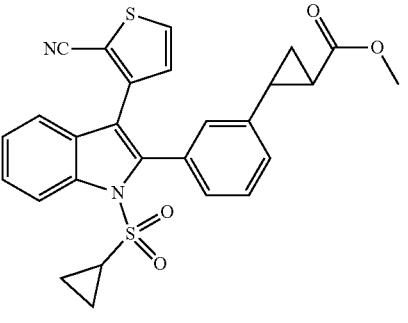 [SMILES: COC(=O)C1CC1c1cccc(-c2c(-c3ccsc3C#N)c3ccccc3n2S(=O)(=O)C2CC2)c1] | |
| 1/70 | 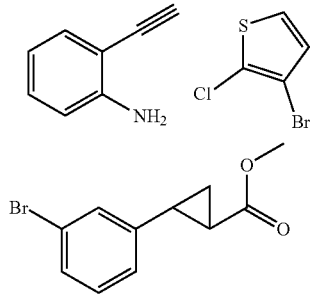 P16 | 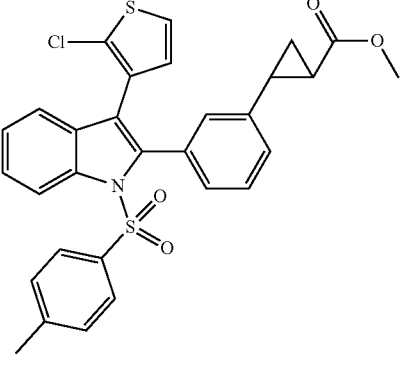 | |
| 1/71 | 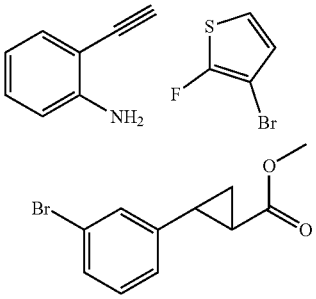 P16 | 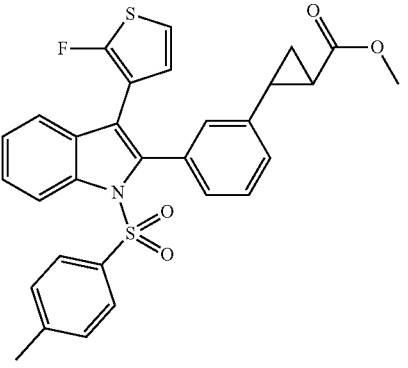 [SMILES: COC(=O)C1CC1c1cccc(-c2c(-c3ccsc3F)c3ccccc3n2S(=O)(=O)c2ccc(C)cc2)c1] | |

-continued
| # | building block(s) | structure | analytical data |
|---|---|---|---|
| 1/72 | 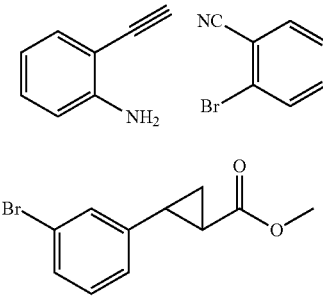 | 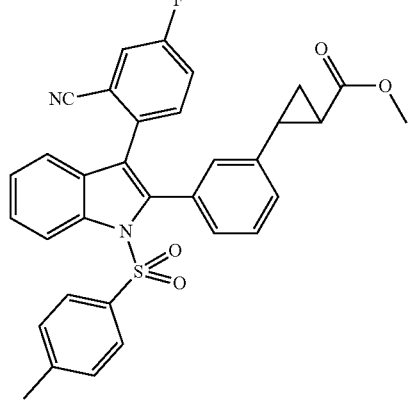 | |
| 1/73 | 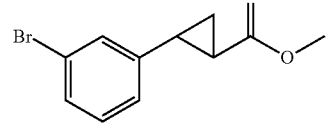 | 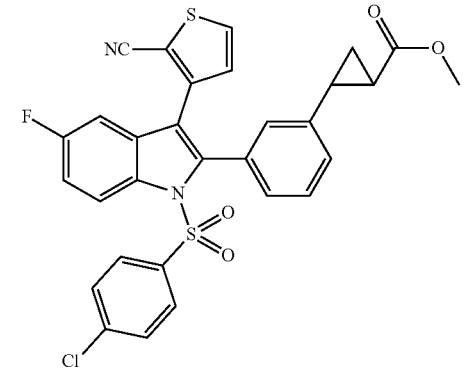 [SMILES: COC(=O)C1CC1c1cccc(-c2c(-c3ccsc3C#N)c3cc(F)ccc3n2S(=O)(=O)c2ccc(Cl)cc2)c1] | |
| 1/74 | 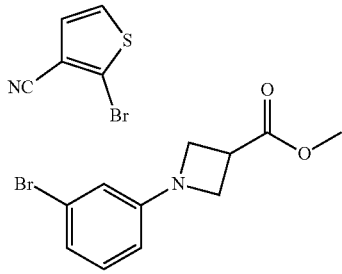 | 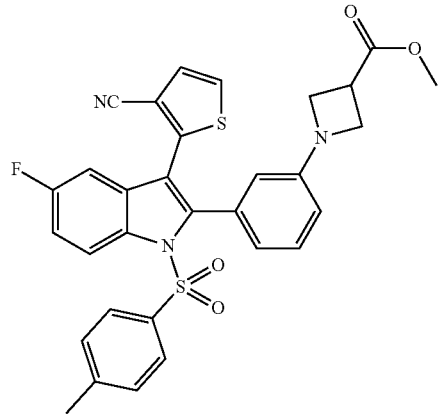 [SMILES: COC(=O)C1CN(c2cccc(-c3c(-c4sccc4C#N)c4cc(F)ccc4n3S(=O)(=O)c3ccc(C)cc3)c2)C1] | |

-continued
| # | building block(s) | structure | analytical data |
|---|---|---|---|
| 1/75 | 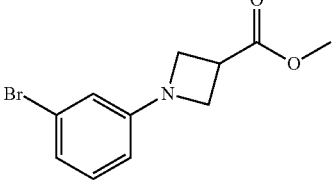 P12 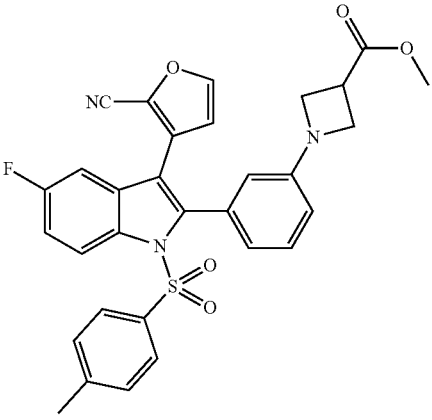 P19 | 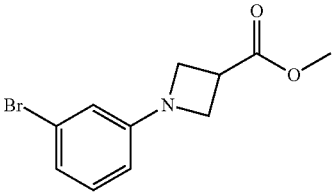 | |
| 1/76 | 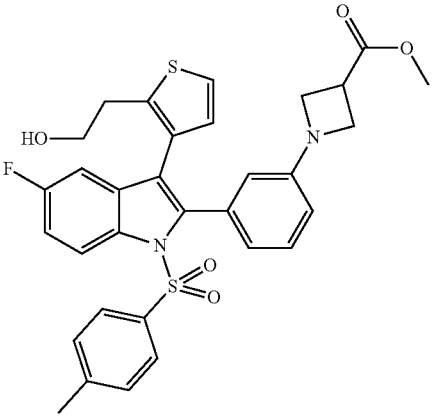 P12 | 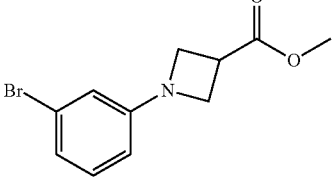 | |
| 1/77 | 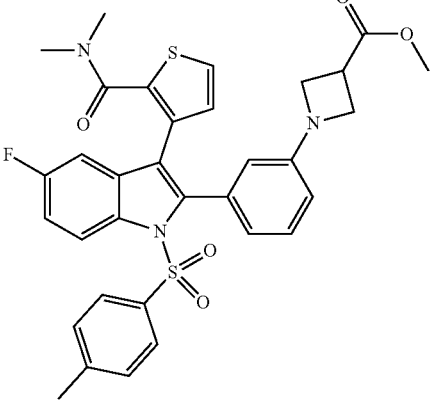 P12 | 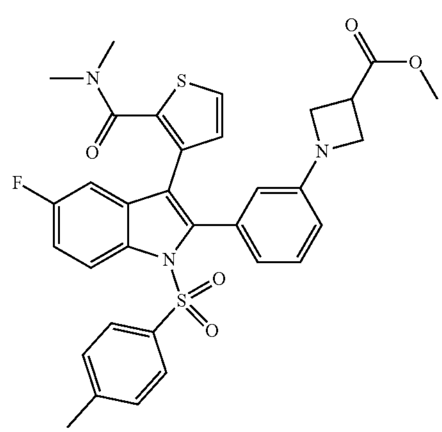 [SMILES: COC(=O)C1CN(c2cccc(-c3c(-c4ccsc4C(=O)N(C)C)c4cc(F)ccc4n3S(=O)(=O)c3ccc(C)cc3)c2)C1] | |

| # | building block(s) | structure | analytical data |
|---|---|---|---|
| C1/78 | 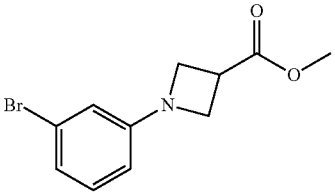 P12 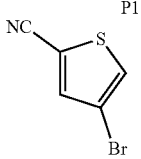 | 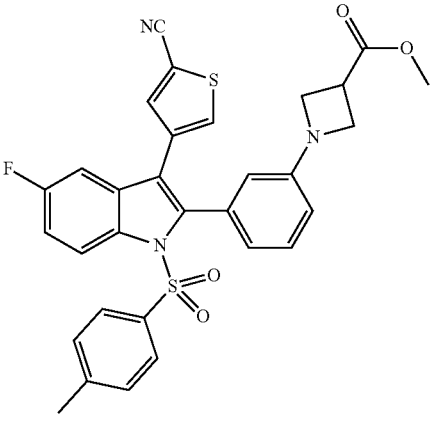 [SMILES: COC(=O)C1CN(c2cccc(-c3c(-c4csc(C#N)c4)c4cc(F)ccc4n3S(=O)(=O)c3ccc(C)cc3)c2)C1] | |
| 1/79 | 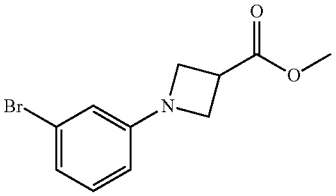 P12 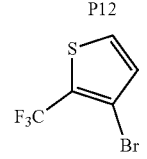 | 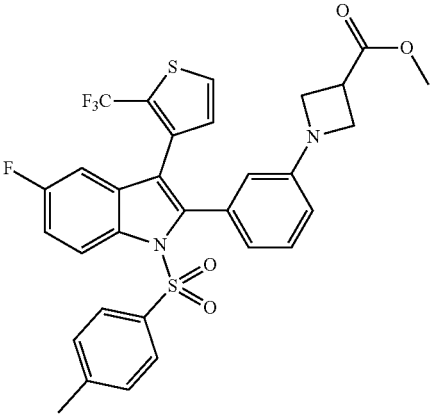 [SMILES: COC(=O)C1CN(c2cccc(-c3c(-c4ccsc4C(F)(F)F)c4cc(F)ccc4n3S(=O)(=O)c3ccc(C)cc3)c2)C1] | |
| 1/80 | 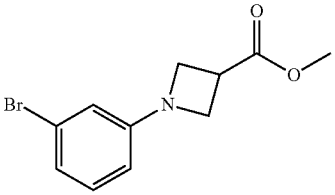 P12 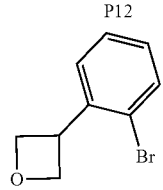 | 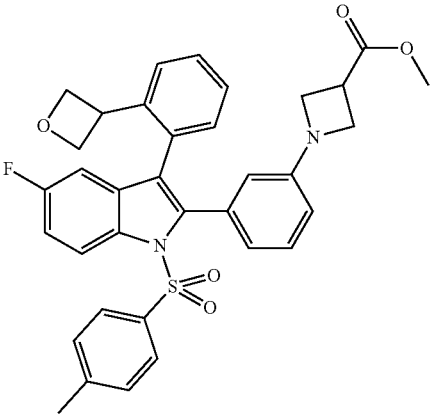 [SMILES: COC(=O)C1CN(c2cccc(-c3c(-c4ccccc4C4COC4)c4cc(F)ccc4n3S(=O)(=O)c3ccc(C)cc3)c2)C1] | |

| # | building block(s) | structure | analytical data |
|---|---|---|---|
| 1/81 | P12 | 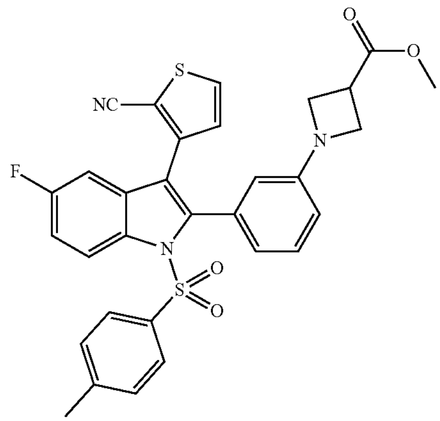 [SMILES: COC(=O)C1CN(c2cccc(-c3c(-c4ccsc4C#N)c4cc(F)ccc4n3S(=O)(=O)c3ccc(C)cc3)c2)C1] | |
| 1/82 | P12 | 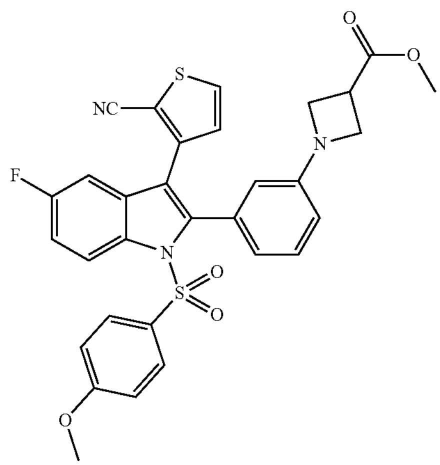 [SMILES: COC(=O)C1CN(c2cccc(-c3c(-c4ccsc4C#N)c4cc(F)ccc4n3S(=O)(=O)c3ccc(OC)cc3)c2)C1] | |
| 1/83 | P12 | 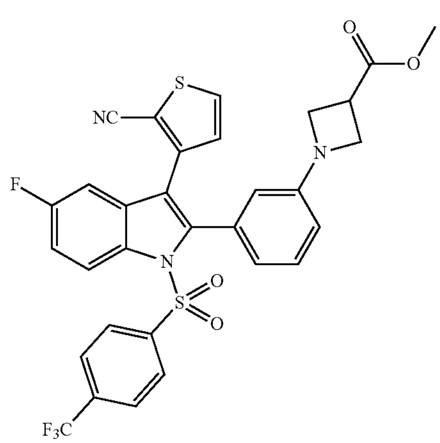 [SMILES: COC(=O)C1CN(c2cccc(-c3c(-c4ccsc4C#N)c4cc(F)ccc4n3S(=O)(=O)c3ccc(C(F)F)cc3)c2)C1] | |

-continued
| # | building block(s) | structure | analytical data |
|---|---|---|---|
| 1/84 | 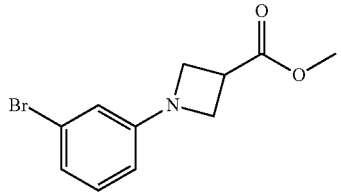 | 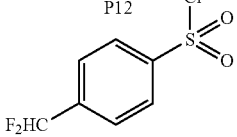 | |
| 1/85 | 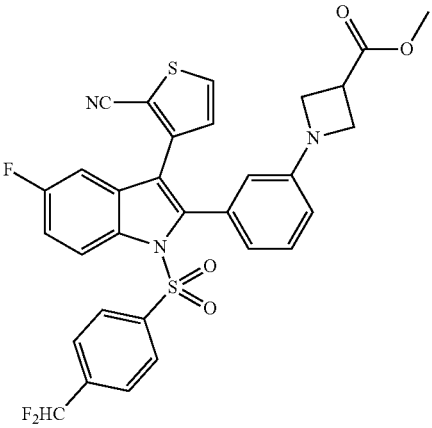 | 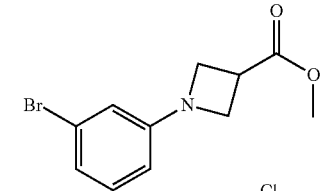 | |
| 1/86 | 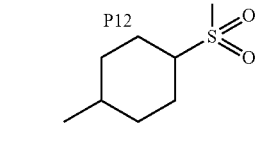 | 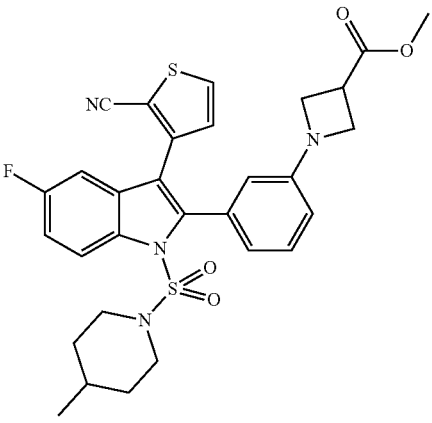 [SMILES: COC(=O)C1CN(c2cccc(-c3c(-c4ccsc4C#N)c4cc(F)ccc4n3S(=O)(=O)N3CCC(C)CC3)c2)C1] | |

-continued

| # | building block(s) | structure | analytical data |
|---|---|---|---|
| 1/87 | P13/1 | 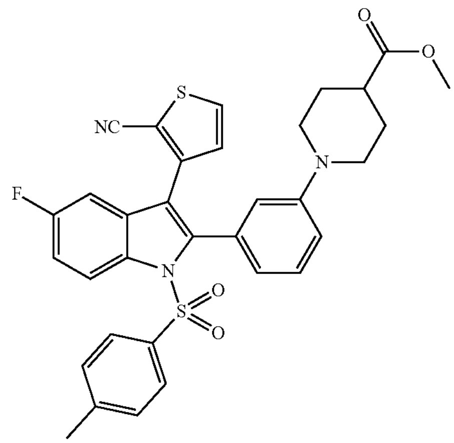 [SMILES: COC(=O)C1CCN(c2cccc(-c3c(-c4ccsc4C#N)c4cc(F)ccc4n3S(=O)(=O)c3ccc(C)cc3)c2)CC1] | |
| 1/88 | P15 | 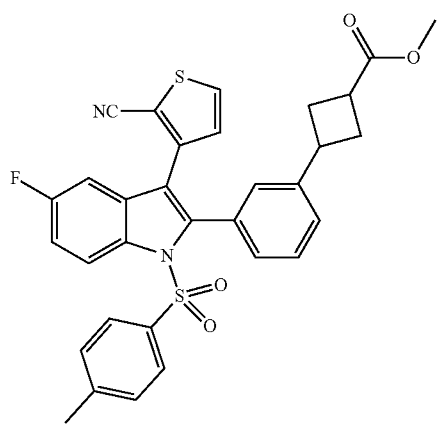 [SMILES: COC(=O)C1CC(c2cccc(-c3c(-c4ccsc4C#N)c4cc(F)ccc4n3S(=O)(=O)c3ccc(C)cc3)c2)C1] | |
| 1/89 | P13/2 | 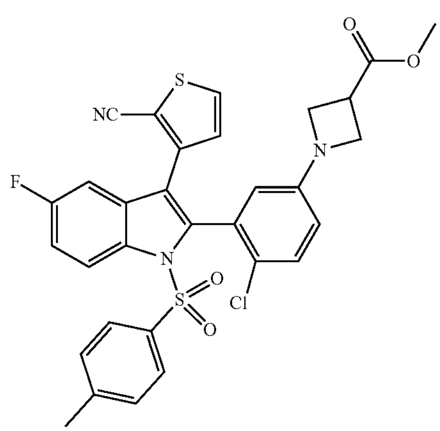 [SMILES: COC(=O)C1CN(c2ccc(Cl)c(-c3c(-c4ccsc4C#N)c4cc(F)ccc4n3S(=O)(=O)c3ccc(C)cc3)c2)C1] | |

-continued
| # | building block(s) | structure | analytical data |
|---|---|---|---|
1/90 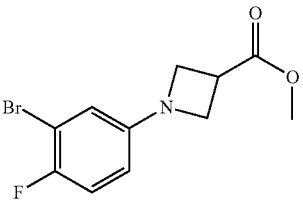 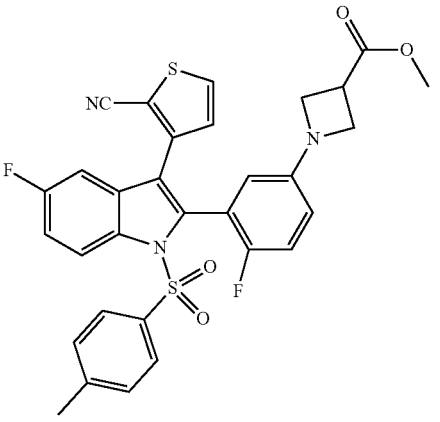 [SMILES: COC(=O)C1CN(c2ccc(F)c(-c3c(-c4ccsc4C#N)c4cc(F)ccc4n3S(=O)(=O)c3ccc(C)cc3)c2)C1]
1/91 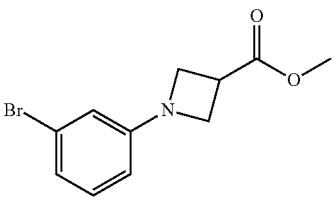 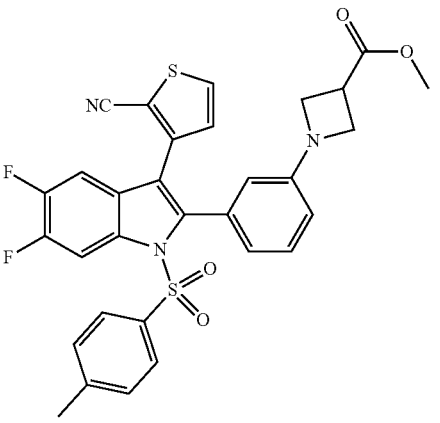 [SMILES: COC(=O)C1CN(c2cccc(-c3c(-c4ccsc4C#N)c4cc(F)c(F)cc4n3S(=O)(=O)c3ccc(C)cc3)c2)C1]
1/92 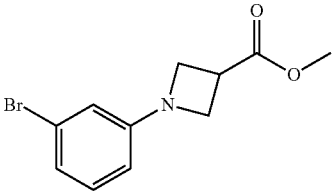 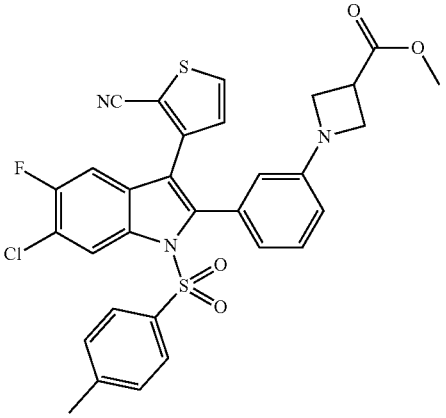 [SMILES: COC(=O)C1CN(c2cccc(-c3c(-c4ccsc4C#N)c4cc(F)c(Cl)cc4n3S(=O)(=O)c3ccc(C)cc3)c2)C1]

| # | building block(s) | structure | analytical data |
|---|---|---|---|
| 1/93 | 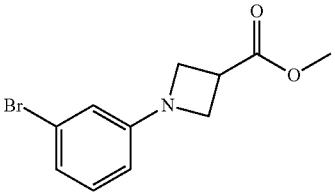 P12 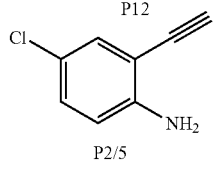 P2/5 | 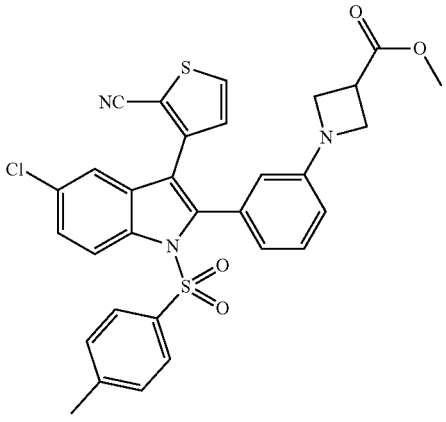 [SMILES: COC(=O)C1CN(c2cccc(-c3c(-c4ccsc4C#N)c4cc(Cl)ccc4n3S(=O)(=O)c3ccc(C)cc3)c2)C1] | |
| 1/94 | 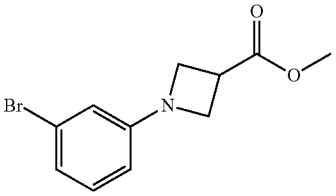 P12 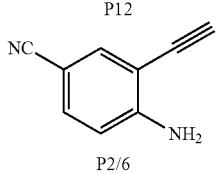 P2/6 | 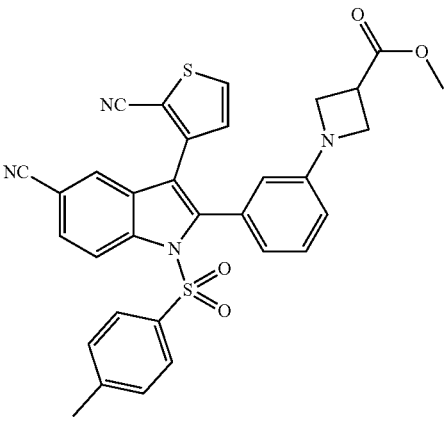 | |
| 1/95 | 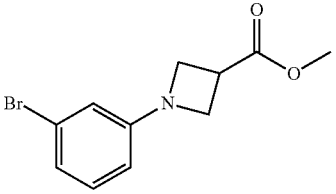 P12 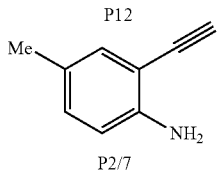 P2/7 | 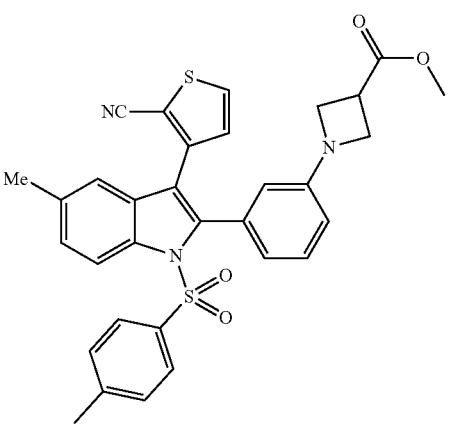 [SMILES: COC(=O)C1CN(c2cccc(-c3c(-c4ccsc4C#N)c4cc(C#N)ccc4n3S(=O)(=O)c3ccc(C)cc3)c2)C1] | |

-continued
| # | building block(s) | structure | analytical data |
|---|---|---|---|
| 1/96 | 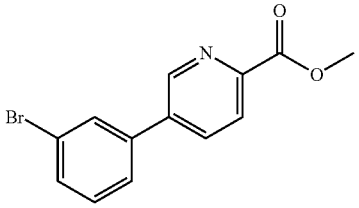  P17/3 | 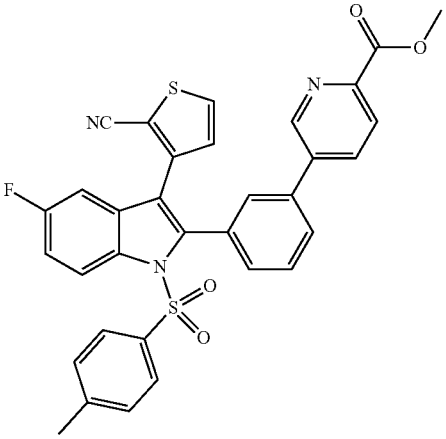 [SMILES: COC(=O)c1ccc(-c2cccc(-c3c(-c4ccsc4C#N)c4cc(F)ccc4n3S(=O)(=O)c3ccc(C)cc3)c2)cn1] | |
| 1/97 | 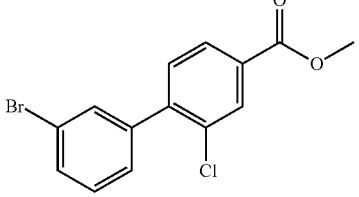  P5 | 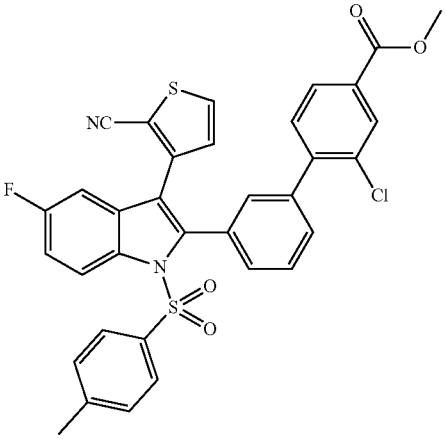 [SMILES: COC(=O)c1ccc(-c2cccc(-c3c(-c4ccsc4C#N)c4cc(F)ccc4n3S(=O)(=O)c3ccc(C)cc3)c2)c(Cl)c1] | |
| 1/98 | 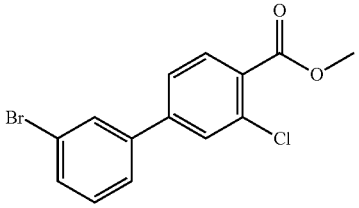  P17/4 | 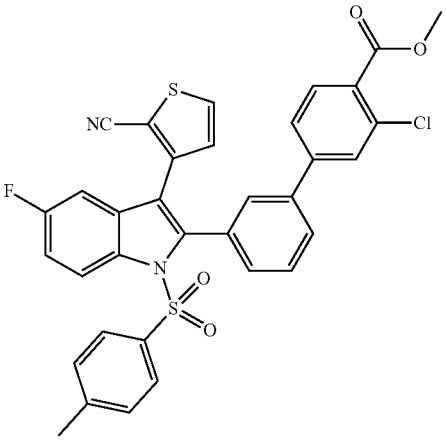 [SMILES: COC(=O)c1ccc(-c2cccc(-c3c(-c4ccsc4C#N)c4cc(F)ccc4n3S(=O)(=O)c3ccc(C)cc3)c2)cc1Cl] | |

| # | building block(s) | structure | analytical data |
|---|---|---|---|
| 1/99 | 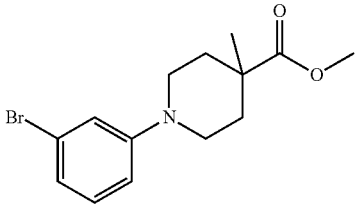 P13/4 | 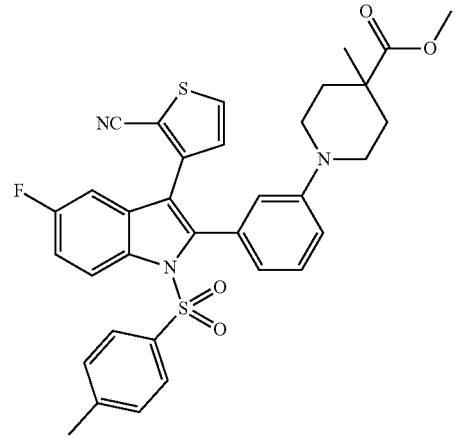 [SMILES: COC(=O)C1(C)CCN(c2cccc(-c3c(-c4ccsc4C#N)c4cc(F)ccc4n3S(=O)(=O)c3ccc(C)cc3)c2)CC1] | |
| 1/100 | 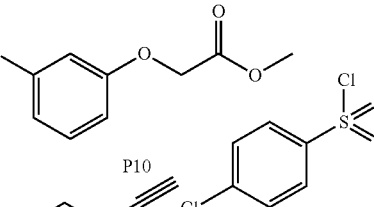 P10 | 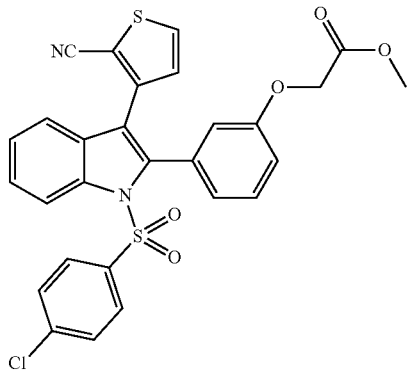 [SMILES: COC(=O)COc1cccc(-c2c(-c3ccsc3C#N)c3ccccc3n2S(=O)(=O)c2ccc(Cl)cc2)c1] | |
| 1/101 | 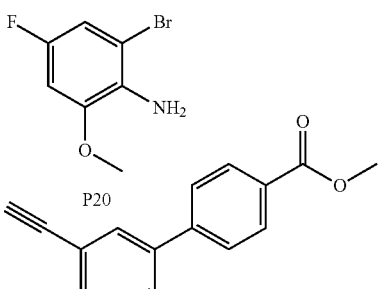 P20 | 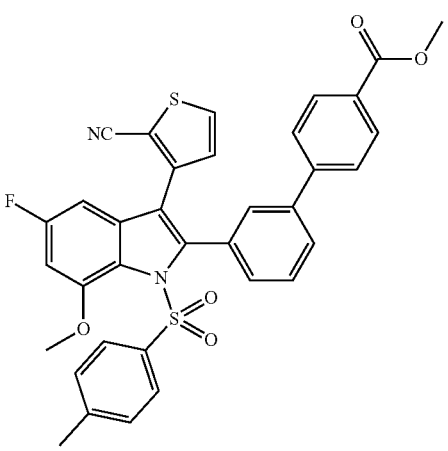 [SMILES: COC(=O)c1ccc(-c2cccc(-c3c(-c4ccsc4C#N)c4cc(F)cc(OC)c4n3S(=O)(=O)c3ccc(C)cc3)c2)cc1] | |

| # | building block(s) | structure | analytical data |
| --- | --- | --- | --- |
| 1/102 | | 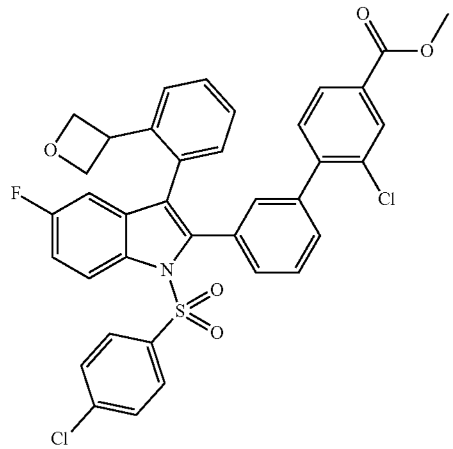 [SMILES: COC(=O)c1ccc(-c2cccc(-c3c(-c4ccccc4C4COC4)c4cc(F)ccc4n3S(=O)(=O)c3ccc(Cl)cc3)c2)c(Cl)c1] | |
| 1/103 | | 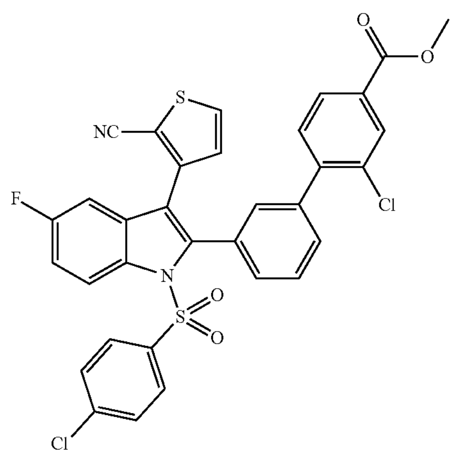 | |
| 1/104 | | 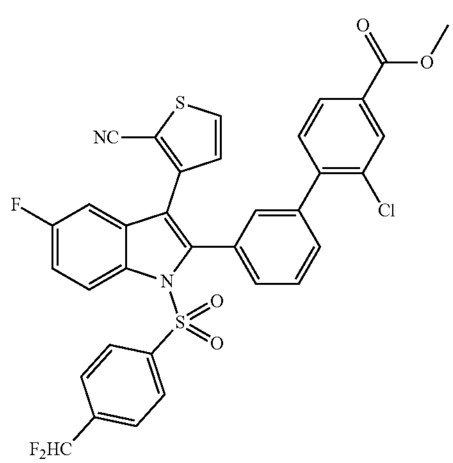 | |

| # | building block(s) | structure | analytical data |
|---|---|---|---|
| 1/ 105 | 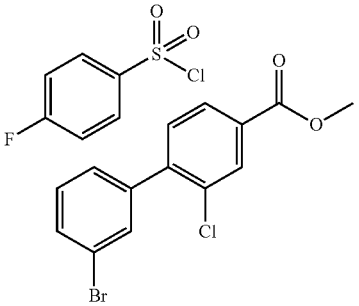 P5 | 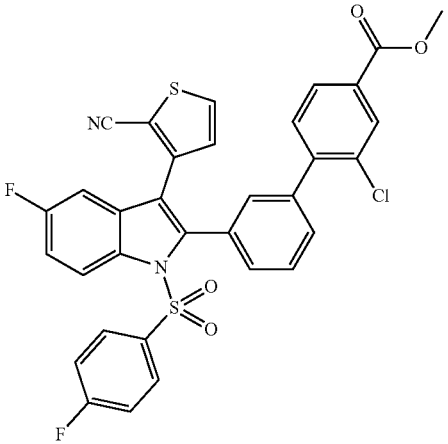 [SMILES: COC(=O)c1ccc(-c2cccc(-c3c(-c4ccsc4C#N)c4cc(F)ccc4n3S(=O)(=O)c3ccc(Cl)cc3)c2)c(Cl)c1] | |
| 1/ 106 | 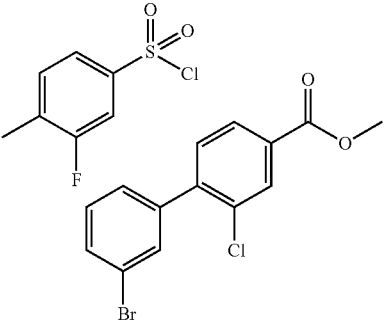 P5 | 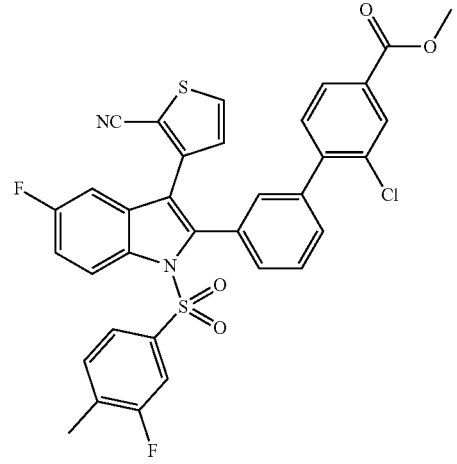 [SMILES: COC(=O)c1ccc(-c2cccc(-c3c(-c4ccsc4C#N)c4cc(F)ccc4n3S(=O)(=O)c3ccc(C)c(F)c3)c2)c(Cl)c1] | |
| 1/ 107 | 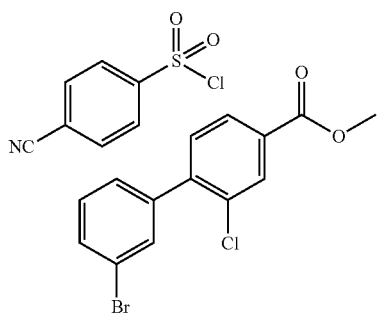 P5 | 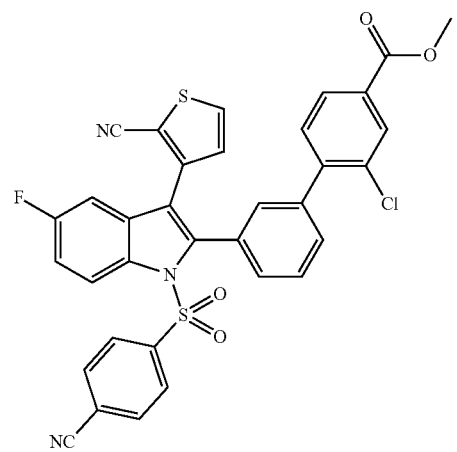 [SMILES: COC(=O)c1ccc(-c2cccc(-c3c(-c4ccsc4C#N)c4cc(F)ccc4n3S(=O)(=O)c3ccc(C#N)cc3)c2)c(Cl)c1] | |

| # | building block(s) | structure | analytical data |
|---|---|---|---|
| 1/ 108 | 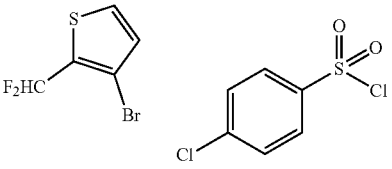 | 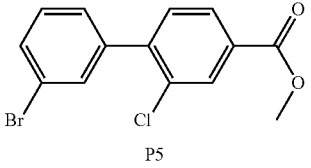 | |
| 1/ 109 | 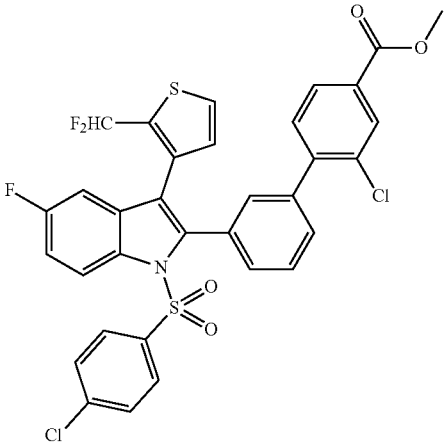 [SMILES: COC(=O)c1ccc(-c2cccc(-c3c(-c4ccsc4C(F)F)c4cc(F)ccc4n3S(=O)(=O)c3ccc(Cl)cc3)c2)c(Cl)c1] | 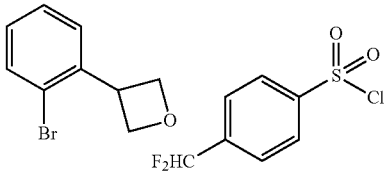 | |
| 1/ 110 | 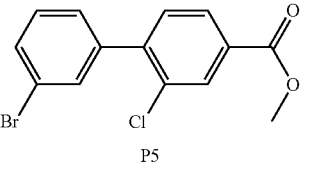 | 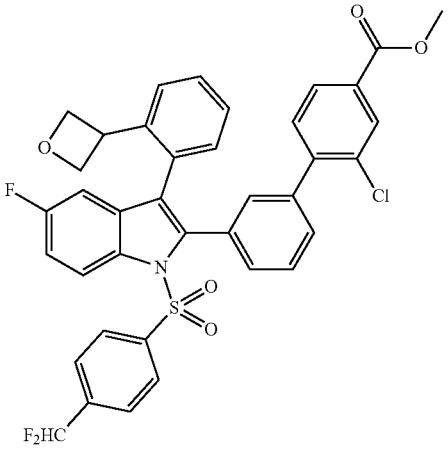 [SMILES: COC(=O)c1ccc(-c2cccc(-c3c(-c4ccccc4C4COC4)c4cc(F)ccc4n3S(=O)(=O)c3ccc(C(F)F)cc3)c2)c(Cl)c1] | |

-continued

| # | building block(s) | structure | analytical data |
|---|---|---|---|
| 1/111 | (structures shown: 3-bromo-4-(trifluoromethyl)pyridine; 4-(difluoromethyl)benzenesulfonyl chloride; methyl 3'-bromo-2-chloro-[1,1'-biphenyl]-4-carboxylate P5) | (indole-based product structure) | |
| 1/112 | (structures shown: 4-(difluoromethyl)benzenesulfonyl chloride; methyl 1-(3-bromophenyl)piperidine-4-carboxylate P13/1) | (indole-based product structure with thiophene-CN) | |
| 1/113 | (structures shown: 4-bromo-3-(trifluoromethyl)-1-trityl-1H-pyrazole P26; 4-(difluoromethyl)benzenesulfonyl chloride; methyl 3'-bromo-2-chloro-[1,1'-biphenyl]-4-carboxylate P5) | (indole-based product structure with trityl-pyrazole) | |

| # | building block(s) | structure | analytical data |
|---|---|---|---|
| 1/114 | 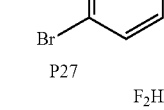 | 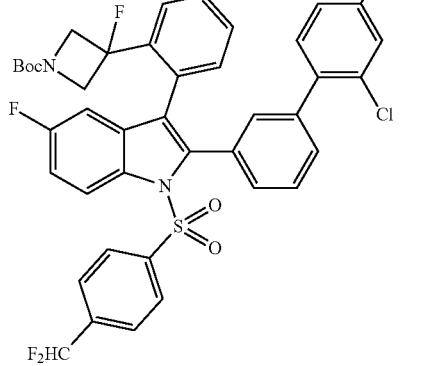 | |
| 1/115 |  | 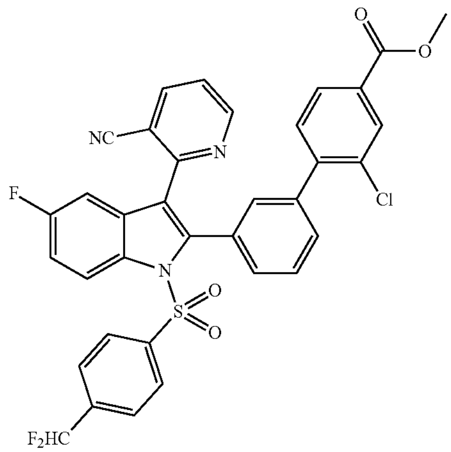 [SMILES: COC(=O)c1ccc(-c2cccc(-c3c(-c4ncccc4C(F)(F)F)c4cc(F)ccc4n3S(=O)(=O)c3ccc(C(F)F)cc3)c2)c(Cl)c1] | |
| 1/116 | 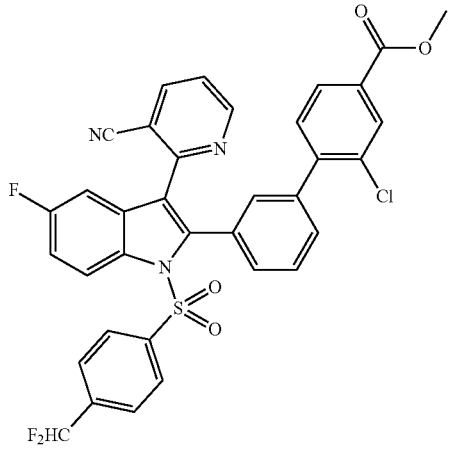 | 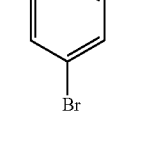 | |

-continued

| # | building block(s) | structure | analytical data |
|---|---|---|---|
| 1/117 | | 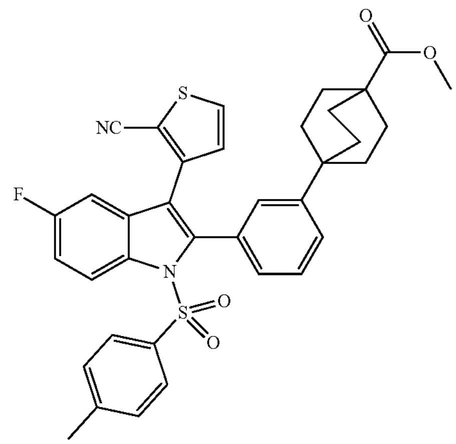 [SMILES: COC(=O)C12CCC(c3cccc(-c4c(-c5ccsc5C#N)c5cc(F)ccc5n4S(=O)(=O)c4ccc(C)cc4)c3)(CC1)CC2] | |
| 1/118 | | 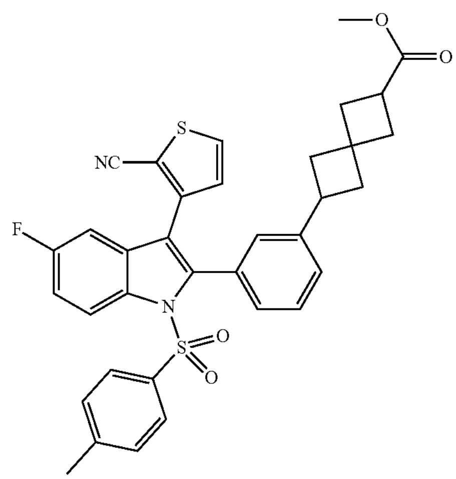 [SMILES: COC(=O)C1CC2(C1)CC(c1cccc(-c3c(-c4ccsc4C#N)c4cc(F)ccc4n3S(=O)(=O)c3ccc(C)cc3)c1)C2] | |
| 1/119 | | 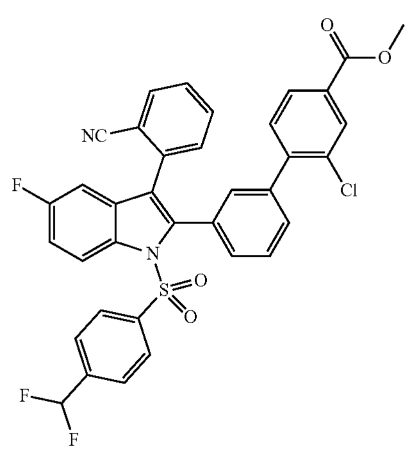 [SMILES: COC(=O)c1ccc(-c2cccc(-c3c(-c4ccccc4C#N)c4cc(F)ccc4n3S(=O)(=O)c3ccc(C(F)F)cc3)c2)c(Cl)c1] | |

| # | building block(s) | structure | analytical data |
|---|---|---|---|
| 1/120 | 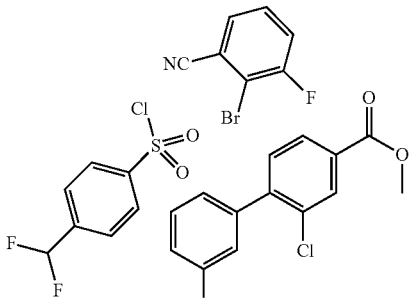 | 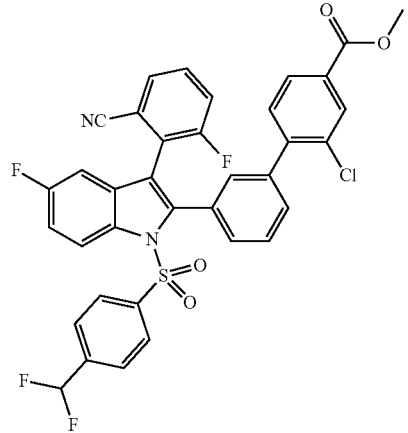 [SMILES: COC(=O)c1ccc(-c2cccc(-c3c(-c4c(F)cccc4C#N)c4cc(F)ccc4n3S(=O)(=O)c3ccc(C(F)F)cc3)c2)c(Cl)c1] | |
| 1/121 | 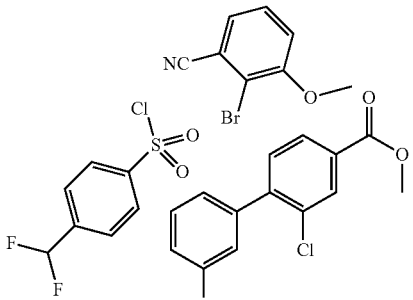 | 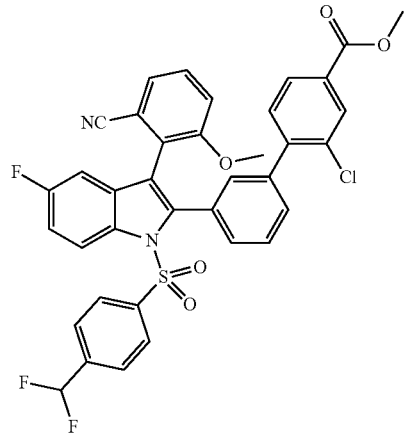 [SMILES: COC(=O)c1ccc(-c2cccc(-c3c(-c4c(C#N)cccc4OC)c4cc(F)ccc4n3S(=O)(=O)c3ccc(C(F)F)cc3)c2)c(Cl)c1] | |
| 1/122 | 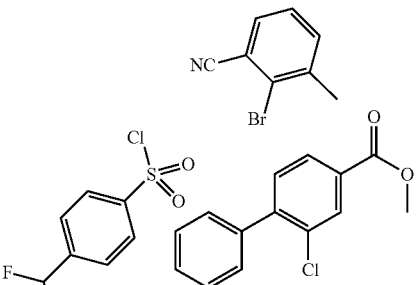 | 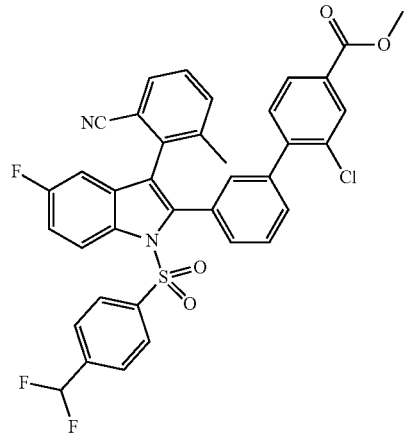 [SMILES: COC(=O)c1ccc(-c2cccc(-c3c(-c4c(C)cccc4C#N)c4cc(F)ccc4n3S(=O)(=O)c3ccc(C(F)F)cc3)c2)c(Cl)c1] | $^1$H-NMR (400 MHz, CD$_3$OD) δ: 8.41 (dd, J = 9.2, 4.4 Hz, 1H), 8.09 (d, J = 1.6 Hz, 1H), 8.00 (dd, J = 8.0, 1.6 Hz, 1H), 7.60-7.15 (m, 13H), 6.73 (dd, J = 2.4, 8.4 Hz, 1H), 6.71 (t, J = 55.6 Hz, 1H), 3.96 (s, 3H), 1.88 (s, 3H). |

-continued
| # | building block(s) | structure | analytical data |
|---|---|---|---|
| C1/ 123 | 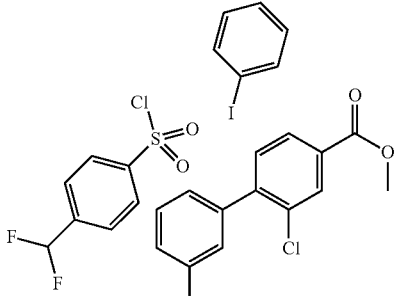 | 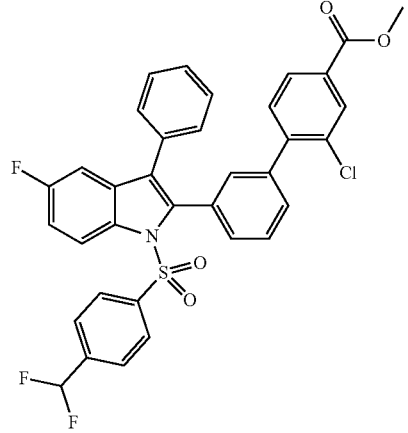 [SMILES: COC(=O)c1ccc(-c2cccc(-c3c(-c4ccccc4)c4cc(F)ccc4n3S(=O)(=O)c3ccc(C(F)F)cc3)c2)c(Cl)c1] | |
| 1/ 124 | 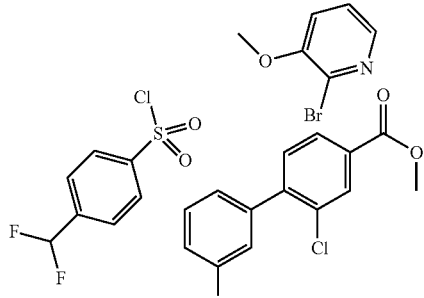 | 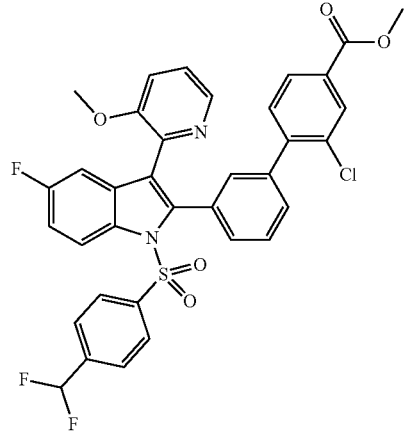 [SMILES: COC(=O)c1ccc(-c2cccc(-c3c(-c4ncccc4OC)c4cc(F)ccc4n3S(=O)(=O)c3ccc(C(F)F)cc3)c2)c(Cl)c1] | |
| 1/ 125 | 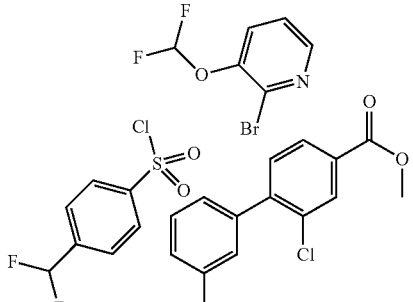 | 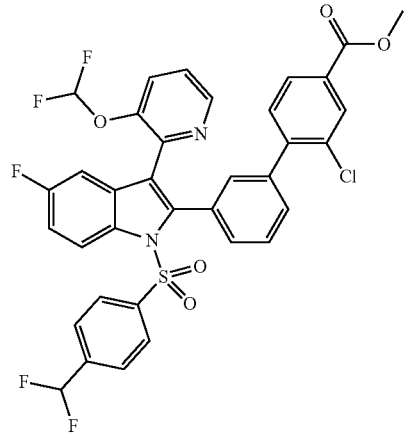 [SMILES: COC(=O)c1ccc(-c2cccc(-c3c(-c4ncccc4OC(F)F)c4cc(F)ccc4n3S(=O)(=O)c3ccc(C(F)F)cc3)c2)c(Cl)c1] | |

-continued
| # | building block(s) | structure | analytical data |
|---|---|---|---|
| 1/126 | 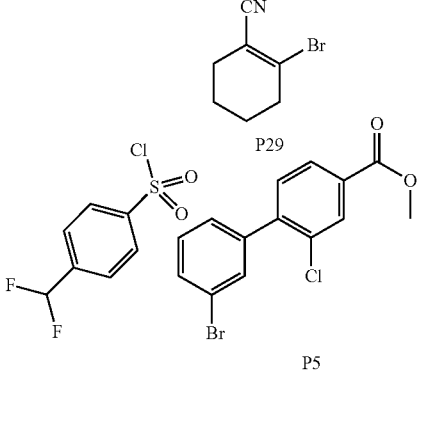 | 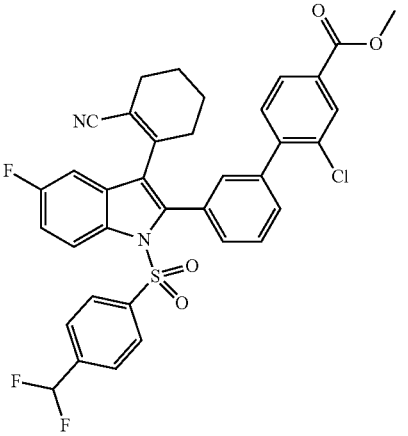 [SMILES: COC(=O)c1ccc(-c2cccc(-c3c(C4=C(C#N)CCCC4)c4cc(F)ccc4n3S(=O)(=O)c3ccc(C(F)F)cc3)c2)c(Cl)c1] | |
| 1/127 | 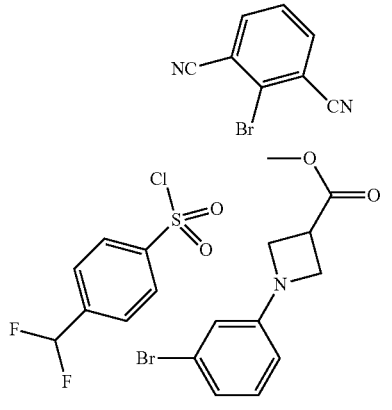 | 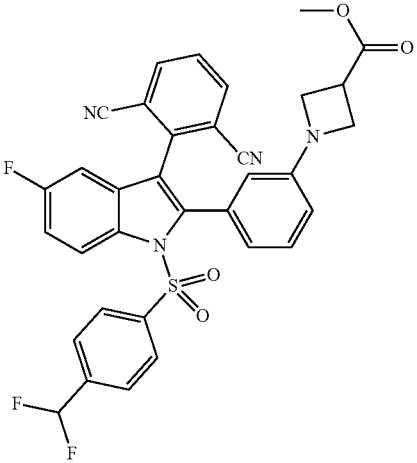 [SMILES: COC(=O)C1CN(c2cccc(-c3c(-c4c(C#N)cccc4C#N)c4cc(F)ccc4n3S(=O)(=O)c3ccc(C(F)F)cc3)c2)C1] | |
| 1/128 | 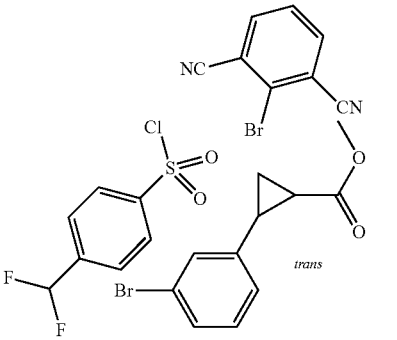 | 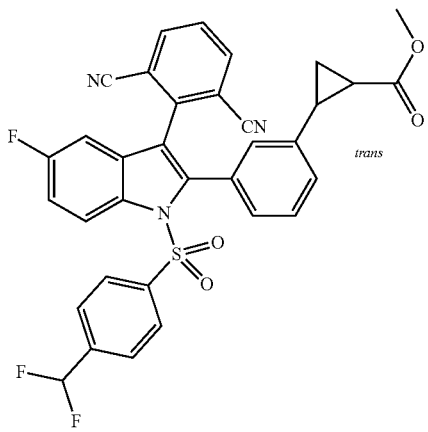 [SMILES: COC(=O)C1CC1c1cccc(-c2c(-c3c(C#N)cccc3C#N)c3cc(F)ccc3n2S(=O)(=O)c2ccc(C(F)F)cc2)c1] | |

| # | building block(s) | structure | analytical data |
|---|---|---|---|
| 1/129 | 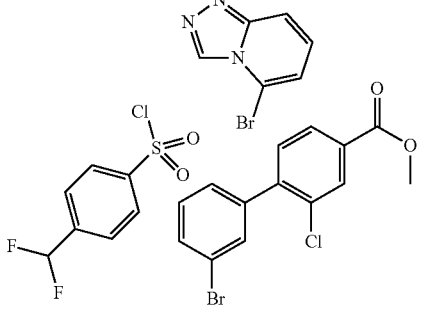 | 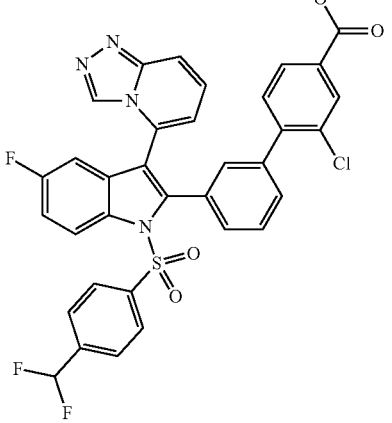 | |
| 1/130 | 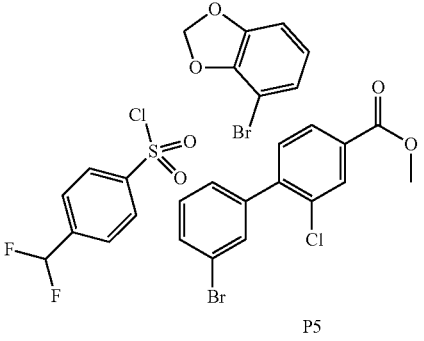 | 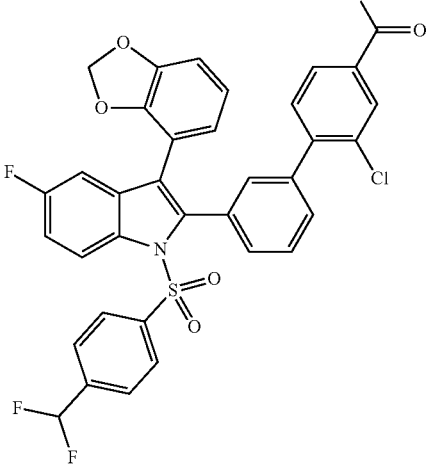 | |
| 1/131 | 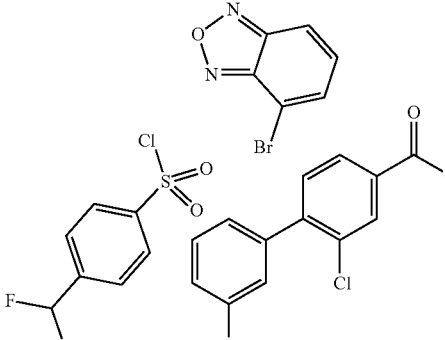 | 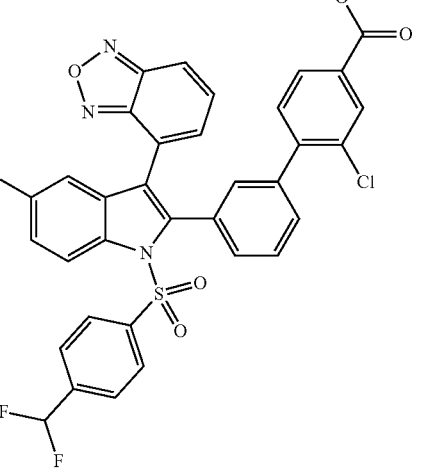 | |

| # | building block(s) | structure | analytical data |
|---|---|---|---|
| 1/132 | | 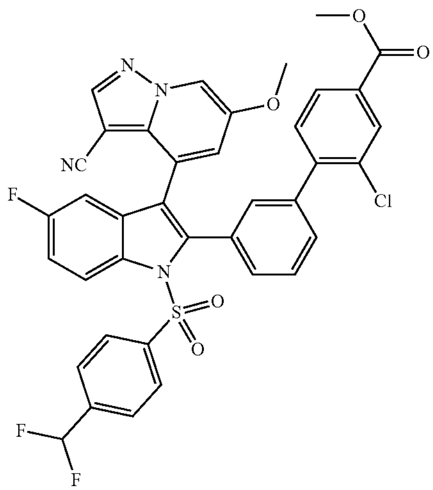 [SMILES: COC(=O)c1ccc(-c2cccc(-c3c(-c4cc(OC)cn5ncc(C#N)c45)c4cc(F)ccc4n3S(=O)(=O)c3ccc(C(F)F)cc3)c2)c(Cl)c1] | |
| 1/133 | | 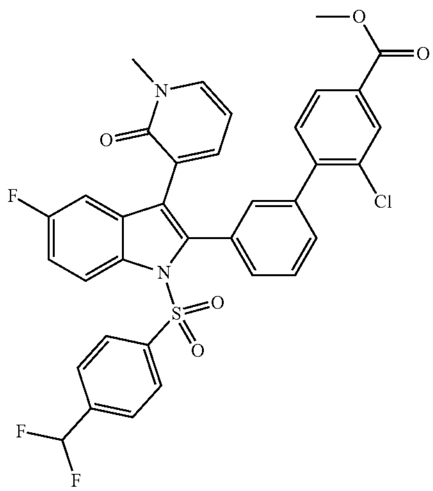 [SMILES: COC(=O)c1ccc(-c2cccc(-c3c(-c4cccn(C)c4=O)c4cc(F)ccc4n3S(=O)(=O)c3ccc(C(F)F)cc3)c2)c(Cl)c1] | |
| C1/134 | | 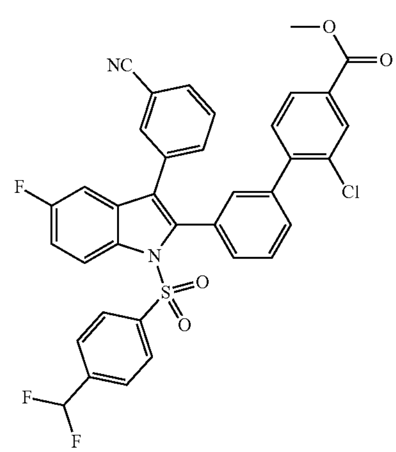 [SMILES: COC(=O)c1ccc(-c2cccc(-c3c(-c4cccc(C#N)c4)c4cc(F)ccc4n3S(=O)(=O)c3ccc(C(F)F)cc3)c2)c(Cl)c1] | |

| # | building block(s) | structure | analytical data |
|---|---|---|---|
| 1/135 | | 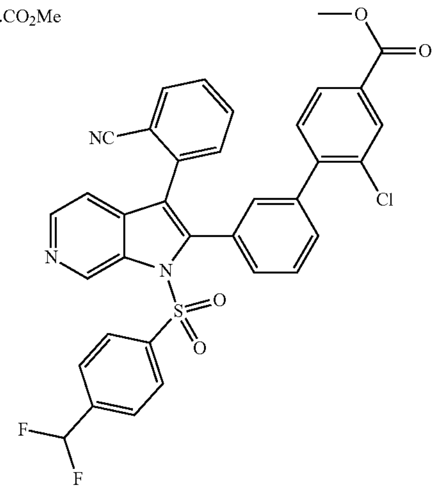 | |
| 1/136 | | 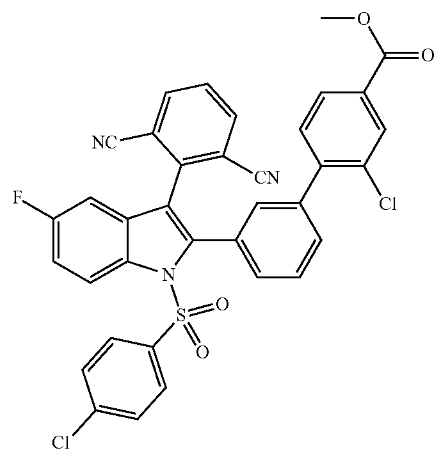 [SMILES: COC(=O)c1ccc(-c2cccc(-c3c(-c4c(C#N)cccc4C#N)c4cc(F)ccc4n3S(=O)(=O)c3ccc(Cl)cc3)c2)c(Cl)c1] | |
| 1/137 | | 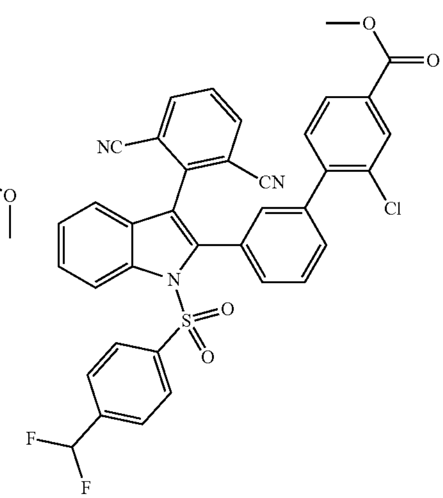 | |

| # | building block(s) | structure | analytical data |
|---|---|---|---|
| 1/138 | 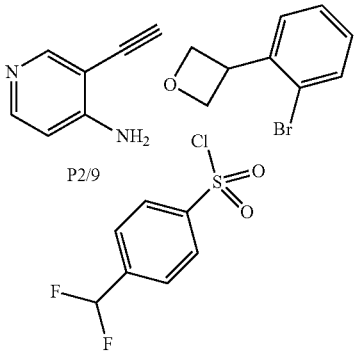 | 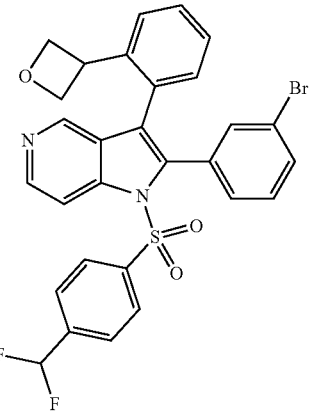 | |
| 1/139 | 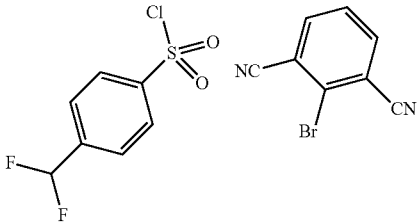 | 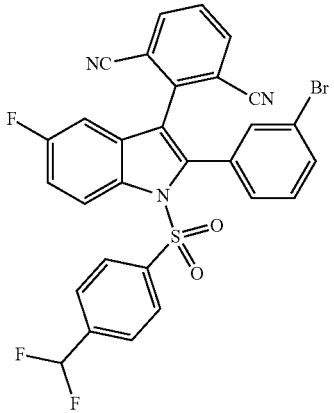 [SMILES: N#Cc1cccc(C#N)c1-c1c(-c2cccc(Br)c2)n(S(=O)(=O)c2ccc(C(F)F)cc2)c2ccc(F)cc12] | ¹H-NMR (500 MHz, DMSO-d₆) δ: 8.32 (dd, J = 9.3, 4.3 Hz, 1H), 8.24 (d, J = 8.5 Hz, 2H), 7.80 (t, J = 8.0 Hz, 1H), 7.72-7.59 (m, 5H), 7.45 (dt, J = 2.5, 9.0 Hz, 1H), 7.35-7.24 (m, 2H), 7.23 (d, J = 2.5 Hz, 1H), 7.25 (d, J = 8.5 Hz, 1H), 7.08 (t, J = 55.0 Hz, 1H). |
| 1/140 | 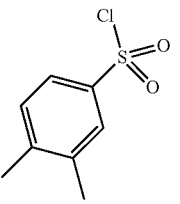 | 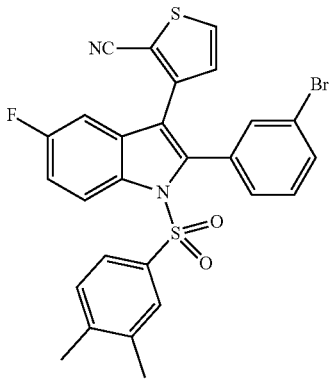 [SMILES: Cc1ccc(S(=O)(=O)n2c(-c3cccc(Br)c3)c(-c3ccsc3C#N)c3cc(F)ccc32)cc1C] | |
| 1/141 | 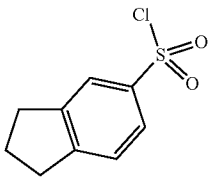 [SMILES: O=S(=O)(Cl)c1ccc2c(c1)CCC2] | 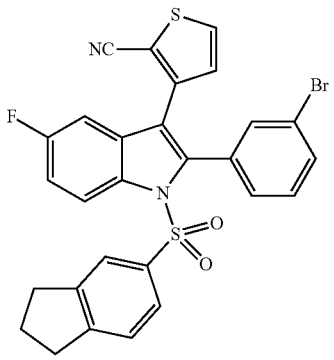 [SMILES: N#Cc1sccc1-c1c(-c2cccc(Br)c2)n(S(=O)(=O)c2ccc3c(c2)CCC3)c2ccc(F)cc12] | |

-continued

| # | building block(s) | structure | analytical data |
|---|---|---|---|
| 1/142 | | 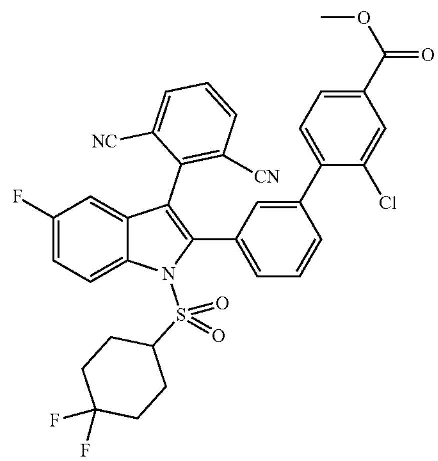 [SMILES: COC(=O)c1ccc(-c2cccc(-c3c(-c4c(C#N)cccc4C#N)c4cc(F)ccc4n3S(=O)(=O)C3CCC(F)(F)CC3)c2)c(Cl)c1] | |
| 1/143 | | 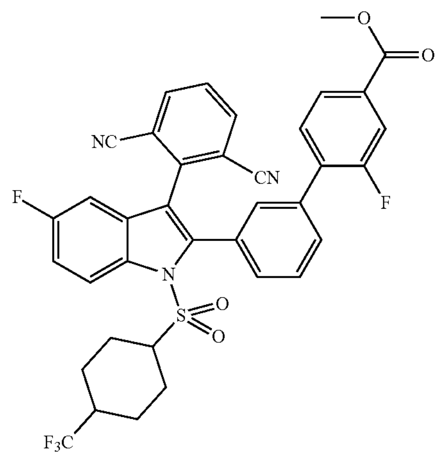 [SMILES: COC(=O)c1ccc(-c2cccc(-c3c(-c4c(C#N)cccc4C#N)c4cc(F)ccc4n3S(=O)(=O)C3CCC(C(F)(F)F)CC3)c2)c(F)c1] | |
| 1/144 | | 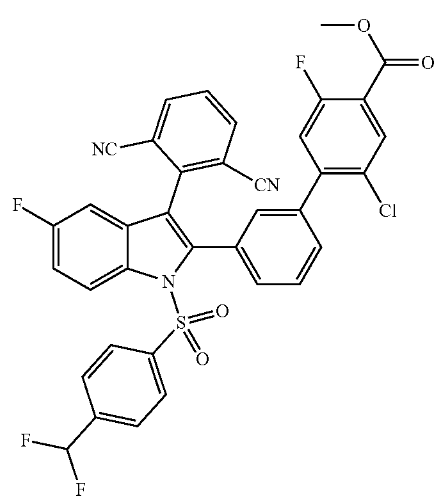 [SMILES: COC(=O)c1cc(Cl)c(-c2cccc(-c3c(-c4c(C#N)cccc4C#N)c4cc(F)ccc4n3S(=O)(=O)c3ccc(C(F)F)cc3)c2)cc1F] | |

| # | building block(s) | structure | analytical data |
|---|---|---|---|
| 1/145 | 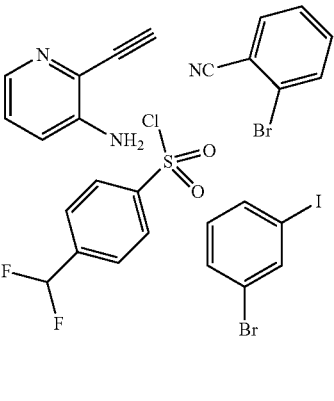 | 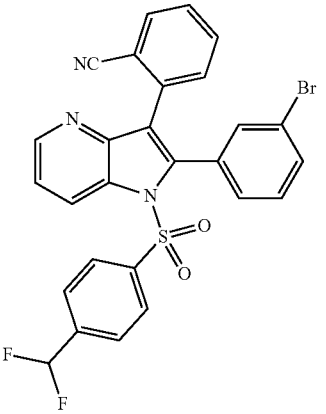 [SMILES: N#Cc1ccccc1-c1c(-c2cccc(Br)c2)n(S(=O)(=O)c2ccc(C(F)F)cc2)c2cccnc12] | |
| 1/146 | 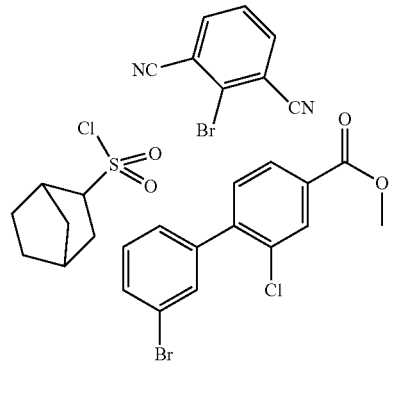 | 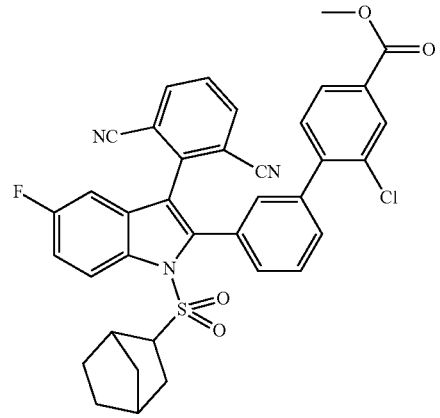 [SMILES: COC(=O)c1ccc(-c2cccc(-c3c(-c4c(C#N)cccc4C#N)c4cc(F)ccc4n3S(=O)(=O)C3CC4CCC3C4)c2)c(Cl)c1] | |
| 1/147 | 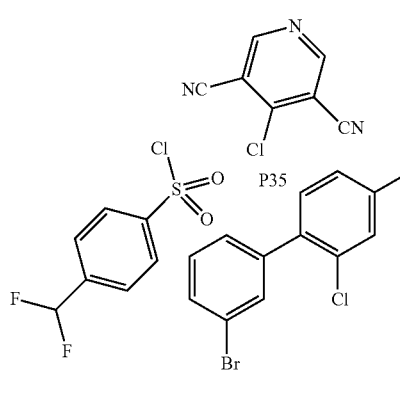 | 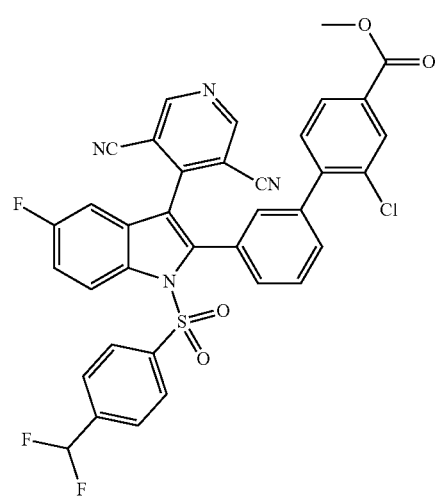 [SMILES: COC(=O)c1ccc(-c2cccc(-c3c(-c4c(C#N)cncc4C#N)c4cc(F)ccc4n3S(=O)(=O)c3ccc(C(F)F)cc3)c2)c(Cl)c1] | |

-continued
| # | building block(s) | structure | analytical data |
|---|---|---|---|
| 1/148 | | 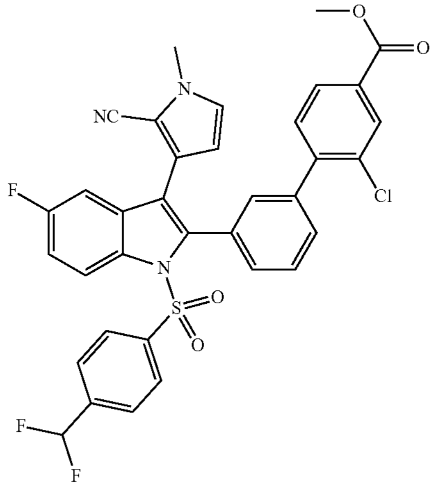 [SMILES: COC(=O)c1ccc(-c2cccc(-c3c(-c4ccn(C)c4C#N)c4cc(F)ccc4n3S(=O)(=O)c3ccc(C(F)F)cc3)c2)c(Cl)c1] | |
| 1/149 | | trans | trans |
Example 2
Step 1: 3-(5-Fluoro-2-(3-(4,4,5,5-tetramethyl-1,3,2-dioxaborolan-2-yl)phenyl)-1-tosyl-1H-indol-3-yl)thiophene-2-carbonitrile (2a)
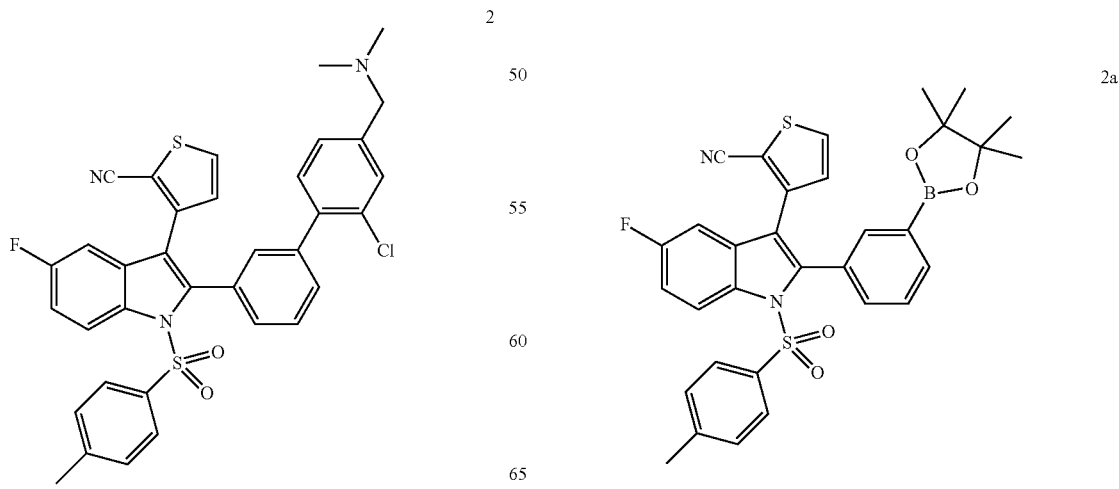

To a solution of compound 1 (2.61 g, 4.73 mmol) in dioxane (40 mL) was added B$_2$Pin$_2$ (1.44 g, 5.68 mmol), KOAc (928 mg, 9.46 mmol) and Pd(dppf)Cl$_2$ (344 mg, 0.47 mmol). The mixture was stirred at 80° C. overnight under N$_2$, cooled, filtered, concentrated and purified by FCC (EA:PE=1:3) to give compound 2a as a white solid.

Step 2: 3-(2-(2'-Chloro-4'-((dimethylamino)methyl)-[1,1'-biphenyl]-3-yl)-5-fluoro-1-tosyl-1H-indol-3-yl)thiophene-2-carbonitrile (2)

To a solution of compound 2a (150 mg, 0.25 mmol) in dioxane (8 mL) was added 1-(4-bromo-3-chlorophenyl)-N,N-dimethylmethanamine (65 mg, 0.26 mmol), Cs$_2$CO$_3$ (163 mg, 0.50 mmol) and Pd(PPh$_3$)$_4$ (30 mg, 25 μmol). The mixture was stirred at 100° C. overnight under N$_2$, cooled, filtered, concentrated and purified by prep-HPLC to give compound 2 as a white solid. $^1$H-NMR (500 MHz, DMSO-d$_6$) δ: 8.29 (dd, J=9.5, 4.5 Hz, 1H), 8.02 (d, J=5.0 Hz, 1H), 7.51-7.32 (m, 8H), 7.26-7.17 (m, 4H), 7.02-6.99 (m, 2H), 3.42 (s, 2H), 2.21 (s, 3H), 2.18 (s, 6H); MS: 639.9 (M+1)$^+$.

Example 2/1 to 2/34

The following Examples were prepared similar as described for Example 2 (and optionally for Example 1) using the appropriate building blocks.

| # | building block(s) | structure | analytical data |
|---|---|---|---|
| 2/1 | 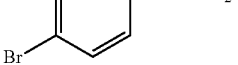 | 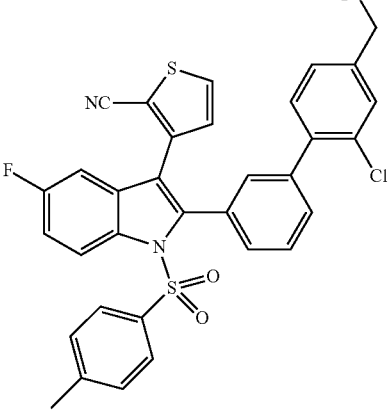 | $^1$H-NMR (500 MHz, CD$_3$OD) δ: 8.41 (dd, J = 9.0, 4.5 Hz, 1H), 7.83 (d, J = 5.5 Hz, 1H), 7.65 (d, J = 1.5 Hz, 1H), 7.50-7.43 (m, 4H), 7.35-7.26 (m, 4H), 7.20-7.15 (m, 3H), 7.05 (dd, J = 8.5, 2.5 Hz, 1H), 6.96 (d, J = 5.0 Hz, 1H), 4.19 (s, 2H), 2.29 (s, 3H); MS: 611.8 (M + 1)$^+$. |
| 2/2 | 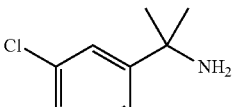 | 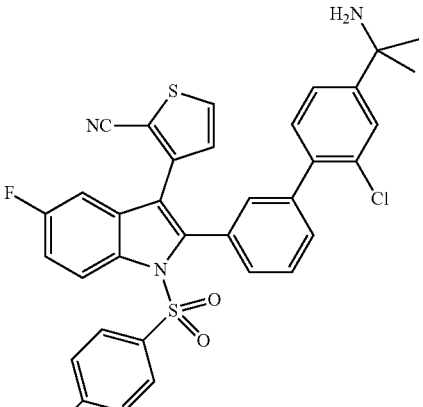 | $^1$H-NMR (500 MHz, CD$_3$OD) δ: 8.41 (dd, J = 9.0, 4.5 Hz, 1H), 7.81 (d, J = 5.0 Hz, 1H), 7.64 (d, J = 2.0 Hz, 1H), 7.52-7.41 (m, 4H), 7.29-7.25 (m, 4H), 7.16-7.14 (m, 2H), 7.06 (dd, J = 8.5, 3.0 Hz, 1H), 6.97 (s, 1H), 6.93 (d, J = 5.0 Hz, 1H), 2.25 (s, 3H), 1.54 (s, 6H); MS: 639.0 (M + 1)$^+$. |

-continued
| # | building block(s) | structure | analytical data |
|---|---|---|---|
| 2/3 | 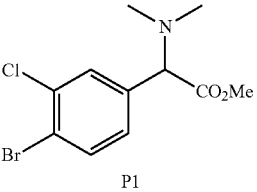 P1 | 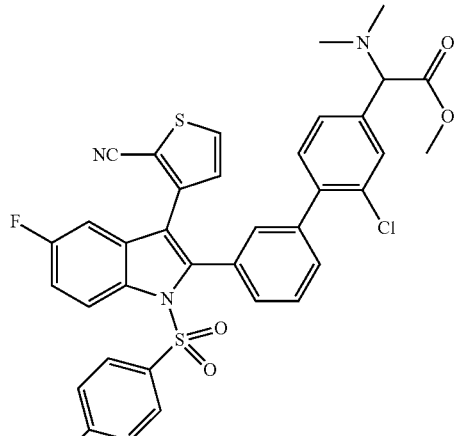 | |
| 2/4 | 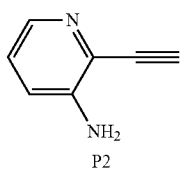 P2 | 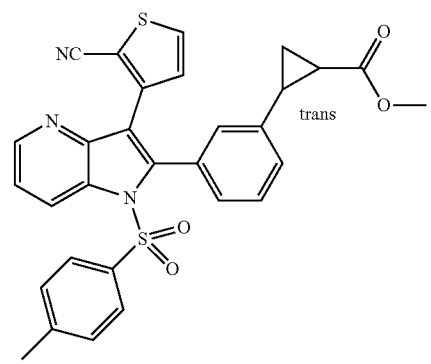 [SMILES: COC(=O)C1CC1c1cccc(-c2c(-c3ccsc3C#N)c3ncccc3n2S(=O)(=O)c2ccc(C)cc2)c1] | |
| 2/5 | 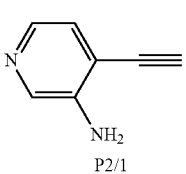 P2/1 | 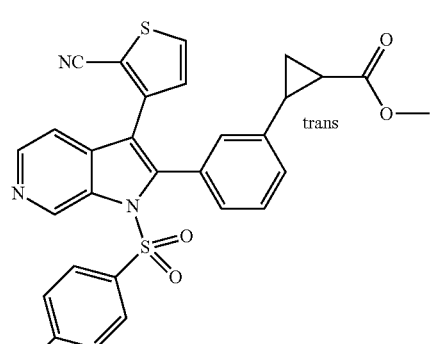 | |
| 2/6 | 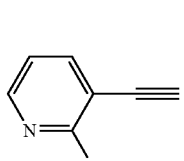 P2/2 | 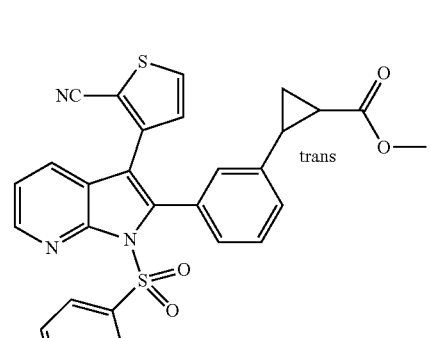 | |

| # | building block(s) | structure | analytical data |
|---|---|---|---|
| 2/7 | 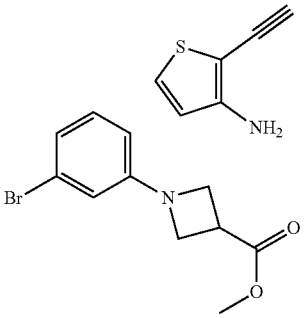<br>P2/3 | 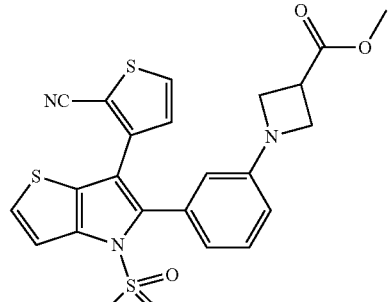 | |
| 2/8 | 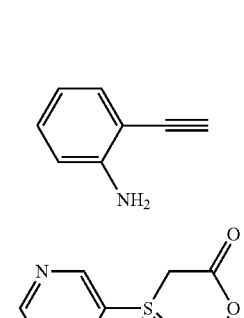<br>coupling with Na$_2$CO$_3$ (2 eq)<br>Pd(dppf)Cl$_2$, 90° C., 3 h,<br>dioxane/water 10:1 | 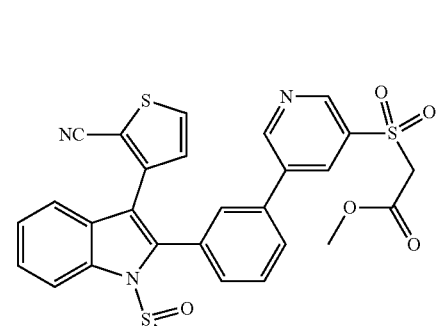 | |
| 2/9 | 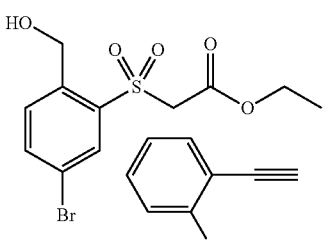<br>P3<br>coupling with Na$_2$CO$_3$ (2 eq)<br>Pd(dppf)Cl$_2$, 90° C., 3 h,<br>dioxane/water 10:1 | 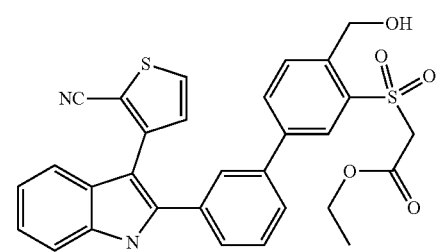 | |

| # | building block(s) | structure | analytical data |
|---|---|---|---|
| 2/10 | 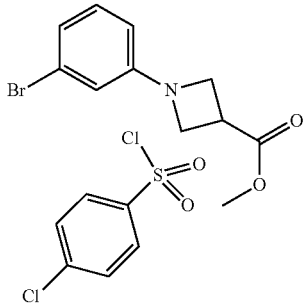 | 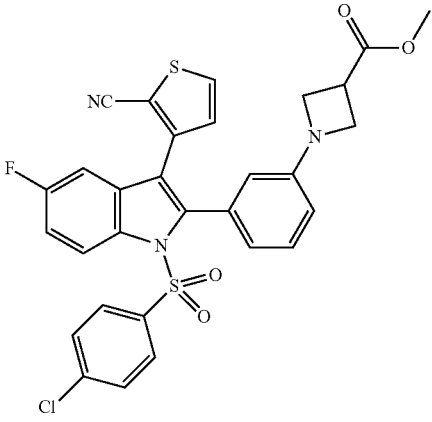 [SMILES: COC(=O)C1CN(c2cccc(-c3c(-c4ccsc4C#N)c4cc(F)ccc4n3S(=O)(=O)c3ccc(Cl)cc3)c2)C1] | |
| 2/11 | 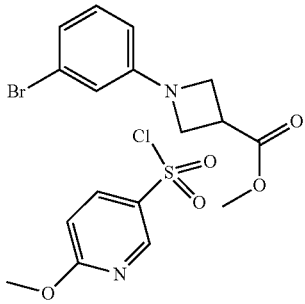 | 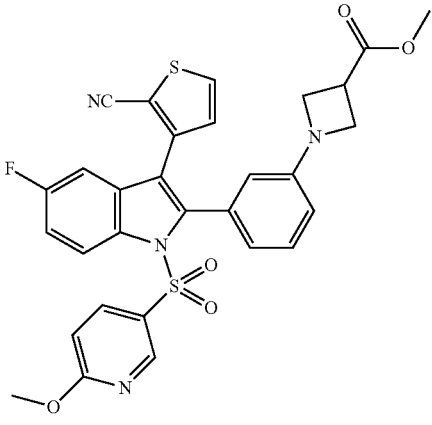 [SMILES: COC(=O)C1CN(c2cccc(-c3c(-c4ccsc4C#N)c4cc(F)ccc4n3S(=O)(=O)c3ccc(OC)nc3)c2)C1] | |
| 2/12 | 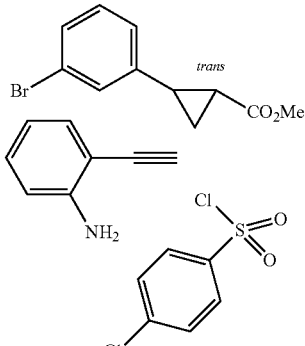<br>P16 | 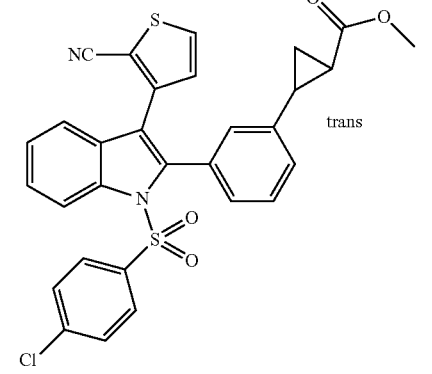 | |

-continued
| # | building block(s) | structure | analytical data |
|---|---|---|---|
| 2/13 | 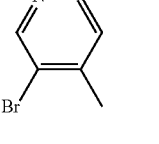 | 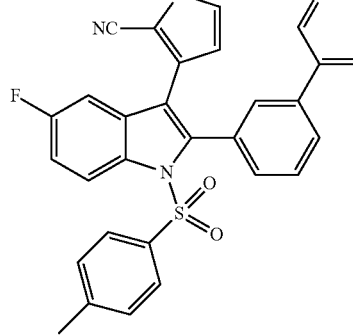 | |
| 2/14 | 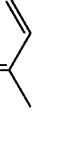 | 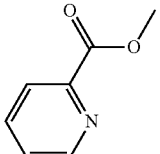 | |
| P2/15 | 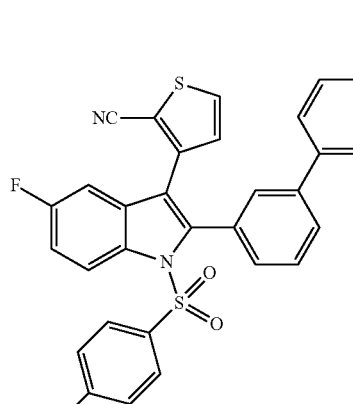 P22 | 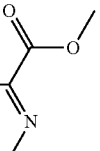 | |

| # | building block(s) | structure | analytical data |
|---|---|---|---|
| 2/16 | 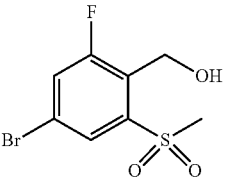<br>prepared according to ACS Med. Chem. Lett. 2016;7:1207 | 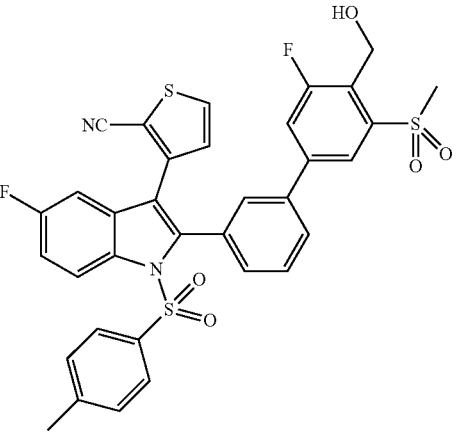 [SMILES: Cc1ccc(S(=O)(=O)n2c(-c3cccc(-c4cc(F)c(CO)c(S(C)(=O)=O)c4)c3)c(-c3ccsc3C#N)c3cc(F)ccc32)cc1] | ¹H-NMR (500 MHz, DMSO-d₆) δ: 8.34-8.29 (m, 1H), 8.01 (d, J = 5.0 Hz, 1H), 7.96 (d, J = 1.5 Hz, 1H), 7.86-7.84 (m, 2H), 7.61 (s, 1H), 7.53 (t, J = 7.5 Hz, 1H), 7.41-7.28 (m, 6H), 7.21-7.18 (m, 1H), 7.08 (d, J = 5.5 Hz, 1H), 5.59-5.55 (m, 1H), 4.96-4.94 (m, 2H), 3.45 (s, 3H), 2.27 (s, 3H); MS: 691.8 (M + 18)⁺. |
| P2/17 | 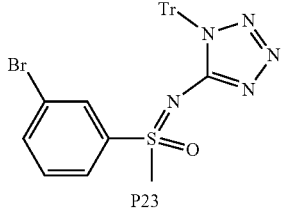<br>P23 | 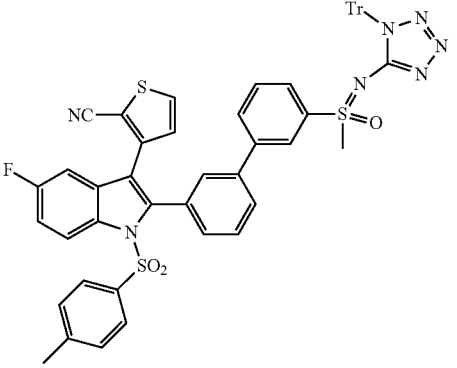 | |
| 2/18 | 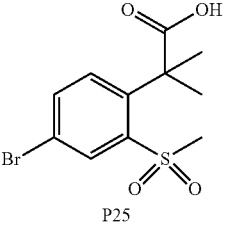<br>P25 | 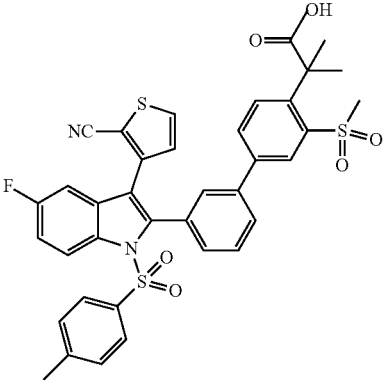 | ¹H-NMR (500 MHz, CD₃OD) δ: 8.44-8.41 (m, 1H), 8.16 (s, 1H), 7.85-7.76 (m, 4H), 7.51-7.48 (m, 1H), 7.39-7.26 (m, 5H), 7.19-7.17 (m, 2H), 7.06-7.01 (m, 2H), 3.23 (s, 3H), 2.26 (s, 3H), 1.77 (s, 6H); MS: 730.1 (M + 18)⁺. |

| # | building block(s) | structure | analytical data |
|---|---|---|---|
| 2/19 | 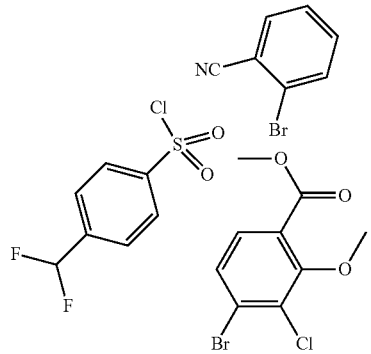 | 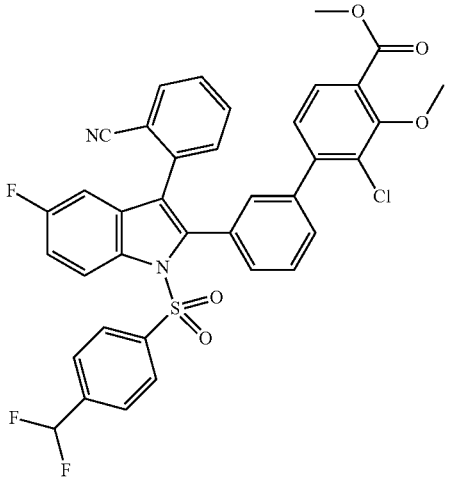 [SMILES: COC(=O)c1ccc(-c2cccc(-c3c(-c4ccccc4C#N)c4cc(F)ccc4n3S(=O)(=O)c3ccc(C(F)F)cc3)c2)c(Cl)c1OC] | |
| 2/20 | 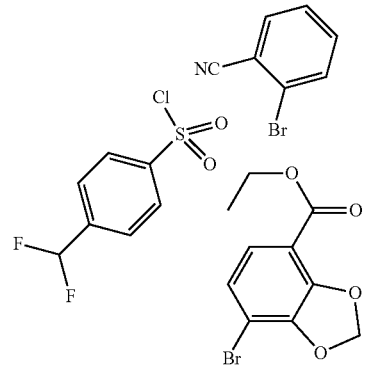 | 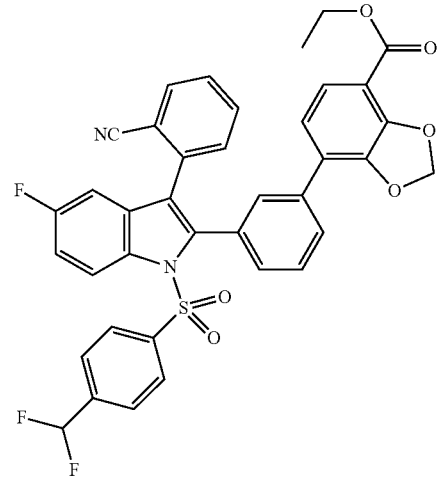 [SMILES: CCOC(=O)c1ccc(-c2cccc(-c3c(-c4ccccc4C#N)c4cc(F)ccc4n3S(=O)(=O)c3ccc(C(F)F)cc3)c2)c2c1OCO2] | |
| 2/21 | 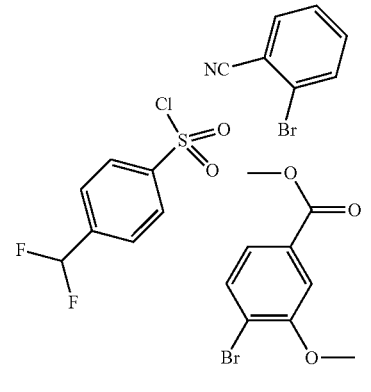 | 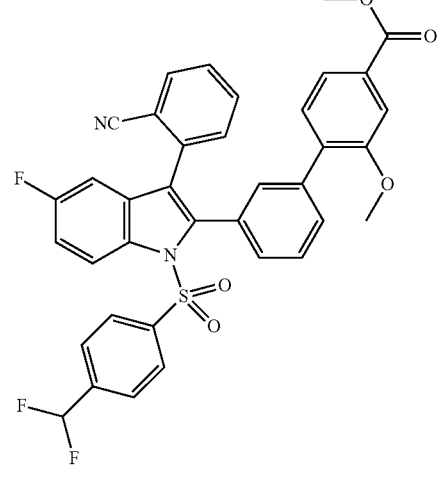 | |

| # | building block(s) | structure | analytical data |
|---|---|---|---|
| 2/22 | 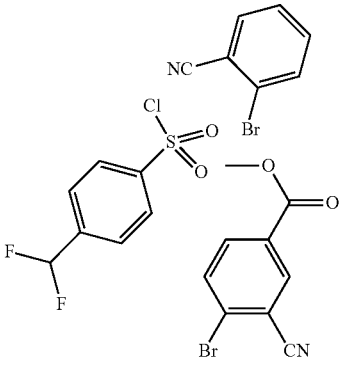 | 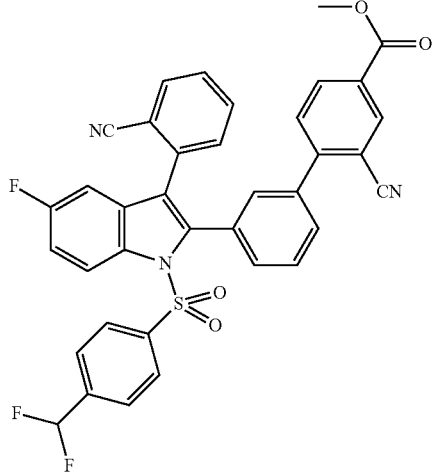 [SMILES: COC(=O)c1ccc(-c2cccc(-c3c(-c4ccccc4C#N)c4cc(F)ccc4n3S(=O)(=O)c3ccc(C(F)F)cc3)c2)c(C#N)c1] | |
| 2/23 | 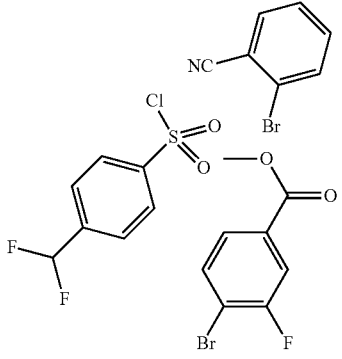 | 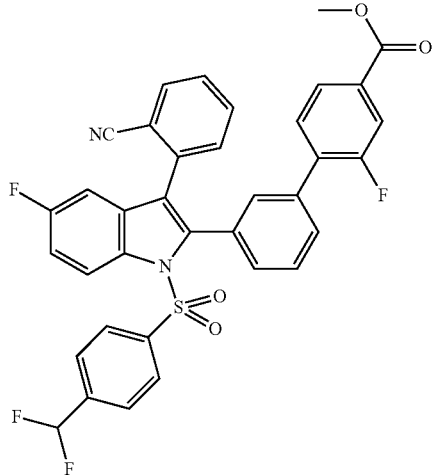 [SMILES: COC(=O)c1ccc(-c2cccc(-c3c(-c4ccccc4C#N)c4cc(F)ccc4n3S(=O)(=O)c3ccc(C(F)F)cc3)c2)c(F)c1] | |
| 2/24 | 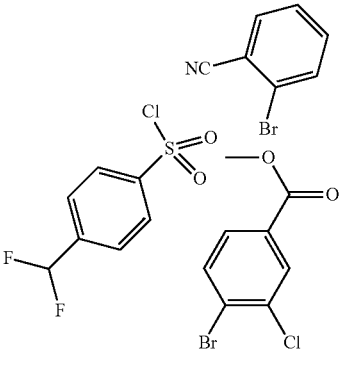 | 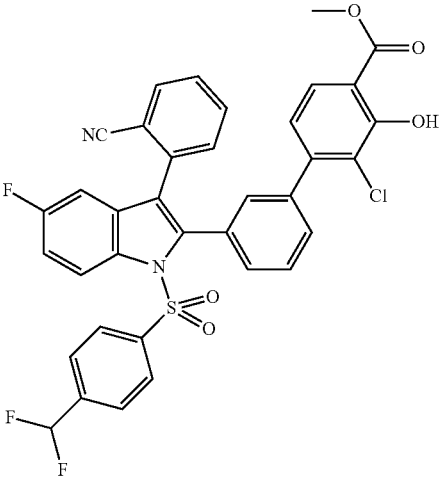 [SMILES: COC(=O)c1ccc(-c2cccc(-c3c(-c4ccccc4C#N)c4cc(F)ccc4n3S(=O)(=O)c3ccc(C(F)F)cc3)c2)c(Cl)c1O] | |

| # | building block(s) | structure | analytical data |
|---|---|---|---|
| 2/25 | 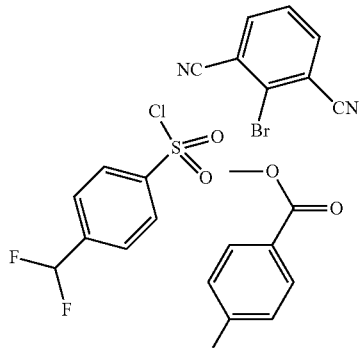 | 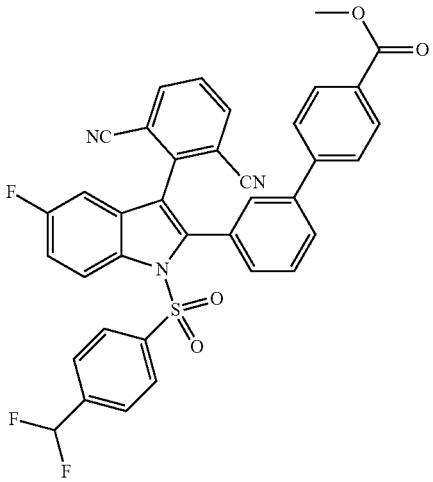 [SMILES: COC(=O)c1ccc(-c2cccc(-c3c(-c4c(C#N)cccc4C#N)c4cc(F)ccc4n3S(=O)(=O)c3ccc(C(F)F)cc3)c2)cc1] | |
| 2/26 | 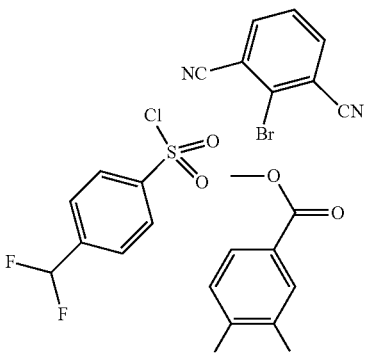 | 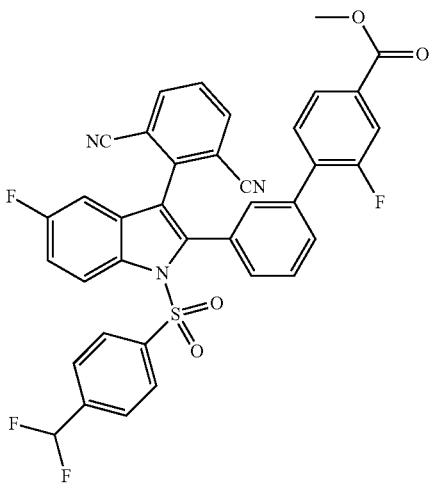 [SMILES: COC(=O)c1ccc(-c2cccc(-c3c(-c4c(C#N)cccc4C#N)c4cc(F)ccc4n3S(=O)(=O)c3ccc(C(F)F)cc3)c2)c(F)c1] | |
| 2/27 | 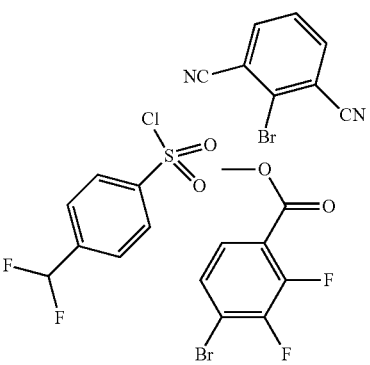 | 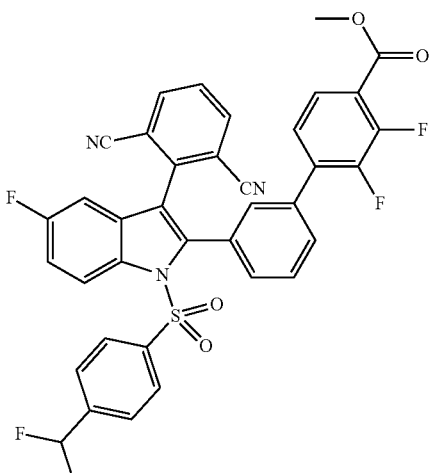 | |

| # | building block(s) | structure | analytical data |
|---|---|---|---|
| 2/28 | 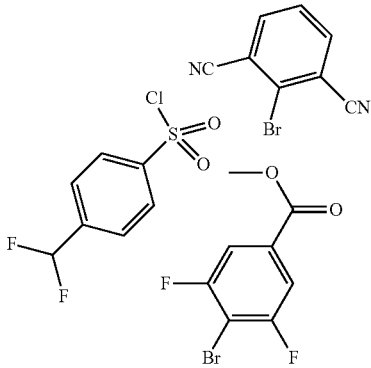 | 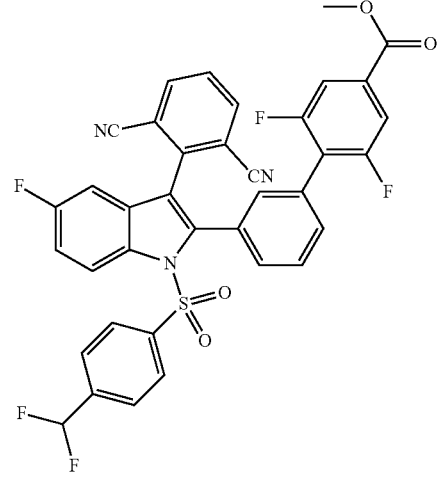 [SMILES: COC(=O)c1cc(F)c(-c2cccc(-c3c(-c4c(C#N)cccc4C#N)c4cc(F)ccc4n3S(=O)(=O)c3ccc(C(F)F)cc3)c2)c(F)c1] | |
| 2/29 | 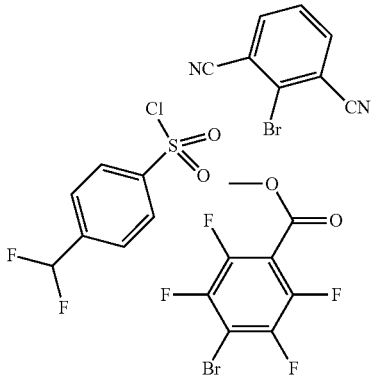 | 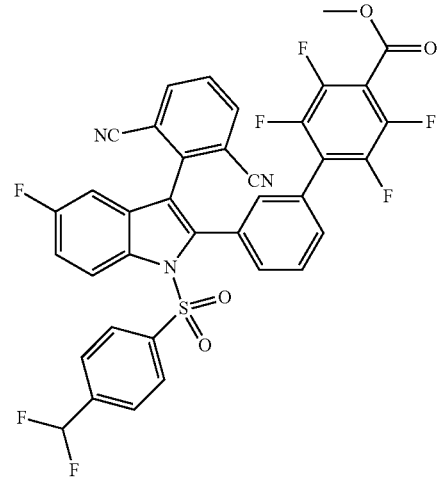 [SMILES: COC(=O)c1c(F)c(F)c(-c2cccc(-c3c(-c4c(C#N)cccc4C#N)c4cc(F)ccc4n3S(=O)(=O)c3ccc(C(F)F)cc3)c2)c(F)c1F] | |
| 2/30 | 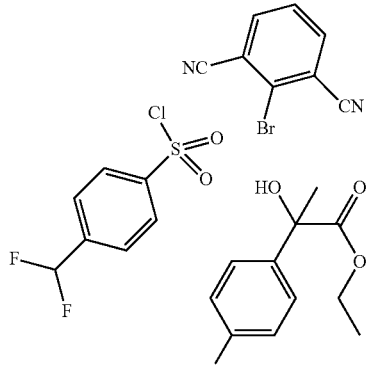 P32 | 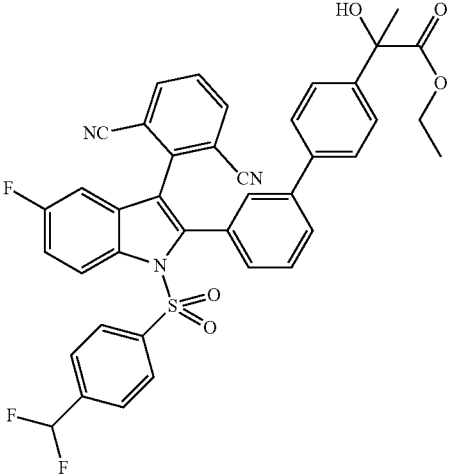 [SMILES: CCOC(=O)C(C)(O)c1ccc(-c2cccc(-c3c(-c4c(C#N)cccc4C#N)c4cc(F)ccc4n3S(=O)(=O)c3ccc(C(F)F)cc3)c2)cc1] | |

| # | building block(s) | structure | analytical data |
|---|---|---|---|
| 2/31 | P32/1 | 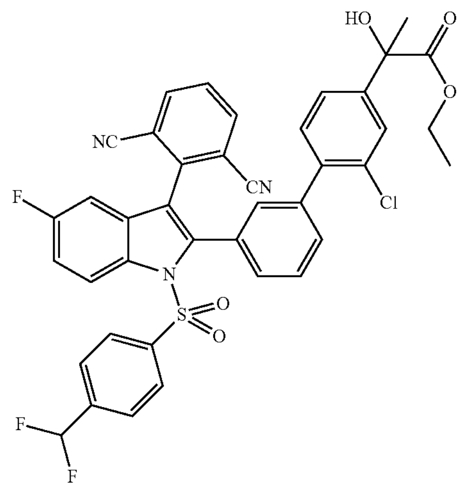 [SMILES: CCOC(=O)C(C)(O)c1ccc(-c2cccc(-c3c(-c4c(C#N)cccc4C#N)c4cc(F)ccc4n3S(=O)(=O)c3ccc(C(F)F)cc3)c2)c(Cl)c1] | |
| 2/32 | P10/1 | 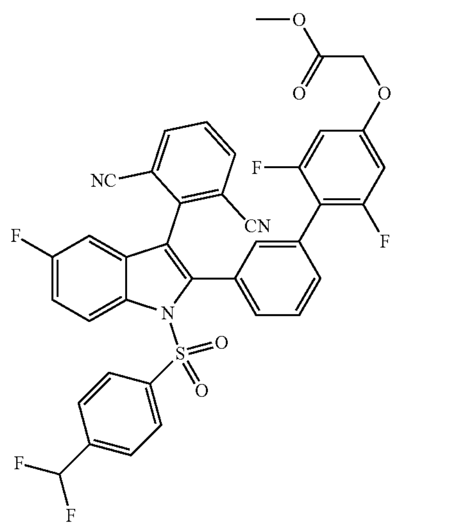 [SMILES: COC(=O)COc1cc(F)c(-c2cccc(-c3c(-c4c(C#N)cccc4C#N)c4cc(F)ccc4n3S(=O)(=O)c3ccc(C(F)F)cc3)c2)c(F)c1] | |
| 2/33 | P21/1 | 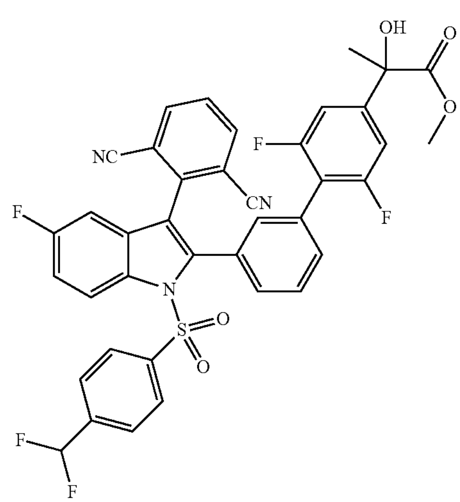 [SMILES: COC(=O)C(C)(O)c1cc(F)c(-c2cccc(-c3c(-c4c(C#N)cccc4C#N)c4cc(F)ccc4n3S(=O)(=O)c3ccc(C(F)F)cc3)c2)c(F)c1] | |

| # | building block(s) | structure | analytical data |
|---|---|---|---|

2/34

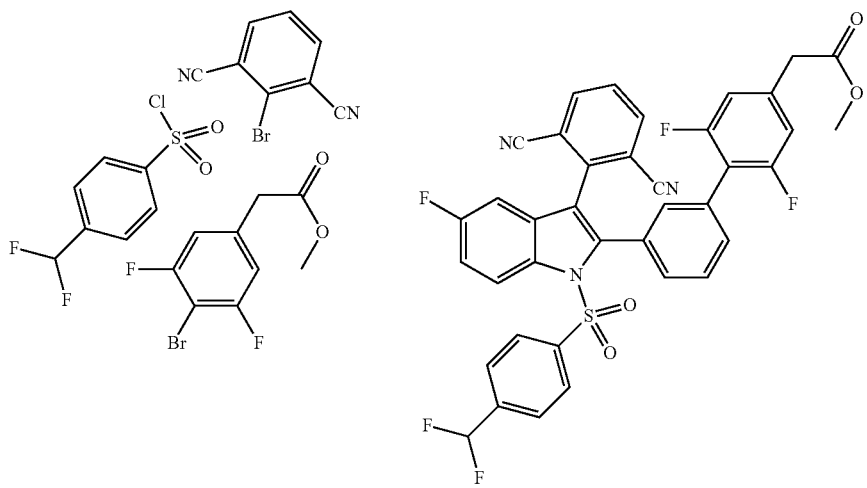

Example 3

2-(2-Chloro-3'-(3-(2-cyanothiophen-3-yl)-5-fluoro-1-tosyl-1H-indol-2-yl)-[1,1'-biphenyl]-4-yl)-2-(dimethylamino)acetic Acid (3)

To a solution of compound 2/3 (80 mg, 0.11 mmol) in THF (8 mL), MeOH (3 mL) and H$_2$O (3 mL) was added LiOH·H$_2$O (24 mg, 0.57 mmol). The mixture was stirred at rt for 30 min, concentrated, diluted with H$_2$O (6 mL), adjusted to pH=3 with 2N HCl and extracted with EA (2×50 mL). The combined organic layer was dried over Na$_2$SO$_4$, filtered, concentrated and purified by prep-HPLC to afford compound 3 as a white solid. $^1$H-NMR (500 MHz, DMSO-d$_6$) δ: 8.41 (dd, J=9.3, 4.3 Hz, 1H), 7.82 (d, J=5.0 Hz, 1H), 7.74 (d, J=2.0 Hz, 1H), 7.57 (dd, J=7.8, 1.7 Hz, 1H), 7.50-7.41 (m, 4H), 7.30-7.25 (m, 3H), 7.18-7.15 (m, 2H), 7.07-7.05 (m, 2H), 6.95 (d, J=5.0 Hz, 1H), 4.53 (s, 1H), 2.84 (s, 6H), 2.27 (s, 3H); MS: 683.8 (M+1)$^+$.

3

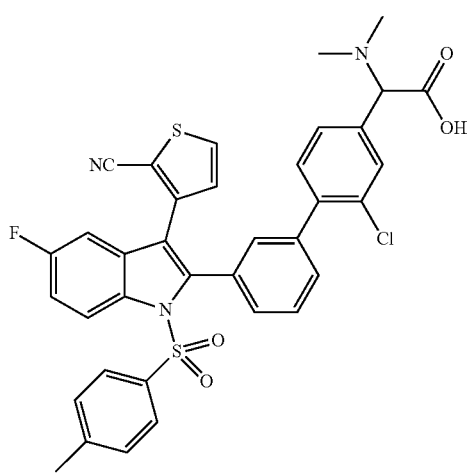

Example 3/1 to 3/73

The following Examples were saponified similar as described for Example 3 using the appropriate starting material (ester).

| # | starting material | structure | analytical data |
|---|---|---|---|
| 3/1 | 1/5 first eluting isomer | 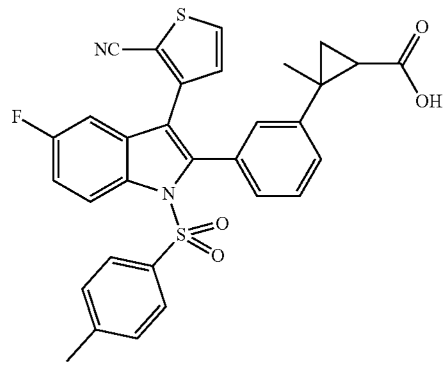 [SMILES: Cc1ccc(S(=O)(=O)n2c(-c3cccc(C4(C)CC4C(=O)O)c3)c(-c3ccsc3C#N)c3cc(F)ccc32)cc1] | ¹H-NMR (500 MHz, CD₃OD) δ: 8.42 (dd, J = 4.5, 9.0 Hz, 1H), 7.80 (d, J = 5.0 Hz, 1H), 7.40 (d, J = 8.0 Hz, 1H), 7.32-7.17 (m, 7H), 7.04 (dd, J = 2.8, 8.8 Hz, 1H), 6.99 (s, 1H), 6.88 (d, J = 5.5 Hz, 1H), 2.36 (s, 3H), 1.83-1.80 (m, 1H), 1.43 (s, 3H), 1.31-1.29 (m, 1H), 1.22-1.19 (m, 1H); MS: 568.8 (M − 1)⁻. |
| 3/2 | 1/6 second eluting isomer | 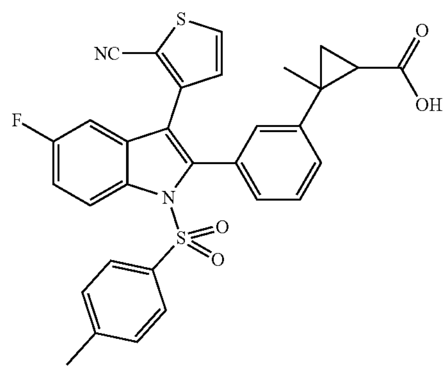 [SMILES: Cc1ccc(S(=O)(=O)n2c(-c3cccc(C4(C)CC4C(=O)O)c3)c(-c3ccsc3C#N)c3cc(F)ccc32)cc1] | ¹H-NMR (500 MHz, CD₃OD) δ: 8.43 (dd, J = 4.3, 8.8 Hz, 1H), 7.74 (d, J = 5.0 Hz, 1H), 7.36-7.21 (m, 8H), 7.13-7.04 (m, 2H), 6.75 (d, J = 5.0 Hz, 1H), 2.35 (s, 3H), 1.94-1.92 (m, 1H), 1.63-1.62 (m, 1H), 1.38 (s, 3H), 1.20-1.17 (m, 1H); MS: 568.8 (M − 1)⁻. |
| 3/3 | 1/7 | 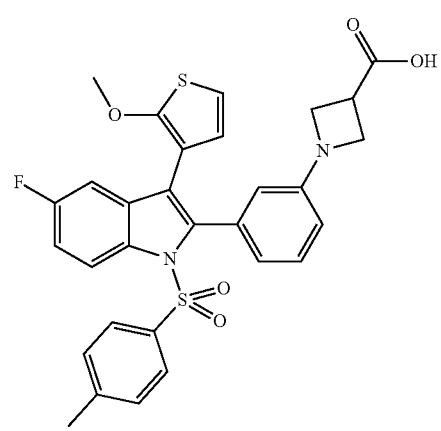 [SMILES: COc1sccc1-c1c(-c2cccc(N3CC(C(=O)O)C3)c2)n(S(=O)(=O)c2ccc(C)cc2)c2ccc(F)cc12] | ¹H-NMR (500 MHz, DMSO-d₆) δ: 8.21 (dd, J = 4.5, 9.0 Hz, 1H), 6.68 (d, J = 9.0 Hz, 2H), 7.31-7.26 (m, 3H), 7.17 (t, J = 8.0 Hz, 1H), 6.97 (dd, J = 2.5, 9.0 Hz, 1H), 6.75 (d, J = 6.0 Hz, 1H), 6.64 (d, J = 8.0 Hz, 1H), 6.48 (dd, J = 2.0, 8.0 Hz, 1H), 6.39 (d, J = 6.0 Hz, 1H), 6.26 (s, 1H), 3.93 (t, J = 8.0 Hz, 2H), 3.79 (t, J = 6.5 Hz, 2H), 3.60 (s, 3H), 3.54-3.47 (m, 1H), 2.32 (s, 3H); MS: 577.1 (M + 1)⁺. |

| # | starting material | structure | analytical data |
|---|---|---|---|
| 3/4 | [structure 1/8] | [structure] | $^1$H-NMR (500 MHz, CD$_3$OD) δ: 8.36 (dd, J = 4.3, 8.8 Hz, 1H), 7.60 (d, J = 5.5 Hz, 1H), 7.30 (d, J = 8.5 Hz, 2H), 7.25-7.17 (m, 4H), 6.84 (dd, J = 2.5, 8.5 Hz, 1H), 6.75-6.70 (m, 2H), 6.55 (dd, J = 1.8, 8.3 Hz, 1H), 6.19 (t, J = 55.0 Hz, 1H), 6.16 (s, 1H), 3.99-3.82 (m, 4H), 3.58-3.52 (m, 1H), 2.38 (s, 3H); MS: 597.1 (M + 1)$^-$. |
| 3/5 | [structure 1/9] | [structure] | $^1$H-NMR (500 MHz, DMSO-d$_6$) δ: 12.64 (br s, 1H), 9.31 (d, J = 1.0 Hz, 1H), 8.26 (dd, J = 4.0, 9.0 Hz, 1H), 8.10 (dd, J = 1.3, 4.8 Hz, 1H), 7.40-7.32 (m, 5H), 7.14-7.06 (m, 3H), 6.60 (br s, 1H), 6.46 (dd, J = 1.8, 8.3 Hz, 1H), 6.20 (br s, 1H), 3.87 (t, J = 8.0 Hz, 2H), 3.74 (t, J = 6.5 Hz, 2H), 3.54-3.48 (m, 1H), 2.33 (s, 3H); MS: 575.0 (M + 1)$^+$. |
| 3/6 | [structure 1/10] | [structure] | $^1$H-NMR (500 MHz, DMSO-d$_6$) δ: 8.23 (dd, J = 4.5, 9.0 Hz, 1H), 7.46 (d, J = 5.0 Hz, 1H), 7.33-7.27 (m, 5H), 7.14 (t, J = 7.8 Hz, 1H), 6.87 (dd, J = 2.5, 8.5 Hz, 1H), 6.63-6.60 (m, 2H), 6.45 (dd, J = 2.0, 8.0 Hz, 1H), 6.18 (s, 1H), 4.14-4.09 (m, 1H), 3.89-3.73 (m, 5H), 3.54-3.48 (m, 1H), 2.99 (s, 3H), 2.31 (s, 3H); MS: 591.1 (M + 1)$^+$. |

| # | starting material | structure | analytical data |
|---|---|---|---|
| 3/7 | 1/11 | 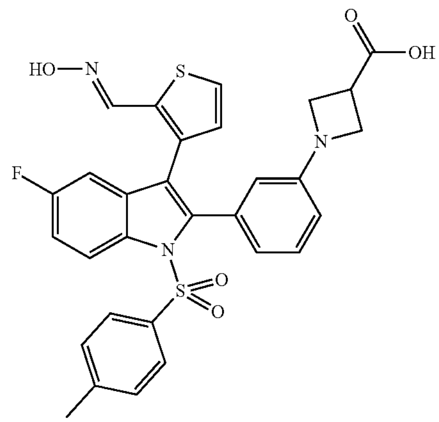 [SMILES: Cc1ccc(S(=O)(=O)n2c(-c3cccc(N4CC(C(=O)O)C4)c3)c(-c3ccsc3/C=N/O)c3cc(F)ccc32)cc1] | $^1$H-NMR (500 MHz, DMSO-d$_6$) δ: 12.69 (br s, 1H), 11.24 (s, 1H), 8.25 (dd, J = 4.3, 9.3 Hz, 1H), 7.49 (d, J = 5.0 Hz, 1H), 7.38-7.29 (m, 6H), 7.13 (d, J = 7.8 Hz, 1H), 6.83 (dd, J = 2.5, 8.5 Hz, 1H), 6.72 (d, J = 5.5 Hz, 1H), 6.60-6.57 (m, 1H), 6.45 (dd, J = 2.0, 8.0 Hz, 1H), 6.19 (s, 1H), 3.91-3.87 (m, 2H), 3.79-3.75 (m, 2H), 3.54-3.50 (m, 1H), 2.32 (m, 3H); MS: 590.0 (M + 1)$^+$. |
| 3/8 | 1/12 | 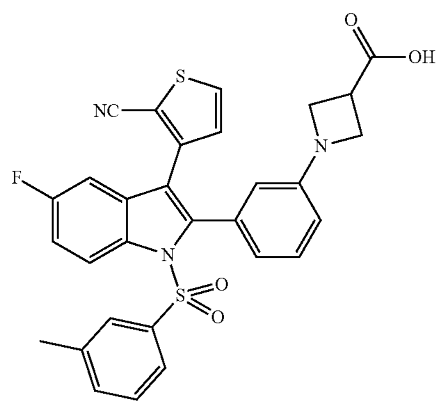 [SMILES: Cc1cccc(S(=O)(=O)n2c(-c3cccc(N4CC(C(=O)O)C4)c3)c(-c3ccsc3C#N)c3cc(F)ccc32)c1] | $^1$H-NMR (500 MHz, DMSO-d$_6$) δ: 8.28 (dd, J = 4.8, 9.3 Hz, 1H), 8.24 (d, J = 5.0 Hz, 1H), 7.49 (d, J = 7.5 Hz, 1H), 7.42-7.33 (m, 3H), 7.23 (s, 1H), 7.15-7.11 (m, 2H), 6.94 (d, J = 5.0 Hz, 1H), 6.52 (d, J = 7.5 Hz, 1H), 6.47 (dd, J = 1.3, 8.3 Hz, 1H), 6.17 (s, 1H), 3.86 (t, J = 8.0 Hz, 2H), 3.75 (t, J = 6.5 Hz, 2H), 3.45-3.40 (m, 1H), 2.28 (s, 3H); MS: 569.8 (M − 1)$^-$. |
| 3/9 | 1/13 | 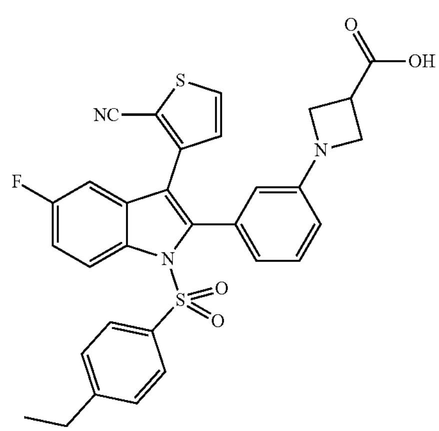 | $^1$H-NMR (500 MHz, DMSO-d$_6$) δ: 8.28 (dd, J = 4.5, 9.5 Hz, 1H), 7.98 (d, J = 4.5 Hz, 1H), 7.71-7.67 (m, 1H), 7.54-7.50 (m, 4H), 7.37-7.33 (m, 1H), 7.14-7.11 (m, 2H), 6.93 (d, J = 5.0 Hz, 1H), 6.53 (d, J = 7.5 Hz, 1H), 6.45 (dd, J = 1.8, 8.3 Hz, 1H), 6.18 (s, 1H), 3.83 (t, J = 7.8 Hz, 2H), 3.74 (t, J = 6.3 Hz, 2H), 3.34-3.30 (m, 1H); MS: 557.9 (M + 1)$^+$. |

-continued

| # | starting material | structure | analytical data |
|---|---|---|---|
| 3/10 | 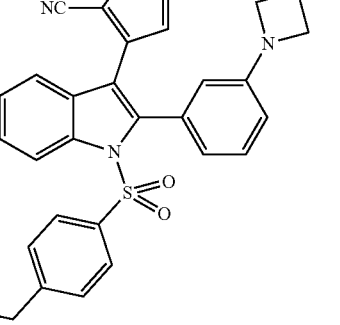<br>1/14 | 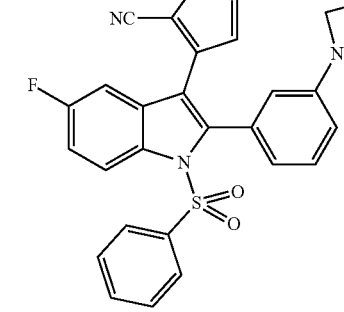 | $^1$H-NMR (500 MHz, DMSO-$d_6$) δ: 8.28 (dd, J = 4.0, 9.0 Hz, 1H), 7.98 (d, J = 5.0 Hz, 1H), 7.44 (d, J = 8.0 Hz, 2H), 7.37-7.33 (m, 3H), 7.16-7.11 (m, 2H), 6.94 (d, J = 5.0 Hz, 1H), 6.55 (d, J = 7.5 Hz, 1H), 6.48 (dd, J = 1.5, 8.0 Hz, 1H), 6.21 (s, 1H), 3.89 (t, J = 7.5 Hz, 2H), 3.77 (t, J = 6.3 Hz, 2H), 3.49-3.44 (m, 1H), 2.63 (q, J = 7.5 Hz, 2H), 1.12 (t, J = 7.5 Hz, 3H); MS: 586.8 (M + 1)$^+$. |
| 3/11 | 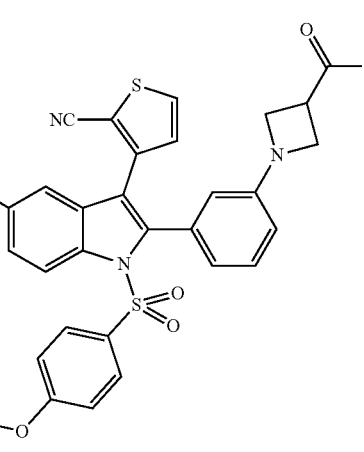<br>1/15 | 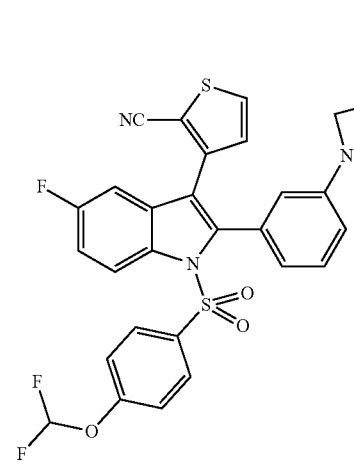 | $^1$H-NMR (500 MHz, DMSO-$d_6$) δ: 8.28 (dd, J = 4.3, 9.3 Hz, 1H), 7.99 (d, J = 5.0 Hz, 1H), 7.58 (d, J = 9.0 Hz, 2H), 7.52-7.23 (m, 4H), 7.15-7.12 (m, 2H), 6.95 (d, J = 5.0 Hz, 1H), 6.53 (d, J = 7.5 Hz, 1H), 6.49-6.48 (m, 1H), 6.27 (s, 1H), 3.90 (t, J = 8.0 Hz, 2H), 3.79 (t, J = 6.5 Hz, 2H), 3.46-3.41 (m, 1H); MS: 623.7 (M + 1)$^+$. |
| 3/12 | 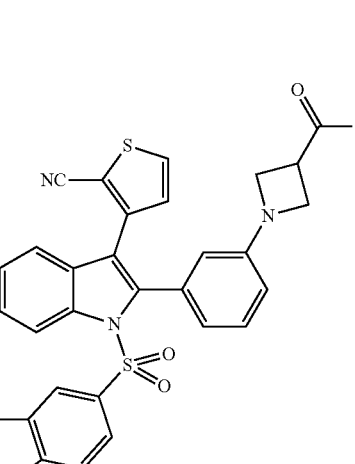<br>1/16 | 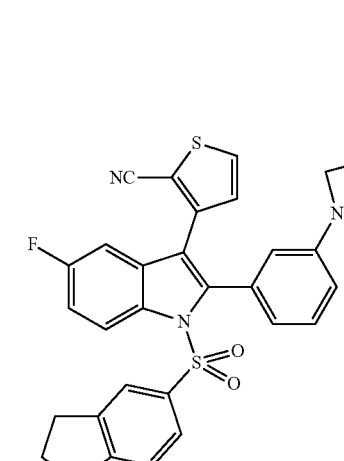 | $^1$H-NMR (500 MHz, DMSO-$d_6$) δ: 8.28 (dd, J = 4.5, 9.0 Hz, 1H), 7.97 (d, J = 5.0 Hz, 1H), 7.37-7.30 (m, 3H), 7.27 (s, 1H), 7.15-7.10 (m, 2H), 6.94 (d, J = 5.5 Hz, 1H), 6.54 (d, J = 7.5 Hz, 1H), 6.46 (dd, J = 1.8, 8.3 Hz, 1H), 6.14 (s, 1H), 3.84 (t, J = 8.0 Hz, 2H), 3.74 (t, J = 6.5 Hz, 2H), 3.41-3.35 (m, 1H), 2.88-2.80 (m, 4H), 2.02-1.97 (m, 2H); MS: 598.2 (M + 1)$^+$. |

| # | starting material | structure | analytical data |
|---|---|---|---|
| 3/13 1/17 | (structure) | (structure) | $^1$H-NMR (500 MHz, DMSO-$d_6$) δ: 8.38 (dd, J = 4.0, 9.5 Hz, 1H), 8.18 (s, 1H), 8.06-7.96 (m, 4H), 7.76-7.68 (m, 2H), 7.46 (d, J = 9.0 Hz, 1H), 7.39-7.36 (m, 1H), 7.15-7.12 (m, 2H), 6.95 (d, J = 5.0 Hz, 1H), 6.59 (d, J = 7.0 Hz, 1H), 6.45 (d, J = 7.5 Hz, 1H), 6.08 (s, 1H), 3.69-3.59 (m, 4H), 3.42-3.32 (m, 1H); MS: 608.2 (M + 1)$^+$. |
| 3/14 1/18 | (structure) | (structure) | $^1$H-NMR (500 MHz, DMSO-$d_6$) δ: 8.16 (dd, J = 4.5, 9.0 Hz, 1H), 7.98 (d, J = 5.5 Hz, 1H), 7.36-7.17 (m, 4H), 7.05 (t, J = 7.5 Hz, 2H), 6.99 (d, J = 5.0 Hz, 1H), 6.45-6.40 (m, 2H), 5.97 (s, 1H), 3.79 (t, J = 8.0 Hz, 2H), 3.68 (t, J = 6.3 Hz, 2H), 3.45-3.40 (m, 1H), 2.36 (s, 3H); MS: 589.9 (M + 1)$^+$. |
| 3/15 1/19 | (structure) | (structure) | $^1$H-NMR (500 MHz, DMSO-$d_6$) δ: 8.42 (d, J = 8.5 Hz, 1H), 8.03-8.01 (m, 1H), 7.83 (d, J = 5.0 Hz, 1H), 7.79 (s, 1H), 7.67-7.62 (m, 2H), 7.56-7.53 (m, 1H), 7.42-7.39 (m, 2H), 7.34 (d, J = 8.0 Hz, 2H), 7.24 (d, J = 8.5 Hz, 2H), 6.97 (d, J = 5.0 Hz, 1H), 4.26 (s, 2H), 2.35 (s, 3H); MS: 576.7 (M + 1)$^+$. |

| # | starting material | structure | analytical data |
|---|---|---|---|
| 3/16 | (structure) 1/20 | (structure) | ¹H-NMR (500 MHz, DMSO-d₆) δ: 12.07 (br s, 1H), 8.28 (d, J = 8.0 Hz, 1H), 8.02 (d, J = 5.0 Hz, 1H), 7.53-7.50 (m, 1H), 7.44 (d, J = 8.0 Hz, 2H), 7.38 (d, J = 4.0 Hz, 2H), 7.31 (d, J = 8.5 Hz, 2H), 7.05 (d, J = 3.5 Hz, 1H), 6.99 (d, J = 5.5 Hz, 1H), 6.83 (d, J = 4.0 Hz, 1H), 2.97 (s, 2H), 2.31 (s, 3H), 1.09 (s, 6H); MS: 559.0 (M − 1)⁻. |
| 3/17 | (structure) 1/21 | (structure) | ¹H-NMR (500 MHz, DMSO-d₆) δ: 8.26 (d, J = 11.0 Hz, 1H), 8.05 (d, J = 6.0 Hz, 1H), 7.54-7.32 (m, 8H), 7.04 (d, J = 6.0 Hz, 1H), 6.91 (d, J = 2.0 Hz, 1H), 2.39-2.34 (m, 1H), 2.32 (s, 3H), 1.75-1.70 (m, 1H), 1.39-1.35 (m, 1H), 1.20-1.15 (m, 1H); MS: 562.1 (M + 18)⁺. |
| 3/18 | (structure) 1/22 | (structure) | ¹H-NMR (500 MHz, CD₃OD) δ: 8.41 (d, J = 10.0 Hz, 1H), 7.80 (d, J = 6.5 Hz, 1H), 7.65-7.49 (m, 3H), 7.43-7.21 (m, 9H), 6.96 (d, J = 6.5 Hz, 1H), 6.35 (d, J = 20.0 Hz, 1H), 2.36 (s, 3H); MS: 524.6 (M + 1)⁺. |
| 3/19 | (structure) 1/24 | (structure) | ¹H-NMR (500 MHz, DMSO-d₆) δ: 12.47 (br s, 1H), 8.25 (d, J = 10.5 Hz, 1H), 8.07 (d, J = 6.5 Hz, 1H), 7.70 (d, J = 20.0 Hz, 1H), 7.56-7.51 (m, 4H), 7.42-7.32 (m, 4H), 7.23 (d, J = 4.5 Hz, 1H), 7.09 (d, J = 6.5 Hz, 1H), 6.18 (d, J = 20.0 Hz, 1H), 2.31 (s, 3H); MS: 530.7 (M + 1)⁺. |

| # | starting material | structure | analytical data |
|---|---|---|---|
| 3/20 1/25 | | | ¹H-NMR (500 MHz, DMSO-d₆) δ: 12.39 (br s, 1H), 8.29 (d, J = 8.5 Hz, 1H), 7.98 (d, J = 5.0 Hz, 1H), 7.51 (t, J = 7.5 Hz, 1H), 7.40-7.28 (m, 9H), 7.06 (s, 1H), 6.92 (d, J = 4.0 Hz, 1H), 2.30 (s, 3H), 1.36 (s, 6H); MS: 563.1 (M + Na)⁺. |
| 3/21 1/29 | | | ¹H-NMR (500 MHz, CD₃OD) δ: 8.26 (dd, J = 4.5, 9.0 Hz, 1H), 8.10 (d, J = 1.0 Hz, 1H), 7.99 (dd, J = 1.8, 7.8 Hz, 1H), 7.86 (d, J = 5.5 Hz, 1H), 7.56-7.51 (m, 3H), 7.44 (s, 1H), 7.40 (d, J = 8.0 Hz, 1H), 7.25-7.21 (m, 1H), 7.15 (dd, J = 2.8, 8.8 Hz, 1H), 6.98 (d, J = 4.5 Hz, 1H), 3.48 (d, J = 12.5 Hz, 2H), 2.53-2.48 (m, 2H), 1.47 (d, J = 12.5 Hz, 2H), 1.33-1.28 (m, 1H), 0.86-0.77 (m, 5H); MS: 633.9 (M + 1)⁺. |
| 3/22 1/30 | | | ¹H-NMR (500 MHz, CD₃OD) δ: 8.44 (dd, J = 4.5, 9.0 Hz, 1H), 8.09 (d, J = 2.0 Hz, 1H), 8.00 (dd, J = 1.5, 7.5 Hz, 1H), 7.82 (d, J = 5.0 Hz, 1H), 7.52-7.44 (m, 3H), 7.39 (d, J = 8.0 Hz, 1H), 7.29-6.95 (m, 4H); MS: 632.0 (M − 1)⁻. |

| # | starting material | structure | analytical data |
|---|---|---|---|
| 3/23 | (1/31) | 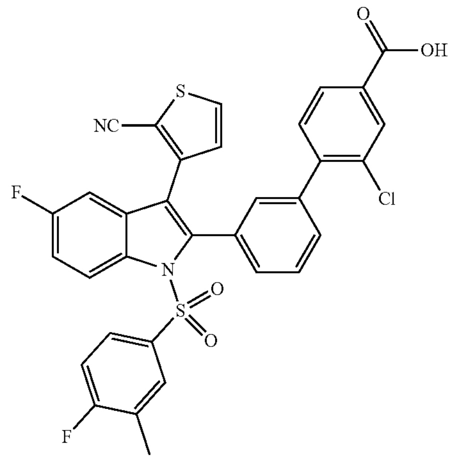 [SMILES: Cc1cc(S(=O)(=O)n2c(-c3cccc(-c4ccc(C(=O)O)cc4Cl)c3)c(-c3ccsc3C#N)c3cc(F)ccc32)ccc1F] | $^1$H-NMR (500 MHz, DMSO-$d_6$) δ: 13.41 (br s, 1H), 8.31 (dd, J = 4.5, 9.0 Hz, 1H), 8.04-7.95 (m, 3H), 7.56-7.48 (m, 3H), 7.42-7.34 (m, 4H), 7.26-7.18 (m, 3H), 7.03 (d, J = 5.0 Hz, 1H), 2.08 (s, 3H); MS: 642.9 (M − 1)$^-$. |
| 3/24 | (1/73) | 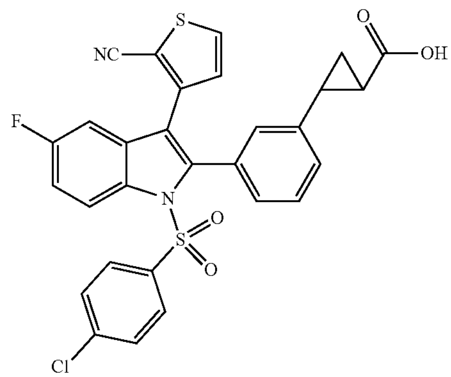 [SMILES: N#Cc1sccc1-c1c(-c2cccc(C3CC3C(=O)O)c2)n(S(=O)(=O)c2ccc(Cl)cc2)c2ccc(F)cc12] | $^1$H-NMR (500 MHz, DMSO-$d_6$) δ: 8.29-8.26 (m, 1H), 8.01 (d, J = 5.5 Hz, 1H), 7.65-7.55 (m, 2H), 7.45-7.35 (m, 3H), 7.26 (d, J = 5.0 Hz, 1H), 7.18-7.14 (m, 1H), 7.06-7.03 (m, 1H), 6.97 (d, J = 5.0 Hz, 1H), 6.91 (s, 1H), 2.35-2.30 (m, 1H), 1.70 (s, 1H), 1.41-1.37 (m, 1H), 1.17 (s, 1H); MS: 575.0 (M − 1)$^-$. |
| 3/25 | (1/74) | 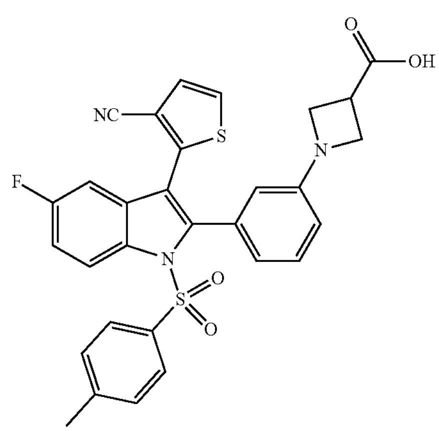 [SMILES: Cc1ccc(S(=O)(=O)n2c(-c3cccc(N4CC(C(=O)O)C4)c3)c(-c3sccc3C#N)c3cc(F)ccc32)cc1] | $^1$H-NMR (500 MHz, DMSO-$d_6$) δ: 12.66 (br s, 1H), 8.31-8.26 (m, 1H), 7.76 (d, J = 5.5 Hz, 1H), 7.46-7.33 (m, 6H), 7.20-7.15 (m, 2H), 6.60 (d, J = 7.5 Hz, 1H), 6.53-6.49 (m, 1H), 6.23 (s, 1H), 3.92 (t, J = 8.0 Hz, 2H), 3.79 (t, J = 6.5 Hz, 2H), 3.54-3.50 (m, 1H), 2.34 (s, 3H); MS: 572.1 (M + 1)$^+$. |

| # | starting material | structure | analytical data |
|---|---|---|---|
| 3/26 | (structure) 1/75 | (structure) | ¹H-NMR (500 MHz, CD₃OD) δ: 8.42-8.39 (m, 1H), 7.72 (d, J = 1.5 Hz, 1H), 7.36 (d, J = 8.5 Hz, 2H), 7.28-7.14 (m, 5H), 6.65 (d, J = 8.0 Hz, 1H), 6.66-6.64 (m, 1H), 6.60-6.57 (m, 1H), 6.35 (d, J = 2.0 Hz, 1H), 6.20 (s, 1H), 4.01 (t, J = 7.5 Hz, 2H), 3.91 (t, J = 6.0 Hz, 2H), 3.54-3.50 (m, 1H), 2.38 (s, 3H); MS: 556.2 (M + 1)⁺. |
| 3/27 | (structure) 1/76 | (structure) | ¹H-NMR (500 MHz, DMSO-d₆) δ: 8.23-8.19 (m, 1H), 7.32-7.26 (m, 6H), 7.14 (t, J = 7.5 Hz, 1H), 6.84-6.81 (m, 1H), 6.66-6.62 (m, 1H), 6.55 (d, J = 5.0 Hz, 1H), 6.45-6.42 (m, 1H), 6.16 (s, 3H), 3.90-3.85 (m, 2H), 3.77-3.73 (m, 2H), 3.52-3.49 (m, 1H), 3.25-3.19 (m, 2H), 2.48-2.33 (m, 2H), 2.31 (s, 1H); MS: 591.0 (M + 1)⁺. |
| 3/28 | (structure) 1/77 | (structure) | ¹H-NMR (500 MHz, CD₃OD) δ: 8.40-8.37 (m, 1H), 7.54 (d, J = 5.5 Hz, 1H), 7.34 (d, J = 8.0 Hz, 2H), 7.25-7.19 (m, 4H), 7.05-7.03 (m, 1H), 6.75 (d, J = 5.0 Hz, 1H), 6.67-6.59 (m, 2H), 6.26 (s, 1H), 4.05-4.01 (m, 2H), 3.95-3.92 (m, 2H), 3.60-3.57 (m, 1H), 2.65 (s, 3H), 2.38 (s, 3H), 2.33 (s, 3H); MS: 618.0 (M + 1)⁺. |

| # | starting material | structure | analytical data |
|---|---|---|---|
| C3/29 (C1/78) | [structure] | [structure] | ¹H-NMR (500 MHz, CD₃OD) δ: 8.41-8.38 (m, 1H), 7.63 (d, J = 1.5 Hz, 1H), 7.40-7.35 (m, 3H), 7.30-7.21 (m, 5H), 6.68-6.61 (m, 2H), 6.18 (d, J = 1.5 Hz, 1H), 4.03-3.99 (m, 2H), 3.93-3.89 (m, 2H), 3.56-3.53 (m, 1H), 2.37 (s, 3H); MS: 572.1 (M + 1)⁺. |
| 3/30 (1/79) | [structure] | [structure] | ¹H-NMR (500 MHz, CD₃OD) δ: 8.35-8.32 (m, 1H), 7.62 (d, J = 5.0 Hz, 1H), 7.31-7.15 (m, 7H), 6.78-6.75 (m, 1H), 6.66 (br s, 2H), 6.51-6.48 (m, 1H), 3.98-3.79 (m, 4H), 3.55-3.50 (m, 1H), 2.37 (s, 3H); MS: 615.1 (M + 1)⁺. |
| 3/31 (1/80) | [structure] | [structure] | ¹H-NMR (500 MHz, DMSO-d₆) δ: 8.27-8.23 (m, 1H), 7.62 (d, J = 7.0 Hz, 1H), 7.41 (t, J = 8.0 Hz, 1H), 7.35-7.28 (m, 5H), 7.20 (t, J = 7.0 Hz, 1H), 7.09 (t, J = 7.0 Hz, 1H), 6.87 (d, J = 7.5 Hz, 1H), 6.63-6.56 (m, 2H), 6.38 (d, J = 6.5 Hz, 1H), 6.05-6.01 (m, 1H), 4.41-4.13 (m, 4H), 3.82-3.79 (m, 2H), 3.70-3.66 (m, 2H), 3.59-3.55 (m, 1H), 3.43-3.39 (m, 1H), 2.33 (s, 3H); MS: 597.2 (M + 1)⁺. |

-continued

| # | starting material | structure | analytical data |
|---|---|---|---|
| 3/32 1/81 | | | ¹H-NMR (500 MHz, DMSO-d₆) δ: 8.29-8.26 (m, 1H), 7.98 (d, J = 5.1 Hz, 1H), 7.41 (d, J = 8.4 Hz, 2H), 7.37-7.31 (m, 3H), 7.17-7.09 (m, 2H), 6.94 (d, J = 5.1 Hz, 1H), 6.56 (d, J = 7.6 Hz, 1H), 6.48 (dd, J = 8.1, 1.8 Hz, 1H), 6.20 (s, 1H), 3.88 (t, J = 7.8 Hz, 2H), 3.77 (t, J = 6.5 Hz, 2H), 3.47-3.43 (m, 1H), 2.33 (s, 3H); MS: 569.7 (M − 1)⁻. |
| 3/33 1/82 | | | ¹H-NMR (500 MHz, DMSO-d₆) δ: 8.30-8.26 (m, 1H), 7.98 (d, J = 5.1 Hz, 1H), 7.46 (d, J = 8.9 Hz, 2H), 7.35 (td, J = 9.2, 2.5 Hz, 1H), 7.16-7.10 (m, 2H), 7.02 (d, J = 9.0 Hz, 2H), 6.94 (d, J = 5.1 Hz, 1H), 6.56 (d, J = 7.5 Hz, 1H), 6.48 (d, J = 8.1 Hz, 1H), 6.23 (s, 1H), 3.90 (t, J = 7.9 Hz, 2H), 3.77-3.80 (m, 5H), 3.48-3.44 (m, 1H); MS: 578.8 (M + 1)⁺. |
| 3/34 1/83 | | | ¹H-NMR (500 MHz, DMSO-d₆) δ: 8.31-8.28 (m, 1H), 7.99 (d, J = 5.1 Hz, 1H), 7.92 (d, J = 8.4 Hz, 2H), 7.70 (d, J = 8.3 Hz, 2H), 7.39 (td, J = 9.1, 2.5 Hz, 1H), 7.15-7.11 (m, 2H), 6.94 (d, J = 5.1 Hz, 1H), 6.54-6.47 (m, 2H), 6.24 (s, 1H), 3.89 (t, J = 7.9 Hz, 2H), 3.78 (t, J = 6.4 Hz, 2H), 3.44-3.47 (m, 1H); MS: 625.8 (M + 1)⁺. |

| # | starting material | structure | analytical data |
|---|---|---|---|
| 3/35 1/84 | (structure with methyl ester, thiophene-CN, 5-fluoroindole, N-sulfonyl-4-(difluoromethyl)phenyl, azetidine) | (corresponding carboxylic acid) | ¹H-NMR (500 MHz, DMSO-d₆) δ: 8.30-8.27 (m, 1H), 7.99 (d, J = 5.1 Hz, 1H), 7.73 (d, J = 8.3 Hz, 2H), 7.65 (d, J = 8.3 Hz, 2H), 7.40-7.35 (m, 1H), 7.15-7.12 (m, 2H), 7.09 (t, J = 55.5 Hz, 1H), 6.96 (d, J = 5.1 Hz, 1H), 6.55 (d, J = 7.5 Hz, 1H), 6.48 (d, J = 8.0 Hz, 1H), 6.24 (s, 1H), 3.88 (t, J = 7.9 Hz, 2H), 3.77 (t, J = 6.5 Hz, 2H), 3.42-3.48 (m, 1H); MS: 607.8 (M + 1)⁺. |
| 3/36 1/85 | (structure with methyl ester, thiophene-CN, 5-fluoroindole, N-sulfonyl-4-methylpiperidine, azetidine) | (corresponding carboxylic acid) | ¹H-NMR (500 MHz, CD₃OD) δ: 8.24-8.21 (m, 1H), 7.79 (d, J = 5.1 Hz, 1H), 7.23-7.15 (m, 2H), 7.11 (dd, J = 8.7, 2.5 Hz, 1H), 6.86 (d, J = 5.1 Hz, 1H), 6.77 (d, J = 7.6 Hz, 1H), 6.56-6.53 (m, 2H), 4.05-4.01 (m, 2H), 3.94-3.90 (m, 2H), 3.50-3.56 (m, 1H), 3.47 (d, J = 12.9 Hz, 2H), 2.48 (t, J = 11.7 Hz, 2H), 1.49 (dd, J = 13.0, 2.1 Hz, 2H), 1.39-1.26 (m, 1H), 0.90-0.76 (m, 5H); MS: 579.0 (M + 1)⁺. |
| 3/37 1/86 | (structure with methyl ester, 3-methylazetidine, thiophene-CN, 5-fluoroindole, N-tosyl) | (corresponding carboxylic acid) | ¹H-NMR (500 MHz, DMSO-d₆) δ: 12.77 (s, 1H), 8.27 (dd, J = 9.2, 4.4 Hz, 1H), 7.99 (d, J = 5.1 Hz, 1H), 7.45-7.28 (m, 5H), 7.19-7.08 (m, 2H), 6.95 (d, J = 5.1 Hz, 1H), 6.59-6.57 (m, 1H), 6.51-6.47 (m, 1H), 6.21 (s, 1H), 3.92 (d, J = 7.2 Hz, 2H), 3.54 (d, J = 7.2 Hz, 2H), 2.33 (s, 3H), 1.52 (s, 3H); MS: 586.2 (M + 1)⁺. |

| # | starting material | structure | analytical data |
|---|---|---|---|
| 3/38 | 1/87 | 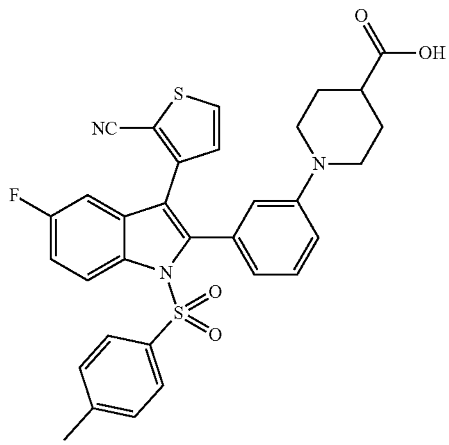 [SMILES: Cc1ccc(S(=O)(=O)n2c(-c3cccc(N4CCC(C(=O)O)CC4)c3)c(-c3ccsc3C#N)c3cc(F)ccc32)cc1] | ¹H-NMR (400 MHz, CD₃OD) δ: 8.40 (dd, J = 9.2, 4.4 Hz, 1H), 7.88 (d, J = 5.1 Hz, 1H), 7.41-7.57 (m, 3H), 7.35-7.20 (m, 5H), 7.10-6.98 (m, 3H), 3.73-3.69 (m, 2H), 3.47-3.41 (m, 2H), 2.80-2.67 (m, 1H), 2.36 (s, 3H), 2.26 (d, J = 14.1 Hz, 2H), 2.13-1.98 (m, 2H); MS: 600.2 (M + 1)⁺. |
| 3/39 | 1/88 | 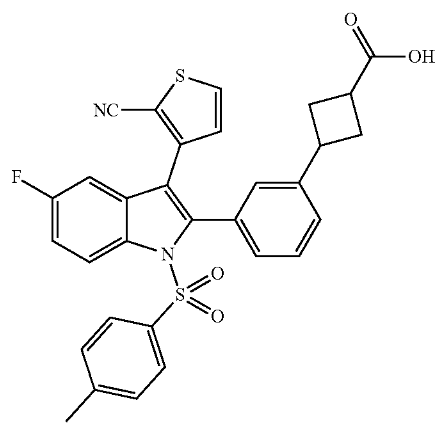 [SMILES: Cc1ccc(S(=O)(=O)n2c(-c3cccc(C4CC(C(=O)O)C4)c3)c(-c3ccsc3C#N)c3cc(F)ccc32)cc1] | ¹H-NMR (500 MHz, DMSO-d₆) δ: 12.14 (s, 1H), 8.30 (dd, J = 9.2, 4.4 Hz, 1H), 8.00-7.97 (m, 1H), 7.43-7.20 (m, 7H), 7.17-7.08 (m, 2H), 7.06-6.91 (m, 2H), 3.62-3.29 (m, 1H), 3.10-2.92 (m, 1H), 2.50-2.39 (m, 2H), 2.32 (s, 3H), 2.24-2.02 (m, 2H); MS: 568.7 (M − 1)⁻. |
| 3/40 | 1/89 | 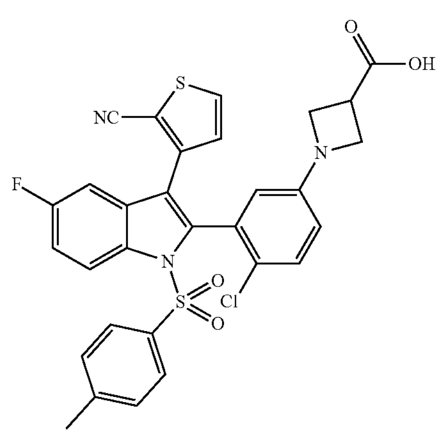 [SMILES: Cc1ccc(S(=O)(=O)n2c(-c3cc(N4CC(C(=O)O)C4)ccc3Cl)c(-c3ccsc3C#N)c3cc(F)ccc32)cc1] | ¹H-NMR (500 MHz, DMSO-d₆) δ: 12.68 (s, 1H), 8.28 (dd, J = 9.2, 4.4 Hz, 1H), 7.98 (d, J = 5.1 Hz, 1H), 7.59 (d, J = 8.4 Hz, 2H), 7.44-7.32 (m, 3H), 7.28-7.17 (m, 2H), 6.94 (d, J = 5.1 Hz, 1H), 6.54 (dd, J = 8.7, 2.8 Hz, 1H), 6.40 (d, J = 2.3 Hz, 1H), 4.02-3.93 (m, 2H), 3.90-3.77 (m, 2H), 3.59-3.48 (m, 1H), 2.36 (s, 3H); MS: 606.1 (M + 1)⁺. |

-continued

| # | starting material | structure | analytical data |
|---|---|---|---|
| 3/41 | 1/90 | 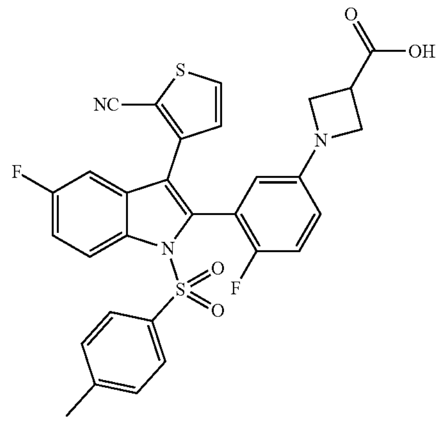 [SMILES: Cc1ccc(S(=O)(=O)n2c(-c3cc(N4CC(C(=O)O)C4)ccc3F)c(-c3ccsc3C#N)c3cc(F)ccc32)cc1] | ¹H-NMR (500 MHz, CDCl₃) δ: 8.30 (dd, J = 9.2, 4.4 Hz, 1H), 7.49 (d, J = 5.1 Hz, 1H), 7.42 (d, J = 8.3 Hz, 2H), 7.20-7.12 (m, 3H), 7.05 (dd, J = 8.4, 2.4 Hz, 1H), 6.90 (t, J = 8.9 Hz, 1H), 6.83 (d, J = 5.1 Hz, 1H), 6.56-6.49 (m, 1H), 6.39-6.35 (m, 1H), 4.12-3.98 (m, 4H), 3.63-3.55 (m, 1H), 2.35 (s, 3H); MS: 590.1 (M + 1)⁺. |
| 3/42 | 1/91 | 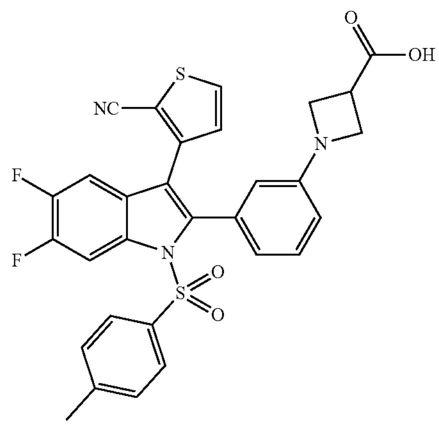 [SMILES: Cc1ccc(S(=O)(=O)n2c(-c3cccc(N4CC(C(=O)O)C4)c3)c(-c3ccsc3C#N)c3cc(F)c(F)cc32)cc1] | ¹H-NMR (500 MHz, CD₃OD) δ: 8.34-8.29 (m, 1H), 7.78 (d, J = 5.0 Hz, 1H), 7.34-7.15 (m, 6H), 6.87 (d, J = 5.0 Hz, 1H), 6.62 (d, J = 7.5 Hz, 1H), 6.57 (dd, J = 1.5 Hz, 1.0 Hz, 1H), 6.18 (s, 1H), 4.00 (t, J = 8.0 Hz, 2H), 3.89 (t, J = 7.5 Hz, 2H), 3.58-3.54 (m, 1H), 2.38 (s, 3H); MS: 589.7 (M + 1)⁺. |
| 3/43 | 1/92 | 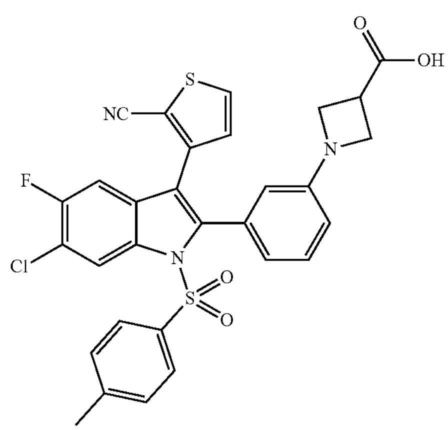 [SMILES: Cc1ccc(S(=O)(=O)n2c(-c3cccc(N4CC(C(=O)O)C4)c3)c(-c3ccsc3C#N)c3cc(F)c(Cl)cc32)cc1] | ¹H-NMR (500 MHz, DMSO-d₆) δ: 12.69 (br s, 1H), 8.40 (d, J = 8.0 Hz, 1H), 7.99 (d, J = 6.5 Hz, 1H), 7.45-7.32 (m, 5H), 7.14 (t, J = 9.5 Hz, 1H), 6.95 (d, J = 6.0 Hz, 1H), 6.55-6.48 (m, 2H), 6.15 (s, 1H), 3.89 (t, J = 9.5 Hz, 2H), 3.74 (t, J = 8.5 Hz, 2H), 3.54-3.49 (m, 1H), 2.34 (s, 3H); MS: 606.1 (M + 1)⁺. |

| # | starting material | structure | analytical data |
|---|---|---|---|
| 3/44 | 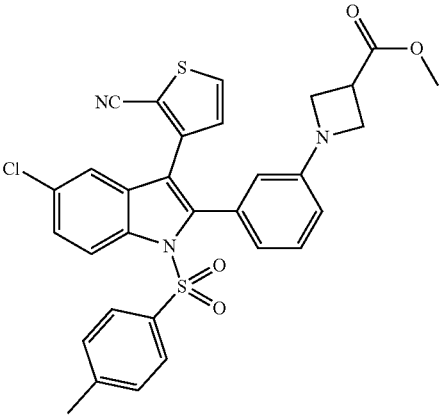   1/93 | 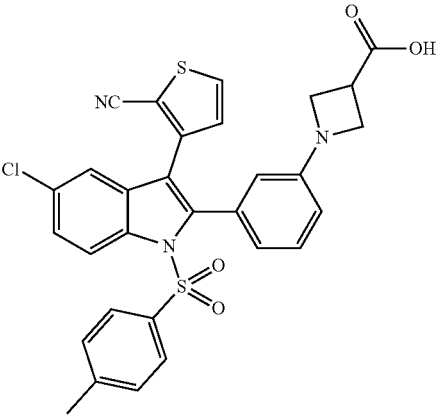 [SMILES: Cc1ccc(S(=O)(=O)n2c(-c3cccc(N4CC(C(=O)O)C4)c3)c(-c3ccsc3C#N)c3cc(Cl)ccc32)cc1] | ¹H-NMR (500 MHz, DMSO-d₆) δ: 8.28 (d, J = 9.0 Hz, 1H), 7.99 (d, J = 5.0 Hz, 1H), 7.52 (dd, J = 2.5, 2.0 Hz, 1H), 7.42 (d, J = 8.5 Hz, 2H), 7.35-7.31 (m, 3H), 7.13 (t, J = 7.5 Hz, 1H), 6.97 (d, J = 5.0 Hz, 1H), 6.55 (d, J = 7.5 Hz, 1H), 6.50-6.46 (m, 1H), 6.19 (s, 1H), 3.89-3.86 (m, 2H), 3.78-3.74 (m, 2H), 3.45-3.40 (m, 1H), 2.33 (s, 3H); MS: 587.8 (M + 1)⁺. |
| 3/45 | 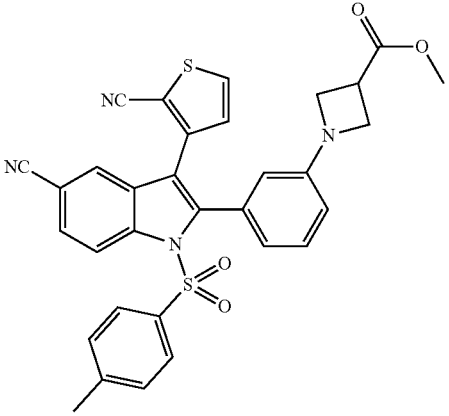   1/94 | 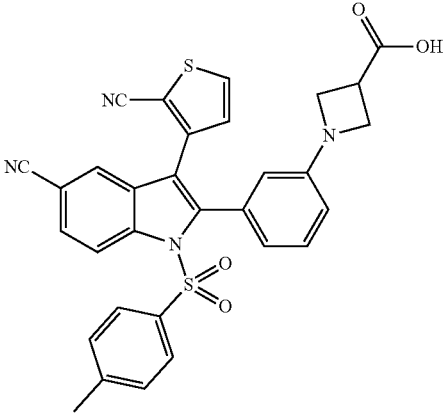 [SMILES: Cc1ccc(S(=O)(=O)n2c(-c3cccc(N4CC(C(=O)O)C4)c3)c(-c3ccsc3C#N)c3cc(C#N)ccc32)cc1] | ¹H-NMR (500 MHz, DMSO-d⁶) δ: 8.46 (d, J = 8.5 Hz, 1H), 8.00 (d, J = 5.0 Hz, 1H), 7.95-7.88 (m, 2H), 7.46 (d, J = 8.5 Hz, 2H), 7.35 (d, J = 8.5 Hz, 2H), 7.16 (t, J = 8.0 Hz, 1H), 7.01 (d, J = 5.0 Hz, 1H), 6.56 (d, J = 7.5 Hz, 1H), 6.50 (dd, J = 1.5, 2.0 Hz, 1H), 6.20 (s, 1H), 3.93-3.87 (m, 2H), 3.80-3.75 (m, 2H), 3.54-3.50 (m, 1H), 2.35 (s, 3H); MS: 579.1 (M + 1)⁺. |
| 3/46 | 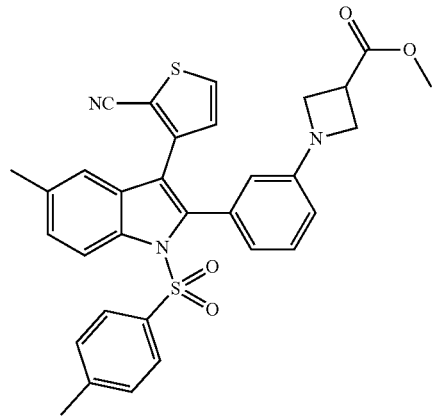   1/95 | 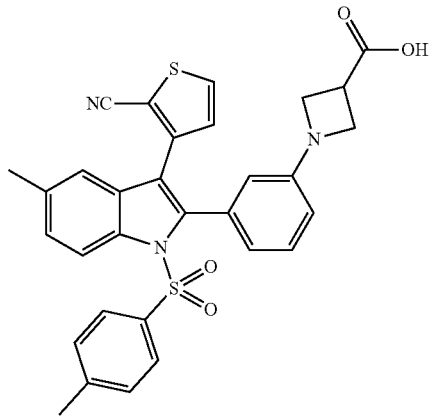 [SMILES: Cc1ccc(S(=O)(=O)n2c(-c3cccc(N4CC(C(=O)O)C4)c3)c(-c3ccsc3C#N)c3cc(C)ccc32)cc1] | ¹H-NMR (500 MHz, DMSO-d₆) δ: 8.12 (d, J = 9.0 Hz, 1H), 7.98 (d, J = 5.0 Hz, 1H), 7.42-7.28 (m, 5H), 7.13 (t, J = 7.5 Hz, 1H), 7.07 (s, 1H), 6.96 (d, J = 5.0 Hz, 1H), 6.57 (d, J = 7.5 Hz, 1H), 6.46 (dd, J = 1.5, 2.0 Hz, 1H), 6.22 (s, 1H), 3.90-3.86 (m, 2H), 3.78-3.74 (m, 2H), 3.45-3.41 (m, 1H), 2.36 (s, 3H), 2.31 (s, 3H); MS: 567.8 (M + 1)⁺. |

| # | starting material | structure | analytical data |
|---|---|---|---|
| 3/47 | (structure 1/96) | 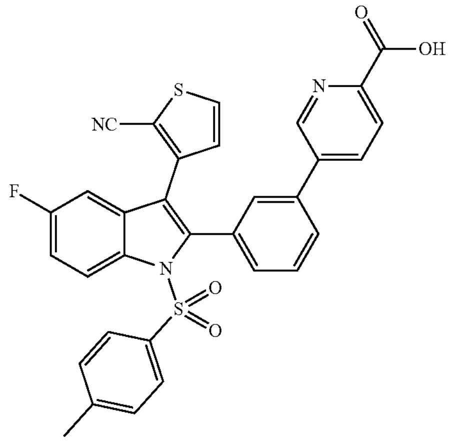 [SMILES: Cc1ccc(S(=O)(=O)n2c(-c3cccc(-c4ccc(C(=O)O)nc4)c3)c(-c3ccsc3C#N)c3cc(F)ccc32)cc1] | $^1$H-NMR (500 MHz, DMSO-d$_6$) δ: 8.81 (s, 1H), 8.33-8.29 (m, 1H), 8.10-8.03 (m, 3H), 7.85 (d, J = 10.0 Hz, 1H), 7.58-7.52 (m, 2H), 7.42-7.32 (m, 4H), 7.27 (d, J = 10.0 Hz, 2H), 7.21 (dd, J = 3.0, 3.5 Hz, 1H), 7.08 (d, J = 6.0 Hz, 1H), 2.25 (s, 3H); MS: 594.1 (M + 1)$^+$. |
| 3/48 | (structure 1/97) | 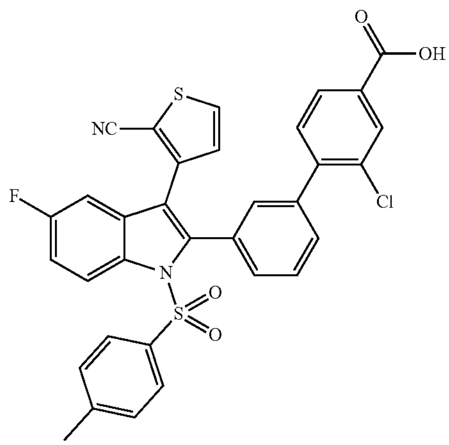 | $^1$H-NMR (500 MHz, CD$_3$OD) δ: 8.43-8.40 (m, 1H), 8.08 (d, J = 2.0 Hz, 1H), 7.99 (dd, J = 10.0, 2.0 Hz, 1H), 7.83 (d, J = 6.5 Hz, 1H), 7.52-7.44 (m, 3H), 7.38 (d, J = 10.0 Hz, 1H), 7.30-7.25 (m, 3H), 7.15 (d, J = 10.0 Hz, 2H), 7.08-6.96 (m, 3H), 2.24 (s, 3H); MS: 624.7 (M − 1)$^-$. |
| 3/49 | (structure 1/98) | 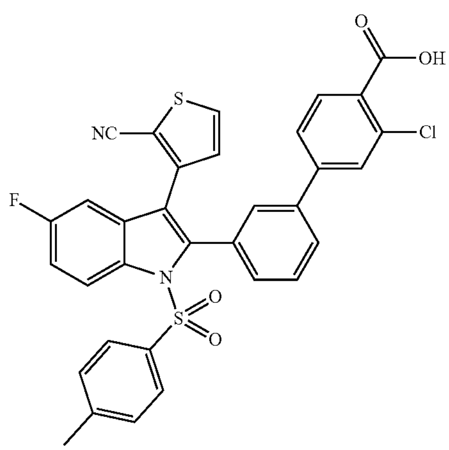 [SMILES: Cc1ccc(S(=O)(=O)n2c(-c3cccc(-c4ccc(C(=O)O)c(Cl)c4)c3)c(-c3ccsc3C#N)c3cc(F)ccc32)cc1] | $^1$H-NMR (500 MHz, CD$_3$OD) δ: 8.44-8.40 (m, 1H), 7.88-7.83 (m, 2H), 7.72 (dd, J = 8.5, 1.5 Hz, 1H), 7.53 (d, J = 2.0 Hz, 1H), 7.51-7.45 (m, 2H), 7.34-7.27 (m, 5H), 7.18 (d, J = 8.5 Hz, 2H), 7.07 (dd, J = 8.5, 2.5 Hz, 1H), 7.00 (d, J = 5.0 Hz, 1H), 2.30 (s, 3H); MS: 624.7 (M − 1)$^-$. |

| # | starting material | structure | analytical data |
|---|---|---|---|
| 3/50 | (structure) 1/99 | (structure) | $^1$H-NMR (500 MHz, DMSO-d$_6$) δ: 12.41 (br s, 1H), 8.29-8.25 (m, 1H), 7.98 (d, J = 5.0 Hz, 1H), 7.39-7.29 (m, 5H), 7.20-7.12 (m, 2H), 7.02-6.95 (m, 2H), 6.72-6.65 (m, 2H), 3.33-3.30 (m, 2H), 2.83-2.79 (m, 2H), 2.32 (s, 3H), 2.01-1.99 (m, 2H), 1.48-1.43 (m, 2H), 1.16 (s, 3H); MS: 614.0 (M + 1)$^+$. |
| 3/51 | (structure) 1/100 | (structure) | $^1$H-NMR (500 MHz, DMSO-d$_6$) δ 13.03 (s, 1H), 8.26 (d, J = 8.5 Hz, 1H), 8.00 (d, J = 5.5 Hz, 1H), 7.61-7.58 (m, 2H), 7.53-7.50 (m, 3H), 7.41-7.34 (m, 2H), 7.28 (t, J = 8.0 Hz, 1H), 7.00-6.96 (m, 2H), 6.87 (d, J = 7.5 Hz, 1H), 6.82 (s, 1H), 4.63 (s, 2H); MS: 549.0 (M + 1)$^+$. |
| 3/52 | (structure) 32/3 | (structure) | $^1$H-NMR (500 MHz, DMSO-d$_6$) δ: 12.24 (s, 1H), 8.28 (dd, J = 9.2, 4.4 Hz, 1H), 8.19 (s, 1H), 7.98 (d, J = 5.1 Hz, 1H), 7.42 (d, J = 8.4 Hz, 2H), 7.37-7.29 (m, 3H), 7.17-7.10 (m, 2H), 6.93 (d, J = 5.1 Hz, 1H), 6.57-6.55 (m, 1H), 6.48-6.45 (m, 1H), 6.20 (s, 1H), 3.87-3.83 (m, 2H), 3.73-3.70 (m, 2H), 3.52-3.39 (m, 1H), 2.33 (s, 3H), 1.36 (s, 6H); MS: 657.0 (M + 1)$^+$. |

| # | starting material | structure | analytical data |
|---|---|---|---|
| 3/53 | (structure shown) 1/101 | (structure shown) | ¹H-NMR (500 MHz, DMSO-d₆) δ: 13.00 (s, 1H), 8.08 (d, J = 5.1 Hz, 1H), 8.00 (d, J = 8.3 Hz, 2H), 7.73 (d, J = 7.8 Hz, 1H), 7.61-7.56 (m, 4H), 7.50-7.45 (m, 2H), 7.33-7.28 (m, 3H), 7.08 (d, J = 5.0 Hz, 1H), 7.00 (dd, J = 11.4, 2.1 Hz, 1H), 6.69 (dd, J = 8.0, 2.2 Hz, 1H), 3.80 (s, 1H), 2.33 (s, 3H); MS: 623.0 (M + 1)⁺. |
| 3/54 | (structure shown) 33 | (structure shown) | ¹H-NMR (500 MHz, DMSO-d₆) δ: 13.02 (s, 1H), 10.68 (s, 1H), 8.08 (d, J = 5.1 Hz, 1H), 8.00 (d, J = 8.4 Hz, 2H), 7.73 (d, J = 8.0 Hz, 1H), 7.60-7.38 (m, 6H), 7.30-7.21 (m, 3H), 7.02 (d, J = 5.1 Hz, 1H), 6.67 (dd, J = 10.9, 2.3 Hz, 1H), 6.51 (dd, J = 8.1, 2.4 Hz, 1H), 2.29 (s, 3H); MS: 609.2 (M + 1)⁺. |
| 3/55 | (structure shown) 8/2 | (structure shown) | ¹H-NMR (500 MHz, DMSO-d₆) δ: 12.74 (br s, 1H), 8.30 (dd, J = 9.0, 5.0 Hz, 1H), 8.01 (d, J = 5.0 Hz, 1H), 7.72 (d, J = 8.0 Hz, 1H), 7.59 (d, J = 8.5 Hz, 2H), 7.49-7.34 (m, 7H), 7.27-7.16 (m, 4H), 7.05 (d, J = 5.0 Hz, 1H), 5.83 (br s, 1H), 2.24 (s, 3H), 1.65 (s, 3H); MS: 634.8 (M − 1)⁻. |

| # | starting material | structure | analytical data |
|---|---|---|---|
| 3/56 | (structure 1/102) | 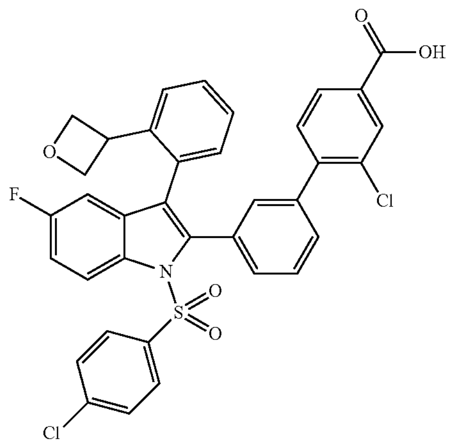 [SMILES: O=C(O)c1ccc(-c2cccc(-c3c(-c4ccccc4C4COC4)c4cc(F)ccc4n3S(=O)(=O)c3ccc(Cl)cc3)c2)c(Cl)c1] | ¹H-NMR (500 MHz, DMSO-d₆) δ: 13.39 (s, 1H), 8.27-8.24 (m, 1H), 7.97 (s, 1H), 7.93 (d, J = 7.0 Hz, 1H), 7.64-7.25 (m, 12H), 7.11 (s, 1H), 7.01 (br s, 1H), 6.75-6.73 (m, 1H), 4.42-4.37 (m, 2H), 4.17-4.13 (m, 2H), 3.67-3.63 (m, 1H); MS: 670.0 (M − 1)⁻. |
| 3/57 | (structure 1/103) | 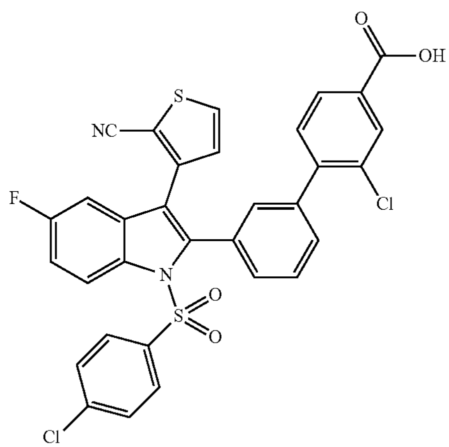 [SMILES: N#Cc1sccc1-c1c(-c2cccc(-c3ccc(C(=O)O)cc3Cl)c2)n(S(=O)(=O)c2ccc(Cl)cc2)c2ccc(F)cc12] | ¹H-NMR (500 MHz, DMSO-d₆) δ: 8.30-8.27 (m, 1H), 8.04 (d, J = 5.0 Hz, 1H), 7.96 (s, 1H), 7.93 (d, J = 8.0 Hz, 1H), 7.55-7.51 (m, 4H), 7.45-7.38 (m, 5H), 7.21-7.19 (m, 1H), 7.09 (s, 1H), 7.04 (d, J = 5.0 Hz, 1H); MS: 644.9 (M − 1)⁻. |
| 3/58 | (structure 38/1, relative stereoisomers) | (relative stereoisomers) | ¹H-NMR (500 MHz, CD₃OD) δ: 8.40 (dd, J = 9.5, 4.0 Hz, 1H), 7.71 (d, J = 5.0 Hz, 1H), 7.33 (d, J = 8.5 Hz, 2H), 7.27-7.16 (m, 4H), 7.04-7.02 (m, 1H), 6.91-6.89 (m, 1H), 6.80 (d, J = 5.5 Hz, 1H), 6.61 (d, J = 8.0 Hz, 1H), 6.46 (s, 1H), 4.16-4.13 (m, 2H), 2.94-2.90 (m, 1H), 2.35 (s, 3H), 2.11-2.07 (m, 2H), 1.89-1.81 (m, 4H), 1.57-1.54 (m, 2H); MS: 626.2 (M + 1)⁺. |

| # | starting material | structure | analytical data |
|---|---|---|---|
| 3/59 | (1/109) | 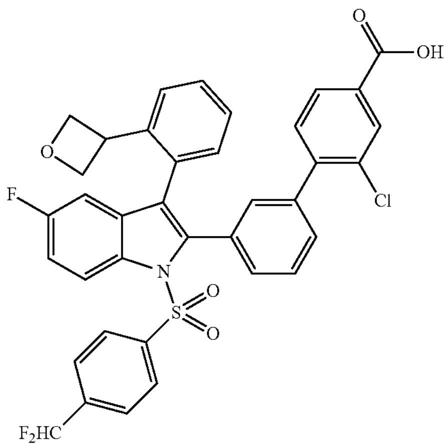 [SMILES: O=C(O)c1ccc(-c2cccc(-c3c(-c4ccccc4C4COC4)c4cc(F)ccc4n3S(=O)(=O)c3ccc(C(F)F)cc3)c2)c(Cl)c1] | ¹H-NMR (500 MHz, CD₃OD) δ: 8.41-8.38 (m, 1H), 8.07 (s, 1H), 7.97 (d, J = 7.5 Hz, 1H), 7.69 (d, J = 8.0 Hz, 1H), 7.60-7.32 (m, 8H), 7.31-7.24 (m, 3H), 7.15-6.97 (m, 2H), 6.77 (t, J = 55.5 Hz, 1H), 6.69-6.66 (m, 1H), 4.53-4.43 (m, 2H), 4.35-4.29 (m, 2H), 3.72-3.64 (m, 1H); MS: 686.0 (M − 1)⁻. |
| 3/60 | (1/111) | 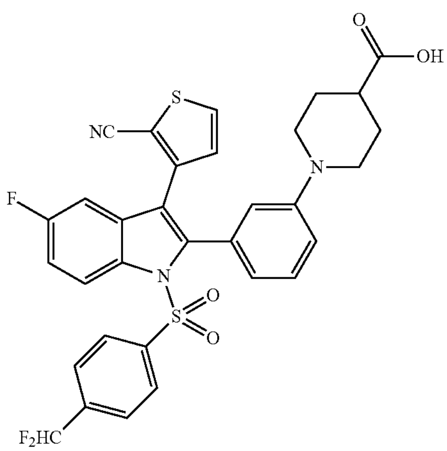 [SMILES: N#Cc1sccc1-c1c(-c2cccc(N3CCC(C(=O)O)CC3)c2)n(S(=O)(=O)c2ccc(C(F)F)cc2)c2ccc(F)cc12] | ¹H-NMR (500 MHz, CD₃OD) δ: 8.41 (dd, J = 9.2, 4.4 Hz, 1H), 7.79 (d, J = 5.1 Hz, 1H), 7.60 (d, J = 8.3 Hz, 2H), 7.53 (d, J = 8.4 Hz, 2H), 7.32-7.15 (m, 2H), 7.08-7.01 (m, 2H), 6.88 (d, J = 5.0 Hz, 1H), 6.81 (t, J = 55.0 Hz, 1H), 6.73-6.67 (m, 2H), 3.53-3.50 (m, 2H), 2.76-2.70 (m, 2H), 2.49-2.32 (m, 1H), 1.98-1.96 (m, 2H), 1.81-1.73 (m, 2H); MS: 634.0 (M − 1)⁻. |
| 3/61 | 39 | 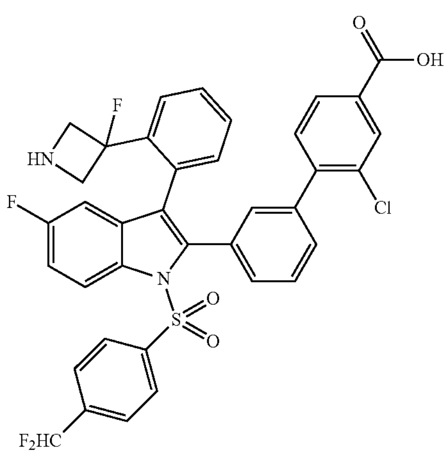 [SMILES: O=C(O)c1ccc(-c2cccc(-c3c(-c4ccccc4C4(F)CNC4)c4cc(F)ccc4n3S(=O)(=O)c3ccc(C(F)F)cc3)c2)c(Cl)c1] | ¹H-NMR (400 MHz, CD₃COCD₃) δ: 8.38-8.34 (m, 1H), 8.07 (s, 1H), 8.00 (d, J = 7.9 Hz, 1H), 7.71 (s, 4H), 7.63-7.23 (m, 9H), 7.14-6.72 (m, 3H), 3.61-3.54 (m, 2H), 3.52-2.98 (m, 3H); MS: 705.0 (M + 1)⁺. |

| # | starting material | structure | analytical data |
|---|---|---|---|
| 3/62 | (structure 40) | 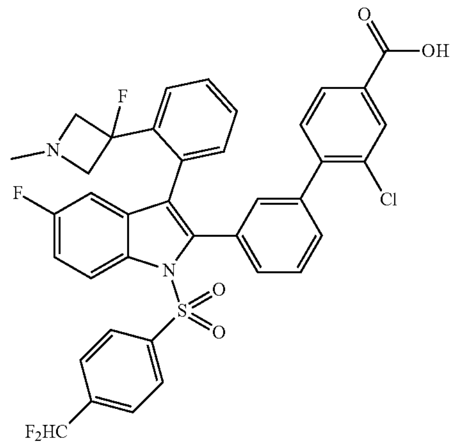 [SMILES: CN1CC(F)(c2ccccc2-c2c(-c3cccc(-c4ccc(C(=O)O)cc4Cl)c3)n(S(=O)(=O)c3ccc(C(F)F)cc3)c3ccc(F)cc23)C1] | ¹H-NMR (500 MHz, CD₃OD) δ: 8.43 (dd, J = 9.2, 4.3 Hz, 1H), 8.09 (s, 1H), 8.00 (br s, 1H), 7.76-7.14 (m, 14H), 6.93-6.63 (m, 2H), 4.61-3.78 (m, 4H), 2.81 (s, 3H); MS: 719.0 (M + 1)⁺. |
| 3/63 | (structure 1/116) | 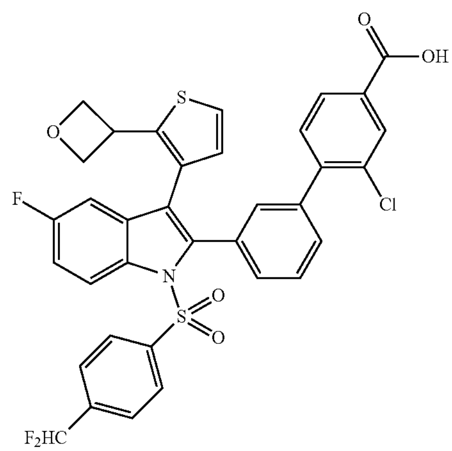 [SMILES: O=C(O)c1ccc(-c2cccc(-c3c(-c4ccsc4C4COC4)c4cc(F)ccc4n3S(=O)(=O)c3ccc(C(F)F)cc3)c2)c(Cl)c1] | ¹H-NMR (400 MHz, CD₃OD) δ: 8.40-8.36 (m, 1H), 8.10 (s, 1H), 8.00 (d, J = 5.5 Hz, 1H), 7.58-7.23 (m, 11H), 6.85-6.80 (m, 2H), 6.75 (t, J = 55.5 Hz, 1H), 4.76-4.73 (m, 1H), 4.58-4.54 (m, 1H), 4.25-4.12 (m, 1H), 4.10-4.09 (m, 1H), 3.89-3.86 (m, 1H); MS: 691.9 (M − 1)⁻. |
| 3/64 | (structure 1/117) | 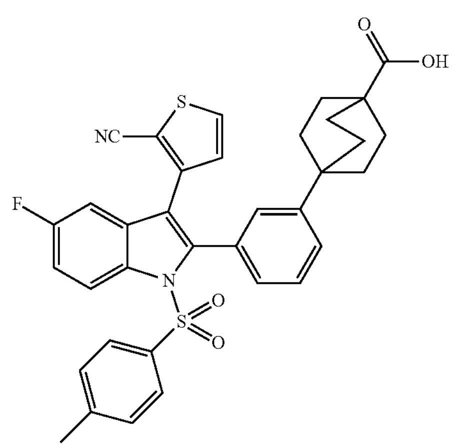 [SMILES: Cc1ccc(S(=O)(=O)n2c(-c3cccc(C45CCC(C(=O)O)(CC4)CC5)c3)c(-c3ccsc3C#N)c3cc(F)ccc32)cc1] | ¹H-NMR (500 MHz, DMSO-d₆) δ: 11.11 (br s, 1H), 8.30 (dd, J = 4.5, 9.5 Hz, 1H). 7.99 (d, J = 5.5 Hz, 1H), 7.39-6.94 (m, 11H), 2.13 (s, 3H), 1.79-1.76 (m, 6H), 1.65-1.62 (m, 6H); MS: 622.8 (M − 1)⁻. |

-continued

| # | starting material | structure | analytical data |
|---|---|---|---|
| 3/65 1/118 | (structure) | (structure) | ¹H-NMR (500 MHz, DMSO-d₆) δ: 8.29 (dd, J = 4.3, 9.3 Hz, 1H), 7.99 (d, J = 5.0 Hz, 1H), 7.39-6.91 (m, 11H), 3.33-3.26 (m, 1H), 2.95-2.90 (m, 1H), 2.41-1.81 (m, 11H); MS: 608.8 (M − 1)⁻. |
| 3/66 1/119 | (structure) | (structure) | ¹H-NMR (400 MHz, CDCl₃) δ: 8.28-8.14 (m, 3H), 7.72-7.37 (m, 11H), 6.79-6.77 (m, 1H), 2.96-2.93 (m, 4H), 1.16-1.10 (m, 4H), 0.75 (s, 6H); MS: 593.7 (M − 1)⁻. |
| 3/67 1/127 | (structure) | (structure) | ¹H-NMR (500 MHz, CD₃OD) δ: 8.43 (dd, J = 9.3, 4.8 Hz, 1H), 8.04 (d, J = 7.5 Hz, 2H), 7.70 (t, J = 8.0 Hz, 1H), 7.61 (d, J = 9.0 Hz, 2H), 7.54 (d, J = 8.0 Hz, 2H), 7.32 (dt, J = 2.5, 9.3 Hz, 1H), 7.12 (t, J = 8.0 Hz, 1H), 6.90 (dd, J = 2.5, 8.5 Hz, 1H), 6.80 (t, J = 55.8 Hz, 1H), 6.32 (d, J = 7.5 Hz, 1H), 6.53 (dd, J = 1.5, 8.0 Hz, 1H), 6.21 (t, J = 1.8 Hz, 1H), 3.96 (br s, 2H), 3.85 (br s, 2H), 3.57-3.51 (m, 1H); MS: 727.2 (M + 1)⁺. |

-continued

| # | starting material | structure | analytical data |
|---|---|---|---|
| 3/68 | 1/128 | trans | ¹H-NMR (500 MHz, CD₃OD) δ: 8.44 (dd, J = 9.4, 4.4 Hz, 1H), 8.06-8.03 (m, 2H), 7.71 (t, J = 8.3 Hz, 1H), 7.61 (d, J = 8.0 Hz, 2H), 7.49 (d, J = 8.0 Hz, 2H), 7.35-7.21 (m, 3H), 7.05-6.84 (m, 4H), 2.42-2.34 (m, 1H), 1.70-1.19 (m, 3H); MS: 610.0 (M − 1)⁻. |
| 3/69 | 20/24 | 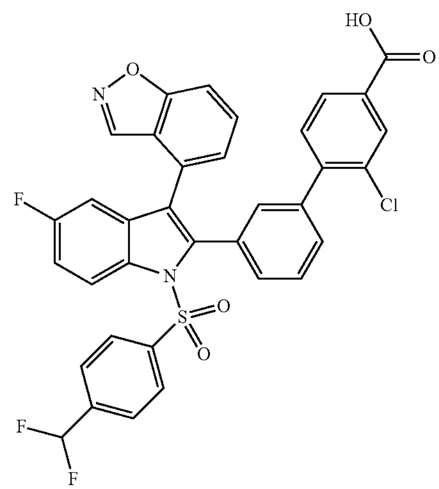 [SMILES: O=C(O)c1ccc(-c2cccc(-c3c(-c4cccc5oncc45)c4cc(F)ccc4n3S(=O)(=O)c3ccc(C(F)F)cc3)c2)c(Cl)c1] | ¹H-NMR (500 MHz, CD₃OD) δ: 8.38 (dd, J = 9.3, 4.3 Hz, 1H), 8.07 (d, J = 1.5 Hz, 1H), 7.97 (dd, J = 8.0, 1.5 Hz, 1H), 7.55-7.47 (m, 8H), 7.39 (t, J = 8.0 Hz, 1H), 7.33 (d, J = 8.0 Hz, 1H), 7.27 (dd, J = 2.5, 9.2 Hz, 1H), 7.26 (br s, 1H), 7.10-6.59 (m, 4H); MS: 670.9 (M − 1)⁻. |
| 3/70 | 44 | 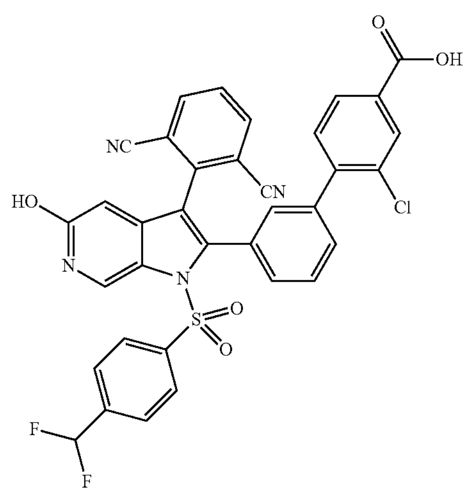 [SMILES: N#Cc1cccc(C#N)c1-c1c(-c2cccc(-c3ccc(C(=O)O)cc3Cl)c2)n(S(=O)(=O)c2ccc(C(F)F)cc2)c2cnc(O)cc12] | ¹H-NMR (500 MHz, CD₃OD) δ: 8.57 (s, 1H), 8.09-8.07 (m, 3H), 8.00 (dd, J = 8.3, 1.8 Hz, 1H), 7.74 (t, J = 7.8 Hz, 1H), 7.61-7.43 (m, 7H), 7.36 (d, J = 8.0 Hz, 1H), 7.02 (s, 1H), 6.70 (t, J = 55.5 Hz, 1H), 6.14 (d, J = 1.0 Hz, 1H); MS: 681.1 (M + 1)⁺. |

-continued

| # | starting material | structure | analytical data |
|---|---|---|---|
| 3/71 | (structure 2/32) | (structure) | ¹H-NMR (500 MHz, CD₃OD) δ: 8.44 (dd, J = 4.3, 9.3 Hz, 1H), 8.07-7.97 (m, 2H), 7.70 (t, J = 8.0 Hz, 1H), 7.53-7.44 (m, 7H), 7.34 (dt, J = 2.5, 9.0 Hz, 1H), 6.94-6.91 (m, 2H), 6.70-6.65 (m, 2H), 6.68 (t, J = 55.5 Hz, 1H), 4.71 (s, 2H); MS: 712.0 (M − 1)⁻. |
| 3/72 | (structure 2/33) | (structure) | ¹H-NMR (500 MHz, CD₃OD) δ: 8.45 (dd, J = 9.0, 4.5 Hz, 1H), 8.17-7.92 (m, 2H), 7.71 (t, J = 8.0 Hz, 1H), 7.57-7.48 (m, 7H), 7.36-7.29 (m, 3H), 6.95-6.92 (m, 2H), 6.65 (t, J = 55.8 Hz, 1H), 1.75 (s, 3H); MS: 726.0 (M − H)⁻. |
| 3/73 | (structure 2/34) | (structure) | ¹H-NMR (500 MHz, CD₃OD) δ: 8.45 (dd, J = 4.3, 9.3 Hz, 1H), 8.07-8.02 (m, 2H), 7.71 (t, J = 8.0 Hz, 1H), 7.56-7.48 (m, 7H), 7.34 (dt, J = 2.5, 9.5 Hz, 1H), 7.02 (d, J = 8.5 Hz, 2H), 7.01-6.93 (m, 2H), 6.66 (t, J = 55.5 Hz, 1H), 3.68 (s, 2H); MS: 652.0 (M − CO₂H)⁻. |

Example 4

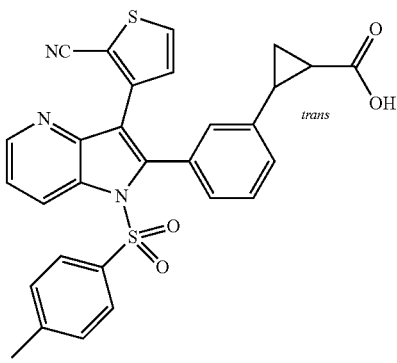

trans-2-(3-(3-(2-Cyanothiophen-3-yl)-1-tosyl-1H-pyrrolo[3,2-b]pyridin-2-yl)phenyl)cyclopropane-1-carboxylic Acid (4)

A mixture of compound 2/4 (178 mg, 0.32 mmol) and LiOH·H$_2$O (67 mg, 1.62 mmol) in THF (4.1 mL), MeOH (4.1 mL) and water (0.81 mL) was stirred at rt for 3 h, adjusted to pH=3 with 1N HCl, concentrated, diluted with EA (50 mL) and washed with water (3×5 mL) and brine (5 mL). The organic layer was concentrated under reduced pressure, the residue was dissolved in DMF (2.5 mL), filtrated and the filtrate was purified by prep-HPLC to give compound 4 as a white solid. $^1$H-NMR (500 MHz, CD$_3$OD) δ: 8.90 (dd, J=8.5, 1.5 Hz, 1H), 8.60 (dd, J=4.8, 0.8 Hz, 1H), 7.79 (d, J=5.0 Hz, 1H), 7.62 (dd, J=8.5, 4.5 Hz, 1H), 7.32-7.25 (m, 6H), 7.15-7.13 (m, 1H), 6.95 (d, J=5.0 Hz, 1H), 6.76 (s, 1H), 2.39-2.38 (m, 4H), 1.77-1.73 (m, 1H), 1.55-1.51 (m, 1H), 1.25 (br s, 1H); MS: 540.1 (M+1)$^+$.

Example 4/1 to 4/3

The following Examples were prepared similar as described for Example 4 using the appropriate starting material.

| # | starting material | structure | analytical data |
|---|---|---|---|
| 4/1 | [structure: NC-thiophene, pyrrolo[2,3-c]pyridine with N-tosyl, phenyl-cyclopropane methyl ester, trans] 2/5 | [structure: NC-thiophene, pyrrolo[2,3-c]pyridine with N-tosyl, phenyl-cyclopropane carboxylic acid, trans] | $^1$H-NMR (500 MHz, CD$_3$OD) δ: 9.84 (s, 1H), 8.65 (d, J = 6.0 Hz, 1H), 8.03 (d, J = 6.0 Hz, 1H), 7.87 (d, J = 5.0 Hz, 1H), 7.34-7.28 (m, 6H), 7.12 (d, J = 6.0 Hz, 1H), 6.99 (d, J = 5.0 Hz, 1H), 6.71 (s, 1H), 2.42-2.36 (m, 4H), 1.76-1.73 (m, 1H), 1.54-1.51 (m, 1H), 1.23 (br s, 1H); MS: 540.1 (M + 1)$^+$. |
| 4/2 | [structure: NC-thiophene, pyrrolo[2,3-b]pyridine with N-tosyl, phenyl-cyclopropane methyl ester, trans] 2/6 | [structure: NC-thiophene, pyrrolo[2,3-b]pyridine with N-tosyl, phenyl-cyclopropane carboxylic acid, trans] | $^1$H-NMR (500 MHz, CD$_3$OD) δ: 8.51 (dd, J = 1.5, 5.0 Hz, 1H), 7.87 (dd, J = 1.5, 8.0 Hz, 1H), 7.79 (d, J = 8.5 Hz, 1H), 7.68 (d, J = 8.5 Hz, 2H), 7.41 (dd, J = 5.3, 7.7 Hz, 1H), 7.34-7.26 (m, 4H), 7.21 (dd, J = 7.5, 1.5 Hz 1H), 7.00 (s, 1H), 6.89 (d, J = 5.0 Hz, 1H), 2.47-2.44 (m, 1H), 2.40 (s, 3H), 1.80-1.78 (m, 1H), 1.56-1.52 (m, 1H), 1.30-1.29 (m, 1H); MS: 540.0 (M + 1)$^+$. |

| # | starting material | structure | analytical data |
|---|---|---|---|
| 4/3 | (structure shown) | (structure shown) 2/7 | $^1$H-NMR (500 MHz, DMSO-$d_6$) δ: 7.91 (d, J = 5.5 Hz, 1H), 7.68 (d, J = 5.5 Hz, 1H), 7.61-7.60 (m, 1H), 7.38-7.32 (m, 4H), 7.15 (t, J = 7.8 Hz, 1H), 6.81 (d, J = 4.5 Hz, 1H), 6.53-6.50 (m, 2H), 6.13 (d, J = 1.5 Hz, 1H), 3.90 (t, J = 7.8 Hz, 2H), 3.76 (t, J = 6.3 Hz, 2H), 3.53-3.49 (m, 1H), 2.35 (s, 3H); MS: 560.0 (M + 1)$^+$. |

Example 5

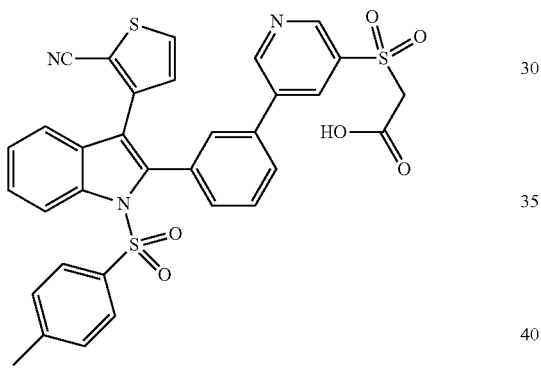

2-((5-(3-(3-(2-Cyanothiophen-3-yl)-1-tosyl-1H-indol-2-yl)phenyl)pyridin-3-yl)sulfonyl)acetic Acid (5)

To a mixture of compound 2/8 (110 mg, 0.17 mmol) in MeOH (2 mL) and THF (1 mL) was added LiOH (2M, 0.3 mL) and the mixture was stirred at rt for 1 h. The mixture was neutralized with 1N HCl and extracted with EA (3×). The combined organic layer was washed with brine, dried over Na$_2$SO$_4$, filtered, concentrated and purified by prep-HPLC to give compound 5 as a white solid. $^1$H-NMR (500 MHz, CD$_3$OD) δ: 9.09 (d, J=2.0 Hz, 1H), 9.03 (d, J=2.0 Hz, 1H), 8.44-8.42 (m, 2H), 7.85-7.80 (m, 2H), 7.57-7.39 (m, 6H), 7.33 (d, J=8.0 Hz, 2H), 7.20 (d, J=8.0 Hz, 2H), 7.06 (d, J=4.5 Hz, 1H), 4.54 (s, 2H), 2.29 (s, 3H); MS: 554.1 (M+1)$^+$.

Example 5/1 to 5/10

The following Examples were prepared similar as described for Example 5 using the appropriate starting material.

| # | starting material | structure | analytical data |
|---|---|---|---|
| 5/1 2/9 | (structure) | (structure) | ¹H-NMR (500 MHz, DMSO-d₆) δ: 13.30 (br s, 1H), 8.30 (d, J = 8.5 Hz, 1H), 8.05-8.00 (m, 2H), 7.92-7.86 (m, 2H), 7.77 (d, J = 8.0 Hz, 1H), 7.55-7.51 (m, 3H), 7.42-7.28 (m, 7H), 7.08 (d, J = 5.5 Hz, 1H), 4.96 (s, 2H), 4.61 (s, 2H), 2.26 (s, 3H); MS: 699.8 (M + 18)⁺. |
| 5/2 1/1 | (structure) | (structure) | ¹H-NMR (500 MHz, DMSO-d₆) δ: 12.43 (s, 1H), 8.27 (d, J = 8.5 Hz, 1H), 8.01 (d, J = 5.0 Hz, 1H), 7.53-7.49 (m, 1H), 7.38-7.22 (m, 9H), 6.98-6.95 (m, 2H), 2.32 (s, 3H), 2.14 (s, 6H); MS: 562.8 (M − 1)⁻. |
| 5/3 1/2 | (structure) | (structure) | ¹H-NMR (500 MHz, DMSO-d₆) δ: 13.05 (s, 1H), 8.31 (dd, J = 9.2, 4.4 Hz, 1H), 8.04-8.02 (m, 3H), 7.80 (d, J = 7.7 Hz, 1H), 7.68 (d, J = 8.3 Hz, 2H), 7.56-7.47 (m, 2H), 7.44-7.33 (m, 3H), 7.30-7.26 (m, 3H), 7.19 (dd, J = 8.6, 2.5 Hz, 1H), 7.07 (d, J = 5.1 Hz, 1H), 2.25 (s, 3H); MS: m/z 590.6 (M − 1)⁻. |

| # | starting material | structure | analytical data |
|---|---|---|---|
| 5/4 | (structure 7) | 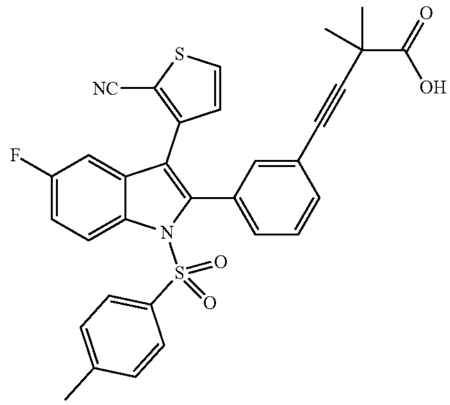 [SMILES: Cc1ccc(S(=O)(=O)n2c(-c3cccc(C#CC(C)(C)C(=O)O)c3)c(-c3ccsc3C#N)c3cc(F)ccc32)cc1] | ¹H-NMR (500 MHz, DMSO-d₆) δ: 12.91 (br s, 1H), 8.27 (dd, J = 9.3, 4.8 Hz, 1H), 8.00 (d, J = 5.0 Hz, 1H), 7.45-7.33 (m, 7H), 7.22-7.17 (m, 3H), 6.97 (d, J = 5.0 Hz, 1H), 2.33 (s, 3H), 1.48 (s, 6H); MS: 583.1 (M + 1)⁺. |
| 5/5 | (structure 1/3) | 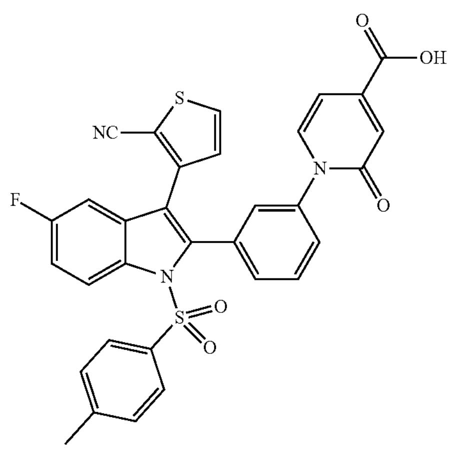 [SMILES: Cc1ccc(S(=O)(=O)n2c(-c3cccc(-n4ccc(C(=O)O)cc4=O)c3)c(-c3ccsc3C#N)c3cc(F)ccc32)cc1] | ¹H-NMR (500 MHz, CD₃OD) δ: 8.41 (dd, J = 9.0, 4.5 Hz, 1H), 7.85 (d, J = 5.0 Hz, 1H), 7.64 (d, J = 7.5 Hz, 1H), 7.57-7.50 (m, 2H), 7.39 (d, J = 8.0 Hz, 2H), 7.32-7.23 (m, 6H), 7.07 (dd, J = 8.5, 2.5 Hz, 1H), 7.02 (d, J = 5.0 Hz, 1H), 6.90 (dd, J = 7.3, 1.8 Hz, 1H), 2.33 (s, 3H); MS: 609.9 (M + 1)⁺. |
| 5/6 | (structure 1/4) | 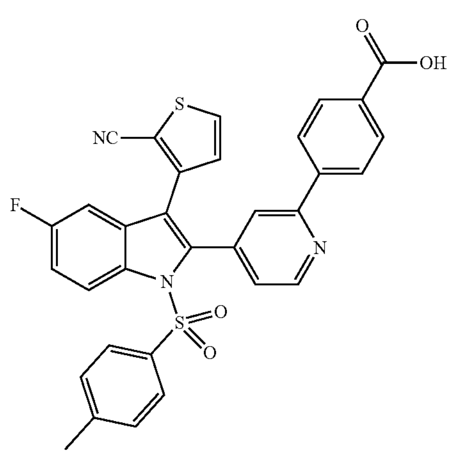 [SMILES: Cc1ccc(S(=O)(=O)n2c(-c3ccnc(-c4ccc(C(=O)O)cc4)c3)c(-c3ccsc3C#N)c3cc(F)ccc32)cc1] | ¹H-NMR (500 MHz, DMSO-d₆) δ: 8.73 (d, J = 5.5 Hz, 1H), 8.30 (dd, J = 9.3, 4.3 Hz, 1H), 8.08-8.04 (m, 5H), 7.92 (s, 1H), 7.48-7.40 (m, 3H), 7.33-7.30 (m, 3H), 7.23 (dd, J = 8.5, 2.0 Hz, 1H), 7.12 (d, J = 5.0 Hz, 1H), 2.29 (s, 3H); MS: 594.1 (M + 1)⁺. |

-continued

| # | starting material | structure | analytical data |
|---|---|---|---|
| 5/7 | (structure 2/10) | (product structure) | ¹H-NMR (500 MHz, DMSO-d₆) δ: 8.28 (dd, J = 9.0, 4.5 Hz, 1H), 7.99 (d, J = 4.5 Hz, 1H), 7.61 (dd, J = 6.8, 2.3 Hz, 2H), 7.50 (dd, J = 6.8, 1.8 Hz, 2H), 7.39-7.35 (m, 1H), 7.16-7.12 (m, 2H), 6.95 (d, J = 5.0 Hz, 1H), 6.54 (d, J = 7.5 Hz, 1H), 6.48 (dd, J = 8.3, 1.8 Hz, 1H), 6.23 (s, 1H), 3.89 (t, J = 7.8 Hz, 2H), 3.79 (t, J = 6.3 Hz, 2H), 3.48-3.43 (m, 1H); MS: 589.6 (M − 1)⁻. |
| 5/8 | (structure 2/11) | (product structure) | ¹H-NMR (500 MHz, DMSO-d₆) δ: 8.32-8.27 (m, 2H), 7.99 (d, J = 5.0 Hz, 1H), 7.68 (dd, J = 8.8, 2.8 Hz, 1H), 7.39-7.35 (m, 1H), 7.17-7.13 (m, 2H), 6.96-6.91 (m, 2H), 6.55 (d, J = 7.5 Hz, 1H), 6.48 (dd, J = 8.0, 2.0 Hz, 1H), 6.23 (s, 1H), 3.90-3.87 (m, 5H), 3.79 (t, J = 6.5 Hz, 2H), 3.46-3.43 (m, 1H); MS: 586.7 (M − 1)⁻. |
| 5/9 | 38 relative stereochemistry cis | relative stereochemistry cis | ¹H-NMR (500 MHz, CD₃OD) δ: 8.41-8.38 (m, 1H), 7.80 (d, J = 5.0 Hz, 1H), 7.34-7.21 (m, 7H), 7.09 (d, J = 7.0 Hz, 1H), 7.04-7.02 (m, 1H), 6.97 (s, 1H), 6.90 (d, J = 5.0 Hz, 1H), 3.11-3.07 (m, 1H), 2.96-2.94 (m, 1H), 2.79-2.74 (m, 1H), 2.50-2.44 (m, 1H), 2.36 (s, 3H), 2.08-1.98 (m, 2H), 1.87-1.82 (m, 1H), 1.59-1.51 (m, 1H), 0.86 (d, J = 6.0 Hz, 3H); MS: 614.0 (M + 1)⁺. |

| # | starting material | structure | analytical data |
|---|---|---|---|
| 5/10 20/25 | (structure) | (structure) | $^1$H-NMR (500 MHz, CD$_3$OD) δ: 8.53 (dd, J = 9.2, 4.3 Hz, 1H), 8.12 (s, 1H), 8.06-8.04 (m, 1H), 7.99-7.97 (m, 1H), 7.70-7.14 (m, 13H), 6.77 (t, J = 55.5 Hz, 1H), 4.37-4.27 (m, 1H), 3.78-3.36 (m, 3H), 3.24-3.20 (m, 1H); MS: 704.1 (M + 1)$^+$. |

Example 6

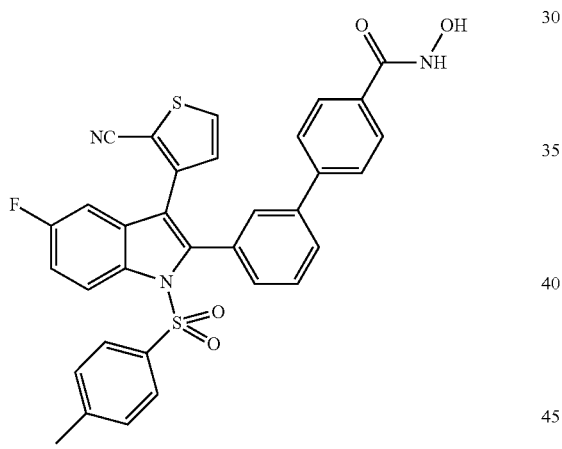

3'-(3-(2-Cyanothiophen-3-yl)-5-fluoro-1-tosyl-1H-indol-2-yl)-N-hydroxy-[1,1'-biphenyl]-4-carboxamide (6)

To a mixture of compound 5/3 (120 mg, 0.20 mmol) in DMF (5 mL) was added hydroxylamine hydrochloride (27 mg, 0.40 mmol), HATU (114 mg, 0.30 mmol) and DIPEA (103 mg, 0.80 mmol) and the mixture was stirred at rt overnight, diluted with EA (40 mL) and washed with H$_2$O (30 mL), 1N HCl (20 mL) and brine (30 mL). The organic layer was dried over Na$_2$SO$_4$, filtered, concentrated and purified by prep-HPLC to give compound 6 as a white solid. $^1$H-NMR (500 MHz, DMSO-d$_6$) δ: 10.69 (br s, 1H), 9.15 (br s, 1H), 8.31 (dd, J=9.3, 4.3 Hz, 1H), 8.02 (d, J=5.0 Hz, 1H), 7.86 (d, J=8.5 Hz, 2H), 7.78 (d, J=8.0 Hz, 1H), 7.62 (d, J=8.5 Hz, 2H), 7.50-7.47 (m, 2H), 7.41-7.25 (m, 6H), 7.19 (dd, J=8.5, 2.5 Hz, 1H), 7.07 (d, J=5.0 Hz, 1H), 2.25 (s, 3H); MS: 605.8 (M−1)$^−$.

Example 6/1 to 6/3

The following Example was prepared similar as described for Example 6 using the appropriate starting material.

| # | starting material | structure | analytical data |
|---|---|---|---|
| 6/1 | (structure, 5/9) | (structure) | $^1$H-NMR (500 MHz, DMSO-$d_6$) δ: 8.39 (d, J = 8.5 Hz, 1H), 7.82 (d, J = 5.5 Hz, 1H), 7.53-7.23 (m, 9H), 7.04-7.01 (m, 2H), 6.94 (d, J = 5.0 Hz, 1H), 2.43-2.38 (m, 1H), 1.76-1.72 (m, 1H), 1.54-1.50 (m, 1H), 1.25-1.20 (m, 1H); MS: 574.1 (M + 1)$^+$. |
| 6/2 | (structure, 5/3) | (structure) | $^1$H-NMR (500 MHz, DMSO-$d_6$) δ: 8.29 (dd, J = 9.0, 4.0 Hz, 1H), 8.04-7.96 (m, 4H), 7.78 (d, J = 8.5 Hz, 1H), 7.61 (d, J = 8.5 Hz, 2H), 7.50-7.36 (m, 6H), 7.26 (d, J = 8.0 Hz, 2H), 7.17 (dd, J = 8.0, 2.5 Hz, 1H), 7.06 (d, J = 5.0 Hz, 1H), 2.25 (s, 3H); MS: 589.8 (M − 1)$^-$. |
| 6/3 | (structure) | (structure) | $^1$H-NMR (400 MHz, CD$_3$OD) δ: 8.43 (dd, J = 4.4, 9.2 Hz, 1H), 8.05 (d, J = 7.6 Hz, 2H), 7.96 (d, J = 1.2 Hz, 1H), 7.84 (dd, J = 1.8, 7.8 Hz, 1H), 7.71 (t, J = 8.0 Hz, 1H), 7.54-7.30 (m, 9H), 7.09 (s, 1H), 6.94 (dd, J = 2.4, 8.4 Hz, 1H), 6.67 (t, J = 55.4 Hz, 1H), 4.03 (s, 2H), 1.51 (s, 9H); MS: 793.1 (M − 1)$^-$. |

Example 7

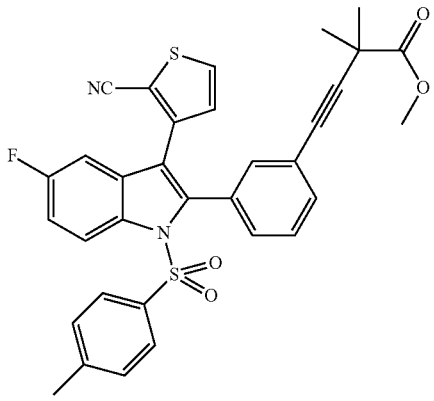 [SMILES: COC(=O)C(C)(C)C#Cc1cccc(-c2c(-c3ccsc3C#N)c3cc(F)ccc3n2S(=O)(=O)c2ccc(C)cc2)c1]

Methyl 4-(3-(3-(2-cyanothiophen-3-yl)-5-fluoro-1-tosyl-1H-indol-2-yl)phenyl)-2,2-dimethylbut-3-ynoate (7)

To a solution of compound 1 (234 mg, 0.52 mmol) in Et-N (1.5 mL) was added Pd(PPh$_3$)$_4$ (47 mg), CuI (80 mg), PPh$_3$ (11 mg) and methyl 2,2-dimethylbut-3-ynoate (78 mg, 0.62 mmol). The mixture was stirred at 60° C. under N$_2$ for 4 h, cooled, filtered, concentrated and purified by FCC (PE: EA=8:1) to give compound 7 as a yellow solid.

Example 8

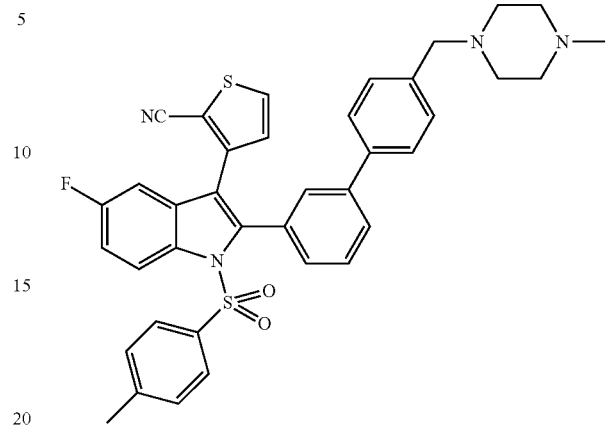

3-(5-Fluoro-2-(4'-((4-methylpiperazin-1-yl)methyl)-[1,1'-biphenyl]-3-yl)-1-tosyl-1H-indol-3-yl)thiophene-2-carbonitrile (8)

To a solution of compound 1 (250 mg, 0.45 mmol) in dioxane (20 mL) was added (3-((4-methylpiperazin-1-yl)methyl)phenyl)boronic acid (116 mg, 0.50 mmol), Cs$_2$CO$_3$ (293 mg, 0.90 mmol) and Pd(PPh$_3$)$_4$ (52 mg, 50 μmol). The mixture was stirred at 100° C. overnight under N$_2$, cooled, filtered, concentrated and purified by prep-HPLC to give compound 8 as a white solid. $^1$H-NMR (500 MHz, CD$_3$OD) δ: 8.43 (dd, J=4.5, 9.5 Hz, 1H), 7.82 (d, J=5.0 Hz, 1H), 7.67 (d, J=8.0 Hz, 1H), 7.47-7.41 (m, 5H), 7.31-7.15 (m, 7H), 7.06 (dd, J=2.5, 8.5 Hz, 1H), 6.96 (d, J=5.0 Hz, 1H), 3.61 (s, 2H), 2.61-2.48 (m, 8H), 2.31 (s, 3H), 2.27 (s, 3H); MS: 661.0 (M+1)$^+$.

Example 8/1 to 8/8

The following Example was prepared similar as described for Example 8 using the appropriate starting materials.

| # | starting material(s) | structure | analytical data |
|---|---|---|---|
| 8/1 | ![boronic acid structure] | ![product structure] | $^1$H-NMR (500 MHz, DMSO-d$_6$) δ: 8.31 (dd, J = 4.5, 9.0 Hz, 1H), 8.02 (d, J = 5.0 Hz, 1H), 7.72 (d, J = 8.0 Hz, 1H), 7.49-7.35 (m, 9H), 7.27-7.17 (m, 4H), 7.06 (d, J = 5.0 Hz, 1H), 3.43 (s, 2H), 2.25 (s, 3H), 2.17 (s, 6H); MS: 606.0 (M + 1)$^+$. |

-continued
| # | starting material(s) | structure | analytical data |
|---|---|---|---|
| 8/2 | 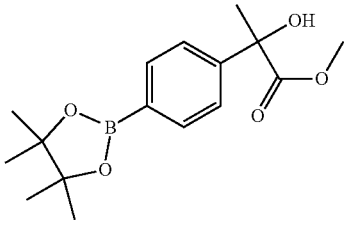 P21 | 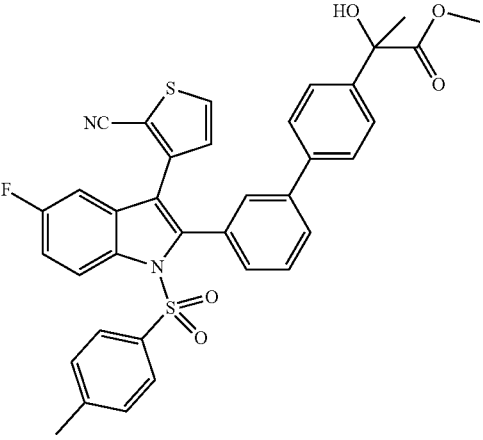 [SMILES: COC(=O)C(C)(O)c1ccc(-c2cccc(-c3c(-c4ccsc4C#N)c4cc(F)ccc4n3S(=O)(=O)c3ccc(C)cc3)c2)cc1] | |
| 8/3 | 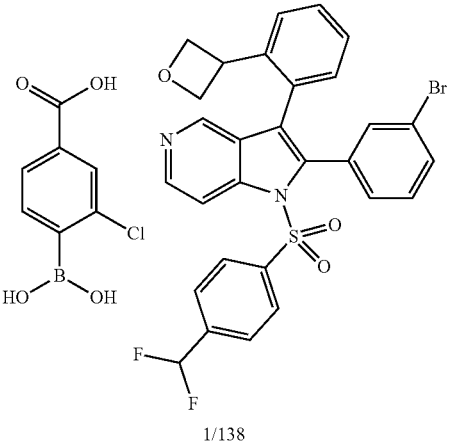 1/138 | 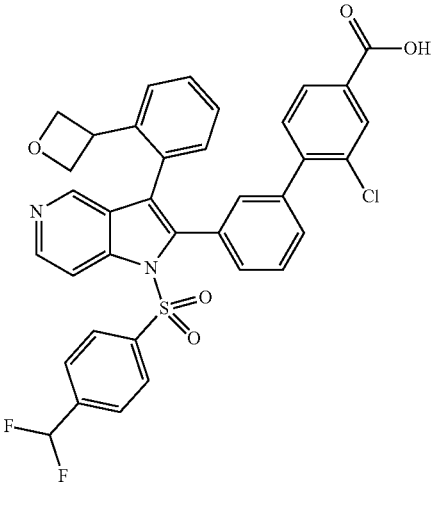 [SMILES: O=C(O)c1ccc(-c2cccc(-c3c(-c4ccccc4C4COC4)c4cnccc4n3S(=O)(=O)c3ccc(C(F)F)cc3)c2)c(Cl)c1] | $^1$H-NMR (500 MHz, CD$_3$OD) δ: 8.60 (d, J = 5.9 Hz, 1H), 8.43 (d, J = 6.0 Hz, 1H), 8.37 (s, 1H), 8.06 (s, 1H), 7.99-7.97 (m, 1H), 7.76-7.08 (m, 13H), 6.74 (t, J = 55.5 Hz, 1H), 4.65-4.56 (m, 1H), 4.53-4.49 (m, 1H), 4.41-4.37 (m, 1H), 4.30-4.26 (m, 1H), 3.90-3.78 (m, 1H); MS: 671.1 (M + 1)$^+$. |
| 8/4 | 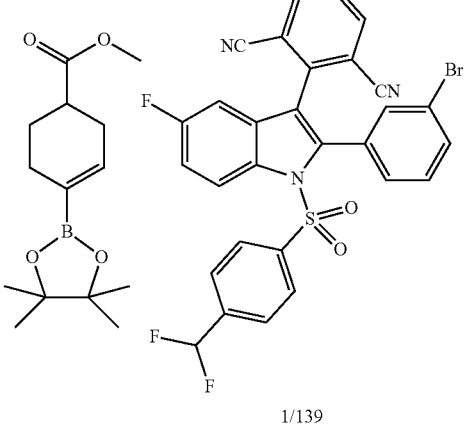 1/139 | 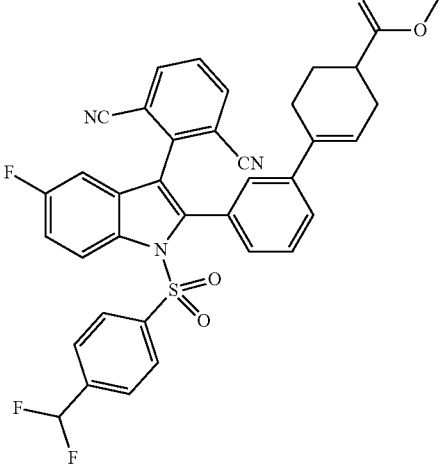 | |

-continued
| # | starting material(s) | structure | analytical data |
|---|---|---|---|
| 8/5 | 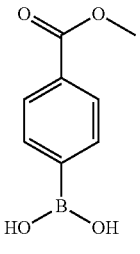 1/140 | 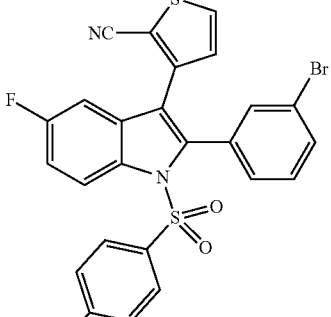 | |
| 8/6 | 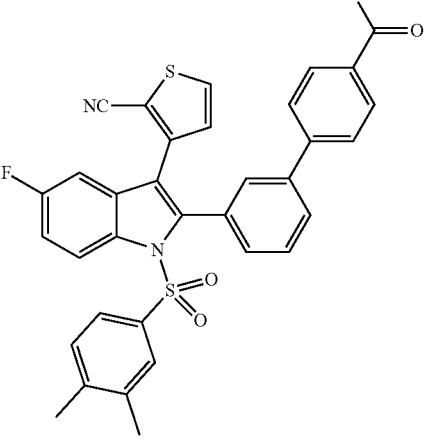 1/141 | 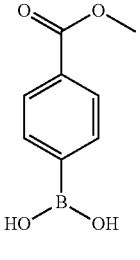 | |
| 8/7 | 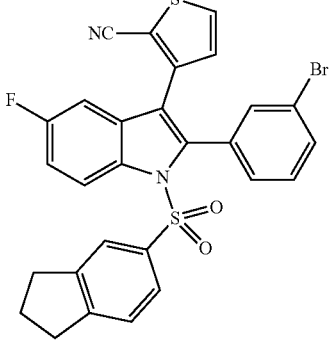 1/145 | 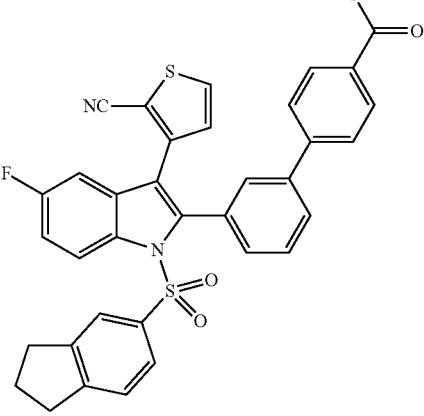 | ¹H-NMR (500 MHz, CD₃OD) δ: 8.81 (dd, J = 8.5, 1.5 Hz, 1H), 8.56 (dd, J = 4.8, 1.3 Hz, 1H), 8.06 (d, J = 1.5 Hz, 1H), 7.98 (d, J = 8.0 Hz, 1H), 7.77 (d, J = 7.5 Hz, 1H), 7.65-7.04 (m, 13H), 6.70 (t, J = 55.5 Hz, 1H); MS: 640.2 (M + 1)⁺. |

| # | starting material(s) | structure | analytical data |
|---|---|---|---|
| 8/8 | 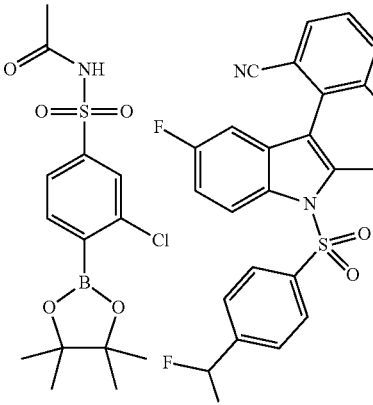<br>P34 | 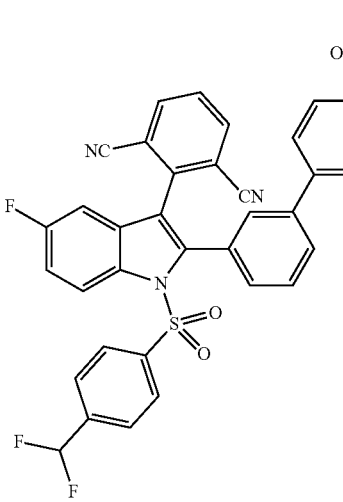 | ¹H-NMR (400 MHz, CD₃OD) δ: 8.42 (dd, J = 9.4, 4.2 Hz, 1H), 8.05-8.03 (m, 3H), 7.96 (dd, J = 8.2, 1.8 Hz, 1H), 7.70 (dd, J = 8.4, 7.6 Hz, 1H), 7.51-7.44 (m, 8H), 7.32 (td, J = 9.2, 2.4 Hz, 1H), 6.97 (s, 1H), 6.94 (dd, J = 8.4, 2.4 Hz, 1H), 6.62 (t, J = 55.4 Hz, 1H), 2.00 (s, 3H); MS: 757.0 (M − 1)⁻. |
|   |   | 1/139<br>Pd(dppf)Cl₂<br>K₂CO₃, 95° C., 8 h<br>in dioxane/water<br>(17:1) |   |

Example 9

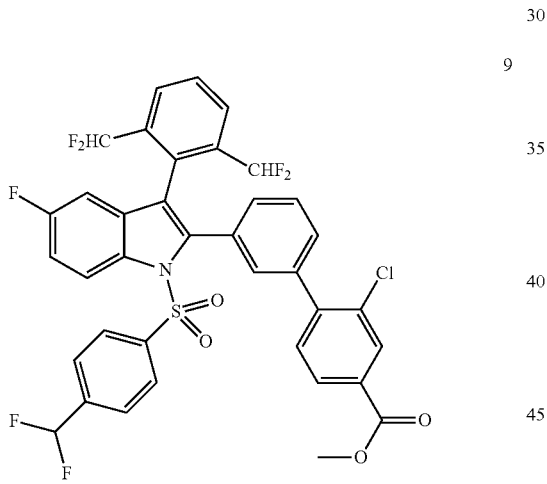

Methyl 3'-(3-(2,6-bis(difluoromethyl)phenyl)-1-((4-(difluoromethyl)phenyl)sulfonyl)-5-fluoro-1H-indol-2-yl)-2-chloro-[1,1'-biphenyl]-4-carboxylate (9)

To a solution of compound 1/55 (180 mg, 0.26 mmol) in DCM (10.0 mL) was added DAST (209 mg, 1.30 mmol) and the mixture was stirred at rt overnight, poured into EA (200 mL) and washed with H₂O (2×20 mL) and brine (20 mL). The organic layer was dried over Na₂SO₄, concentrated and purified by prep-TLC (EA:PE=1:3) to give compound 9 as a colorless oil.

Example 9/1

The following Example was prepared similar as described for Example 9 using the appropriate starting material.

| # | starting material | structure |
|---|---|---|
| 9/1 | | 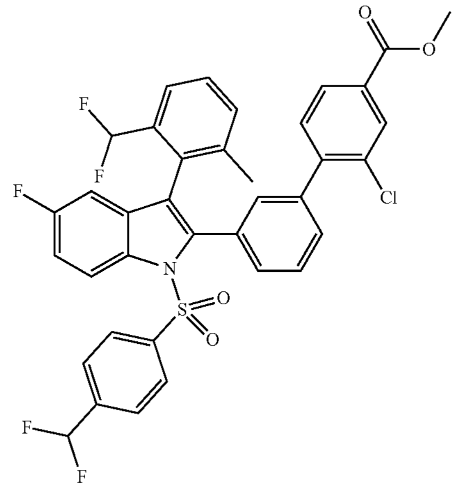 [SMILES: COC(=O)c1ccc(-c2cccc(-c3c(-c4c(C)cccc4C(F)F)c4cc(F)ccc4n3S(=O)(=O)c3ccc(C(F)F)cc3)c2)c(Cl)c1] |

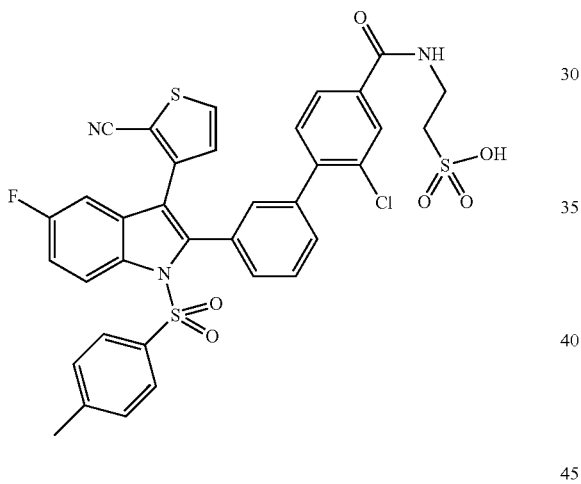

Example 10

2-(2-Chloro-3'-(3-(2-cyanothiophen-3-yl)-5-fluoro-1-tosyl-1H-indol-2-yl)-[1,1'-biphenyl]-4-carboxamido)ethane-1-sulfonic Acid (10)

To a solution of compound 3/48 (100 mg, 0.20 mmol) in DMF (10 mL) was added EDCI (100 mg, 0.50 mmol), DMAP (60 mg, 0.50 mmol) and 2-aminoethane-1-sulfonic acid (22 mg, 0.20 mmol). The mixture was stirred at rt for 12 h, diluted with water (100 mL) and extracted with EA (3×100 mL). The combined organic layer was washed with brine (50 mL), concentrated and purified by FCC (PE:EA=1:4) to give compound 10 as a white solid. $^1$H-NMR (500 MHz, DMSO-$d_6$) δ: 8.68 (t, J=5.3 Hz, 1H), 8.29 (dd, J=4.5, 9.0 Hz, 1H), 8.03 (d, J=5.0 Hz, 1H), 7.92 (d, J=2.0 Hz, 1H), 7.81 (dd, J=1.8, 8.3 Hz, 1H), 7.54-7.17 (m, 10H), 7.03-7.01 (m, 2H), 3.56-3.52 (m, 2H), 2.70-2.67 (m, 2H), 2.21 (s, 3H); MS: 731.9 (M−1)$^-$.

Example 10/1 to 10/4

The following Examples were prepared similar as described for Example 10 using the appropriate starting material.

| # | starting material | structure | analytical data |
|---|---|---|---|
| 10/1 | (structure) 11/12 | (structure) | ¹H-NMR (500 MHz, CD₃OD) δ: 8.45-8.43 (m, 1H), 8.07 (br s, 2H), 7.94 (d, J = 2.0 Hz, 1H), 7.82 (dd, J = 8.0, 1.5 Hz, 1H), 7.78 (t, J = 7.8 Hz, 1H), 7.55-7.43 (m, 7H), 7.36-7.28 (m, 2H), 7.04 (s, 1H), 6.95 (dd, J = 8.5, 2.5 Hz, 1H), 6.68 (t, J = 55.5 Hz, 1H), 3.84 (t, J = 6.5 Hz, 2H), 3.13 (t, J = 6.5 Hz, 2H); MS: 786.9 (M − 1)⁻. |
| 10/2 | (structure) 11/12 | (structure) | ¹H-NMR (500 MHz, CD₃OD) δ: 8.44 (dd, J = 9.3, 4.3 Hz, 1H), 8.06 (br s, 2H), 7.72 (t, J = 7.8 Hz, 1H), 7.59-7.47 (m, 9H), 7.35-7.32 (m, 2H), 7.02-6.58 (m, 3H), 3.97-3.77 (m, 2H), 3.24-3.10 (m, 5H); MS: 801.0 (M − 1)⁻. |
| 10/3 | (structure) | (structure) | ¹H-NMR (500 MHz, CD₃OD) δ: 8.42 (dd, J = 9.0, 4.5 Hz, 1H), 7.97 (d, J = 1.5 Hz, 1H), 7.85-7.81 (m, 2H), 7.56-7.49 (m, 6H), 7.44 (d, J = 7.0 Hz, 1H), 7.39 (d, J = 8.0 Hz, 1H), 7.31 (td, J = 9.0, 2.5 Hz, 1H), 7.09-7.06 (m, 2H), 6.98 (d, J = 5.0 Hz, 1H), 6.71 (t, J = 55.5 Hz, 1H), 3.84 (t, J = 6.8 Hz, 2H), 3.13 (t, J = 6.8 Hz, 2H); MS: 768.0 (M − 1)⁻. |

| # | starting material | structure | analytical data |
|---|---|---|---|
| 10/4 | [structure with OH carboxylic acid, Cl, Cl, F-indole, tosyl with CHF2, trans cyclopropyl] | [structure with taurine amide HN-CH2-CH2-SO2-OH, Cl, Cl, F-indole, tosyl with CHF2, trans cyclopropyl] | $^1$H-NMR (400 MHz, CD$_3$OD) δ: 8.37 (dd, J = 9.2, 4.4 Hz, 1H), 7.59 (d, J = 8.0 Hz, 2H), 7.47 (d, J = 8.0 Hz, 2H), 7.40-7.35 (m, 3H), 7.26-7.14 (m, 4H), 6.95-6.64 (m, 3H), 3.69-3.61 (m, 2H), 3.00 (t, J = 6.6 Hz, 2H), 2.33-2.28 (m, 1H), 1.64 (br s, 1H), 1.47-1.42 (m, 1H), 1.06 (br s, 1H); MS: 735.0 and 737.0 (M − 1)$^-$. |

Example 11

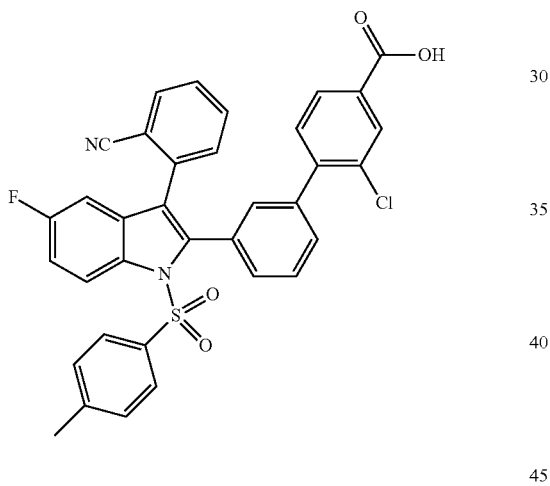

2-Chloro-3'-(3-(2-cyanophenyl)-5-fluoro-1-tosyl-1H-indol-2-yl)-[1,1'-biphenyl]-4-carboxylic Acid (11)

To a solution of compound 1/32 (165 mg, 0.26 mmol) in HCl/dioxane (4N, 5 mL) was added H$_2$O (0.5 mL). The mixture was stirred at 90° C. overnight, cooled, concentrated, diluted with water and extracted with EA (3×). The combined organic layer was washed with brine, dried over Na$_2$SO$_4$, filtered, concentrated and purified by prep-HPLC to give compound 11 as a white solid. $^1$H-NMR (500 MHz, DMSO-d$_6$) δ: 13.36 (br s, 1H), 8.28 (dd, J=4.5, 9.5 Hz, 1H), 7.97-7.94 (m, 2H), 7.86 (d, J=7.5 Hz, 1H), 7.66 (t, J=7.5 Hz, 1H), 7.55-7.31 (m, 9H), 7.24 (d, J=8.5 Hz, 2H), 7.02-7.00 (m, 2H), 2.21 (s, 3H); MS: 619.0 (M−1)$^-$.

Example 11/1 to 11/69

The following Examples were prepared similar as described for Example 11 using the appropriate starting material.

| # | starting material | structure | analytical data |
|---|---|---|---|
| 11/1 | 1/33 | 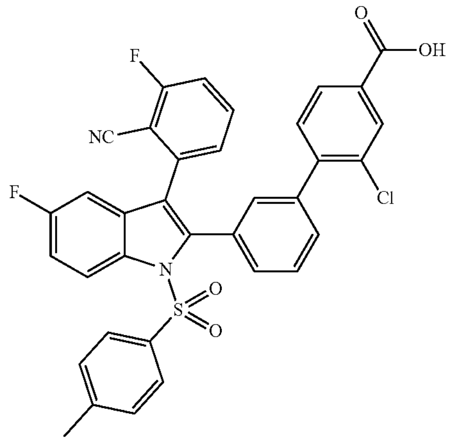 | ¹H-NMR (500 MHz, CD₃OD) δ: 8.41 (dd, J = 9.3, 4.3 Hz, 1H), 8.08 (d, J = 1.0 Hz, 1H), 8.02 (dd, J = 1.8, 8.3 Hz, 1H), 7.69-7.64 (m, 1H), 7.49-7.26 (m, 8H), 7.18-1.15 (m, 3H), 7.02 (s, 1H), 6.97 (dd, J = 2.5, 8.5 Hz, 1H), 2.25 (s, 3H); MS: 637.0 (M − 1)⁻. |
| 11/2 | 1/34 | 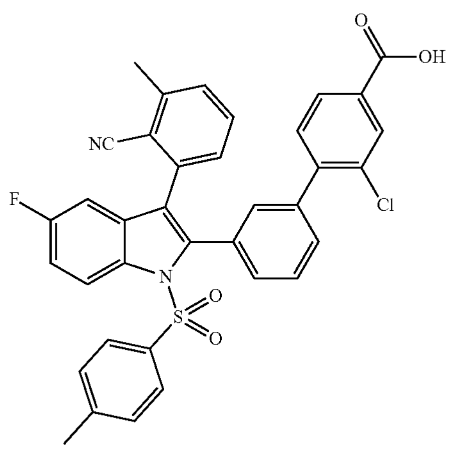 | ¹H-NMR (500 MHz, CD₃OD) δ: 8.39 (dd, J = 9.3, 4.3 Hz, 1H), 8.05 (d, J = 1.5 Hz, 1H), 7.98 (dd, J = 8.0, 1.5 Hz, 1H), 7.51-7.43 (m, 4H), 7.39 (d, J = 8.0 Hz, 1H), 7.31 (d, J = 8.0 Hz, 1H), 7.28-6.98 (m, 7H), 6.88 (dd, J = 8.5, 2.5 Hz, 1H), 2.51 (s, 3H), 2.24 (s, 3H); MS: 633.0 (M − 1)⁻. |
| 11/3 | 1/35 | 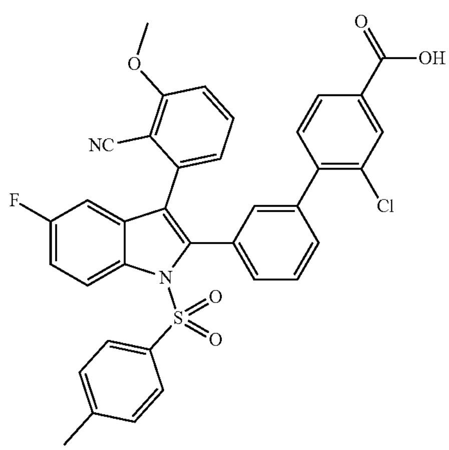 [SMILES: COc1cccc(-c2c(-c3cccc(-c4ccc(C(=O)O)cc4Cl)c3)n(S(=O)(=O)c3ccc(C)cc3)c3ccc(F)cc23)c1C#N] | ¹H-NMR (500 MHz, CD₃OD) δ: 8.38 (dd, J = 9.0, 4.5 Hz, 1H), 8.07 (d, J = 1.5 Hz, 1H), 8.00 (dd, J = 8.0, 1.5 Hz, 1H), 7.57-7.54 (m, 1H), 7.48-7.44 (m, 3H), 7.37 (d, J = 7.5 Hz, 1H), 7.27-7.14 (m, 6H), 7.03 (s, 1H), 6.88 (dd, J = 8.3, 2.8 Hz, 1H), 6.83 (br s, 1H), 3.95 (s, 3H), 2.24 (s, 3H); MS: 649.0 (M − 1)⁻. |

| # | starting material | structure | analytical data |
|---|---|---|---|
| 11/4 | (1/36) | 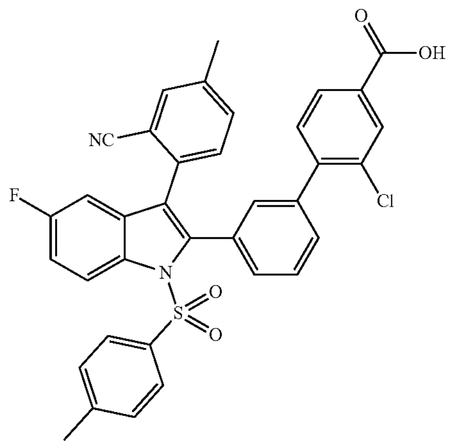 [SMILES: Cc1ccc(S(=O)(=O)n2c(-c3cccc(-c4ccc(C(=O)O)cc4Cl)c3)c(-c3ccc(C)cc3C#N)c3cc(F)ccc32)cc1] | ¹H-NMR (500 MHz, CD₃OD) δ: 8.38 (dd, J = 9.3, 4.3 Hz, 1H), 8.07 (d, J = 1.5 Hz, 1H), 7.99 (dd, J = 8.0, 1.5 Hz, 1H), 7.63-7.54 (m, 1H), 7.45-7.42 (m, 4H), 7.36 (d, J = 8.0 Hz, 1H), 7.30-7.14 (m, 6H), 7.02 (s, 1H), 6.88 (dd, J = 8.5, 2.5 Hz, 1H), 2.39 (s, 3H), 2.24 (s, 3H); MS: 633.0 (M − 1)⁻. |
| 11/5 | (1/37) | 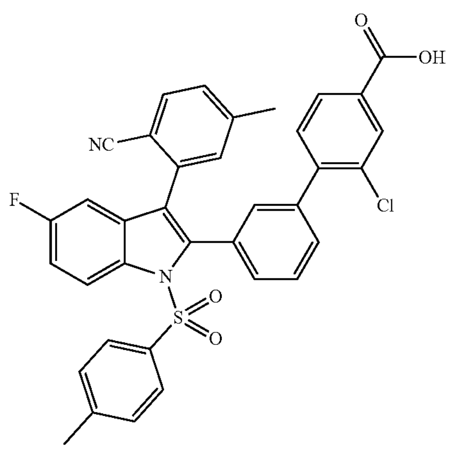 [SMILES: Cc1ccc(S(=O)(=O)n2c(-c3cccc(-c4ccc(C(=O)O)cc4Cl)c3)c(-c3cc(C)ccc3C#N)c3cc(F)ccc32)cc1] | ¹H-NMR (500 MHz, CD₃OD) δ: 8.39 (dd, J = 9.0, 4.5 Hz, 1H), 8.07 (d, J = 2.0 Hz, 1H), 8.00 (dd, J = 8.0, 1.5 Hz, 1H), 7.62 (d, J = 8.0 Hz, 1H), 7.46-7.44 (m, 3H), 7.36 (d, J = 8.5 Hz, 1H), 7.33-7.14 (m, 7H), 7.03 (s, 1H), 6.89 (dd, J = 8.3, 2.8 Hz, 1H), 2.35 (s, 3H), 2.24 (s, 3H); MS: 633.0 (M − 1)⁻. |
| 11/6 | (1/38) | 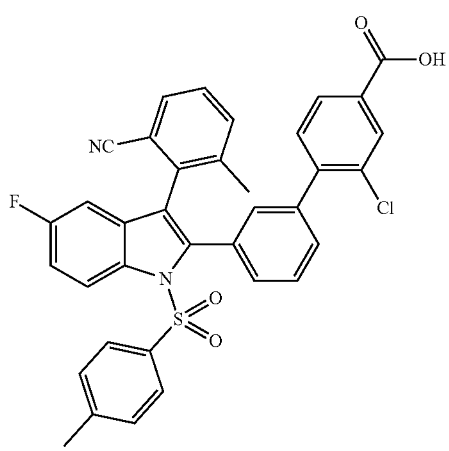 [SMILES: Cc1ccc(S(=O)(=O)n2c(-c3cccc(-c4ccc(C(=O)O)cc4Cl)c3)c(-c3c(C)cccc3C#N)c3cc(F)ccc32)cc1] | ¹H-NMR (500 MHz, CD₃OD) δ: 8.40 (dd, J = 9.3, 4.3 Hz, 1H), 8.08 (s, 1H), 8.00 (dd, J = 8.0, 1.5 Hz, 1H), 7.58-7.15 (m, 13H), 6.71 (dd, J = 8.0, 2.5 Hz, 1H), 2.25 (s, 3H), 1.90 (s, 3H); MS: 633.0 (M − 1)⁻. |

-continued

| # | starting material | structure | analytical data |
|---|---|---|---|
| 11/7 | (structure) 1/48 | (structure) | ¹H-NMR (500 MHz, CD₃OD) δ: 8.43 (dd, J = 9.0, 4.5 Hz, 1H), 8.03 (d, J = 7.0 Hz, 1H), 7.85 (d, J = 5.5 Hz, 1H), 7.57-7.44 (m, 5H), 7.38 (d, J = 8.5 Hz, 2H), 7.30 (dt, J = 2.7, 9.2 Hz, 1H), 7.21 (d, J = 10.5 Hz, 1H), 7.15 (s, 1H), 7.07 (dd, J = 8.5, 2.5 Hz, 1H), 6.99 (d, J = 5.5 Hz, 1H), 5.35 (d, J = 47.0 Hz, 2H); MS: 660.9 (M − 1)⁻. |
| 11/8 | (structure) 1/49 | (structure) | ¹H-NMR (500 MHz, CD₃OD) δ: 8.43 (dd, J = 9.3, 4.3 Hz, 1H), 8.03 (d, J = 6.5 Hz, 1H), 7.86 (d, J = 5.0 Hz, 1H), 7.58-7.49 (m, 6H), 7.43 (d, J = 7.5 Hz, 1H), 7.31 (td, J = 9.0, 2.5 Hz, 1H), 7.22 (d, J = 10.5 Hz, 1H), 7.16 (s, 1H), 7.09 (dd, J = 2.5, 8.5 Hz, 1H), 7.01 (d, J = 5.0 Hz, 1H), 6.73 (t, J = 55.5 Hz, 1H); MS: 678.9 (M − 1)⁻. |
| 11/9 | (structure) 1/50 | (structure) | ¹H-NMR (500 MHz, CD₃OD) δ: 9.33 (s, 1H), 8.46 (dd, J = 9.3, 4.3 Hz, 1H), 8.04 (d, J = 6.5 Hz, 1H), 7.61-7.50 (m, 6H), 7.41 (d, J = 8.0 Hz, 1H), 7.33 (d, J = 2.5 Hz, 1H), 7.27 (d, J = 11.0 Hz, 1H), 7.21-7.18 (m, 2H), 6.73 (t, J = 55.5 Hz, 1H); MS: 679.9 (M − 1)⁻. |

| # | starting material | structure | analytical data |
|---|---|---|---|
| 11/10 | (structure) 1/51 | (structure) | ¹H-NMR (500 MHz, CD₃OD) δ: 8.72 (d, J = 4.5 Hz, 1H), 8.55 (br s, 1H), 8.44 (dd, J = 4.3, 9.3 Hz, 1H), 8.01 (d, J = 6.5 Hz, 1H), 7.78 (d, J = 5.0 Hz, 1H), 7.60-7.04 (m, 11H), 6.73 (t, J = 55.5 Hz, 1H); MS: 673.9 (M − 1)⁻. |
| 11/11 | (structure) 1/52 | (structure) | ¹H-NMR (500 MHz, CD₃OD) δ: 8.90 (d, J = 2.5 Hz, 1H), 8.71 (d, J = 2.5 Hz, 1H), 8.47 (dd, J = 9.5, 4.5 Hz, 1H), 8.01 (d, J = 5.0 Hz, 1H), 7.78-7.18 (m, 11H), 6.73 (t, J = 55.5 Hz, 1H); MS: 674.9 (M − 1)⁻. |
| 11/12 | (structure) 1/53 | (structure) | ¹H-NMR (500 MHz, CD₃OD) δ: 8.45 (dd, J = 4.3, 9.3 Hz, 1H), 8.08-8.00 (m, 4H), 7.72 (t, J = 7.8 Hz, 1H), 7.55-7.32 (m, 9H), 7.08 (s, 1H), 6.95 (dd, J = 2.5, 8.5 Hz, 1H), 6.68 (t, J = 55.5 Hz, 1H); MS: 679.9 (M − 1)⁻. |

| # | starting material | structure | analytical data |
|---|---|---|---|
| 11/13 | 1/54 | 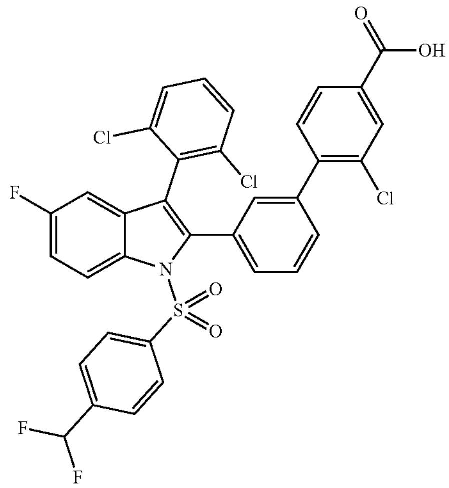 [SMILES: O=C(O)c1ccc(-c2cccc(-c3c(-c4c(Cl)cccc4Cl)c4cc(F)ccc4n3S(=O)(=O)c3ccc(C(F)F)cc3)c2)c(Cl)c1] | ¹H-NMR (500 MHz, CD₃OD) δ: 8.39 (dd, J = 4.8, 9.3 Hz, 1H), 8.08 (d, J = 1.5 Hz, 1H), 7.98 (dd, J = 1.5, 8.0 Hz, 1H), 7.56-7.25 (m, 12H), 7.21 (s, 1H), 6.73 (t, J = 55.3 Hz, 1H), 6.68 (dd, J = 2.5, 8.5 Hz, 1H); MS: 697.9 (M − 1)⁻. |
| 11/14 | 29 | 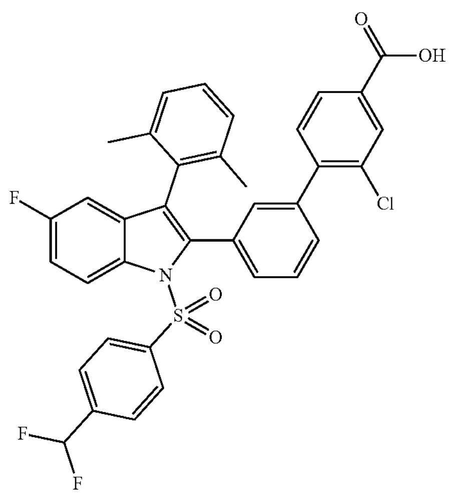 [SMILES: Cc1cccc(C)c1-c1c(-c2cccc(-c3ccc(C(=O)O)cc3Cl)c2)n(S(=O)(=O)c2ccc(C(F)F)cc2)c2ccc(F)cc12] | ¹H-NMR (400 MHz, CD₃OD) δ: 8.41 (dd, J = 4.2, 9.0 Hz, 1H), 8.07 (d, J = 1.6 Hz, 1H), 7.94 (dd, J = 1.6, 8.0 Hz, 1H), 7.57-7.40 (m, 7H), 7.29-7.15 (m, 4H), 7.04 (d, J = 8.4 Hz, 2H), 6.75 (t, J = 55.6 Hz, 1H), 6.57 (d, J = 2.6, 8.2 Hz, 1H), 1.63 (s, 6H); MS: 658.0 (M − 1)⁻. |
| 11/15 | 9 | 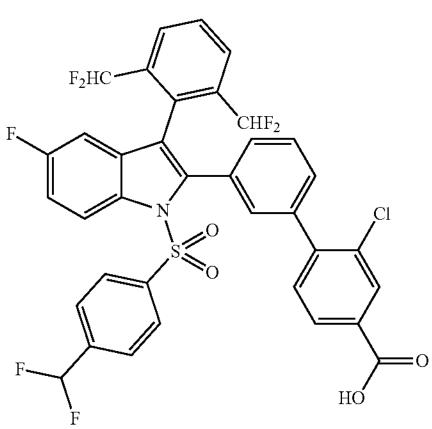 [SMILES: O=C(O)c1ccc(-c2cccc(-c3c(-c4c(C(F)F)cccc4C(F)F)c4cc(F)ccc4n3S(=O)(=O)c3ccc(C(F)F)cc3)c2)c(Cl)c1] | ¹H-NMR (400 MHz, CD₃OD) δ: 8.44 (dd, J = 4.4, 9.2 Hz, 1H), 8.08 (d, J = 1.6 Hz, 1H), 7.97 (dd, J = 1.4, 3.8 Hz, 1H), 7.83 (d, J = 7.6 Hz, 2H), 7.73 (t, J = 7.8 Hz, 1H), 7.61-7.55 (m, 4H), 7.47-7.23 (m, 5H), 6.91 (s, 1H), 6.77-6.63 (m, 2H), 6.01 (t, J = 55.0 Hz, 2H); MS: 729.9 (M − 1)⁻. |

| # | starting material | structure | analytical data |
|---|---|---|---|
| 11/16 | (structure) 35 | (structure) | $^1$H-NMR (500 MHz, DMSO-$d_6$) δ: 13.39 (s, 1H), 8.78 (d, J = 2.5 Hz, 1H), 8.34 (dd, J = 9.0, 4.5 Hz, 1H), 8.12-7.93 (m, 5H) 7.57-7.55 (m, 2H), 7.50-7.41 (m, 3H), 7.23-7.21 (m, 2H), 7.04-7.02 (m, 1H); MS: 679.6 (M − 1)$^−$. |
| 11/17 | (structure) 1/104 | (structure) | $^1$H-NMR (500 MHz, DMSO-$d_6$) δ: 8.30 (dd, J = 9.2, 4.4 Hz, 1H), 8.04 (d, J = 5.1 Hz, 1H), 7.99-7.88 (m, 2H), 7.70-7.49 (m, 6H), 7.47-7.35 (m, 3H), 7.20 (dd, J = 8.6, 2.6 Hz, 1H), 7.12-7.10 (m, 1H), 7.05-7.03 (m, 1H), 7.01 (t, J = 55.0 Hz, 1H); MS: 660.9 (M − 1)$^−$. |
| 11/18 | (structure) 1/105 | (structure) | $^1$H-NMR (500 MHz, DMSO-$d_6$) δ: 8.30 (dd, J = 9.2, 4.4 Hz, 1H), 8.04 (d, J = 5.1 Hz, 1H), 7.99-7.88 (m, 2H), 7.58-7.45 (m, 4H), 7.45-7.35 (m, 3H), 7.31 (t, J = 8.8 Hz, 2H), 7.19 (dd, J = 8.6, 2.6 Hz, 1H), 7.14 (s, 1H), 7.03 (d, J = 4.9 Hz, 1H); MS: 628.9 (M − 1)$^−$. |

| # | starting material | structure | analytical data |
|---|---|---|---|
| 11/19 | (structure 1/106) | (product structure) | $^1$H-NMR (500 MHz, DMSO-d$_6$) δ: 13.42 (s, 1H), 8.31 (dd, J = 9.2, 4.5 Hz, 1H), 8.05-7.93 (m, 3H), 7.55-7.53 (m, 2H), 7.48-7.36 (m, 4H), 7.24-7.11 (m, 4H), 7.05 (d, J = 4.8 Hz, 1H), 2.15 (s, 3H); MS: 642.9 (M − 1)$^-$. |
| 11/20 | (structure 1/107) | (product structure) | $^1$H-NMR (500 MHz, DMSO-d$_6$) δ: 13.46 (s, 1H), 8.31-8.28 (m, 1H), 8.05 (d, J = 5.1 Hz, 1H), 8.02-7.92 (m, 4H), 7.59-7.50 (m, 4H), 7.48-7.37 (m, 3H), 7.22-7.20 (m, 1H), 7.12 (s, 1H), 7.04 (d, J = 5.0 Hz, 1H); MS: 635.9 (M − 1)$^-$. |
| 11/21 | (structure 1/108) | (product structure) | $^1$H-NMR (400 MHz, CD$_3$OD) δ: 8.36 (dd, J = 9.2, 4.4 Hz, 1H), 8.07 (d, J = 1.6 Hz, 1H), 7.97 (dd, J = 8.0, 1.6 Hz, 1H), 7.64 (d, J = 5.0 Hz, 1H), 7.52-7.33 (m, 7H), 7.31-7.22 (m, 2H), 7.12 (s, 1H), 6.91 (dd, J = 8.5, 2.5 Hz, 1H), 6.82 (br s, 1H), 6.34 (t, J = 54.8 Hz, 1H); MS: 669.8 (M − 1)$^-$. |

| # | starting material | structure | analytical data |
|---|---|---|---|
| 11/22 | 1/110 | 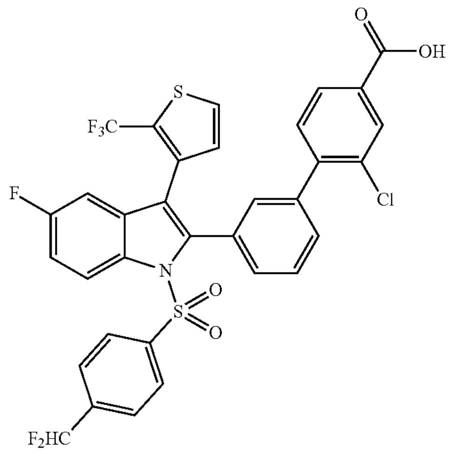 [SMILES: N#Cc1sccc1-c1c(-c2cccc(-c3ccc(C(=O)O)cc3Cl)c2)n(S(=O)(=O)c2ccc(C(F)F)cc2)c2ccc(F)cc12] | $^1$H-NMR (500 MHz, CD$_3$OD) δ: 8.38 (dd, J = 9.2, 4.3 Hz, 1H), 8.11 (d, J = 1.3 Hz, 1H), 8.01 (d, J = 6.9 Hz, 1H), 7.70 (d, J = 4.0 Hz, 1H), 7.57-7.24 (m, 10H), 6.85-6.63 (m, 3H); MS: 703.9 (M − 1)$^-$. |
| 11/23 | 1/111 | 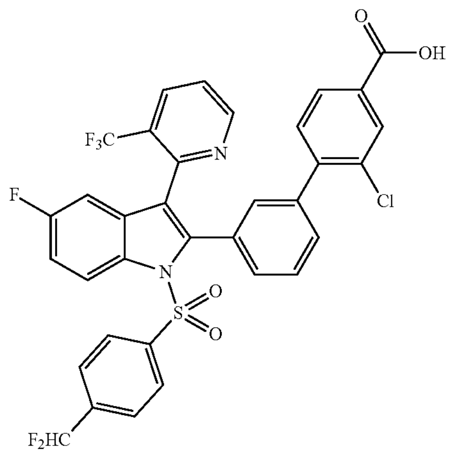 [SMILES: O=C(O)c1ccc(-c2cccc(-c3c(-c4ncccc4C(F)(F)F)c4cc(F)ccc4n3S(=O)(=O)c3ccc(C(F)F)cc3)c2)c(Cl)c1] | $^1$H-NMR (500 MHz, CD$_3$OD) δ: 8.78 (d, J = 4.6 Hz, 1H), 8.42 (dd, J = 9.2, 4.3 Hz, 1H), 8.21 (d, J = 7.5 Hz, 1H), 8.09 (d, J = 1.5 Hz, 1H), 8.01 (dd, J = 8.0, 1.5 Hz, 1H), 7.70-7.06 (m, 11H), 6.79-6.77 (m, 1H), 6.76 (t, J = 56.0, 1H); MS: 699.0 (M − 1)$^-$. |
| 11/24 | 29/1 | 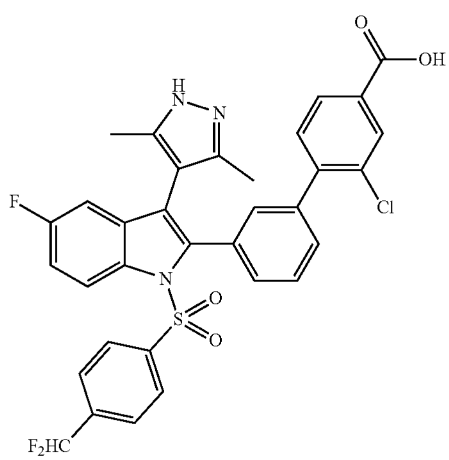 [SMILES: Cc1n[nH]c(C)c1-c1c(-c2cccc(-c3ccc(C(=O)O)cc3Cl)c2)n(S(=O)(=O)c2ccc(C(F)F)cc2)c2ccc(F)cc12] | $^1$H-NMR (400 MHz, CD$_3$OD) δ: 8.36 (dd, J = 9.1, 4.4 Hz, 1H), 8.07 (d, J = 1.5 Hz, 1H), 7.97 (dd, J = 7.9, 1.6 Hz, 1H), 7.56-7.43 (m, 7H), 7.33 (d, J = 8.0 Hz, 1H), 7.25 (dt, J = 4.4, 8.8 Hz, 1H), 7.15 (s, 1H), 6.82-6.79 (m, 1H), 6.73 (t, J = 55.2 Hz, 1H), 1.70 (s, 6H); MS: 650.1 (M + H)$^+$. |

| # | starting material | structure | analytical data |
|---|---|---|---|
| 11/25 | (P1/113 structure: methyl ester, F₃C-pyrazole-Tr, F-indole, N-SO₂-C₆H₄-CHF₂, chlorobiphenyl) | (carboxylic acid analog, 1H-pyrazole) | ¹H-NMR (500 MHz, CD₃OD) δ: 8.37 (dd, J = 9.1, 4.3 Hz, 1H), 8.09 (d, J = 1.4 Hz, 1H), 7.99 (dd, J = 8.0, 1.5 Hz, 1H), 7.68-6.89 (m, 11H), 6.88-6.86 (m, 1H), 6.73 (t, J = 55.0 Hz, 1H); MS: 688.0 (M − 1)⁻. |
| 11/26 | (1/115 structure: methyl ester, NC-pyridine, F-indole, N-SO₂-C₆H₄-CHF₂, chlorobiphenyl) | (carboxylic acid analog) | ¹H-NMR (500 MHz, CD₃OD) δ: 8.84 (dd, J = 5.0, 1.6 Hz, 1H), 8.45 (dd, J = 9.2, 4.3 Hz, 1H), 8.16 (dd, J = 8.0, 1.5 Hz, 1H), 8.07 (s, 1H), 8.00 (d, J = 8.0 Hz, 1H), 7.82-7.10 (m, 11H), 7.05 (dd, J = 8.4, 2.5 Hz, 1H), 6.71 (t, J = 55.6 Hz, 1H); MS: 655.9 (M − 1)⁻. |
| 11/27 | (2/19 structure: methyl ester with OMe, NC-phenyl, F-indole, N-SO₂-C₆H₄-CHF₂, chlorobiphenyl) | (carboxylic acid analog) | ¹H-NMR (500 MHz, DMSO-d₆) δ: 8.28 (dd, J = 9.0, 4.5 Hz, 1H), 7.88 (d, J = 6.0 Hz, 1H), 7.76-7.36 (m, 12H), 7.12-6.90 (m, 4H), 3.82 (s, 3H); MS: 684.9 (M − 1)⁻. |

-continued

| # | starting material | structure | analytical data |
|---|---|---|---|
| 11/28 | | 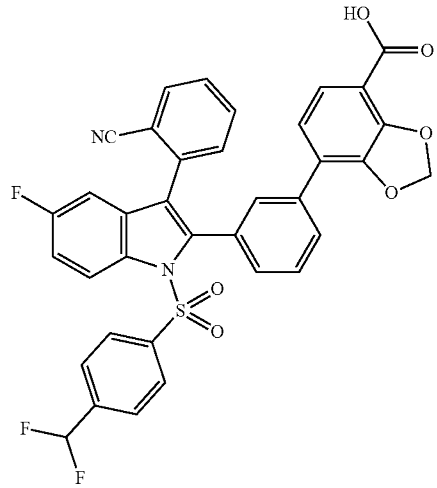 [SMILES: N#Cc1ccccc1-c1c(-c2cccc(-c3ccc(C(=O)O)c4c3OCO4)c2)n(S(=O)(=O)c2ccc(C(F)F)cc2)c2ccc(F)cc12] | ¹H-NMR (500 MHz, CD₃OD) δ: 8.41 (dd, J = 9.0, 4.0 Hz, 1H), 7.78 (d, J = 7.5 Hz, 2H), 7.61-7.39 (m, 10H), 7.30-7.26 (m, 2H), 6.95 (d, J = 8.5 Hz, 1H), 6.90-6.87 (m, 1H), 6.70 (t, J = 55.5 Hz, 1H), 6.08 (d, J = 4.5 Hz, 2H); MS: 665.0 (M − 1)⁻. |
| 11/29 | | 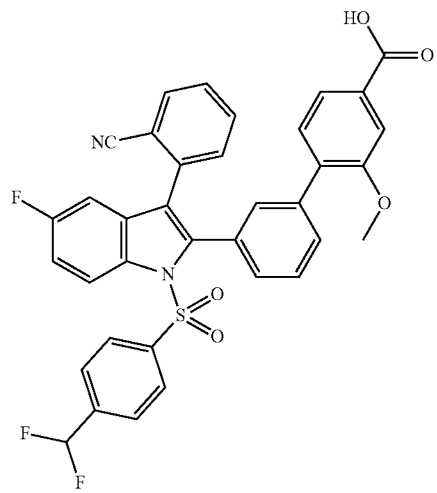 [SMILES: COc1cc(C(=O)O)ccc1-c1cccc(-c2c(-c3ccccc3C#N)c3cc(F)ccc3n2S(=O)(=O)c2ccc(C(F)F)cc2)c1] | ¹H-NMR (400 MHz, CD₃OD) δ: 8.40 (dd, J = 9.2, 4.4 Hz, 1H), 7.79-7.50 (m, 10H), 7.35-7.17 (m, 6H), 6.88 (dd, J = 8.4, 2.4 Hz, 1H), 6.69 (t, J = 55.6 Hz, 1H), 3.83 (s, 3H); MS: 651.0 (M − 1)⁻. |
| 11/30 | | 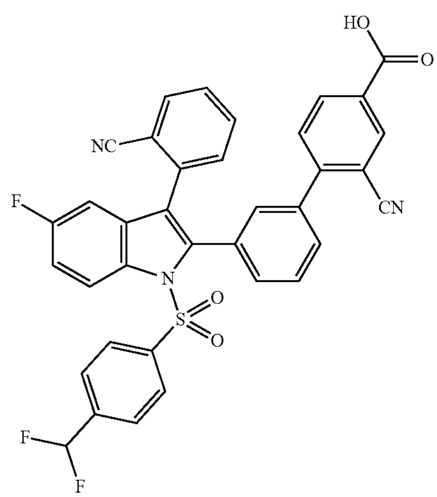 [SMILES: N#Cc1cc(C(=O)O)ccc1-c1cccc(-c2c(-c3ccccc3C#N)c3cc(F)ccc3n2S(=O)(=O)c2ccc(C(F)F)cc2)c1] | ¹H-NMR (400 MHz, CD₃OD) δ: 8.43-8.40 (m, 2H), 8.29 (dd, J = 8.2, 1.4 Hz, 1H), 7.77-7.75 (m, 1H), 7.67-7.26 (m, 13H), 6.91 (dd, J = 2.8, 8.4 Hz, 1H), 6.74 (t, J = 55.6 Hz, 1H); MS: 646.0 (M − 1)⁻. |

-continued

| # | starting material | structure | analytical data |
|---|---|---|---|
| 11/31 | (structure) | (structure) | ¹H-NMR (400 MHz, CD₃OD) δ: 8.41 (dd, J = 9.2, 4.4 Hz, 1H), 7.87 (dd, J = 1.6, 8.0 Hz, 1H), 7.76 (dd, J = 1.4, 11.0 Hz, Hz, 1H), 7.65-7.26 (m, 13H), 6.89 (dd, J = 2.4, 8.4 Hz, 1H), 6.72 (t, J = 55.6 Hz, 1H); MS: 639.0 (M − 1)⁻. |
| 11/32 | (structure) | (structure) | ¹H-NMR (400 MHz, CD₃OD) δ: 8.41 (dd, J = 9.2, 4.4 Hz, 1H), 7.83 (d, J = 8.4 Hz, 1H), 7.78-6.55 (m, 16H); MS: 670.9 (M − 1)⁻. |
| 11/33 | (structure) | (structure) | ¹H-NMR (500 MHz, MeOD) δ: 8.40 (dd, J = 9.3, 4.3 Hz, 1H), 8.07 (d, J = 2.0 Hz, 1H), 7.99 (dd, J = 7.8, 1.8 Hz, 1H), 7.77 (d, J = 7.5 Hz, 1H), 7.64 (t, J = 7.5 Hz, 1H), 7.56-7.44 (m, 8H), 7.35-7.26 (m, 3H), 7.09 (br s, 1H), 6.90 (dd, J = 8.5, 2.5 Hz, 1H), 6.70 (t, J = 55.5 Hz, 1H); MS: 670.9 (M − 1)⁻. |

| # | starting material | structure | analytical data |
|---|---|---|---|
| 11/34 | (structure 1/120) | (product structure) | ¹H-NMR (400 MHz, MeOD) δ: 8.42 (dd, J = 9.4, 4.2 Hz, 1H), 8.06 (d, J = 1.6 Hz, 1H), 7.98 (dd, J = 7.8, 1.4 Hz, 1H), 7.64-7.41 (m, 10H), 7.34-7.28 (m, 2H), 7.05 (br s, 1H), 6.90 (dd, J = 8.2, 2.6 Hz, 1H), 6.70 (t, J = 55.4 Hz, 1H); MS: 670.9 (M − 1)⁻. |
| 11/35 | (structure 1/121) | (product structure) | ¹H-NMR (500 MHz, MeOD) δ: 8.37 (dd, J = 9.3, 4.3 Hz, 1H), 8.08 (d, J = 1.0 Hz, 1H), 7.99 (dd, J = 7.5, 1.5 Hz, 1H), 7.56-7.23 (m, 12H), 7.10 (br s, 1H), 6.76 (dd, J = 1.8, 8.3 Hz, 1H), 6.72 (t, J = 55.5 Hz, 1H), 3.59 (s, 3H); MS: 670.9 (M − 1)⁻. |
| 11/36 | (structure 1/122) | (product structure) | ¹H-NMR (500 MHz, MeOD) δ: 8.41 (dd, J = 9.3, 4.3 Hz, 1H), 8.08 (d, J = 1.5 Hz, 1H), 8.00 (dd, J = 8.0, 1.5 Hz, 1H), 7.60-7.15 (m, 13H), 6.82-6.60 (m, 2H), 1.88 (s, 3H); MS: 670.9 (M − 1)⁻. |

-continued

| # | starting material | structure | analytical data |
|---|---|---|---|
| 11/37 | (35/1) | 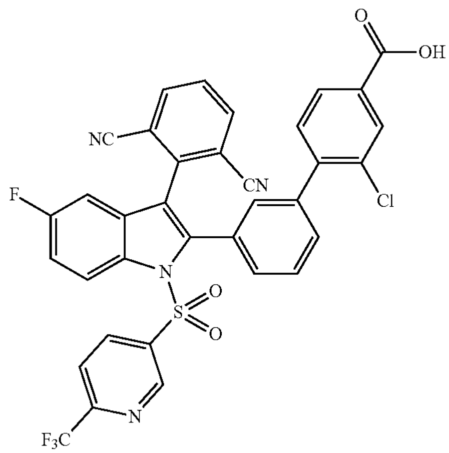 [SMILES: N#Cc1cccc(C#N)c1-c1c(-c2cccc(-c3ccc(C(=O)O)cc3Cl)c2)n(S(=O)(=O)c2ccc(C(F)(F)F)nc2)c2ccc(F)cc12] | ¹H-NMR (400 MHz, MeOD) δ: 8.68 (d, J = 2.0 Hz, 1H), 8.50 (dd, J = 9.2, 4.0 Hz, 1H), 8.09-7.98 (m, 5H), 7.83 (d, J = 8.4 Hz, 1H), 7.74 (t, J = 7.8 Hz, 1H), 7.55-7.38 (m, 5H), 7.20 (s, 1H), 6.97 (dd, J = 8.2, 2.6 Hz, 1H); MS: 698.9 (M − 1)⁻. |
| 11/38 | (9/1) | 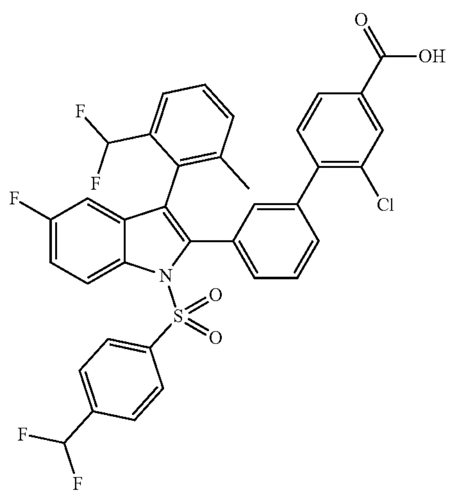 [SMILES: Cc1cccc(C(F)F)c1-c1c(-c2cccc(-c3ccc(C(=O)O)cc3Cl)c2)n(S(=O)(=O)c2ccc(C(F)F)cc2)c2ccc(F)cc12] | ¹H-NMR (500 MHz, MeOD) δ: 8.42 (dd, J = 9.0, 4.5 Hz, 1H), 8.09 (d, J = 2.0 Hz, 1H), 7.98 (dd, J = 8.0, 1.5 Hz, 1H), 7.59-7.25 (m, 12H), 7.21 (br s, 1H), 6.77 (t, J = 55.5 Hz, 1H), 6.59 (dd, J = 8.0, 2.5 Hz, 1H), 5.90 (t, J = 55.5 Hz, 1H), 1.70 (s, 3H); MS: 694.0 (M − 1)⁻. |
| C11/39 | (C1/123) | 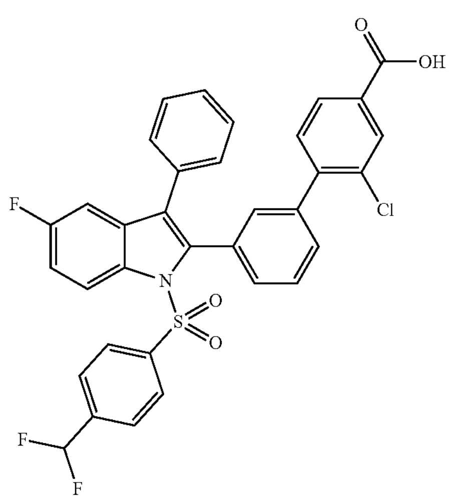 [SMILES: O=C(O)c1ccc(-c2cccc(-c3c(-c4ccccc4)c4cc(F)ccc4n3S(=O)(=O)c3ccc(C(F)F)cc3)c2)c(Cl)c1] | ¹H-NMR (400 MHz, CD₃OD) δ: 8.40 (dd, J = 9.2, 4.4 Hz, 1H), 8.07 (d, J = 1.6 Hz, 1H), 7.97 (dd, J = 8.0, 1.6 Hz, 1H), 7.56-7.45 (m, 7H), 7.34-7.21 (m, 5H), 7.14-7.11 (m, 4H), 6.73 (t, J = 55.6 Hz, 1H); MS: 630.0 (M − 1)⁻. |

| # | starting material | structure | analytical data |
|---|---|---|---|
| 11/40 | 1/124 | 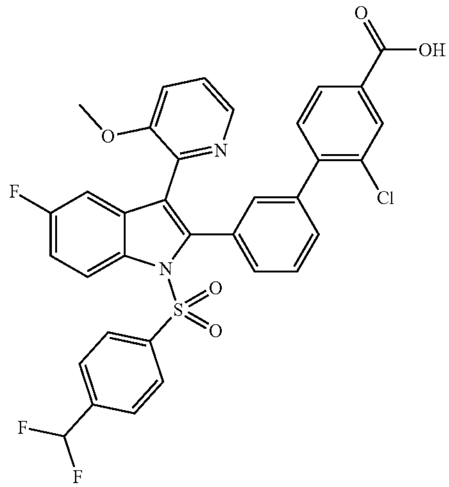 [SMILES: COc1cccnc1-c1c(-c2cccc(-c3ccc(C(=O)O)cc3Cl)c2)n(S(=O)(=O)c2ccc(C(F)F)cc2)c2ccc(F)cc12] | ¹H-NMR (500 MHz, CD₃OD) δ: 8.41 (dd, J = 9.0, 4.5 Hz, 1H), 8.19 (dd, J = 1.0, 4.5 Hz, 1H), 8.08 (d, J = 1.0 Hz, 1H), 8.01 (dd, J = 7.8, 1.8 Hz, 1H), 7.56-7.46 (m, 9H), 7.39 (d, J = 8.0 Hz, 1H), 7.29-7.25 (m, 1H), 7.14 (br s, 1H), 7.00 (dd, J = 9.0, 2.5 Hz, 1H), 6.74 (t, J = 55.5 Hz, 1H), 3.50 (s, 3H); MS: 663.0 (M + 1)⁺. |
| 11/41 | 1/125 | 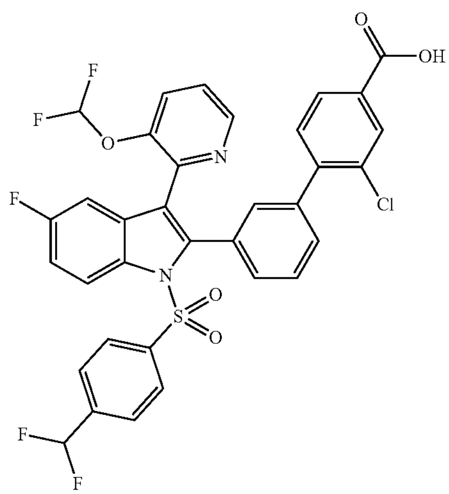 [SMILES: O=C(O)c1ccc(-c2cccc(-c3c(-c4ncccc4OC(F)F)c4cc(F)ccc4n3S(=O)(=O)c3ccc(C(F)F)cc3)c2)c(Cl)c1] | ¹H-NMR (400 MHz, CD₃OD) δ: 8.44-8.40 (m, 2H), 8.07 (d, J = 1.6 Hz, 1H), 8.00 (dd, J = 8.0, 1.2 Hz, 1H), 7.67 (d, J = 8.4 Hz, 1H), 7.57-7.25 (m, 10H), 7.14 (br s, 1H), 6.98 (dd, J = 8.6, 2.6 Hz, 1H), 6.73 (t, J = 55.6 Hz, 1H), 6.51 (t, J = 72.6 Hz, 1H); MS: 699.0 (M + 1)⁺. |
| 11/42 | 1/126 | 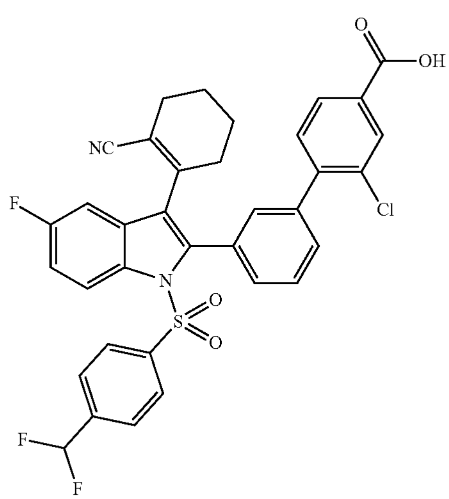 [SMILES: N#CC1=C(c2c(-c3cccc(-c4ccc(C(=O)O)cc4Cl)c3)n(S(=O)(=O)c3ccc(C(F)F)cc3)c3ccc(F)cc23)CCCC1] | ¹H-NMR (400 MHz, CD₃OD) δ: 8.32 (dd, J = 9.0, 4.6 Hz, 1H), 8.16 (d, J = 1.6 Hz, 1H), 8.07 (dd, J = 7.8, 1.4 Hz, 1H), 7.62-7.22 (m, 10H), 7.15 (dd, J = 8.2, 2.6 Hz, 1H), 6.70 (t, J = 55.6 Hz, 1H), 2.43-2.16 (m, 3H), 1.92-1.43 (m, 5H); MS: 659.0 (M − 1)⁻. |

-continued

| # | starting material | structure | analytical data |
|---|---|---|---|
| 11/43 | (1/129) | 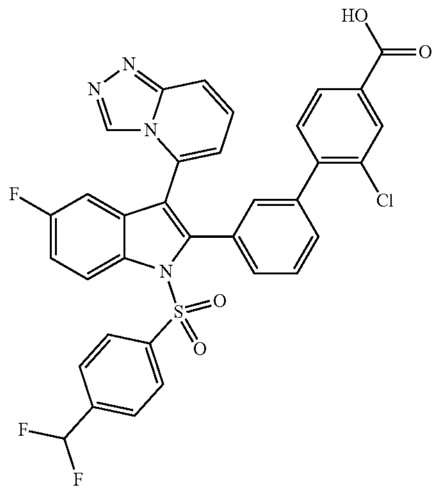 [SMILES: O=C(O)c1ccc(-c2cccc(-c3c(-c4cccc5nncn45)c4cc(F)ccc4n3S(=O)(=O)c3ccc(C(F)F)cc3)c2)c(Cl)c1] | ¹H-NMR (500 MHz, CD₃OD) δ: 8.67 (br s, 1H), 8.51-8.48 (m, 1H), 8.00-7.93 (m, 2H), 7.75 (d, J = 9.5 Hz, 1H), 7.63-7.00 (m, 13H), 6.73 (t, J = 55.3 Hz, 1H); MS: 671.0 (M − 1)⁻. |
| 11/44 | (1/130) | 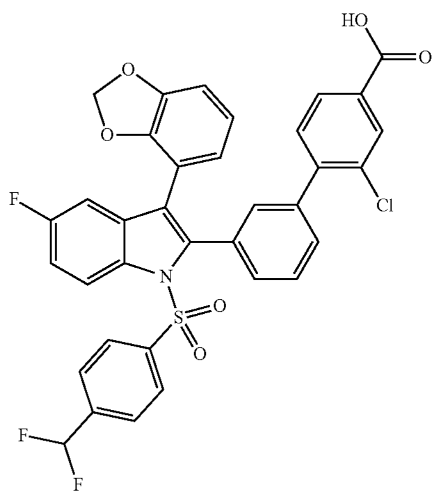 [SMILES: O=C(O)c1ccc(-c2cccc(-c3c(-c4cccc5c4OCO5)c4cc(F)ccc4n3S(=O)(=O)c3ccc(C(F)F)cc3)c2)c(Cl)c1] | ¹H-NMR (500 MHz, CD₃OD) δ: 8.38 (dd, J = 9.1, 4.3 Hz, 1H), 8.08 (d, J = 1.5 Hz, 1H), 7.99 (dd, J = 7.8, 1.4 Hz, 1H), 7.56-7.415 (m, 7H), 7.35 (d, J = 8.0 Hz, 1H), 7.27-7.22 (m, 1H), 7.16 (s, 1H), 7.07 (dd, J = 8.5, 2.5 Hz, 1H), 6.84-6.60 (m, 4H), 5.65 (s, 2H); MS: 674.0 (M − 1)⁻. |
| 11/45 | (1/131) | 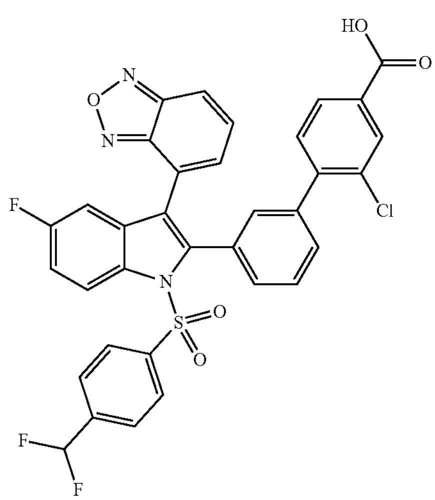 [SMILES: O=C(O)c1ccc(-c2cccc(-c3c(-c4cccc5nonc45)c4cc(F)ccc4n3S(=O)(=O)c3ccc(C(F)F)cc3)c2)c(Cl)c1] | ¹H-NMR (500 MHz, CD₃OD) δ: 8.45 (dd, J = 9.3, 4.3 Hz, 1H), 8.01 (d, J = 1.5 Hz, 1H), 7.98 (dd, J = 8.0, 1.5 Hz, 1H), 7.85 (d, J = 9.0 Hz, 1H), 7.59-7.55 (m, 4H), 7.49-7.28 (m, 7H), 7.07-7.05 (m, 2H), 6.72 (t, J = 55.5 Hz, 1H); MS: 671.9 (M − 1)⁻. |

| # | starting material | structure | analytical data |
|---|---|---|---|
| 11/46 | 1/132 | 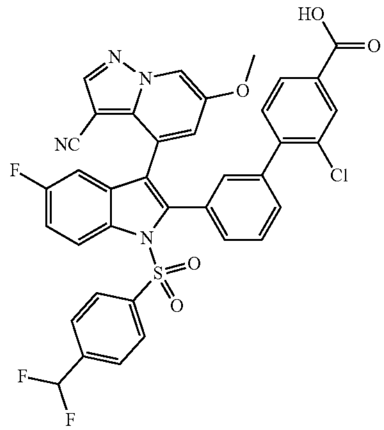 [SMILES: COc1cc(-c2c(-c3cccc(-c4ccc(C(=O)O)cc4Cl)c3)n(S(=O)(=O)c3ccc(C(F)F)cc3)c3ccc(F)cc23)c2c(C#N)cnn2c1] | $^1$H-NMR (500 MHz, CD$_3$OD) δ: 8.43-8.40 (m, 2H), 8.22-7.97 (m, 3H), 7.54-6.72 (m, 13H), 3.86 (s, 3H); MS: 725.0 (M − 1)$^−$. |
| 11/47 | 1/133 | 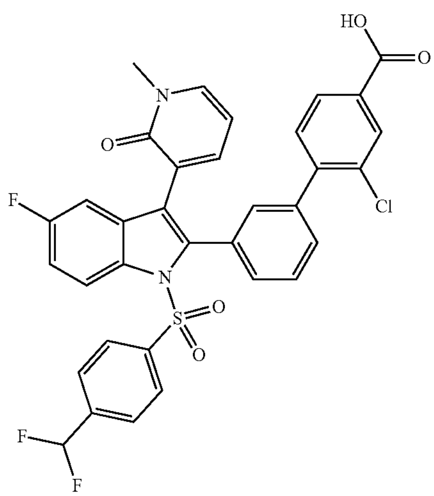 [SMILES: Cn1cccc(-c2c(-c3cccc(-c4ccc(C(=O)O)cc4Cl)c3)n(S(=O)(=O)c3ccc(C(F)F)cc3)c3ccc(F)cc23)c1=O] | $^1$H-NMR (500 MHz, CD$_3$OD) δ: 8.34 (dd, J = 9.3, 4.3 Hz, 1H), 8.08 (s, 1H), 8.01 (d, J = 8.0 Hz, 1H), 7.64 (dd, J = 2.0, 6.5 Hz, 1H), 7.59-7.42 (m, 8H), 7.23-7.18 (m, 3H), 7.00 (dd, J = 2.3, 8.8 Hz, 1H), 6.72 (t, J = 55.5 Hz, 1H), 6.27-6.25 (m, 1H), 3.57 (s, 3H); MS: 661.0 (M − 1)$^−$. |
| C11/48 | C1/134 | 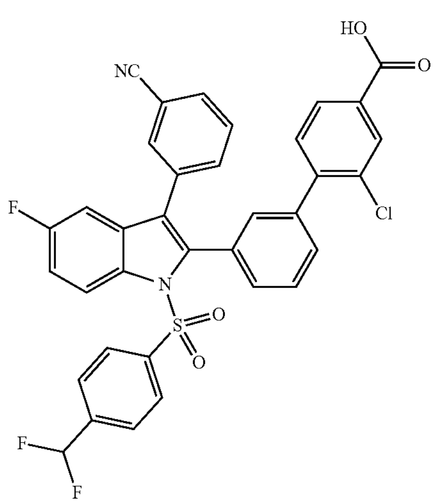 [SMILES: N#Cc1cccc(-c2c(-c3cccc(-c4ccc(C(=O)O)cc4Cl)c3)n(S(=O)(=O)c3ccc(C(F)F)cc3)c3ccc(F)cc23)c1] | $^1$H-NMR (500 MHz, CD$_3$OD) δ: 8.42 (dd, J = 9.0, 4.5 Hz, 1H), 8.06 (d, J = 1.5 Hz, 1H), 7.98 (dd, J = 8.0, 1.5 Hz, 1H), 7.64-7.46 (m, 11H), 7.36 (d, J = 7.5 Hz, 1H), 7.31-7.26 (m, 1H), 7.18 (dd, J = 8.8, 2.8 Hz, 1H), 7.10 (s, 1H), 6.73 (t, J = 55.8 Hz, 1H); MS: 654.9 (M − 1)$^−$. |

| # | starting material | structure | analytical data |
|---|---|---|---|
| 11/49 | (structure with methyl ester, CN, pyrrolopyridine, Cl, sulfonyl-phenyl-CHF2) 1/135 | (corresponding carboxylic acid) | $^1$H-NMR (400 MHz, DMSO-d$_6$) δ: 9.52 (s, 1H), 8.52 (d, J = 5.2 Hz, 1H), 7.94-7.88 (m, 3H), 7.71-7.32 (m, 12H), 7.14-6.86 (m, 2H); MS: 638.0 (M − 1)$^-$. |
| 11/50 | (structure with methyl ester, CN, CN, F-indole, sulfonyl-phenyl-CHF2) 2/25 | (corresponding carboxylic acid) | $^1$H-NMR (500 MHz, DMSO-d$_6$) δ: 8.36 (dd, J = 9.5, 4.0 Hz, 1H), 8.25 (d, J = 8.0 Hz, 2H), 8.03 (d, J = 8.5 Hz, 2H), 7.79 (t, J = 7.8 Hz, 2H), 7.68 (d, J = 8.0 Hz, 2H), 7.60-7.56 (m, 4H), 7.50-7.40 (m, 3H), 7.26 (dd, J = 2.5, 8.5 Hz, 1H), 7.19 (d, J = 7.5 Hz, 1H), 7.04 (t, J = 55.3 Hz, 1H); MS: 646.0 (M − 1)$^-$. |
| 11/51 | (structure with methyl ester, CN, CN, F-indole, F, sulfonyl-phenyl-CHF2) 2/26 | (corresponding carboxylic acid) | $^1$H-NMR (500 MHz, CD$_3$OD) δ: 8.45 (dd, J = 9.5, 4.0 Hz, 1H), 8.06 (br s, 2H), 7.89 (dd, J = 8.0, 1.5 Hz, 1H), 7.78-7.63 (m, 3H), 7.56-7.29 (m, 9H), 6.95 (dd, J = 8.5, 2.5 Hz, 1H), 6.69 (t, J = 55.8 Hz, 1H); MS: 664.0 (M − 1)$^-$. |

-continued

| # | starting material | structure | analytical data |
|---|---|---|---|
| 11/52 | | 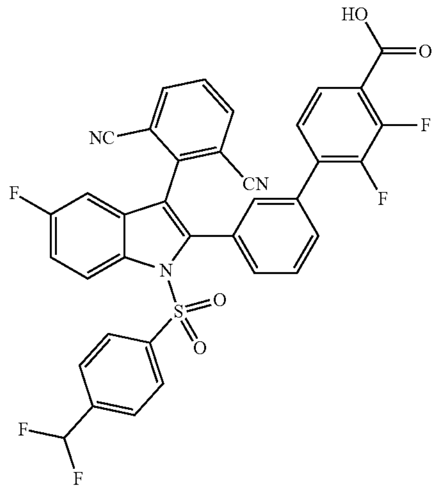 [SMILES: N#Cc1cccc(C#N)c1-c1c(-c2cccc(-c3ccc(C(=O)O)c(F)c3F)c2)n(S(=O)(=O)c2ccc(C(F)F)cc2)c2ccc(F)cc12] | ¹H-NMR (500 MHz, CD₃OD) δ: 8.45 (dd, J = 9.0, 4.5 Hz, 1H), 8.07 (br s, 2H), 7.77-7.64 (m, 3H), 7.57-7.48 (m, 5H), 7.41-7.29 (m, 3H), 7.21-7.18 (m, 1H), 6.96 (dd, J = 8.5, 2.5 Hz, 1H), 6.71 (t, J = 55.8 Hz, 1H); MS: 682.0 (M − 1)⁻. |
| 11/53 | | 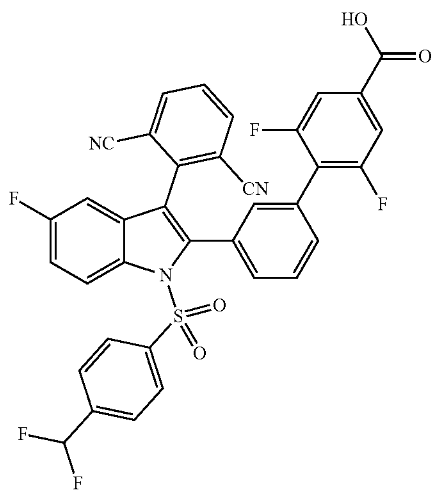 [SMILES: N#Cc1cccc(C#N)c1-c1c(-c2cccc(-c3c(F)cc(C(=O)O)cc3F)c2)n(S(=O)(=O)c2ccc(C(F)F)cc2)c2ccc(F)cc12] | ¹H-NMR (500 MHz, CD₃OD) δ: 8.44 (dd, J = 9.0, 4.0 Hz, 1H), 8.07-8.03 (m, 2H), 7.72 (t, J = 8.3 Hz, 1H), 7.66-7.50 (m, 9H), 7.33 (td, J = 9.0, 2.5 Hz, 1H), 7.00 (s, 1H), 6.95 (dd, J = 8.0, 2.5 Hz, 1H), 6.68 (t, J = 55.5 Hz, 1H); MS: 682.0 (M − 1)⁻. |
| 11/54 | | 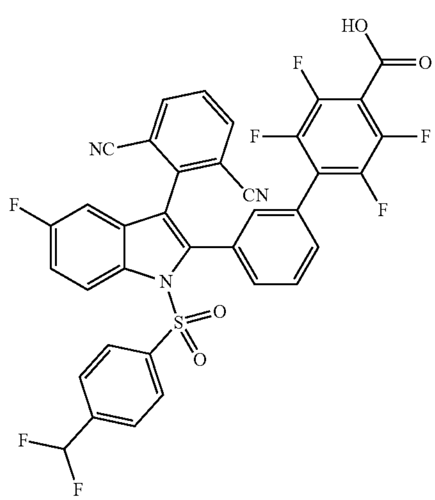 [SMILES: N#Cc1cccc(C#N)c1-c1c(-c2cccc(-c3c(F)c(F)c(C(=O)O)c(F)c3F)c2)n(S(=O)(=O)c2ccc(C(F)F)cc2)c2ccc(F)cc12] | ¹H-NMR (500 MHz, CD₃OD) δ: 8.44 (dd, J = 9.3, 4.8 Hz, 1H), 8.12-8.02 m, 2H), 7.77-7.72 (m, 1H), 7.62-7.51 (m, 7H), 7.35 (td, J = 9.3, 2.8 Hz, 1H), 7.06 (s, 1H), 6.97 (dd, J = 8.0, 2.5 Hz, 1H), 6.71 (t, J = 55.5 Hz, 1H); MS: 737.1 (M + 18)⁺. |

-continued

| # | starting material | structure | analytical data |
|---|---|---|---|
| 11/55 | (structure 1/136) | (product structure) | ¹H-NMR (500 MHz, CD₃OD) δ: 8.42 (dd, J = 9.5, 4.0 Hz, 1H), 8.09-8.04 (m, 3H), 8.00 (dd, J = 1.5, 8.0 Hz, 1H), 7.73 (t, J = 7.8 Hz, 1H), 7.49-7.44 (m, 3H), 7.38-7.29 (m, 6H), 7.05 (d, J = 1.0 Hz, 1H), 6.95 (dd, J = 8.5, 2.5 Hz, 1H); MS: 663.9/666.0 (M − 1)⁻. |
| 11/56 | (structure 1/137) | (product structure) | ¹H-NMR (500 MHz, CD₃OD) δ: 8.43 (d, J = 8.5 Hz, 1H), 8.09-8.04 (m, 3H), 7.98 (dd, J = 7.5, 1.5 Hz, 1H), 7.72 (t, J = 8.0 Hz, 1H), 7.58-7.47 (m, 8H), 7.42 (t, J = 7.8 Hz, 1H), 7.34 (d, J = 8.0 Hz, 1H), 7.19 (d, J = 7.5 Hz, 1H), 7.07 (s, 1H), 6.66 (t, J = 55.5 Hz, 1H); MS: 661.9 (M − 1)⁻. |
| 11/57 | (structure 35/2) | (product structure) | ¹H-NMR (400 MHz, CD₃OD) δ: 8.60 (d, J = 2.0 Hz, 1H), 8.44 (dd, J = 4.4, 9.2 Hz, 1H), 8.10 (s, 1H), 8.03-7.31 (m, 9H), 7.21 (s, 1H), 7.09 (dd, J = 2.8, 8.4 Hz, 1H), 7.00 (d, J = 4.8 Hz, 1H), 6.65 (t, J = 54.6 Hz, 1H); MS: 663.8 (M + 1)⁺. |

-continued

| # | starting material | structure | analytical data |
|---|---|---|---|
| 11/58 | 1/138 | 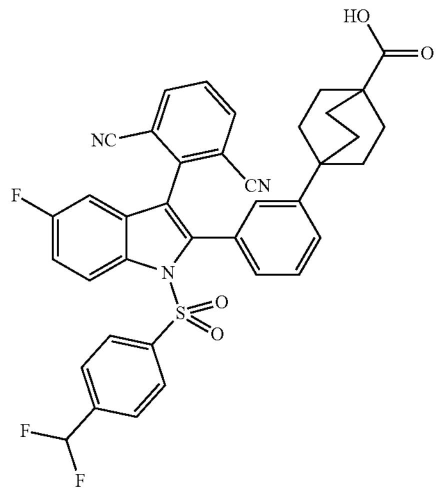 [SMILES: N#Cc1cccc(C#N)c1-c1c(-c2cccc(C34CCC(C(=O)O)(CC3)CC4)c2)n(S(=O)(=O)c2ccc(C(F)F)cc2)c2ccc(F)cc12] | ¹H-NMR (500 MHz, CD₃OD) δ: 8.45 (dd, J = 9.3, 4.3 Hz, 1H), 8.07-7.98 (m, 2H), 7.69 (t, J = 8.0 Hz, 1H), 7.58 (d, J = 8.5 Hz, 2H), 7.43 (d, J = 8.0 Hz, 2H), 7.37-7.31 (m, 2H), 7.24 (t, J = 7.8 Hz, 1H), 7.11 (d, J = 8.0 Hz, 1H), 6.97-6.93 (m, 2H), 6.79 (t, J = 55.8 Hz, 1H), 1.90-1.87 (m, 6H), 1.70-1.67 (m, 6H); MS: 678.0 (M − 1)⁻. |
| 11/59 | 2/30 | 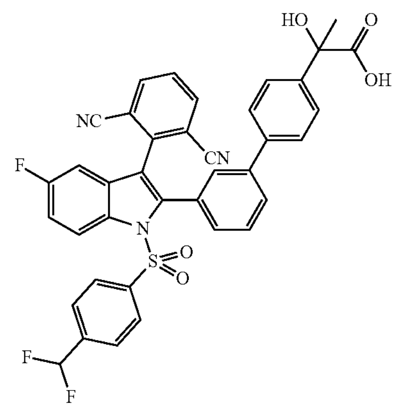 | ¹H-NMR (500 MHz, CD₃OD) δ: 8.46 (dd, J = 9.2, 4.3 Hz, 1H), 8.05 (d, J = 7.9 Hz, 2H), 7.75-7.62 (m, 4H), 7.52 (q, J = 8.6 Hz, 4H), 7.47-7.28 (m, 5H), 7.21 (d, J = 7.8 Hz, 1H), 6.96 (dd, J = 8.3, 2.5 Hz, 1H), 6.67 (t, J = 55.6 Hz, 1H), 1.79 (s, 3H); MS: 690.0 (M − 1)⁻. |
| 11/60 | 2/31 | 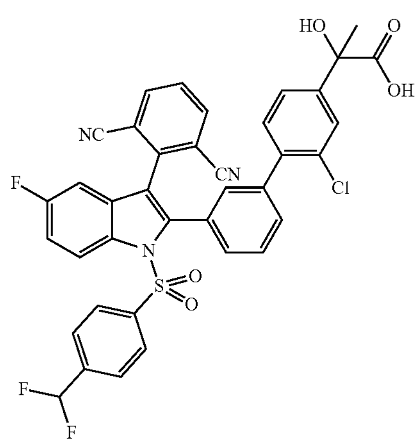 | ¹H-NMR (500 MHz, CD₃OD) δ: 8.44 (dd, J = 9.5, 4.3 Hz, 1H), 8.06 (br s, 2H), 7.75-7.70 (m, 2H), 7.62-7.59 (m, 1H), 7.52-7.48 (m, 4H), 7.45-7.43 (m, 2H), 7.35-7.31 (m, 1H), 7.21 (d, J = 7.5 Hz, 1H), 6.98-6.93 (m, 2H), 6.64 (t, J = 55.6 Hz, 1H), 1.77 (s, 3H); MS: 724.0 (M − 1)⁻. |

-continued

| # | starting material | structure | analytical data |
|---|---|---|---|
| 11/61 | (structure 43/1) | 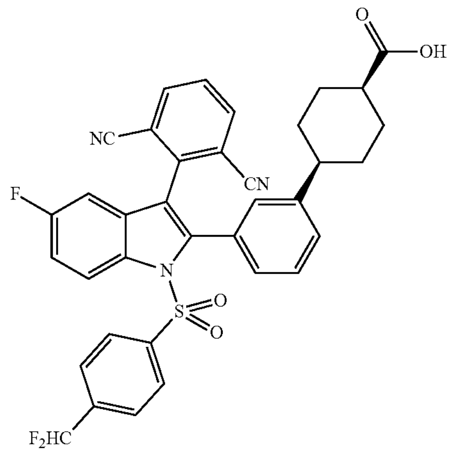 [SMILES: N#Cc1cccc(C#N)c1-c1c(-c2cccc([C@H]3CC[C@@H](C(=O)O)CC3)c2)n(S(=O)(=O)c2ccc(C(F)F)cc2)c2ccc(F)cc12] | ¹H-NMR (500 MHz, CD₃OD) δ: 8.45-8.42 (m, 1H), 8.02 (br s, 2H), 7.68 (t, J = 7.9 Hz, 1H), 7.57 (d, J = 8.3 Hz, 2H), 7.45 (d, J = 8.3 Hz, 2H), 7.37-7.13 (m, 4H), 6.98-6.60 (m, 3H), 2.65 (s, 1H), 2.50-2.45 (m, 1H), 2.17-2.14 (m, 2H), 1.71-1.11 (m, 6H); MS: 652.0 (M − 1)⁻. |
| 11/62 | (structure 43/2) | 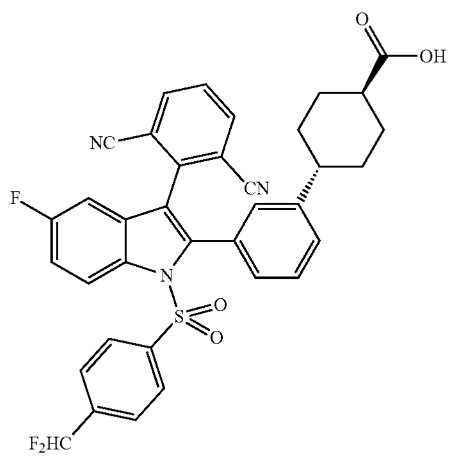 [SMILES: N#Cc1cccc(C#N)c1-c1c(-c2cccc([C@H]3CC[C@H](C(=O)O)CC3)c2)n(S(=O)(=O)c2ccc(C(F)F)cc2)c2ccc(F)cc12] | ¹H-NMR (500 MHz, CD₃OD) δ: 8.44 (dd, J = 9.2, 4.3 Hz, 1H), 8.04-8.00 (m, 2H), 7.69 (t, J = 7.9 Hz, 1H), 7.58 (d, J = 8.3 Hz, 2H), 7.47 (d, J = 8.3 Hz, 2H), 7.32 (td, J = 9.1, 2.5 Hz, 1H), 7.29-7.16 (m, 2H), 7.09-7.07 (m, 1H), 7.01-6.61 (m, 3H), 2.46-2.41 (m, 1H), 2.31-2.25 (m, 1H), 2.08 (d, J = 11.8 Hz, 2H), 1.79 (br s, 2H), 1.55 (qd, J = 13.0, 3.3 Hz, 2H), 1.32 (br s, 2H); MS: 652.0 (M − 1)⁻. |
| 11/63 | (structure 1/142) | 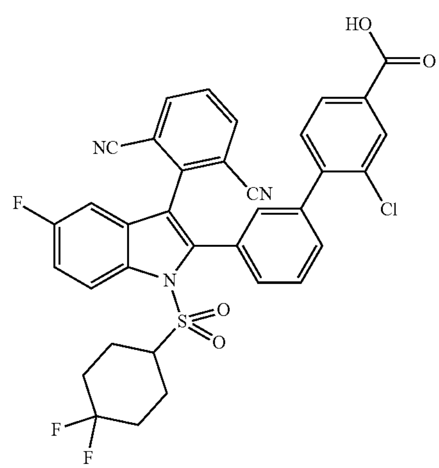 [SMILES: N#Cc1cccc(C#N)c1-c1c(-c2cccc(-c3ccc(C(=O)O)cc3Cl)c2)n(S(=O)(=O)C2CCC(F)(F)CC2)c2ccc(F)cc12] | ¹H-NMR (500 MHz, CD₃OD) δ: 8.28 (dd, J = 4.3, 9.3 Hz, 1H), 8.12 (d, J = 7.5 Hz, 2H), 9.09 (d, J = 2.0 Hz, 1H), 7.99 (dd, J = 1.5, 8.0 Hz, 1H), 7.77 (t, J = 7.8 Hz, 1H), 7.53-7.33 (m, 6H), 7.04 (dd, J = 2.5, 9.0 Hz, 1H), 3.48-3.43 (m, 1H), 2.04 (br s, 2H), 1.80-1.67 (m, 6H); MS: 672.0 (M − 1)⁻. |

| # | starting material | structure | analytical data |
|---|---|---|---|
| 11/64 | 1/143 | 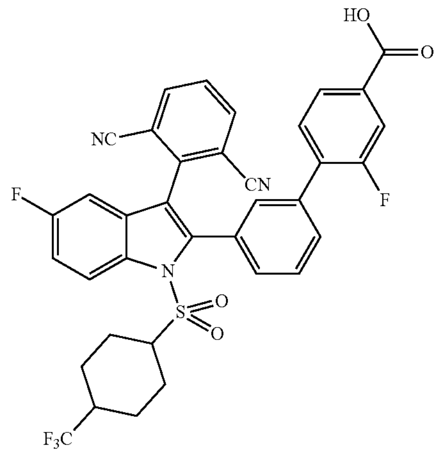 [SMILES: N#Cc1cccc(C#N)c1-c1c(-c2cccc(-c3ccc(C(=O)O)cc3F)c2)n(S(=O)(=O)C2CCC(C(F)(F)F)CC2)c2ccc(F)cc12] | ¹H-NMR (500 MHz, DMSO-d₆) δ: 8.29 (d, J = 7.5 Hz, 2H), 8.16 (dd, J = 4.3, 9.3 Hz, 1H), 7.84-7.81 (m, 2H), 7.71 (dd, J = 11.3, 1.3 Hz, 1H), 7.62 (d, J = 7.0 Hz, 1H), 7.51-7.43 (m, 4H), 7.38 (d, J = 8.0 Hz, 1H), 7.30 (dd, J = 2.5, 8.5 Hz, 1H), 3.56-3.51 (m, 1H), 2.30-2.22 (m, 1H), 1.79-1.67 (m, 4H), 1.44 (q, J = 11.8 Hz, 2H), 1.22 (q, J = 11.8 Hz, 2H); MS: 688.0 (M − 1)⁻. |
| 11/65 | 1/144 | 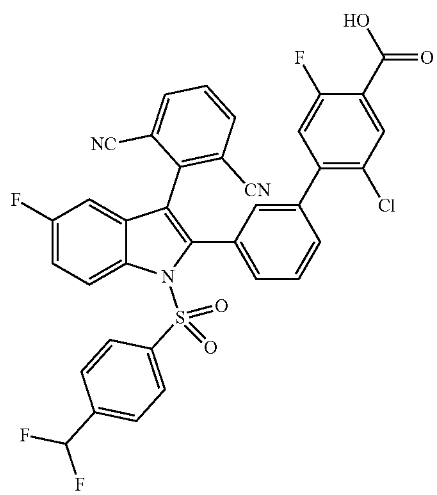 [SMILES: N#Cc1cccc(C#N)c1-c1c(-c2cccc(-c3cc(F)c(C(=O)O)cc3Cl)c2)n(S(=O)(=O)c2ccc(C(F)F)cc2)c2ccc(F)cc12] | ¹H-NMR (500 MHz, DMSO-d₆) δ: 8.44 (dd, J = 4.3, 9.3 Hz, 1H), 8.07 (d, J = 7.0 Hz, 2H), 8.01 (d, J = 6.5 Hz, 1H), 7.73 (t, J = 8.0 Hz, 1H), 7.56-7.32 (m, 8H), 7.19 (d, J = 11.0 Hz, 1H), 7.11 (s, 1H), 6.96 (dd, J = 2.5, 8.0 Hz, 1H), 6.70 (t, J = 55.8 Hz, 1H); MS: 697.9 (M − 1)⁻. |
| 11/66 | 1/146 | 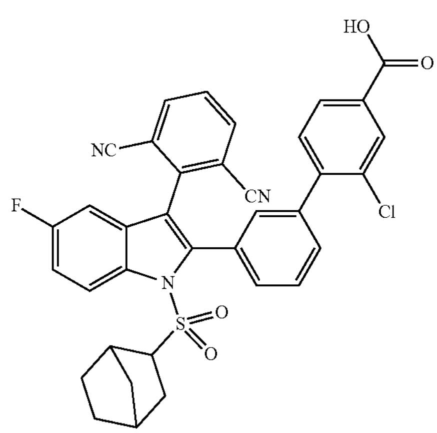 [SMILES: N#Cc1cccc(C#N)c1-c1c(-c2cccc(-c3ccc(C(=O)O)cc3Cl)c2)n(S(=O)(=O)C2CC3CCC2C3)c2ccc(F)cc12] | ¹H-NMR (500 MHz, CD₃OD) δ: 8.29 (dd, J = 9.0, 4.0 Hz, 1H), 8.13-8.08 (m, 3H), 7.99 (dd, J = 8.5, 1.5 Hz, 1H), 7.78-7.74 (m, 1H), 7.57-7.29 (m, 6H), 7.03-6.99 (m, 1H), 3.18 (dd, J = 8.5, 6.0 Hz, 1H), 2.38-2.25 (m, 2H), 1.85-1.05 (m, 8H); MS: 648.0 (M − 1)⁻. |

| # | starting material | structure | analytical data |
|---|---|---|---|
| 11/67 | 1/147 | 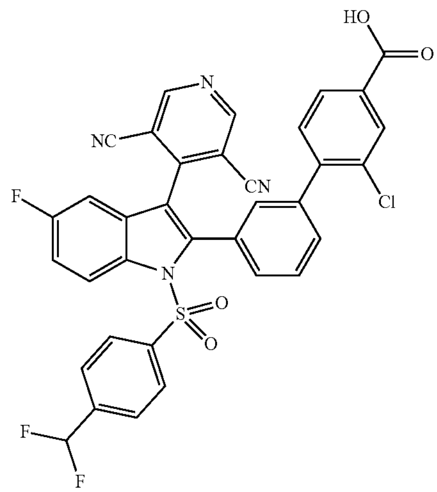 [SMILES: N#Cc1cncc(C#N)c1-c1c(-c2cccc(-c3ccc(C(=O)O)cc3Cl)c2)n(S(=O)(=O)c2ccc(C(F)F)cc2)c2ccc(F)cc12] | $^1$H-NMR (500 MHz, CD$_3$OD) δ: 9.15 (br s, 2H), 8.48 (dd, J = 9.3, 4.3 Hz, 1H), 8.08 (d, J = 1.0 Hz, 1H), 8.00 (dd, J = 8.0, 1.5 Hz, 1H), 7.55-7.48 (m, 6H), 7.44-7.38 (m, 3H), 7.13 (dd, J = 8.0, 2.5 Hz, 1H), 7.01 (s, 1H), 6.68 (t, J = 55.8 Hz, 1H); MS: 681.0 (M − 1)$^-$. |
| 11/68 | 1/148 | 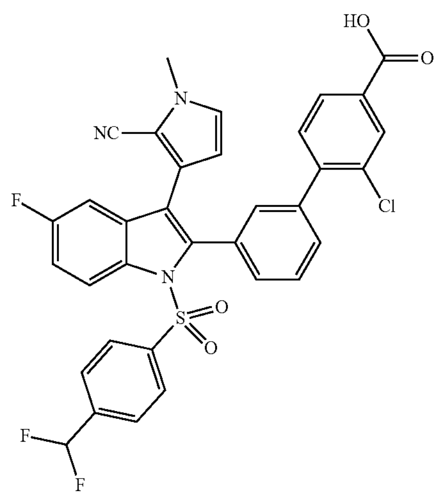 [SMILES: Cn1ccc(-c2c(-c3cccc(-c4ccc(C(=O)O)cc4Cl)c3)n(S(=O)(=O)c3ccc(C(F)F)cc3)c3ccc(F)cc23)c1C#N] | $^1$H-NMR (400 MHz, CD$_3$OD) δ: 8.37 (dd, J = 9.2, 4.4 Hz, 1H), 8.10 (s, 1H), 8.00 (d, J = 7.6 Hz, 1H), 7.55-7.41 (m, 8H), 7.27-7.22 (m, 1H), 7.16 (s, 1H), 7.10 (dd, J = 8.8, 2.4 Hz, 1H), 6.99 (d, J = 2.8 Hz, 1H), 6.70 (t, J = 55.4 Hz, 1H), 6.03 (d, J = 2.8 Hz, 1H), 3.72 (s, 3H); MS: 658.0 (M − 1)$^-$. |
| 11/69 | 1/149 | 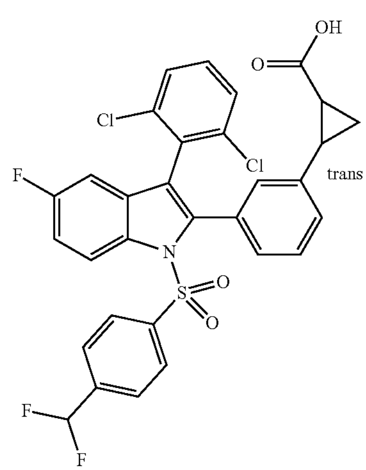 [SMILES: O=C(O)C1CC1c1cccc(-c2c(-c3c(Cl)cccc3Cl)c3cc(F)ccc3n2S(=O)(=O)c2ccc(C(F)F)cc2)c1] | $^1$H-NMR (400 MHz, CD$_3$OD) δ: 8.38 (dd, J = 9.2, 4.4 Hz, 1H), 7.58 (d, J = 8.4 Hz, 2H), 7.45 (d, J = 8.4 Hz, 2H), 7.39-7.16 (m, 7H), 6.94-6.65 (m, 3H), 2.38-2.34 (m, 1H), 1.61-1.55 (m, 1H), 1.50-1.45 (m, 1H), 1.10 (br s, 1H); MS: 628.0 and 630.0 (M − 1)$^-$. |

Example 12

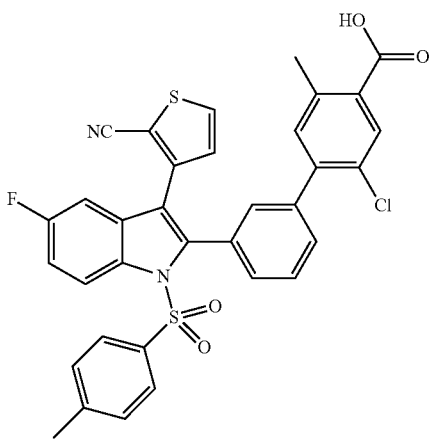

Step 1: Methyl 2-chloro-3'-(3-(2-cyanothiophen-3-yl)-5-fluoro-1-tosyl-1H-indol-2-yl)-5-methyl-[1,1'-biphenyl]-4-carboxylate (12a)

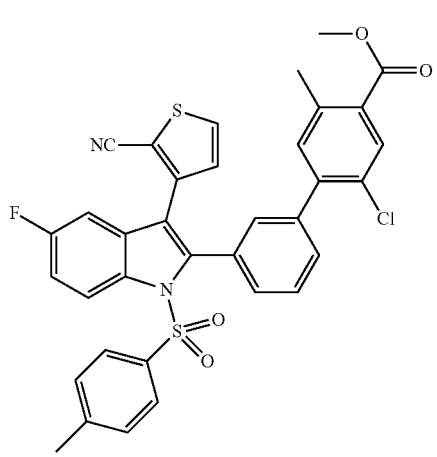

To a solution of compound 2a (200 mg, 0.33 mmol) in dioxane (2 mL) and water (0.4 mL) was added methyl 4-bromo-5-chloro-2-methylbenzoate (105 mg, 0.40 mmol), $Cs_2CO_3$ (215 mg, 0.66 mmol) and $Pd(dppf)Cl_2$ (20 mg). The mixture was stirred under $N_2$ at 100° C. for 8 h, cooled to rt, poured into EA (40 mL) and washed with $H_2O$ (40 mL) and brine (40 mL). The organic layer was dried over $Na_2SO_4$, filtered, concentrated and purified by FCC (EA:PE=1:8) to give compound 12a as a white solid.

Step 2: 2-Chloro-3'-(3-(2-cyanothiophen-3-yl)-5-fluoro-1-tosyl-1H-indol-2-yl)-5-methyl-[1,1'-biphenyl]-4-carboxylic Acid (12)

To a solution of compound 12a (150 mg, 0.23 mmol) in HCl/dioxane (4N, 5 mL) was added $H_2O$ (0.5 mL) and the mixture was stirred at 90° C. overnight, concentrated, diluted with water and extracted with EA (3×). The combined organic layer was washed with brine, dried over $Na_2SO_4$, filtered, concentrated and purified by prep-HPLC to give compound 12 as a white solid. $^1$H-NMR (500 MHz, DMSO-$d_6$) δ: 8.29 (dd, J=9.0, 4.5 Hz, 1H), 8.03 (d, J=5.0 Hz, 1H), 7.82 (s, 1H), 7.54-7.46 (m, 3H), 7.40-7.32 (m, 3H), 7.24 (d, J=8.0 Hz, 2H), 7.18 (dd, J=8.0, 3.0 Hz, 2H), 7.04-7.00 (m, 2H), 2.53 (s, 3H), 2.21 (s, 3H); MS: 638.9 (M−1)⁻.

Example 12/1 to 12/10

The following Examples were prepared similar as described for Example 12 using the appropriate building block.

| # | building block | structure | analytical data |
|---|---|---|---|
| 12/1 | (structure shown) | (structure shown) | $^1$H-NMR (500 MHz, DMSO-$d_6$) δ: 8.29 (dd, J = 9.3, 4.3 Hz, 1H), 8.03 (d, J = 5.0 Hz, 1H), 7.68 (d, J = 8.0 Hz, 1H), 7.53-7.15 (m, 10H), 7.03 (d, J = 5.0 Hz, 1H), 6.98 (s, 1H), 2.55 (s, 3H), 2.23 (s, 3H); MS: 639.0 (M − 1)⁻. |

-continued

| # | building block | structure | analytical data |
|---|---|---|---|
| 12/2 | | 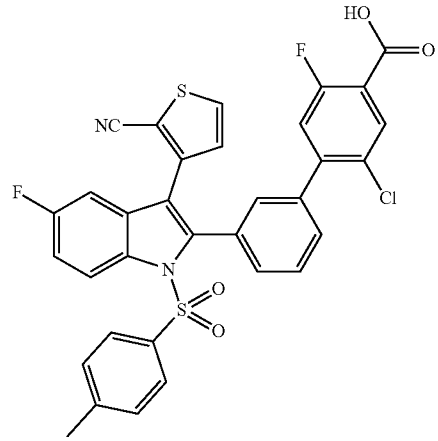 [SMILES: Cc1ccc(S(=O)(=O)n2c(-c3cccc(-c4cc(F)c(C(=O)O)cc4Cl)c3)c(-c3ccsc3C#N)c3cc(F)ccc32)cc1] | $^1$H-NMR (500 MHz, DMSO-d$_6$) δ: 8.42 (dd, J = 9.0, 4.5 Hz, 1H), 7.92 (d, J = 7.5 Hz, 1H), 7.84 (d, J = 5.0 Hz, 1H), 7.53-7.46 (m, 3H), 7.30-7.26 (m, 3H), 7.19-6.97 (m, 6H), 2.28 (s, 3H); MS: 643.0 (M − 1)$^-$. |
| 12/3 | | 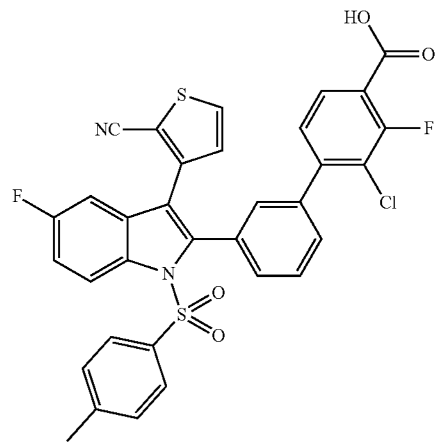 [SMILES: Cc1ccc(S(=O)(=O)n2c(-c3cccc(-c4ccc(C(=O)O)c(F)c4Cl)c3)c(-c3ccsc3C#N)c3cc(F)ccc32)cc1] | $^1$H-NMR (500 MHz, CD$_3$OD) δ: 8.42 (dd, J = 9.3, 4.3 Hz, 1H), 7.85-7.80 (m, 2H), 7.53-7.47 (m, 3H), 7.30-7.25 (m, 3H), 7.17 (d, J = 8.0 Hz, 3H), 7.07 (dd, J = 7.8, 2.8 Hz, 1H), 7.04-6.96 (m, 2H), 2.27 (s, 3H); MS: 642.9 (M − 1)$^-$. |
| 12/4 | | 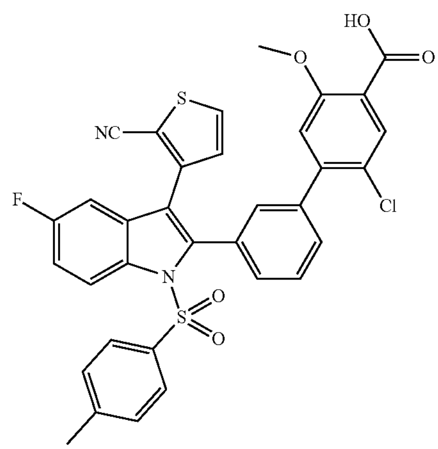 | $^1$H-NMR (500 MHz, DMSO-d$_6$) δ: 8.29 (dd, J = 9.3, 4.3 Hz, 1H), 8.03 (d, J = 5.0 Hz, 1H), 7.59-7.50 (m, 3H), 7.43 (d, J = 7.5 Hz, 1H), 7.40-7.34 (m, 3H), 7.24 (d, J = 8.5 Hz, 2H), 7.17 (dd, J = 8.5, 2.5 Hz, 1H), 7.10 (s, 1H), 7.06 (d, J = 5.5 Hz, 1H), 6.94 (s, 1H), 3.82 (s, 3H), 2.22 (s, 3H); MS: 655.0 (M − 1)$^-$. |

| # | building block | structure | analytical data |
|---|---|---|---|
| 12/5 | | 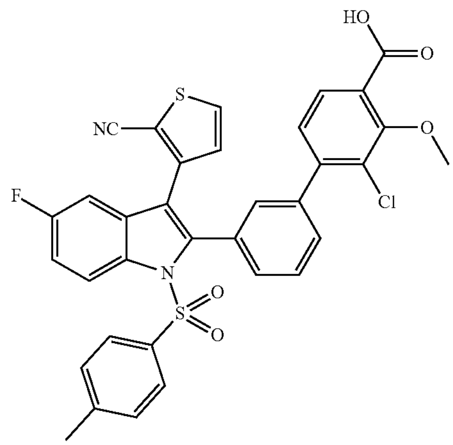 [SMILES: COc1c(C(=O)O)ccc(-c2cccc(-c3c(-c4ccsc4C#N)c4cc(F)ccc4n3S(=O)(=O)c3ccc(C)cc3)c2)c1Cl] | ¹H-NMR (500 MHz, CD₃OD) δ: 8.42 (dd, J = 9.3, 4.3 Hz, 1H), 7.84 (d, J = 5.0 Hz, 1H), 7.69 (d, J = 7.5 Hz, 1H), 7.51-7.45 (m, 3H), 7.29-7.24 (m, 3H), 7.16 (d, J = 8.0 Hz, 2H), 7.09-7.05 (m, 2H), 6.97-6.95 (m, 2H), 3.95 (s, 3H), 2.27 (s, 3H); MS: 655.0 (M − 1)⁻. |
| 12/6 | | 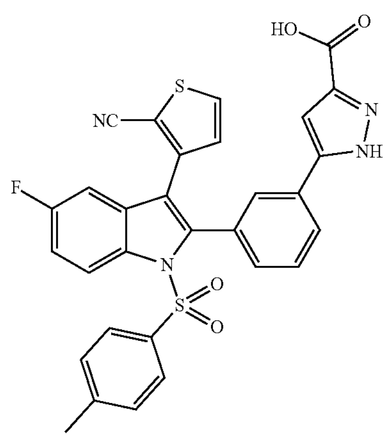 [SMILES: Cc1ccc(S(=O)(=O)n2c(-c3cccc(-c4cc(C(=O)O)n[nH]4)c3)c(-c3ccsc3C#N)c3cc(F)ccc32)cc1] | ¹H-NMR (500 MHz, DMSO-d₆) δ: 8.30 (dd, J = 9.2, 4.4 Hz, 1H), 7.98 (d, J = 5.1 Hz, 1H), 7.88 (d, J = 7.8 Hz, 1H), 7.61 (s, 1H), 7.48-7.33 (m, 4H), 7.29 (d, J = 8.3 Hz, 2H), 7.25-7.13 (m, 2H), 6.99 (d, J = 5.0 Hz, 1H), 6.93 (br s, 1H), 2.28 (s, 3H); MS: 581.0 (M − 1)⁻. |
| 12/7 | | 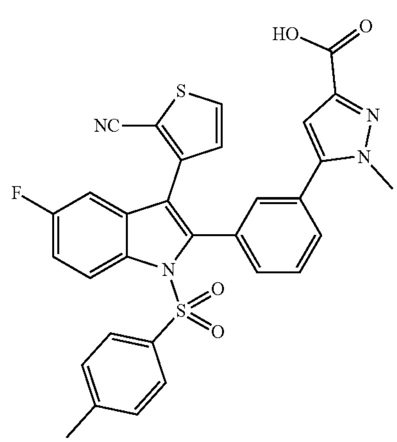 [SMILES: Cc1ccc(S(=O)(=O)n2c(-c3cccc(-c4cc(C(=O)O)nn4C)c3)c(-c3ccsc3C#N)c3cc(F)ccc32)cc1] | ¹H-NMR (500 MHz, DMSO-d₆) δ: 8.30 (dd, J = 9.2, 4.4 Hz, 1H), 7.98 (d, J = 5.1 Hz, 1H), 7.61 (br s, 1H), 7.52 (br s, 1H), 7.48-7.28 (m, 7H), 7.20-7.17 (m, 1H), 7.06 (d, J = 4.5 Hz, 1H), 6.64 (br s, 1H), 3.76 (br s, 3H), 2.28 (s, 3H); MS: 597.2 (M + H)⁺. |

-continued

| # | building block | structure | analytical data |
|---|---|---|---|
| 12/8 | | 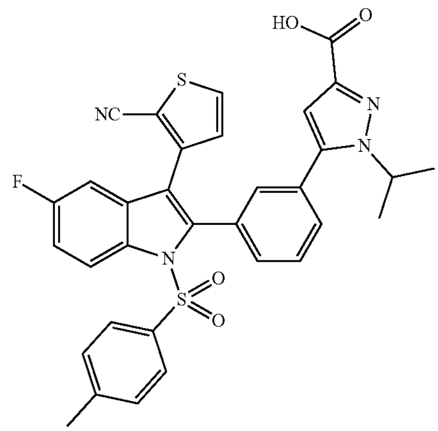 [SMILES: Cc1ccc(S(=O)(=O)n2c(-c3cccc(-c4cc(C(=O)O)nn4C(C)C)c3)c(-c3ccsc3C#N)c3cc(F)ccc32)cc1] | $^1$H-NMR (500 MHz, DMSO-d$_6$) δ: 8.29 (dd, J = 9.2, 4.4 Hz, 1H), 8.07 (d, J = 5.1 Hz, 1H), 7.59-7.49 (m, 2H), 7.45-7.31 (m, 4H), 7.28 (d, J = 8.3 Hz, 2H), 7.20 (dd, J = 8.6, 2.6 Hz, 1H), 7.10-7.00 (m, 2H), 6.61 (s, 1H), 4.25-4.22 (m, 1H), 2.26 (s, 3H), 1.30 (d, J = 6.5 Hz, 6H); MS: 623.0 (M − 1)$^-$. |
| 12/9 | | 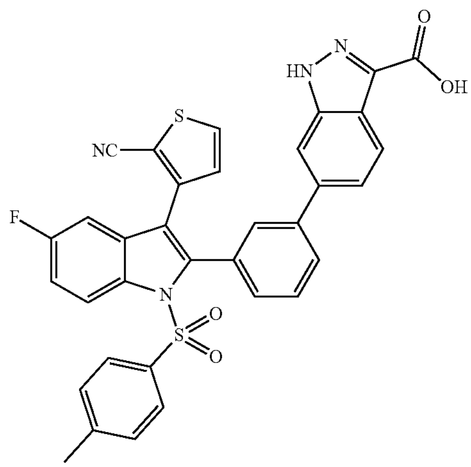 [SMILES: Cc1ccc(S(=O)(=O)n2c(-c3cccc(-c4ccc5c(C(=O)O)n[nH]c5c4)c3)c(-c3ccsc3C#N)c3cc(F)ccc32)cc1] | $^1$H-NMR (500 MHz, DMSO-d$_6$) δ: 8.31 (dd, J = 9.2, 4.4 Hz, 1H), 8.17 (d, J = 8.2 Hz, 1H), 8.04 (d, J = 5.1 Hz, 1H), 7.80 (d, J = 7.6 Hz, 1H), 7.68 (s, 1H), 7.55-7.44 (m, 2H), 7.40-7.36 (m, 4H), 7.28-7.24 (m, 3H), 7.19 (dd, J = 8.5, 2.5 Hz, 1H), 7.09 (d, J = 5.1 Hz, 1H), 2.22 (s, 3H); MS: 631.0 (M − 1)$^-$. |
| 12/10 | P33 | 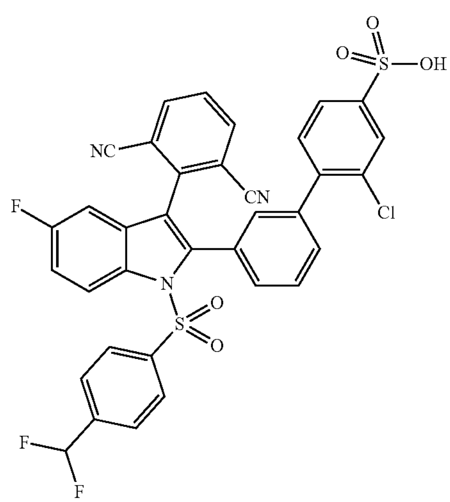 [SMILES: N#Cc1cccc(C#N)c1-c1c(-c2cccc(-c3ccc(S(=O)(=O)O)cc3Cl)c2)n(S(=O)(=O)c2ccc(C(F)F)cc2)c2ccc(F)cc12] | $^1$H-NMR (500 MHz, CD$_3$OD) δ: 8.44 (dd, J = 9.5, 4.5 Hz, 1H), 8.06 (br s, 2H), 7.89 (d, J = 1.5 Hz, 1H), 7.80 (dd, J = 1.3, 7.8 Hz, 1H), 7.72 (t, J = 8.0 Hz, 1H), 7.55-7.48 (m, 7H), 7.36-7.31 (m, 2H), 7.02 (s, 1H), 6.95 (dd, J = 2.3, 8.3 Hz, 1H), 6.68 (t, J = 55.8 Hz, 1H); MS: 715.9 (M − 1)$^-$. |

Example 13

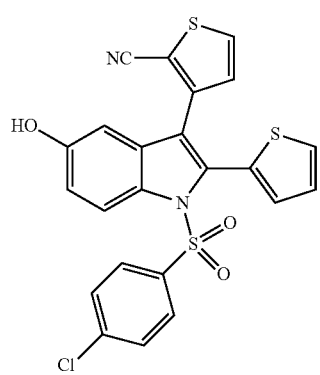

3-(1-((4-Chlorophenyl)sulfonyl)-5-hydroxy-2-(thiophen-2-yl)-1H-indol-3-yl)thiophene-2-carbonitrile (13)

To a solution of compound 1/39 (775 mg, 1.52 mmol) in DCM (10 mL) was added BBr$_3$ (2 mL, 3N in DCM) at 0° C. and the mixture was stirred for 2 h, poured into water (50 mL) and extracted with EA (3×20 mL). The combined organic layer was washed with aq. K$_2$CO$_3$ (30 mL) and brine (2×30 mL), dried over Na$_2$SO$_4$, filtered, concentrated and purified by prep-HPLC to give compound 13 as a yellow solid. $^1$H-NMR (500 MHz, DMSO-d$_6$) δ: 9.63 (s, 1H), 8.05-8.03 (m, 2H), 7.73 (d, J=5.0 Hz, 1H), 7.59 (d, J=8.5 Hz, 2H), 7.47 (d, J=8.5 Hz, 2H), 7.19 (d, J=3.0 Hz, 1H), 7.12-7.10 (m, 1H), 7.01-6.96 (m, 2H), 6.58 (s, 1H); MS: 496.9 (M+1)$^+$.

Example 13/1

The following Example was prepared similar as described for Example 13 using the appropriate starting material.

Example 14

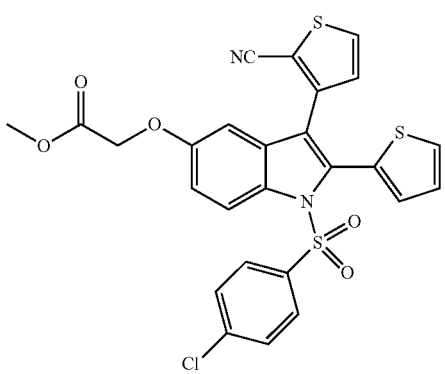

Methyl 2-((1-((4-chlorophenyl)sulfonyl)-3-(2-cyanothiophen-3-yl)-2-(thiophen-2-yl)-1H-indol-5-yl)oxy)acetate (14)

To a solution of compound 13 (120 mg, 0.25 mmol) in DMF (5 mL) was added K$_2$CO$_3$ (69 mg, 0.50 mmol) and methyl 2-bromoacetate (46 mg, 0.30 mmol). The mixture was stirred at rt overnight, diluted with water and extracted with EA (3×20 mL). The combined organic layer was washed with brine (20 mL), dried over Na$_2$SO$_4$, filtered, concentrated and purified by FCC to give compound 14 as a brown solid.

| # | starting material | structure | analytical data |
|---|---|---|---|
| 13/1 | 1/40 | 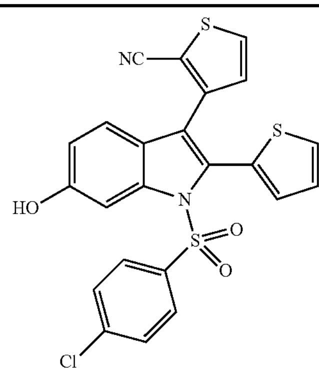 | $^1$H-NMR (500 MHz, DMSO-d$_6$) δ: 9.99 (s, 1H), 8.01 (d, J = 5.0 Hz, 1H), 7.70-7.68 (m, 2H), 7.63 (d, J = 9.0 Hz, 2H), 7.50 (d, J = 8.5 Hz, 2H), 7.16-7.15 (m, 2H), 7.09-7.08 (m, 1H), 7.00 (d, J = 5.0 Hz, 1H), 6.87 (dd, J = 2.0, 8.5 Hz, 1H); MS: 496.7 (M + 1)$^+$. |

Example 15

2-((1-((4-Chlorophenyl)sulfonyl)-3-(2-cyanothiophen-3-yl)-2-(thiophen-2-yl)-1H-indol-5-yl)oxy) acetic Acid (15)

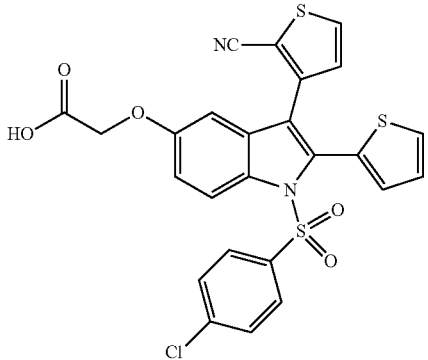

To a solution of compound 14 (74 mg, 0.13 mmol) in MeOH (3 mL) was added LiOH (1 mL, 2N) and the mixture was stirred at rt overnight, evaporated, adjusted to pH<2 with 2N HCl and extracted with EA (3×20 mL). The combined organic layer was washed with brine (20 mL), dried over $Na_2SO_4$, filtered, concentrated and purified by prep-HPLC to give compound 15 as a white solid. $^1$H-NMR (500 MHz, DMSO-$d_6$) δ: 13.02 (br s, 1H), 8.16 (d, J=9.0 Hz, 1H), 8.05 (d, J=5.0 Hz, 1H), 7.74 (d, J=5.0 Hz, 1H), 7.60 (d, J=8.5 Hz, 2H), 7.49 (d, J=8.5 Hz, 2H), 7.21-7.11 (m, 3H), 7.03 (d, J=5.0 Hz, 1H), 6.77 (d, J=2.5 Hz, 1H), 4.67 (s, 2H); MS: 554.6 (M+1)$^+$.

Example 15/1 to 15/6

The following Examples were prepared similar as described for Example 14 (optional) and Example 15 using the appropriate building blocks.

| # | building block(s) | structure | analytical data |
|---|---|---|---|
| 15/1 | | 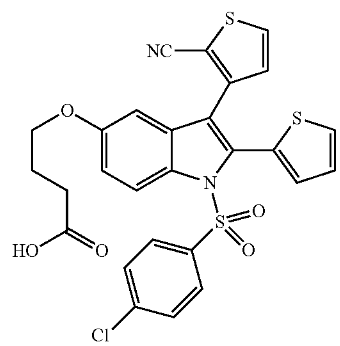 [SMILES: N#Cc1sccc1-c1c(-c2cccs2)n(S(=O)(=O)c2ccc(Cl)cc2)c2ccc(OCCCC(=O)O)cc12] | $^1$H-NMR (500 MHz, DMSO-$d_6$) δ: 12.12 (s, 1H), 8.14 (d, J = 9.0 Hz, 1H), 8.03 (d, J = 5.0 Hz, 1H), 7.73 (d, J = 4.5 Hz, 1H), 7.59 (d, J = 9.0 Hz, 2H), 7.48 (d, J = 9.0 Hz, 2H), 7.20 (d, J = 2.5 Hz, 1H), 7.15-7.11 (m, 2H), 7.02 (d, J = 5.0 Hz, 1H), 6.77 (d, J = 3.0 Hz, 1H), 3.97 (t, J = 6.5 Hz, 2H), 2.37 (t, J = 7.3 Hz, 2H), 1.93 (t, J = 6.8 Hz, 2H); MS: 582.7 (M + 1)$^+$. |
| 15/2 | | 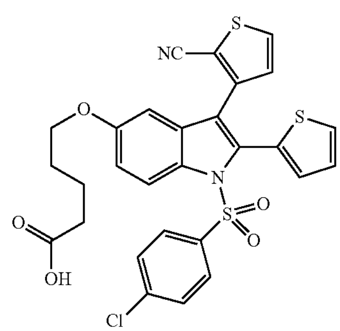 [SMILES: N#Cc1sccc1-c1c(-c2cccs2)n(S(=O)(=O)c2ccc(Cl)cc2)c2ccc(OCCCCC(=O)O)cc12] | $^1$H-NMR (500 MHz, DMSO-$d_6$) δ: 12.03 (br s, 1H), 8.14 (d, J = 9.5 Hz, 1H), 8.04 (d, J = 5.0 Hz, 1H), 7.74 (d, J = 5.0 Hz, 1H), 7.59 (d, J = 8.0 Hz, 2H), 7.48 (d, J = 9.0 Hz, 2H), 7.21-7.20 (m, 1H), 7.15-7.11 (m, 2H), 7.02 (d, J = 4.5 Hz, 1H), 6.77 (d, J = 2.5 Hz, 1H), 3.96 (t, J = 6.0 Hz, 2H), 2.27 (t, J = 7.3 Hz, 2H), 1.75-1.62 (m, 4H); MS: 596.9 (M + 1)$^+$. |

| # | building block(s) | structure | analytical data |
|---|---|---|---|
| 15/3 | (structure) 13/1 | (structure) | $^1$H-NMR (500 MHz, DMSO-d$_6$) δ: 13.20 (s, 1H), 8.03 (d, J = 5.0 Hz, 1H), 7.72 (d, J = 5.0 Hz, 2H), 7.60 (d, J = 8.5 Hz, 2H), 7.54 (d, J = 8.5 Hz, 2H), 7.26 (d, J = 9.0 Hz, 1H), 7.19 (d, J = 3.5 Hz, 1H), 7.12-7.10 (m, 1H), 7.05 (dd, J = 2.0, 9.0 Hz, 1H), 7.01 (d, J = 5.0 Hz, 1H), 4.86 (s, 2H); MS: 554.6 (M + 1)$^+$. |
| 15/4 | (structure) 13/1 | (structure) | $^1$H-NMR (500 MHz, DMSO-d$_6$) δ: 8.02 (d, J = 5.0 Hz, 1H), 7.74 (d, J = 2.0 Hz, 1H), 7.71 (d, J = 5.5 Hz, 1H), 7.61 (d, J = 8.5 Hz, 2H), 7.54 (d, J = 8.0 Hz, 2H), 7.25 (d, J = 9.0 Hz, 1H), 7.18 (d, J = 3.0 Hz, 1H), 7.11-7.00 (m, 3H), 4.13 (t, J = 6.5 Hz, 2H), 2.38 (t, J = 7.3 Hz, 2H), 2.03-1.97 (m, 2H); MS: 583.0 (M + 1)$^+$. |
| 15/5 | (structure) 13/1 | (structure) | $^1$H-NMR (500 MHz, DMSO-d$_6$) δ: 8.03 (d, J = 5.0 Hz, 1H), 7.74 (d, J = 1.5 Hz, 1H), 7.71 (d, J = 5.5 Hz, 1H), 7.61 (d, J = 8.5 Hz, 2H), 7.54 (d, J = 8.5 Hz, 2H), 7.25 (d, J = 9.0 Hz, 1H), 7.18 (d, J = 4.0 Hz, 1H), 7.10 (t, J = 4.3 Hz, 1H), 7.05-7.03 (m, 1H), 7.01 (d, J = 5.0 Hz, 1H), 4.12 (t, J = 6.0 Hz, 2H), 2.31 (t, J = 7.3 Hz, 2H), 1.83-1.78 (m, 2H), 1.73-1.68 (m, 2H); MS: 597.0 (M + 1)$^+$. |
| 15/6 | (structure) 1/47 | (structure) | $^1$H-NMR (500 MHz, DMSO-d$_6$) δ: 12.20 (br s, 1H), 8.26 (d, J = 8.5 Hz, 1H), 7.98 (d, J = 5.0 Hz, 1H), 7.50-7.47 (m, 1H), 7.40-7.32 (m, 4H), 7.22 (d, J = 8.5 Hz, 2H), 7.16 (d, J = 8.5 Hz, 2H), 6.99 (d, J = 9.0 Hz, 2H), 6.93 (d, J = 5.0 Hz, 1H), 3.78 (s, 3H), 2.87 (t, J = 7.5 Hz, 2H), 2.59 (t, J = 7.5 Hz, 2H); MS: 542.9 (M + 1)$^+$. |

Example 16

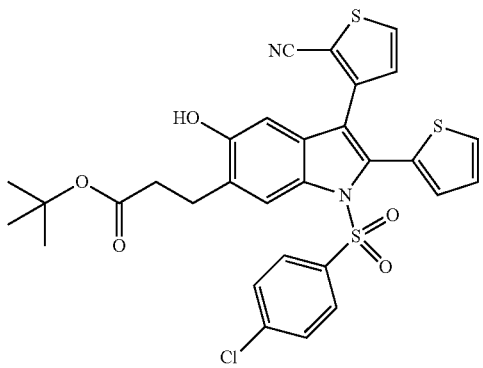

tert-Butyl 3-(1-((4-chlorophenyl)sulfonyl)-3-(2-cyanothiophen-3-yl)-5-hydroxy-2-(thiophen-2-yl)-1H-indol-6-yl)propanoate (16)

To a solution of compound 13 (120 mg, 0.25 mmol) in DMF (3 mL) was added $K_2CO_3$ (69 mg, 0.50 mmol) and methyl 2-bromoacetate (38 mg, 0.30 mmol). The mixture was stirred at rt overnight, diluted with water and extracted with EA (3×20 mL). The combined organic layer was washed with brine (20 mL), dried over $Na_2SO_4$, filtered, concentrated and purified by FCC to give compound 16 as a brown solid; MS: 624.7 $(M+1)^+$.

Example 17

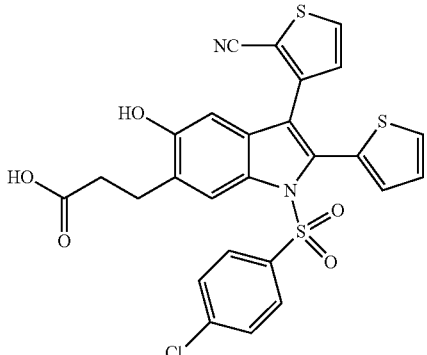

3-(1-((4-Chlorophenyl)sulfonyl)-3-(2-cyanothiophen-3-yl)-5-hydroxy-2-(thiophen-2-yl)-1H-indol-6-yl)propanoic Acid (17)

To a solution of compound 16 (32 mg, 50 μmol) in MeOH (2 mL) was added NaOH (0.5 mL, 2N) and the mixture was stirred at rt overnight, concentrated, adjusted to pH<2 with 2N HCl and extracted with EA (3×20 mL). The combined organic layer was washed with brine (20 mL), dried over $Na_2SO_4$, filtered, concentrated and purified by prep-HPLC to give compound 17 as a white solid. $^1$H-NMR (500 MHz, DMSO-$d_6$) δ: 12.46 (s, 1H), 10.42 (s, 1H), 7.95 (d, J=9.0 Hz, 1H), 7.77 (d, J=5.0 Hz, 1H), 7.70 (d, J=5.0 Hz, 1H), 7.64 (d, J=8.5 Hz, 2H), 7.57 (d, J=9.0 Hz, 2H), 7.18 (d, J=3.0 Hz, 1H), 7.13-7.11 (m, 1H), 7.06 (d, J=5.0 Hz, 1H), 6.89 (d, J=9.0 Hz, 1H), 4.43-4.37 (m, 2H), 2.61 (t, J=7.8 Hz, 2H); MS: 568.7 $(M+1)^+$.

Example 18

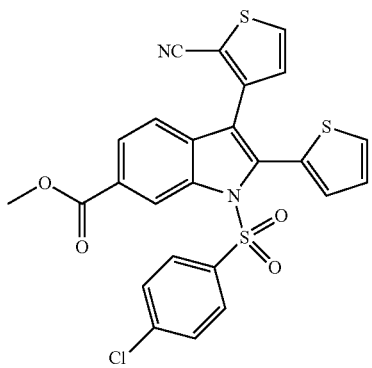

Step 1: Methyl 3-amino-4-(thiophen-2-ylethynyl)benzoate (18a)

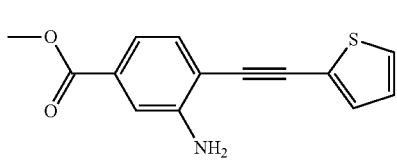

Methyl 3-amino-4-iodo-benzoate (1.0 g, 3.6 mmol) was dissolved in degassed THF (10 mL) and the mixture was degassed by bubbling a gentle stream of $N_2$ through the solution. After ~5 min DIPEA (5.0 mL, 29 mmol) was added and the bubbling was continued for a few minutes before addition of 2-ethynylthiophene (0.41 mL, 4.3 mmol). Then CuI (28 mg, 0.15 mmol) was added directly followed by $PdCl_2(PPh_3)_2$ (49 mg, 70 μmol). The mixture was stirred at rt for 2.5 h, filtered through Celite and washed with THF. EA (200 mL) was added and the mixture was washed with water (50 mL) and brine (50 mL). The organic layer was dried over $Na_2SO_4$, filtered, concentrated and purified by FCC to give compound 18a. $^1$H-NMR (400 MHz, CDCl$_3$): 3.90 (s, 3H), 4.36 (br s, 2H), 7.02-7.04 (m, 1H), 7.30-7.34 (m, 2H), 7.35-7.41 (m, 3H).

Step 2: Methyl 4-(thiophen-2-ylethynyl)-3-(2,2,2-trifluoroacetamido)benzoate (18b)

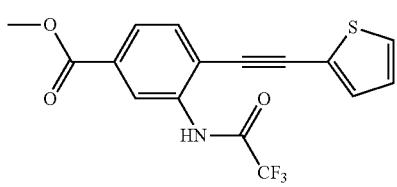

Compound 18a (450 mg, 1.68 mmol) was dissolved in dry THF (1 mL) and the mixture was cooled to 0° C. Then 2,2,2-trifluoroacetic anhydride (0.47 mL, 3.4 mmol) was added dropwise and the mixture was stirred for 15 min, diluted with EA (100 mL) and washed with NaHCO$_3$-water (1:1, 50 mL) and brine (50 mL). The organic layer was dried over Na$_2$SO$_4$, filtered, concentrated and purified by FCC to give the compound 18b as a yellow solid. $^1$H-NMR (400 MHz, CDCl$_3$): 3.95 (s, 3H), 7.08-7.10 (m, 1H), 7.37-7.38 (m, 1H), 7.43-7.44 (m, 1H), 7.60-7.63 (m, 1H), 7.90-7.92 (m, 1H), 8.75 (br s, 1H), 8.97 (d, 1H).

Step 3: Methyl 3-(2-cyanothiophen-3-yl)-2-(thiophen-2-yl)-1H-indole-6-carboxylate (18c)

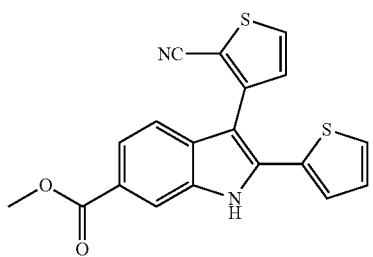

18c

A dried microwave-tube was charged with compound 18b (187 mg, 0.53 mmol), Cs$_2$CO$_3$ (259 mg, 0.79 mmol), Pd(PPh$_3$)$_4$ (31 mg, 0.03 mmol) and 3-bromothiophene-2-carbonitrile (149 mg, 0.79 mmol). Degassed CH$_3$CN (2.5 mL) was added and the tube was purged with N$_2$. The mixture was stirred at 100° C. for 1 h, cooled, diluted with EA (80 mL) and washed with NaHCO$_3$:water (1:1, 40 mL), water (20 mL) and brine (15 mL). The organic layer was dried (Na$_2$SO$_4$), filtered and concentrated to give compound 18c as a yellow solid. $^1$H-NMR (400 MHz, DMSO-d$_6$): 3.88 (s, 3H), 7.17-7.19 (m, 1H), 7.33-7.46 (m, 3H), 7.64-7.71 (m, 2H), 8.10 (s, 1H), 8.19-8.21 (m, 1H), 12.32 (s, 1H).

Step 4: Methyl 1-((4-chlorophenyl)sulfonyl)-3-(2-cyanothiophen-3-yl)-2-(thiophen-2-yl)-1H-indole-6-carboxylate (18)

Compound 18c (180 mg, 0.49 mmol) was dissolved in THF (15 mL) and NaH (3.9 mmol dispersed in mineral oil) was added followed by 4-chlorobenzenesulfonyl chloride (188 mg, 0.89 mmol). The mixture was stirred at rt for 1 h, quenched by careful addition of water, diluted with EA (250 mL) and washed with water (100 mL) and brine (100 mL). The organic layer was dried over Na$_2$SO$_4$, filtered, concentrated and purified by FCC and then prep-HPLC (55-60% acetonitrile in 15 mM NH$_4$HCO$_3$ buffer, pH 10) to give compound 18 as a white solid.

Example 19

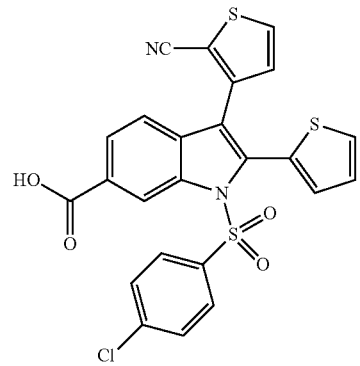

19

1-((4-Chlorophenyl)sulfonyl)-3-(2-cyanothiophen-3-yl)-2-(thiophen-2-yl)-1H-indole-6-carboxylic Acid (19)

Compound 18 (77 mg, 0.14 mmol) was dissolved in THF (4 mL) and cooled to 0° C. In a separate 4 mL vial LiOH (48 mg, 2.0 mmol) was dissolved in water (4 mL) and cooled to 0° C. The base solution was added dropwise to the solution of compound 18 and the resulting mixture was stirred vigorously overnight (the reaction slowly adapted rt). The reaction was re-cooled to 0° C., quenched with 2N HCl (1.4 mL) and extracted with EA (3×20 mL). The combined organic layer was dried over MgSO$_4$, filtered, concentrated and purified by prep-HPLC (Xbridge, 30-60% acetonitrile in 0.1% TFA buffer) to give compound 19 as a white solid. $^1$H-NMR (400 MHz, DMSO-d$_6$): 7.07 (d, 1H), 7.12-7.15 (dd, 1H), 7.24-7.25 (dd, 1H), 7.40-7.50 (m, 3H), 7.55-7.63 (m, 2H), 7.76-7.77 (dd, 1H), 7.97-8.00 (dd, 1H), 8.06 (d, 1H), 8.89 (m, 1H), 13.29 (br s, 1H); MS: 542 (M+NH$_3$+1)$^+$.

Example 20

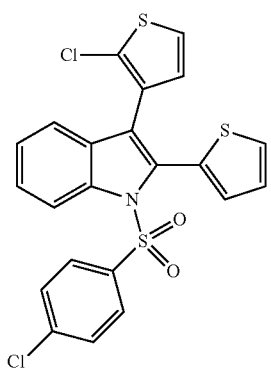

20

363

Step 1: 2-(Thiophen-2-ylethynyl)aniline (20a)

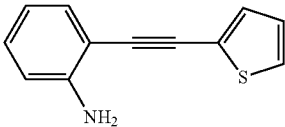

To a mixture of 2-iodoaniline (40.0 g, 183 mmol), CuI (700 mg, 3.70 mmol), Pd(PPh$_3$)$_2$Cl$_2$ (1.30 g, 1.83 mmol) and TEA (120 mL) in ACN (1 L) was added 2-ethynylthiophene (24.0 g, 219 mmol) under N$_2$ via a syringe. The mixture was stirred at 50° C. overnight, cooled, filtered, concentrated and purified by FCC (PE:EA=50:1) to afford compound 20a as a yellow solid.

Step 2: 4-Chloro-N-(2-(thiophen-2-ylethynyl)phenyl)benzenesulfonamide (20b)

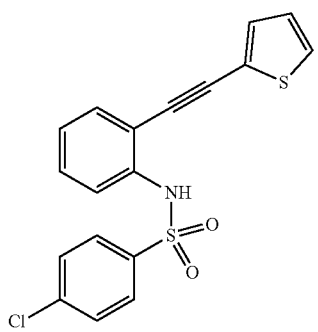

To a solution of compound 20a (10.0 g, 50.3 mmol), 4-chlorobenzenesulfonyl chloride (13.1 g, 62.3 mmol) and pyridine (4.17 g, 52.8 mmol) in DCM (150 mL) was added DMAP (306 mg, 2.5 mmol) at rt. The mixture was heated to reflux overnight, cooled, washed with 2N HCl and extracted with DCM. The organic layer was dried over Na$_2$SO$_4$, filtered, concentrated and then the residue was washed with PE to give compound 20b as a yellow solid.

364

Step 3: 1-((4-Chlorophenyl)sulfonyl)-3-(4,4,5,5-tetramethyl-1,3,2-dioxaborolan-2-yl)-2-(thiophen-2-yl)-1H-indole (20c)

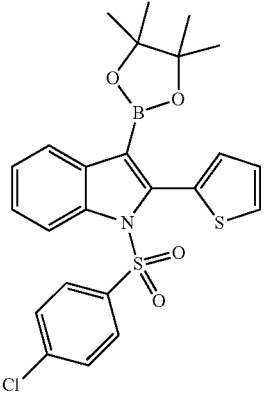

A mixture of compound 20b (11.0 g, 29.4 mmol), Cs$_2$CO$_3$ (19 g, 59 mmol), AsPh$_3$ (1.36 g, 4.40 mmol), Pd$_2$(dba)$_3$ (1.34 g, 1.48 mmol) and B$_2$Pin$_2$ (15 g, 59 mmol) in dioxane (175 mL) was stirred under N$_2$ at 60° C. for 2 h, cooled, filtered, concentrated and purified by FCC (PE:EA=20:1 to 5:1) to afford compound 20c as a white solid.

Step 4: 1-((4-Chlorophenyl)sulfonyl)-3-(2-chlorothiophen-3-yl)-2-(thiophen-2-yl)-1H-indole (20)

A solution of compound 20c (200 mg, 0.40 mmol), 3-bromo-2-chlorothiophene (79 mg, 0.40 mmol), Pd(PPh$_3$)$_4$ (46 mg, 40 µmol) and K$_3$PO$_4$ (404 mg, 1.6 mmol) in dioxane/H$_2$O (10:1, 22 mL) was stirred under N$_2$ at 100° C. overnight, cooled, filtered and washed with DCM. Then the filtrate was concentrated and purified by prep-HPLC to afford compound 20 as a white solid. $^1$H-NMR (CDCl$_3$, 300 MHz) δ: 8.35 (d, J=6.6 Hz, 1H), 7.40-7.25 (m, 8H), 7.13 (d, J=0.6 Hz, 1H), 7.05-7.03 (m, 2H), 6.61 (d, J=4.2 Hz, 1H); MS: 589.0 (M+1)$^+$.

Example 20/1 to 20/25

The following Examples were prepared similar as described for Example 20 using the appropriate building blocks.

| # | building block(s) | structure | analytical data |
|---|---|---|---|
| 20/1 | ![bb] | ![str] | $^1$H-NMR (CDCl$_3$, 300 MHz) δ: 1.02 (s, 9H), 6.67 (s, 1H), 6.98-7.01 (m, 1H), 7.08 (s, 1H), 7.19 (s, 1H), 7.28-7.30 (m, 3H), 7.35-7.43 (m, 3H), 7.47-7.50 (m, 2H), 8.32 (s, 1H). |

| # | building block(s) | structure | analytical data |
|---|---|---|---|
| 20/2 | 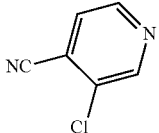 | 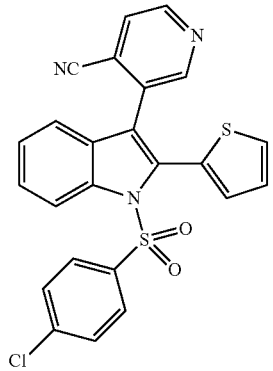 [SMILES: N#Cc1ccncc1-c1c(-c2cccs2)n(S(=O)(=O)c2ccc(Cl)cc2)c2ccccc12] | ¹H-NMR (CDCl₃, 300 MHz) δ: 7.04-7.01 (m, 1H), 7.42-7.19 (m, 8H), 7.48-7.57 (m, 2H), 8.41 (d, J = 8.4 Hz, 1H), 8.55 (s, 1H), 8.70 (d, J = 4.5 Hz, 1H); MS: 476.0 (M + 1)⁺. |
| 20/3 | 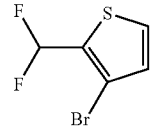 | 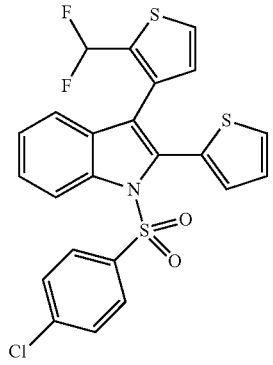 [SMILES: O=S(=O)(c1ccc(Cl)cc1)n1c(-c2cccs2)c(-c2ccsc2C(F)F)c2ccccc21] | ¹H-NMR (CDCl₃, 300 MHz) δ: 6.29 (t, J = 54.9 Hz, 1H), 6.72-6.73 (m, 1H), 7.03 (dd, J = 3.8, 5.0 Hz, 1H), 7.10 (d, J = 2.7 Hz, 1H), 7.25-7.46 (m, 9H), 8.37 (d, J = 8.4 Hz, 1H); MS: 505.9 (M + 1)⁺. |
| 20/4 | 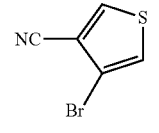 | 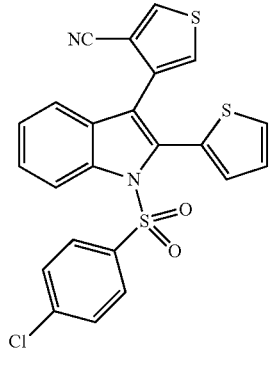 [SMILES: N#Cc1cscc1-c1c(-c2cccs2)n(S(=O)(=O)c2ccc(Cl)cc2)c2ccccc12] | ¹H-NMR (CDCl₃, 300 MHz) δ: 7.04 (dd, J = 3.8, 5.3 Hz, 1H), 7.15 (d, J = 3.3 Hz, 1H), 7.20 (dd, J = 0.9, 3.6 Hz, 1H), 7.26-7.47 (m, 8H), 7.94 (d, J = 3.3 Hz, 1H), 8.36 (d, J = 8.4 Hz, 1H); MS: 498.0 (M + 18)⁺. |
| 20/5 | 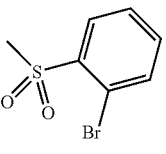 | 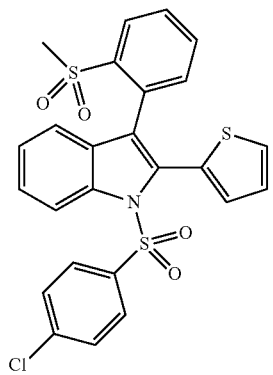 [SMILES: CS(=O)(=O)c1ccccc1-c1c(-c2cccs2)n(S(=O)(=O)c2ccc(Cl)cc2)c2ccccc12] | ¹H-NMR (CDCl₃, 300 MHz) δ: 2.54 (s, 3H), 6.97 (dd, J = 3.8, 8.6 Hz, 1H), 7.02 (s, 1H), 7.07-7.10 (m, 1H), 7.23-7.57 (m, 10H), 8.14-8.17 (m, 1H), 8.32 (d, J = 8.4 Hz, 1H); MS: 545.0 (M + 18)⁺. |

| # | building block(s) | structure | analytical data |
|---|---|---|---|
| 20/6 | 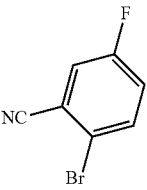 | 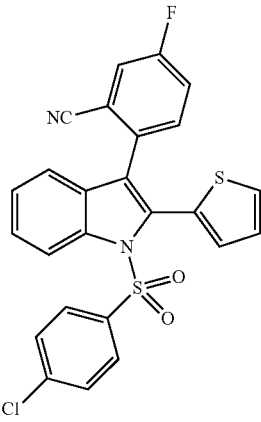 [SMILES: N#Cc1cc(F)ccc1-c1c(-c2cccs2)n(S(=O)(=O)c2ccc(Cl)cc2)c2ccccc12] | ¹H-NMR (CDCl₃, 300 MHz) δ: 6.99-7.02 (m, 1H), 7.16-7.42 (m, 11H), 7.47 (t, J = 8.4 Hz, 1H), 8.36 (d, J = 8.4 Hz, 1H); MS: 493.0 (M + 1)⁺. |
| 20/7 | 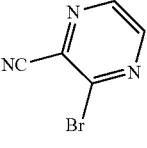 | 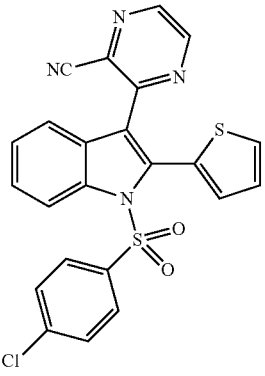 [SMILES: N#Cc1nccnc1-c1c(-c2cccs2)n(S(=O)(=O)c2ccc(Cl)cc2)c2ccccc12] | ¹H-NMR (CDCl₃, 300 MHz) δ: 7.09 (dd, J = 3.9, 5.1 Hz, 1H), 7.26-7.28 (m, 2H), 7.36-7.41 (m, 6H), 7.48-7.52 (m, 1H), 8.43 (d, J = 8.4 Hz, 1H), 8.60 (d, J = 2.4 Hz, 1H), 8.79 (d, J = 2.4 Hz, 1H); MS: 477.0 (M + 1)⁺. |
| 20/8 | 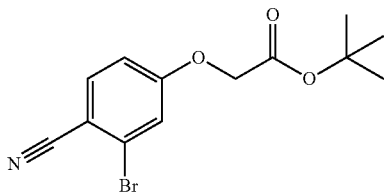 P7 | 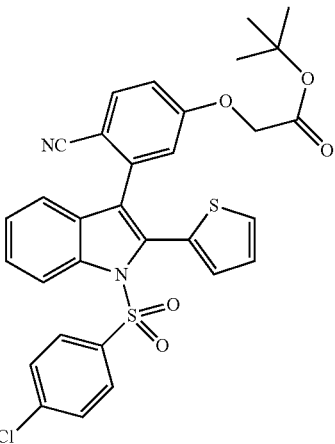 | |

| # | building block(s) | structure | analytical data |
|---|---|---|---|
| 20/9 | 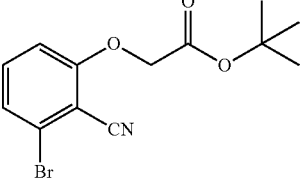 P7/1 | 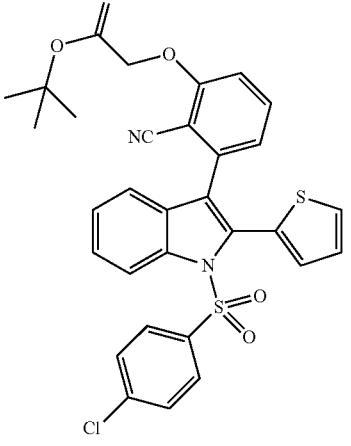 | |
| 20/10 | 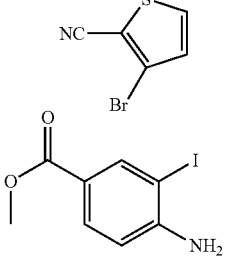 | 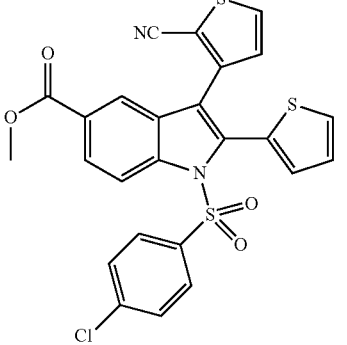 | |
| 20/11 | 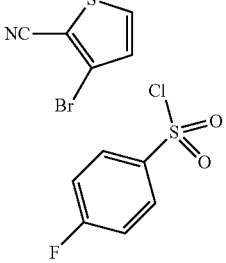 | 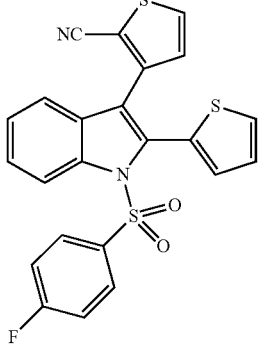 | ¹H-NMR (CDCl₃, 300 MHz) δ: 6.80 (d, J = 5.1 Hz, 1H), 6.98-7.08 (m, 3H), 7.20-7.22 (m, 1H), 7.33-7.53 (m, 7H), 8.39 (d, J = 8.4 Hz, 1H); MS 482.0 (M + 18)⁺. |
| 20/12 | 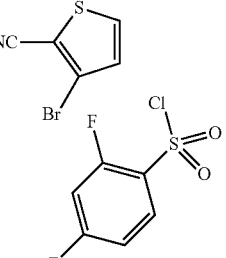 | 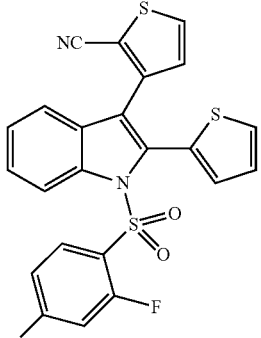 | ¹H-NMR (CDCl₃, 300 MHz) δ: 6.74-6.84 (m, 2H), 6.89 (d, J = 5.1 Hz, 1H), 7.00-7.03 (m, 1H), 7.20 (d, J = 2.7 Hz, 1H), 7.32-7.51 (m, 6H), 8.30 (d, J = 9.0 Hz, 1H); MS: 483.0 (M + 1)⁺. |

-continued
| # | building block(s) | structure | analytical data |
|---|---|---|---|
| 20/13 | 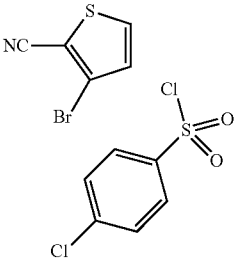 | 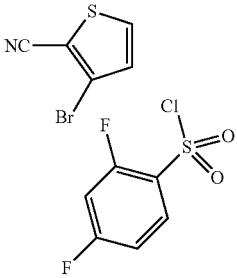 | ¹H NMR (CDCl₃, 300 MHz) δ: 6.81 (d, J = 4.8 Hz, 1H), 7.06 (dd, J = 3.2, 5.0 Hz, 1H), 7.21 (d, J = 2.7 Hz, 1H), 7.29-7.49 (m, 9H), 8.38 (d, J = 8.7 Hz, 1H). |
| 20/14 | 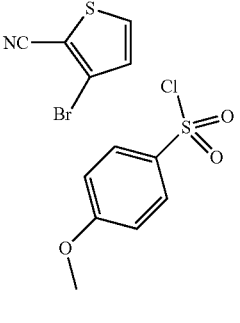 | 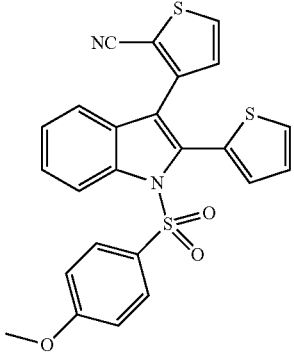 [SMILES: COc1ccc(S(=O)(=O)n2c(-c3cccs3)c(-c3ccsc3C#N)c3ccccc32)cc1] | ¹H-NMR (CDCl₃, 300 MHz) δ: 3.79 (s, 3H), 6.77-6.79 (m, 3H), 7.05 (dd, J = 3.8, 5.0 Hz, 1H), 7.19 (dd, J = 0.9, 3.6 Hz, 1H), 7.31-7.49 (m, 7H), 8.41 (d, J = 8.4 Hz, 1H); MS: 477.0 (M + 1)⁺. |
| 20/15 | 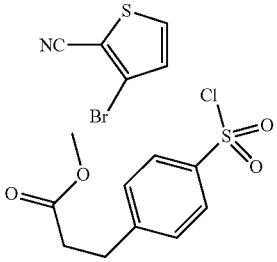 | 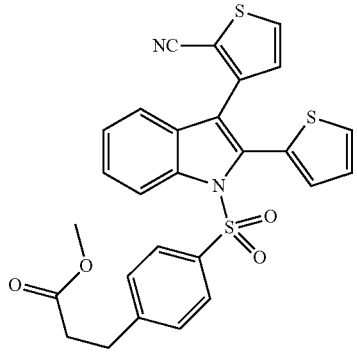 [SMILES: COC(=O)CCc1ccc(S(=O)(=O)n2c(-c3cccs3)c(-c3ccsc3C#N)c3ccccc32)cc1] | ¹H-NMR (CDCl₃, 300 MHz) δ: 2.55-2.60 (m, 2H), 2.93 (t, J = 7.5 Hz, 2H), 3.63 (s, 3H), 6.79 (d, J = 5.1 Hz, 1H), 7.04 (dd, J = 3.9, 5.1 Hz, 1H), 7.15-7.18 (m, 3H), 7.33-7.50 (m, 7H), 8.40 (d, J = 8.4 Hz, 1H); MS: 550.0 (M + 18)⁺. |
| 20/16 | 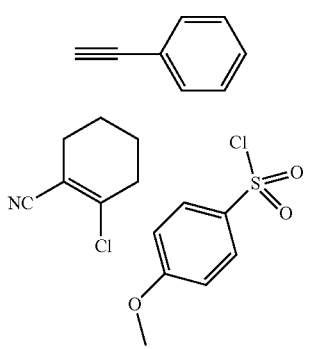 | 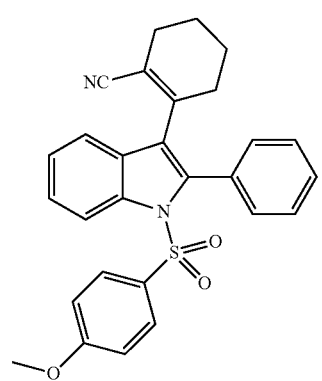 [SMILES: COc1ccc(S(=O)(=O)n2c(-c3ccccc3)c(C3=C(C#N)CCCC3)c3ccccc32)cc1] | ¹H-NMR (DMSO-d₆, 400 MHz) δ: 8.17 (d, J = 8.4 Hz, 1H), 7.48-7.33 (m, 10H), 6.98-6.94 (m, 2H), 3.75 (s, 3H), 2.29-2.08 (m, 3H), 1.77-1.36 (m, 5H); MS: 486.2 (M + 18)⁺. |

-continued

| # | building block(s) | structure | analytical data |
|---|---|---|---|
| 20/17 | | 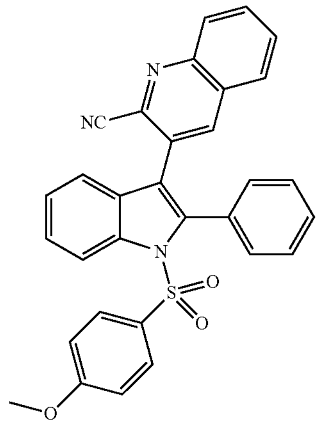 [SMILES: COc1ccc(S(=O)(=O)n2c(-c3ccccc3)c(-c3cc4ccccc4nc3C#N)c3ccccc32)cc1] | $^1$H-NMR (DMSO-d$_6$, 400 MHz) δ: 8.61 (s, 1H), 8.30 (d, J = 8.4 Hz, 1H), 8.12 (d, J = 8.4 Hz, 1H), 8.04 (d, J = 8.0 Hz, 1H), 7.96-7.92 (m, 1H), 7.83-7.79 (m, 1H), 7.55-7.48 (m, 3H), 7.37-7.29 (m, 7H), 7.05-7.03 (m, 2H), 3.79 (s, 3H); MS: 516.1 (M + 1)$^+$. |
| 20/18 | | 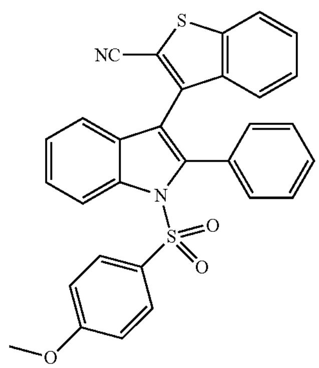 [SMILES: COc1ccc(S(=O)(=O)n2c(-c3ccccc3)c(-c3c(C#N)sc4ccccc34)c3ccccc32)cc1] | $^1$H-NMR (DMSO-d$_6$, 300 MHz) δ: 8.31 (d, J = 8.4 Hz, 1H), 8.16 (d, J = 8.4 Hz, 1H), 7.61-7.50 (m, 2H), 7.43-7.01 (m, 13H), 3.79 (s, 3H); MS 538.1 (M + 18)$^+$. |
| 20/19 | | 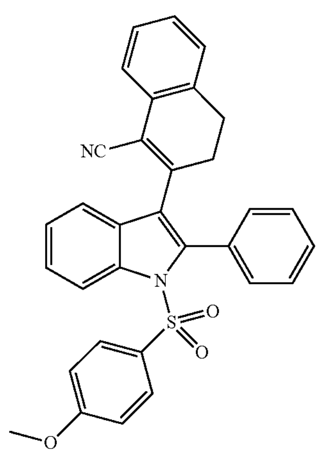 [SMILES: COc1ccc(S(=O)(=O)n2c(-c3ccccc3)c(C3=C(C#N)c4ccccc4CC3)c3ccccc32)cc1] | $^1$H-NMR (DMSO-d$_6$, 400 MHz) δ: 8.23 (d, J = 8.4 Hz, 1H), 7.51-7.21 (m, 14H), 7.00 (d, J = 8.8 Hz, 2H), 3.77 (s, 3H), 2.86-2.80 (m, 1H), 2.60-2.49 (m, 2H), 2.15-2.09 (m, 1H); MS: 534.1 (M + 18)$^+$. |

-continued
| # | building block(s) | structure | analytical data |
|---|---|---|---|
| 20/20 | 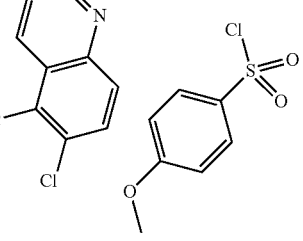 | 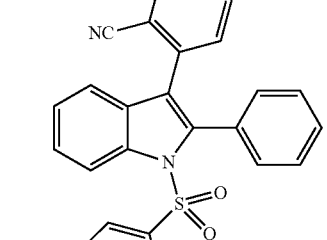 | $^1$H-NMR (DMSO-d$_6$, 400 MHz) δ: 9.07 (dd, J = 1.2, 4.0 Hz, 1H), 8.44 (d, J = 8.0 Hz, 1H), 8.29 (d, J = 8.4 Hz, 1H), 8.24 (d, J = 8.8 Hz, 1H), 7.79 (dd, J = 4.2, 8.6 Hz, 1H), 7.60 (d, J = 8.8 Hz, 1H), 7.53-7.45 (m, 3H), 7.36-7.27 (m, 7H), 7.03 (d, J = 9.2 Hz, 2H), 3.79 (s, 3H); MS: 516.1 (M + 1)$^+$. |
| 20/21 | 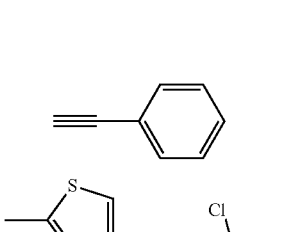 | 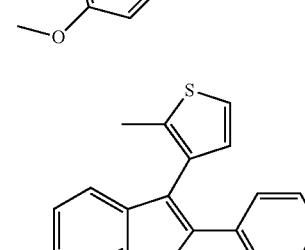 | $^1$H-NMR (DMSO-d$_6$, 400 MHz) δ: 8.21 (d, J = 8.4 Hz, 1H), 7.47-7.25 (m, 10H), 7.14 (d, J = 8.0 Hz, 1H), 7.01-6.97 (m, 2H), 6.65 (d, J = 4.8 Hz, 1H), 3.76 (s, 3H), 1.85 (s, 3H); MS: 460.1 (M + 1)$^+$. |
| 20/22 | 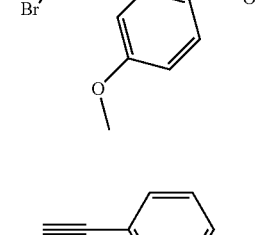 | 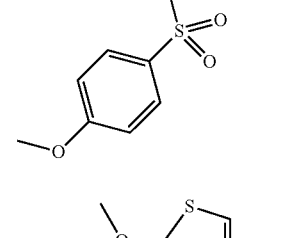 | $^1$H-NMR (DMSO-d$_6$, 400 MHz) δ: 8.20 (d, J = 8.4 Hz, 1H), 7.44-7.29 (m, 10H), 7.02-6.98 (m, 2H), 6.75 (d, J = 6.0 Hz, 1H), 6.41 (d, J = 5.6 Hz, 1H), 3.77 (s, 3H), 3.54 (s, 3H); MS: 476.1 (M + 1)$^+$. |
| 20/23 | 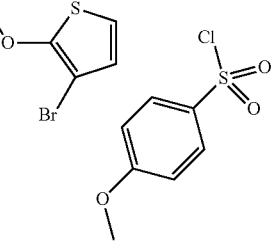 | 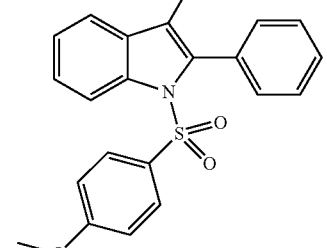 | $^1$H-NMR (DMSO-d$_6$, 400 MHz) δ: 8.26 (d, J = 8.0 Hz, 1H), 7.52-7.28 (m, 10H), 7.01 (d, J = 9.2 Hz, 2H), 6.77 (s, 1H), 3.77 (s, 3H), 2.43 (s, 3H); MS: 502.1 (M + 18)$^+$. |

-continued

| # | building block(s) | structure | analytical data |
|---|---|---|---|
| 20/24 | | 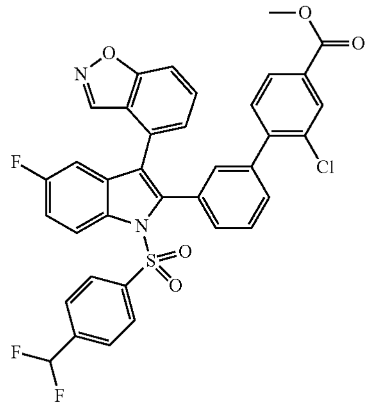 [SMILES: COC(=O)c1ccc(-c2cccc(-c3c(-c4cccc5oncc45)c4cc(F)ccc4n3S(=O)(=O)c3ccc(C(F)F)cc3)c2)c(Cl)c1] | |
| 20/25 | | 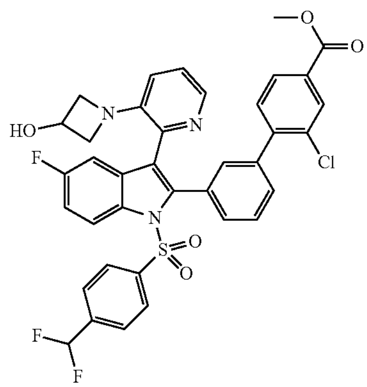 [SMILES: COC(=O)c1ccc(-c2cccc(-c3c(-c4ncccc4N4CC(O)C4)c4cc(F)ccc4n3S(=O)(=O)c3ccc(C(F)F)cc3)c2)c(Cl)c1] | |

Example 21

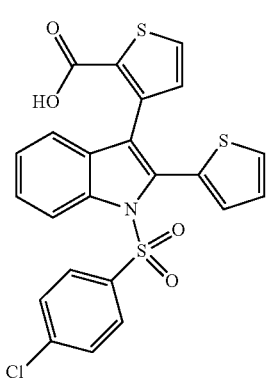

3-(1-((4-Chlorophenyl)sulfonyl)-2-(thiophen-2-yl)-1H-indol-3-yl)thiophene-2-carboxylic Acid (21)

A solution of compound 20/1 (95 mg, 0.24 mmol) and TFA (0.5 mL) in DCM (2.5 mL) was stirred at rt for 4 h, concentrated and then the residue was triturated with PE including a little amount of EA to give compound 21 as a white solid. $^1$H-NMR (CDCl$_3$, 400 MHz) δ: 6.79 (d, J=3.9 Hz, 1H), 7.02-7.04 (m, 1H), 7.11 (dd, J=1.1, 2.6 Hz, 1H), 7.21 (d, J=5.7 Hz, 1H), 7.26-7.40 (m, 6H), 7.45-7.49 (m, 1H), 7.55 (d, J=3.9 Hz, 1H), 8.35 (d, J=6.3 Hz, 1H); MS: 497.9 (M−1)$^-$.

Example 21/1 to 21/3

The following Examples were prepared similar as described for Example 20 using the appropriate starting material.

| # | starting material | structure | analytical data |
|---|---|---|---|
| 21/1 | (20/8) | 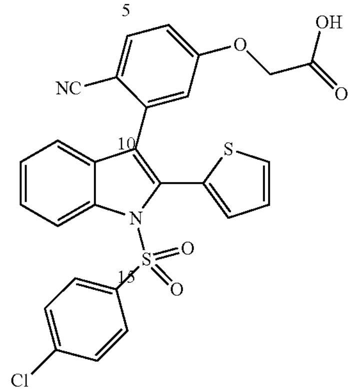 | ¹H-NMR (CDCl₃, 400 MHz) δ: 8.34 (d, J = 6.3 Hz, 1H), 7.58-7.13 (m, 10H), 6.97-6.87 (m, 2H), 6.66 (s, 1H), 4.49 (br s, 2H); MS: 547.0 (M − 1)⁻. |
| 21/2 | (20/9) | 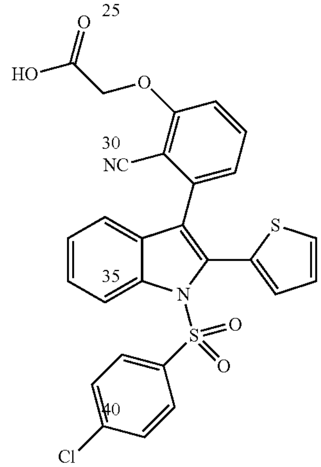 | ¹H-NMR (DMSO-d₆, 300 MHz) δ: 8.21 (d, J = 8.1 Hz, 1H), 7.65 (d, J = 4.8 Hz, 1H), 7.58-7.48 (m, 6H), 7.37-7.32 (m, 1H), 7.16-7.04 (m, 4H), 6.87 (d, J = 7.8 Hz, 1H), 4.83 (s, 2H); MS: 546.9 (M − 1)⁻. |
| 21/3 | (6/3) | 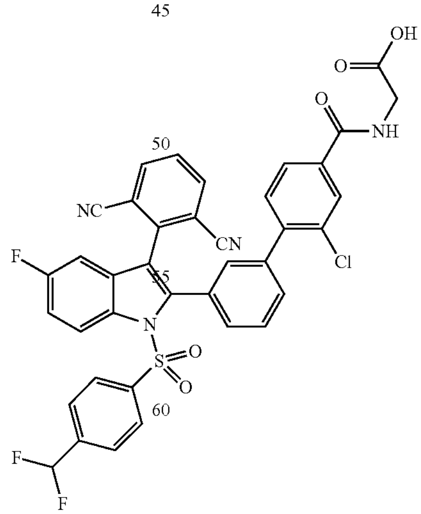 | ¹H-NMR (CD₃OD, 400 MHz) δ: 8.43 (dd, J = 9.4, 4.2 Hz, 1H), 8.05 (d, J = 8.0 Hz, 2H), 7.98 (d, J = 2.0 Hz, 1H), 7.86 (dd, J = 8.0, 2.0 Hz, 1H), 7.71 (t, J = 8.0 Hz, 1H), 7.54-7.30 (m, 9H), 7.09 (s, 1H), 6.94 (dd, J = 8.4, 2.8 Hz, 1H), 6.67 (t, J = 55.6 Hz, 1H), 4.12 (s, 2H); MS: 737.0 (M − 1)⁻. |

Example 22

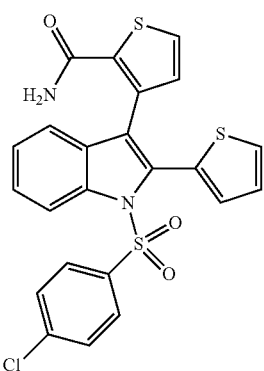

3-(1-((4-Chlorophenyl)sulfonyl)-2-(thiophen-2-yl)-1H-indol-3-yl)thiophene-2-carboxamide (22)

To a solution of compound 21 (90 mg, 0.18 mmol) and HATU (137 mg, 0.36 mmol) in DMF (5 mL) was added DIEA (116 mg, 0.90 mmol) at rt. The solution was stirred for 20 min, then NH$_4$Cl (19 mg, 0.36 mmol) was added and the mixture was stirred at rt for 2 h, cooled, diluted with water and stirred for 10 min. The mixture was filtered to give compound 22 as a yellow solid. $^1$H-NMR (CDCl$_3$, 300 MHz) δ: 5.16 (br s, 2H), 6.68 (d, J=5.1 Hz, 1H), 7.03 (dd, J=3.6, 5.1 Hz, 1H), 7.14 (dd, J=1.2, 3.6 Hz, 1H), 7.23-7.49 (m, 9H), 8.39 (d, J=8.4 Hz, 1H); MS: 499.0 (M+1)$^+$.

Example 23

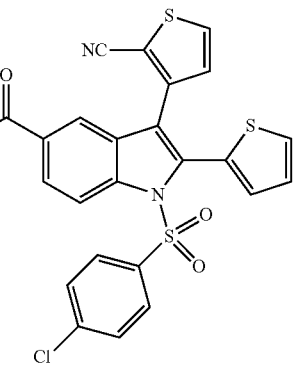

1-((4-Chlorophenyl) sulfonyl)-3-(2-cyanothiophen-3-yl)-2-(thiophen-2-yl)-1H-indole-5-carboxylic Acid (23)

A solution of compound 20/10 (49 mg, 90 μmol) and LiOH·H$_2$O (12 mg, 0.27 mmol) in THF/H$_2$O (3:1, 8 mL) was stirred at rt overnight, concentrated, adjusted to pH to 5-6 with 1N HCl and purified by prep-HPLC to give compound 23 as a yellow solid. $^1$H-NMR (CDCl$_3$, 300 MHz) δ: 8.48 (d, J=8.7 Hz, 1H), 8.22-8.18 (m, 2H), 7.53 (d, J=5.1 Hz, 1H), 7.44-7.26 (m, 6H), 7.10-7.07 (m, 1H), 6.88 (d, J=4.8 Hz, 1H); MS: 522.8 (M−1)$^−$.

Example 23/1 to 23/3

The following Example was prepared similar as described for Example 23 using the appropriate starting material.

| # | starting material | structure | analytical data |
|---|---|---|---|
| 23/1 | 20/15 | 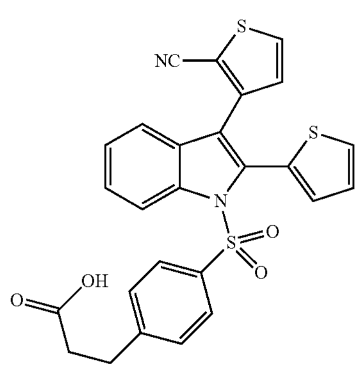 [SMILES: N#Cc1sccc1-c1c(-c2cccs2)n(S(=O)(=O)c2ccc(CCC(=O)O)cc2)c2ccccc12] | $^1$H-NMR (CDCl$_3$, 400 MHz) δ: 8.37 (d, J = 8.7 Hz, 1H), 7.77 (d, J = 5.1, 1H), 7.52-7.45 (m, 2H), 7.39-7.25 (m, 6H), 7.15 (d, J = 3.6 Hz, 1H), 7.07-7.04 (m, 1H), 6.91 (d, J = 5.4 Hz, 1H), 2.92-2.86 (m, 2H), 2.56 (t, J = 7.4 Hz, 2H); MS: 519.0 (M + 1)$^+$, 536.1 (M + 18)$^+$. |

-continued

| # | starting material | structure | analytical data |
|---|---|---|---|
| 23/2 | | 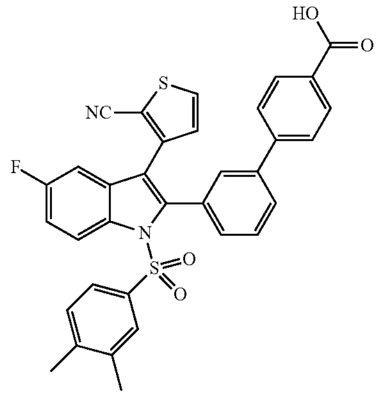 [SMILES: Cc1ccc(S(=O)(=O)n2c(-c3cccc(-c4ccc(C(=O)O)cc4)c3)c(-c3ccsc3C#N)c3cc(F)ccc32)cc1C] | 8/5 |
| 23/3 | | 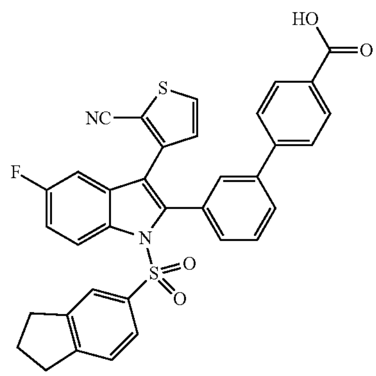 [SMILES: N#Cc1sccc1-c1c(-c2cccc(-c3ccc(C(=O)O)cc3)c2)n(S(=O)(=O)c2ccc3c(c2)CCC3)c2ccc(F)cc12] | 8/6 |

Example 24

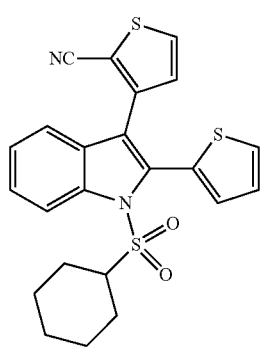

24

Step 1: Methyl 3-((2-iodophenyl)amino)propanoate (24a)

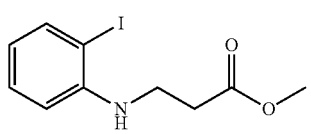

24a

A mixture of 2-iodoaniline (50 g, 288 mmol) and methyl acrylate (103 mL, 1.14 mol) in AcOH (60 mL) was stirred at 90° C. in a sealed tube for 48 h, cooled and filtered. The filtrate was concentrated, diluted with aq. Na$_2$CO$_3$ and extracted with EA (2×100 mL). The combined organic layer was washed with brine, dried over Na$_2$SO$_4$ and concentrated to afford compound 24a as a yellow oil.

Step 2: Methyl 3-((2-iodophenyl)(methyl)amino)propanoate (24b)

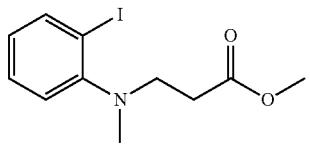

A mixture of compound 24a (17.7 g, 58.1 mmol), CH₃I (29 mL, 46 mmol) and K₂CO₃ (16.3 g, 118 mmol) in ACN (120 mL) was stirred at 80° C. in a sealed tube for 48 h, cooled and filtered. The filtrate was concentrated, diluted with H₂O and extracted with EA (2×100 mL). The combined organic layer was washed with brine, dried over Na₂SO₄ and concentrated to afford crude compound 24b as a yellow oil.

Step 3: Methyl 3-(methyl(2-(thiophen-2-ylethynyl)phenyl)amino)propanoate (24c)

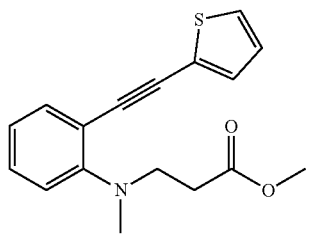

A mixture of compound 24b (24.8 g, 77.7 mmol), 2-ethynyl-thiophene (15.6 mL, 154 mmol), CuI (296 mg, 1.56 mmol), Pd(PPh₃)₂Cl₂ (546 mg, 0.778 mmol) and TEA (39.3 g, 389 mmol) in ACN (90 mL) was stirred at 80° C. in a sealed tube overnight, cooled and filtered. The filtrate was concentrated and purified by FCC (PE:EA=20:1) to afford compound 24c as a brown oil.

Step 4: Methyl 3-(3-(2-cyanothiophen-3-yl)-2-(thiophen-2-yl)-1H-indol-1-yl)propanoate (24d)

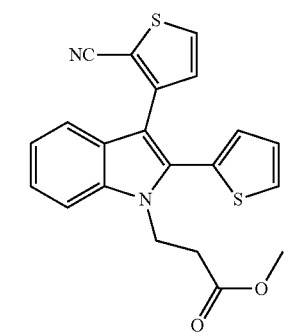

A mixture of compound 24c (23.2 g, 77.6 mmol), 3-bromo-thiophene-2-carbonitrile (16.1 g, 85.6 mmol), n-Bu₄NI (2.90 g, 7.76 mmol) and PdCl₂(dppf) (1.70 g, 2.33 mmol) in ACN (150 mL) was stirred at 90° C. under N₂ overnight, cooled, quenched with H₂O and extracted with EA (2×150 mL). The combined organic layer was washed with brine, dried over Na₂SO₄, concentrated and purified by FCC (PE:EA=5:1) to afford compound 24d as a brown oil; MS: 393.0 (M+1)⁺.

Step 5: 3-(2-(Thiophen-2-yl)-1H-indol-3-yl)thiophene-2-carbonitrile (24e)

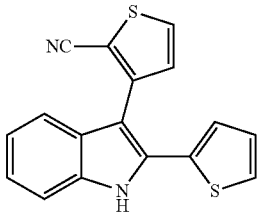

A mixture of compound 24d (12.6 g, 32.1 mmol) and DBU (10.1 mL, 64.2 mmol) in DMF (100 mL) was stirred at 120° C. overnight, cooled, diluted with H₂O and extracted with EA (2×100 mL). The combined organic layer was washed with H₂O (2×100 mL) and brine, dried over Na₂SO₄, concentrated and purified by FCC (PE:EA=5:1) to afford compound 24e as a yellow solid; MS: 307.0 (M+1)⁺.

Step 6: 3-(1-(Cyclohexylsulfonyl)-2-(thiophen-2-yl)-1H-indol-3-yl)thiophene-2-carbonitrile (24)

To a solution of compound 24e (200 mg, 0.65 mmol) in THF (20 mL) at −78° C. under N₂ was added LiHMDS (1.0 M in THF, 0.8 mL, 0.8 mmol) dropwise. The mixture was stirred at −78° C. for 30 min, then cyclohexanesulfonyl chloride (144 mg, 0.80 mmol) was added. The mixture was stirred at −78° C. for 2 h, diluted with aq. NH₄Cl and extracted with DCM (3×). The combined organic layer was dried over Na₂SO₄, filtered, concentrated and purified by prep-HPLC to afford compound 24 as a yellow solid. ¹H-NMR (CDCl₃, 300 MHz) δ: 1.08-1.12 (m, 3H), 1.46-1.60 (m, 3H), 1.73-1.77 (m, 4H), 3.06-3.16 (m, 1H), 6.86 (d, J=5.4 Hz, 1H), 7.05 (dd, J=3.6, 4.8 Hz, 1H), 7.27-7.51 (m, 6H), 8.19 (d, J=8.4 Hz, 1H); MS: 467.7 (M+Na)⁺.

Example 25

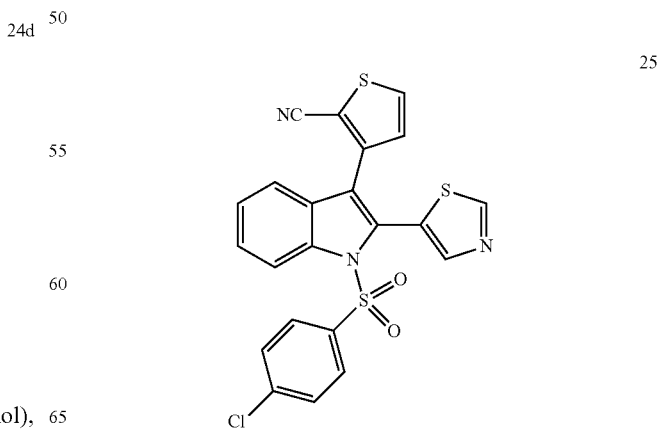

Step 1: tert-Butyl 2-(thiazol-5-yl)-1H-indole-1-carboxylate (25a)

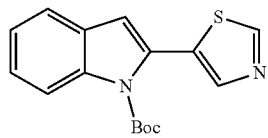

A mixture of tert-butyl 2-(4,4,5,5-tetramethyl-1,3,2-dioxaborolan-2-yl)-1H-indole-1-carboxylate (4.20 g, 12.2 mmol), 5-bromo-thiazole (2.00 g, 12.2 mmol), Pd(dppf)Cl$_2$ (877 mg, 1.20 mmol) and K$_2$CO$_3$ (5.10 g, 36.6 mmol) in dioxane/H$_2$O (50 mL/5 mL) was stirred at 100° C. under N$_2$ overnight, cooled, diluted with EA (300 mL) and washed with brine. The organic layer was dried over Na$_2$SO$_4$, filtered, concentrated and purified by FCC (PE:EA=5:1) to give compound 25a as a colorless oil.

Step 2: tert-Butyl 3-bromo-2-(thiazol-5-yl)-1H-indole-1-carboxylate (25b)

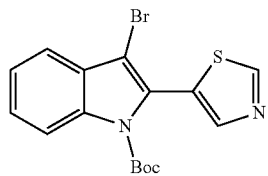

A mixture of compound 25a (2.6 g, 8.7 mmol) and NBS (1.85 g, 10.4 mmol) in DMF (50 mL) was stirred at rt under N$_2$ overnight, diluted with water and extracted with EA (3×50 mL). The combined organic layer was washed with brine, dried over Na$_2$SO$_4$, filtered, concentrated and purified by FCC (PE:EA=10:1) to give compound 25b as a yellow solid.

Step 3: tert-Butyl 3-(2-cyanothiophen-3-yl)-2-(thiazol-5-yl)-1H-indole-1-carboxylate (25c)

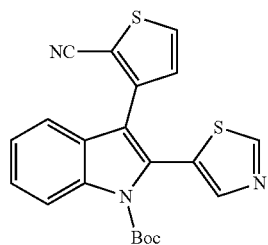

A mixture of compound 25b (620 mg, 1.60 mmol), 3-(4,4,5,5-tetramethyl-[1,3,2]dioxaborolan-2-yl)-thiophene-2-carbonitrile (376 mg, 1.60 mmol), Pd(dppf)Cl$_2$ (117 mg, 160 µmol) and K$_2$CO$_3$ (662 mg, 4.80 mmol) in dioxane/H$_2$O (20 mL/2 mL) was stirred at 100° C. under N$_2$ overnight, cooled, diluted with EA (200 mL) and washed with brine. The organic layer was dried over Na$_2$SO$_4$, filtered, concentrated and purified by FCC (PE:EA=5:1) to give compound 25c as a yellow oil.

Step 4: 3-(2-(Thiazol-5-yl)-1H-indol-3-yl)thiophene-2-carbonitrile (25d)

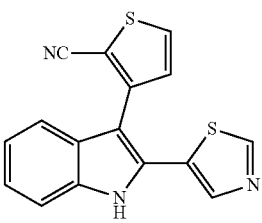

A mixture of compound 25c (320 mg, 0.79 mmol) and TFA (4 mL) in DCM (10 mL) was stirred at rt overnight, concentrated, neutralized with sat. aq. NaHCO$_3$ and extracted with EA (3×30 mL). The combined organic layer was washed with brine, dried over Na$_2$SO$_4$, filtered and concentrated to afford compound 25d, which was used in the next step without further purification.

Step 5: 3-(1-((4-Chlorophenyl)sulfonyl)-2-(thiazol-5-yl)-1H-indol-3-yl)thiophene-2-carbonitrile (25)

To a solution of compound 25d (200 mg, 0.65 mmol) in THF (10 mL) was added NaH (39 mg, 0.98 mmol) under N$_2$ at 0° C. The mixture was stirred at 0° C. for 30 min, then 4-chloro-benzenesulfonyl chloride (165 mg, 0.78 mmol) was added. The mixture was stirred at 0° C. for 30 min, poured into sat. aq. NH$_4$Cl (50 mL) and extracted with EA (3×50 mL). The combined organic layer was washed with brine, dried over Na$_2$SO$_4$, filtered, concentrated and purified by prep-HPLC (CH$_3$CN/H$_2$O=20% to 95%, 5 mmol NH$_4$HCO$_3$) to afford compound 25 as a yellow solid. $^1$H-NMR (DMSO-d$_6$, 400 MHz) δ: 9.28 (d, J=0.8 Hz, 1H), 8.27 (d, J=8.4 Hz, 1H), 8.08 (d, J=5.2 Hz, 1H), 7.91 (d, J=0.8 Hz, 1H), 7.66-7.56 (m, 5H), 7.43-7.39 (m, 2H), 7.11 (d, J=5.2 Hz, 1H); MS: 481.8 (M+1)$^+$.

Example 26

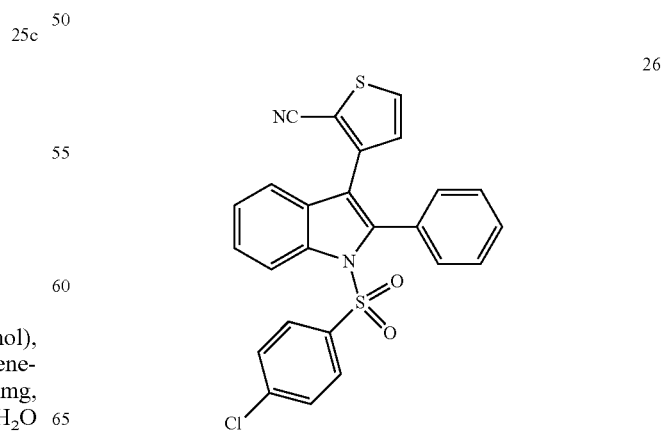

Step 1: tert-Butyl 3-(2-cyanothiophen-3-yl)-1H-indole-1-carboxylate (26a)

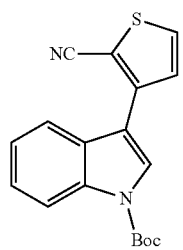

26a

To a solution of tert-butyl 3-(4,4,5,5-tetramethyl-1,3,2-dioxaborolan-2-yl)-1H-indole-1-carboxylate (2.0 g, 5.8 mmol), 3-bromo-thiophene-2-carbonitrile (1.1 g, 5.8 mmol) and K₂CO₃ (2.40 g, 17.4 mmol) in dioxane/H₂O (20 mL/2 mL) was added Pd(dppf)Cl₂ (413 mg, 0.58 mmol) under N₂. The mixture was stirred at 90° C. for 4 h, evaporated and purified by FCC (PE:EA=20:1 to 10:1) to afford compound 26a as a yellow oil.

Step 2: tert-Butyl 2-bromo-3-(2-cyanothiophen-3-yl)-1H-indole-1-carboxylate (26b)

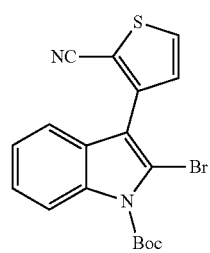

26b

To a solution compound 26a (1.30 g, 4.01 mmol) in CCl₄ (20 mL) were added NBS (1.40 g, 8.02 mmol) and AIBN (65.4 mg, 401 μmol). The mixture was stirred at 100° C. for 48 h, evaporated and purified by FCC (PE:EA=10:1) to afford compound 26b as a yellow oil.

Step 3: tert-Butyl 3-(2-cyanothiophen-3-yl)-2-phenyl-1H-indole-1-carboxylate (26c)

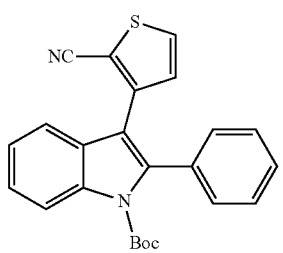

26c

To a solution of compound 26b (500 mg, 1.24 mmol), PhB(OH)₂ (302 mg, 2.48 mmol) and K₂CO₃ (513 mg, 3.72 mmol) in dioxane (15 mL) was added Pd(dppf)Cl₂ (88.4 mg, 124 μmol) under N₂. The mixture was stirred at 90° C. overnight, concentrated and purified by FCC (PE:EA=10:1) to afford compound 26c as a yellow oil.

Step 4: 3-(2-Phenyl-1H-indol-3-yl)thiophene-2-carbonitrile (26d)

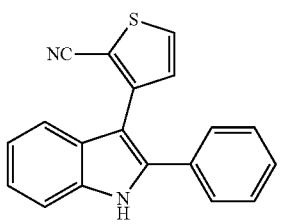

26d

To a solution of compound 26c (616 mg, 1.54 mmol) in DCM (4 mL) was added TFA (2 mL). The mixture was stirred at rt for 2 h, concentrated and purified to afford compound 26d as a white solid.

Step 5: 3-(1-((4-Chlorophenyl)sulfonyl)-2-phenyl-1H-indol-3-yl)thiophene-2-carbonitrile (26)

To a solution of compound 26d (147 mg, 488 μmol) in DMF (5 mL) was added NaH (78 mg, 2.0 mmol) under N₂ at 0° C. The mixture was stirred at 0° C. for 30 min, then 4-chloro-benzenesulfonyl chloride (310 mg, 1.46 mmol) was added. The mixture was stirred at 0° C. for 30 min, quenched with sat. aq. NH₄Cl and extracted with DCM (3×20 mL). The combined organic layer was washed with brine, dried over Na₂SO₄, filtered, concentrated and purified by FCC (PE:EA=20:1) to afford compound 26 as a white solid. ¹H-NMR (DMSO-d₆, 400 MHz) δ: 8.25 (d, J=8.0 Hz, 1H), 7.99 (d, J=5.2 Hz, 1H), 7.59 (dd, J=2.0, 6.8 Hz, 2H), 7.53-7.27 (m, 10H), 6.96 (d, J=4.8 Hz, 1H); MS: 491.7 (M+18)⁺.

Example 26/1

The following Example was prepared similar as described for Example 26 using the appropriate starting material.

| # | starting material | structure | analytical data |
|---|---|---|---|
| 26/1 | HO-B(OH)-C6H4-F | (structure with cyanothiophene, indole, 4-F-phenyl, 4-Cl-phenylsulfonyl) | $^1$H-NMR (DMSO-d$_6$, 400 MHz) δ: 8.25 (d, J = 8.4 Hz, 1H), 8.03 (d, J = 5.6 Hz, 1H), 7.61-7.58 (m, 2H), 7.55-7.48 (m, 3H), 7.43-7.32 (m, 4H), 7.25-7.21 (m, 2H), 7.00 (d, J = 4.8 Hz, 1H); MS: 509.6 (M + 18)$^+$. |

Example 27

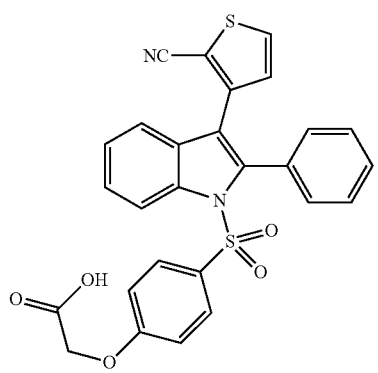

27

2-(4-((3-(2-Cyanothiophen-3-yl)-2-phenyl-1H-indol-1-yl)sulfonyl)phenoxy)acetic Acid (27)

To a solution of compound 1/43 (70 mg, 130 µmol) in MeOH (5 mL) was added NaOH (2N, 0.5 mL) and the mixture was stirred overnight. Then the MeOH was removed and the solution was adjusted to pH<2 with 2N HCl, extracted with EA (10 mL) and washed with brine (10 mL). The organic layer was dried over Na$_2$SO$_4$, filtered, concentrated and purified by prep-HPLC to afford compound 27 as a white solid. $^1$H-NMR (500 MHz, DMSO-d$_6$) δ: 13.21 (br s, 1H), 8.26 (d, J=8.5 Hz, 1H), 7.99 (d, J=5.0 Hz, 1H), 7.52-7.34 (m, 8H), 7.27 (d, J=7.0 Hz, 2H), 7.01-6.99 (m, 3H), 4.75 (s, 2H); MS: 515.1 (M+1)$^+$.

Example 27/1 to 27/3

The following Examples were prepared similar as described for Example 27 using the appropriate starting material.

| # | starting material | structure | analytical data |
|---|---|---|---|
| 27/1 | (structure with methyl ester) | (structure with carboxylic acid) 1/44 | $^1$H-NMR (500 MHz, DMSO-d$_6$) δ: 12.55 (br s, 1H), 8.26 (d, J = 9.0 Hz, 1H), 8.00 (d, J = 5.0 Hz, 1H), 7.55-7.34 (m, 10H), 7.28 (d, J = 7.0 Hz, 2H), 6.98 (d, J = 5.0 Hz, 1H), 3.61 (s, 2H); MS: 499.1 (M + 1)$^+$. |

-continued

| # | starting material | structure | analytical data |
|---|---|---|---|
| 27/2 | | 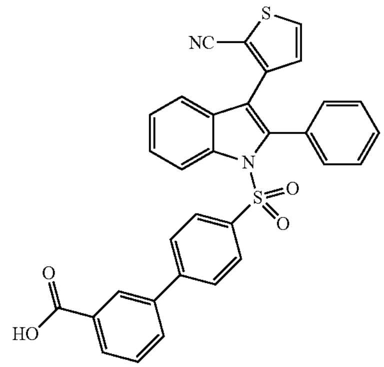 [SMILES: N#Cc1sccc1-c1c(-c2ccccc2)n(S(=O)(=O)c2ccc(-c3cccc(C(=O)O)c3)cc2)c2ccccc12] | 1H-NMR (500 MHz, DMSO-d6) δ: 13.18 (br s, 1H), 8.32 (d, J = 8.5 Hz, 1H), 8.17 (s, 1H), 8.00 (d, J = 5.0 Hz, 2H), 7.93 (d, J = 8.0 Hz, 1H), 7.86 (d, J = 8.5 Hz, 2H), 7.63-7.52 (m, 4H), 7.45-7.32 (m, 7H), 6.97 (d, J = 5.0 Hz, 1H); MS: 561.2 (M + 1)$^+$. |
| | 1/45 | | |
| 27/3 | | 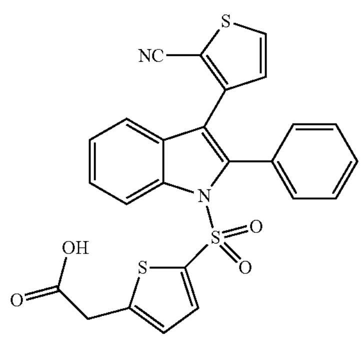 [SMILES: N#Cc1sccc1-c1c(-c2ccccc2)n(S(=O)(=O)c2ccc(CC(=O)O)s2)c2ccccc12] | $^1$H-NMR (500 MHz, DMSO-d$_6$) δ: 12.85 (br s, 1H), 8.21 (d, J = 8.0 Hz, 1H), 8.01 (d, J = 5.5 Hz, 1H), 7.54-7.51 (m, 1H), 7.44-7.32 (m, 8H), 7.00 (d, J = 5.0 Hz, 1H), 6.95 (d, J = 3.5 Hz, 1H), 3.91 (s, 2H); MS: 505.0 (M + 1)$^+$. |
| | 1/46 | | |

Example 28

3-(4-(3-(2-Cyanothiophen-3-yl)-1-((4-methoxyphenyl)sulfonyl)-1H-indol-2-yl)phenyl)propanamide (28)

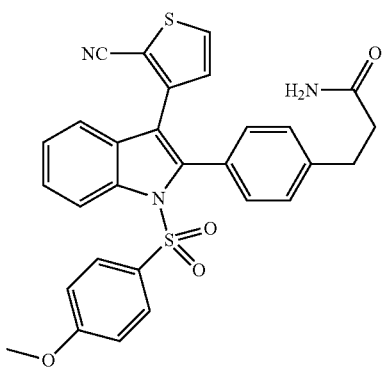

To a solution of compound 15/6 (200 mg, 0.40 mmol) in DMF (10 mL) was added EDCI (100 mg, 0.50 mmol), DMAP (60 mg, 0.50 mmol) and NH$_4$Cl (70 mg, 0.50 mmol) and the mixture was stirred at rt for 12 h, diluted with water (100 mL) and extracted with EA (3×100 mL). The combined organic layer was washed with brine (50 mL), dried over Na$_2$SO$_4$, filtered, concentrated and purified by prep-HPLC to give compound 28 as a white solid. $^1$H-NMR (500 MHz, DMSO-d$_6$) δ: 8.26 (d, J=8.0 Hz, 1H), 7.98 (d, J=5.5 Hz, 1H), 7.50-7.47 (m, 1H), 7.40-7.33 (m, 5H), 7.20 (d, J=8.0 Hz, 2H), 7.15 (d, J=8.0 Hz, 2H), 7.00 (d, J=9.0 Hz, 2H), 6.93 (d, J=5.0 Hz, 1H), 6.84 (s, 1H), 3.78 (s, 3H), 2.85 (t, J=8.0 Hz, 2H), 2.41 (t, J=8.0 Hz, 2H); MS: 542.1 (M+1)$^+$.

Example 29

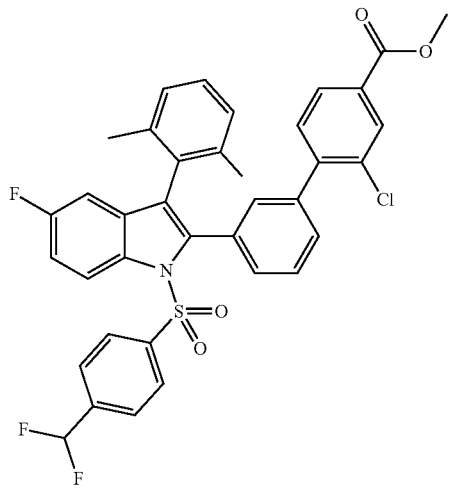

Step 1: Methyl 2-chloro-3'-((2-((4-(difluoromethyl)phenyl)sulfonamido)-5-fluorophenyl)ethynyl)-[1,1'-biphenyl]-4-carboxylate (29a)

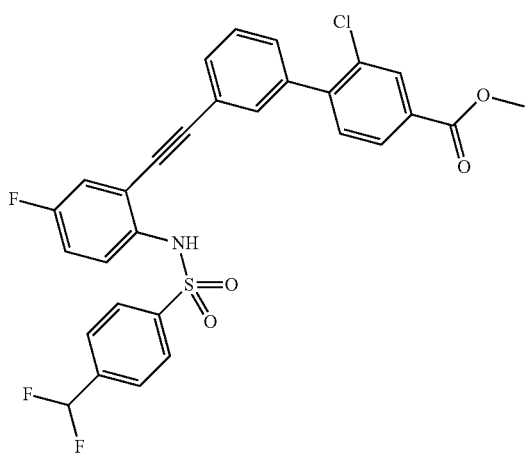

Compound 29a was synthesized similar as described in Example 1, Step 1 and 2 using the appropriate building blocks.

Step 2: Methyl 2-chloro-3'-(1-((4-(difluoromethyl)phenyl)sulfonyl)-5-fluoro-1H-indol-2-yl)-[1,1'-biphenyl]-4-carboxylate (29b)

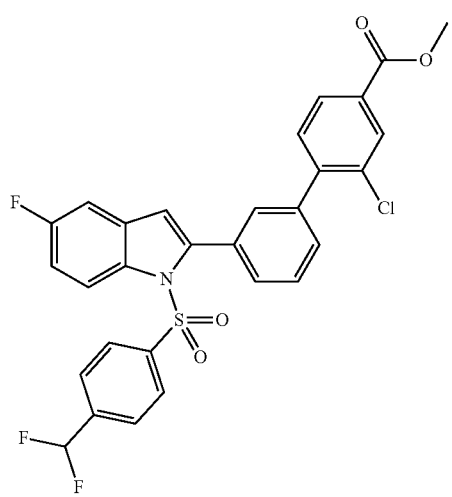

To a solution of compound 29a (400 mg, 0.70 mmol) in MeCN (12.0 mL) was added $K_2CO_3$ (193 mg, 1.40 mmol) and $Pd(PPh_3)_4$ (81 mg, 70 µmol) under $N_2$. The mixture was stirred at 100° C. for 2 h, cooled to rt, poured into EA (200 mL) and washed with $H_2O$ (2×20 mL) and brine (20 mL). The organic layer was dried over $Na_2SO_4$, concentrated and purified by FCC (EA:PE=1:4) to give compound 29b as a colorless oil.

Step 3: Methyl 3'-(3-bromo-1-((4-(difluoromethyl)phenyl)sulfonyl)-5-fluoro-1H-indol-2-yl)-2-chloro-[1,1'-biphenyl]-4-carboxylate (29c)

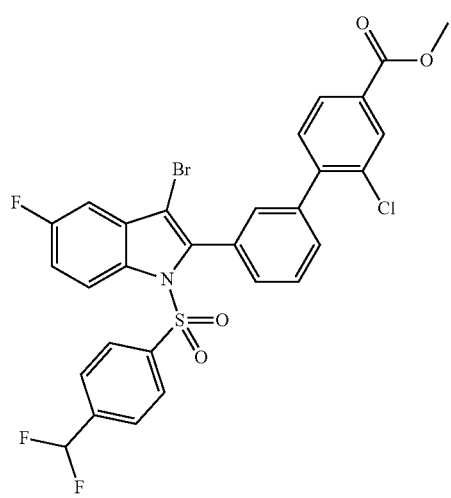

To a solution of compound 29b (150 mg, 0.26 mmol) in THF (15 mL) was added NBS (56 mg, 0.31 mmol). The mixture was stirred at rt overnight, poured into EA (200 mL) and washed with $H_2O$ (2×20 mL) and brine (20 mL). The organic layer was dried over Na₂SO₄, concentrated and purified by prep-TLC (EA:PE=1:4) to give compound 29c as a white solid.

Step 4: Methyl 2-chloro-3'-(1-((4-(difluoromethyl)phenyl)sulfonyl)-3-(2,6-dimethylphenyl)-5-fluoro-1H-indol-2-yl)-[1,1'-biphenyl]-4-carboxylate (29)

To a solution of compound 29c (150 mg, 0.23 mmol) in dioxane (8 mL) was added 2,6-dimethyl-phenylboronic acid (45 mg, 0.30 mmol), Cs₂CO₃ (176 mg, 0.46 mmol) and Pd(dppf)Cl₂ (17 mg, 23 μmol) under N₂. The mixture was stirred at 90° C. overnight, cooled to rt, poured into EA (200 mL) and washed with H₂O (2×20 mL) and brine (20 mL). The organic layer was dried over Na₂SO₄, concentrated and purified by prep-TLC (EA:PE=1:4) to give compound 29 as a colorless oil.

Example 29/1 to 29/3

The following Examples were prepared similar as described for Example 29 using the appropriate starting material(s).

| # | starting material(s) | structure |
|---|---|---|
| 29/1 | 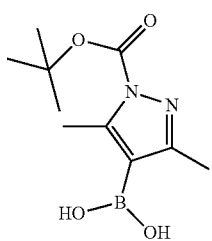 [SMILES: Cc1nn(C(=O)OC(C)(C)C)c(C)c1B(O)O] | 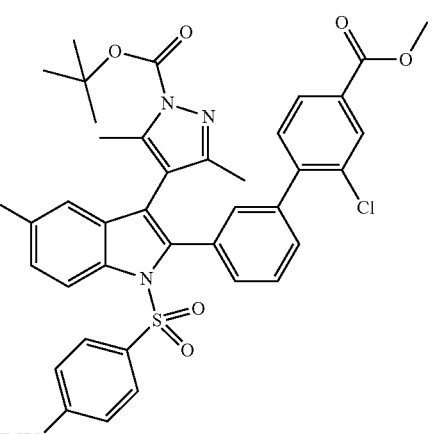 |
| 29/2 | 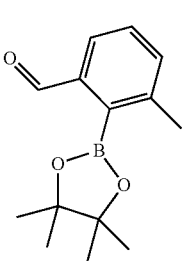 | 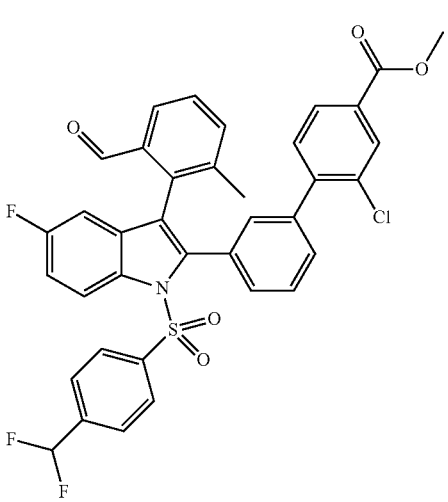 [SMILES: COC(=O)c1ccc(-c2cccc(-c3c(-c4c(C)cccc4C=O)c4cc(F)ccc4n3S(=O)(=O)c3ccc(C(F)F)cc3)c2)c(Cl)c1] |

-continued

| # | starting material(s) | structure |
|---|---|---|
| 29/3 | 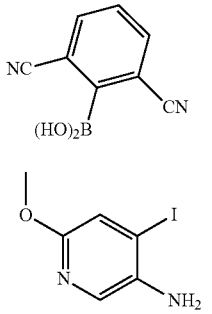 | 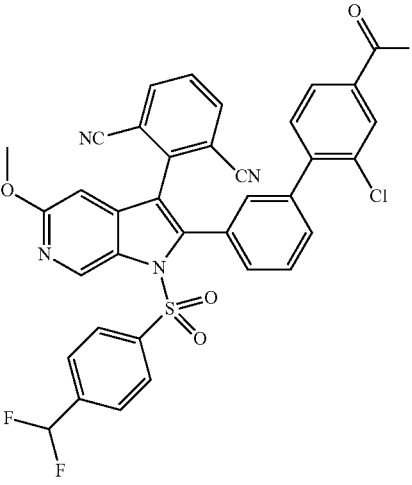 |

Example 30

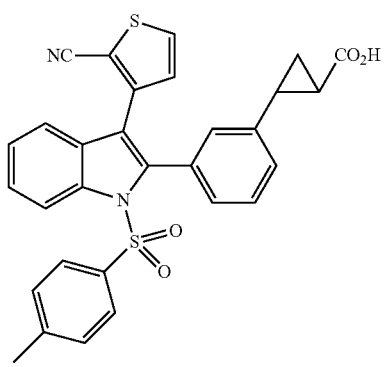

rac-(1R,2R)-2-(3-(3-(2-Cyanothiophen-3-yl)-1-tosyl-1H-indol-2-yl)phenyl)cyclopropane-1-carboxylic Acid (30)

To a solution of compound 1/56 (130 mg, 0.23 mmol) in MeOH (10 mL) was added LiOH·H$_2$O (49 mg, 1.18 mmol) and the mixture was stirred at rt for 1 h. Then the mixture was concentrated, adjusted to pH<4 with 2N aq. HCl and extracted with EA (3×30 mL). The combined organic layer was washed with brine (10 mL), dried over Na$_2$SO$_4$, concentrated and purified by prep-HPLC to give compound 30 as a white solid. $^1$H-NMR (500 MHz, DMSO-d$_6$) δ: 12.36 (s, 1H), 8.27 (d, J=10.0 Hz, 2H), 8.01 (d, J=5.5 Hz, 1H), 7.52-7.48 (m, 1H), 7.41-7.26 (m, 8H), 7.10-7.08 (m, 1H), 7.02-6.98 (m, 1H), 6.88 (s, 1H), 2.38-2.33 (m, 1H), 2.31 (s, 3H), 1.73-1.68 (m, 1H), 1.44-1.39 (m, 1H), 1.25-1.18 (m, 1H). MS: 521 (M−18+H)$^+$.

Example 30/1 to 30/16

The following Examples were prepared similar as described for Example 30 using the appropriate starting materials.

| # | starting material | structure | analytical data |
|---|---|---|---|
| 30/1 | 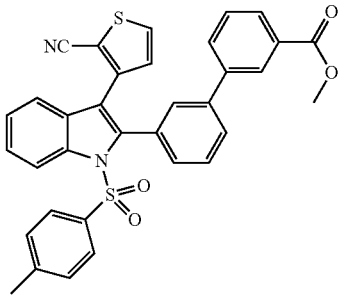 | 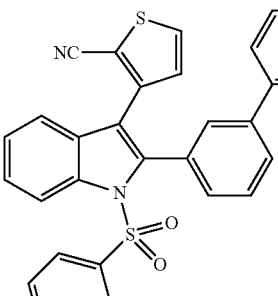 | $^1$H-NMR (500 MHz, DMSO-d$_6$) δ: 13.12 (s, 1H), 8.31 (d, J = 8.5 Hz, 1H), 8.07 (s, 1H), 8.01 (d, J = 5.0 Hz, 1H), 7.96 (d, J = 8.0 Hz, 1H), 7.81 (d, J = 7.5 Hz, 1H), 7.76 (d, J = 8.0 Hz, 1H), 7.63-7.60 (m, 1H), 7.55-7.47 (m, 2H), 7.42-7.37 (m, 4H), 7.31-7.25 (m, 3H), 7.07 (d, J = 5.0 Hz, 1H), 2.24 (s, 3H); MS: 574.8 (M + 1)$^+$. |

| # | starting material | structure | analytical data |
|---|---|---|---|
| 30/2 | (structure 1/58) | (structure) | ¹H-NMR (500 MHz, CD₃OD) δ: 8.43 (d, J = 8.5 Hz, 1H), 7.83 (d, J = 5.0 Hz, 1H), 7.65 (d, J = 8.0 Hz, 1H), 7.51-7.32 (m, 9H), 7.27 (d, J = 8.5 Hz, 2H), 7.22 (s, 1H), 7.12 (d, J = 8.5 Hz, 2H), 6.98 (d, J = 5.0 Hz, 1H), 2.22 (s, 3H), 1.62 (s, 6H); MS: 615.0 (M + 1)⁺. |
| 30/3 | (structure 1/59) | (structure) | ¹H-NMR (500 MHz, DMSO-d₆) δ: 12.75 (s, 1H), 8.75 (s, 1H), 8.66 (d, J = 2.0 Hz, 1H), 8.28 d, J = 8.5 Hz, 1H), 8.05-8.02 (m, 2H), 7.84 (d, J = 7.5 Hz, 1H), 7.62 (s, 1H), 7.54-7.25 (m, 9H), 7.11 (d, J = 5.0 Hz, 1H), 2.23 (s, 3H), 1.61 (s, 6H); MS: 618.1 (M + 1)⁺. |
| 30/4 | (structure 1/60) | (structure) | ¹H-NMR (500 MHz, DMSO-d₆) δ: 12.35 (s, 1H), 8.26 (d, J = 9.0 Hz, 1H), 8.02 (d, J = 5.0 Hz, 1H), 7.61-7.44 (m, 5H), 7.42-7.08 (m, 4H), 7.07-7.06 (m, 1H), 7.00-6.94 (m, 2H), 2.39-2.34 (m, 1H), 1.72 (s, 1H), 1.44-1.40 (m, 1H), 1.25-1.23 (m, 1H); MS: 540.8 (M + 1)⁺. |
| 30/5 | (structure 1/61) | (structure) | ¹H-NMR (500 MHz, DMSO-d₆) δ: 12.05 (s, 1H), 8.27 (d, J = 8.5 Hz, 1H), 7.98 (d, J = 5.0 Hz, 1H), 7.60-7.46 (m, 5H), 7.40-7.23 (m, 4H), 7.13 (d, J = 7.5 Hz, 1H), 7.03 (s, 1H), 6.96 (d, J = 5.0 Hz, 1H), 2.56 (t, J = 8.0 Hz, 2H), 2.15 (t, J = 7.0 Hz, 2H), 1.74-1.70 (m, 2H); MS: 560.8 (M + 1)⁺. |

-continued

| # | starting material | structure | analytical data |
|---|---|---|---|
| 30/6 | 1/63 | 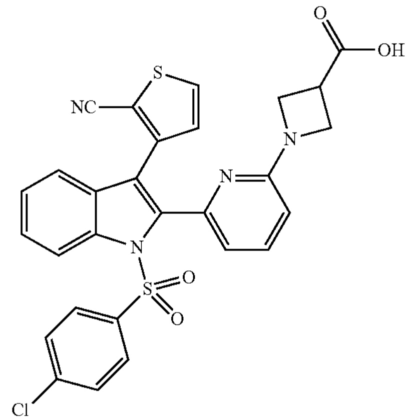 [SMILES: N#Cc1sccc1-c1c(-c2cccc(N3CC(C(=O)O)C3)n2)n(S(=O)(=O)c2ccc(Cl)cc2)c2ccccc12] | ¹H-NMR (500 MHz, CD₃OD) δ: 8.34 (d, J = 8.5 Hz, 1H), 7.96 (d, J = 5.0 Hz, 1H), 7.83-7.79 (m, 1H), 7.73 (d, J = 9.0 Hz, 2H), 7.62-7.58 (m, 1H), 7.53-7.42 (m, 4H), 7.23 (d, J = 5.0 Hz, 1H), 6.87 (d, J = 8.5 Hz, 1H), 6.77 (d, J = 7.0 Hz, 1H), 4.54-4.43 (m, 4H), 3.77-3.73 (m, 1H); MS: 574.7 (M + 1)⁺. |
| 30/7 | 1/64 | 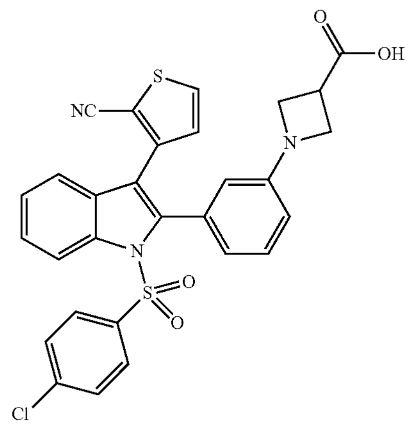 [SMILES: N#Cc1sccc1-c1c(-c2cccc(N3CC(C(=O)O)C3)c2)n(S(=O)(=O)c2ccc(Cl)cc2)c2ccccc12] | ¹H-NMR (500 MHz, CD₃OD) δ: 8.38 (d, J = 8.0 Hz, 1H), 7.77 (d, J = 5.0 Hz, 1H), 7.51-7.34 (m, 7H), 7.16 (t, J = 7.5 Hz, 1H), 6.88 (d, J = 5.0 Hz, 1H), 6.65 (d, J = 7.5 Hz, 1H), 6.55-6.53 (m, 1H), 6.23 (s, 1H), 4.01-3.97 (m, 2H), 3.91-3.88 (m, 2H), 3.54-3.50 (m, 1H); MS: 574.1 (M + 1)⁺. |
| 30/8 | 1/65 | 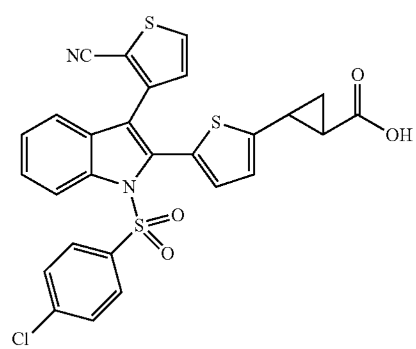 [SMILES: N#Cc1sccc1-c1c(-c2ccc(C3CC3C(=O)O)s2)n(S(=O)(=O)c2ccc(Cl)cc2)c2ccccc12] | ¹H-NMR (400 MHz, DMSO-d₆) δ: 8.26 (d, J = 8.8 Hz, 1H), 8.06 (d, J = 5.5 Hz, 1H), 7.64-7.51 (m, 5H), 7.42-7.36 (m, 2H), 7.05 (d, J = 5.0 Hz, 1H), 7.02 (d, J = 5.0 Hz, 1H), 6.88 (d, J = 3.5 Hz, 1H), 2.52-2.45 (m, 1H), 1.78-1.75 (m, 1H), 1.48-1.42 (m, 1H), 1.24-1.18 (m, 1H); MS: 582.1 (M + 18)⁺. |
| 30/9 | 1/66 | 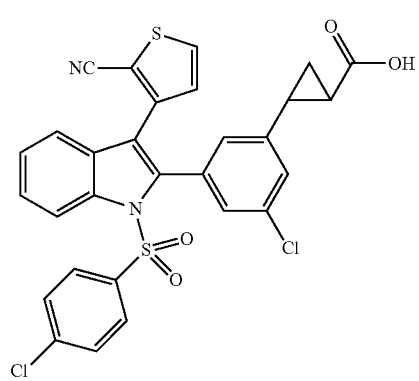 [SMILES: N#Cc1sccc1-c1c(-c2cc(Cl)cc(C3CC3C(=O)O)c2)n(S(=O)(=O)c2ccc(Cl)cc2)c2ccccc12] | ¹H-NMR (500 MHz, DMSO-d₆) δ: 8.25 (d, J = 8.5 Hz, 1H), 8.05 (d, J = 5.0 Hz, 1H), 7.60 (d, J = 8.5 Hz, 2H), 7.55-7.47 (m, 3H), 7.42-7.36 (m, 3H), 7.10 (s, 1H), 7.05 (d, J = 5.0 Hz, 1H), 6.90 (s, 1H), 2.39-2.35 (m, 1H), 1.79-1.72 (m, 1H), 1.43-1.38 (m, 1H), 1.25-1.20 (m, 1H); MS: 610.0 (M + 18)⁺. |

| # | starting material | structure | analytical data |
|---|---|---|---|
| 30/ 10 1/67 | | | $^1$H-NMR (500 MHz, DMSO-d$_6$) δ: 12.29 (s, 1H), 8.14 (d, J = 8.5 Hz, 1H), 8.00 (d, J = 5.5 Hz, 1H), 7.89 (s, 1H), 7.82 (s, 1H), 7.46-7.34 (m, 3H), 7.25-7.19 (m, 2H), 7.14-7.10 (m, 2H), 6.99 (d, J = 5.0 Hz, 1H), 3.65 (s, 3H), 2.37-2.35 (m, 1H), 1.82-1.75 (m, 1H), 1.45-1.38 (m, 1H), 1.28-1.22 (m, 1H); MS: 529.2 (M + 1)$^+$. |
| 30/ 11 1/68 | | | $^1$H-NMR (500 MHz, DMSO-d$_6$) δ: 12.49 (s, 1H), 8.26 (d, J = 8.5 Hz, 1H), 7.99 (d, J = 5.0 Hz, 1H), 7.58-7.40 (m, 5H), 7.40-7.32 (m, 2H), 7.16-7.13 (m, 1H), 6.98 (d, J = 5.0 Hz, 1H), 6.57 (d, J = 8.0 Hz, 1H), 6.52 (d, J = 7.5 Hz, 1H), 6.27 (s, 1H), 3.33-3.28 (m, 2H), 3.21-3.14 (m, 3H), 2.21-2.13 (m, 2H); MS: 587.8 (M + 1)$^+$. |
| 30/ 12 1/69 | | | $^1$H-NMR (500 MHz, DMSO-d$_6$) δ: 12.35 (br s, 1H), 8.13 (d, J = 8.0 Hz, 1H), 8.04 (s, 1H), 7.52-7.39 (m, 3H), 7.27-7.13 (m, 4H), 7.04 (d, J = 5.0 Hz, 1H), 2.88-2.83 (m, 1H), 2.41-2.36 (m, 1H), 1.75-1.72 (m, 1H), 1.43-1.39 (m, 1H), 1.28-1.25 (m, 1H), 0.99-0.94 (m, 4H); MS: 471.0 (M − 18 + H)$^+$. |
| 30/ 13 1/70 | | | $^1$H-NMR (500 MHz, CD$_3$OD) δ: 8.37 (d, J = 8.0 Hz, 1H), 7.46-7.42 (m, 1H), 7.33-7.30 (m, 1H), 7.27-7.17 (m, 9H), 6.74 (s, 1H), 6.60 (d, J = 5.5 Hz, 1H), 2.40-2.36 (m, 1H), 2.35 (s, 3H), 1.76-1.72 (m, 1H), 1.51-1.48 (m, 1H), 1.17-1.13 (m, 1H); MS: 548.0 (M + 1)$^+$. |

| # | starting material | structure | analytical data |
|---|---|---|---|
| 30/14 | (structure 1/71) | (carboxylic acid structure) | ¹H-NMR (500 MHz, DMSO-d₆) δ: 12.38 (s, 1H), 8.25 (d, J = 8.0 Hz, 1H), 7.49-7.45 (m, 1H), 7.36-7.13 (m, 8H), 7.15 (d, J = 7.0 Hz, 1H), 6.9 6-6.92 (m, 2H), 6.48-6.46 (m, 1H), 2.39-2.34 (m, 1H), 2.31 (s, 3H), 1.73-1.69 (m, 1H), 1.45-1.40 (m, 1H), 1.27-1.23 (m, 1H); MS: 530.0 (M − 1)⁺. |
| 30/15 | (structure 1/72) | (carboxylic acid structure) | ¹H-NMR (500 MHz, DMSO-d₆) δ: 12.35 (br s, 1H), 8.25 (d, J = 8.5 Hz, 1H), 7.88-7.85 (m, 1H), 7.57-7.34 (m, 8H), 7.32-7.18 (m, 3H), 7.06 (s, 1H), 6.84 (s, 1H), 2.32-2.29 (m, 4H), 1.64-1.61 (m, 1H), 1.43-1.39 (m, 1H), 1.19-1.16 (m, 1H); MS: 549.0 (M − 1)⁻. |
| 30/16 | (structure 42) | (carboxylic acid structure) | ¹H-NMR (400 MHz, DMSO-d₆) δ: 8.32-8.28 (m, 1H), 7.94-7.88 (m, 3H), 7.65-7.24 (m, 12H), 7.04-6.85 (m, 2H), 5.19 (br s, 1H), 1.23 (s, 6H); MS: 663.0 (M − 1)⁻ |

Example 31

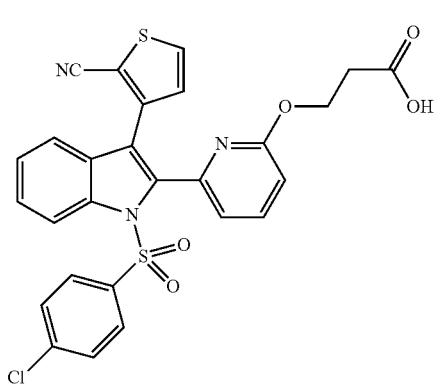

3-((6-(1-(((4-Chlorophenyl)sulfonyl)-3-(2-cyanothiophen-3-yl)-1H-indol-2-yl)pyridin-2-yl)oxy)propanoic Acid (31)

A solution of compound 1/62 (110 mg, 0.19 mmol) in 4N HCl in dioxane (30 mL) was stirred at rt overnight. The solvent was removed, EA (20 mL) was added and the mixture was washed with water (10 mL) and brine (10 mL). The organic layer was dried over $Na_2SO_4$, concentrated and purified by prep-HPLC to give compound 31 as a white solid. $^1$H-NMR (400 MHz, DMSO-$d_6$) δ: 12.38 (s, 1H), 8.13 (d, J=8.5 Hz, 1H), 8.02 (d, J=5.0 Hz, 1H), 7.94-7.91 (m, 2H), 7.77-7.65 (m, 3H), 7.54-7.42 (m, 1H), 7.41-7.37 (m, 2H), 7.13 (d, J=6.8 Hz, 1H), 7.00 (d, J=4.8 Hz, 1H), 6.86 (d, J=8.0 Hz, 1H), 4.32 (t, J=6.4 Hz, 2H), 2.67 (t, J=6.4 Hz, 2H); MS: 563.8 (M+1)$^+$.

Example 32

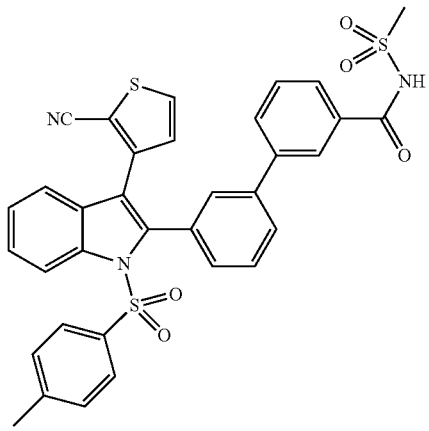

3'-(3-(2-Cyanothiophen-3-yl)-1-tosyl-1H-indol-2-yl)-N-(methylsulfonyl)-[1,1'-biphenyl]-3-carboxamide (32)

A cloudy solution of compound 30/1 (100 mg, 0.17 mmol), methanesulfonamide (17 mg, 0.17 mmol), DMAP (21 mg, 0.17 mmol) and EDCI (50 mg, 0.26 mmol) in DMF (4 mL) was stirred for 14 h at rt. The product was purified from the mixture by prep-HPLC to give compound 32 as a white solid. $^1$H-NMR (500 MHz, DMSO-$d_6$) δ: 12.30 (s, 1H), 8.31-7.92 (m, 4H), 7.83 (t, J=7.5 Hz, 2H), 7.65-7.62 (m, 2H), 7.55-7.49 (m, 2H), 7.42-7.39 (m, 4H), 7.30-7.26 (m, 3H), 7.07 (d, J=2.5 Hz, 1H), 3.42 (s, 3H), 2.25 (s, 3H); MS: 652.1 (M+1)$^+$.

Example 32/1 to 32/5

The following Examples were prepared similar as described for Example 32 using the appropriate starting materials.

| # | starting material | structure | analytical data |
|---|---|---|---|
| 32/1 | ![sm](30/4) | ![struct] | $^1$H-NMR (500 MHz, DMSO-$d_6$) δ: 12.09 (s, 1H), 8.25 (d, J = 8.5 Hz, 1H), 8.01 (d, J = 5.0 Hz, 1H), 7.62-7.59 (m, 2H), 7.54-7.23 (m, 7H), 7.10-6.96 (m, 3H), 3.28 (s, 1H), 2.46-2.42 (m, 1H), 2.09-2.06 (m, 1H), 1.51-1.46 (m, 1H), 1.35-1.32 (m, 1H); MS: 658.0 (M + Na)$^+$. |

| # | starting material | structure | analytical data |
|---|---|---|---|
| 32/2 | (structure) 3/32 | (structure) | ¹H-NMR (500 MHz, DMSO-d₆) δ: 8.27 (dd, J = 9.1, 4.4 Hz, 1H), 7.98 (d, J = 5.1 Hz, 1H), 7.46-7.28 (m, 5H), 7.20-7.07 (m, 2H), 6.94 (d, J = 5.1 Hz, 1H), 6.57-6.48 (m, 2H), 6.24 (s, 1H), 3.95 (t, J = 7.5 Hz, 2H), 3.89-3.80 (m, 1H), 3.72 (t, J = 6.2 Hz, 2H), 3.52 (s, 3H), 2.87 (s, 3H), 2.33 (s, 3H), 1.34 (s, 6H); MS: 685.0 (M + 1)⁺. |
| 32/3 | (structure) 3/32 | (structure) | |
| 32/4 | (structure) 30/4 | (structure) 32/4 | ¹H-NMR (500 MHz, DMSO-d₆) δ: 12.32 (s, 1H), 8.31-8.28 (m, 1H), 8.11 (d, J = 1.5 Hz, 1H), 8.03 (d, J = 5.0 Hz, 1H), 7.99-7.97 (m, 2H), 7.55-.35 (m, 4H), 7.41-7.33 (m, 3H), 7.26-7.18 (m, 3H), 7.07-7.03 (m, 2H), 3.38 (s, 3H), 2.22 (s, 3H); MS: 701.9 (M − 1)⁻. |
| 32/5 | (structure) 11/12 | (structure) | ¹H-NMR (500 MHz, CD₃OD) δ: 8.44 (dd, J = 9.0, 4.0 Hz, 1H), 8.08-8.04 (m, 3H), 7.93 (dd, J = 8.5, 1.5 Hz, 1H), 7.73 (t, J = 8.3 Hz, 1H), 7.55-7.32 (m, 9H), 7.12 (s, 1H), 6.95 (dd, J = 8.0, 2.5 Hz, 1H), 6.69 (t, J = 55.5 Hz, 1H), 3.36 (s, 3H); MS: 756.8 (M − 1)⁻. |

Example 33

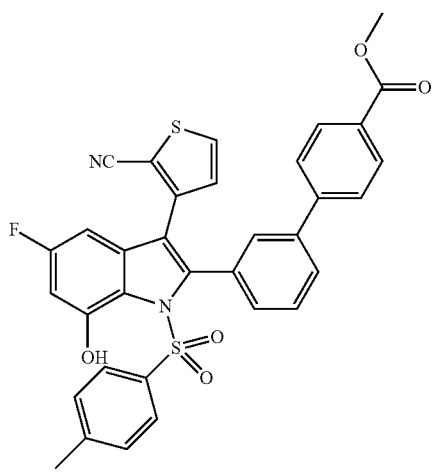

Methyl 3'-(3-(2-cyanothiophen-3-yl)-5-fluoro-7-hydroxy-1-tosyl-1H-indol-2-yl)-[1,1'-biphenyl]-4-carboxylate (33)

To a solution of compound 1/101 (120 mg, 0.19 mmol) in DCM (6 mL) at −78° C. was slowly added BBr$_3$ (10 mL, 1M in DCM). The mixture was stirred at this temperature for 40 min and at rt for 1 h, quenched with H$_2$O (20 mL) and extracted with EA (2×100 mL). The combined organic layer was washed with brine (20 mL), dried over Na$_2$SO$_4$ and concentrated. The residue was purified by prep-TLC (EA:PE=1:1) to afford compound 33 as a yellow oil.

Example 34

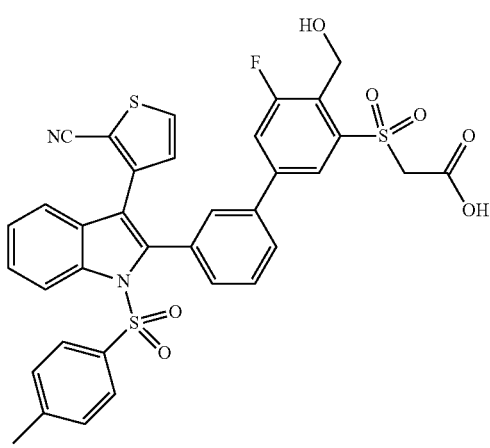

Step 1: Ethyl 2-((3'-(3-(2-cyanothiophen-3-yl)-1-tosyl-1H-indol-2-yl)-5-fluoro-4-(hydroxymethyl)-[1,1'-biphenyl]-3-yl)sulfonyl)acetate (34a)

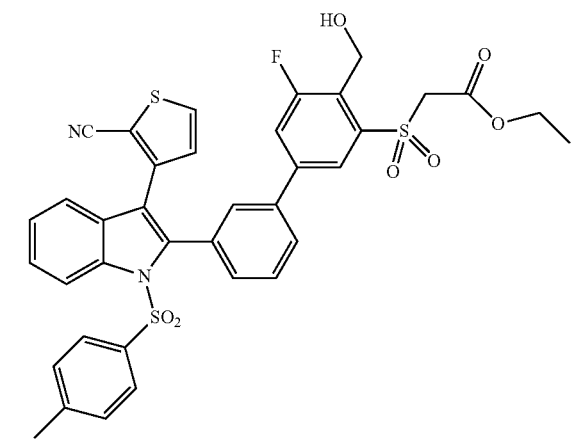

To a solution of compound 1 (290 mg, 0.54 mmol) in dioxane (15 mL) was added compound P3-1 (193 mg, 0.54 mmol), B$_2$Pin$_2$ (166 mg, 0.65 mmol), Pd(dppf)Cl$_2$ (39 mg, 0.05 mmol) and KOAc (107 mg, 1.09 mmol). The mixture was stirred at 100° C. overnight. After cooling to rt the mixture was filtered, the filtrate was concentrated und reduced pressure and the residue was purified by prep-TLC (EA:PE=1:1) to afford compound 34a as a yellow oil.

Step 2: 2-((3'-(3-(2-Cyanothiophen-3-yl)-1-tosyl-1H-indol-2-yl)-5-fluoro-4-(hydroxymethyl)-[1,1'-biphenyl]-3-yl)sulfonyl)acetic Acid (34)

To a solution of compound 34a (90 mg, 0.12 mmol) in EtOH (10 mL) was added LiOH·H$_2$O (26 mg, 0.62 mmol) and the mixture was stirred at rt for 1.5 h. Then the EtOH was removed, water was added and the pH was adjusted to <4 by addition of 2N HCl. The mixture was extracted with EA (3×40 mL) and the combined organic layer was washed with brine (10 mL), dried over Na$_2$SO$_4$, concentrated and purified by prep-HPLC to afford compound 34 as a white solid. $^1$H-NMR (500 MHz, CD$_3$OD) δ: 8.42 (d, J=8.5 Hz, 1H), 7.99 (s, 1H), 7.84 (d, J=4.5 Hz, 1H), 7.75 (d, J=8.0 Hz, 1H), 7.64-7.30 (m, 9H), 7.20 (d, J=8.5 Hz, 2H), 7.03 (d, J=5.0 Hz, 1H), 5.11 (s, 2H), 4.50 (s, 2H), 2.29 (s, 3H); MS: 718.1 (M+18)$^+$.

Example 35

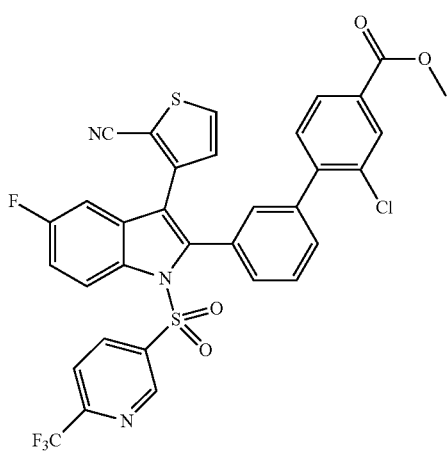

Step 1: Methyl 3'-((2-amino-5-fluorophenyl)ethynyl)-2-chloro-[1,1'-biphenyl]-4-carboxylate (35a)

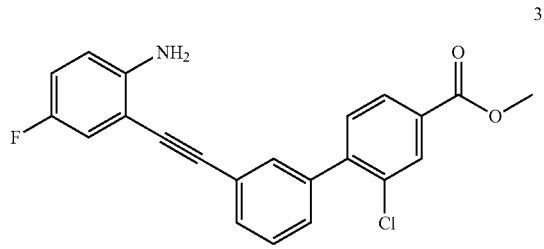

To a solution of compound P5 (5.00 g, 15.4 mmol) in TEA (60 mL) was added Pd(PPh₃)₄ (710 mg, 0.61 mmol), CuI (175 mg, 0.92 mmol), PPh₃ (241 mg, 0.92 mmol), and 2-ethynyl-4-fluoroaniline (2.70 g, 20.0 mmol). The mixture was stirred at 60° C. under N₂ overnight. After cooling to rt the mixture was filtered, the filtrate was concentrated and the residue was purified by FCC (PE:EA=2:1) to give compound 35a as a light yellow solid.

Step 2: Methyl 2-chloro-3'-((5-fluoro-2-(2,2,2-trifluoroacetamido)phenyl)ethynyl)-[1,1'-biphenyl]-4-carboxylate (35b)

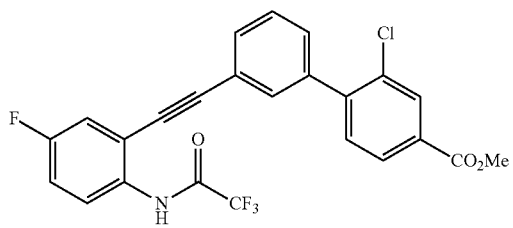

To a solution of compound 35a (300 mg, 0.79 mmol) in DCM (15 mL) was added TFAA (199 mg, 0.95 mmol) and TEA (120 mg, 1.19 mmol). The mixture was stirred at rt for 15 min, then DCM (20 mL) was added and the mixture was washed with H₂O (2×10 mL) and brine (20 mL). The organic layer was dried over Na₂SO₄ and concentrated to dryness to afford crude compound 35b as a yellow solid.

Step 3: Methyl 2-chloro-3'-(3-(2-cyanothiophen-3-yl)-5-fluoro-1H-indol-2-yl)-[1,1'-biphenyl]-4-carboxylate (35c)

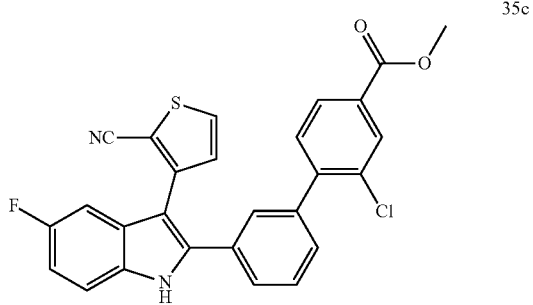 [SMILES: COC(=O)c1ccc(-c2cccc(-c3[nH]c4ccc(F)cc4c3-c3ccsc3C#N)c2)c(Cl)c1]

To a solution of compound 35b (320 mg, 0.67 mmol) in ACN (20 mL) was added 3-bromothiophene-2-carbonitrile (190 mg, 1.01 mmol), K₂CO₃ (185 mg, 1.34 mmol), and Pd(PPh₃)₄ (77 mg, 67 µmol) under N₂ and the mixture was stirred at 100° C. for 2 h, cooled to rt, poured into EA (20 mL) and washed with H₂O (2×20 mL) and brine (20 mL). The organic layer was dried over Na₂SO₄, concentrated and purified by FCC (EA:PE=1:3) to give compound 35c as a yellow solid.

Step 4: Methyl 2-chloro-3'-(3-(2-cyanothiophen-3-yl)-5-fluoro-1-((6-(trifluoromethyl)pyridin-3-yl)sulfonyl)-1H-indol-2-yl)-[1,1'-biphenyl]-4-carboxylate (35)

To a solution of compound 35c (200 mg, 0.41 mmol) in THF (8 mL) at 0° C. was added NaH (60% in mineral oil, 50 mg, 1.23 mmol) and 6-(trifluoromethyl)pyridine-3-sulfonyl chloride (201 mg, 0.82 mmol). The mixture was stirred at rt for 1 h and poured into cold sat. aq. NH₄Cl (50 mL). The mixture was extracted with EA (2×50 mL) and washed with brine (20 mL). The combined organic layer was dried over Na₂SO₄, concentrated and purified by prep-TLC (EA:PE=1:3) to give compound 35 as a yellow solid.

Example 35/1 to 35/2

The following Examples were prepared similar as described for Example 35 using the appropriate starting materials.

| # | starting material | structure |
|---|---|---|
| 35/1 | 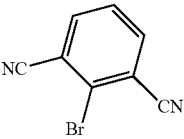 [SMILES: N#Cc1cccc(C#N)c1Br] | 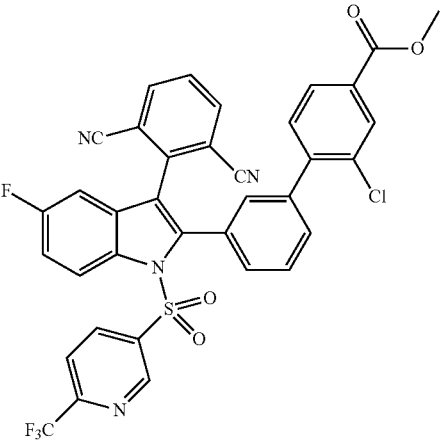 [SMILES: COC(=O)c1ccc(-c2cccc(-c3c(-c4c(C#N)cccc4C#N)c4cc(F)ccc4n3S(=O)(=O)c3ccc(C(F)(F)F)nc3)c2)c(Cl)c1] |
| 35/2 | 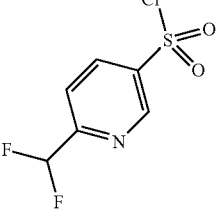 | 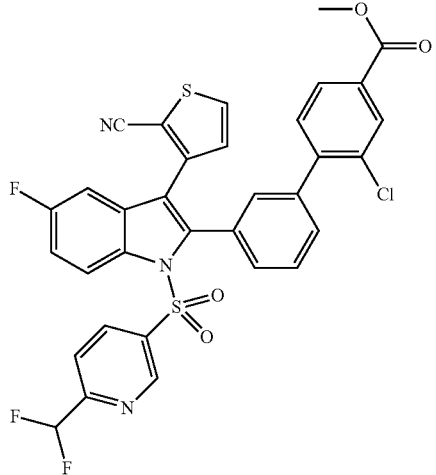 [SMILES: COC(=O)c1ccc(-c2cccc(-c3c(-c4ccsc4C#N)c4cc(F)ccc4n3S(=O)(=O)c3ccc(C(F)F)nc3)c2)c(Cl)c1] |

Example 36

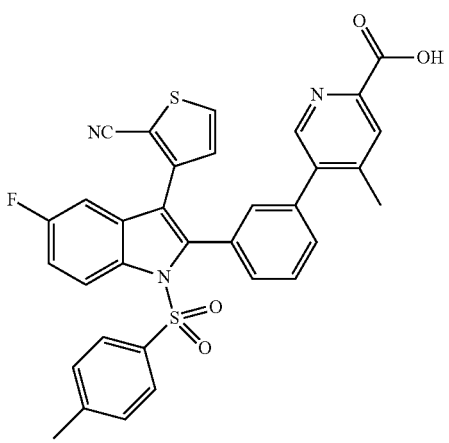

5-(3-(3-(2-Cyanothiophen-3-yl)-5-fluoro-1-tosyl-1H-indol-2-yl)phenyl)-4-methylpicolinic Acid (36)

To a stirred solution of compound 2/13 (150 mg, 0.24 mmol) in THF (10 mL) at rt was added 1N LiOH (1 mL) and stirring was continued at rt for 2 h. The mixture was extracted with EA (100 mL), the organic layer was washed with brine, dried over $Na_2SO_4$, filtered, concentrated and purified by prep-HPLC to give compound 36 as a white solid. $^1$H-NMR (500 MHz, DMSO-$d_6$) δ: 8.39 (s, 1H), 8.28 (dd, J=10.0, 4.5 Hz, 1H), 8.05 (d, J=5.0 Hz, 1H), 8.01 (s, 1H), 7.57-7.51 (m, 2H), 7.42-7.36 (m, 4H), 7.27 (d, J=8.5 Hz, 2H), 7.20-7.18 (m, 1H), 7.13 (s, 1H), 7.06 (d, J=5.0 Hz, 1H), 2.24 (s, 3H), 2.19 (s, 3H); MS: 606.0 (M−1)⁻.

Example 36/1

The following Example was prepared similar as described for Example 36 using the appropriate starting material.

| # | starting material | structure | analytical data |
|---|---|---|---|
| 36/1 | 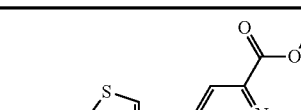<br>2/14 | 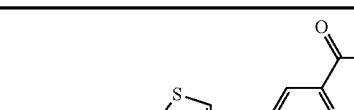 | ¹H-NMR (500 MHz, DMSO-d₆) δ: 8.30-8.27 (m, 1H), 8.04 (d, J = 5.0 Hz, 1H), 7.91 (d, J = 7.5 Hz, 1H), 7.65 (d, J = 7.5 Hz, 1H), 7.54-7.48 (m, 2H), 7.40-7.36 (m, 4H), 7.28-7.26 (m, 2H), 7.19-7.17 (m, 1H), 7.12 (s, 1H), 7.05 (d, J = 5.0 Hz, 1H), 2.30 (s, 3H), 2.25 (s, 3H); MS: 607.8 (M + 1)⁺. |

Example 37

3-(2-(2'-Chloro-4'-(1H-tetrazol-5-yl)-[1,1'-biphenyl]-3-yl)-5-fluoro-1-tosyl-1H-indol-3-yl)thiophene-2-carbonitrile (37)

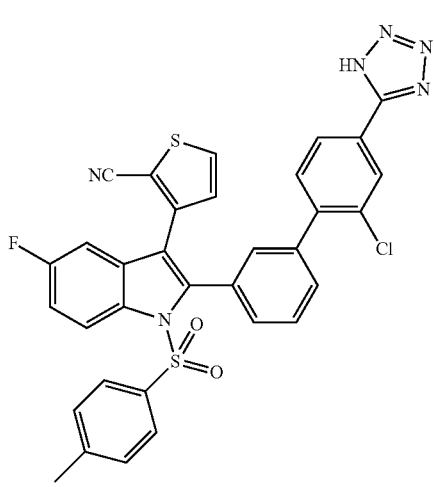

To a stirred solution of compound P2/15 (150 mg, 0.17 mmol) in acetone (10 mL) at rt was added 1N HCl (1 mL) and stirring was continued for 2 h. Water was added and the mixture was extracted with EA (100 mL). The organic layer was washed with brine, dried over Na₂SO₄, filtered, concentrated and purified by prep-HPLC to give compound 37 as a white solid. ¹H-NMR (500 MHz, DMSO-d₆) δ: 8.31-8.28 (m, 1H), 8.19 (s, 1H), 8.11-8.09 (m, 1H), 8.03 (d, J=5.0 Hz, 1H), 7.59-7.56 (m, 3H), 7.47-7.20 (m, 7H), 7.11 (s, 1H), 7.04 (d, J=5.0 Hz, 1H), 2.21 (s, 3H); MS: 649.0 (M−1)⁻.

Example 37/1

The following Example was prepared similar as described for Example 37 using the appropriate starting material.

| # | starting material | structure | analytical data |
|---|---|---|---|
| 37/1 | P2/17 | 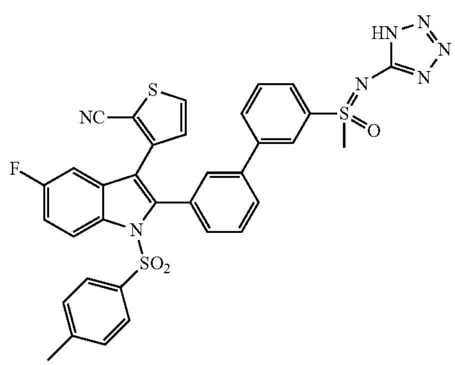 [SMILES: Cc1ccc(S(=O)(=O)n2c(-c3cccc(-c4cccc(S(C)(=O)=Nc5nnn[nH]5)c4)c3)c(-c3ccsc3C#N)c3cc(F)ccc32)cc1] | ¹H-NMR (500 MHz, DMSO-d₆) δ: 8.33-8.30 (m, 1H), 8.16 (s, 1H), 8.02-7.76 (m, 5H), 7.61 (s, 1H), 7.51 (t, J = 7.5 Hz, 1H), 7.41-7.37 (m, 3H), 7.30-7.26 (m, 3H), 7.20 (dd, J = 8.5, 2.5 Hz, 1H), 7.07 (d, J = 5.0 Hz, 1H), 3.71 (s, 3H), 2.24 (s, 3H); MS: 694.0 (M + 1)⁺. |

Example 38

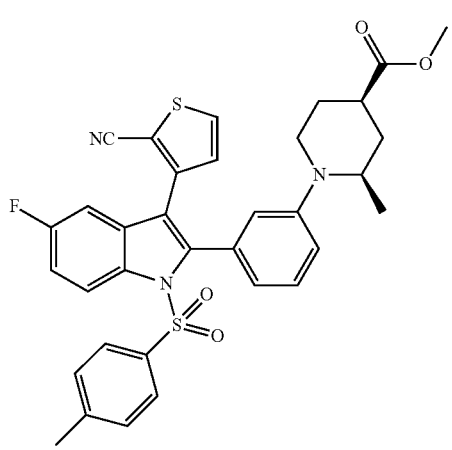

relative stereochemistry
cis rel-Methyl (2R,4R)-1-(3-(3-(2-cyanothiophen-3-yl)-5-fluoro-1-tosyl-1H-indol-2-yl)phenyl)-2-methylpiperidine-4-carboxylate (38)

To a solution of compound 1 (500 mg, 0.91 mmol) in toluene (15 mL) was added rel-methyl (2R,4R)-2-methylpiperidine-4-carboxylate (215 mg, 1.36 mmol), $Cs_2CO_3$ (869 mg, 2.27 mmol), $Pd_2(dba)_3$ (83 mg, 90 μmol) and BINAP (113 mg, 0.18 mmol) under $N_2$. The mixture was stirred at 100° C. overnight, cooled to rt, poured into EA (200 mL) and washed with $H_2O$ (30 mL) and brine (30 mL). The organic layer was dried over $Na_2SO_4$, concentrated and purified by prep-TLC (EA:PE=1:1) to give compound 38 as a yellow oil.

Example 38/1

The following Example was prepared similar as described for Example 38 using the appropriate starting materials.

Example 39

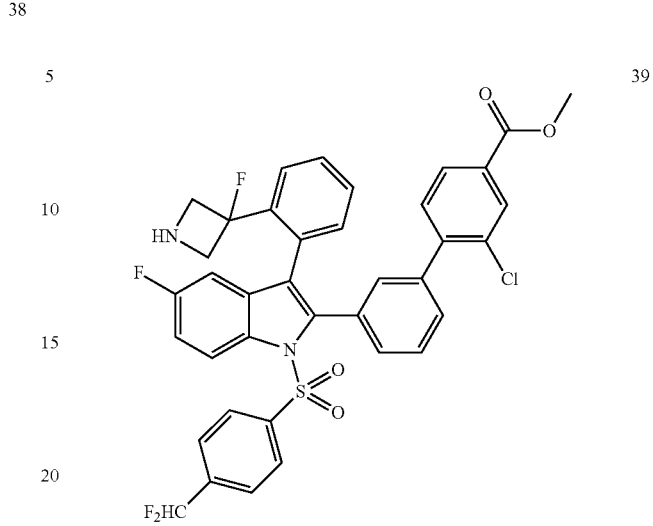

Methyl 2-chloro-3'-(1-((4-(difluoromethyl)phenyl)sulfonyl)-5-fluoro-3-(2-(3-fluoroazetidine-3-yl)phenyl)-1H-indol-2-yl)-[1,1'-biphenyl]-4-carboxylate (39)

To a solution of compound 1/114 (30 mg, 40 μmol) in DCM (2 mL) was added TFA (0.2 mL) and the mixture was stirred at rt for 4 h. The mixture was poured into water and the pH was adjusted to 8 with sat. aq. $NaHCO_3$. Then the mixture was extracted with EA and the organic layer was washed with brine, dried over $Na_2SO_4$ and concentrated to dryness to give compound 39 as a yellow solid.

| # | starting materials | | structure |
|---|---|---|---|
| 38/1 | (structure 1, HCl) | P24 | (structure, relative stereoisomers) |

Example 40

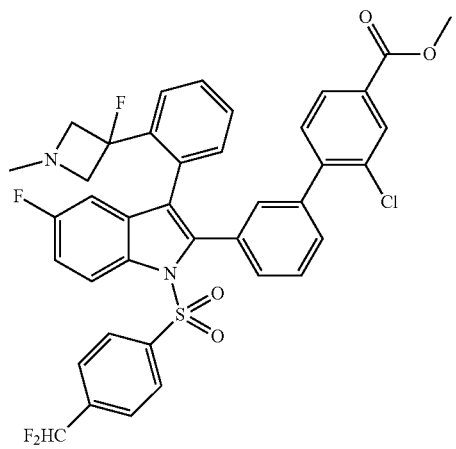

Methyl 2-chloro-3'-(1-((4-(difluoromethyl)phenyl)sulfonyl)-5-fluoro-3-(2-(3-fluoro-1-methyl-azetidin-3-yl)phenyl)-1H-indol-2-yl)-[1,1'-biphenyl]-4-carboxylate (40)

To a solution of compound 39 (27 mg, 40 μmol) in MeOH (2 mL) was added formaldehyde (0.2 mL) and the mixture was stirred at rt for 1 h. Then NaBH(OAc)₃ (82 mg, 0.37 mmol) was added and the mixture was stirred at rt for overnight. Water (40 mL) was added and the mixture was extracted with DCM (3×20 mL). The combined organic layer was washed with brine (30 mL), dried over Na₂SO₄, filtered, concentrated and purified by FCC (PE:EA=1:1) to afford compound 40 as a yellow solid.

Example 41/1 and Example 41/2

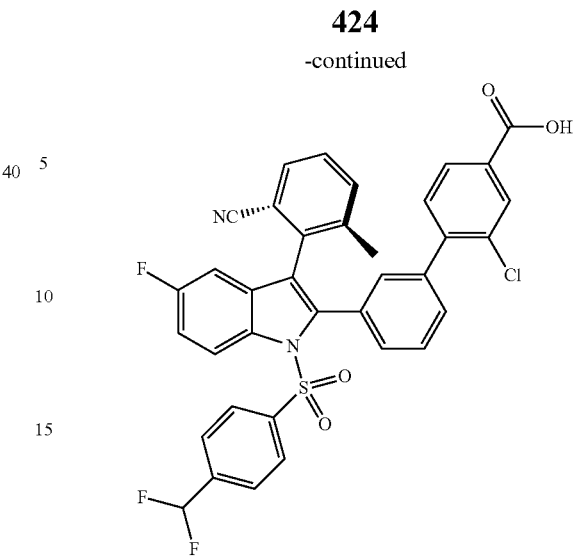

Separated Atropisomers of 2-chloro-3'-(3-(2-cyano-6-methylphenyl)-1-((4-(difluoro-methyl)phenyl)sulfonyl)-5-fluoro-1H-indol-2-yl)-[1,1'-biphenyl]-4-carboxylic Acid (41/1 and 41/2)

Compound 11/36 (300 mg) was separated by chiral-HPLC (instrument: Gilson-281; column: IE 20*250, 10 μm; mobile phase: n-hexane (0.1% DEA):EtOH (0.1% DEA)=55:45; run time per injection: 14 min; injection: 0.4 mL; sample solution: 75 mg in 3 mL MeOH) to give as first eluting isomer (retention time: 10.28 min) compound 41/1 and as second eluting isomer (retention time: 14.35 min) compound 41/2. NMR corresponds with Example 11/36; MS: 669.0 (M−1)⁻.

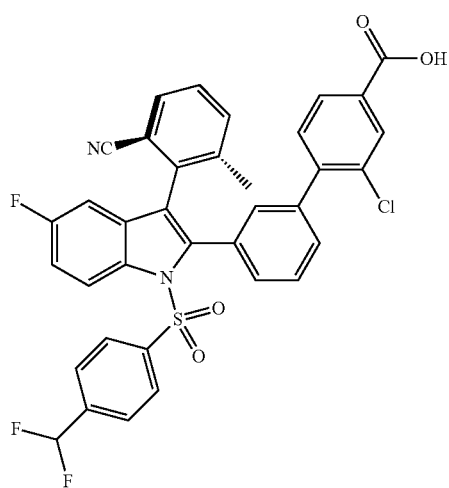

Example 42

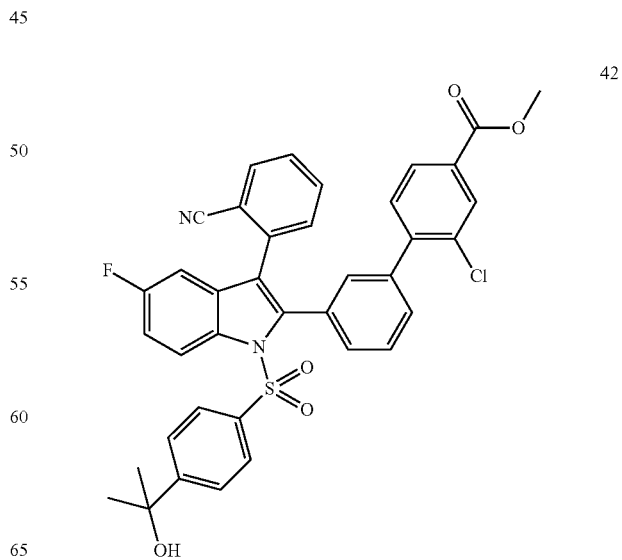

Step 1: Methyl 4-(N-(4-fluoro-2-iodophenyl)sulfamoyl)benzoate (42a)

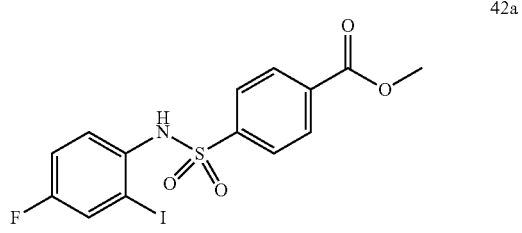 [SMILES: COC(=O)c1ccc(S(=O)(=O)Nc2ccc(F)cc2I)cc1]

To a solution of 4-fluoro-2-iodoaniline (2.00 g, 8.43 mmol) in pyridine (10 mL) was added methyl 4-(chlorosulfonyl)benzoate (2.20 g, 9.40 mmol). The mixture was stirred at rt overnight. Brine (40 mL) was added and the formed solid was filtered off, washed with EA (30 mL) and water (30 mL). The crude product was lyophilized to give compound 42a as a white solid.

Step 2: N-(4-Fluoro-2-iodophenyl)-4-(2-hydroxypropan-2-yl)benzenesulfonamide (42b)

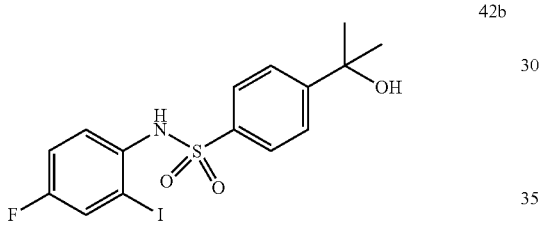

To a solution of compound 42a (3.50 g, 8.04 mmol) in THF (30 mL) was added a solution of MeMgBr (2.0M in THF, 20 mL, 40.0 mmol) at −78° C. slowly during 20 min. The mixture was stirred at −78° C. for 6 h before the mixture was allowed to warm to rt. Saturated aq. $NH_4Cl$ (50 mL) was added and the resulting mixture was extracted with EA (3×50 mL). The combined organic layer was dried over $Na_2SO_4$ and concentrated in vacuo to afford compound 42b as a white solid.

Step 3: Methyl 2-chloro-3'-((5-fluoro-2-((4-(2-hydroxypropan-2-yl)phenyl)sulfonamido)phenyl)-ethynyl)-[1,1'-biphenyl]-4-carboxylate (42c)

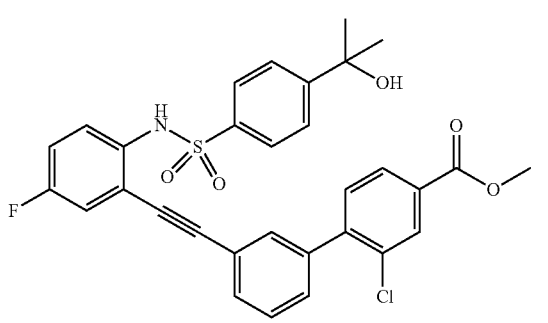

To a solution of compound 42b (1.30 g, 2.98 mmol) and compound P30 (740 mg, 2.74 mmol) in dry THF (20 mL) were added CuI (23 mg, 0.12 mmol), $Pd(PPh_3)_2Cl_2$ (130 mg) and TEA (830 mg, 8.22 mmol). The mixture was stirred at 0° C. for 30 min under argon and then stirred at rt overnight, diluted with water (30 mL) and extracted with EA (3×40 mL). The combined organic layer was washed by brine (2×50 mL), dried over $Na_2SO_4$, filtered, concentrated and purified by FCC (PE:EA=5:1) to give compound 42c as a pale yellow solid.

Step 4: Methyl 2-chloro-3'-(5-fluoro-1-((4-(2-hydroxypropan-2-yl)phenyl)sulfonyl)-3-iodo-1H-indol-2-yl)-[1,1'-biphenyl]-4-carboxylate (42d)

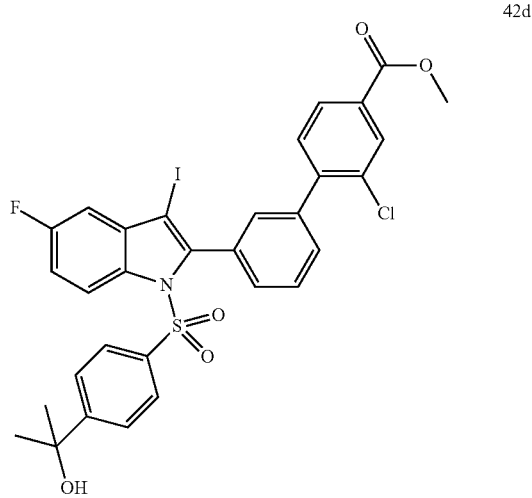 [SMILES: COC(=O)c1ccc(-c2cccc(-c3c(I)c4cc(F)ccc4n3S(=O)(=O)c3ccc(C(C)(C)O)cc3)c2)c(Cl)c1]

To a solution of compound 42c (500 mg, 0.86 mmol) and $K_2CO_3$ (368 mg, 2.67 mmol) in ACN (30 mL) was added NIS (608 mg, 2.67 mmol) at −10° C. under argon. The mixture was allowed to warm to rt during 30 min and stirred overnight. The mixture was washed with aq. sat. $Na_2S_2O_3$ (3×20 mL) and extracted with DCM (2×20 mL). The combined organic layer was dried over $Na_2SO_4$, filtered, concentrated and purified by prep-HPLC to give compound 42d as a white solid.

Step 5: Methyl 2-chloro-3'-(3-(2-cyanophenyl)-5-fluoro-1-((4-(2-hydroxypropan-2-yl)phenyl)sulfonyl)-1H-indol-2-yl)-[1,1'-biphenyl]-4-carboxylate (42)

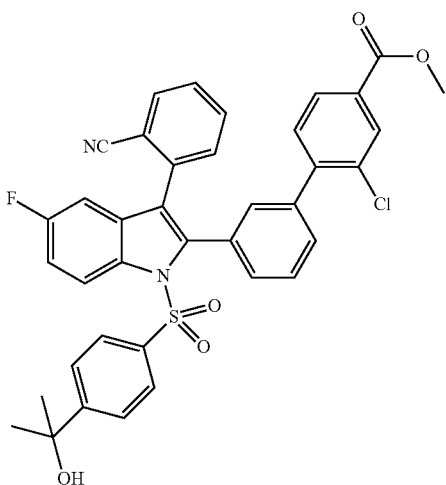

To a solution of compound 42d (350 mg, 0.49 mmol), (2-cyanophenyl)boronic acid (217 mg, 1.47 mmol) and K₂CO₃ (210 mg, 1.47 mmol) in a mixture of dioxane and H₂O (15 mL, 10:1) was added Pd(dppf)Cl₂ (45 mg) under argon. The mixture was stirred at 60° C. for 4 h, cooled, quenched with water (20 mL) and extracted with EA (3×20 mL). The combined organic layer was washed with brine (20 mL), dried over Na₂SO₄, filtered, concentrated and purified by prep-TLC (PE:EA=8:5) to give compound 42 as a yellow solid.

Example 43/1 and Example 43/2

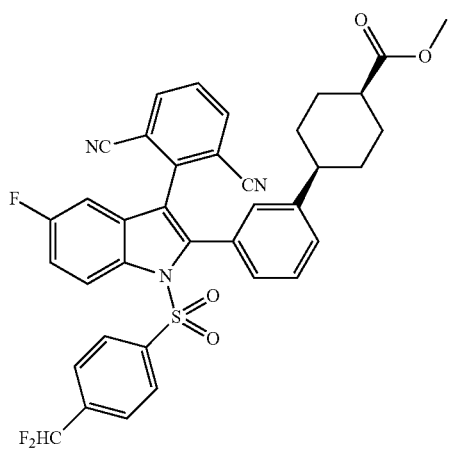

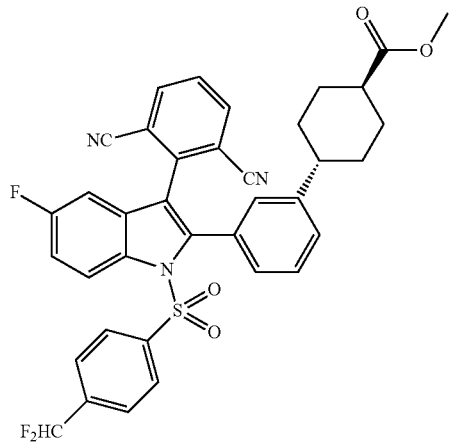

Separated Isomers Methyl (1s,4s)-4-(3-(3-(2,6-dicyanophenyl)-1-((4-(difluoro-methyl)phenyl)sulfonyl)-5-fluoro-1H-indol-2-yl)phenyl)cyclohexane-1-carboxylate (43/1) and methyl (1r,4r)-4-(3-(3-(2,6-dicyanophenyl)-1-((4-(difluoromethyl)phenyl)sulfonyl)-5-fluoro-1H-indol-2-yl)phenyl)cyclohexane-1-carboxylate (43/2)

To a solution of compound 8/4 (665 mg, 1.00 mmol) in MeOH (10 mL) was added Pd/C (100 mg). The mixture was stirred at rt for 16 h under H₂. The catalyst was filtered off and washed with MeOH (15 mL). The combined filtrates were concentrated. The residue was purified by prep-TLC (EA:PE=1:3) to give the two separated compounds 43/1 and 43/2 as white solids, respectively.

Example 44

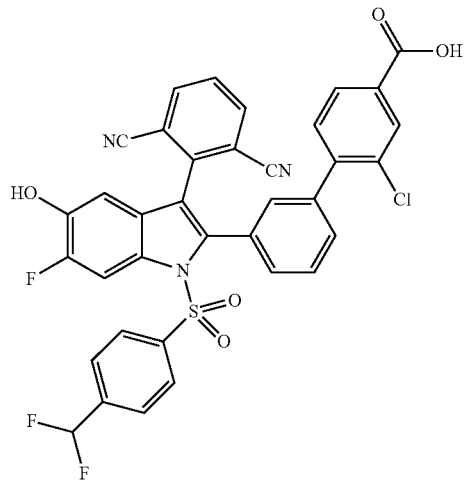

429

Step 1: Methyl 3'-((2-amino-4-fluoro-5-methoxy-phenyl)ethynyl)-2-chloro-[1,1'-biphenyl]-4-carboxylate (44a)

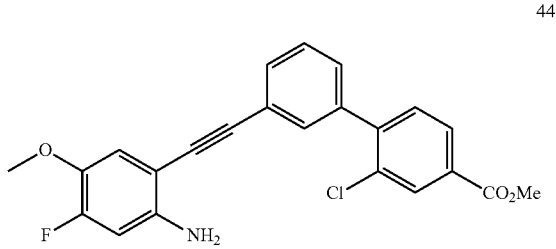

44a

To a solution of compound P30 (1.39 g, 5.10 mmol) in TEA (20 mL) was added Pd(PPh$_3$)$_4$ (237 mg, 205 µmol), CuI (78 mg, 0.41 mmol), PPh$_3$ (108 mg, 0.41 mmol) and 2-bromo-5-fluoro-4-methoxyaniline (1.34 g, 6.12 mmol). The mixture was stirred at 60° C. under N$_2$ overnight. The reaction was cooled, filtered, concentrated and purified by FCC (PE:EA=1:1) to give compound 44a as a light yellow solid.

Step 2: Methyl 2-chloro-3'-((2-((4-(difluoromethyl) phenyl)sulfonamido)-4-fluoro-5-methoxy-phenyl) ethynyl)-[1,1'-biphenyl]-4-carboxylate (44b)

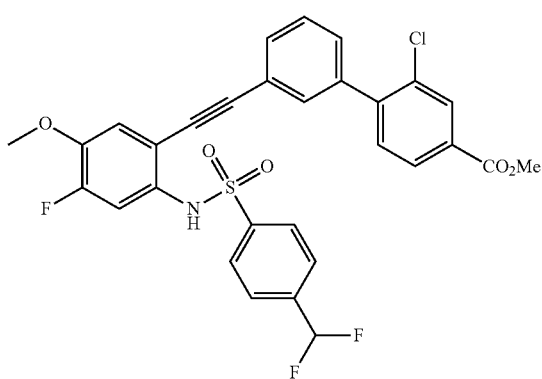

44b

To a solution of compound 44a (818 mg, 2.00 mmol) in DCM (10 mL) was added 4-(difluoromethyl)benzene-1-sulfonyl chloride (542 mg, 2.40 mmol), pyridine (316 mg, 4.00 mmol) and DMAP (89 mg). The mixture was stirred at rt overnight, then DCM (20 mL) was added and the mixture was washed with 2N aq. HCl (2×20 mL) and brine (40 mL). The organic layer was dried over Na$_2$SO$_4$, concentrated and purified by FCC (PE:DCM=1:1) to give compound 44b as a white solid.

430

Step 3: Methyl 2-chloro-3'-(3-(2,6-dicyanophenyl)-1-((4-(difluoromethyl)phenyl)sulfonyl)-6-fluoro-5-methoxy-1H-indol-2-yl)-[1,1'-biphenyl]-4-carboxylate (44c)

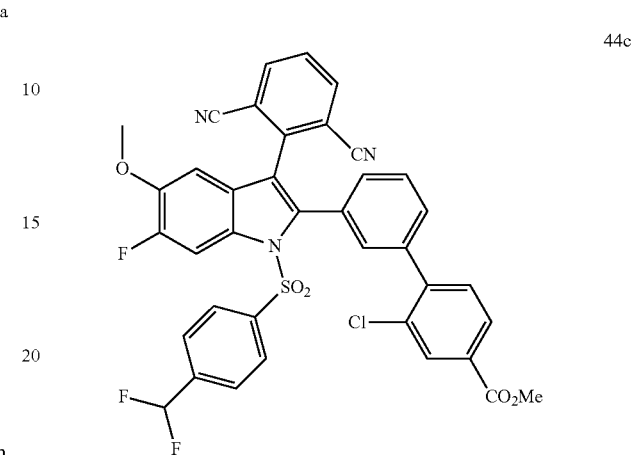

44c

To a solution of compound 44b (599 mg, 1.00 mmol) in dioxane (5 mL) was added 2-bromo-isophthalonitrile (310 mg, 1.50 mmol), K$_2$CO$_3$ (276 mg, 2.00 mmol) and Pd(PPh$_3$)$_4$ (47 mg, 40 µmol) under N$_2$. The mixture was stirred at 90° C. for 4 h under N$_2$. Upon completion, the mixture was cooled to rt, poured into EA (20 mL) and washed with H$_2$O (2×20 mL) and brine (20 mL). The organic layer was dried over Na$_2$SO$_4$, concentrated and purified by FCC (EA:PE=1:1) to give compound 44c as a yellow solid.

Step 4: 2-Chloro-3'-(3-(2,6-dicyanophenyl)-1-((4-(difluoromethyl)phenyl)sulfonyl)-6-fluoro-5-hydroxy-1H-indol-2-yl)-[1,1'-biphenyl]-4-carboxylic Acid (44)

To a solution of compound 44c (390 mg, 0.53 mmol) in CCl$_4$ (10 mL) was added iodotrimethylsilane (5 mL) and NaI (159 mg, 1.06 mmol) and the mixture was stirred at 85° C. overnight. The solvent was removed and the residue was partitioned between sat. aq. NaS$_2$O$_3$ and EA. The aq. phase was again extracted with EA (3×20 mL). The combined organic layer was washed with brine, dried over Na$_2$SO$_4$, filtered, concentrated and purified by prep-HPLC to afford compound 44 as a white solid. $^1$H-NMR (400 MHz, CD$_3$OD) δ: 8.12 (d, J=11.7 Hz, 1H), 8.10-7.93 (m, 4H), 7.70 (t, J=7.9 Hz, 1H), 7.58-7.29 (m, 8H), 7.00 (s, 1H), 6.83-6.48 (m, 2H). MS: 696.0 (M−1)$^−$.

Example 45

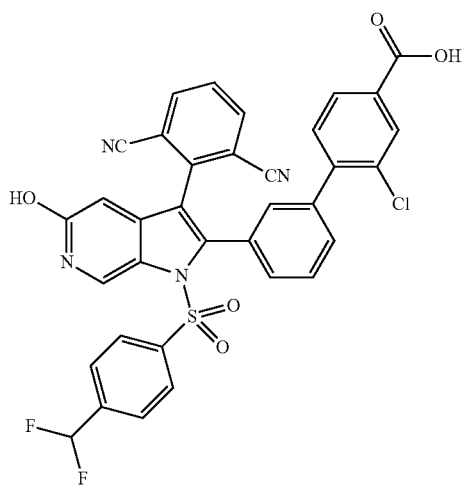

2-Chloro-3'-(3-(2,6-dicyanophenyl)-1-((4-(difluoromethyl)phenyl)sulfonyl)-5-hydroxy-1H-pyrrolo[2,3-c]pyridin-2-yl)-[1,1'-biphenyl]-4-carboxylic Acid (45)

If one were to treat a solution of compound 29/3 in ACN (10 mL) with chlorotrimethylsilane and sodium iodide under reflux one would obtain compound 45.

If one were to follow the procedures described above using appropriate building blocks, the following compounds can be prepared:

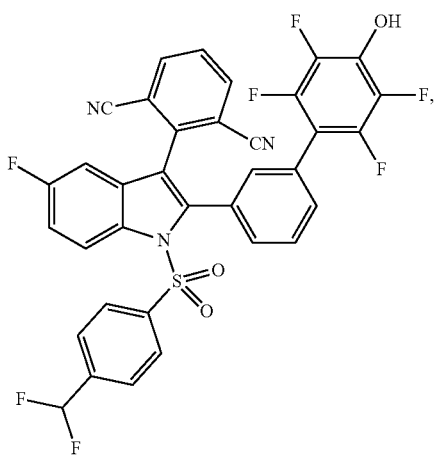

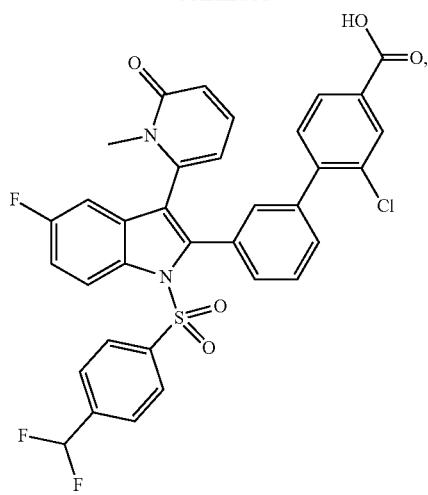

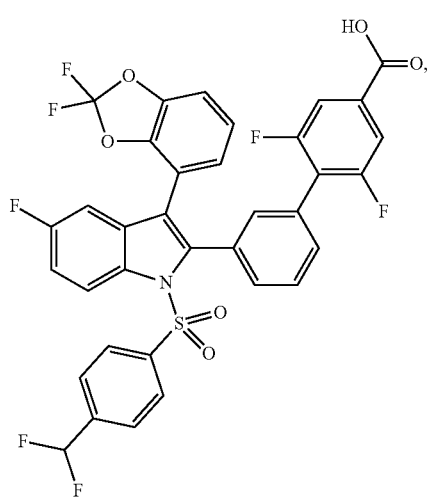

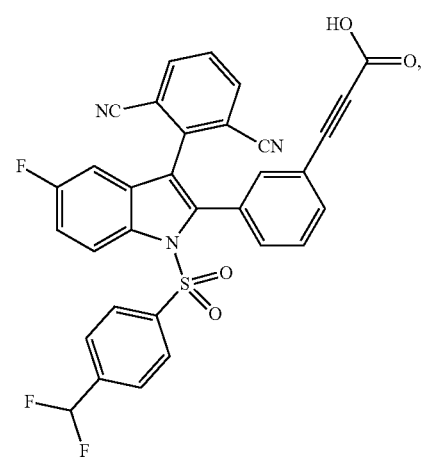

433
-continued
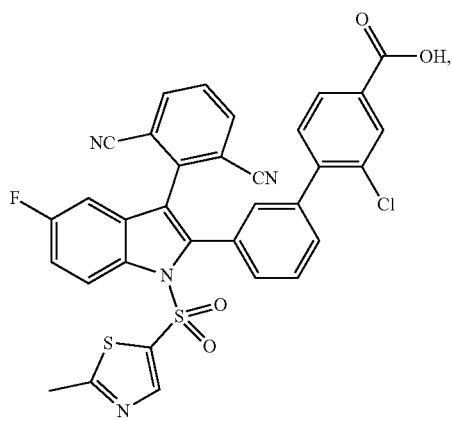
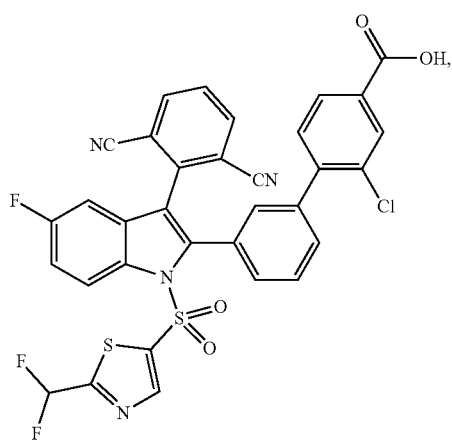
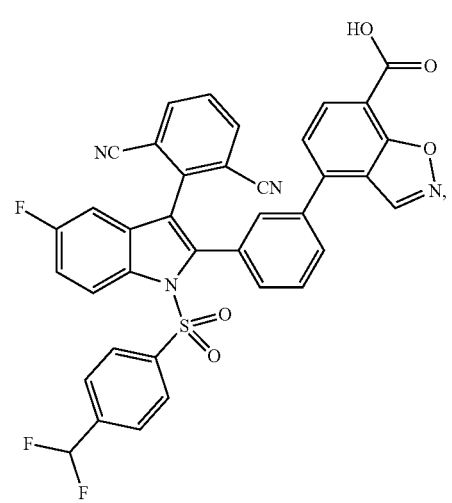
434
-continued
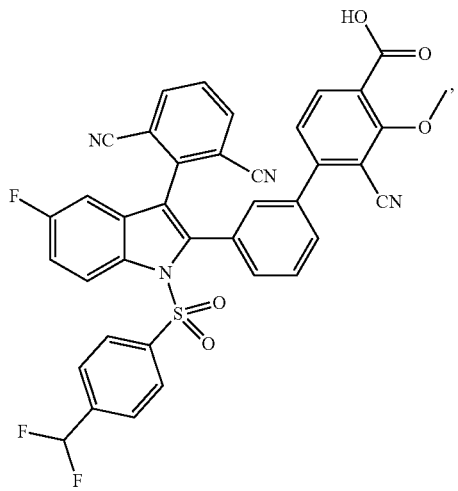
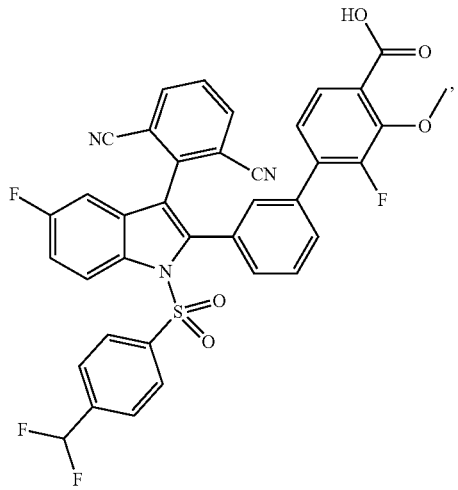
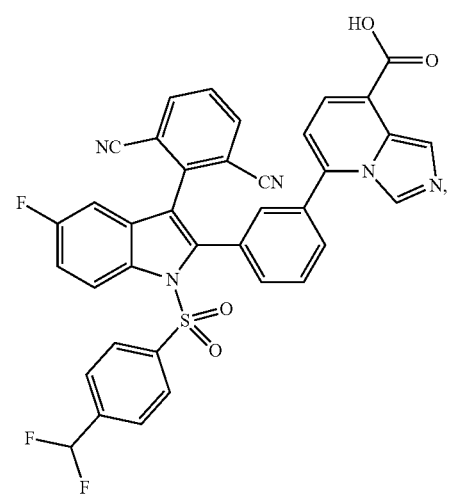

435
-continued
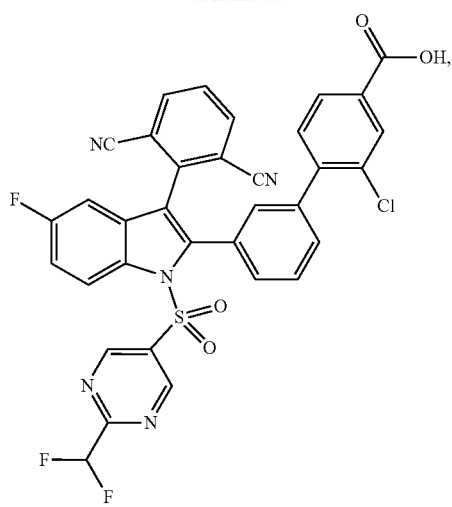
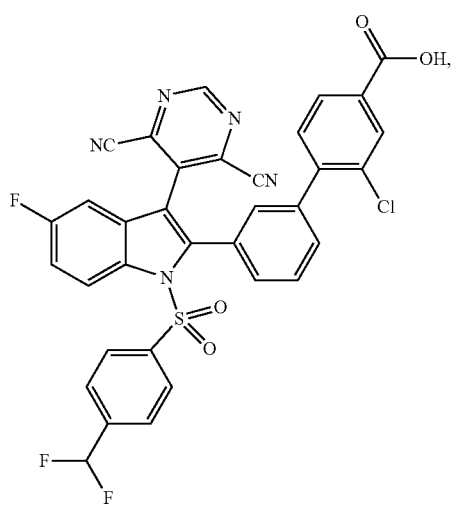
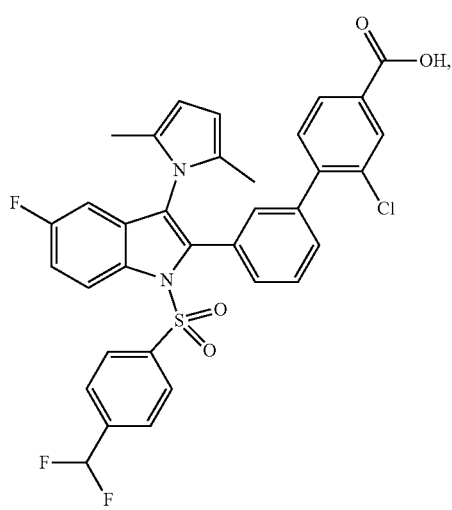
436
-continued
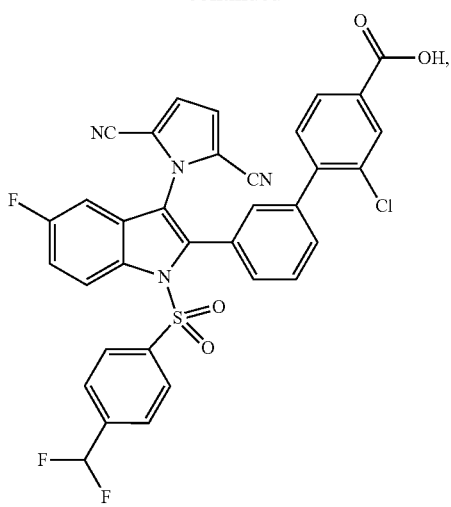
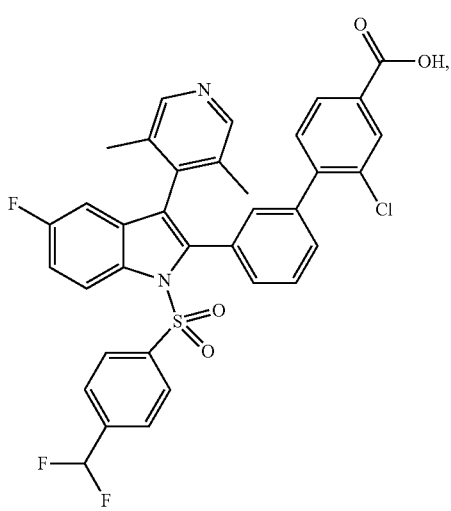
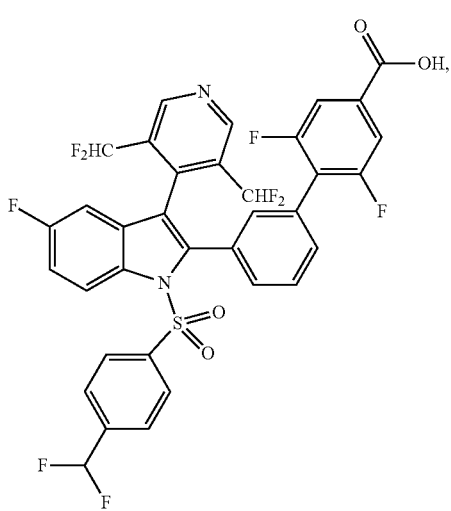

437
-continued
438
-continued
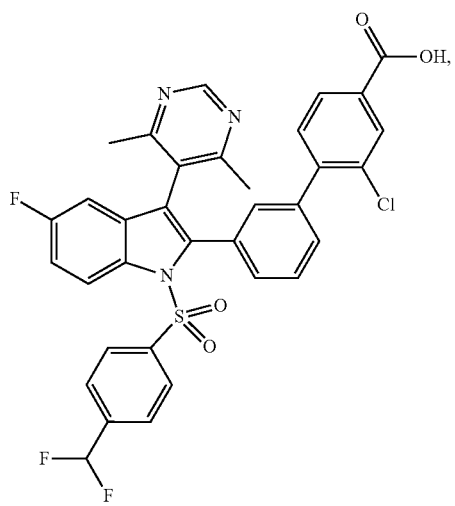
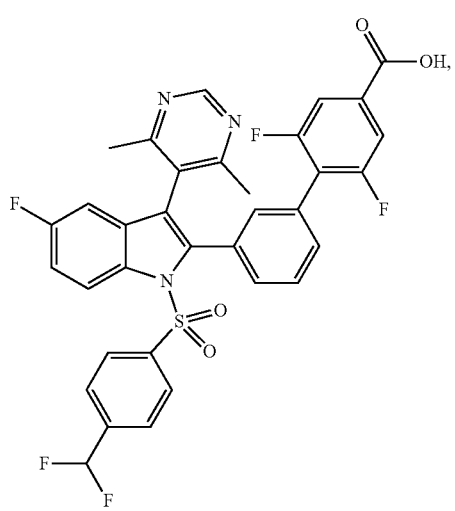
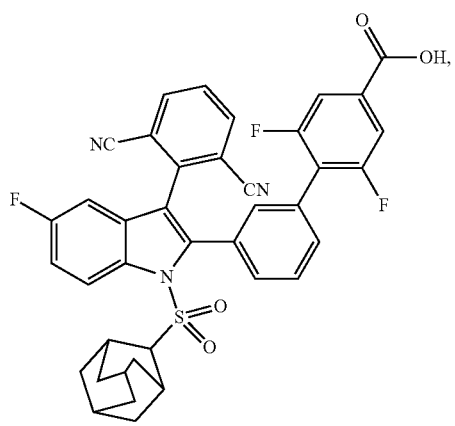
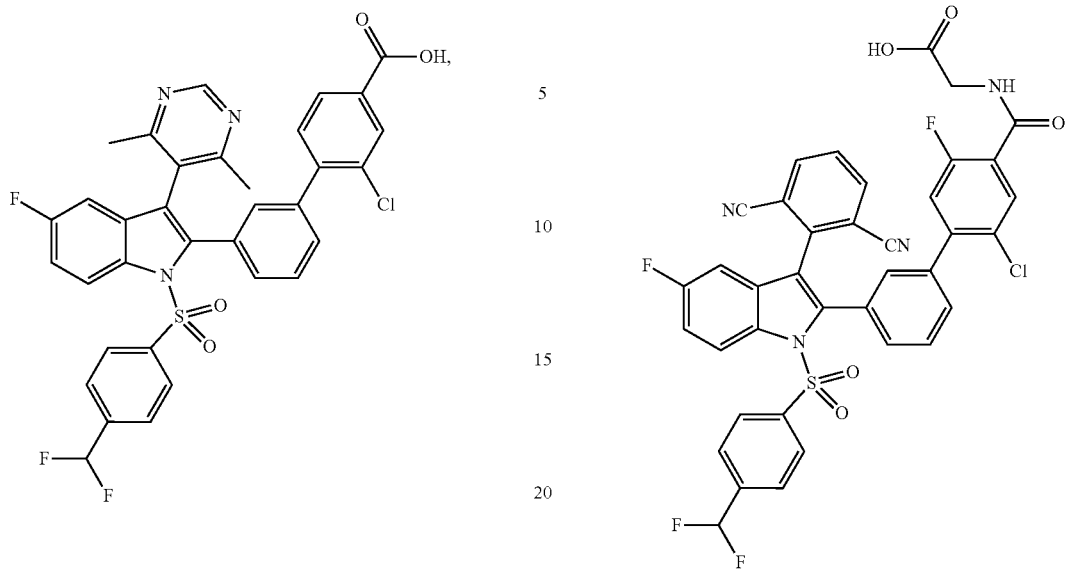
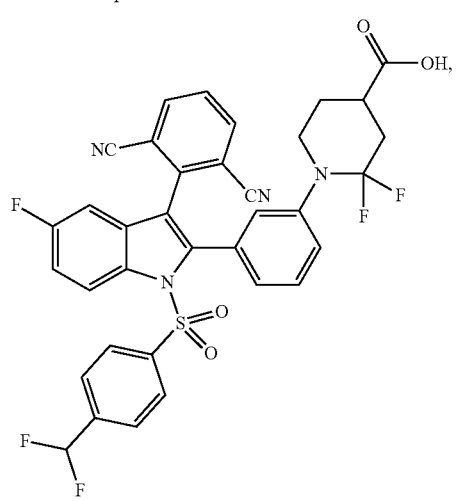
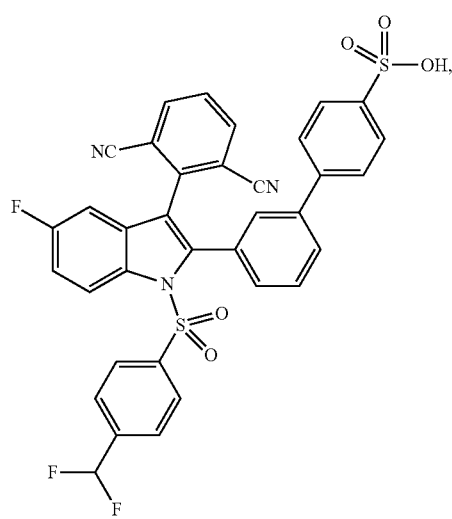

439
-continued
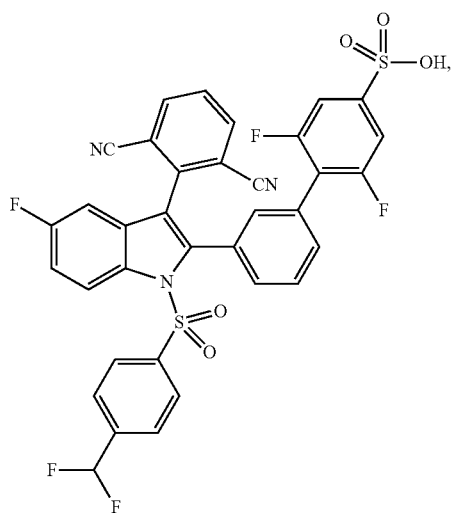
440
-continued
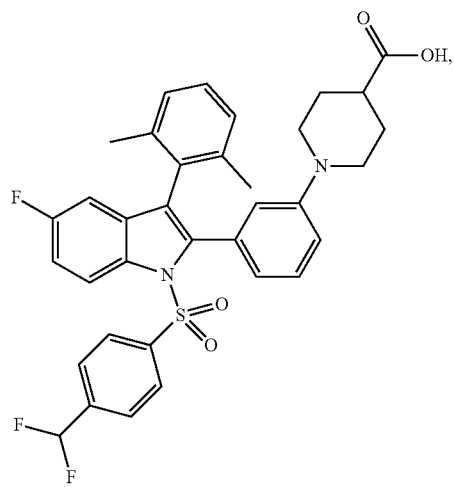
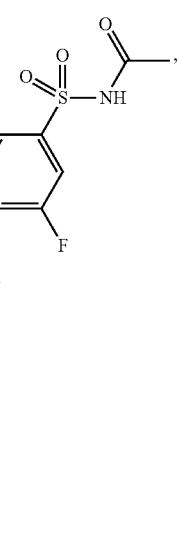
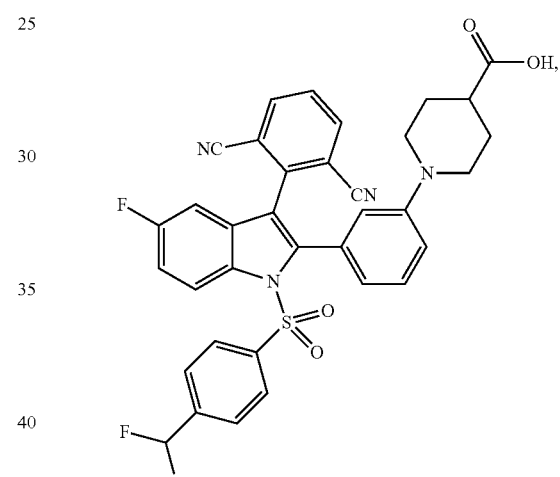
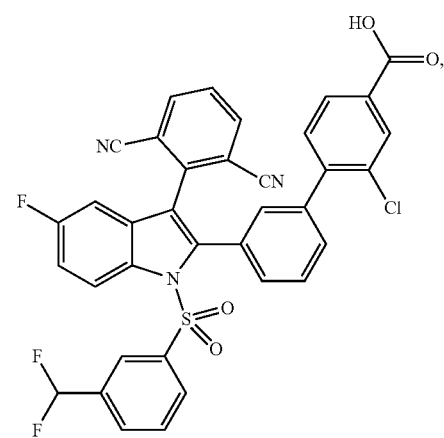
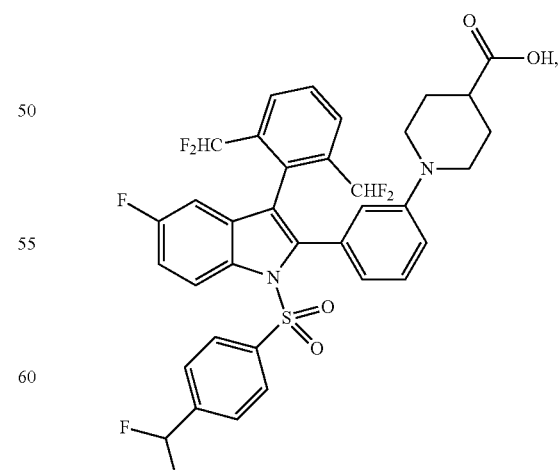

441
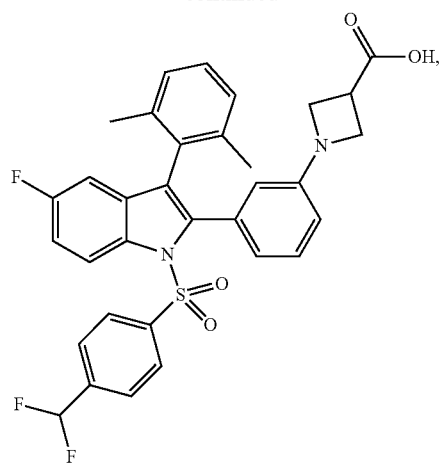
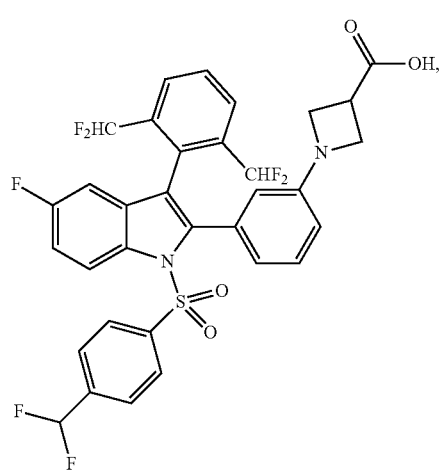
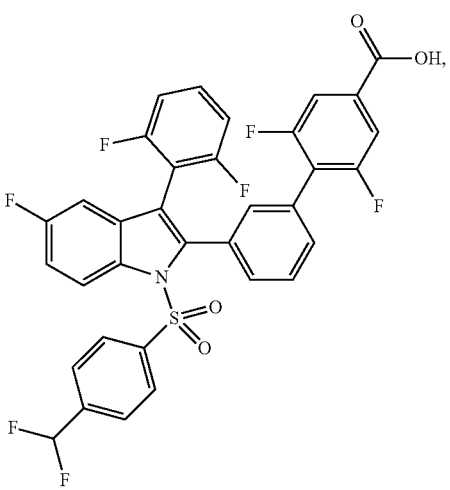
442
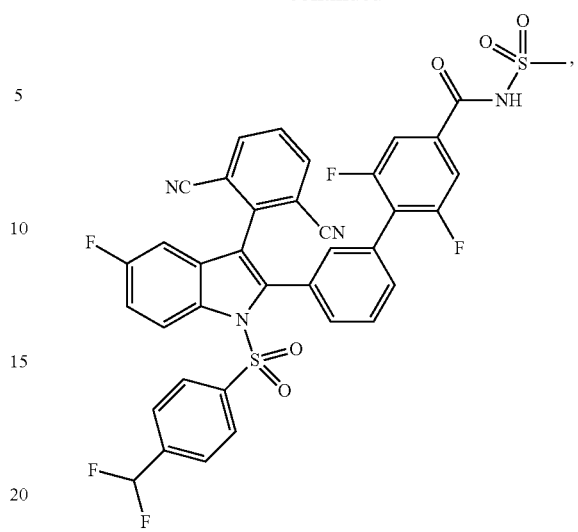
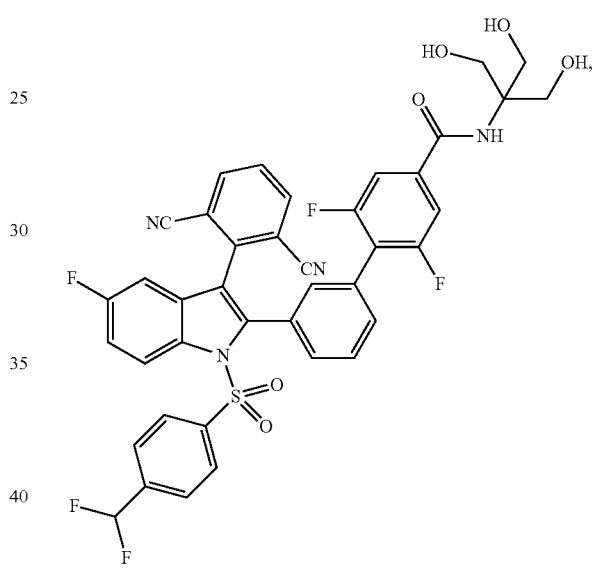
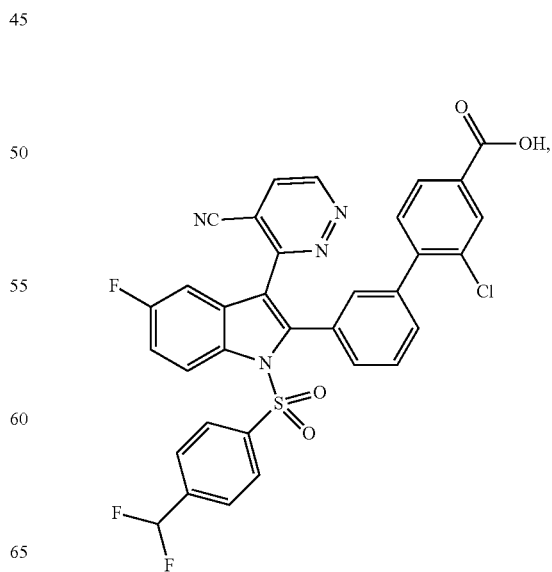

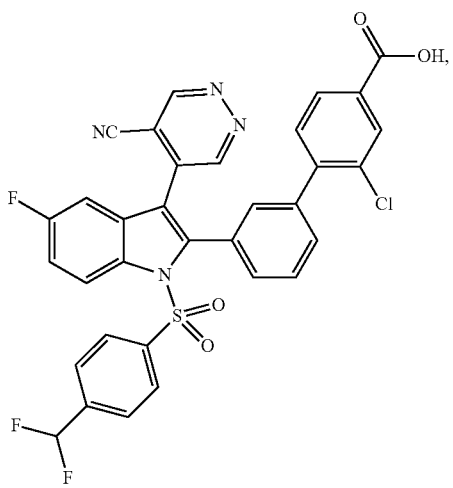
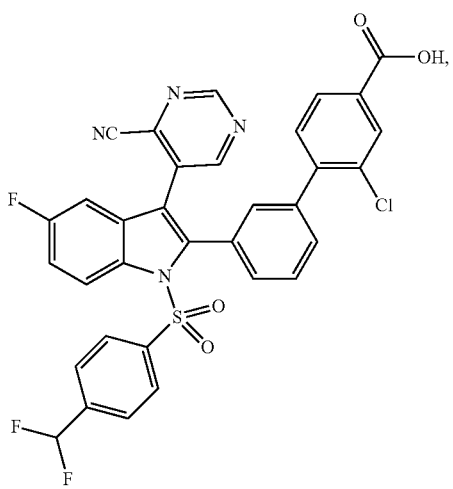
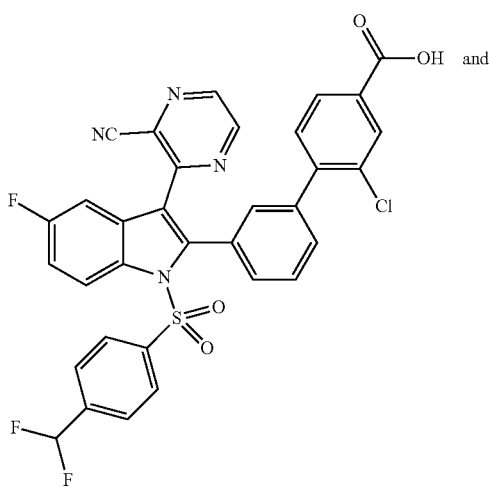

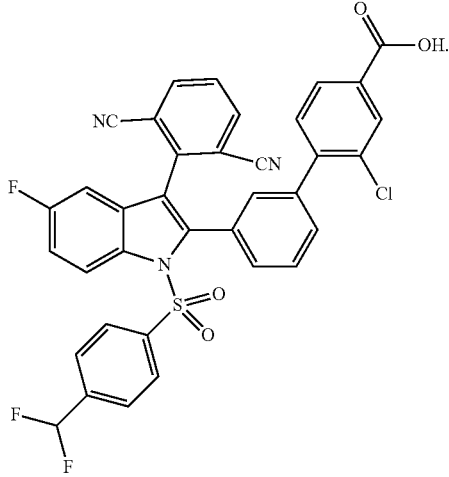

Compound Stock Solutions

The tested compounds were usually dissolved, tested and stored as 20 mM stock solutions in DMSO. Since sulfonyl acetic acid derivatives tend to decarboxylate under these conditions, these stock solutions were prepared, tested and stored as 20 mM DMSO stock solutions containing 100 mM trifluoroacetic acid (5 equivalents). Sulfonyl acetic acid derivatives are shelf stable as solid at rt for long time as reported by Griesbrecht et al. (Synlett 2010:374) or Faucher et al. (J. Med. Chem. 2004; 47:18).

TR-FRETβ Activity Assay

Recombinant GST-LXRβ ligand-binding domain (LBD; amino acids 156-461; NP009052; SEQ ID NO:4) was expressed in *E. coli* and purified via gluthathione-sepharose affinity chromatography. N-terminally biotinylated NCoA3 coactivator peptide (SEQ ID NO:7) was chemically synthesized (Eurogentec). Assays were done in 384 well format (final assay volume of 25 μL/well) in a Tris/HCl buffer (pH 6.8) containing KCl, bovine serum albumin, Triton-X-100 and 1 μM 24(S)-25-epoxycholesterol as LXR-prestimulating agonist. Assay buffer was provided and test articles (potential LXR inverse agonists) were titrated to yield final assay concentrations of 50 μM, 16.7 μM, 5.6 μM, 1.9 μM, 0.6 μM, 0.2 μM, 0.07 μM, 0.02 μM, 0.007 μM, 0.002 μM with one vehicle control. Finally, a detection mix was added containing anti GST-Tb cryptate (CisBio; 610SAXLB) and Streptavidin-XL665 (CisBio; 610SAXLB) as fluorescent donor and acceptor, respectively, as well as the coactivator peptide and LXRβ-LBD protein (SEQ ID NO:4). The reaction was mixed thoroughly, equilibrated for 1 h at 4° C. and vicinity of LXRβ and coactivator peptide was detected by measurement of fluorescence in a VictorX4 multiplate reader (PerkinElmer Life Science) using 340 nm as excitation and 615 and 665 nm as emission wavelengths. Assays were performed in triplicates.

Final Assay Concentrations of Components:

240 mM KCl, 1 μg/μL BSA, 0.002% Triton-X-100, 125 pg/μL anti GST-Tb cryptate, 2.5 ng/μL Streptavidin-XL665, coactivator peptide (400 nM), LXRβ protein (530 μg/mL, i.e. 76 nM).

LXR Gal4 Reporter Transient Transfection Assays

LXRα and LXRβ activity status was determined via detection of interaction with coactivator and corepressor proteins in mammalian two-hybrid experiments (M2H). For this, via transient transfection the full length (FL) proteins of LXRα (amino acids 1-447; NP005684; SEQ ID NO:1) or LXRβ-(amino acids 1-461; NP009052; SEQ ID NO:2) or the ligand-binding domains (LBD) of LXRα (amino acids 155-447 SEQ ID NO:3) or LXRβ (amino acids 156-461; SEQ ID NO:4) were expressed from pCMV-AD (Stratagene) as fusions to the transcriptional activation domain of NFkB. As cofactors, domains of either the steroid receptor coactivator 1 (SRC1; amino acids 552-887; SEQ ID NO:5) or of the corepressor NCoR (amino acids 1906-2312; NP006302; SEQ ID NO:6) were expressed as fusions to the DNA binding domain of the yeast transcription factor GAL4 (from pCMV-BD; Stratagene). Interaction was monitored via activation of a coexpressed Firefly Luciferase Reporter gene under control of a promoter containing repetitive GAL4 response elements (vector pFRLuc; Stratagene). Transfection efficiency was controlled via cotransfection of constitutively active pRL-CMV *Renilla reniformis* luciferase reporter (Promega). HEK293 cells were grown in minimum essential medium (MEM) with 2 mM L-glutamine and Earle's balanced salt solution supplemented with 8.3% fetal bovine serum, 0.1 mM non-essential amino acids, 1 mM sodium pyruvate, at 37° C. in 5% $CO_2$. $3.5 \times 10^4$ cells/well were plated in 96-well cell culture plates in growth medium supplemented with 8.3% fetal bovine serum for 16-20 h to ~90% confluency. For transfection, medium was taken off and LXR and cofactor expressing plasmids as well as the reporter plasmids are added in 30 μL OPTIMEM/well including polyethylene-imine (PEI) as vehicle. Typical amounts of plasmids transfected/well: pCMV-AD-LXR (5 ng), pCMV-BD-cofactor (5 ng), pFR-Luc (100 ng), pRL-CMV (0.5 ng). Compound stocks were prepared in DMSO, prediluted in MEM to a total volume of 120 μL, and added 4 h after addition of the transfection mixture (final vehicle concentration not exceeding 0.2%). Cells were incubated for additional 16 h, lysed for 10 min in 1× Passive Lysis Buffer (Promega) and Firefly and *Renilla* luciferase activities were measured sequentially in the same cell extract using buffers containing D-luciferin and coelenterazine, respectively. Measurements of luminescence were done in a BMG-luminometer.

| Materials | Company | Cat.No. |
| --- | --- | --- |
| HEK293 cells | DSMZ | ACC305 |
| MEM | Sigma-Aldrich | M2279 |
| OPTIMEM | LifeTechnologies | 11058-021 |
| FCS | Sigma-Aldrich | F7542 |
| Glutamax | Invitrogen | 35050038 |
| Pen/Strep | Sigma Aldrich | P4333 |
| Sodium Pyruvate | Sigma Aldrich | S8636 |
| Non Essential Amino Acids | Sigma Aldrich | M7145 |
| Trypsin | Sigma-Aldrich | T3924 |
| PBS | Sigma Aldrich | D8537 |
| PEI | Sigma Aldrich | 40.872-7 |
| Passive Lysis Buffer (5×) | Promega | E1941 |
| D-Luciferine | PJK | 260150 |
| Coelentrazine | PJK | 26035 |

TABLE 1

LXR activity data

| Ex. # | FRETβ | LBD-M2H Gal4α | LBD-M2H Gal4β | FL-M2H Gal4α | FL-M2H Gal4β |
| --- | --- | --- | --- | --- | --- |
| 1/23 | C | D | D | | |
| 1/26 | *B* | C | *D* | | |
| 1/27 | B | C | D | | |
| 1/28 | B | *C* | *D* | | |
| 1/39 | A | *B* | — | | |
| 1/40 | B | C | D | | |
| 1/41 | B | *C* | *D* | | |
| 1/42 | B | *D* | D | | |
| 1/122 | C | | | D | D |
| 1/139 | C | | | D | D |
| 2 | C | | | D | D |
| 2/1 | C | | | C | C |
| 2/2 | C | | | C | C |
| 2/16 | D | | | D | D |
| 2/18 | C | | | C | D |
| 3 | D | | | D | D |
| 3/1 | C | | | C | C |
| 3/2 | B | | | C | D |
| 3/3 | B | | | C | C |
| 3/4 | C | | | C | D |
| 3/5 | C | | | C | C |
| 3/6 | B | | | C | C |
| 3/7 | B | | | — | D |
| 3/8 | B | C | D | | |
| 3/9 | B | C | D | | |
| 3/10 | C | | | C | D |
| 3/11 | B | | | C | — |
| 3/12 | C | | | D | D |
| 3/13 | B | | | D | D |
| 3/14 | B | | | C | C |
| 3/15 | B | | | — | |
| 3/16 | B | *C* | C | | |
| 3/17 | B | C | D | | |
| 3/18 | B | C | D | | |
| 3/19 | B | C | C | | |
| 3/20 | B | C | D | | |
| 3/21 | C | | | D | D |
| 3/22 | D | | | D | D |
| 3/23 | C | | | D | D |
| 3/24 | | D | D | D | D |
| 3/25 | B | | | C | D |
| 3/26 | B | | | C | D |
| 3/27 | B | | | C | C |
| 3/28 | A | | | — | B |
| 3/29 | B | | | — | — |
| 3/30 | C | | | D | D |
| 3/31 | C | | | C | C |
| 3/32 | C | | | C | D |
| 3/33 | B | | | C | D |
| 3/34 | C | | | C | D |
| 3/35 | C | | | C | D |
| 3/36 | B | | | C | C |
| 3/37 | C | | | D | D |
| 3/38 | C | | | D | D |
| 3/39 | C | | | C | D |
| 3/40 | B | | | C | D |
| 3/41 | B | | | D | D |
| 3/42 | B | C | D | C | D |
| 3/43 | B | *C* | *C* | *C* | *D* |
| 3/44 | B | D | D | D | D |
| 3/45 | B | | | C | C |
| 3/46 | C | D | D | D | D |
| 3/47 | C | | | D | D |
| 3/48 | C | | | D | D |
| 3/49 | C | | | D | D |
| 3/50 | C | | | D | D |
| 3/51 | B | C | C | | |
| 3/52 | C | | | C | C |
| 3/53 | D | | | D | D |
| 3/54 | C | | | D | D |
| 3/55 | C | | | D | D |
| 3/56 | D | | | D | D |
| 3/57 | C | | | D | D |
| 3/58 | B | | | D | D |
| 3/59 | D | | | D | D |
| 3/60 | C | | | D | D |
| 3/61 | C | | | C | C |
| 3/62 | C | | | C | D |
| 3/63 | D | | | D | D |
| 3/64 | C | | | D | D |

TABLE 1-continued

LXR activity data

| Ex. # | FRETβ | LBD-M2H Gal4α | LBD-M2H Gal4β | FL-M2H Gal4α | FL-M2H Gal4β |
|---|---|---|---|---|---|
| 3/65 | C | | | D | D |
| 3/66 | B | | | C | C |
| 3/67 | C | | | C | C |
| 3/68 | C | | | D | D |
| 3/69 | C | | | C | C |
| 3/70 | C | | | C | C |
| 3/71 | D | | | D | D |
| 3/72 | D | | | D | D |
| 3/73 | D | | | D | D |
| 4 | B | | | D | C |
| 4/1 | B | | | C | D |
| 4/2 | B | | | C | C |
| 4/3 | B | | | D | D |
| 5 | C | | | B | B |
| 5/1 | C | | | B | C |
| 5/2 | C | | | C | |
| 5/3 | C | | | | D |
| 5/4 | B | | | C | D |
| 5/5 | C | | | C | C |
| 5/6 | C | | | D | D |
| 5/7 | C | | | C | D |
| 5/8 | C | | | C | C |
| 5/9 | C | | | C | D |
| 5/10 | B | | | C | C |
| 6 | C | | | D | D |
| 6/1 | C | | | D | D |
| 6/2 | C | | | D | D |
| 6/3 | D | | | D | D |
| 8 | C | | | C | D |
| 8/1 | C | | | D | D |
| 8/3 | C | | | C | D |
| 8/7 | C | | | C | D |
| 8/8 | D | | | D | D |
| 10 | C | | | D | C |
| 10/1 | D | | | D | D |
| 10/2 | D | | | D | D |
| 10/3 | D | | | D | D |
| 10/4 | D | | | C | D |
| 11 | D | | | D | D |
| 11/1 | D | | | D | D |
| 11/2 | D | | | D | D |
| 11/3 | D | | | D | D |
| 11/4 | C | | | D | D |
| 11/5 | D | | | D | D |
| 11/6 | D | | | D | D |
| 11/7 | D | | | D | D |
| 11/8 | D | | | D | D |
| 11/9 | D | | | D | D |
| 11/10 | D | | | D | D |
| 11/11 | D | | | D | D |
| 11/12 | D | | | D | D |
| 11/13 | D | | | D | D |
| 11/14 | D | | | D | D |
| 11/15 | D | | | D | D |
| 11/16 | C | | | D | D |
| 11/17 | D | | | D | D |
| 11/18 | C | | | D | D |
| 11/19 | C | | | D | D |
| 11/20 | C | | | D | D |
| 11/21 | D | | | D | D |
| 11/22 | D | | | D | D |
| 11/23 | D | | | D | D |
| 11/24 | C | | | C | C |
| 11/25 | C | | | C | D |
| 11/26 | D | | | D | D |
| 11/27 | D | | | D | D |
| 11/28 | D | | | D | D |
| 11/29 | D | | | D | D |
| 11/30 | D | | | D | D |
| 11/31 | D | | | D | D |
| 11/32 | D | | | D | D |
| 11/33 | D | | | D | D |
| 11/34 | D | | | D | D |
| 11/35 | D | | | D | D |
| 11/36 | D | | | D | D |
| 11/37 | D | | | D | D |
| 11/38 | D | | | D | D |
| C11/39 | C | | | D | D |
| 11/40 | C | | | D | D |
| 11/41 | D | | | D | D |
| 11/42 | A | | | C | C |
| 11/43 | C | | | C | C |
| 11/44 | D | | | D | D |
| 11/45 | D | | | D | D |
| 11/46 | D | | | D | D |
| 11/47 | C | | | C | C |
| C11/48 | D | | | D | D |
| 11/49 | D | | | D | D |
| 11/50 | D | | | D | D |
| 11/51 | D | | | D | D |
| 11/52 | D | | | D | D |
| 11/53 | D | | | D | D |
| 11/54 | D | | | D | D |
| 11/55 | D | | | D | D |
| 11/56 | D | | | D | D |
| 11/57 | D | | | D | D |
| 11/58 | D | | | D | D |
| 11/59 | D | | | D | D |
| 11/60 | | | | D | D |
| 11/61 | C | | | D | D |
| 11/62 | C | | | D | D |
| 11/63 | C | | | D | D |
| 11/64 | C | | | D | D |
| 11/65 | D | | | D | D |
| 11/66 | C | | | D | D |
| 11/67 | C | | | D | D |
| 11/68 | D | | | D | D |
| 11/69 | D | | | D | D |
| 12 | C | | | D | D |
| 12/1 | C | | | D | D |
| 12/2 | C | | | D | D |
| 12/3 | C | | | D | D |
| 12/4 | C | | | D | D |
| 12/5 | D | | | D | D |
| 12/6 | B | | | C | B |
| 12/7 | C | | | C | C |
| 12/8 | B | | | C | C |
| 12/9 | C | | | C | C |
| 12/10 | D | | | D | D |
| 13 | C | D | D | | |
| 13/1 | B | D | D | | |
| 15 | A | B | A | | |
| 15/1 | B | *C* | *C* | | |
| 15/2 | A | *C* | C | | |
| 15/3 | A | — | — | | |
| 15/4 | B | *C* | D | | |
| 15/5 | B | *D* | D | | |
| 15/6 | B | — | C | | |
| 17 | A | — | *B* | | |
| 19 | A | — | — | | |
| 20 | C | D | D | | |
| 20/2 | B | C | D | | |
| 20/3 | C | D | D | | |
| 20/4 | B | D | D | | |
| 20/5 | B | C | C | | |
| 20/6 | C | C | D | | |
| 20/7 | B | C | D | | |
| 20/11 | C | D | D | | |
| 20/12 | B | D | *D* | | |
| 20/13 | C | D | D | | |
| 20/14 | C | D | D | | |
| 20/15 | C | — | *C* | | |
| 20/16 | B | C | C | | |
| 20/17 | — | — | C | | |
| 20/18 | — | C | D | | |
| 20/19 | A | *C* | C | | |
| 20/20 | B | *B* | C | | |
| 20/21 | *B* | C | D | | |
| 20/22 | C | C | C | | |
| 20/23 | *B* | C | C | | |

TABLE 1-continued

LXR activity data

| Ex. # | FRETβ | LBD-M2H Gal4α | LBD-M2H Gal4β | FL-M2H Gal4α | FL-M2H Gal4β |
|---|---|---|---|---|---|
| 21 | A | — | B | | |
| 21/1 | B | B | B | | |
| 21/2 | B | B | B | | |
| 21/3 | D | | | D | D |
| 22 | B | C | C | | |
| 23 | A | C | C | | |
| 23/1 | B | — | *D* | | |
| 23/2 | C | | | D | D |
| 23/3 | C | | | D | D |
| 24 | B | C | D | | |
| 25 | B | C | D | | |
| 26 | C | D | D | | |
| 26/1 | B | C | D | | |
| 27 | B | — | *C* | | |
| 27/1 | B | — | — | | |
| 27/2 | B | | | | |
| 27/3 | A | — | — | | |
| 28 | B | B | *C* | | |
| 30 | C | D | D | | |
| 30/1 | C | C | D | | |
| 30/2 | B | C | C | | |
| 30/3 | | C | C | | |
| 30/4 | B | C | D | | |
| 30/5 | B | C | D | | |
| 30/6 | B | C | C | | |
| 30/7 | C | D | D | | |
| 30/8 | B | C | C | | |
| 30/9 | B | C | D | | |
| 30/10 | A | — | — | | |
| 30/11 | C | C | D | | |
| 30/12 | B | B | C | | |
| 30/13 | C | C | D | | |
| 30/14 | B | C | C | | |
| 30/15 | B | C | C | | |
| 30/16 | B | | | C | C |
| 31 | B | C | C | | |
| 32 | C | C | C | | |
| 32/1 | C | C | D | | |
| 32/2 | C | | | C | C |
| 32/4 | D | | | D | D |
| 32/5 | D | | | D | D |
| 36 | B | | | C | C |
| 36/1 | C | | | D | D |
| 37 | C | | | D | D |
| 37/1 | C | | | C | C |
| 41/1 | D | | | D | D |
| 41/2 | D | | | D | D |
| 44 | C | | | D | D |

Ranges (EC$_{50}$): —: no activity measured; A: >10 μM, B: 1 μM to <10 μM, C: 100 nM to <1 μM, D: <100 nM; italic numbers indicate that efficacy (compared to GW2033) is below 40%.

Pharmacokinetics

The pharmacokinetics of the compounds was assessed in mice after single dosing and oral administrations. Blood/plasma and liver exposure was measured via LC-MS.

The study design was as follows:

Animals: C57/bl6/J (Janvier) males

Diet: standard rodent chow

Dose: 20 mg/kg

Animal handling: animals were withdrawn from food at least 12 h before administration Design: single dose oral administration, n=3 animals per group Sacrifice: at stated time point (4, 12 or 24 h) after administration Bioanalytics: LC-MS of liver and blood/plasma samples

TABLE 2

Study results

| Example # | time point (h) | blood/plasma exposure | liver exposure | liver/blood ratio |
|---|---|---|---|---|
| GSK2033 (comparative example) | 4 | below LLOQ (14.4 ng/mL) | below LLOQ (9.6 ng/mL) | — |
| SR9238 (comparative example) | 4 | below LLOQ | below LLOQ | — |
| 3/24 | 4 | D | C | D |
| 3/48 | 12 | below LLOQ (1.2 ng/mL) | A | — |
| 5/3 | 4 | C | C | C |
| 8 | 4 | B | D | B |
| 23/2 | 4 | B | D | C |
| 30/4 | 4 | C | C | C |
| 30/7 | 4 | D | B | D |

Ranges:
blood/plasma exposure: A: >1 μM, B: 300 nM to ≤1 μM, C: 100 nM to <300 nM, D: <100 nM;
liver exposure: A: <300 nM, B: 300 nM to ≤1 μM, C: 1 μM to ≤3 μM, D: >3 μM;
liver/plasma ratio: A: <3, B: 3 to ≤10, C: 10 to ≤30, D: >30;

We confirmed that structurally unrelated LXR inverse agonists GSK2033 and SR9238 are not orally bioavailable. We found, that compounds from the present invention are orally bioavailable and the target tissue liver was effectively reached by such compounds and a systemic exposure, which is not desired, could be minimized.

Short Term HFD Mouse Model:

The in vivo transcriptional regulation of several LXR target genes by LXR modulators was assessed in mice.

For this, C57BL/6J were purchased from Elevage Janvier (Rennes, France) at the age of 8 weeks. After an acclimation period of two weeks, animals were prefed on a high fat diet (HFD) (Ssniff Spezialdiäten GmbH, Germany, Surwit EF D12330 mod, Cat. No. E15771-34), with 60 kcal % from fat plus 1% (w/w) extra cholesterol (Sigma-Aldrich, St. Louis, MO) for 5 days. Animals were maintained on this diet during treatment with LXR modulators. The test compounds were formulated in 0.5% hydroxypropylmethylcellulose (HPMC) and administered in three doses (from 1.5 to 20 mg/kg each) by oral gavage according to the following schedule: on day one, animals received treatment in the morning and the evening (ca. 17:00), on day two animals received the final treatment in the morning after a 4 h fast and were sacrificed 4 h thereafter. Animal work was conducted according to the national guidelines for animal care in Germany.

Upon termination, liver was collected, dipped in ice cold PBS for 30 seconds and cut into appropriate pieces. Pieces were snap frozen in liquid nitrogen and stored at −80° C. For the clinical chemistry analysis from plasma, alanine aminotransferase (ALT, IU/mL), cholesterol (CHOL, mg/dL) and triglycerides (TG, mg/dL) were determined using a fully-automated bench top analyzer (Respons®910, DiaSys Greiner GmbH, Flacht, Germany) with system kits provided by the manufacturer.

Analysis of gene expression in liver tissue. To obtain total RNA from frozen liver tissue, samples (25 mg liver tissue) were first homogenized with RLA buffer (4M guanidin thiocyanate, 10 mM Tris, 0.97% w:v β-mercapto-ethanol). RNA was prepared using a SV 96 total RNA Isolation system (Promega, Madison, Wisconsin, USA) following the manufacturer's instructions. cDNAs were synthesized from 0.8-1 μg of total RNA using All-in-One cDNA Supermix reverse transcriptase (Absource Diagnostics, Munich, Germany). Quantitative PCR was performed and analyzed using Prime time Gene expression master mix (Integrated DNA Technologies, Coralville, Iowa, USA) and a 384-format ABI 7900HT Sequence Detection System (Applied Biosystems, Foster City, USA). The expression of the following genes was analysed: Stearoyl-CoA desaturase1 (Scd1), fatty acid synthase (Fas) and sterol regulatory element-binding protein1 (Srebp1). Specific primer and probe sequences (commercially available) are listed in Table 3. qPCR was conducted at 95° C. for 3 min, followed by 40 cycles of 95° C. for 15 s and 60° C. for 30 s. All samples were run in duplicates from the same RT-reaction. Gene expression was expressed in arbitrary units and normalized relative to the mRNA of the housekeeping gene TATA box binding protein (Tbp) using the comparative Ct method.

TABLE 3

Primers used for quantitative PCR

| Gene | Forward Primer | Reverse Primer | Sequence Probe |
|---|---|---|---|
| Fasn | CCCCTCTGTTAATTGGC TCC (SEQ ID NO: 8) | TTGTGGAAGTGCAGGT TAGG (SEQ ID NO: 9) | CAGGCTCAGGGTGTCCC ATGTT (SEQ ID NO: 10) |
| Scd1 | CTGACCTGAAAGCCGA GAAG (SEQ ID NO: 11) | AGAAGGTGCTAACGAA CAGG (SEQ ID NO: 12) | TGTTTACAAAAGTCTCGC CCCAGCA (SEQ ID NO: 13) |
| Srebp1c | CCATCGACTACATCCGC TTC (SEQ ID NO: 14) | GCCCTCCATAGACACA TCTG (SEQ ID NO: 15) | TCTCCTGCTTGAGCTTCT GGTTGC (SEQ ID NO: 16) |
| Tbp | CACCAATGACTCCTATG ACCC (SEQ ID NO: 17) | CAAGTTTACAGCCAAG ATTCACG (SEQ ID NO: 18) | ACTCCTGCCACACCAGC CTC (SEQ ID NO: 19) |

TABLE 4

Study results

| Example # | dose [mg/kg] | plasma exposure 4 h | liver exposure 4 h | liver/plasma ratio 4 h |
|---|---|---|---|---|
| 3/48 | 20 | D | C | C |
| 3/59 | 20 | C | C | B |
| 3/64 | 20 | C | D | D |
| 3/73 | 10 | D | B | C |
| 5/3 | 20 | D | C | B |
| 8/8 | 10 | C | B | B |
| 10/1 | 10 | D | B | C |
| 10/2 | 10 | D | D | B |
| 11/11 | 20 | D | D | D |
| 11/12 | 20 | D | C | C |
| 11/13 | 20 | A | C | A |
| 11/16 | 20 | C | C | B |
| 11/17 | 20 | C | D | C |
| 11/23 | 20 | C | C | B |
| 11/26 | 10 | C | C | C |
| 11/27 | 20 | D | C | C |
| 11/33 | 20 | C | C | C |
| 11/37 | 10 | D | C | C |
| 11/49 | 20 | D | C | D |
| 11/51 | 10 | D | C | C |
| 11/53 | 10 | D | C | C |
| 11/62 | 10 | C | C | B |
| 11/63 | 10 | D | C | B |
| 11/65 | 10 | D | C | C |
| 21/3 | 10 | D | C | D |
| 23/2 | 20 | C | A | A |
| 32/5 | 10 | D | B | B |

| Example # | | Fasn suppression compared to vehicle | Srebp1c suppr. compared to vehicle | Scd1 suppression compared to vehicle |
|---|---|---|---|---|
| 3/48 | 20 | D | D | D |
| 3/59 | 20 | C | D | C |
| 3/64 | 20 | B | B | D |
| 3/73 | 10 | A | D | D |
| 5/3 | 20 | D | C | C |
| 8/8 | 10 | D | D | D |
| 10/1 | 10 | D | D | D |
| 10/2 | 10 | C | C | C |
| 11/11 | 20 | C | D | D |
| 11/12 | 20 | C | D | D |
| 11/13 | 20 | C | D | D |
| 11/16 | 20 | A | B | C |
| 11/17 | 20 | C | D | D |
| 11/23 | 20 | C | D | D |
| 11/26 | 10 | D | D | C |
| 11/27 | 20 | C | A | D |
| 11/33 | 20 | B | D | D |
| 11/37 | 10 | D | D | D |
| 11/49 | 20 | C | C | D |
| 11/51 | 10 | D | D | D |
| 11/53 | 10 | D | D | D |
| 11/62 | 10 | D | D | D |
| 11/63 | 10 | C | D | C |
| 11/65 | 10 | D | D | D |
| 21/3 | 10 | C | D | D |
| 23/2 | 20 | C | D | D |
| 32/5 | 10 | C | C | C |

Ranges:
plasma exposure: A: >1 μM, B: 300 nM to ≤1 μM, C: 100 nM to <300 nM, D: <100 nM;
liver exposure: A: <300 nM, B: 300 nM to ≤1 μM, C: 1 μM to ≤10 μM, D: >10 μM;
liver/plasma ratio: A: <5, B: 5 to ≤30, C: 30 to ≤100, D: >100;
gene suppression: A: >0.9, B: 0.6 to ≤0.9, C: 0.3 to ≤0.6, D: <0.3;

Triple oral dosing over two days (day one morning and evening, day two morning) of compounds from the present invention in mice lead to a high liver exposure with a favourable liver-to-plasma ratio. Hepatic LXR target genes were effectively suppressed. These genes are involved in the transcriptional regulation of hepatic de-novo lipogenesis (Wang et al., Nat. Rev. Mol. Cell Biol. 2015; 16:678). A suppression of these genes will reduce liver fat (liver triglycerides).

Comparative Examples

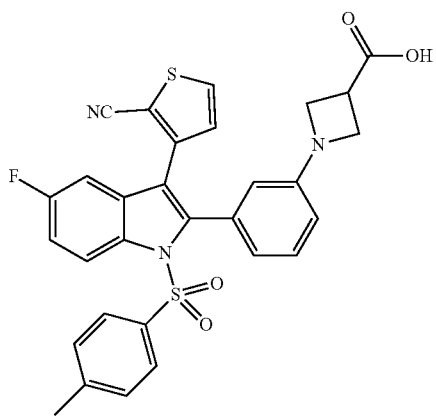

Example 3/32
FRET β           551 nM (−98%)
LBD-M2H Gal4α 106 nM (103%)
LBD-M2H Gal4β   13 nM (81%)

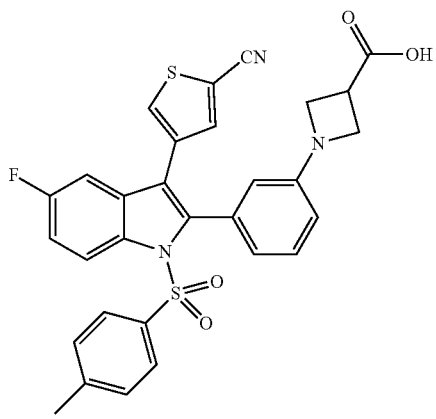

Comparative Example C3/29
FRET β           4228 nM (−102%)
FL-M2H Gal4α    inactive
FL-M2H Gal4β    inactive -continued

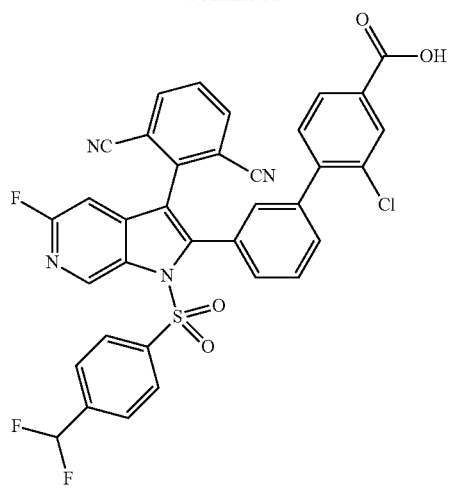

Example 11/33
FRET β           19 nM (−99%)
FL-M2H Gal4α  1.3 Nm (164%)
FL-M2H Gal4β  1.7 Nm (130%)

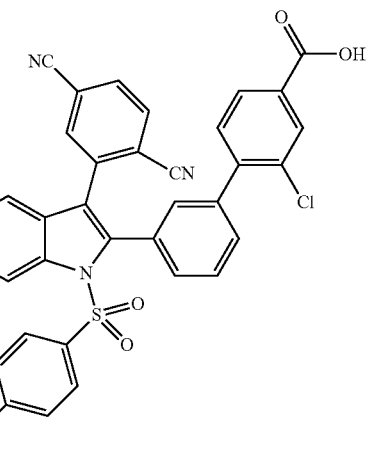

Comparative Example C11/48
FRET β           49 nM (−96%)
FL-M2H Gal4α  62 nM (118%)
FL-M2H Gal4β  32 nM (123%)

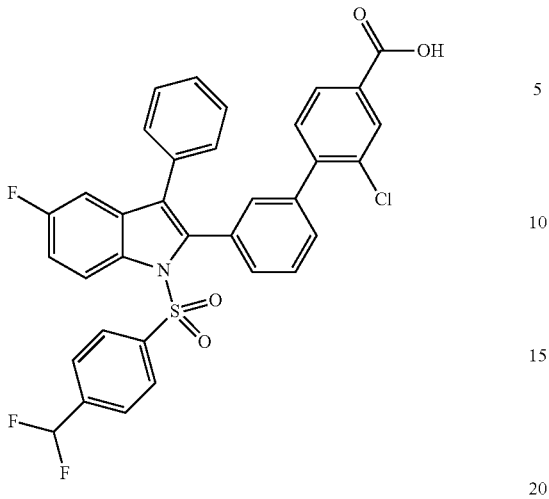

Comparative Example C11/39
FRET β     104 nM (−91%)
FL-M2H Gal4α  14 nM (117%)
FL-M2H Gal4β  14 nM (140%)

The Comparative Examples illustrate that it can be advantageous, when the cyclic moiety in 3-position of the indole (or analog) has at least one substituent in 1,2-orientation (ortho-substituent).

We claim:

1. A compound that is

2. A compound that is

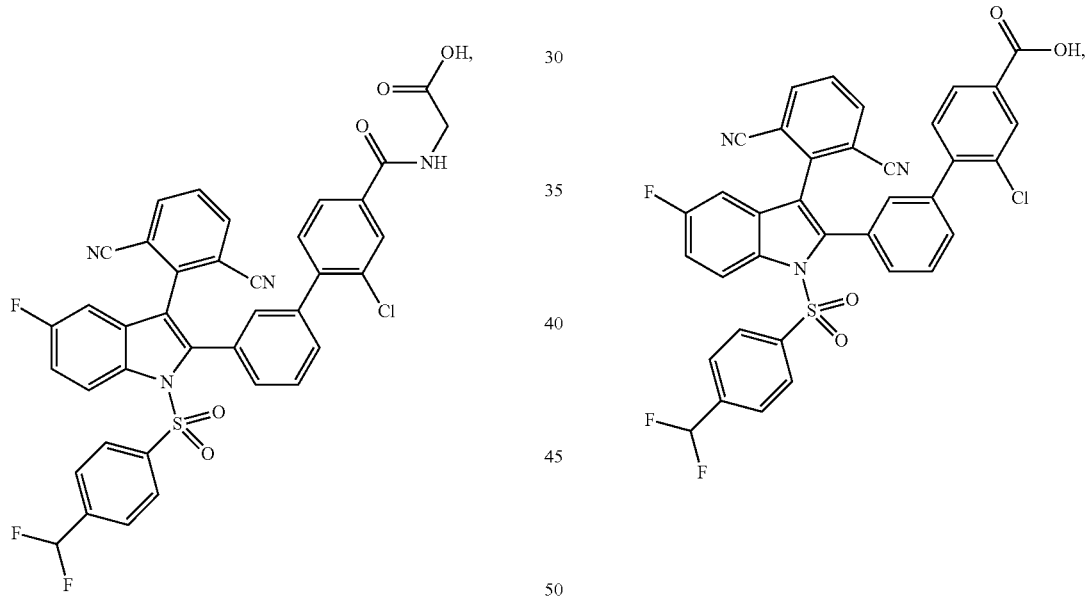

or a pharmaceutically acceptable salt thereof.

or a pharmaceutically acceptable salt thereof.

* * * * *

SEQUENCE LISTING

```
Sequence total quantity: 19
SEQ ID NO: 1           moltype = DNA   length = 1344
FEATURE                Location/Qualifiers
misc_feature           1..1344
                       note = DNA-Sequence LXR alpha-full length
source                 1..1344
                       mol_type = other DNA
                       organism = synthetic construct
SEQUENCE: 1
atgtccttgt ggctgggggc ccctgtgcct gacattcctc ctgactctgc ggtggagctg   60
tggaagccag gcgcacagga tgcaagcagc caggcccagg gaggcagcag ctgcatcctc  120
agagaggaag ccaggatgcc ccactctgct gggggtactg caggggtggg gctggaggct  180
gcagagccca cagccctgct caccagggca gagccccctt cagaacccac agagatccgt  240
ccacaaaagc ggaaaaaggg gccagccccc aaaatgctgg ggaacgagct atgcagtgtg  300
tgtggggaca aggcctcggg cttccactac aatgttctga gctgcgaggg ctgcaaggga  360
ttcttccgcc gcagcgtcat caagggagcg cactacatct gccacagtgg cggccactgc  420
cccatggaca cctacatgcg tcgcaagtgc caggagtgtc ggcttcgcaa atgccgtcag  480
gctggcatgc gggaggagtg tgtcctgtca gaagaacaga tccgcctgaa gaaactgaag  540
cggcaagagg aggaacaggc tcatgccaca tccttgcccc ccagggcttc ctcaccccc   600
caaatcctgc cccagctcag cccggaacaa ctgggcatga tcgagaagct cgtcgctgcc  660
cagcaacagt gtaaccggcg ctcctttttct gaccggcttc gagtcacgcc ttggcccatg  720
gcaccagatc cccatagccg ggaggcccgt cagcagcgct tgcccacttt cactgagctg  780
gccatcgtct ctgtgcagga gatagttgac tttgctaaac agctaccgg  cttcctgcag  840
ctcagccggg aggaccagat tgccctgctg aagacctctg cgatcgaggt gatgcttctg  900
gagacatctc ggaggtacaa ccctgggagt gagagtatca ccttcctcaa ggatttcagt  960
tataaccggg aagactttgc caaagcaggg ctgcaagtgg aattcatcaa ccccatcttc 1020
gagttctcca gggccatgaa tgagctgcaa ctcaatgatg ccgagtttgc cttgctcatt 1080
gctatcagca tcttctctgc agaccggccc aacgtgcagg accactcca  ggtagagagg 1140
ctgcagcaca catatgtgga agccctgcat gcctacgtct ccatccgtct ccccatgac  1200
cgactgatgt tcccacggat gctaatgaaa ctggtgagcc tccggaccct gagcagcgtc 1260
cactcagagc aagtgttttgc actgcgtctg caggacaaaa agctcccacc gctgctctct 1320
gagatctggg atgtgcacga atga                                        1344

SEQ ID NO: 2           moltype = DNA   length = 1386
FEATURE                Location/Qualifiers
misc_feature           1..1386
                       note = DNA-Sequence LXR beta-full length
source                 1..1386
                       mol_type = other DNA
```

```
                        organism = synthetic construct
SEQUENCE: 2
atgtcctctc ctaccacgag ttccctggat accccctgc ctggaaatgg ccccctcag    60
cctggcgccc cttcttcttc acccactgta aggaggagg gtccggagcc gtggcccggg   120
ggtccggacc ctgatgtccc aggcactgat gaggccagct cagcctgcag cacagactgg  180
gtcatcccag atcccgaaga ggaaccagag cgcaagcgaa agaagggccc agccccgaag  240
atgctgggcc acgagctttg ccgtgtctgt ggggacaagg cctccggctt ccactacaac  300
gtgctcagct gcgaaggctg caagggcttc ttccggcgca gtgtggtccg tggtggggcc  360
aggcgctatg cctgccgggg tggcggaacc tgccagatga acgctttcat gcggcgcaag  420
tgccagcagt gccggctgcg caagtgcaag gaggcaggga tgagggagca gtgcgtcctt  480
tctgaagaac agatccggaa gaagaagatt cggaaacaac agcagcagga gtcacagtca  540
cagtcgcagt cacctgtggg gccgcagggc agcagcagct cagcctctgg gcctgggct   600
tccctggtg gatctgaggc aggcagccag ggctccgggg aaggcgaggg cgtccagcta  660
acagcggctc aagaactaat gatccagcag ttggtggcgg cccaactgca gtgcaacaaa  720
cgctccttct ccgaccagcc caaagtcacg ccctggcccc tgggcgcaga cccccagtcc  780
cgagatgccc gccagcaacg cttttgccac ttcacggagc tggccatcat ctcagtccag  840
gagatcgtga acttcgctaa gcaagtgcct ggtttcctgc agctgggccg ggaggaccag  900
atcgcctcc tgaaggcatc cactatcgag atcatgctgc tagagacagc caggcgctac  960
aaccacgaga cagagtgtat caccttcttg aaggacttca cctacagcaa ggacgacttc 1020
caccgtgcag gcctgcaggt ggagttcatc aaccccatct tcgagttctc gcgggccatg 1080
cggcggctgg gcctggacga cgctgagtac gccctgctca tcgccatcaa catcttctcg 1140
gccgacgcc ccaacgtgca ggagccgggc cgcgtggagg cgttgcagca gccctacgtg 1200
gaggcgctgc tgtcctacac gcgcatcaag aggccgcagg accagctgcg cttcccgcgc 1260
atgctcatga agctggtgag cctgcgcacg ctgagctctg tgcactcgga gcaggtcttc 1320
gccttgcggc tccaggacaa gaagctgccg cctctgctgt cggagatctg ggacgtccac 1380
gagtga                                                            1386

SEQ ID NO: 3                moltype = DNA   length = 882
FEATURE                     Location/Qualifiers
misc_feature                1..882
                            note = DNA-Sequence LXR alpha-LBD
source                      1..882
                            mol_type = other DNA
                            organism = synthetic construct
SEQUENCE: 3
cttcgcaaat gccgtcaggc tggcatgcgg gaggagtgtg tcctgtcaga gaacagatc    60
cgcctgaaga aactgaagcg gcaagaggag aacaggctc atgccacatc cttgccccc   120
agggcttcct cacccccca atcctgccc cagctcagcc cggaacaact gggcatgatc   180
gagaagctcg tcgctgccca gcaacagtgt aaccggcgct ccttttctga ccggcttcga  240
gtcacgcctt ggcccatggc accagatccc catagccggg aggcccgtca gcagcgcttt  300
gcccacttca ctgagctggc catcgtctct gtgcaggaga tagttgactt tgctaaacag  360
ctacccggct tcctgcagct cagccgggag gaccagattg ccctgctgaa gacctctgcg  420
atcgggtga tgcttctgga gacatctcgg aggtacaacc ctgggagtga gagtatccac  480
ttcctcaagg atttcagtta taaccgggaa gactttgcca aagcagggct gcaagtggaa  540
ttcatcaacc ccatcttcga gttctccagg gccatgaatg agctgcaact caatgatgcc  600
gagtttgcct tgctcattgc tatcagcatc ttctctgcag accggcccaa cgtgcaggac  660
cagctccagg tagagaggct gcagcacaca tatgtgaagg ccctgcatgc ctacgtctcc  720
atccaccatc cccatgaccg actgatgttc ccacggatgc taatgaaact ggtgagcctc  780
cggaccctga gcagcgtcca ctcagagcaa gtgtttgcac tgcgtctgca ggacaaaaag  840
ctcccaccgc tgctctctga gatctgggat gtgcacgaat ga                     882

SEQ ID NO: 4                moltype = DNA   length = 1011
FEATURE                     Location/Qualifiers
misc_feature                1..1011
                            note = DNA-sequence LXR beta-LBD
source                      1..1011
                            mol_type = other DNA
                            organism = synthetic construct
SEQUENCE: 4
gagcagtgcg tcctttctga gaacagatc cggaagaaga agattcggaa acaacagcag    60
caggagtcac agtcacagtc gcagtcacct gtggggccgc agggcagcag cagctcagcc   120
tctgggcctg ggcttcccc tggtggatct gaggcaggca gccagggctc ggggaaggc    180
gagggtgtcc agctaacagc ggctcaagaa ctaatgatcc agcagttggt ggcggcccaa   240
ctgcagtgca acaaacgctc cttctccgac cagcccaaag tcacgccctg gccctttga    300
gcagacccc agtcccgaga tgcccgccag caacgctttg cccacttcac ggagctggcc   360
atcatctcag tccaggagat cgtggacttc gctaagcaag tgcctggttt cctgcagctg   420
ggccgggagg accagatcgc cctcctgaag gcatccacta tcgagatcat gctgctagag   480
acagccaggc gctacaacca cgagacagag tgtatcacct tcttgaagga cttcacctac   540
agcaaggacg acttccaccg tgcaggcctg caggtggagt tcatcaaccc catcttcgag   600
ttctcgcggg ccatgcggcg gctgggcctg gacgacgctg agtacgccct gctcatcgcc   660
atcaacatct ctcggccga ccggcccaac gtgcaggagc cgggccgcgt ggaggcgttg   720
cagcagccct acgtggaggc gctgctgtcc tacacgcgca tcaagaggcc gcaggaccag   780
ctgcgcttcc cgcgcatgct catgaagctg gtgagcctgc gcacgctgag ctctgtgcac   840
tcggagcaga gtcttcgcct tgcggctcag gacaagaagc tgccgcctct gctgtcggag   900
atctgggacg tccacgagtg aggggctggc cacccagccc acagccttg cctgaccacc   960
ctccagcaga tagacgccgg caccccttcc tcttcctctg ctttattta a            1011

SEQ ID NO: 5                moltype = DNA   length = 1011
FEATURE                     Location/Qualifiers
```

```
misc_feature            1..1011
                        note = DNA-sequence SRC1-fragment
source                  1..1011
                        mol_type = other DNA
                        organism = synthetic construct
SEQUENCE: 5
gttggcttct ctgccagttc tccagtcctc aggcagatga gctcacagaa ttcacctagc    60
agattaaata tacaaccagc aaaagctgag tccaaagata caaagagat tgcctcaatt    120
ttaaatgaaa tgattcaatc tgacaacagc tctagtgatg gcaaacctct ggattcaggg   180
cttctgcata caatgacag actttcagat ggagacagta aatactctca aaccagtgac   240
aaactagtgc agcttttgac aacaactgcc gaacagcagt tacggcatgc tgatatagac   300
acaagctgca aagatgtcct gtcttgcaca ggcacttcca actctgcctc tgctaactct   360
tcaggaggtt cttgtccctc ttctcatagc tcattgcaca acggcataa aattctacac   420
cggctcttac aggagggtag cccctcagat atcaccactt tgtctgtcga gcctgataaa   480
aaggacagtg catctacttc tgtgtcagtg actggacagg tacaaggaaa ctccagtata   540
aaactagaac tggatgcttc aaagaaaaaa gaatcaaaag accatcagct cctacgctat   600
cttttagata aagatgagaa agatttaaga tcaactccaa acctgagcct ggatgatgta   660
aaggtgaaag tggaaaagaa agaacagatg gatccatgta atacaaaccc aaccccaatg   720
accaaaccca ctcctgagga aataaaactg gaggcccaga gccagtttac agctgacctt   780
gaccagtttg atcagttact gcccacgctg gagaaggcag cacagtttgc cc aggcttatgt   840
gagacagaca ggatggatgg tgcggtcacc agtgtaacca tcaaatcgga gatcctgcca   900
gcttcacttc agtccgccac tgccagaccc acttccaggc taaatagatt acctgagctg   960
gaattggaag caattgataa ccaatttgga caaccaggaa caggcgatta g            1011

SEQ ID NO: 6             moltype = DNA  length = 1225
FEATURE                  Location/Qualifiers
misc_feature             1..1225
                         note = DNA-sequence NCoR-fragment
source                   1..1225
                         mol_type = other DNA
                         organism = synthetic construct
SEQUENCE: 6
gataaagggc ctcctccaaa atccagatat gaggaagagc taaggaccag agggaagact    60
accattactg cagctaactt catagacgtg atcatcaccc ggcaaattgc tcggacaag   120
gatgcgaggg aacgtggctc tcaaagttca gactcttcta gtagcttatc ttctcacagg   180
tatgaaacac ctagcgatgc tattgaggtg ataagtcctg ccagctcacc tgcgccaccc   240
caggagaaac tgcagaccta tcagccgag gttgttaagg caaatcaagc ggaaaatgat    300
cctaccagac aatatgaagg accattacat cactatcgac cacagcagga atcaccatct   360
ccccaacaac agctgccccc ttcttcacag gcagagggaa tgggcaagt gccc aggacc    420
catcggctga tcacacttgc tgatcacatc tgtcaaatta tcacacaaga ttttgctaga   480
aatcaagttt cctcgcagac tccccagcag cctcctactt ctacattcca gaactcacct   540
tctgctttga tatctacacc tgtgaggact aaaacatcaa accgttacag cccagaatcc   600
caggctcagt ctgtccatca tcaaagacca ggttcaaggg tctctacaga aaatcttgtg   660
gacaaatcca ggggaagtag gcctggaaaa tccccagaga ggagtcacgt ctcttcggag   720
ccctacgagc ccatctcccc accccaggtt ccggttgtgc atgagaaaca ggacagcttg   780
ctgctcttgt tcagaggggg cgcagagcct gcagagcaga ggaatgatgc ccgctcacca   840
gggagtataa gctacttgcc ttcattcttc accaagcttg aaaatacat ccccatggtt   900
aaatcaaaga agcaggagat ttttcgtaag ttgaactcct ctggtggagg tgactctgat   960
atggcagctg ctcagccagg aactgagatc tttaatctgc cagcagttac tacgtcaggc   1020
tcagttagct ctagaggcca ttcttttgct gatcctgcca gtaatcttgg gctggaagac   1080
attatcagga aggctctcat gggaagcttt gatgacaaag ttgaggatca tggagttgtc   1140
atgtcccagc ctatgggagt agtgcctggt actgccaaca cctcagttgt gaccagtggt   1200
gagacacgaa gagaggaagg ggtga                                        1225

SEQ ID NO: 7             moltype = AA  length = 25
FEATURE                  Location/Qualifiers
REGION                   1..25
                         note = Peptide
source                   1..25
                         mol_type = protein
                         organism = synthetic construct
SEQUENCE: 7
ENQRGPLESK GHKKLLQLLT CSSDD                                          25

SEQ ID NO: 8             moltype = DNA  length = 20
FEATURE                  Location/Qualifiers
misc_feature             1..20
                         note = Forward primer
source                   1..20
                         mol_type = other DNA
                         organism = synthetic construct
SEQUENCE: 8
cccctctgtt aattggctcc                                                20

SEQ ID NO: 9             moltype = DNA  length = 20
FEATURE                  Location/Qualifiers
misc_feature             1..20
                         note = Reverse primer
source                   1..20
```

```
                        mol_type = other DNA
                        organism = synthetic construct
SEQUENCE: 9
ttgtggaagt gcaggttagg                                                    20

SEQ ID NO: 10           moltype = DNA   length = 22
FEATURE                 Location/Qualifiers
misc_feature            1..22
                        note = Sequence probe
source                  1..22
                        mol_type = other DNA
                        organism = synthetic construct
SEQUENCE: 10
caggctcagg gtgtcccatg tt                                                 22

SEQ ID NO: 11           moltype = DNA   length = 20
FEATURE                 Location/Qualifiers
misc_feature            1..20
                        note = Forward primer
source                  1..20
                        mol_type = other DNA
                        organism = synthetic construct
SEQUENCE: 11
ctgacctgaa agccgagaag                                                    20

SEQ ID NO: 12           moltype = DNA   length = 20
FEATURE                 Location/Qualifiers
misc_feature            1..20
                        note = Reverse primer
source                  1..20
                        mol_type = other DNA
                        organism = synthetic construct
SEQUENCE: 12
agaaggtgct aacgaacagg                                                    20

SEQ ID NO: 13           moltype = DNA   length = 25
FEATURE                 Location/Qualifiers
misc_feature            1..25
                        note = Sequence probe
source                  1..25
                        mol_type = other DNA
                        organism = synthetic construct
SEQUENCE: 13
tgtttacaaa agtctcgccc cagca                                              25

SEQ ID NO: 14           moltype = DNA   length = 20
FEATURE                 Location/Qualifiers
misc_feature            1..20
                        note = Forward primer
source                  1..20
                        mol_type = other DNA
                        organism = synthetic construct
SEQUENCE: 14
ccatcgacta catccgcttc                                                    20

SEQ ID NO: 15           moltype = DNA   length = 20
FEATURE                 Location/Qualifiers
misc_feature            1..20
                        note = Reverse primer
source                  1..20
                        mol_type = other DNA
                        organism = synthetic construct
SEQUENCE: 15
gccctccata gacacatctg                                                    20

SEQ ID NO: 16           moltype = DNA   length = 24
FEATURE                 Location/Qualifiers
misc_feature            1..24
                        note = Sequence probe
source                  1..24
                        mol_type = other DNA
                        organism = synthetic construct
SEQUENCE: 16
tctcctgctt gagcttctgg ttgc                                               24

SEQ ID NO: 17           moltype = DNA   length = 21
FEATURE                 Location/Qualifiers
misc_feature            1..21
                        note = Forward primer
```

-continued

```
source              1..21
                    mol_type = other DNA
                    organism = synthetic construct
SEQUENCE: 17
caccaatgac tcctatgacc c                                      21

SEQ ID NO: 18       moltype = DNA  length = 23
FEATURE             Location/Qualifiers
misc_feature        1..23
                    note = Reverse primer
source              1..23
                    mol_type = other DNA
                    organism = synthetic construct
SEQUENCE: 18
caagtttaca gccaagattc acg                                    23

SEQ ID NO: 19       moltype = DNA  length = 20
FEATURE             Location/Qualifiers
misc_feature        1..20
                    note = Sequence probe
source              1..20
                    mol_type = other DNA
                    organism = synthetic construct
SEQUENCE: 19
actcctgcca caccagcctc                                        20
```